US012692252B2

(12) United States Patent
Song et al.

(10) Patent No.: US 12,692,252 B2
(45) Date of Patent: Jul. 28, 2026

(54) COMPOUND HAVING ANTI-TUMOR ACTIVITY AND USE THEREOF

(71) Applicant: Innovstone Therapeutics Limited, Shanghai (CN)

(72) Inventors: Yunlong Song, Shanghai (CN); Wenqing Xu, Shanghai (CN); Hongyan Kou, Shanghai (CN); Yongzhao Mu, Shanghai (CN); Qun Dang, Shanghai (CN); Pan Li, Shanghai (CN); Zhou Yin, Shanghai (CN); Jianbin Ma, Shanghai (CN); Xiaodan Fu, Shanghai (CN); Xin Cai, Shanghai (CN); Yan Li, Shanghai (CN)

(73) Assignee: Innovstone Therapeutics Limited, Shanghai (CN)

( * ) Notice: Subject to any disclaimer, the term of this patent is extended or adjusted under 35 U.S.C. 154(b) by 393 days.

(21) Appl. No.: 18/560,632

(22) PCT Filed: May 12, 2022

(86) PCT No.: PCT/CN2022/092346
§ 371 (c)(1),
(2) Date: Nov. 13, 2023

(87) PCT Pub. No.: WO2022/237858
PCT Pub. Date: Nov. 17, 2022

(65) Prior Publication Data

US 2025/0206717 A1 Jun. 26, 2025

(30) Foreign Application Priority Data

May 13, 2021 (CN) ......................... 202110521548.0

(51) Int. Cl.

| | |
|---|---|
| *C07D 401/14* | (2006.01) |
| *A61K 31/4725* | (2006.01) |
| *A61K 31/506* | (2006.01) |
| *A61K 31/519* | (2006.01) |
| *A61K 31/52* | (2006.01) |
| *A61K 31/53* | (2006.01) |
| *A61K 31/5377* | (2006.01) |
| *A61P 35/00* | (2006.01) |
| *C07D 401/04* | (2006.01) |
| *C07D 405/14* | (2006.01) |
| *C07D 409/14* | (2006.01) |
| *C07D 413/14* | (2006.01) |

(Continued)

(52) U.S. Cl.
CPC ........ *C07D 401/14* (2013.01); *A61K 31/4725* (2013.01); *A61K 31/506* (2013.01); *A61K 31/519* (2013.01); *A61K 31/52* (2013.01); *A61K 31/53* (2013.01); *A61K 31/5377* (2013.01); *A61P 35/00* (2018.01); *C07D 401/04* (2013.01); *C07D 405/14* (2013.01); *C07D 409/14* (2013.01); *C07D 413/14* (2013.01); *C07D 417/14* (2013.01); *C07D 471/04* (2013.01); *C07D 471/08* (2013.01); *C07D 473/00* (2013.01); *C07D 513/04* (2013.01)

(58) Field of Classification Search
CPC .. C07D 401/14; C07D 401/04; C07D 405/14; C07D 409/14; C07D 413/14; C07D 417/14; C07D 471/04; C07D 471/08; C07D 473/00; C07D 513/04; A61K 31/4725; A61K 31/506; A61K 31/519; A61K 31/52; A61K 31/53; A61K 31/5377; A61P 35/00
See application file for complete search history.

(56) References Cited

U.S. PATENT DOCUMENTS

| | | | |
|---|---|---|---|
| 2002/0019531 | A1 | 2/2002 | Kitazawa et al. |
| 2011/0311474 | A1 | 12/2011 | Wishart et al. |
| 2016/0304491 | A1 | 10/2016 | Becker-Pelster et al. |

FOREIGN PATENT DOCUMENTS

| | | |
|---|---|---|
| CN | 105980374 A | 9/2016 |
| CN | 108570059 A | 9/2018 |

(Continued)

OTHER PUBLICATIONS

WO2020182018A1, Machine Translation (Year: 2020).*

(Continued)

*Primary Examiner* — Jeffrey S Lundgren
*Assistant Examiner* — Ibrahim D Bori
(74) *Attorney, Agent, or Firm* — Buchanan Ingersoll & Rooney PC

(57) ABSTRACT

Provided is a compound having anti-tumor activity and a use thereof. As a PRMT5 inhibitor, the compound has a structure represented by formula (I). Experiments have confirmed that these compounds have strong inhibitory effects on PRMT5 enzyme activity and tumor cell growth, and can be used as promising compounds for treating PRMT5-mediated diseases. Furthermore, a specific synthesis method is further studied. The synthesis method is simple in process, convenient to operate, and beneficial to large-scale industrial production and application.

(I)

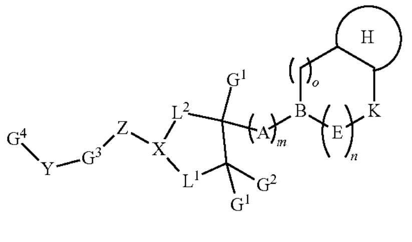

12 Claims, No Drawings

(51) Int. Cl.

| | |
|---|---|
| *C07D 417/14* | (2006.01) |
| *C07D 471/04* | (2006.01) |
| *C07D 471/08* | (2006.01) |
| *C07D 473/00* | (2006.01) |
| *C07D 513/04* | (2006.01) |

(56) References Cited

FOREIGN PATENT DOCUMENTS

| | | | | |
|---|---|---|---|---|
| CN | 111592522 A | | 8/2020 | |
| EP | 1849781 A1 | | 10/2007 | |
| JP | 2013512280 A | | 4/2013 | |
| JP | 2016514118 A | | 5/2016 | |
| WO | 9843956 A1 | | 10/1998 | |
| WO | 0000472 A1 | | 1/2000 | |
| WO | 2014100695 A1 | | 6/2014 | |
| WO | 2014100716 A1 | | 6/2014 | |
| WO | 2014100719 A2 | | 6/2014 | |
| WO | 2014100730 A1 | | 6/2014 | |
| WO | 2014100764 A2 | | 6/2014 | |
| WO | 2014140310 A1 | | 9/2014 | |
| WO | 2015200677 A2 | | 12/2015 | |
| WO | 2015200680 A2 | | 12/2015 | |
| WO | 2018167269 A1 | | 9/2018 | |
| WO | WO-2019002074 A1 | * | 1/2019 | ........... C07D 417/14 |
| WO | 2019102494 A1 | | 5/2019 | |
| WO | 2019173804 A1 | | 9/2019 | |
| WO | WO-2020182018 A1 | * | 9/2020 | ........... C07D 401/14 |
| WO | 2021032323 A1 | | 2/2021 | |
| WO | 2021126728 A1 | | 6/2021 | |
| WO | 2021126731 A1 | | 6/2021 | |
| WO | 2022048631 A1 | | 3/2022 | |

OTHER PUBLICATIONS

Chauhan et al., "Computational elucidation, mutational and hot spot-based designing of potential inhibitors to treat various physiological conditions", Journal of Biomolecular Structure and Dynamics, (month unknown 2018), vol. 36 (13), pp. 3513-3530.

Office Action (Notice of Reasons for Refusal) issued Jan. 28, 2025, by the Japanese Patent Office in corresponding Japanese Patent Application No. 2023-570323 and an English translation of the Office Action. (16 pages).

Scheunemann et al., "Sequential ring-opening of trans-1,4-cyclohexadiene dioxide for an expedient modular approach to 6,7-disubstituted (±)-hexahydro-benzo[1,4]oxazin-3-ones", Tetrahedron Letters, (month unknown 2007), vol. 48(31), pp. 5497-5501.

International Search Report and Written Opinion for International Application No. PCT/CN2022/092346, dated Aug. 18, 2022, 13 pages.

* cited by examiner

COMPOUND HAVING ANTI-TUMOR ACTIVITY AND USE THEREOF

REFERENCES TO RELATED APPLICATIONS

This application is a U.S. national phase application of International Application No. PCT/CN2022/092346, filed May 12, 2022, claiming the benefit of priority of the invention patent application No. 202110521548.0 filed in China, titled "Compound having anti-tumor activity and use thereof", filed May 13, 2021, the contents of which are incorporated herein by reference in their entirety.

TECHNICAL FIELD

The present invention relates to the field of pharmaceutical technology, in particular, to a compound as a PRMT5 inhibitor and a preparation process and use of the compound.

BACKGROUND OF ART

PRMT5, the abbreviation of the English name Protein arginine N-methyltransferase 5, is one of the protein arginine methyltransferases (PRMTs), and it is a new anti-tumor target related to epigenetic modifications. It has several aliases, namely Hsl7, Jbpl, Skbl, Capsuleen or Dart5. PRMT5 is the main enzyme responsible for monomethylation and symmetric dimethylation of arginine. More and more literature demonstrate that protein arginine methyltransferases play a key role in different biological processes, such as cell growth and proliferation, apoptosis, metastasis, and the like.

The function of protein arginine methyltransferase is to transfer a methyl group from S-adenosylmethionine (AdoMet or SAM) to an arginine residue in histones or other proteins, forming methylarginine and S-adenosylhomocysteine (SAH). Currently, 9 members of this family (PRMT 1-9) have been identified. According to the different ways in which they catalyze the arginine methylation, PRMTs can be divided into three types: Type I PRMT, including PRMT1, PRMT2, PRMT3, PRMT4, PRMT6 and PRMT8, and catalyzing monomethylarginine (MMA) and asymmetric dimethylarginine (aDMA); Type II PRMT, including PRMT5 and PRMT9, and catalyzing MMA and symmetric dimethylarginine (sDMA); and III Type PRMT, PRMT7, which can only catalyze MMA. As an epigenetic enzyme, PRMT5 can symmetrically methylate arginine residues of histones or non-histone substrates, affecting multiple target genes and multiple signaling pathways. It plays an important role in protein methylation, such as participating in alternative splicing, post-transcriptional regulation, RNA processing, cell proliferation, cell differentiation, apoptosis and tumor formation. Substances that selectively inhibit PRMT5 may serve as a potentially powerful new anticancer drug. The development of new drugs based on PRMT5 as the target has a positive role in filling gaps to solve unmet clinical needs.

In the past few years, there have been many reports about PRMT5 inhibitors. Such reports can be found in WO2014100719A, WO2019102494A, WO2015200677A, WO2015200680A, WO2014100764A, WO2014100730A, WO2014100716A, WO2014100695A, WO2019173804A, CN108570059 A, WO2018167269A, and the like. Moreover, two compounds, JNJ-64619178 and GSK-3326595, have been used in the clinical treatment of solid tumors and mantle cell lymphoma.

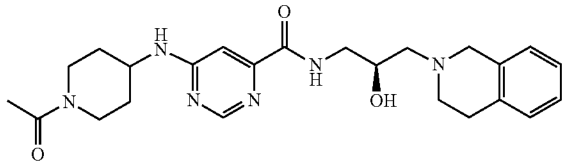

GSK3326595

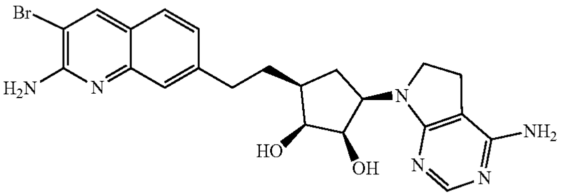

JNJ-64619178

JNJ-64619178 is a selective PRMT5 inhibitor developed by Johnson & Johnson, and has an inhibitory effect on the growth of various tumor cells in vitro. A number of xenograft animal models were selected by Johnson & Johnson to demonstrate its effective anti-tumor effect, for example, Xenograft models of small cell lung cancer (SCLC), non-small cell lung cancer (NSCLC), acute myeloid leukemia (AML) and non-Hodgkin's lymphoma were selected for antitumor experiments. Significant tumor growth inhibition of up to 99% was observed in the model, with continued tumor growth inhibition for weeks after drug withdrawal. JNJ-64619178 can inhibit Sym-Arg dimethylation of SMD1/3 proteins, core components of the tumor spliceosome, and Sym-Arg dimethylation of serum proteins. These can serve as pharmacodynamic markers for the inhibition of tumor growth by PRMT5 in the Xenograft model. In SCLC models, potent and long-term inhibition of SMD1/3 dimethylation by PRMT5 was observed both during and after dosing. Based on these high selectivity and efficiency, good pharmacokinetics and safety, and significant preclinical efficacy and pharmacodynamic results, Phase I clinical trials of JNJ-64619178 began in 2018.

GSK-3326595 is optimized from EPZ015666 (having a structure as follows). It is a highly selective, orally available small molecule, and is the first-generation PRMT5 inhibitor. EPZ015666 showed significant in vitro and in vivo activity in mantle cell lymphoma. After two years of optimization and preclinical research, GlaxoSmithKline (GSK) announced in September 2016 that GSK-3326595 had entered the clinic for the first time. At the 2019 ESMO conference, GlaxoSmithKline announced the Phase I clinical data of GSK-3326595. In Phase I clinical trials of GSK-3326595, adult patients with solid tumors were selected, with the main purpose of testing the safety, tolerance and PK/PD, and collecting drug efficacy data (ORR and DCR). Data show that the PK of GSK3326595 is dose-dependent in plasma.

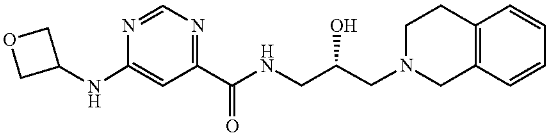

EPZ 015666

Although some PRMT5 small molecule inhibitors have been disclosed, no PRMT5 inhibitor has yet been developed and marketed. Therefore, there is still an urgent need to develop new compounds with market potential, better efficacy and pharmacokinetic results.

SUMMARY OF THE INVENTION

The object of the present invention is to provide a compound with a new structure as a PRMT5 inhibitor, a preparation process of the compound, and its use in treating PRMT5-mediated diseases.

The first aspect of the present invention provides a compound represented by the following formula (I), and stereoisomers, geometric isomers, tautomers, pharmaceutical salts, prodrugs, hydrates, solvates or isotope-labeled analogues thereof, (I)

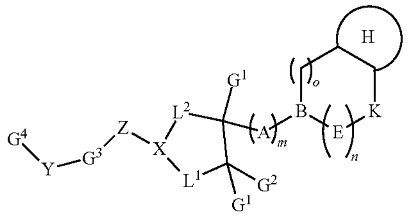

wherein $L^1$ and $L^2$ are each independently one of —$C(R^1)(R^2)$—, —$C(R^1)(R^2)C(R^1)(R^2)$—, and —$C(R^1)(R^2)C(R^1)(R^2)C(R^1)(R^2)$—; wherein $R^1$ and $R^2$ are independently selected at each occurrence from hydrogen, halogen, hydroxy, mercapto, amino, cyano, $C_{1-6}$alkyl, $C_{3-6}$cycloalkyl, 4-6 membered heterocyclyl, —$OR^3$, —$NHR^3$, and —$NR^3R^4$; $R^3$ and $R^4$ are independently selected at each occurrence from $C_{1-6}$alkyl, $C_{2-6}$alkenyl, $C_{2-6}$alkynyl, $C_{3-6}$cycloalkyl, 4-6 membered heterocyclyl, aryl, and 5-6 membered heteroaryl;

X is $C(R^5)$ or N; wherein $R^5$ is independently selected at each occurrence from hydrogen, halogen, hydroxy, mercapto, amino, and cyano;

Y is selected from — (chemical bond), —H, —OH, —$NH_2$, halogen, —O—, —S—, —CO—, —$C(R^6)F$—, —$CF_2$—, —SO—, —$SO_2$—, —$(CH_2)_pN(R^6)$—, —$N(R^6)(CH_2)_p$—, —$S(O)N(R^6)$—, —$S(O)_2N(R^6)$—, —$N(R^6)SO$—, —$N(R^6)S(O)_2$—, —$C(O)N(R^6)$—, —$N(R^6)C(O)$—, and —$CH(R^6)$—; wherein p=0, 1, 2 or 3; $R^6$ can be selected from hydrogen, optionally substituted $C_{1-6}$alkyl, optionally substituted $C_{3-6}$cycloalkyl, optionally substituted and 4-6 membered heterocyclyl; said "optionally substituted" means that the hydrogen on the group to be substituted is unsubstituted or one or more substitutable sites of the group to be substituted are independently substituted by a substituent selected from a group consisting of halogen, hydroxy, mercapto, amino, cyano, $C_{1-6}$alkyl, $C_{2-6}$alkenyl, $C_{2-6}$alkynyl, $C_{3-6}$cycloalkyl, 4-6 membered heterocyclyl, aryl, and 5-6 membered heteroaryl; when Y is selected from —H, —OH, —$NH_2$, and halogen, $G^4$ is absent;

Z is selected from — (chemical bond), —O—, —S—, —CO—, —$N(R^7)$—, —$S(O)N(R^7)$—, —$S(O)_2N(R^7)$—, —$N(R^7)SO$—, —$N(R^7)S(O)_2$—, —$C(O)N(R^7)$—, —$N(R^7)C(O)$—, —$N(R^7)C(O)N(R^7)$—, —$CH(R^7)$—, —CH(OH)—, —$CH(CF_3)$—, —$CH(NHR^7)$—, —$C{=}N(R^7)$—, —SO—, —$SO_2$—, —$CF(R^7)$—, $CF_2$, and

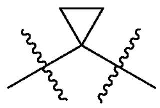

;

wherein $R^7$ is independently selected at each occurrence from hydrogen, optionally substituted $C_{1-6}$alkyl, optionally substituted $C_{3-6}$cycloalkyl, optionally substituted $C_{1-6}$alkyloxy, and optionally substituted 4-6 membered heterocyclyl; said "optionally substituted" means that the hydrogen on the group to be substituted is unsubstituted or one or more substitutable sites of the group to be substituted are independently substituted by a substituent selected from a group consisting of halogen, hydroxy, mercapto, amino, cyano, $C_{1-6}$alkyl, $C_{2-6}$alkenyl, $C_{2-6}$alkynyl, $C_{3-6}$ cycloalkyl, 4-6 membered heterocyclyl, aryl, and 5-6 membered heteroaryl;

$G^1$ is independently selected at each occurrence from hydrogen, halogen, hydroxy, mercapto, amino, cyano, and $C_{1-5}$ linear or branched alkyl;

$G^2$ is halogen, hydroxy, mercapto, amino, cyano, optionally substituted $R^8$, optionally substituted —$O(R^8)$, optionally substituted —$S(R^8)$, optionally substituted —$NH(R^8)$, and optionally substituted —$N(R^8)(R^8)$; wherein $R^8$ is independently selected at each occurrence from $C_{1-6}$alkyl, $C_{3-6}$cycloalkyl, and 4-6 membered heterocyclyl; said "optionally substituted" means that the hydrogen on the group to be substituted is unsubstituted or one or more substitutable sites of the group to be substituted are independently substituted by a substituent selected from a group consisting of halogen, hydroxy, mercapto, amino, cyano, $C_{1-6}$alkyl, $C_{2-6}$alkenyl, $C_{2-6}$alkynyl, $C_{3-6}$cycloalkyl, 4-6 membered heterocyclyl, aryl, and 5-6 membered heteroaryl;

$G^3$ is selected from optionally substituted $C_{6-10}$aryl, optionally substituted 5-10 membered heteroaryl, optionally substituted $C_{3-7}$cycloalkyl, and optionally substituted 4-10 membered heterocyclyl; said "optionally substituted" means that the hydrogen on the group to be substituted is unsubstituted or one or more substitutable sites of the group to be substituted are independently substituted by $R^{16}$, wherein $R^{16}$ is independently selected at each occurrence from hydrogen, deuterium, halogen, hydroxy, mercapto, amino, nitro, cyano, —$R^9$, —$OR^9$, —$OR^9$—$N(R^9)(R^{10})$, —$OR^9$—$OR^{10}$, —$SR^9$, $SO(R^9)$, —$SO_2(R^9)$, —$COOR^9$, —$NH(R^9)$, —$N(R^9)(R^{10})$, —$N(R^9)(R^{10})$—$N(R^9)(R^{10})$, —$CONHR^9$, —$CON(R^9)(R^{10})$, —$SONH(R^9)$, —$SON(R^9)(R^{10})$, $SO_2NH(R^9)$, and —$SO_2N(R^9)(R^{10})$; wherein $R^9$ and $R^{10}$ are independently selected at each occurrence from hydrogen; or $C_{1-6}$ alkyl, $C_{2-6}$alkenyl, $C_{2-6}$alkynyl, $C_{3-10}$cycloalkyl, 4-10 membered heterocyclyl, aryl, and 5-10 membered heteroaryl, which can be optionally substituted by one or more of hydrogen, halogen, hydroxy, mercapto, amino, cyano, nitro, methoxy, —$COOCH_3$, —$COCH_3$, —$COOC(CH_3)_3$, —$CH_2$—$N(CH_3)(CH_3)$, —$N(CH_3)(CH_3)$, —$NH(CH_3)$, $C_{1-6}$alkyl, $C_{2-6}$alkenyl, $C_{1-6}$alkyloxy, $C_{3-6}$cycloalkyl, 4-6 membered heterocyclyl, aryl, and 5-6 membered heteroaryl;

$G^4$ is selected from —$SO_2(CH_3)$, optionally substituted $C_{1-12}$alkyl, optionally substituted $C_{2-12}$alkenyl, optionally substituted $C_{2-12}$alkynyl, optionally substituted $C_{3-12}$cycloalkyl, optionally substituted 4-10 membered heterocyclyl, optionally substituted $C_{6-10}$aryl, and optionally substituted 5-10 membered heteroaryl; said "optionally substituted" means that the hydrogen on the group to be substituted is unsubstituted or one or more substitutable sites of the group to be substituted are independently substituted by $R^{17}$, $R^{17}$ is independently selected at each occurrence from hydrogen, halogen, hydroxy mercapto, amino, cyano, carboxyl, oxo, sulfoxide, —$R^{11}$, —$OR^{11}$, —$SR^{11}$, —$NH(R^{11})$, —$N(R^{11})(R^{11})$,

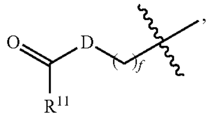

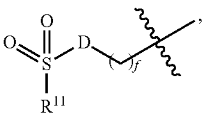

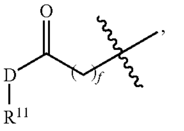

and

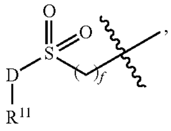

wherein $R^{11}$ is independently selected at each occurrence from $C_{1-6}$alkyl, $C_{1-6}$alkyloxy, $C_{2-6}$alkenyl, $C_{2-6}$alkynyl, $C_{3-6}$cycloalkyl, $C_{3-6}$cycloalkyloxy, 4-10 membered heterocyclyl, aryl, and 5-6 membered heteroaryl, which can be optionally substituted with one or more of hydrogen, halogen, hydroxy, mercapto, amino, cyano, oxo, $C_{1-6}$alkyl, trifluoromethyl, $C_{3-6}$cycloalkyl, 4-6 membered heterocycloalkyl, aryl, and 5-6 membered heteroaryl; D is independently selected at each occurrence from a bond, —$CH_2$—, —C(═O)—, —NH—, —$N(CH_3)$—, —O— and —S—, f is independently selected at each occurrence from 0, 1, 2, 3, 4, 5, 6, 7 and 8.

m=0 or 1, when m=1, A can be selected from —$N(R^{12})$—, —$CH(R^{12})$— and —$CH(NHR^{12})$—, wherein $R^{12}$ can be selected from hydrogen, hydroxy, halogen, $C_{1-6}$alkyl, $C_{3-6}$cycloalkyl, and 4-6 membered heterocyclyl; when m=0, A is absent; B can be selected from N and CH;

n=0 or 1, when n=1, E can be selected from —$NR^{13}$— and —$C(R^{13})R^{13}$—, $R^{13}$ is independently selected at each occurrence from hydrogen, hydroxy, halogen, $C_{1-6}$alkyl, $C_{3-6}$cycloalkyl, and 4-6 membered heterocyclyl; when n=0, E is absent; at least one of A, B, and E is an N atom that meets their respective definitions;

o=0, 1, 2 or 3;

K can be selected from —$CH_2$—, —C(═O)—, —CHF—, —CH(—OH)—, —$CF_2$—, —CHD-, —CD(—OH)—, —CDF—, —$CD_2$- and —$CH(R^{18})$—; $R^{18}$ is independently selected at each occurrence from halogen, mercapto, nitro, cyano, amino, $C_{1-6}$alkyl, $C_{3-6}$cycloalkyl, and 4-6 membered heterocyclyl;

ring H is selected from $C_{6-10}$ aryl ring and 5-10 membered heteroaryl ring; the aryl ring or heteroaryl ring can be independently substituted by one or more $R^{15}$s, wherein $R^{15}$ is independently selected at each occurrence from hydrogen, halogen, hydroxy, mercapto, amino, cyano, optionally substituted —$R^{14}$, optionally substituted —$OR^{14}$, optionally substituted —$NHR^{14}$, and optionally substituted —$N(R^{14})(R^{14})$; wherein $R^{14}$ is independently selected at each occurrence from $C_{1-6}$alkyl, $C_{2-6}$alkenyl, $C_{2-6}$alkynyl, $C_{3-6}$cycloalkyl, 4-6 membered heterocyclyl, aryl, and 5-6 membered heteroaryl; said "optionally substituted" means that the hydrogen on the group to be substituted is unsubstituted or one or more substitutable sites of the group to be substituted are independently substituted by a substituent selected from a group consisting of halogen, hydroxy, mercapto, amino, cyano, $C_{1-6}$alkyl, $C_{2-6}$alkenyl, $C_{2-6}$alkynyl, $C_{3-6}$cycloalkyl, 4-6 membered heterocyclyl, aryl, and 5-6 membered heteroaryl.

In a preferred embodiment of the present invention, the compound represented by formula (I) is further a structure represented by formula (II)B:

(II)B

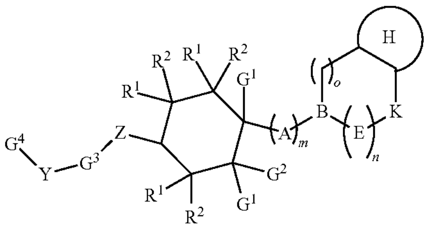

wherein, each substituent in formula (II)B is defined as described in formula (I).

In a further preferable embodiment, $R^1$ and $R^2$ are independently selected at each occurrence from hydrogen, halogen, hydroxy, mercapto, amino, cyano, $C_{1-6}$alkyl, $C_{3-6}$cycloalkyl, 4-6 membered heterocyclyl, —$OR^3$, —$NH(R^3)$, and —$N(R^3)(R^4)$; $R^3$ and $R^4$ are independently selected at each occurrence from $C_{1-6}$alkyl, $C_{2-6}$alkenyl, $C_{2-6}$alkynyl, $C_{3-6}$cycloalkyl, 4-6 membered heterocyclyl, aryl, and 5-6 membered heteroaryl. Even further preferably $R^1$ and $R^2$ are independently at each occurrence hydrogen, halogen, hydroxy, amino, methyl, methylamino, or dimethylamino; most preferably hydrogen.

In some preferable embodiments of the present invention, X is preferably CH, C(OH), or N; most preferably N. Preferably, Y is selected from — (chemical bond), —H, —OH, —$NH_2$, halogen, —O—, —S—, —CO—, —$C(R^6)F$—, —$CF_2$—, —SO—, —$SO_2$—, —$(CH_2)_pN(R^6)$—, —$N(R^6)(CH_2)_p$—, —$S(O)N(R^6)$—, —$S(O)_2N(R^6)$—, —$N(R^6)SO$—, —$N(R^6)S(O)_2$—, —$C(O)N(R^6)$—, —$N(R^6)C(O)$—, and —$CH(R^6)$—, wherein p=0, 1, 2 or 3; $R^6$ can be selected from hydrogen, $C_{1-6}$alkyl, $C_{3-6}$cycloalkyl, and 4-6 membered heterocyclyl, when Y is selected from —H, —OH, —$NH_2$, and halogen, $G^4$ is absent.

More preferably, Y is selected from — (chemical bond), —H, —OH, —$NH_2$, —NH—, —O—, —S—, —CO—, —CHF—, —$CF_2$—, —SO—, —$SO_2$—, —$(CH_2)_pNH$—, —$N(CH_3)$—, —S(O)NH—, —$S(O)_2NH$—, —NHSO—, —$NHS(O)_2$—, —C(O)NH—, —NHC(O)—, and —$CH_2$—, wherein p=1, 2 or 3.

Further preferably, Y is selected from — (chemical bond), —H, —OH, —$NH_2$, —NH—, —$CH_2NH$—, —$(CH_2)_2NH$—, —$N(CH_3)$—, —O—, and —S—.

Further preferably, Y is selected from — (chemical bond), —OH, —$NH_2$, —NH—, —O—, and —S—.

Most preferably, Y is selected from — (chemical bond) and —NH—.

In some preferable embodiments of the present invention, Z is selected from — (chemical bond), —O—, —S—, —CO—, —$N(R^7)$—, —$S(O)N(R^7)$—, —$S(O)_2N(R^7)$—, —$N(R^7)SO$—, —$N(R^7)S(O)_2$—, —$C(O)N(R^7)$—, —$N(R^7)C(O)$—, —$N(R^7)C(O)N(R^7)$—, —$CH(R^7)$—, —CH (OH)—, —CH($CF_3$)—, —CH($NHR^7$)—, —C═N($R^7$)—, —SO—, —$SO_2$—, —CF($R^7$)—, $CF_2$, and

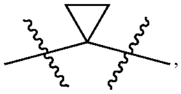, wherein $R^7$ is independently selected at each occurrence from hydrogen, $C_{1-6}$alkyl, $C_{3-6}$cycloalkyl, $C_{1-6}$alkyloxy, and 4-6 membered heterocyclyl. More preferably, Z is selected from — (chemical bond), —O—, —S—, —CO—, —NH—, —$S(O)_2NH$—, —$NHS(O)_2$—, —C(O)NH—, —NHC(O)—, —NHC(O)NH—, —$CH_2$—, —CH(OH)—, —CH($CF_3$)—, —CH($NH_2$)—, —C═N($CH_3$)—, —C═N($OCH_3$)—, —SO—, —$SO_2$—, —CHF—, $CF_2$, and

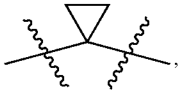 [SMILES: *C1(*)CC1],

Most preferably, Z is selected from — (chemical bond), —O—, —CO—, —NH—, —C(O)NH—, —$CH_2$—, —CH(OH)—, —CH($CF_3$)—, —CH($NH_2$)—, —C═N($CH_3$)—, —C═N($OCH_3$)—, —$SO_2$—, —CHF—, $CF_2$, and

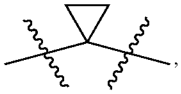 [SMILES: *C1(*)CC1],

Further preferably, Z is —CO—, or —$SO_2$—; most preferably, Z is —CO—.

In some preferable embodiments of the present invention, $G^1$ is independently selected at each occurrence from hydrogen, halogen, hydroxy, mercapto, amino, cyano, and methyl; more preferably, $G^1$ is hydrogen.

In some preferable embodiments of the present invention, $G^2$ is selected from halogen, hydroxy, mercapto, amino, cyano, —$R^8$, —O($R^8$), —S($R^8$), —NH($R^8$), and —N($R^8$)($R^8$), wherein $R^8$ is independently selected at each occurrence from $C_{1-6}$alkyl, $C_{3-6}$ cycloalkyl, and 4-6 membered heterocyclyl; more preferably, $G^2$ is selected from halogen, hydroxy, mercapto, amino, cyano, —$CH_3$, cyclopropyl, —$OCH_3$, —$SCH_3$, —$NHCH_3$, —N($CH_3$)($CH_3$), and —NH($CH_3$); more preferably, $G^2$ is selected from fluoro, hydroxy, and amino; most preferably, $G^2$ is selected from hydroxy, and amino.

In some preferable embodiments of the present invention, $G^3$ is selected from optionally substituted $C_{6-10}$aryl, optionally substituted 5-10 membered heteroaryl, and optionally substituted 4-10 membered heterocyclyl, wherein the heteroatom in 5-10 membered heteroaryl is N, O, or S, and the number of heteroatoms is 1, 2, 3 or 4, said “optionally substituted” means that the hydrogen on the group to be substituted is unsubstituted or one or more substitutable sites of the group to be substituted are independently substituted by $R^{16}$.

In an even further preferable embodiment of the present invention, $G^3$ is optionally substituted $C_{6-10}$aryl, optionally substituted 5-10 membered heteroaryl, or optionally substituted 4-10 membered heterocyclyl, the $C_{6-10}$aryl, 5-10 membered heteroaryl or 4-10 membered heterocyclyl is selected from:

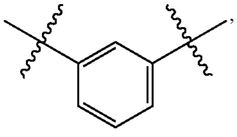, 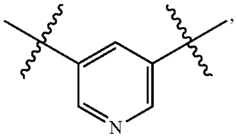,
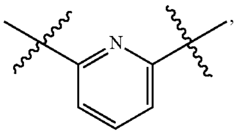, 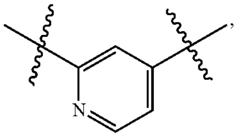,
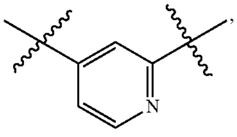, 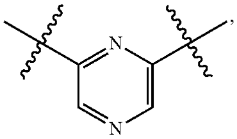,
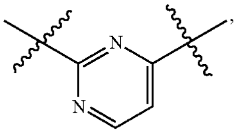, 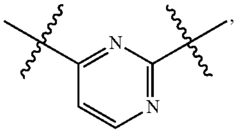,
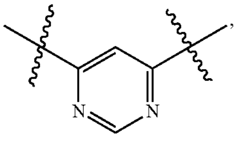, 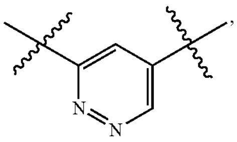,
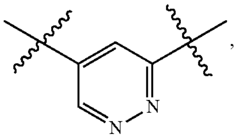, 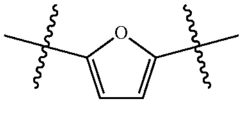,
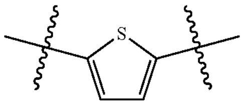, 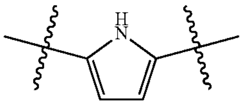,
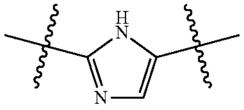, 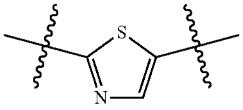,
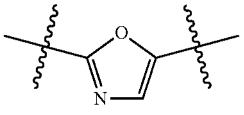, 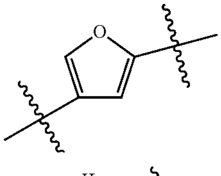,
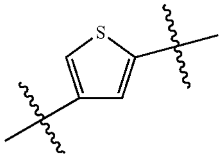, 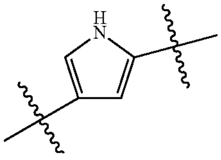,
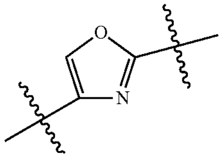, 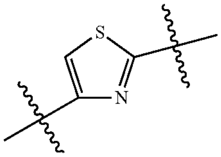,
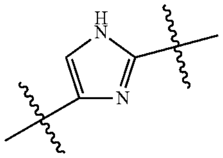, 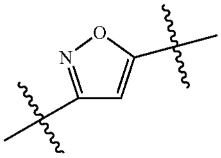, -continued

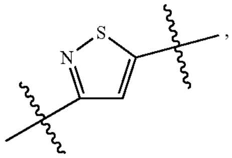,
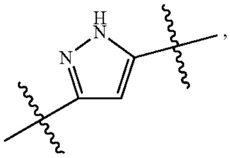,
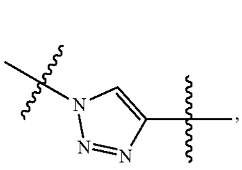,
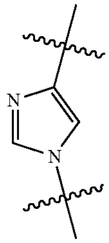,
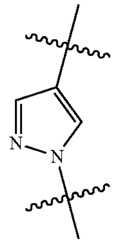,
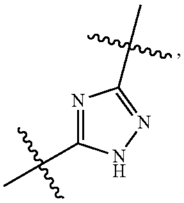,
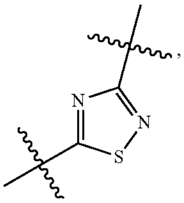,
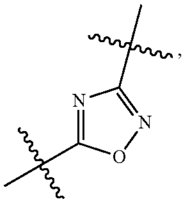,
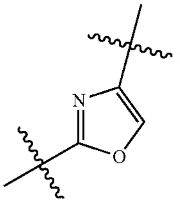,
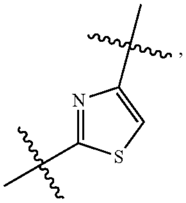,
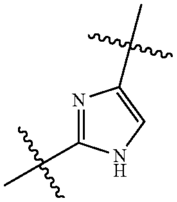
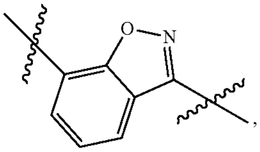,
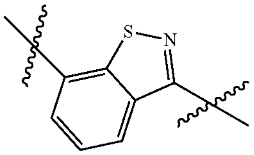,
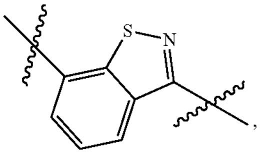,
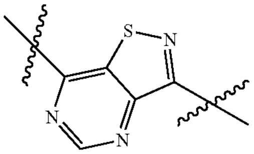,
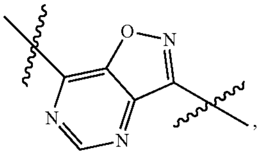,
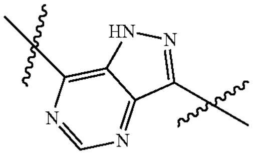,
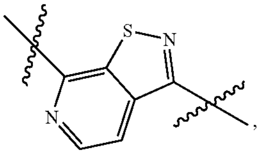,
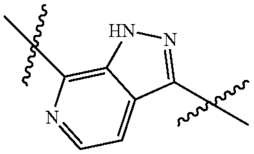,
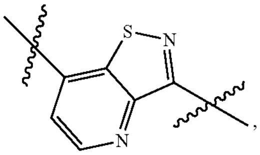,
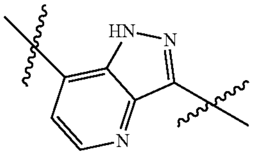, -continued

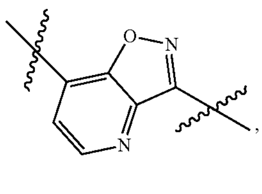,
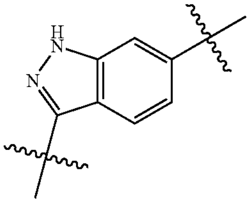, and
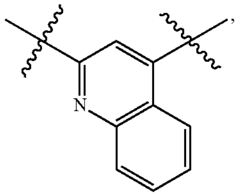, said "optionally substituted" means that the hydrogen on the group to be substituted is unsubstituted or one or more substitutable sites of the group to be substituted are independently substituted by $R^{16}$. $R^{16}$ is independently selected at each occurrence from hydrogen, deuterium, halogen, hydroxy, mercapto, amino, cyano, —$R^9$, —$OR^9$, —$SR^9$, $SO(R^9)$, —$SO_2(R^9)$, —$COOR^9$, —$NH(R^9)$, —$N(R^9)(R^{10})$, —$CONHR^9$, —$CON(R^9)(R^{10})$, —$SONH(R^9)$, —$SON(R^9)(R^{10})$, $SO_2NH(R^9)$, and —$SO_2N(R^9)(R^{10})$; further preferably, $R^{16}$ is independently selected at each occurrence from hydrogen, deuterium, halogen, hydroxy, mercapto, amino, cyano, —$R^9$, —$OR^9$, —$SR^9$, $SO(R^9)$, —$COOR^9$, —$NH(R^9)$, —$N(R^9)(R^{10})$, and —$CON(R^9)(R^{10})$; most preferably, $R^{16}$ is independently selected at each occurrence from hydrogen, deuterium, halogen, cyano, —$R^9$, —$OR^9$, —$SR^9$, $SO(R^9)$, and —$N(R^9)(R^{10})$.

Further preferably, $R^9$ and $R^{10}$ are independently selected at each occurrence from $C_{1-6}$alkyl, $C_{2-6}$alkenyl, $C_{2-6}$alkynyl, $C_{3-6}$ cycloalkyl, 4-10 membered heterocyclyl, aryl, and 5-10 membered heteroaryl, which can be optionally substituted with one or more of hydrogen, halogen, hydroxy, mercapto, amino, methylamino, dimethylamino, methoxy, —$C(O)CH_3$, —$COOC(CH_3)_3$, —$COOCH_3$, cyano, $C_{1-6}$alkyl, $C_{3-6}$cycloalkyl, 4-6 membered heterocyclyl, aryl, and 5-6 membered heteroaryl; most preferably, $R^9$ and $R^{10}$ are independently selected at each occurrence from $C_{1-6}$alkyl, $C_{2-6}$alkenyl, $C_{2-6}$alkynyl, $C_{3-6}$cycloalkyl, 4-10 membered heterocyclyl, phenyl, and 5-10 membered heteroaryl, which can be optionally substituted with one or more of hydrogen, halogen, hydroxy, amino, cyano, $C_{1-3}$alkyl, $C_{3-6}$cycloalkyl, 4-5 membered heterocyclyl, methylamino, dimethylamino, methoxy, —$C(O)CH_3$, —$COOC(CH_3)_3$, and —$COOCH_3$.

In an even further preferable embodiment of the present invention, $G^3$ is

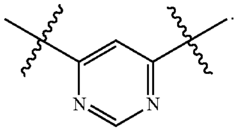 [SMILES: *c1cc(*)ncn1].

In an even further preferable embodiment of the present invention, $R^{16}$ is independently selected at each occurrence from hydrogen, deuterium, —$OCH_3$, —$OCH_2CH_3$, —$SCH_3$, —$SCH_2CH_3$, —S—$C(CH_3)_3$, —O—$C(CH_3)_3$, —O—$CH(CH_3)_2$, —O—$CH_2CH(CH_3)_2$, —O—$CH(CH_2CH_3)_2$, —S—$CH(CH_3)_2$, —S—$CH_2CH(CH_3)_2$, and —S—$CH(CH_2CH_3)_2$.

In some preferable embodiments of the present invention, $G^4$ is selected from $-SO_2(CH_3)$, optionally substituted $C_{1-6}$alkyl, optionally substituted $C_{3-12}$cycloalkyl, optionally substituted 4-10 membered heterocyclyl, optionally substituted $C_{6-10}$aryl, and optionally substituted 5-10 membered heteroaryl, said "optionally substituted" means that the hydrogen on the group to be substituted is unsubstituted or one or more substitutable sites of the group to be substituted are independently substituted by $R^{17}$, $R^{17}$ is independently selected at each occurrence from hydrogen, halogen, hydroxy, mercapto, amino, cyano, carboxyl, oxo, $-R^{11}$, $-OR^{11}$, $-SR^{11}$, $-NH(R^{11})$, $-N(R^{11})(R^{11})$,

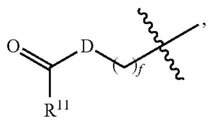

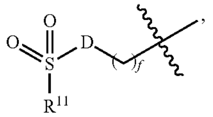

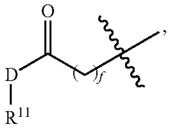

and

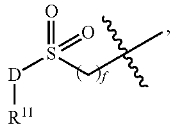

wherein $R^{11}$ is independently selected at each occurrence from $C_{1-6}$alkyl, $C_{2-6}$alkenyl, $C_{2-6}$alkynyl, $C_{3-6}$ cycloalkyl, 4-10 membered heterocyclyl, aryl, and 5-6 membered heteroaryl, which can be optionally substituted with one or more of hydrogen, halogen, hydroxy, mercapto, amino, cyano, oxo, $C_{1-6}$alkyl, trifluoromethyl, $C_{3-6}$cycloalkyl, 4-6 membered heterocycloalkyl, aryl, and 5-6 membered heteroaryl; D is independently selected at each occurrence from a bond, $-CH_2-$, $-C(=O)-$, $-NH-$, $-N(CH_3)-$, $-O-$ and $-S-$, f is independently selected at each occurrence from 0, 1 and 2.

In an even further preferable embodiment of the present invention, $G^4$ is selected from:

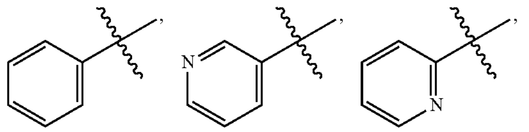

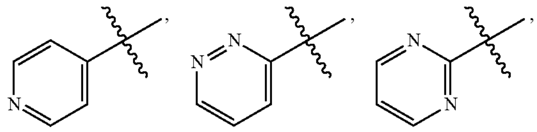

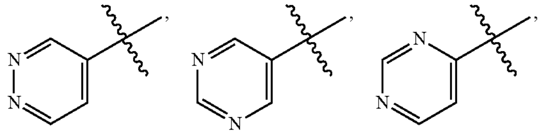

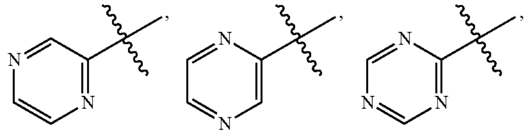

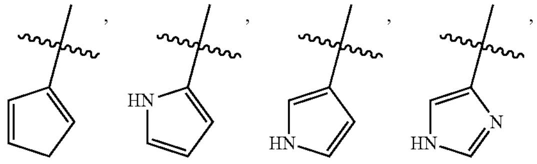

-continued

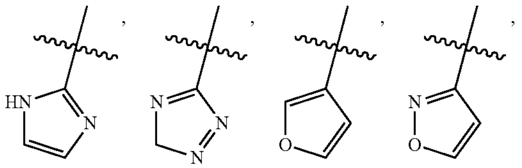

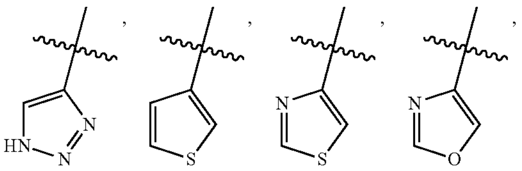

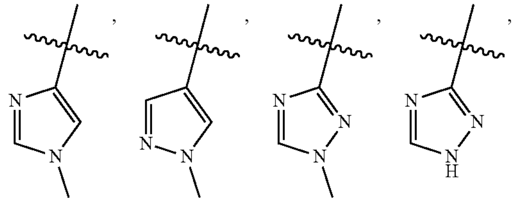

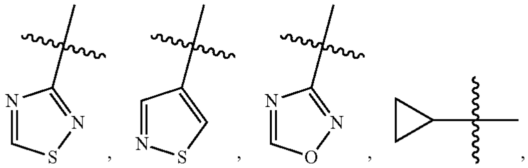

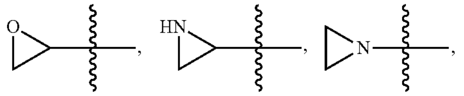

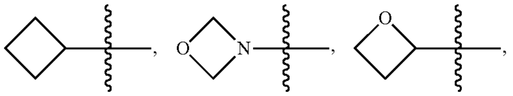

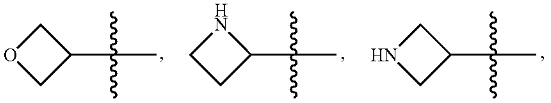

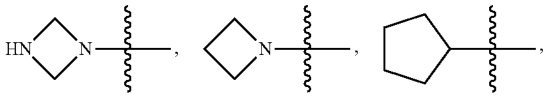

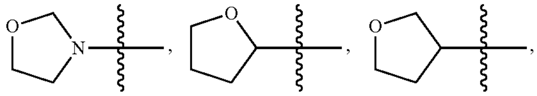

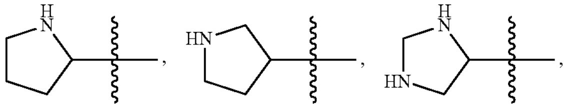

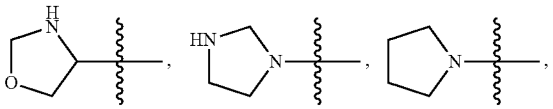

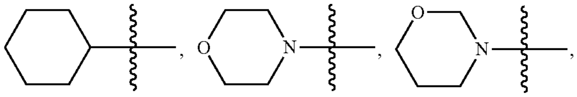

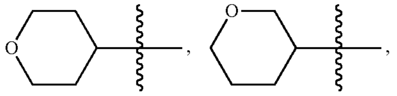

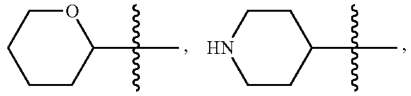

-continued
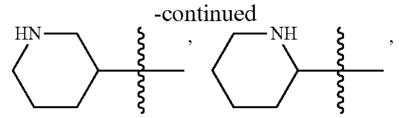
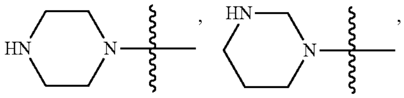
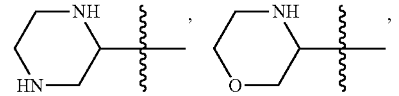
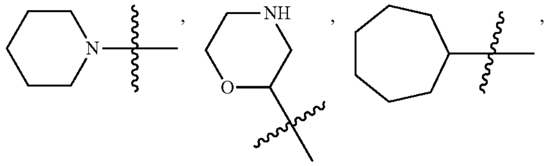
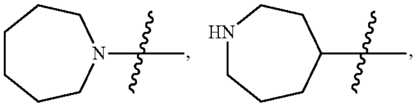
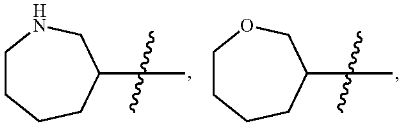
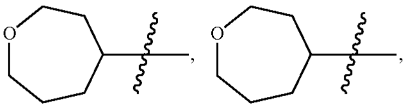
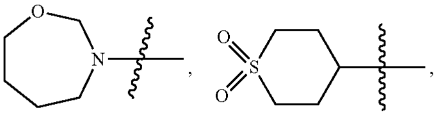
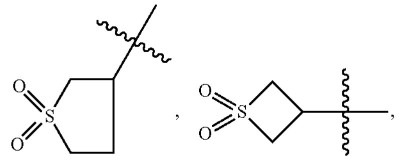
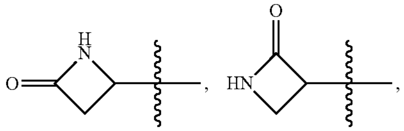
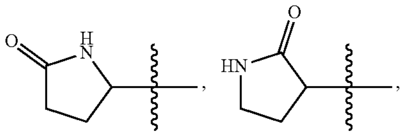
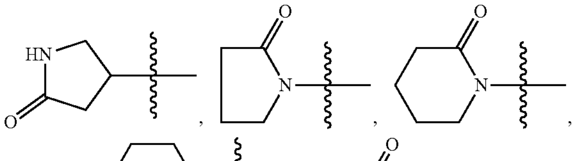
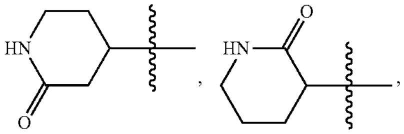
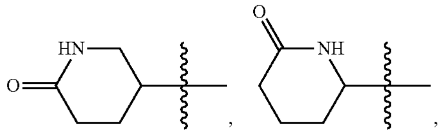
-continued
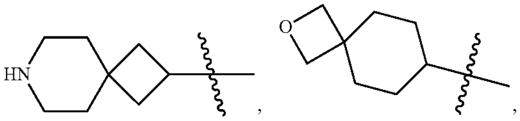
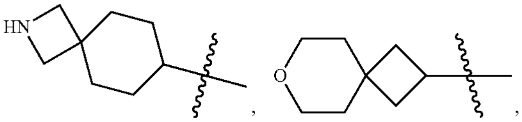
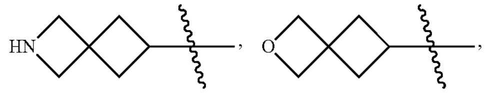
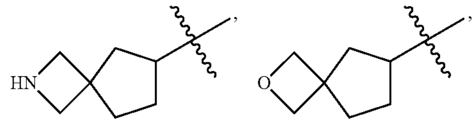
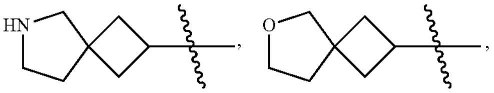
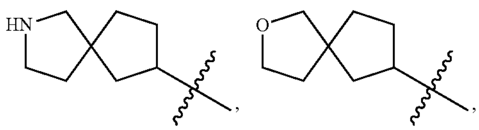
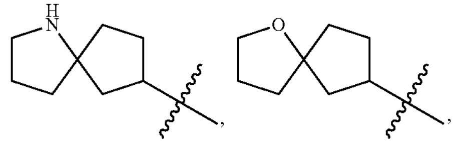
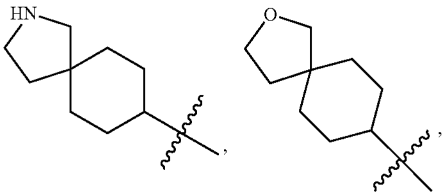
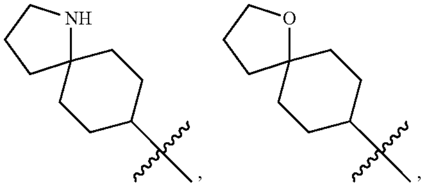
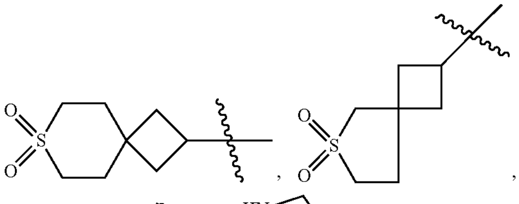
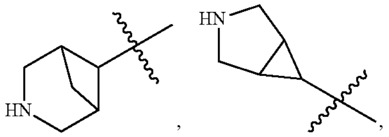
and
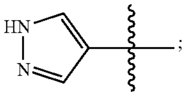

most preferably, $G^4$ is

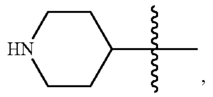

wherein one or more $R^{17}$ substitutions are present in the above groups and located at any substitutable site of t e groups.

Preferably, $R^7$ is independently selected at each occurrence from hydrogen, halogen, hydroxy, mercapto, amino, cyano, carboxyl, oxo, sulfoxide, sulfone, $—R^{11}$, $—OR^{11}$, $—SR^{11}$, $—NH(R^{11})$, $—N(R^{11})(R^{11})$,

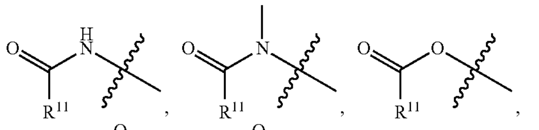

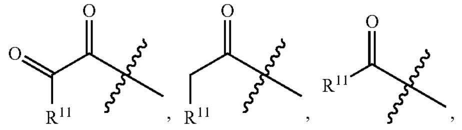

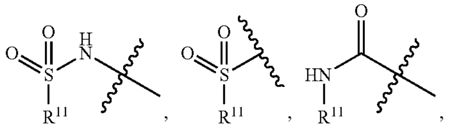

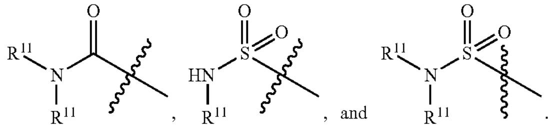

Preferably, $R^{11}$ is independently selected at each occurrence from hydrogen, hydroxy, cyano, amino, trifluoromethyl, difluoromethyl, trifluoroethyl, difluoroethyl, methyl, ethyl, n-propyl, isopropyl, n-butyl, iso-butyl, tert-butyl, sec-butyl, methoxy, ethoxy, n-propoxy, isopropoxy, cyclopropoxy, n-butoxy, iso-butoxy, tert-butoxy, sec-butoxy, $C_{3-6}$cycloalkyl, 4-6 membered heterocyclyl, $C_{6-8}$aryl, and 5-6 membered heteroaryl.

Most preferably, $R^{17}$ is

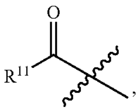

wherein $R^{11}$ is selected from hydrogen, methyl, ethyl, cyclopropyl, cyclobutyl, and phenyl.

In some preferable embodiments of the present invention, A is absent.

In some preferable embodiments of the present invention, B is N.

In some preferable embodiments of the present invention, n=1, E is $—CH(R^{13})—$ or $—N(R^{13})—$, $R^{13}$ is selected from hydrogen, hydroxy, halogen, and methyl; more preferably, n=1, E is $—CH_2—$ or —NH—; most preferably, n=1, E is $—CH_2—$.

In some preferable embodiments of the present invention, o=0, 1 or 2, more preferably, o=1.

In some preferable embodiments of the present invention, K can be selected from $—CH_2—$, —C(═O)—, —CHF—, —CH(—OH)—, $—CF_2—$, —CHD-, —CD(—OH)—, —CDF—, and $—CD_2$-; more preferably, K can be selected from $—CH_2—$, —C(═O)—, $—CF_2—$, —CHD-, —CHF—, and $—CD_2$-; most preferably, K can be selected from $—CH_2—$, —C(═O)—, $—CF_2—$, $—CD_2$-, and —CHD-; most preferably, K can be $—CD_2$-.

In some preferable embodiments of the present invention, ring H is selected from benzene ring, 5-6 membered heteroaryl ring, 5-membered fused to 6-membered heteroaryl ring, and 6-membered fused to 5-membered heteroaryl ring, and the benzene ring, 5-6 membered heteroaryl ring, 5-membered fused to 6-membered heteroaryl ring, and 6-membered fused to 5-membered heteroaryl ring can be independently substituted with one or more $R^{15}$s, wherein $R^{15}$ is selected from hydrogen, halogen, hydroxy, mercapto, amino, cyano, $C_{1-6}$alkyl, $C_{2-6}$alkenyl, $C_{2-6}$alkynyl, $C_{3-6}$cycloalkyl, 4-6 membered heterocyclyl, aryl, and 5-6 membered heteroaryl.

As a preferred embodiment herein, ring H is benzene ring, the benzene ring can be independently substituted with one or more $R^{15}$s.

As a preferred embodiment herein, ring H is 5-6 membered heteroaryl ring, selected from:

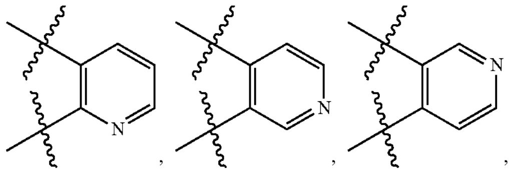

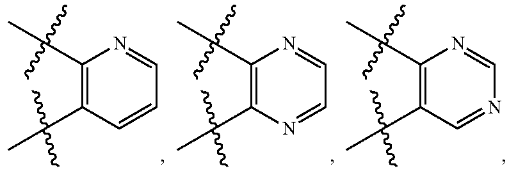

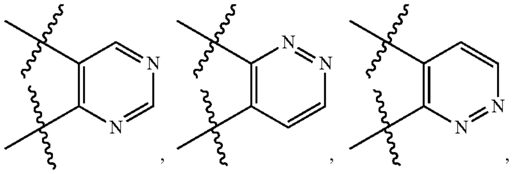

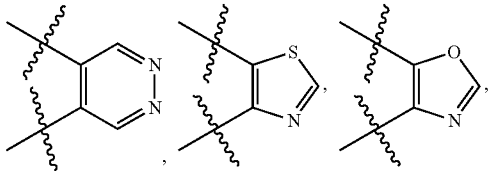

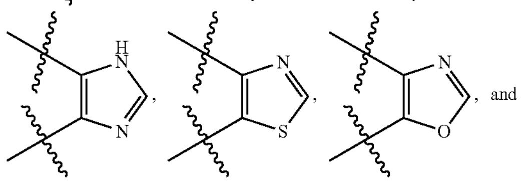

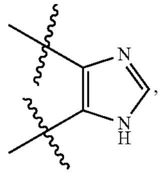

the 5-6 membered heteroaryl ring can be independently substituted with one or more $R^{15}$s.

As a preferred embodiment herein, ring H is 5-membered fused to 6-membered heteroaryl ring, selected from:

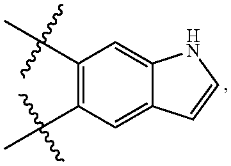
,
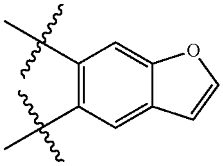
,
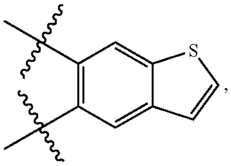
,
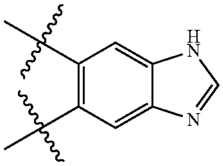
,
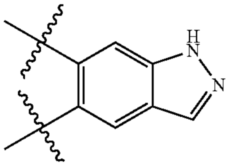
,
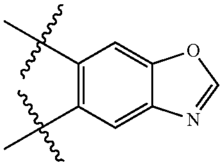
, and
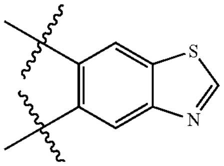
, the 5-membered fused to 6-membered heteroaryl ring can be independently substituted with one or more As a preferred embodiment, ring H is 6-membered fused to 5-membered heteroaryl ring selected from

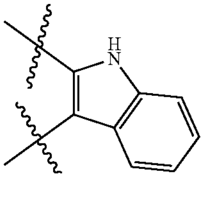
,
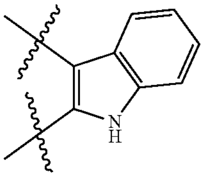
,
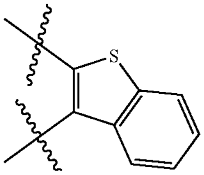
,
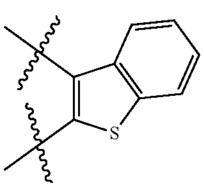
,
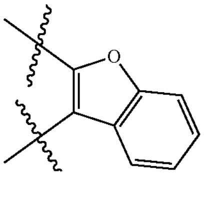
, and
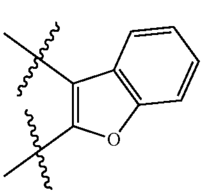
, the 6-membered fused to 5-membered heteroaryl ring can be independently substituted with one or more $R^{15}$s.

Further preferably, $R^{15}$ is selected from hydrogen, halogen, hydroxy, mercapto, amino, cyano, $C_{1-6}$alkyl, $C_{2-6}$alkenyl, $C_{2-6}$alkynyl, $C_{3-6}$cycloalkyl, 4-6 membered heterocyclyl, aryl, and 5-6 membered heteroaryl.

In some preferable embodiments of the present invention,

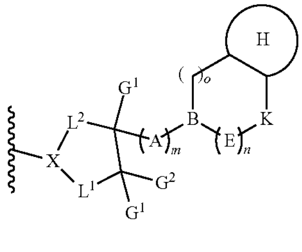

in formula (I) is

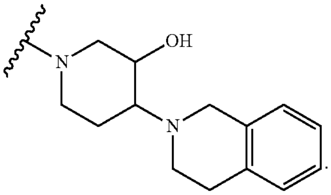 [SMILES: *N1CCC(N2CCc3ccccc3C2)C(O)C1]
.

In some preferable embodiments of the present invention,

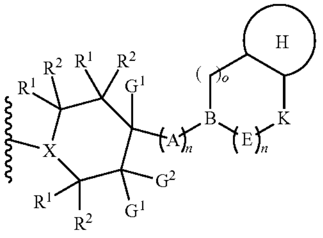

in formula (II)B is

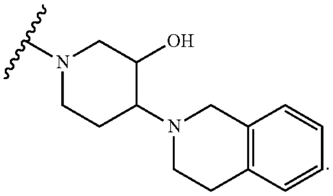 [SMILES: *N1CCC(N2CCc3ccccc3C2)C(O)C1]
.

In some preferable embodiments of the present invention, $G^3$ in formula (I) or formula (II)B is

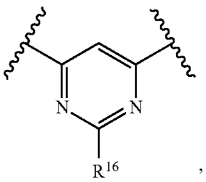
, wherein $R^{16}$ is as defined in formula (I);

Preferably, $R^{16}$ is selected from hydrogen, deuterium, halogen, hydroxy, mercapto, amino, cyano, —$R^9$, —$OR^9$, —$SR^9$, —$NH(R^9)$ and —$N(R^9)(R^{10})$.

At each occurrence, $R^9$ and $R^{10}$ are each independently selected from $C_{1-6}$alkyl and $C_{3-6}$cycloalkyl, or $R^9$ and $R^{10}$ together with the N atom to which they are connected form 4-6 membered heterocyclyl.

In some preferable embodiments of the present invention, $G^4$ in formula (I) or formula (II)B is

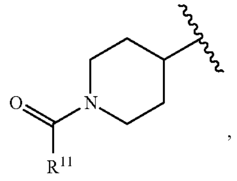

wherein $R^{11}$ is as defined in formula (I);

Preferably, $R^{11}$ is selected from $C_6$Saryl and 5-6 membered heteroaryl, and the aryl or heteroaryl is optionally substituted by one or more of halogen, $C_{1-6}$alkyl, and trifluoromethyl;

The heterocyclyl or heteroaryl contains 1, 2 or 3 heteroatoms, which are each independently selected from N, O and S.

In some preferable embodiments of the present invention, the compound represented by formula (I) is further a structure represented by formula (III):

(III)

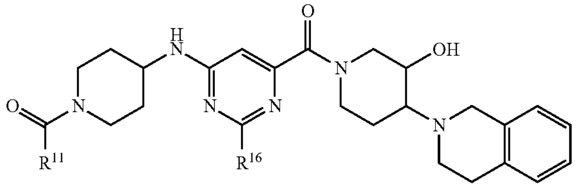

wherein, $R^{16}$ is selected from hydrogen, deuterium, halogen, hydroxy, mercapto, amino, cyano, —$R^9$, —$OR^9$, —$SR^9$, —$NH(R^9)$ and —$N(R^9)(R^{10})$;

At each occurrence, $R^9$ and $R^{10}$ are each independently selected from $C_{1-6}$alkyl and $C_{3-6}$cycloalkyl, or $R^9$ and $R^{10}$ together with the N atom to which they are connected form 4-6 membered heterocyclyl;

$R^{11}$ is selected from $C_{6-8}$aryl and 5-6 membered heteroaryl, and the aryl or heteroaryl is optionally substituted by one or more of halogen, $C_{1-6}$alkyl, and trifluoromethyl;

The heterocyclyl or heteroaryl contains 1, 2 or 3 heteroatoms, which are each independently selected from N, O and S.

In some more preferred embodiments of the present invention, $R^{16}$ is selected from hydrogen, deuterium, —$R^9$, —$OR^9$, —$SR^9$ and —$N(R^9)(R^{10})$, wherein $R^9$ and $R^{10}$ are as defined in formula (III).

In some further preferred embodiments of the present invention, $R^{16}$ is selected from hydrogen, deuterium, —$OCH_3$, —$OCH_2CH_3$, —$OCH(CH_3)_2$, —$OCH_2CH(CH_3)_2$, —$OC(CH_3)_3$, —$OCH(CH_2CH_3)_2$, —O-cyclopropyl, —O-cyclobutyl, —O-cyclopentyl, —O-cyclohexyl, —$SCH_3$, —$SCH_2CH_3$, —$SCH(CH_3)_2$, —$SCH_2CH(CH_3)_2$, —$SC(CH_3)_3$, —$SCH(CH_2CH_3)_2$, —S-cyclopropyl, —S—cyclobutyl, —S-cyclopentyl, —S-cyclohexyl, azetidin-1-yl, pyrrolidin-1-yl, piperidine-1-yl and 3-azabicyclo[3.1.0]hexan-3-yl.

In some more preferred embodiments of the present invention, $R^{11}$ is selected from phenyl, pyrrolyl, furyl, thienyl, imidazolyl, pyrazolyl, oxazolyl, isoxazolyl, thiazolyl, isothiazolyl, pyridyl, pyrimidinyl, pyridazinyl and pyrazinyl, wherein the phenyl, pyrrolyl, furyl, thienyl, imidazolyl, pyrazolyl, oxazolyl, isoxazolyl, thiazolyl, isothiazolyl, pyridyl, pyrimidinyl, pyridazinyl or pyrazinyl is optionally substituted by one or more of halogen, methyl, and trifluoromethyl.

In some further preferred embodiments of the present invention, $R^{11}$ is selected from phenyl, 2-fluorophenyl, 3-fluorophenyl, 4-fluorophenyl, 2-methylphenyl, 3-methylphenyl, 4-methylphenyl, 2-(trifluoromethyl)phenyl, 3-(trifluoromethyl)phenyl, 4-(trifluoromethyl)phenyl, thien-2-yl, thien-3-yl, 1-methyl-1H-pyrazol-3-yl, 1-methyl-1H-pyrazol-4-yl, 1-methyl-1H-pyrazol-5-yl, isoxazol-3-yl, isoxazol-4-yl, isoxazol-5-yl, thiazol-2-yl, thiazol-4-yl, thiazol-5-yl, pyridin-2-yl, pyridin-3-yl, pyridin-4-yl, pyrimidin-2-yl, pyrimidin-4-yl and pyrimidin-5-yl.

In some more preferred embodiments of the present invention, the compound represented by formula (I) is further a structure represented by formula (III)A or formula (III)B:

(III)A

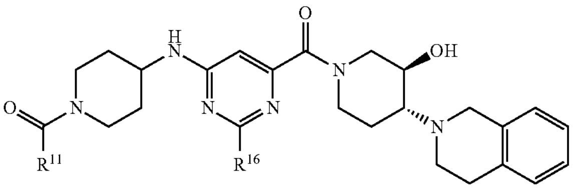

(III)B

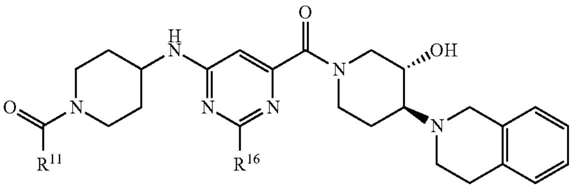

wherein $R^{11}$ and $R^{16}$ are as defined in formula (III).

The compounds of the present invention, and stereoisomers, geometric isomers, tautomers, pharmaceutical salts, prodrugs, hydrates, solvates or isotope-labeled analogues thereof are selected from the following compounds:

| No. | Structure |
| --- | --- |
| 1 | 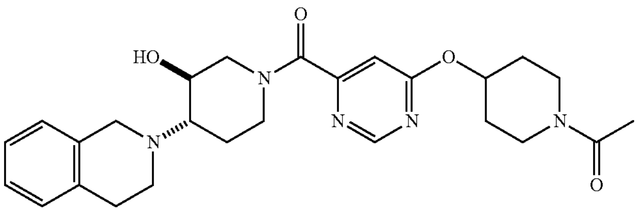 |
| 2 | 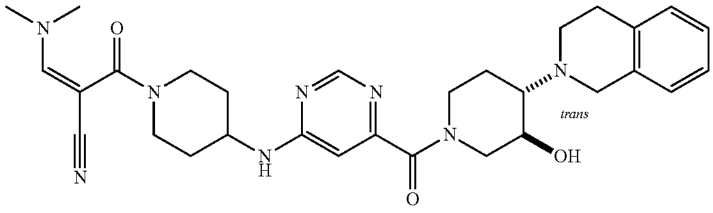 [SMILES: CN(C)/C=C(/C#N)C(=O)N1CCC(Nc2cc(C(=O)N3CC[C@H](N4CCc5ccccc5C4)[C@@H](O)C3)ncn2)CC1] |
| 3 | 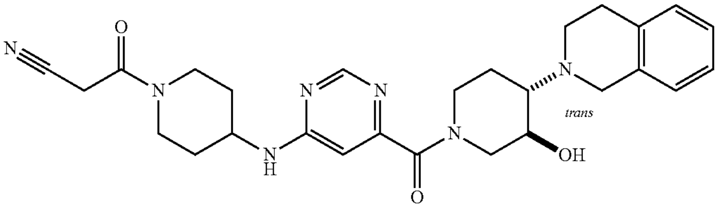 [SMILES: N#CCC(=O)N1CCC(Nc2cc(C(=O)N3CC[C@H](N4CCc5ccccc5C4)[C@@H](O)C3)ncn2)CC1] |
| 4 | 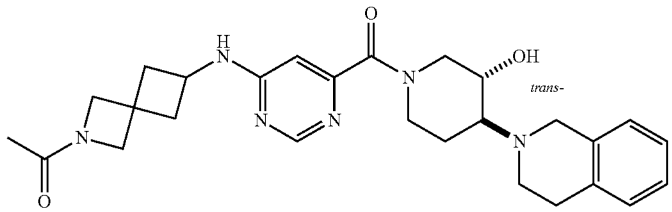 |
| 5 | 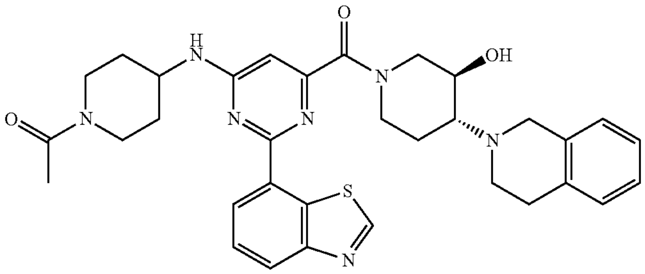 [SMILES: CC(=O)N1CCC(Nc2cc(C(=O)N3CC[C@@H](N4CCc5ccccc5C4)[C@H](O)C3)nc(-c3cccc4ncsc34)n2)CC1] |
| 6 | 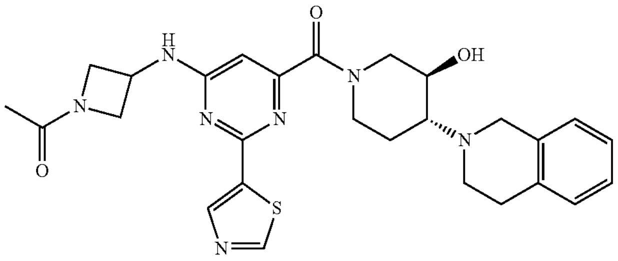 [SMILES: CC(=O)N1CC(Nc2cc(C(=O)N3CC[C@@H](N4CCc5ccccc5C4)[C@H](O)C3)nc(-c3cncs3)n2)C1] |

-continued
| No. | Structure |
| --- | --- |
| 7 | 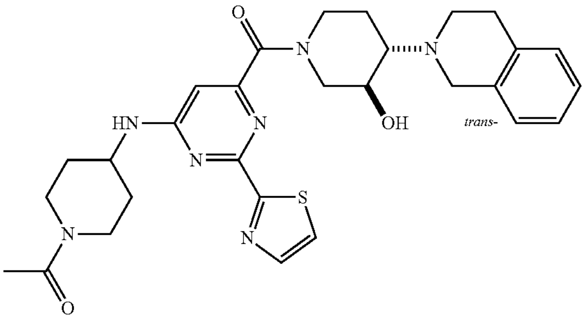 trans- |
| 8 | 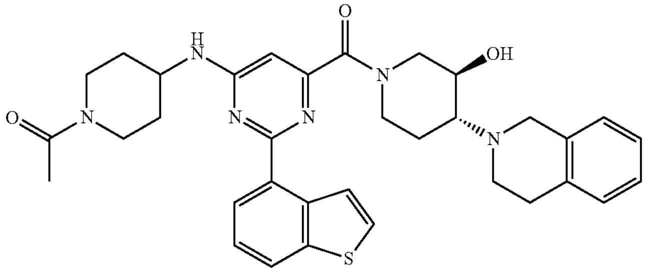 [SMILES: CC(=O)N1CCC(Nc2cc(C(=O)N3CC[C@@H](N4CCc5ccccc5C4)[C@H](O)C3)nc(-c3cccc4sccc34)n2)CC1] |
| 9 | 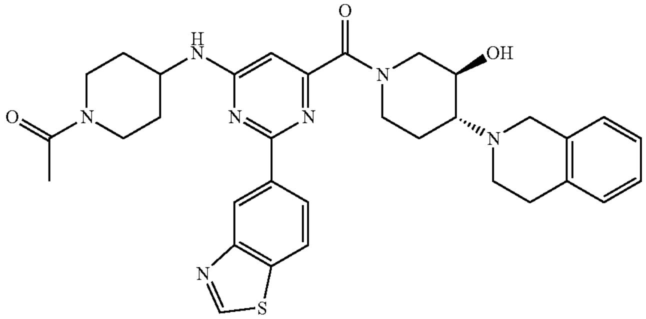 [SMILES: CC(=O)N1CCC(Nc2cc(C(=O)N3CC[C@@H](N4CCc5ccccc5C4)[C@H](O)C3)nc(-c3ccc4scnc4c3)n2)CC1] |
| 10 | 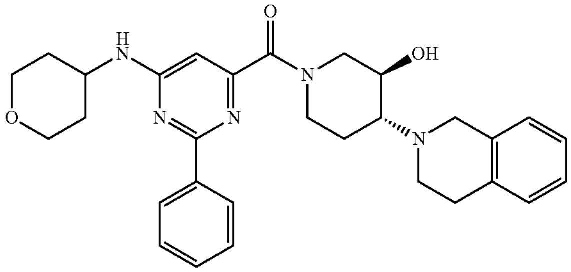 [SMILES: O=C(c1cc(NC2CCOCC2)nc(-c2ccccc2)n1)N1CC[C@@H](N2CCc3ccccc3C2)[C@H](O)C1] |
| 11 | 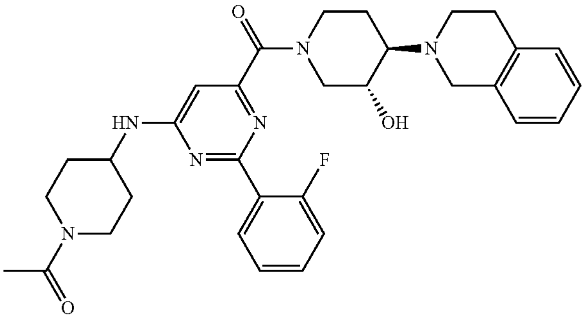 [SMILES: CC(=O)N1CCC(Nc2cc(C(=O)N3CC[C@@H](N4CCc5ccccc5C4)[C@H](O)C3)nc(-c3ccccc3F)n2)CC1] |

-continued
| No. | Structure |
| --- | --- |
| 12 | 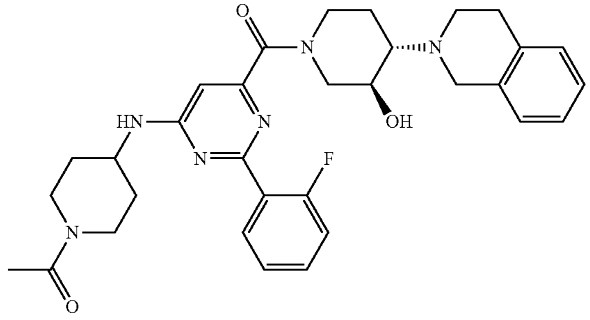 [SMILES: CC(=O)N1CCC(Nc2cc(C(=O)N3CC[C@H](N4CCc5ccccc5C4)[C@@H](O)C3)nc(-c3ccccc3F)n2)CC1] |
| 13 | 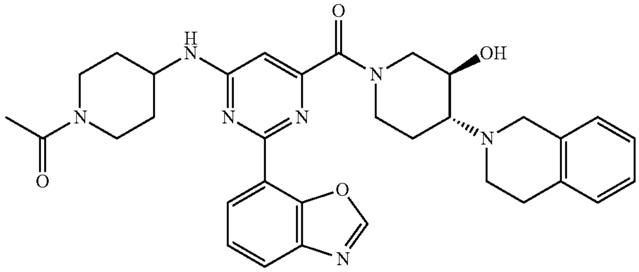 [SMILES: CC(=O)N1CCC(Nc2cc(C(=O)N3CC[C@@H](N4CCc5ccccc5C4)[C@H](O)C3)nc(-c3cccc4ncoc34)n2)CC1] |
| 14 | 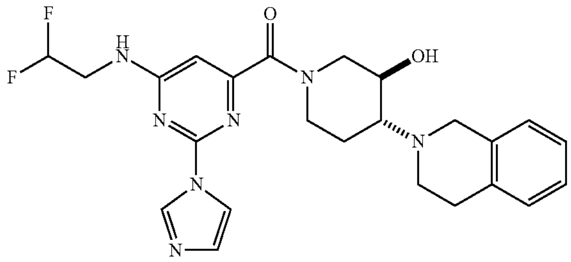 |
| 15 | 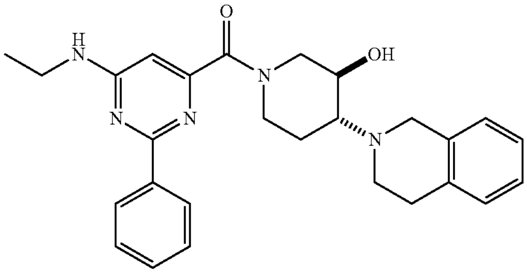 |
| 16 | 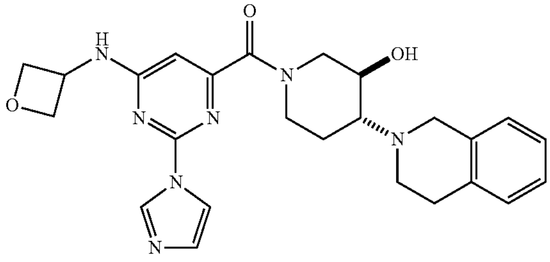 |

-continued
| No. | Structure |
|---|---|
| 17 | 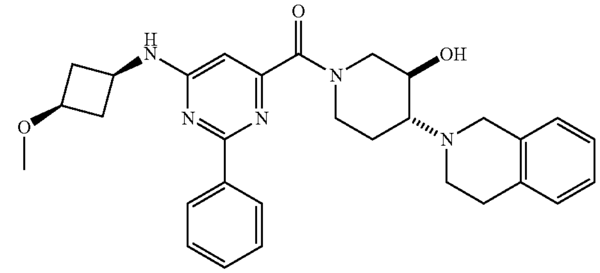 |
| 18 | 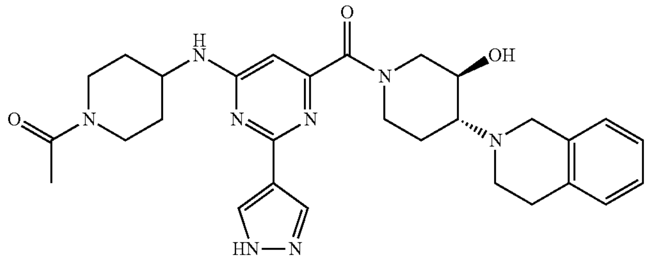 [SMILES: CC(=O)N1CCC(Nc2cc(C(=O)N3CC[C@@H](N4CCc5ccccc5C4)[C@H](O)C3)nc(-c3cn[nH]c3)n2)CC1] |
| 19 | 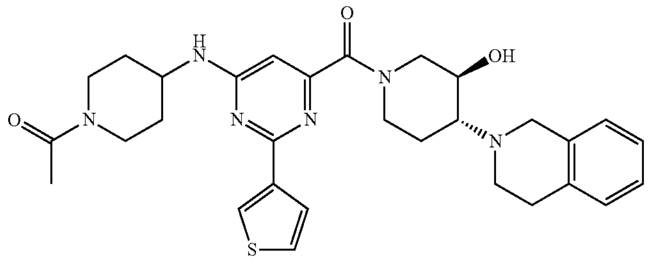 [SMILES: CC(=O)N1CCC(Nc2cc(C(=O)N3CC[C@@H](N4CCc5ccccc5C4)[C@H](O)C3)nc(-c3ccsc3)n2)CC1] |
| 20 | 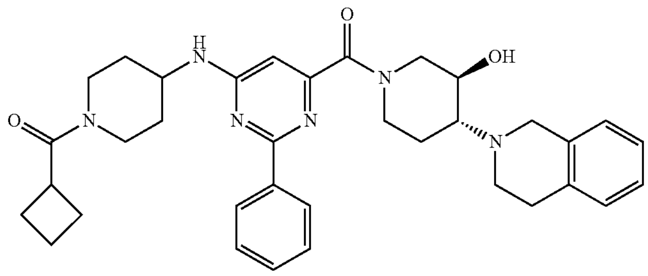 [SMILES: O=C(c1cc(NC2CCN(C(=O)C3CCC3)CC2)nc(-c2ccccc2)n1)N1CC[C@@H](N2CCc3ccccc3C2)[C@H](O)C1] |
| 21 | 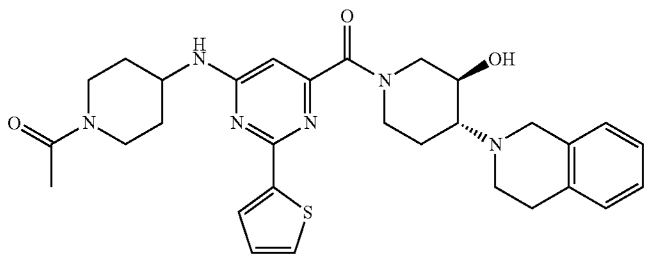 [SMILES: CC(=O)N1CCC(Nc2cc(C(=O)N3CC[C@@H](N4CCc5ccccc5C4)[C@H](O)C3)nc(-c3cccs3)n2)CC1] |

-continued
| No. | Structure |
| --- | --- |
| 22 | 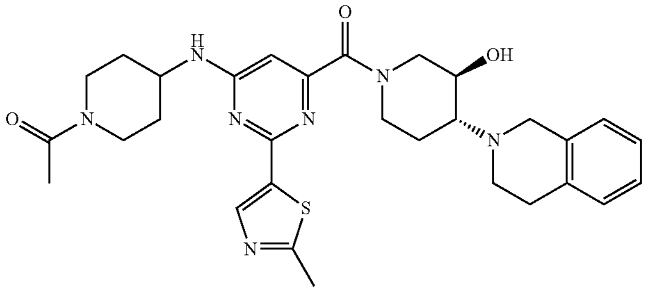 |
| 23 | 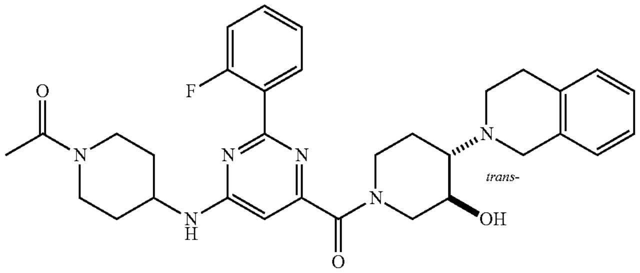 [SMILES: CC(=O)N1CCC(Nc2cc(C(=O)N3CC[C@H](N4CCc5ccccc5C4)[C@@H](O)C3)nc(-c3ccccc3F)n2)CC1] |
| 24 | 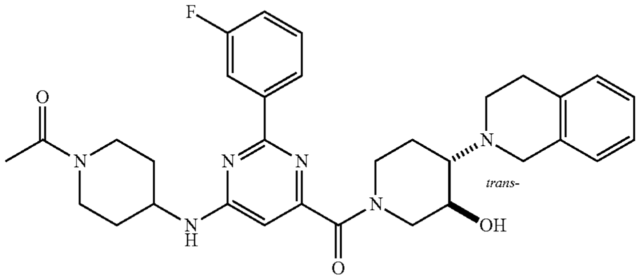 [SMILES: CC(=O)N1CCC(Nc2cc(C(=O)N3CC[C@H](N4CCc5ccccc5C4)[C@@H](O)C3)nc(-c3cccc(F)c3)n2)CC1] |
| 25 | 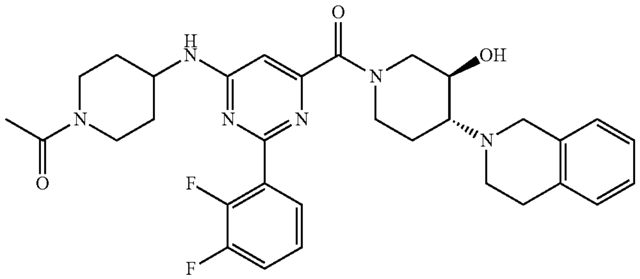 [SMILES: CC(=O)N1CCC(Nc2cc(C(=O)N3CC[C@@H](N4CCc5ccccc5C4)[C@H](O)C3)nc(-c3cccc(F)c3F)n2)CC1] |
| 26 | 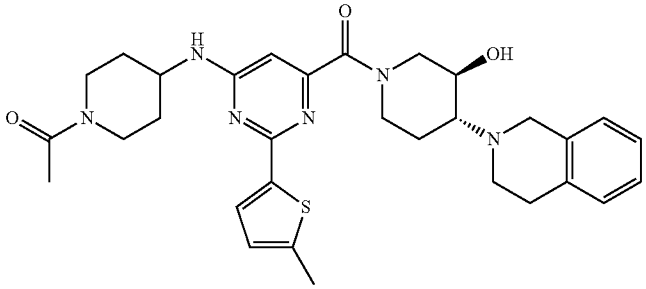 [SMILES: CC(=O)N1CCC(Nc2cc(C(=O)N3CC[C@@H](N4CCc5ccccc5C4)[C@H](O)C3)nc(-c3ccc(C)s3)n2)CC1] |

-continued
| No. | Structure |
|---|---|
| 27 | 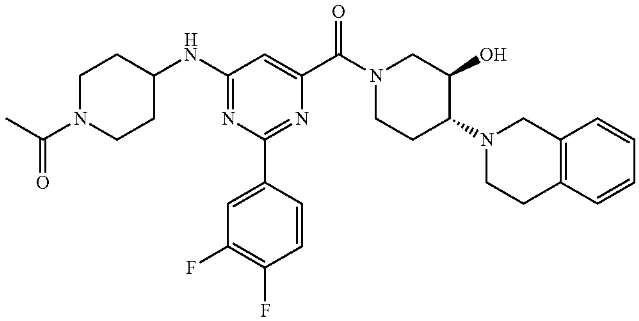 [SMILES: CC(=O)N1CCC(Nc2cc(C(=O)N3CC[C@@H](N4CCc5ccccc5C4)[C@H](O)C3)nc(-c3ccc(F)c(F)c3)n2)CC1] |
| 28 | 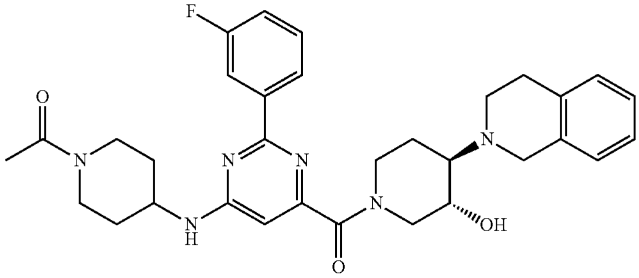 [SMILES: CC(=O)N1CCC(Nc2cc(C(=O)N3CC[C@@H](N4CCc5ccccc5C4)[C@H](O)C3)nc(-c3cccc(F)c3)n2)CC1] |
| 29 | 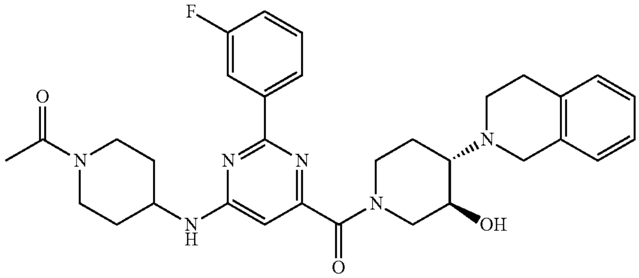 [SMILES: CC(=O)N1CCC(Nc2cc(C(=O)N3CC[C@H](N4CCc5ccccc5C4)[C@@H](O)C3)nc(-c3cccc(F)c3)n2)CC1] |
| 30 | 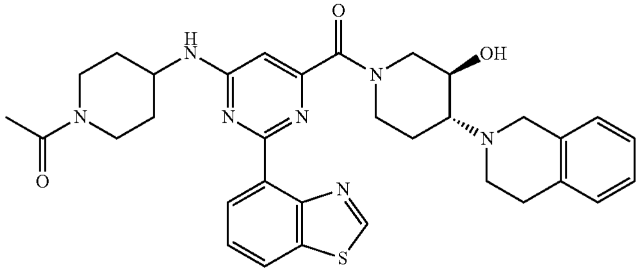 [SMILES: CC(=O)N1CCC(Nc2cc(C(=O)N3CC[C@@H](N4CCc5ccccc5C4)[C@H](O)C3)nc(-c3cccc4scnc34)n2)CC1] |
| 31 | 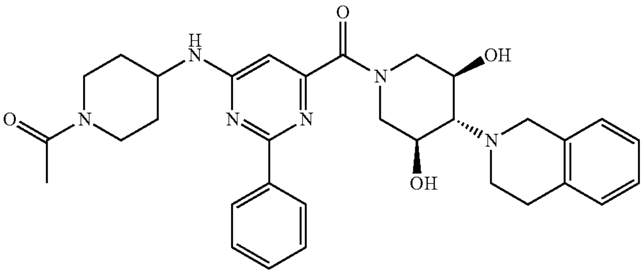 [SMILES: CC(=O)N1CCC(Nc2cc(C(=O)N3C[C@@H](O)[C@H](N4CCc5ccccc5C4)[C@@H](O)C3)nc(-c3ccccc3)n2)CC1] |

-continued
| No. | Structure |
| --- | --- |
| 32 | 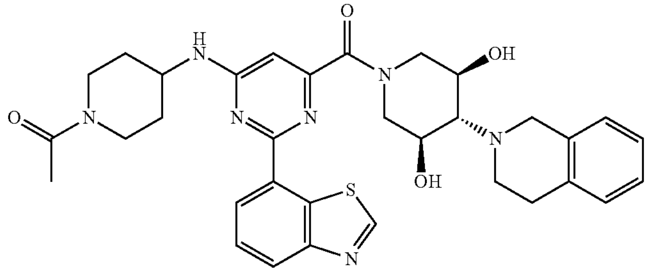 [SMILES: CC(=O)N1CCC(Nc2cc(C(=O)N3C[C@@H](O)[C@H](N4CCc5ccccc5C4)[C@@H](O)C3)nc(-c3cccc4ncsc34)n2)CC1] |
| 33 | 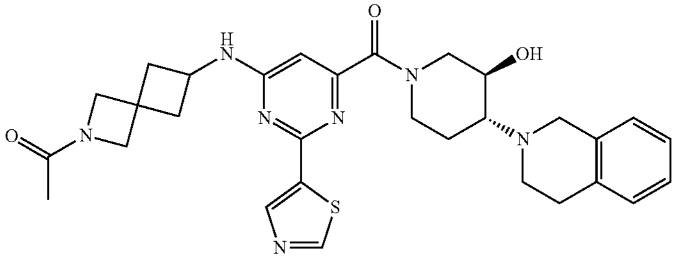 [SMILES: CC(=O)N1CC2(CC(Nc3cc(C(=O)N4CC[C@@H](N5CCc6ccccc6C5)[C@H](O)C4)nc(-c4cncs4)n3)C2)C1] |
| 34 | 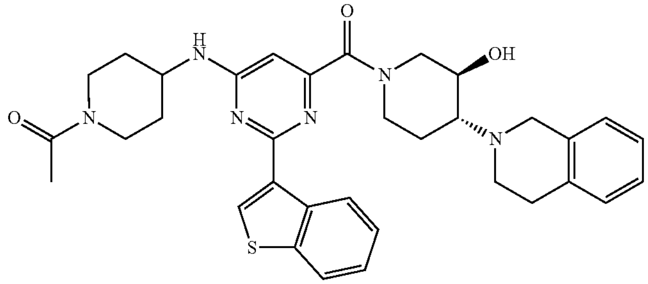 [SMILES: CC(=O)N1CCC(Nc2cc(C(=O)N3CC[C@@H](N4CCc5ccccc5C4)[C@H](O)C3)nc(-c3csc4ccccc34)n2)CC1] |
| 35 | 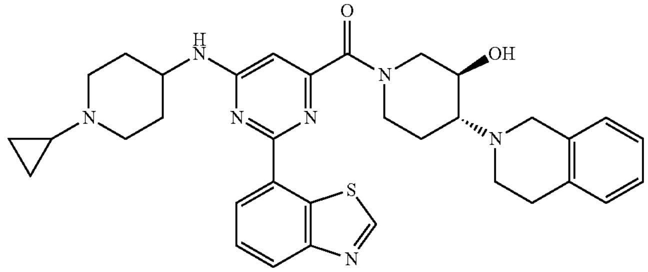 [SMILES: O=C(c1cc(NC2CCN(C3CC3)CC2)nc(-c2cccc3ncsc23)n1)N1CC[C@@H](N2CCc3ccccc3C2)[C@H](O)C1] |
| 36 | 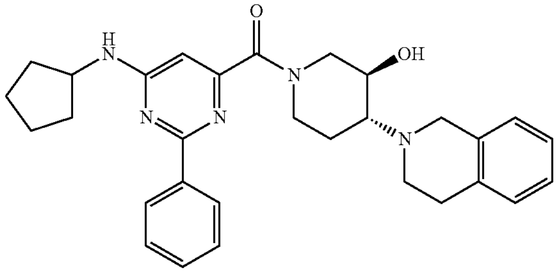 [SMILES: O=C(c1cc(NC2CCCC2)nc(-c2ccccc2)n1)N1CC[C@@H](N2CCc3ccccc3C2)[C@H](O)C1] |

-continued
| No. | Structure |
|---|---|
| 37 | 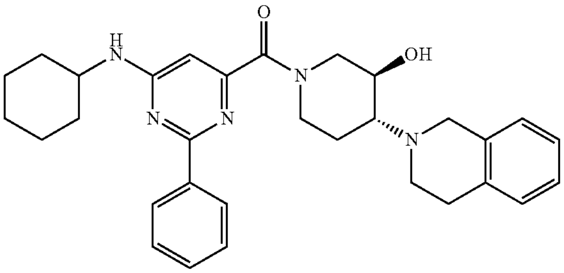 [SMILES: O=C(c1cc(NC2CCCCC2)nc(-c2ccccc2)n1)N1CC[C@@H](N2CCc3ccccc3C2)[C@H](O)C1] |
| 38 | 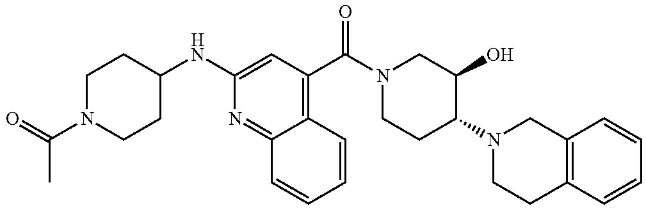 [SMILES: CC(=O)N1CCC(Nc2cc(C(=O)N3CC[C@@H](N4CCc5ccccc5C4)[C@H](O)C3)c3ccccc3n2)CC1] |
| 39 | 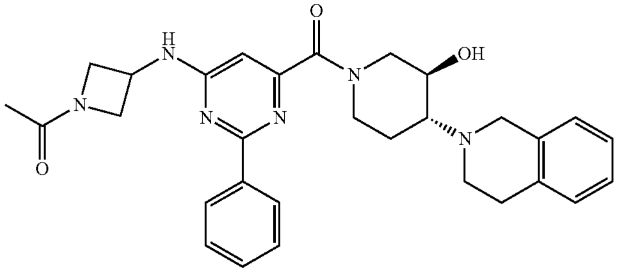 [SMILES: CC(=O)N1CC(Nc2cc(C(=O)N3CC[C@@H](N4CCc5ccccc5C4)[C@H](O)C3)nc(-c3ccccc3)n2)C1] |
| 40 | 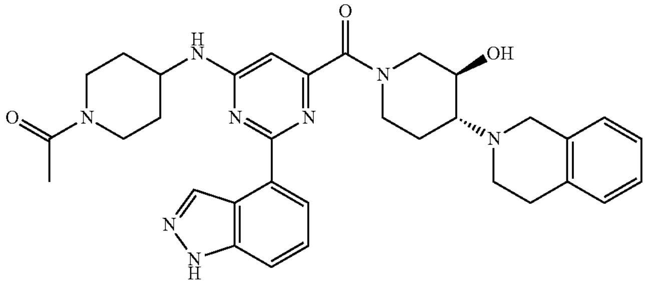 [SMILES: CC(=O)N1CCC(Nc2cc(C(=O)N3CC[C@@H](N4CCc5ccccc5C4)[C@H](O)C3)nc(-c3cccc4[nH]ncc34)n2)CC1] |
| 41 | 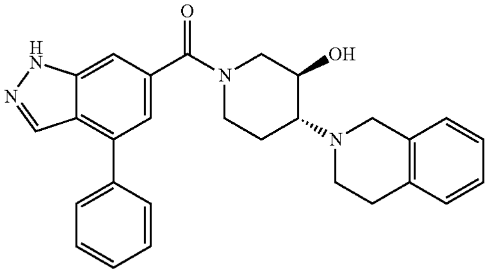 [SMILES: O=C(c1cc(-c2ccccc2)c2cn[nH]c2c1)N1CC[C@@H](N2CCc3ccccc3C2)[C@H](O)C1] |

-continued
| No. | Structure |
|---|---|
| 42 | 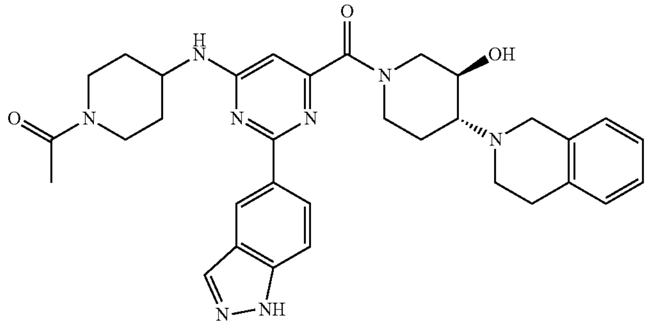 [SMILES: CC(=O)N1CCC(Nc2cc(C(=O)N3CC[C@@H](N4CCc5ccccc5C4)[C@H](O)C3)nc(-c3ccc4[nH]ncc4c3)n2)CC1] |
| 43 | 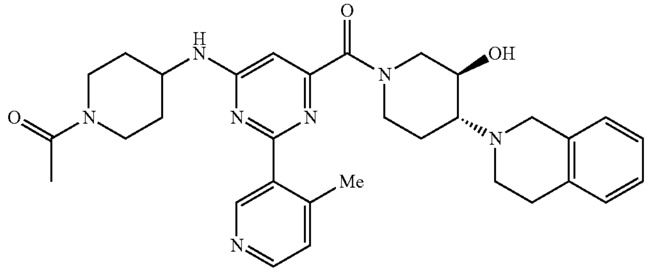 [SMILES: CC(=O)N1CCC(Nc2cc(C(=O)N3CC[C@@H](N4CCc5ccccc5C4)[C@H](O)C3)nc(-c3cnccc3C)n2)CC1] |
| 44 | 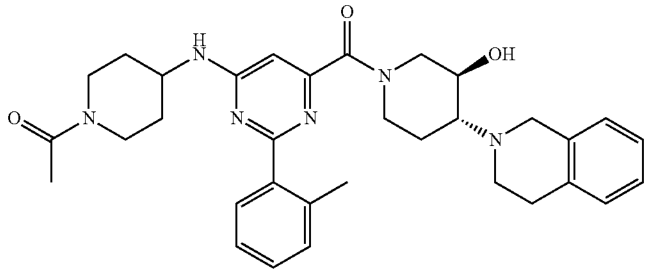 [SMILES: CC(=O)N1CCC(Nc2cc(C(=O)N3CC[C@@H](N4CCc5ccccc5C4)[C@H](O)C3)nc(-c3ccccc3C)n2)CC1] |
| 45 | 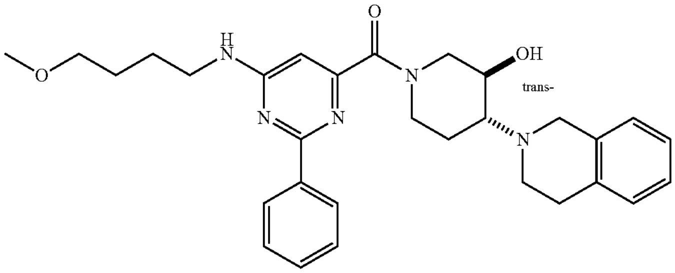 |
| 46 | 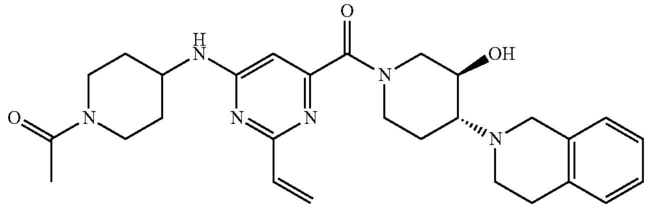 [SMILES: C=Cc1nc(NC2CCN(C(C)=O)CC2)cc(C(=O)N2CC[C@@H](N3CCc4ccccc4C3)[C@H](O)C2)n1] |

-continued
| No. | Structure |
| --- | --- |
| 47 | 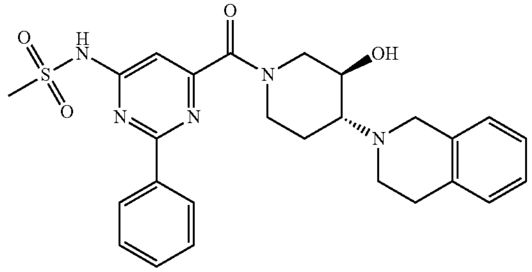 [SMILES: CS(=O)(=O)Nc1cc(C(=O)N2CC[C@@H](N3CCc4ccccc4C3)[C@H](O)C2)nc(-c2ccccc2)n1] |
| 48 | 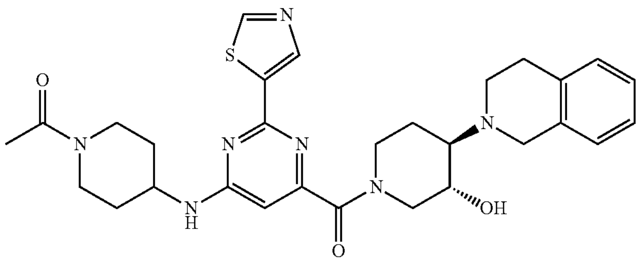 [SMILES: CC(=O)N1CCC(Nc2cc(C(=O)N3CC[C@@H](N4CCc5ccccc5C4)[C@H](O)C3)nc(-c3cncs3)n2)CC1] |
| 49 | 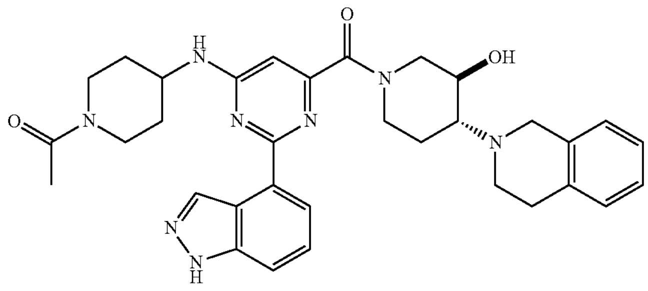 [SMILES: CC(=O)N1CCC(Nc2cc(C(=O)N3CC[C@@H](N4CCc5ccccc5C4)[C@H](O)C3)nc(-c3cccc4[nH]ncc34)n2)CC1] |
| 50 | 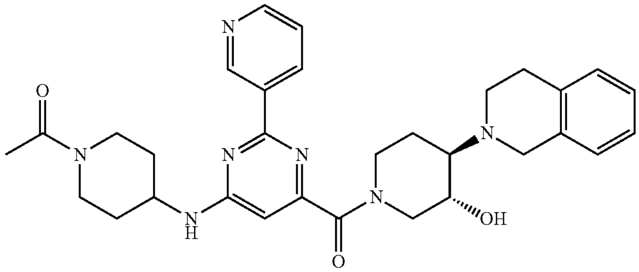 |
| 51 | 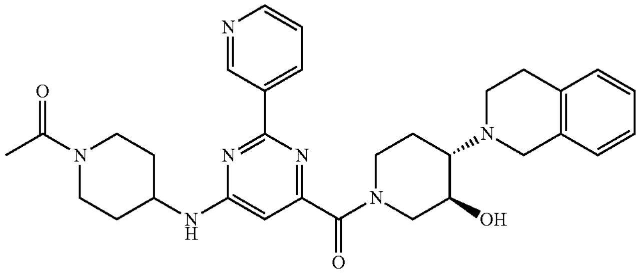 [SMILES: CC(=O)N1CCC(Nc2cc(C(=O)N3CC[C@H](N4CCc5ccccc5C4)[C@@H](O)C3)nc(-c3cccnc3)n2)CC1] |

-continued
| No. | Structure |
|---|---|
| 52 | 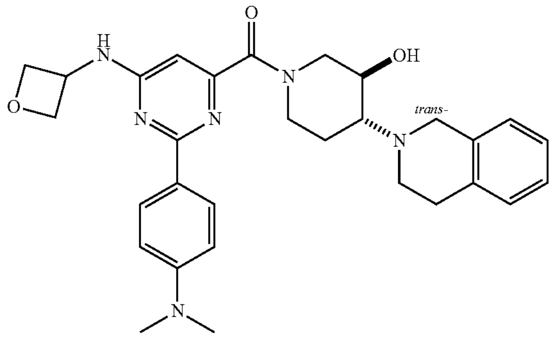 [SMILES: CN(C)c1ccc(-c2nc(NC3COC3)cc(C(=O)N3CC[C@@H](N4CCc5ccccc5C4)[C@H](O)C3)n2)cc1] |
| 53 | 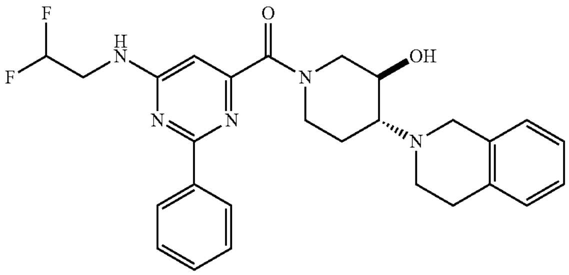 [SMILES: O=C(c1cc(NCC(F)F)nc(-c2ccccc2)n1)N1CC[C@@H](N2CCc3ccccc3C2)[C@H](O)C1] |
| 54 | 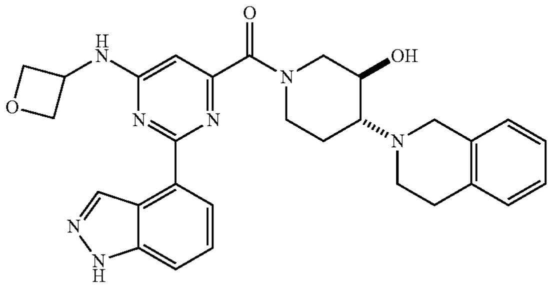 [SMILES: O=C(c1cc(NC2COC2)nc(-c2cccc3[nH]ncc23)n1)N1CC[C@@H](N2CCc3ccccc3C2)[C@H](O)C1] |
| 55 | 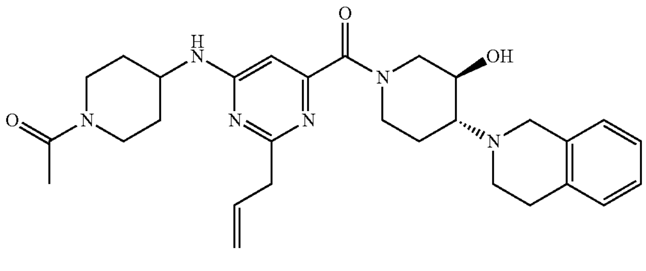 [SMILES: C=CCc1nc(NC2CCN(C(C)=O)CC2)cc(C(=O)N2CC[C@@H](N3CCc4ccccc4C3)[C@H](O)C2)n1] |
| 56 | 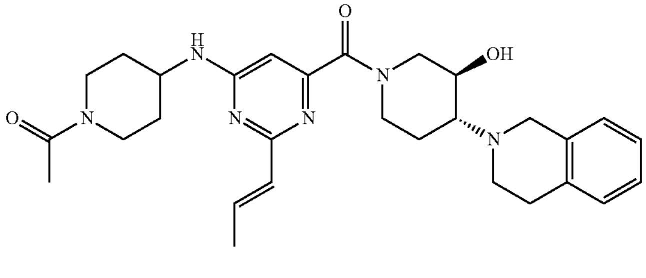 [SMILES: C/C=C/c1nc(NC2CCN(C(C)=O)CC2)cc(C(=O)N2CC[C@@H](N3CCc4ccccc4C3)[C@H](O)C2)n1] |

-continued
| No. | Structure |
| --- | --- |
| 57 | 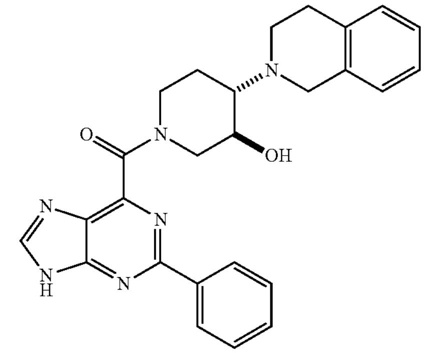 [SMILES: O=C(c1nc(-c2ccccc2)nc2[nH]cnc12)N1CC[C@H](N2CCc3ccccc3C2)[C@@H](O)C1] |
| 58 | 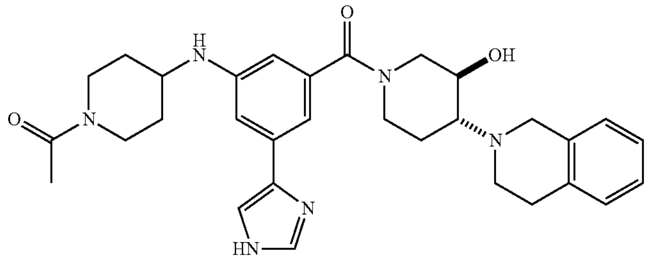 [SMILES: CC(=O)N1CCC(Nc2cc(C(=O)N3CC[C@@H](N4CCc5ccccc5C4)[C@H](O)C3)cc(-c3c[nH]cn3)c2)CC1] |
| 59 | 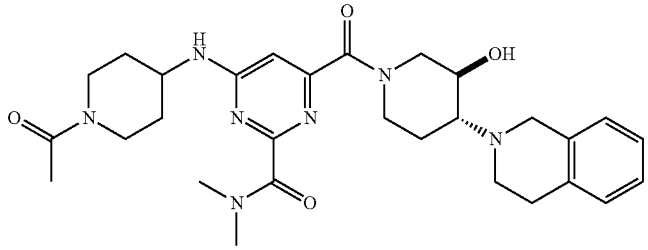 [SMILES: CC(=O)N1CCC(Nc2cc(C(=O)N3CC[C@@H](N4CCc5ccccc5C4)[C@H](O)C3)nc(C(=O)N(C)C)n2)CC1] |
| 60 | 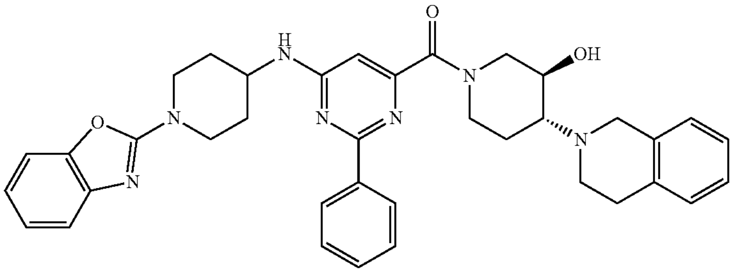 [SMILES: O=C(c1cc(NC2CCN(c3nc4ccccc4o3)CC2)nc(-c2ccccc2)n1)N1CC[C@@H](N2CCc3ccccc3C2)[C@H](O)C1] |
| 61 | 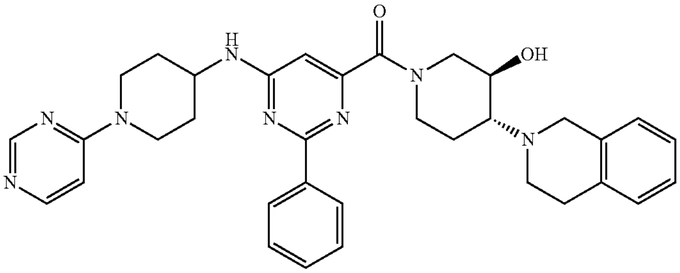 [SMILES: O=C(c1cc(NC2CCN(c3ccncn3)CC2)nc(-c2ccccc2)n1)N1CC[C@@H](N2CCc3ccccc3C2)[C@H](O)C1] |

-continued
| No. | Structure |
|---|---|
| 62 | 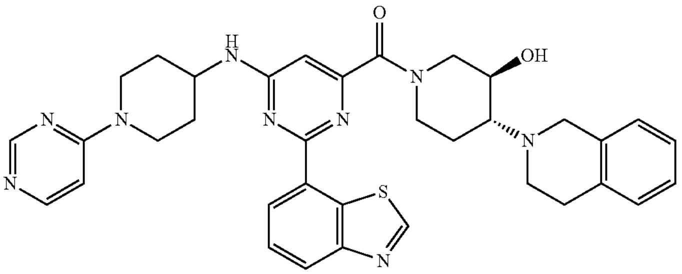 [SMILES: O=C(c1cc(NC2CCN(c3ccncn3)CC2)nc(-c2cccc3ncsc23)n1)N1CC[C@@H](N2CCc3ccccc3C2)[C@H](O)C1] |
| 63 | 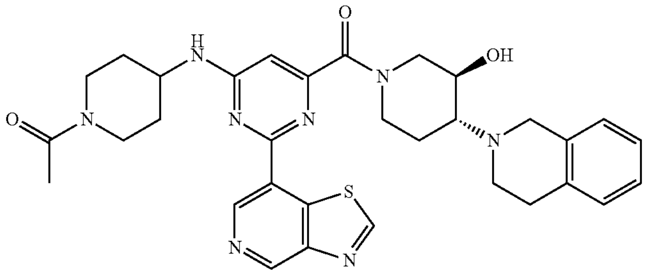 [SMILES: CC(=O)N1CCC(Nc2cc(C(=O)N3CC[C@@H](N4CCc5ccccc5C4)[C@H](O)C3)nc(-c3cncc4ncsc34)n2)CC1] |
| 64 | 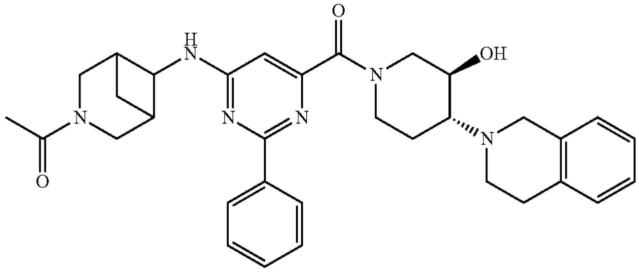 [SMILES: CC(=O)N1CC2CC(C1)C2Nc1cc(C(=O)N2CC[C@@H](N3CCc4ccccc4C3)[C@H](O)C2)nc(-c2ccccc2)n1] |
| 65 | 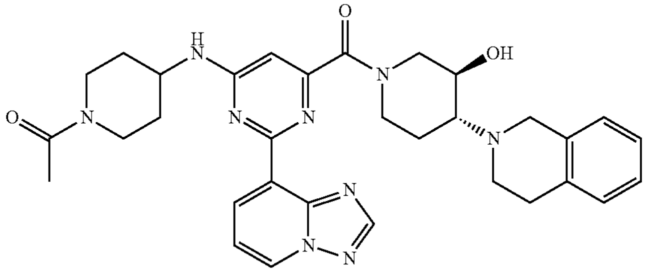 [SMILES: CC(=O)N1CCC(Nc2cc(C(=O)N3CC[C@@H](N4CCc5ccccc5C4)[C@H](O)C3)nc(-c3cccn4ncnc34)n2)CC1] |
| 66 | 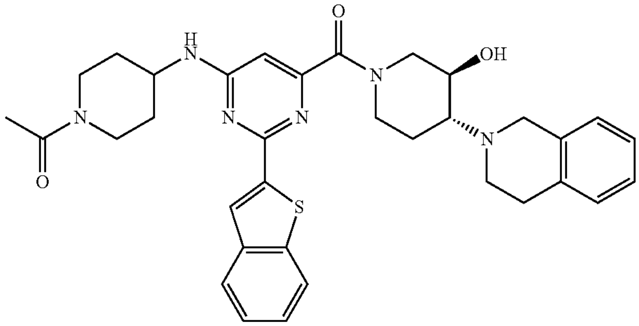 [SMILES: CC(=O)N1CCC(Nc2cc(C(=O)N3CC[C@@H](N4CCc5ccccc5C4)[C@H](O)C3)nc(-c3cc4ccccc4s3)n2)CC1] |

-continued
| No. | Structure |
|---|---|
| 67 | 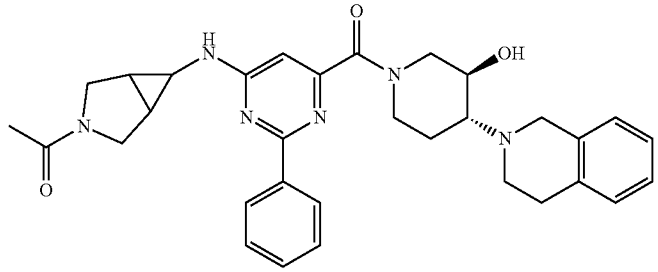 [SMILES: CC(=O)N1CC2C(C1)C2Nc1cc(C(=O)N2CC[C@@H](N3CCc4ccccc4C3)[C@H](O)C2)nc(-c2ccccc2)n1] |
| 68 | 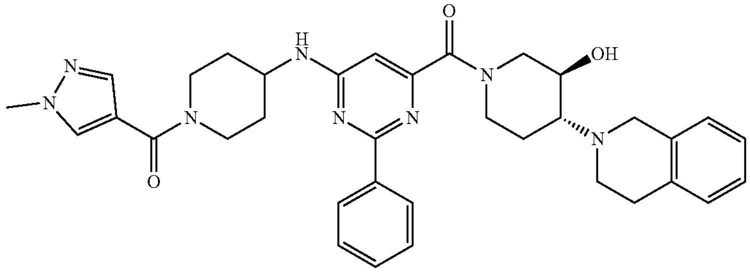 [SMILES: Cn1cc(C(=O)N2CCC(Nc3cc(C(=O)N4CC[C@@H](N5CCc6ccccc6C5)[C@H](O)C4)nc(-c4ccccc4)n3)CC2)cn1] |
| 69 | 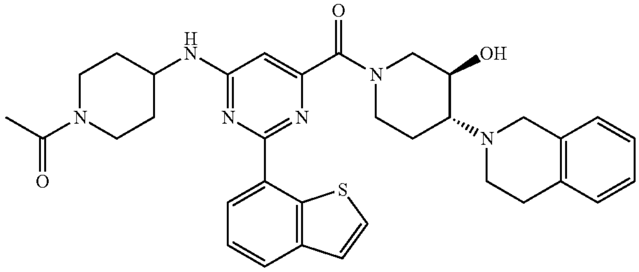 [SMILES: CC(=O)N1CCC(Nc2cc(C(=O)N3CC[C@@H](N4CCc5ccccc5C4)[C@H](O)C3)nc(-c3cccc4ccsc34)n2)CC1] |
| 70 | 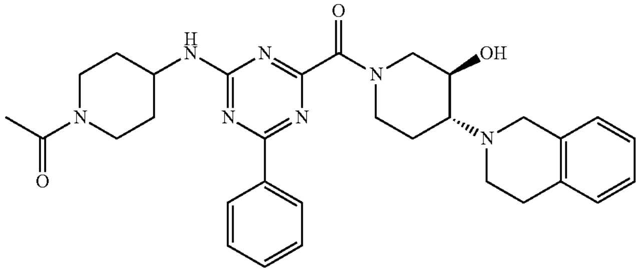 [SMILES: CC(=O)N1CCC(Nc2nc(C(=O)N3CC[C@@H](N4CCc5ccccc5C4)[C@H](O)C3)nc(-c3ccccc3)n2)CC1] |
| 71 | 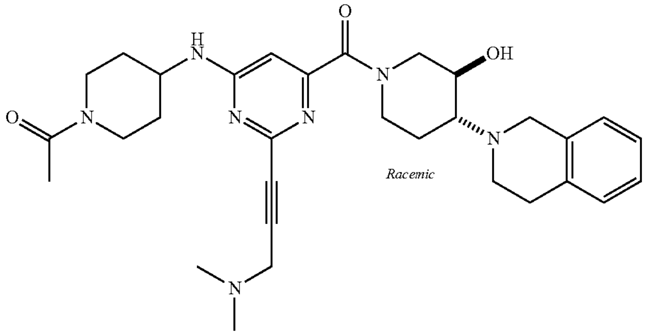 [SMILES: CC(=O)N1CCC(Nc2cc(C(=O)N3CC[C@@H](N4CCc5ccccc5C4)[C@H](O)C3)nc(C#CCN(C)C)n2)CC1] |

-continued
| No. | Structure |
| --- | --- |
| 72 | 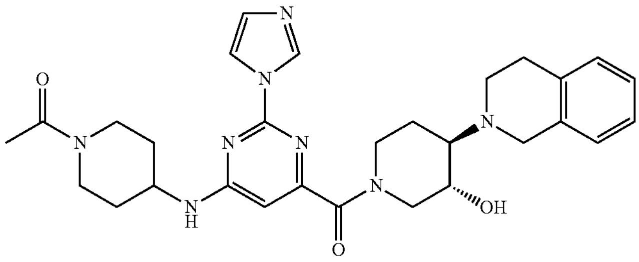 [SMILES: CC(=O)N1CCC(Nc2cc(C(=O)N3CC[C@@H](N4CCc5ccccc5C4)[C@H](O)C3)nc(-n3ccnc3)n2)CC1] |
| 73 | 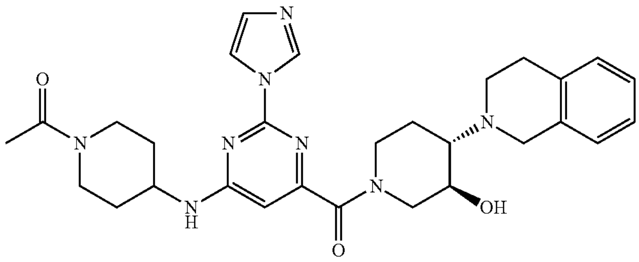 [SMILES: CC(=O)N1CCC(Nc2cc(C(=O)N3CC[C@H](N4CCc5ccccc5C4)[C@@H](O)C3)nc(-n3ccnc3)n2)CC1] |
| 74 | 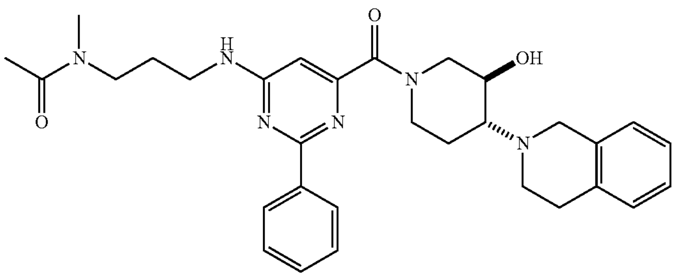 [SMILES: CC(=O)N(C)CCCNc1cc(C(=O)N2CC[C@@H](N3CCc4ccccc4C3)[C@H](O)C2)nc(-c2ccccc2)n1] |
| 75 | 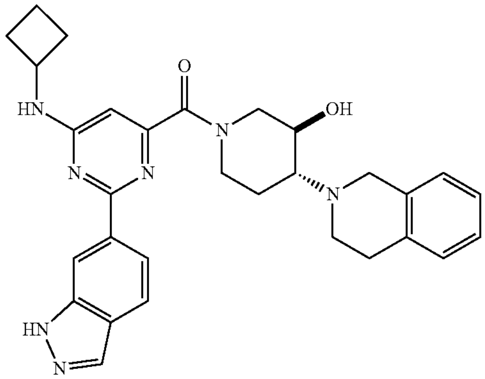 [SMILES: O=C(c1cc(NC2CCC2)nc(-c2ccc3cn[nH]c3c2)n1)N1CC[C@@H](N2CCc3ccccc3C2)[C@H](O)C1] |
| 76 | 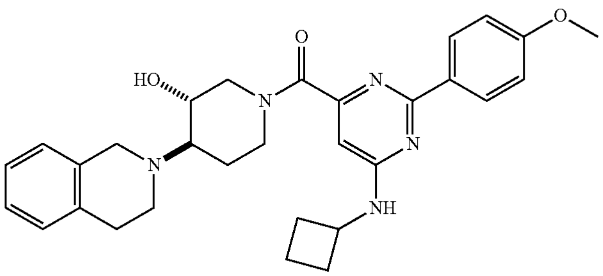 [SMILES: COc1ccc(-c2nc(NC3CCC3)cc(C(=O)N3CC[C@@H](N4CCc5ccccc5C4)[C@H](O)C3)n2)cc1] |

-continued
| No. | Structure |
| --- | --- |
| 77 | 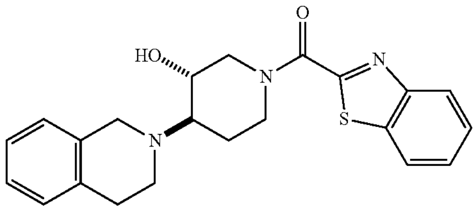 [SMILES: O=C(c1nc2ccccc2s1)N1CC[C@@H](N2CCc3ccccc3C2)[C@H](O)C1] |
| 78 | 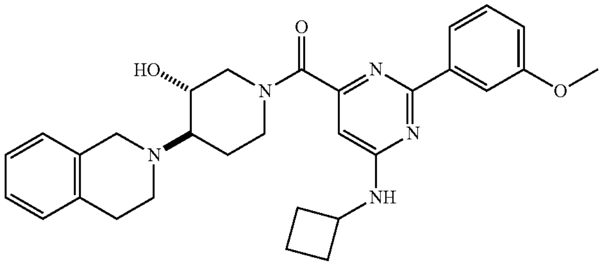 [SMILES: COc1cccc(-c2nc(NC3CCC3)cc(C(=O)N3CC[C@@H](N4CCc5ccccc5C4)[C@H](O)C3)n2)c1] |
| 79 | 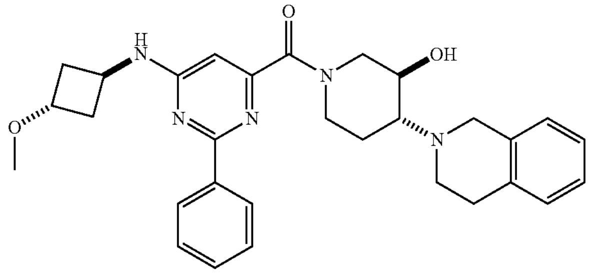 |
| 80 | 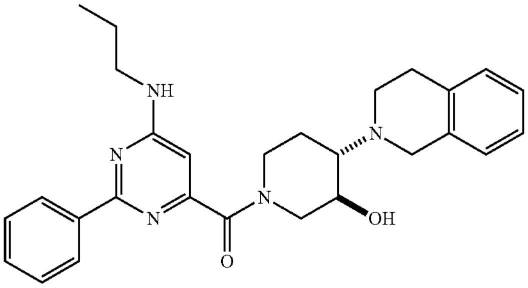 [SMILES: CCCNc1cc(C(=O)N2CC[C@H](N3CCc4ccccc4C3)[C@@H](O)C2)nc(-c2ccccc2)n1] |
| 81 | 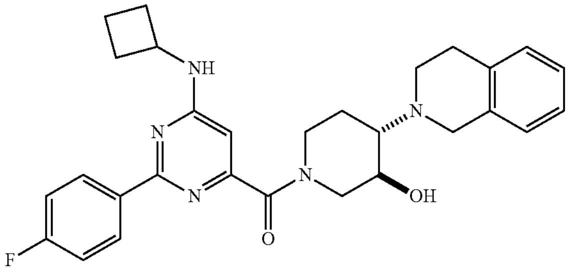 [SMILES: O=C(c1cc(NC2CCC2)nc(-c2ccc(F)cc2)n1)N1CC[C@H](N2CCc3ccccc3C2)[C@@H](O)C1] |

-continued
| No. | Structure |
|---|---|
| 82 | 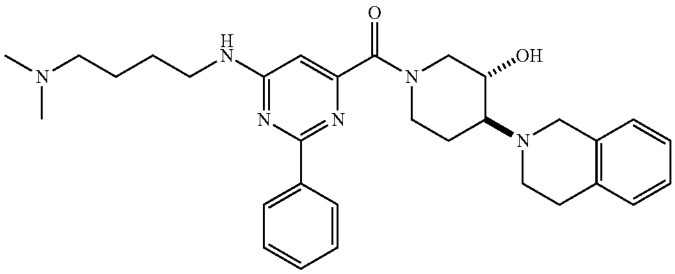 [SMILES: CN(C)CCCCNc1cc(C(=O)N2CC[C@H](N3CCc4ccccc4C3)[C@@H](O)C2)nc(-c2ccccc2)n1] |
| 83 | 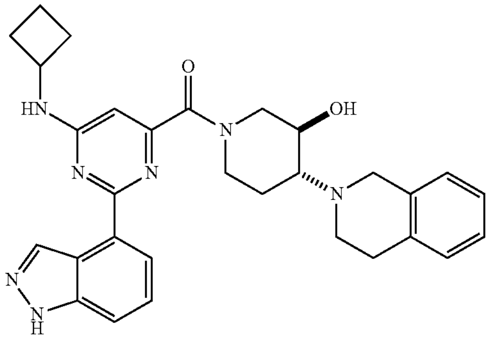 [SMILES: O=C(c1cc(NC2CCC2)nc(-c2cccc3[nH]ncc23)n1)N1CC[C@@H](N2CCc3ccccc3C2)[C@H](O)C1] |
| 84 | 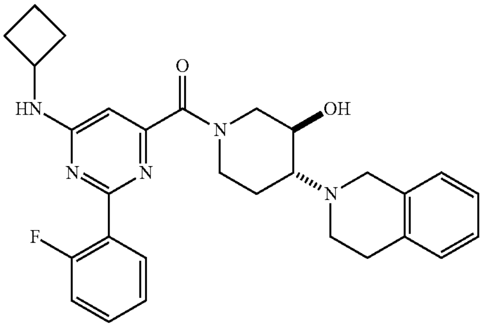 [SMILES: O=C(c1cc(NC2CCC2)nc(-c2ccccc2F)n1)N1CC[C@@H](N2CCc3ccccc3C2)[C@H](O)C1] |
| 85 | 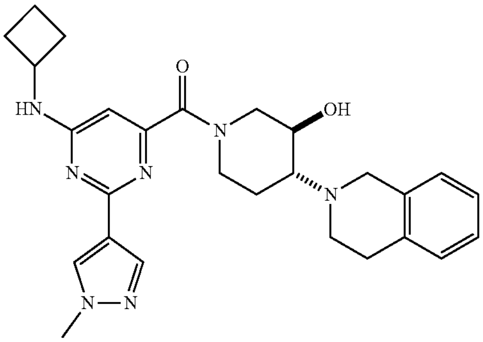 [SMILES: Cn1cc(-c2nc(NC3CCC3)cc(C(=O)N3CC[C@@H](N4CCc5ccccc5C4)[C@H](O)C3)n2)cn1] |
| 86 | 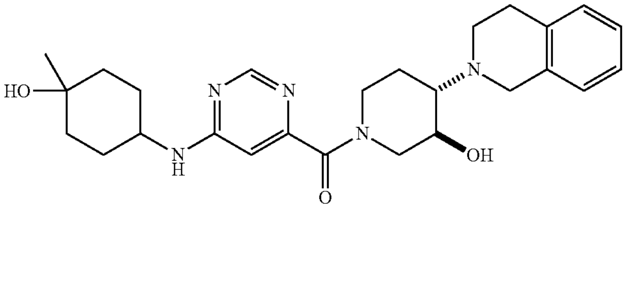 [SMILES: CC1(O)CCC(Nc2cc(C(=O)N3CC[C@H](N4CCc5ccccc5C4)[C@@H](O)C3)ncn2)CC1] |

-continued
| No. | Structure |
| --- | --- |
| 87 | 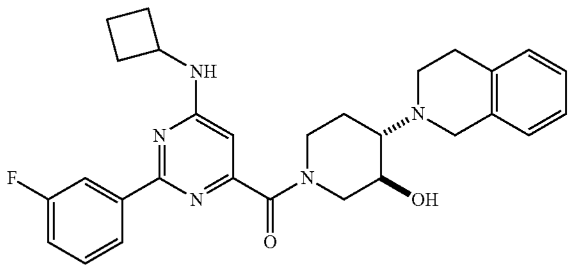 [SMILES: O=C(c1cc(NC2CCC2)nc(-c2cccc(F)c2)n1)N1CC[C@H](N2CCc3ccccc3C2)[C@@H](O)C1] |
| 88 | 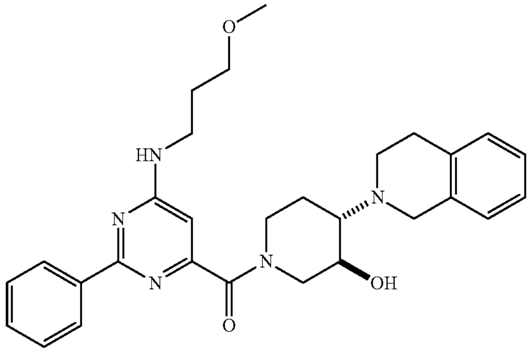 [SMILES: COCCCNc1cc(C(=O)N2CC[C@H](N3CCc4ccccc4C3)[C@@H](O)C2)nc(-c2ccccc2)n1] |
| 89 | 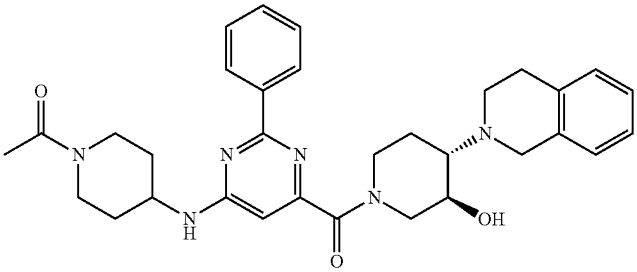 |
| 90 | 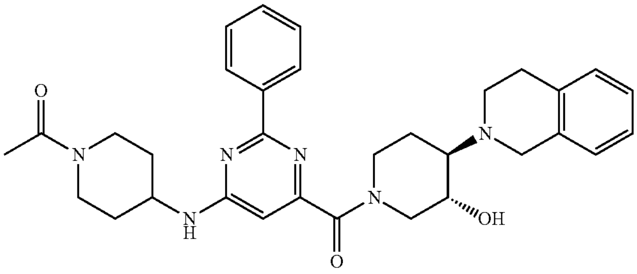 [SMILES: CC(=O)N1CCC(Nc2cc(C(=O)N3CC[C@@H](N4CCc5ccccc5C4)[C@H](O)C3)nc(-c3ccccc3)n2)CC1] |
| 91 | 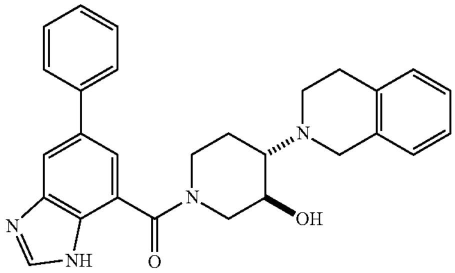 [SMILES: O=C(c1cc(-c2ccccc2)cc2nc[nH]c12)N1CC[C@H](N2CCc3ccccc3C2)[C@@H](O)C1] |

-continued
| No. | Structure |
|---|---|
| 92 | 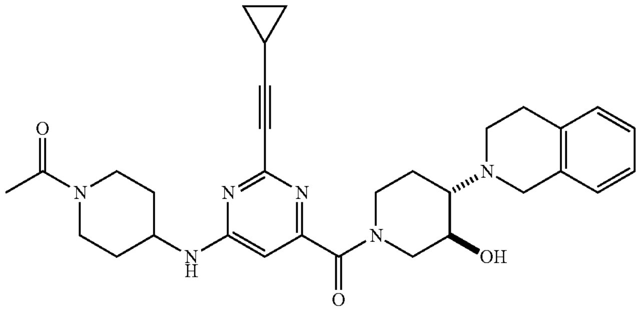 [SMILES: CC(=O)N1CCC(Nc2cc(C(=O)N3CC[C@H](N4CCc5ccccc5C4)[C@@H](O)C3)nc(C#CC3CC3)n2)CC1] |
| 93 | 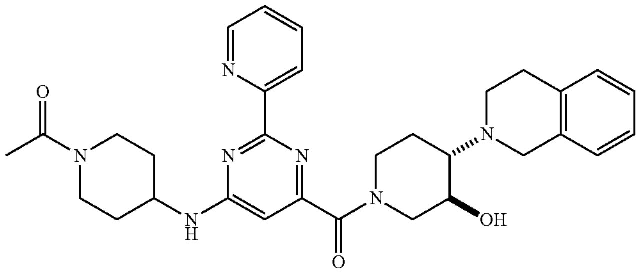 [SMILES: CC(=O)N1CCC(Nc2cc(C(=O)N3CC[C@H](N4CCc5ccccc5C4)[C@@H](O)C3)nc(-c3ccccn3)n2)CC1] |
| 94 | 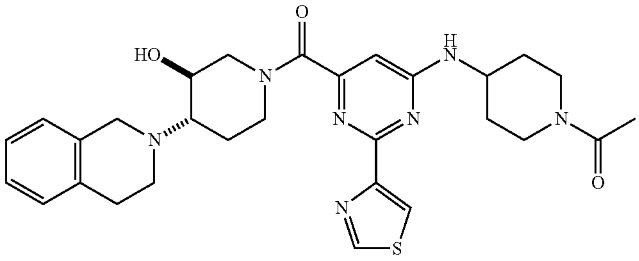 [SMILES: CC(=O)N1CCC(Nc2cc(C(=O)N3CC[C@H](N4CCc5ccccc5C4)[C@@H](O)C3)nc(-c3cscn3)n2)CC1] |
| 95 | 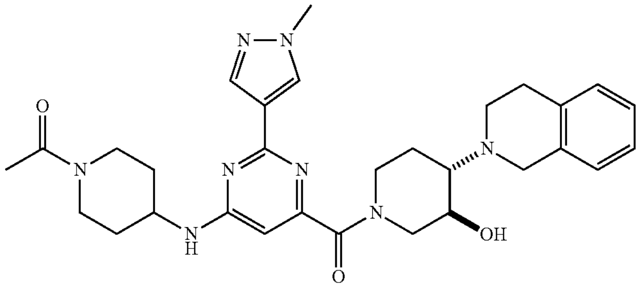 [SMILES: CC(=O)N1CCC(Nc2cc(C(=O)N3CC[C@H](N4CCc5ccccc5C4)[C@@H](O)C3)nc(-c3cnn(C)c3)n2)CC1] |
| 96 | 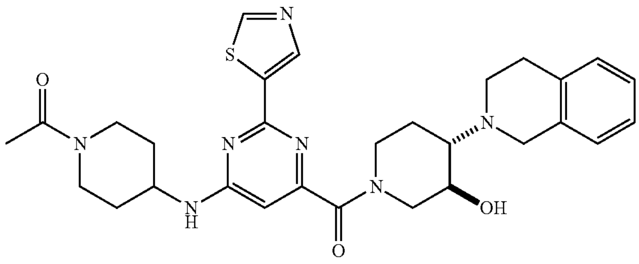 [SMILES: CC(=O)N1CCC(Nc2cc(C(=O)N3CC[C@H](N4CCc5ccccc5C4)[C@@H](O)C3)nc(-c3cncs3)n2)CC1] |

-continued
| No. | Structure |
|---|---|
| 97 | 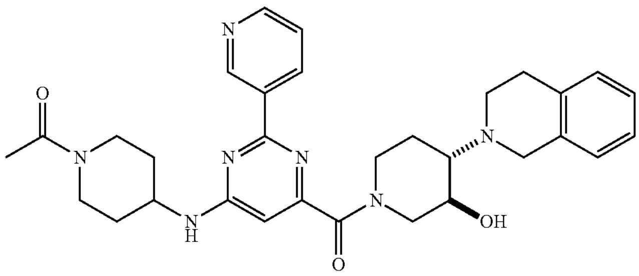 [SMILES: CC(=O)N1CCC(Nc2cc(C(=O)N3CC[C@H](N4CCc5ccccc5C4)[C@@H](O)C3)nc(-c3cccnc3)n2)CC1] |
| 98 | 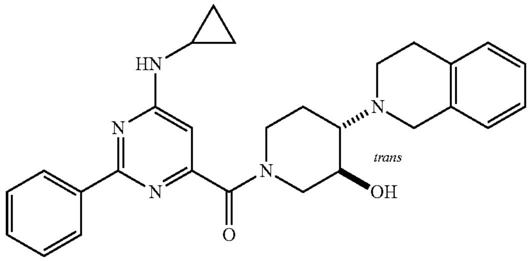 [SMILES: O=C(c1cc(NC2CC2)nc(-c2ccccc2)n1)N1CC[C@H](N2CCc3ccccc3C2)[C@@H](O)C1] |
| 99 | 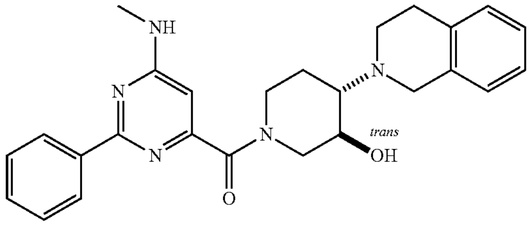 [SMILES: CNc1cc(C(=O)N2CC[C@H](N3CCc4ccccc4C3)[C@@H](O)C2)nc(-c2ccccc2)n1] |
| 100 | 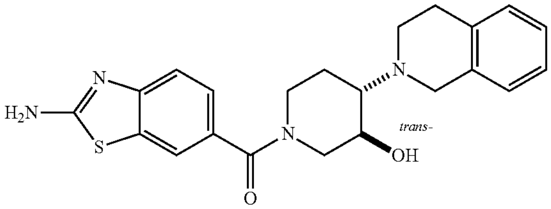 [SMILES: Nc1nc2ccc(C(=O)N3CC[C@H](N4CCc5ccccc5C4)[C@@H](O)C3)cc2s1] |
| 101 | 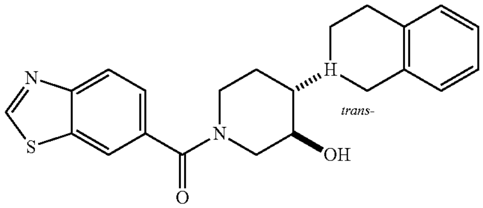 |
| 102 | 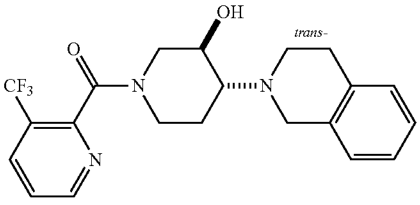 [SMILES: O=C(c1ncccc1C(F)(F)F)N1CC[C@@H](N2CCc3ccccc3C2)[C@H](O)C1] |

-continued
| No. | Structure |
| --- | --- |
| 103 | 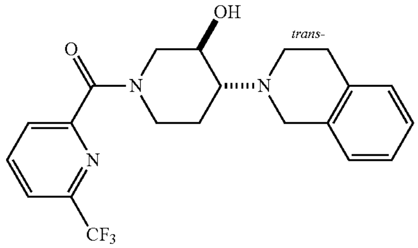 [SMILES: O=C(c1cccc(C(F)(F)F)n1)N1CC[C@@H](N2CCc3ccccc3C2)[C@H](O)C1] |
| 104 | 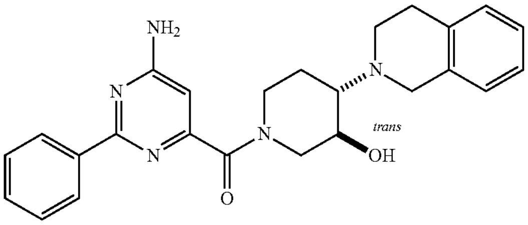 [SMILES: Nc1cc(C(=O)N2CC[C@H](N3CCc4ccccc4C3)[C@@H](O)C2)nc(-c2ccccc2)n1] |
| 105 | 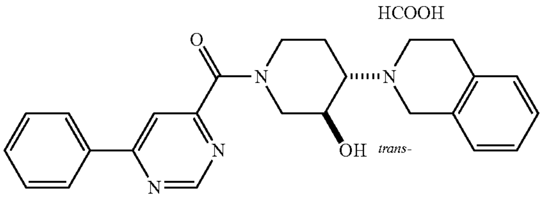 [SMILES: "HCOOH" ; O=C(c1cc(-c2ccccc2)ncn1)N1CC[C@H](N2CCc3ccccc3C2)[C@@H](O)C1] |
| 106 | 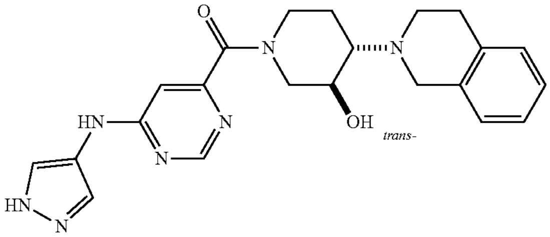 [SMILES: O=C(c1cc(Nc2cn[nH]c2)ncn1)N1CC[C@H](N2CCc3ccccc3C2)[C@@H](O)C1] |
| 107 | 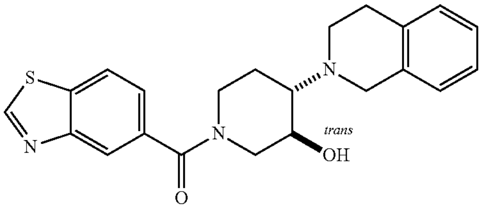 [SMILES: O=C(c1ccc2scnc2c1)N1CC[C@H](N2CCc3ccccc3C2)[C@@H](O)C1] |
| 108 | 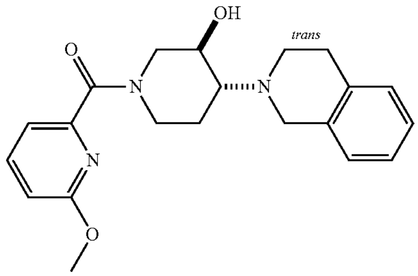 [SMILES: COc1cccc(C(=O)N2CC[C@@H](N3CCc4ccccc4C3)[C@H](O)C2)n1] |

-continued
| No. | Structure |
| --- | --- |
| 109 | 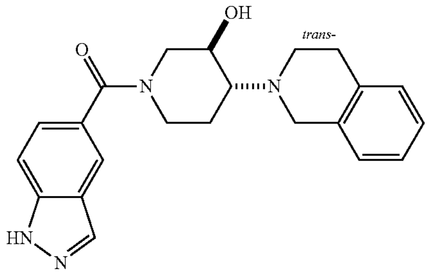 [SMILES: O=C(c1ccc2[nH]ncc2c1)N1CC[C@@H](N2CCc3ccccc3C2)[C@H](O)C1] |
| 110 | 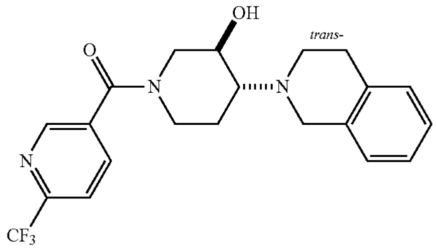 [SMILES: O=C(c1ccc(C(F)(F)F)nc1)N1CC[C@@H](N2CCc3ccccc3C2)[C@H](O)C1] |
| 111 | 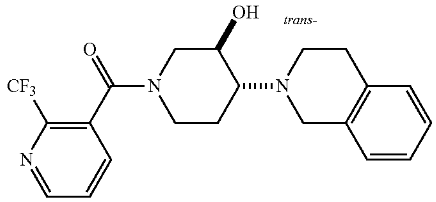 [SMILES: O=C(c1cccnc1C(F)(F)F)N1CC[C@@H](N2CCc3ccccc3C2)[C@H](O)C1] |
| 112 | 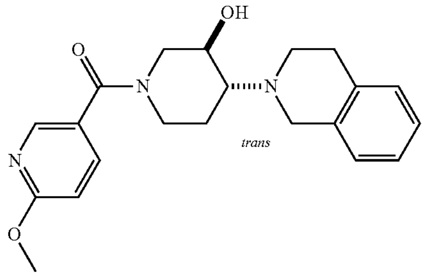 [SMILES: COc1ccc(C(=O)N2CC[C@@H](N3CCc4ccccc4C3)[C@H](O)C2)cn1] |
| 113 | 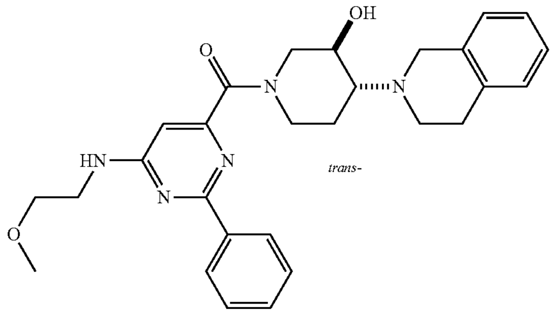 [SMILES: COCCNc1cc(C(=O)N2CC[C@@H](N3CCc4ccccc4C3)[C@H](O)C2)nc(-c2ccccc2)n1] |

-continued
| No. | Structure |
|---|---|
| 114 | 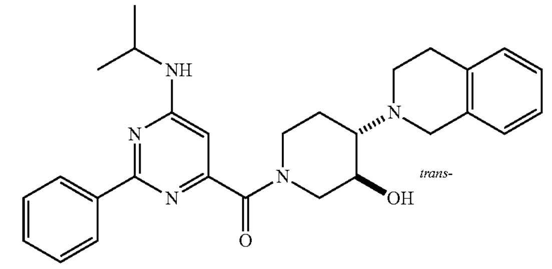 [SMILES: CC(C)Nc1cc(C(=O)N2CC[C@H](N3CCc4ccccc4C3)[C@@H](O)C2)nc(-c2ccccc2)n1] |
| 115 | 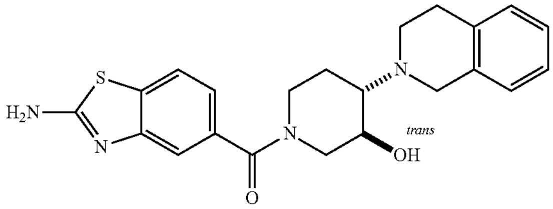 [SMILES: Nc1nc2cc(C(=O)N3CC[C@H](N4CCc5ccccc5C4)[C@@H](O)C3)ccc2s1] |
| 116 | 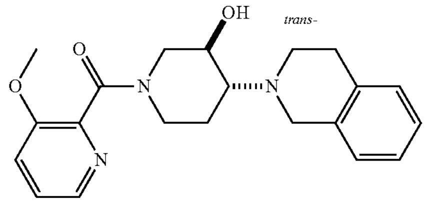 [SMILES: COc1cccnc1C(=O)N1CC[C@@H](N2CCc3ccccc3C2)[C@H](O)C1] |
| 117 | 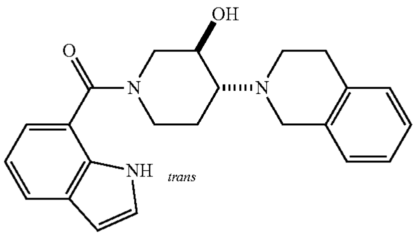 [SMILES: O=C(c1cccc2cc[nH]c12)N1CC[C@@H](N2CCc3ccccc3C2)[C@H](O)C1] |
| 118 | 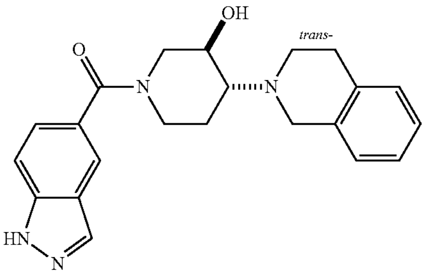 [SMILES: O=C(c1ccc2[nH]ncc2c1)N1CC[C@@H](N2CCc3ccccc3C2)[C@H](O)C1] |
| 119 | 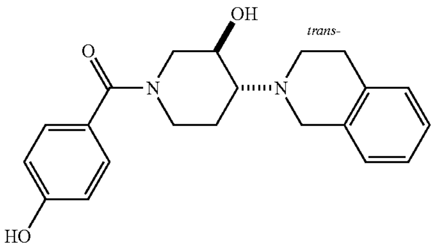 [SMILES: O=C(c1ccc(O)cc1)N1CC[C@@H](N2CCc3ccccc3C2)[C@H](O)C1] |

-continued
| No. | Structure |
|---|---|
| 120 | 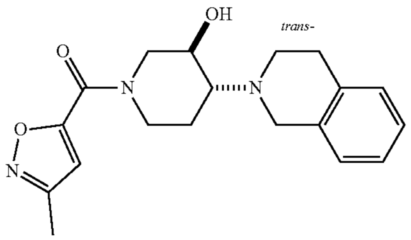 [SMILES: Cc1cc(C(=O)N2CC[C@@H](N3CCc4ccccc4C3)[C@H](O)C2)on1] trans- |
| 121 | 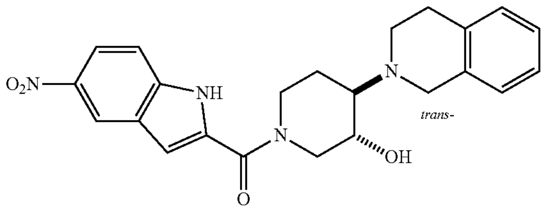 [SMILES: O=C(c1cc2cc([N+](=O)[O-])ccc2[nH]1)N1CC[C@@H](N2CCc3ccccc3C2)[C@H](O)C1] trans- |
| 122 | 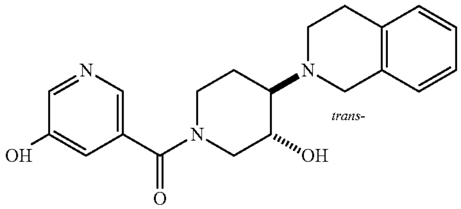 [SMILES: O=C(c1cncc(O)c1)N1CC[C@@H](N2CCc3ccccc3C2)[C@H](O)C1] trans- |
| 123 | 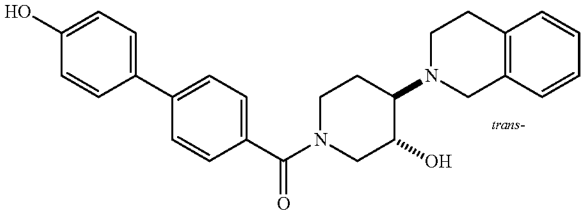 [SMILES: O=C(c1ccc(-c2ccc(O)cc2)cc1)N1CC[C@@H](N2CCc3ccccc3C2)[C@H](O)C1] trans- |
| 124 | 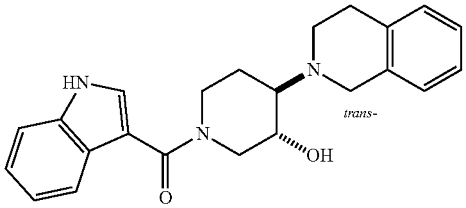 [SMILES: O=C(c1c[nH]c2ccccc12)N1CC[C@@H](N2CCc3ccccc3C2)[C@H](O)C1] trans- |
| 125 | 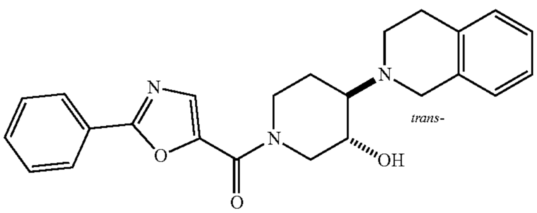 [SMILES: O=C(c1cnc(-c2ccccc2)o1)N1CC[C@@H](N2CCc3ccccc3C2)[C@H](O)C1] trans- |
| 126 | 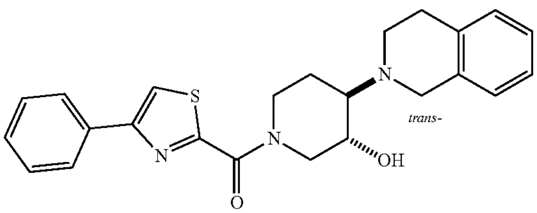 [SMILES: O=C(c1nc(-c2ccccc2)cs1)N1CC[C@@H](N2CCc3ccccc3C2)[C@H](O)C1] trans- |

-continued
| No. | Structure |
|---|---|
| 127 | 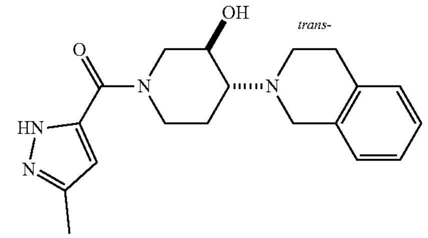 [SMILES: Cc1cc(C(=O)N2CC[C@@H](N3CCc4ccccc4C3)[C@H](O)C2)[nH]n1] |
| 128 | 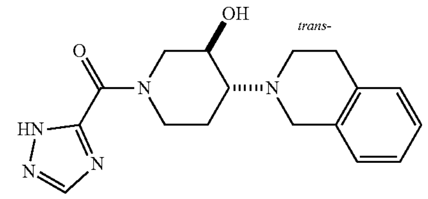 [SMILES: O=C(c1ncn[nH]1)N1CC[C@@H](N2CCc3ccccc3C2)[C@H](O)C1] |
| 129 | 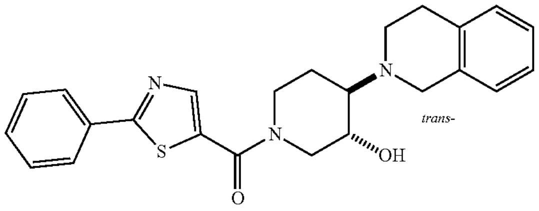 [SMILES: O=C(c1cnc(-c2ccccc2)s1)N1CC[C@@H](N2CCc3ccccc3C2)[C@H](O)C1] |
| 130 | 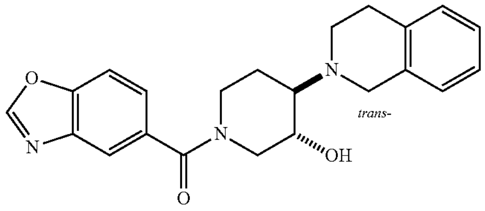 [SMILES: O=C(c1ccc2ocnc2c1)N1CC[C@@H](N2CCc3ccccc3C2)[C@H](O)C1] |
| 131 | 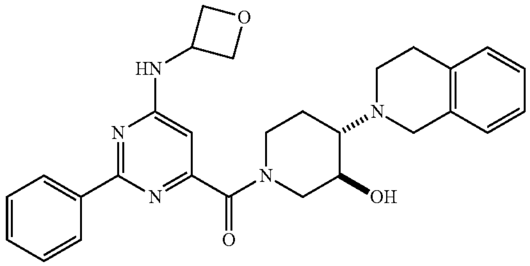 [SMILES: O=C(c1cc(NC2COC2)nc(-c2ccccc2)n1)N1CC[C@H](N2CCc3ccccc3C2)[C@@H](O)C1] |
| 132 | 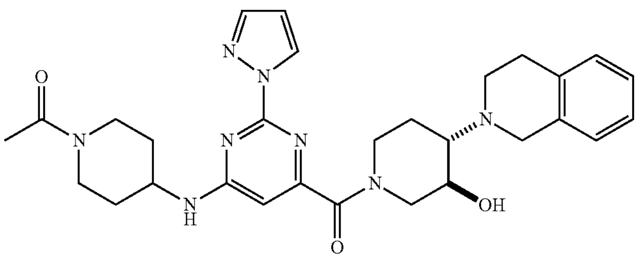 [SMILES: CC(=O)N1CCC(Nc2cc(C(=O)N3CC[C@H](N4CCc5ccccc5C4)[C@@H](O)C3)nc(-n3cccn3)n2)CC1] |

-continued
| No. | Structure |
|---|---|
| 133 | 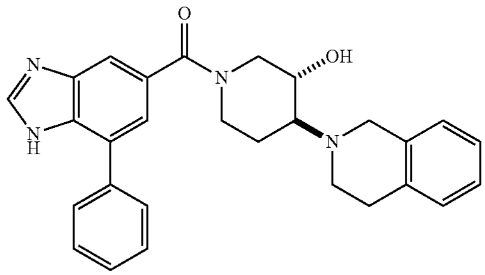 [SMILES: O=C(c1cc(-c2ccccc2)c2[nH]cnc2c1)N1CC[C@H](N2CCc3ccccc3C2)[C@@H](O)C1] |
| 134 | 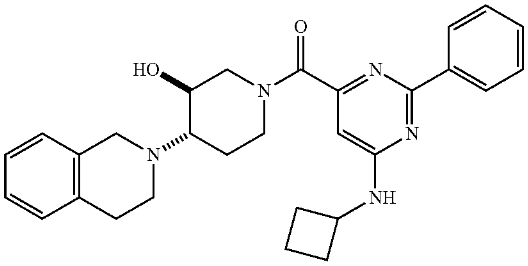 [SMILES: O=C(c1cc(NC2CCC2)nc(-c2ccccc2)n1)N1CC[C@H](N2CCc3ccccc3C2)[C@@H](O)C1] |
| 135 | 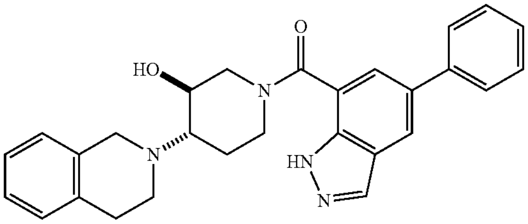 [SMILES: O=C(c1cc(-c2ccccc2)cc2cn[nH]c12)N1CC[C@H](N2CCc3ccccc3C2)[C@@H](O)C1] |
| 136 | 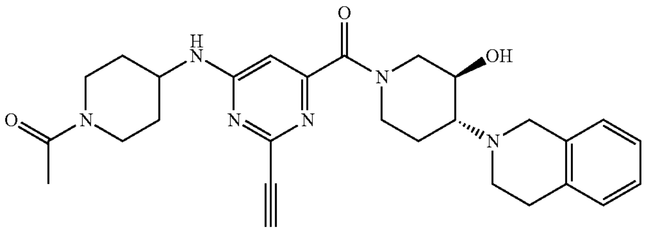 [SMILES: C#Cc1nc(NC2CCN(C(C)=O)CC2)cc(C(=O)N2CC[C@@H](N3CCc4ccccc4C3)[C@H](O)C2)n1] |
| 137 | 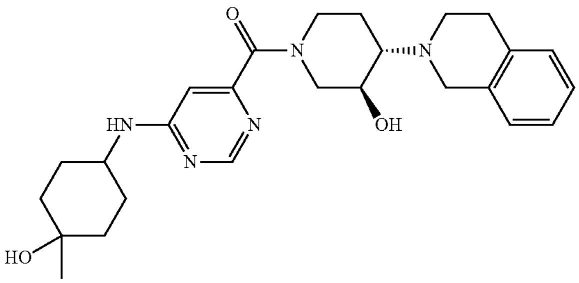 [SMILES: CC1(O)CCC(Nc2cc(C(=O)N3CC[C@H](N4CCc5ccccc5C4)[C@@H](O)C3)ncn2)CC1] |
| 138 | 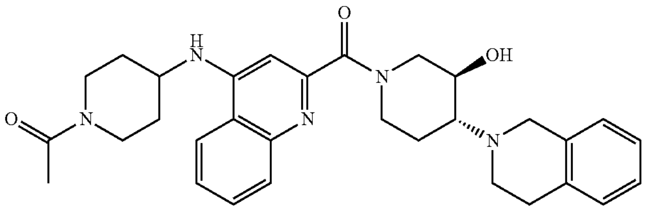 [SMILES: CC(=O)N1CCC(Nc2cc(C(=O)N3CC[C@@H](N4CCc5ccccc5C4)[C@H](O)C3)nc3ccccc23)CC1] |

-continued
| No. | Structure |
| --- | --- |
| 139 | 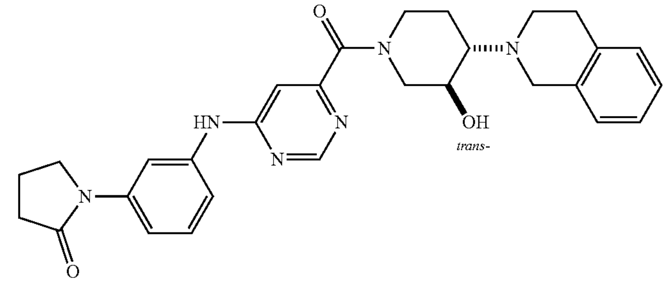 [SMILES: O=C(c1cc(Nc2cccc(N3CCCC3=O)c2)ncn1)N1CC[C@H](N2CCc3ccccc3C2)[C@@H](O)C1] |
| 140 | 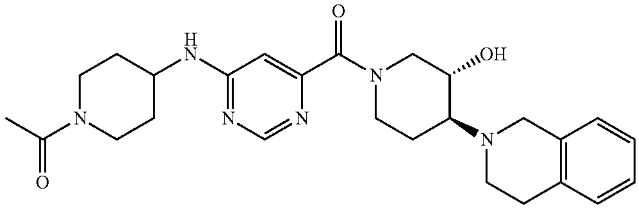 [SMILES: CC(=O)N1CCC(Nc2cc(C(=O)N3CC[C@H](N4CCc5ccccc5C4)[C@@H](O)C3)ncn2)CC1] |
| 141 | 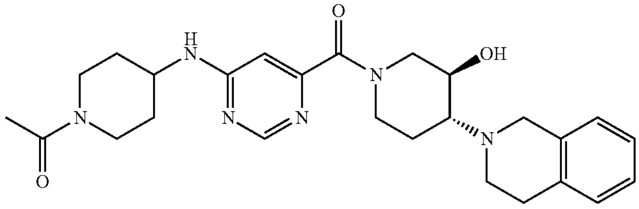 [SMILES: CC(=O)N1CCC(Nc2cc(C(=O)N3CC[C@@H](N4CCc5ccccc5C4)[C@H](O)C3)ncn2)CC1] |
| 142 | 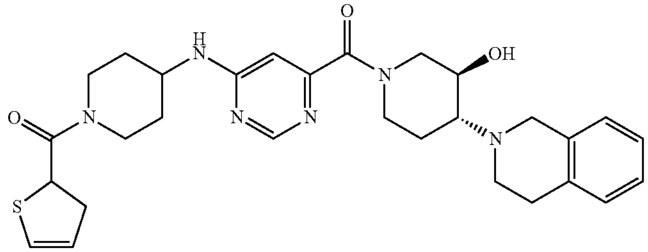 [SMILES: O=C(c1cc(NC2CCN(C(=O)C3CC=CS3)CC2)ncn1)N1CC[C@@H](N2CCc3ccccc3C2)[C@H](O)C1] |
| 143 | 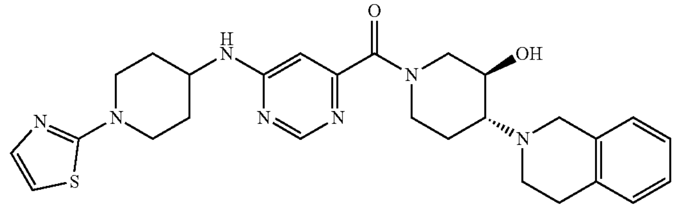 [SMILES: O=C(c1cc(NC2CCN(c3nccs3)CC2)ncn1)N1CC[C@@H](N2CCc3ccccc3C2)[C@H](O)C1] |
| 144 | 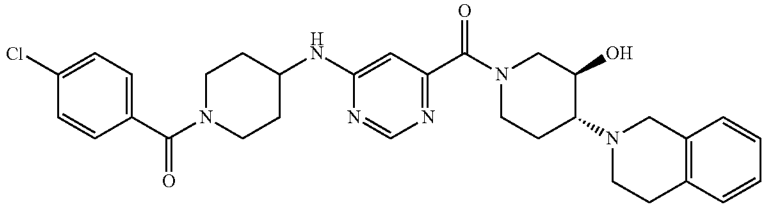 [SMILES: O=C(c1ccc(Cl)cc1)N1CCC(Nc2cc(C(=O)N3CC[C@@H](N4CCc5ccccc5C4)[C@H](O)C3)ncn2)CC1] |

-continued
| No. | Structure |
| --- | --- |
| 145 | 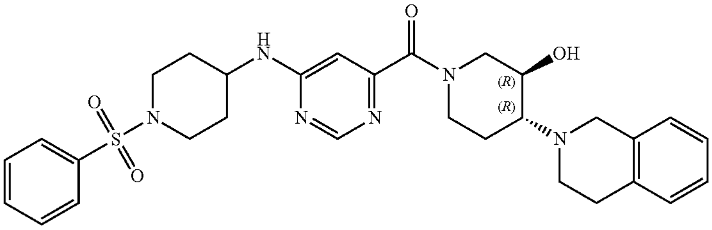 |
| 146 | 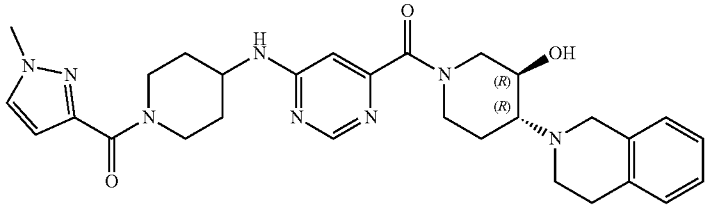 |
| 147 | 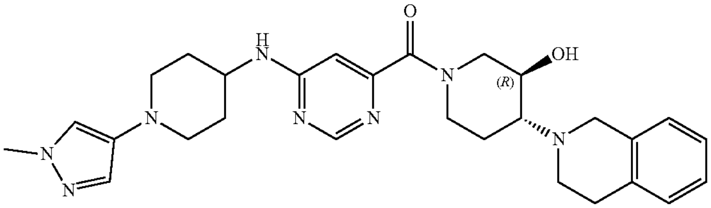 |
| 148 | 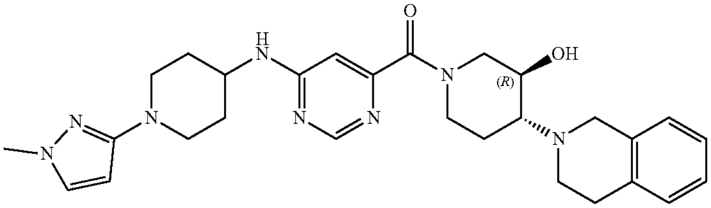 |
| 149 | 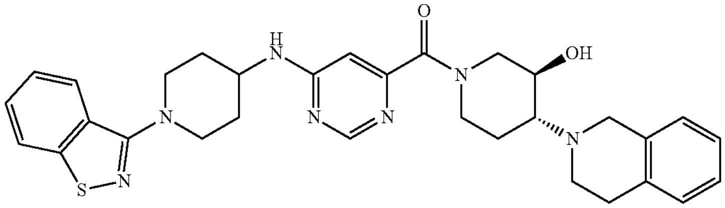 [SMILES: O=C(c1cc(NC2CCN(c3nsc4ccccc34)CC2)ncn1)N1CC[C@@H](N2CCc3ccccc3C2)[C@H](O)C1] |
| 150 | 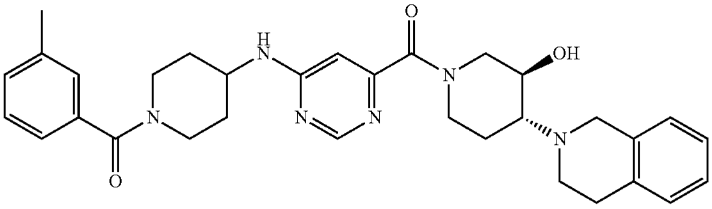 [SMILES: Cc1cccc(C(=O)N2CCC(Nc3cc(C(=O)N4CC[C@@H](N5CCc6ccccc6C5)[C@H](O)C4)ncn3)CC2)c1] |
| 151 | 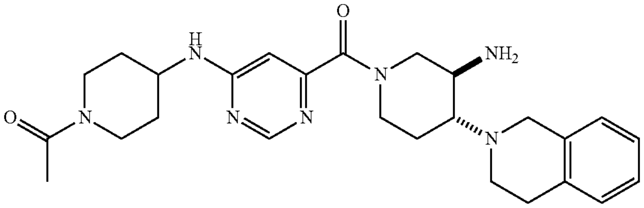 [SMILES: CC(=O)N1CCC(Nc2cc(C(=O)N3CC[C@@H](N4CCc5ccccc5C4)[C@H](N)C3)ncn2)CC1] |

-continued
| No. | Structure |
|---|---|
| 152 | 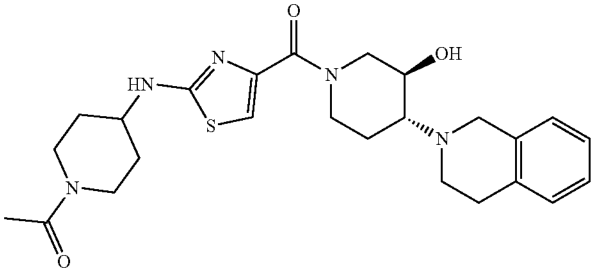 [SMILES: CC(=O)N1CCC(Nc2nc(C(=O)N3CC[C@@H](N4CCc5ccccc5C4)[C@H](O)C3)cs2)CC1] |
| 153 | 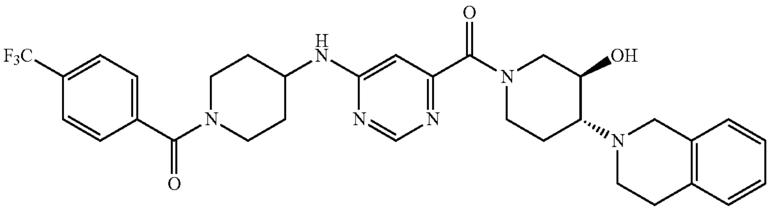 [SMILES: O=C(c1ccc(C(F)(F)F)cc1)N1CCC(Nc2cc(C(=O)N3CC[C@@H](N4CCc5ccccc5C4)[C@H](O)C3)ncn2)CC1] |
| 154 | 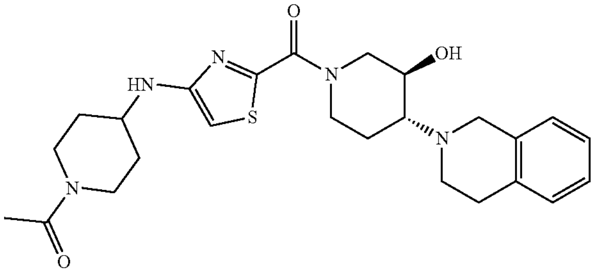 [SMILES: CC(=O)N1CCC(Nc2csc(C(=O)N3CC[C@@H](N4CCc5ccccc5C4)[C@H](O)C3)n2)CC1] |
| 155 | 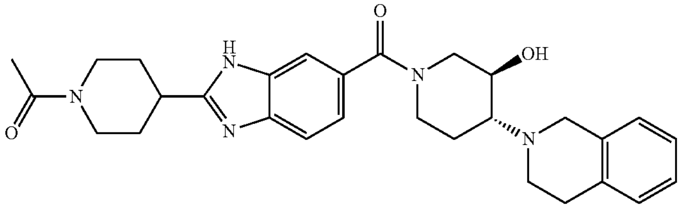 [SMILES: CC(=O)N1CCC(c2nc3ccc(C(=O)N4CC[C@@H](N5CCc6ccccc6C5)[C@H](O)C4)cc3[nH]2)CC1] |
| 156 | 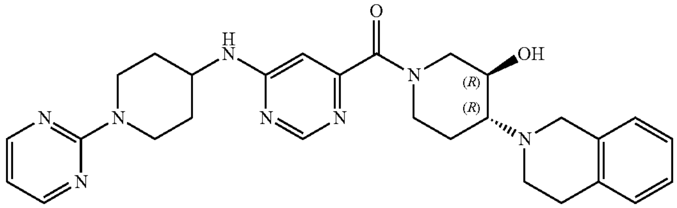 |
| 157 | 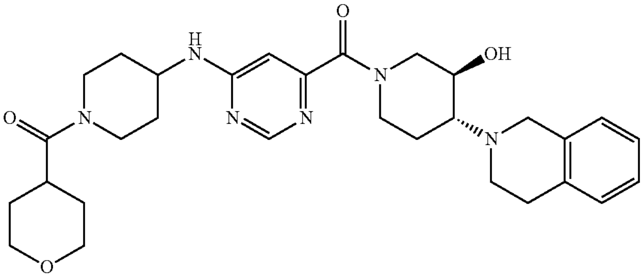 [SMILES: O=C(c1cc(NC2CCN(C(=O)C3CCOCC3)CC2)ncn1)N1CC[C@@H](N2CCc3ccccc3C2)[C@H](O)C1] |

-continued
| No. | Structure |
|---|---|
| 158 | 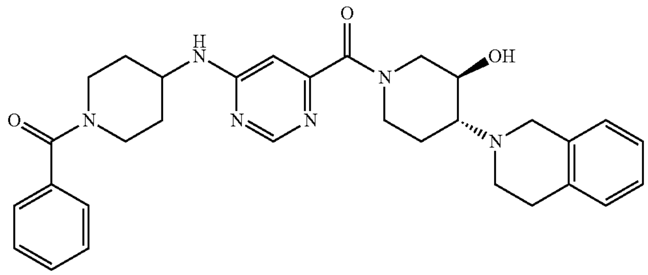 [SMILES: O=C(c1ccccc1)N1CCC(Nc2cc(C(=O)N3CC[C@@H](N4CCc5ccccc5C4)[C@H](O)C3)ncn2)CC1] |
| 159 | 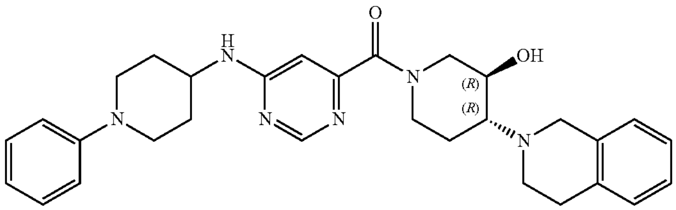 |
| 160 | 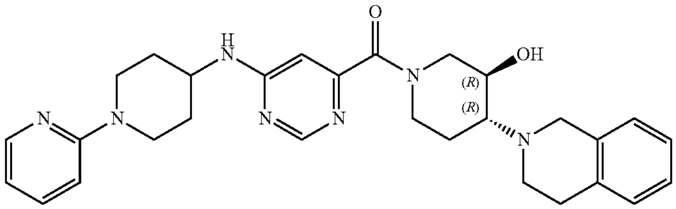 |
| 161 | 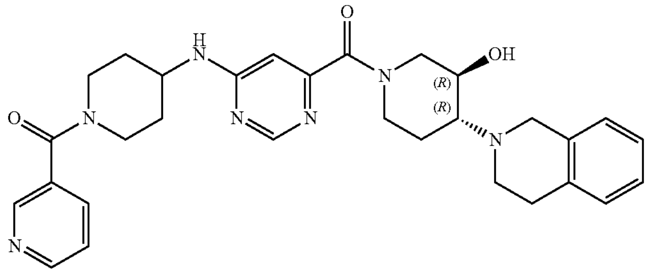 |
| 162 | 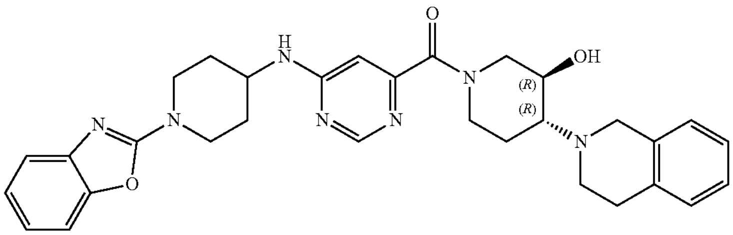 |
| 163 | 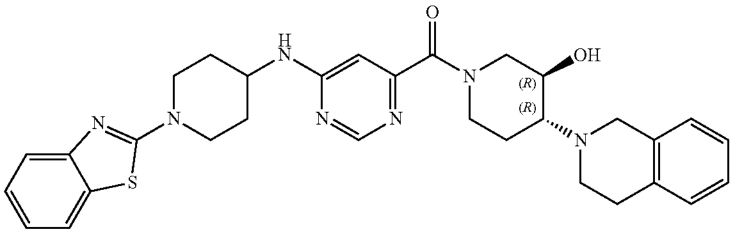 |

-continued
| No. | Structure |
| --- | --- |
| 164 | 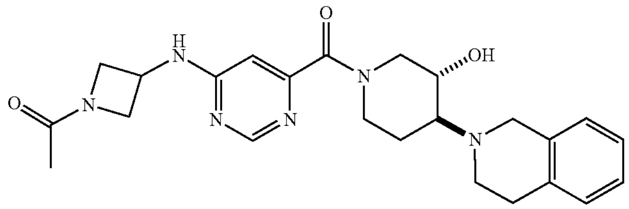 [SMILES: CC(=O)N1CC(Nc2cc(C(=O)N3CC[C@H](N4CCc5ccccc5C4)[C@@H](O)C3)ncn2)C1] |
| 165 | 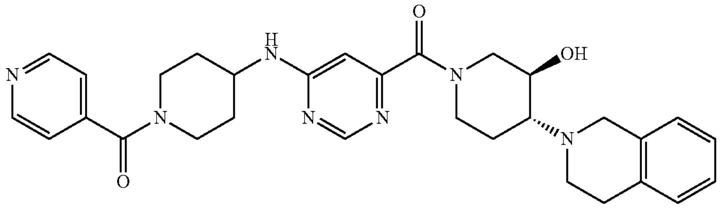 [SMILES: O=C(c1ccncc1)N1CCC(Nc2cc(C(=O)N3CC[C@@H](N4CCc5ccccc5C4)[C@H](O)C3)ncn2)CC1] |
| 166 | 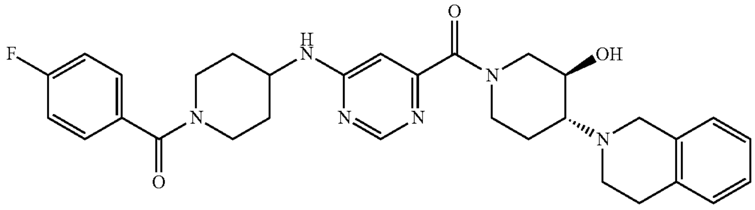 [SMILES: O=C(c1ccc(F)cc1)N1CCC(Nc2cc(C(=O)N3CC[C@@H](N4CCc5ccccc5C4)[C@H](O)C3)ncn2)CC1] |
| 167 | 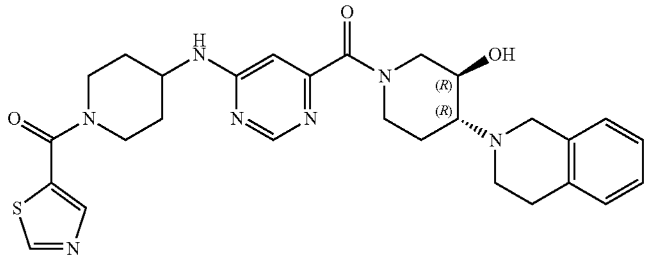 |
| 168 | 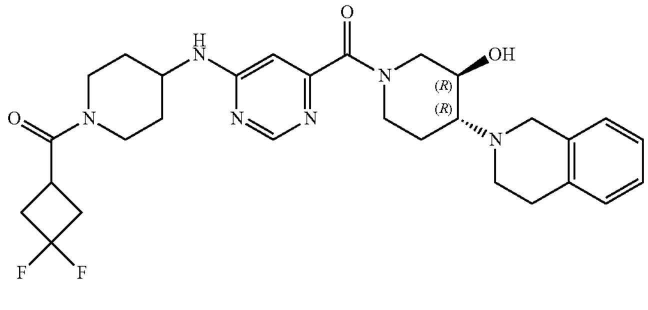 |
| 169 | 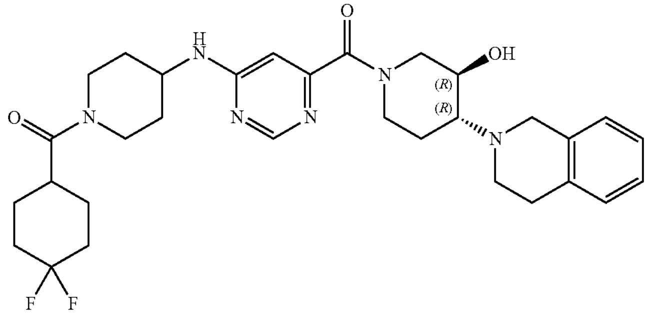 |

-continued
| No. | Structure |
| --- | --- |
| 170 | 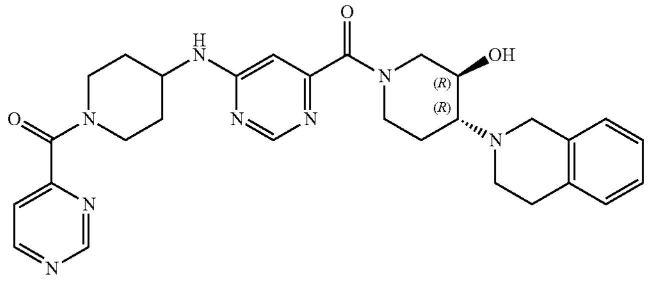 |
| 171 | 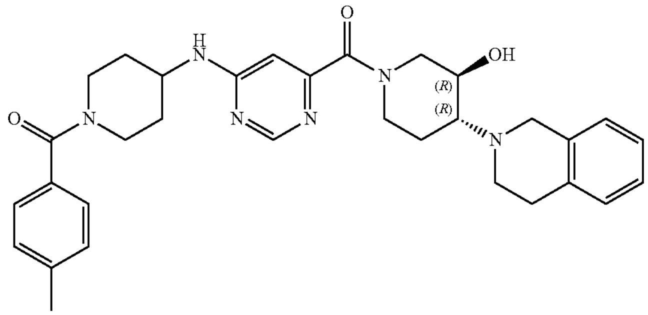 |
| 172 | 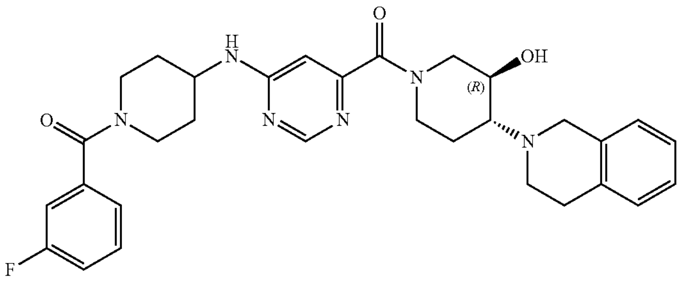 |
| 173 | 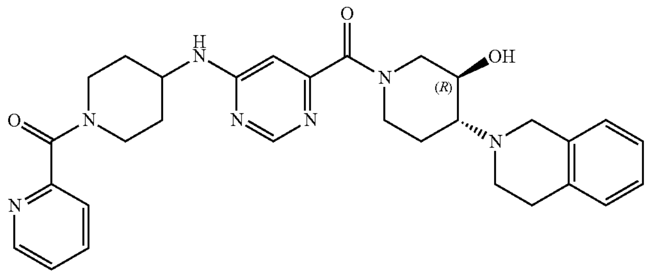 |
| 174 | 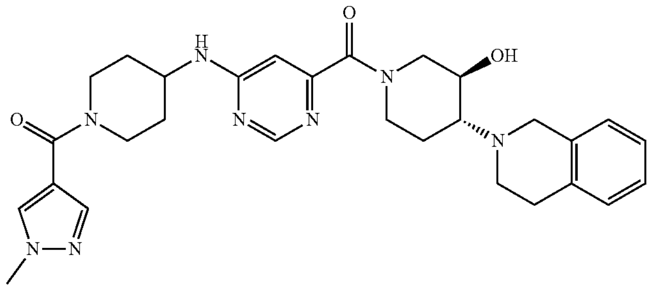 [SMILES: Cn1cc(C(=O)N2CCC(Nc3cc(C(=O)N4CC[C@@H](N5CCc6ccccc6C5)[C@H](O)C4)ncn3)CC2)cn1] |

-continued
| No. | Structure |
|---|---|
| 175 | 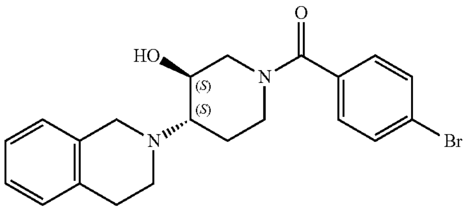 |
| 176 | 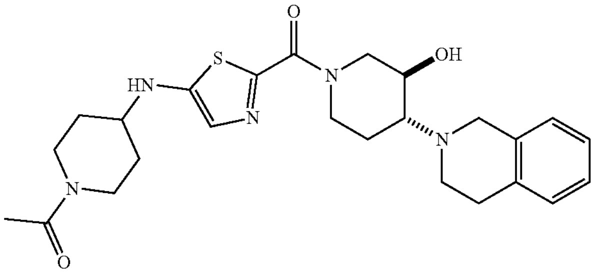 [SMILES: CC(=O)N1CCC(Nc2cnc(C(=O)N3CC[C@@H](N4CCc5ccccc5C4)[C@H](O)C3)s2)CC1] |
| 177 | 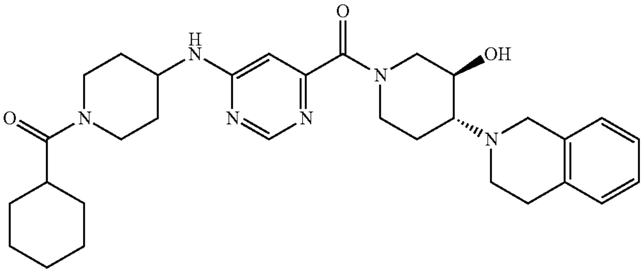 [SMILES: O=C(c1cc(NC2CCN(C(=O)C3CCCCC3)CC2)ncn1)N1CC[C@@H](N2CCc3ccccc3C2)[C@H](O)C1] |
| 178 | 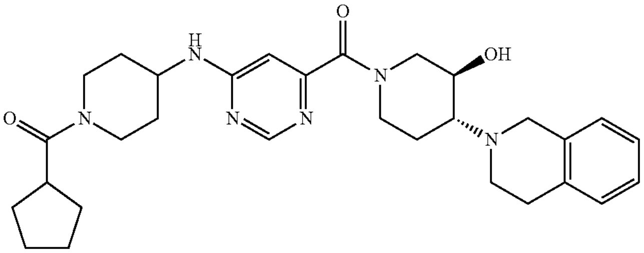 [SMILES: O=C(c1cc(NC2CCN(C(=O)C3CCCC3)CC2)ncn1)N1CC[C@@H](N2CCc3ccccc3C2)[C@H](O)C1] |
| 179 | 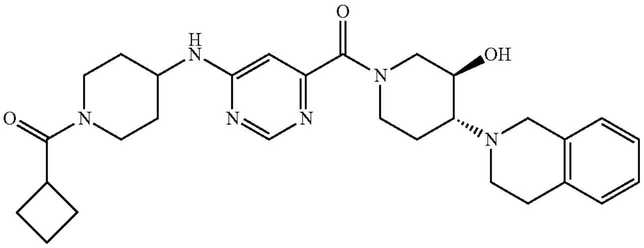 [SMILES: O=C(c1cc(NC2CCN(C(=O)C3CCC3)CC2)ncn1)N1CC[C@@H](N2CCc3ccccc3C2)[C@H](O)C1] |
| 180 | 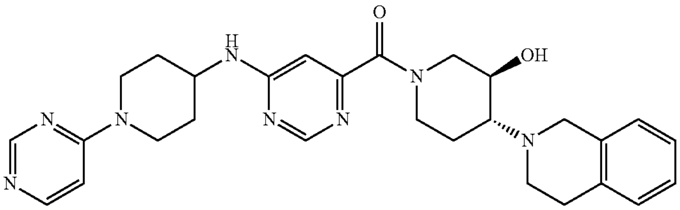 [SMILES: O=C(c1cc(NC2CCN(c3ccncn3)CC2)ncn1)N1CC[C@@H](N2CCc3ccccc3C2)[C@H](O)C1] |

-continued
| No. | Structure |
| --- | --- |
| 181 | 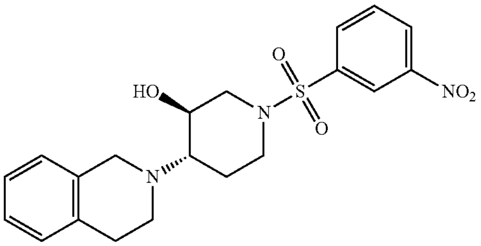 [SMILES: O=[N+]([O-])c1cccc(S(=O)(=O)N2CC[C@H](N3CCc4ccccc4C3)[C@@H](O)C2)c1] |
| 182 | 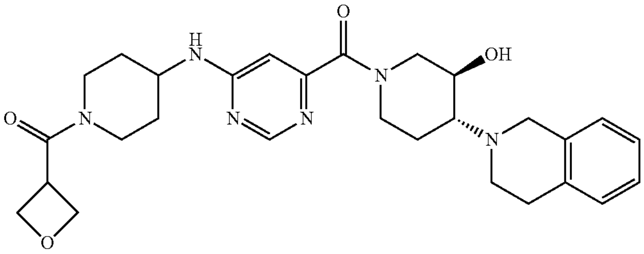 [SMILES: O=C(c1cc(NC2CCN(C(=O)C3COC3)CC2)ncn1)N1CC[C@@H](N2CCc3ccccc3C2)[C@H](O)C1] |
| 183 | 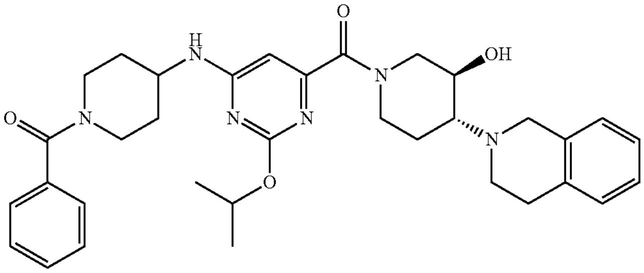 [SMILES: CC(C)Oc1nc(NC2CCN(C(=O)c3ccccc3)CC2)cc(C(=O)N2CC[C@@H](N3CCc4ccccc4C3)[C@H](O)C2)n1] |
| 184 | 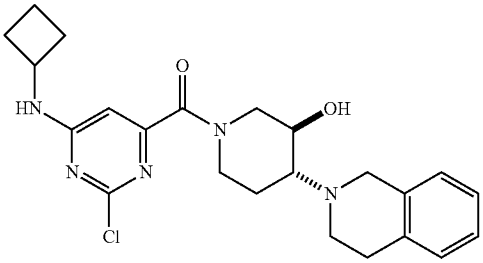 [SMILES: O=C(c1cc(NC2CCC2)nc(Cl)n1)N1CC[C@@H](N2CCc3ccccc3C2)[C@H](O)C1] |
| 185 | 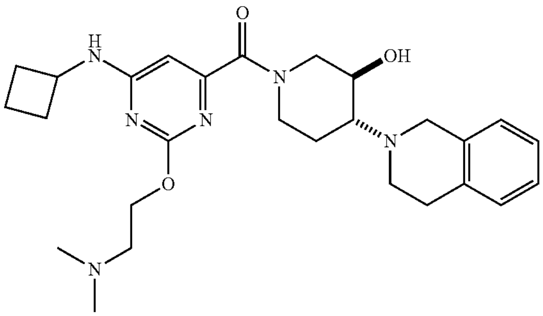 [SMILES: CN(C)CCOc1nc(NC2CCC2)cc(C(=O)N2CC[C@@H](N3CCc4ccccc4C3)[C@H](O)C2)n1] |

-continued
| No. | Structure |
| --- | --- |
| 186 | 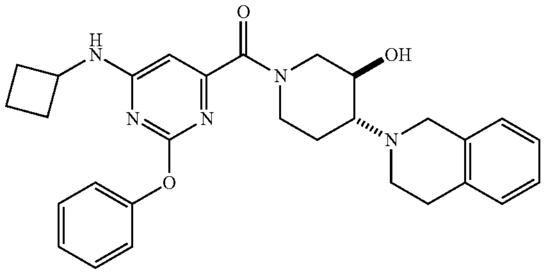 [SMILES: O=C(c1cc(NC2CCC2)nc(Oc2ccccc2)n1)N1CC[C@@H](N2CCc3ccccc3C2)[C@H](O)C1] |
| 187 | 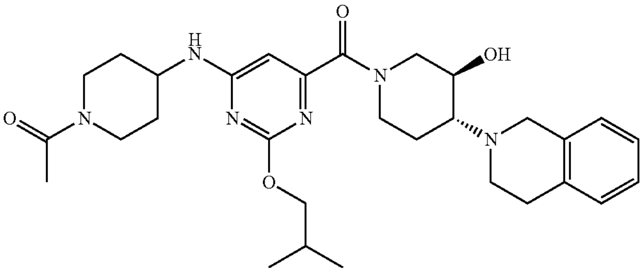 [SMILES: CC(=O)N1CCC(Nc2cc(C(=O)N3CC[C@@H](N4CCc5ccccc5C4)[C@H](O)C3)nc(OCC(C)C)n2)CC1] |
| 188 | 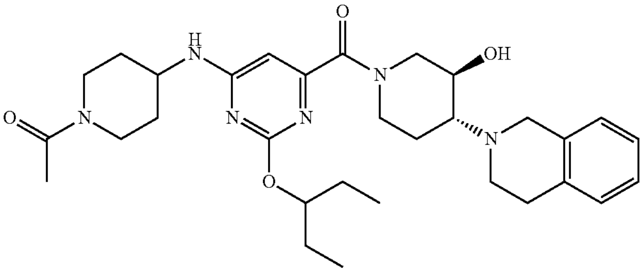 [SMILES: CCC(CC)Oc1nc(NC2CCN(C(C)=O)CC2)cc(C(=O)N2CC[C@@H](N3CCc4ccccc4C3)[C@H](O)C2)n1] |
| 189 | 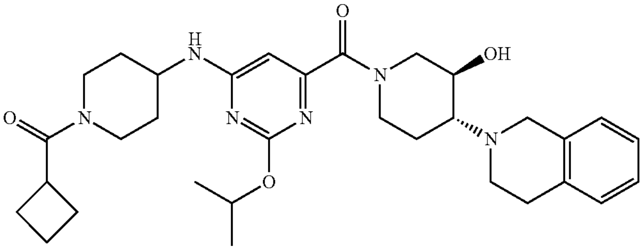 [SMILES: CC(C)Oc1nc(NC2CCN(C(=O)C3CCC3)CC2)cc(C(=O)N2CC[C@@H](N3CCc4ccccc4C3)[C@H](O)C2)n1] |
| 190 | 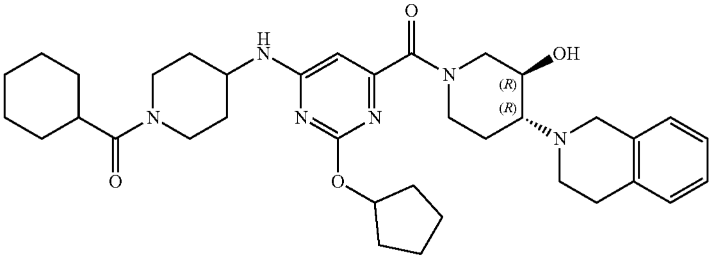 |

-continued
| No. | Structure |
|---|---|
| 191 | 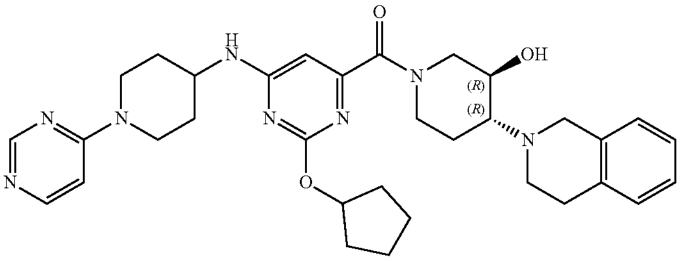 |
| 192 | 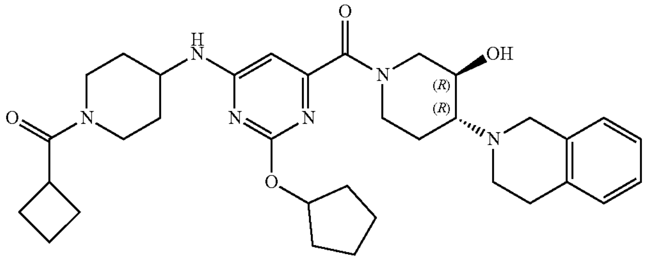 |
| 193 | 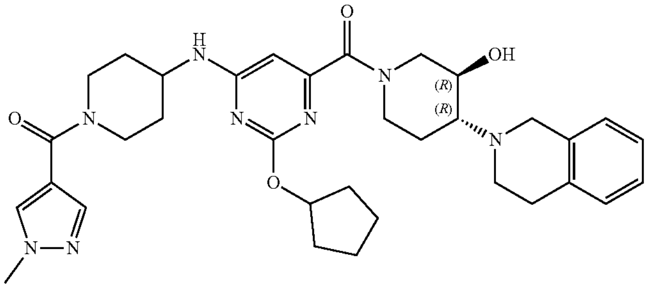 |
| 194 | 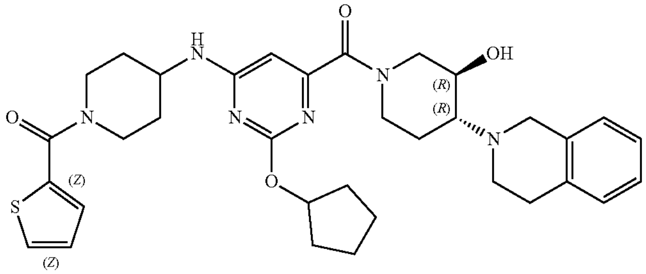 |
| 195 | 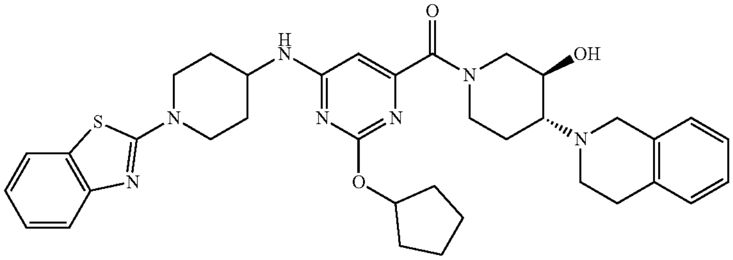 |

-continued
| No. | Structure |
| --- | --- |
| 196 | 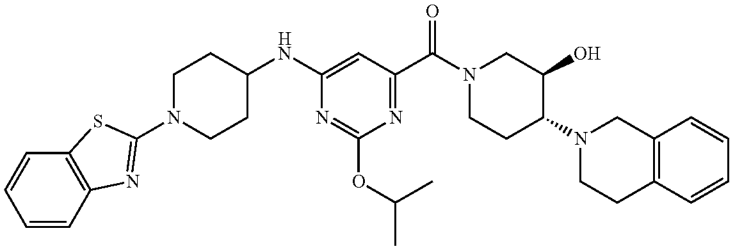 [SMILES: CC(C)Oc1nc(NC2CCN(c3nc4ccccc4s3)CC2)cc(C(=O)N2CC[C@@H](N3CCc4ccccc4C3)[C@H](O)C2)n1] |
| 197 | 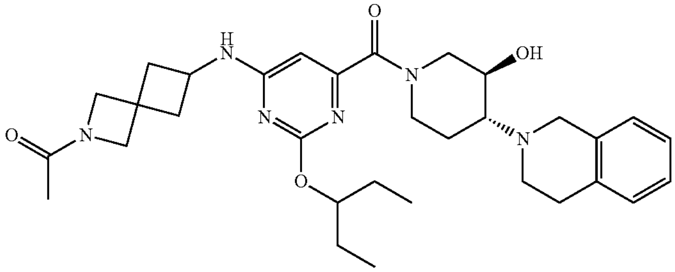 [SMILES: CCC(CC)Oc1nc(NC2CC3(C2)CN(C(C)=O)C3)cc(C(=O)N2CC[C@@H](N3CCc4ccccc4C3)[C@H](O)C2)n1] |
| 198 | 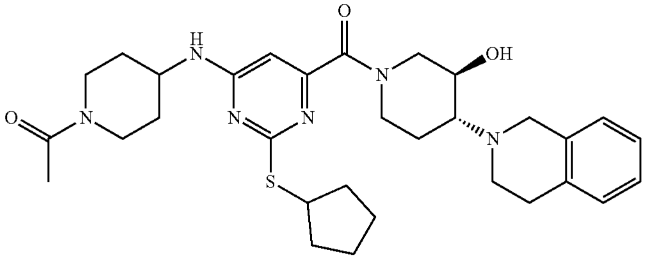 [SMILES: CC(=O)N1CCC(Nc2cc(C(=O)N3CC[C@@H](N4CCc5ccccc5C4)[C@H](O)C3)nc(SC3CCCC3)n2)CC1] |
| 199 | 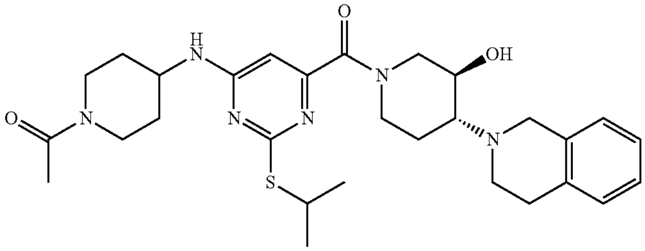 |
| 200 | 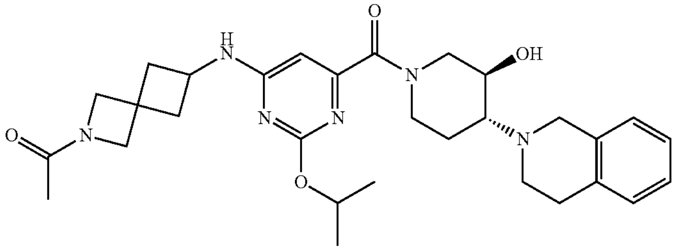 [SMILES: CC(=O)N1CC2(CC(Nc3cc(C(=O)N4CC[C@@H](N5CCc6ccccc6C5)[C@H](O)C4)nc(OC(C)C)n3)C2)C1] |

-continued
| No. | Structure |
|---|---|
| 201 | 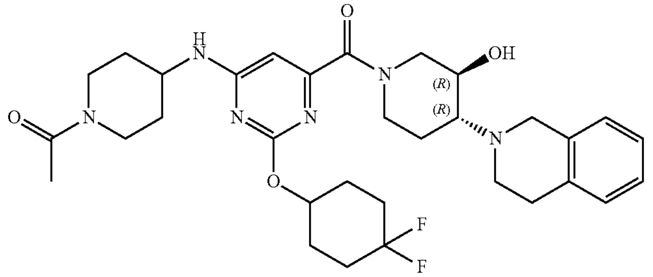 |
| 202 | 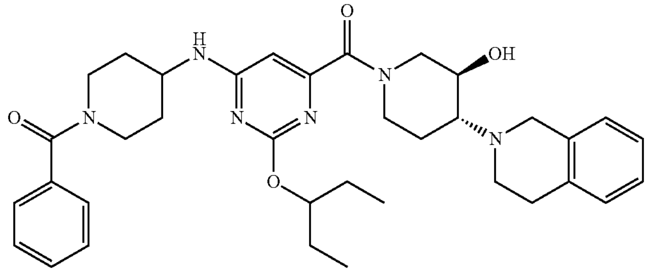 [SMILES: CCC(CC)Oc1nc(NC2CCN(C(=O)c3ccccc3)CC2)cc(C(=O)N2CC[C@@H](N3CCc4ccccc4C3)[C@H](O)C2)n1] |
| 203 | 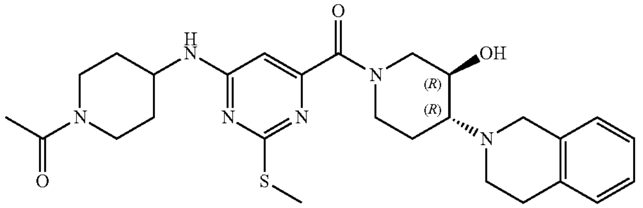 |
| 204 | 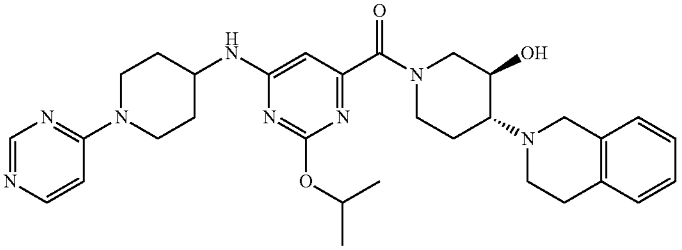 [SMILES: CC(C)Oc1nc(NC2CCN(c3ccncn3)CC2)cc(C(=O)N2CC[C@@H](N3CCc4ccccc4C3)[C@H](O)C2)n1] |
| 205 | 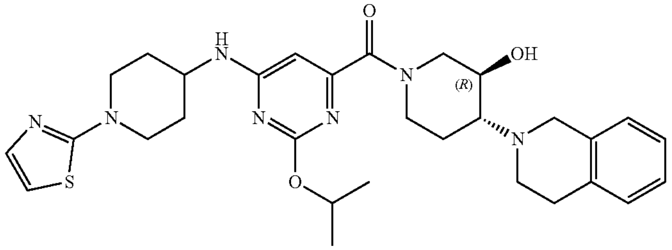 |
| 206 | 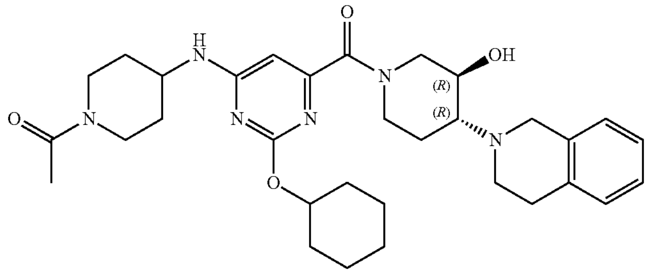 |

-continued
| No. | Structure |
|---|---|
| 207 | 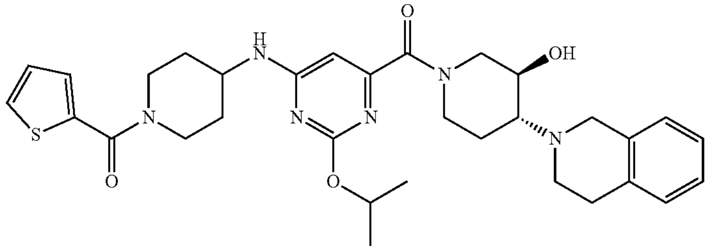 [SMILES: CC(C)Oc1nc(NC2CCN(C(=O)c3cccs3)CC2)cc(C(=O)N2CC[C@@H](N3CCc4ccccc4C3)[C@H](O)C2)n1] |
| 208 | 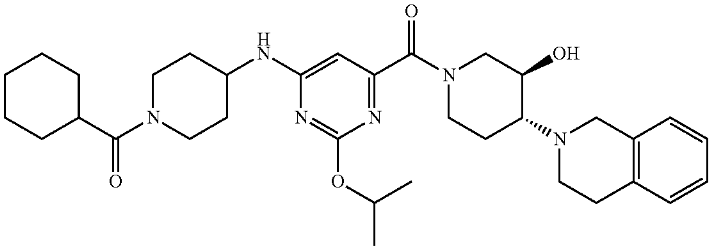 [SMILES: CC(C)Oc1nc(NC2CCN(C(=O)C3CCCCC3)CC2)cc(C(=O)N2CC[C@@H](N3CCc4ccccc4C3)[C@H](O)C2)n1] |
| 209 | 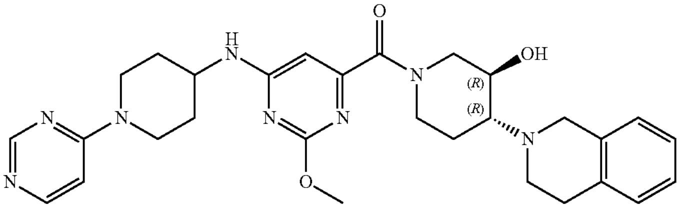 |
| 210 | 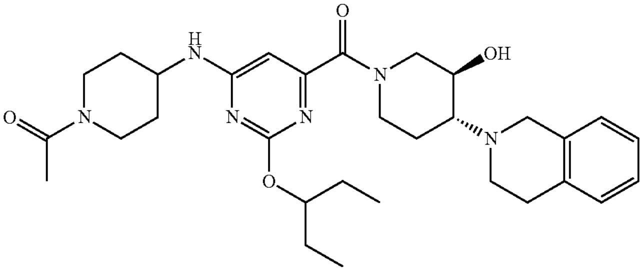 [SMILES: CCC(CC)Oc1nc(NC2CCN(C(C)=O)CC2)cc(C(=O)N2CC[C@@H](N3CCc4ccccc4C3)[C@H](O)C2)n1] |
| 211 | 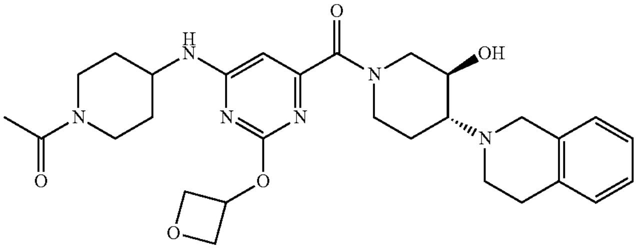 [SMILES: CC(=O)N1CCC(Nc2cc(C(=O)N3CC[C@@H](N4CCc5ccccc5C4)[C@H](O)C3)nc(OC3COC3)n2)CC1] |
| 212 | 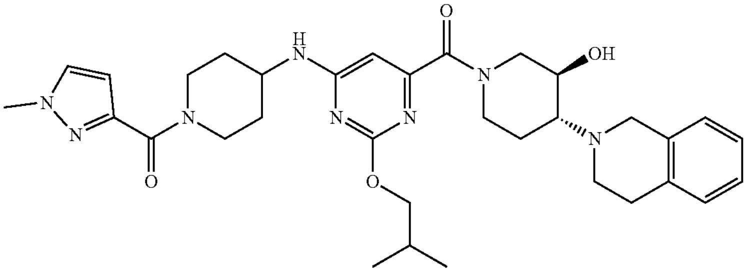 |

-continued
| No. | Structure |
|---|---|
| 213 | 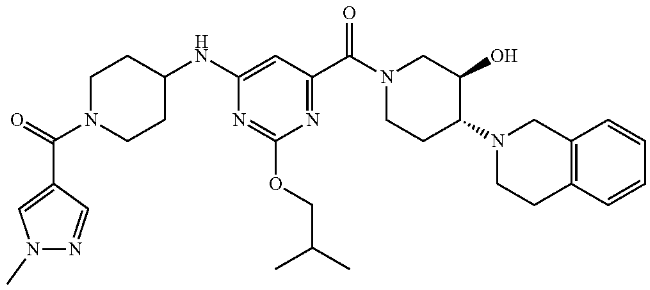 [SMILES: CC(C)COc1nc(NC2CCN(C(=O)c3cnn(C)c3)CC2)cc(C(=O)N2CC[C@@H](N3CCc4ccccc4C3)[C@H](O)C2)n1] |
| 214 | 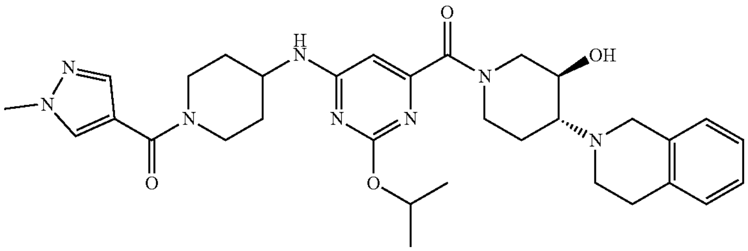 [SMILES: CC(C)Oc1nc(NC2CCN(C(=O)c3cnn(C)c3)CC2)cc(C(=O)N2CC[C@@H](N3CCc4ccccc4C3)[C@H](O)C2)n1] |
| 215 | 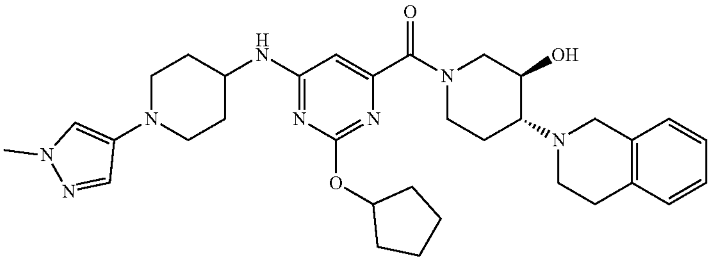 [SMILES: Cn1cc(N2CCC(Nc3cc(C(=O)N4CC[C@@H](N5CCc6ccccc6C5)[C@H](O)C4)nc(OC4CCCC4)n3)CC2)cn1] |
| 216 | 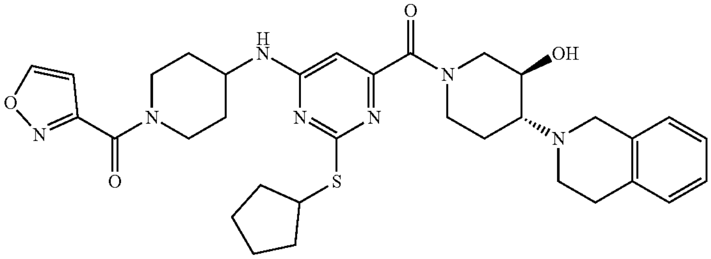 [SMILES: O=C(c1ccon1)N1CCC(Nc2cc(C(=O)N3CC[C@@H](N4CCc5ccccc5C4)[C@H](O)C3)nc(SC3CCCC3)n2)CC1] |
| 217 | 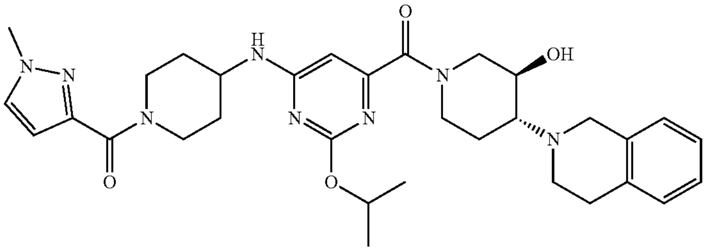 [SMILES: CC(C)Oc1nc(NC2CCN(C(=O)c3ccn(C)n3)CC2)cc(C(=O)N2CC[C@@H](N3CCc4ccccc4C3)[C@H](O)C2)n1] |

-continued
| No. | Structure |
|---|---|
| 218 | 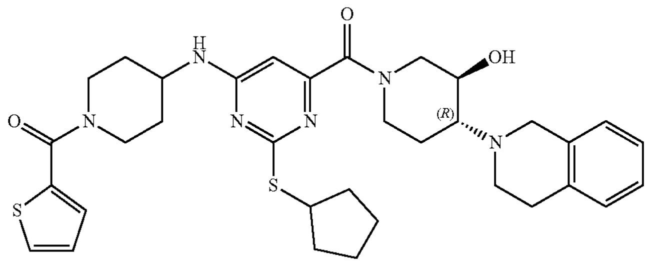 |
| 219 | 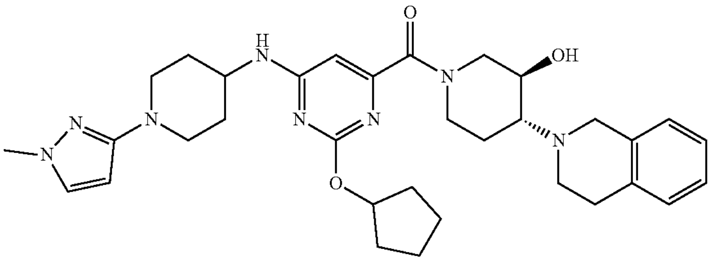 [SMILES: Cn1ccc(N2CCC(Nc3cc(C(=O)N4CC[C@@H](N5CCc6ccccc6C5)[C@H](O)C4)nc(OC4CCCC4)n3)CC2)n1] |
| 220 | 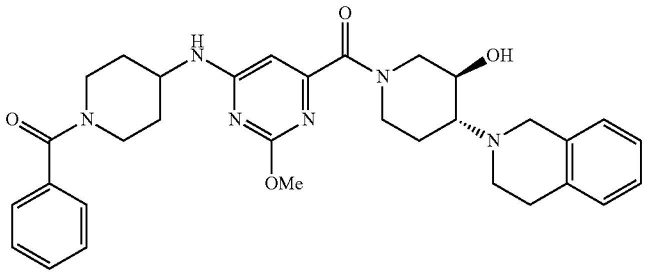 [SMILES: COc1nc(NC2CCN(C(=O)c3ccccc3)CC2)cc(C(=O)N2CC[C@@H](N3CCc4ccccc4C3)[C@H](O)C2)n1] |
| 221 | 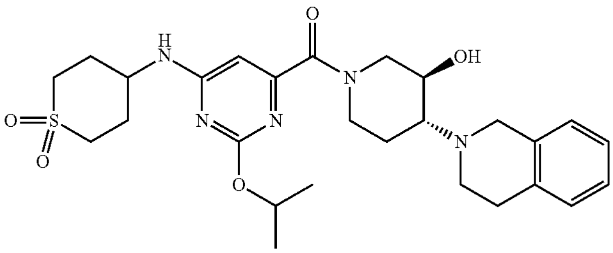 [SMILES: CC(C)Oc1nc(NC2CCS(=O)(=O)CC2)cc(C(=O)N2CC[C@@H](N3CCc4ccccc4C3)[C@H](O)C2)n1] |
| 222 | 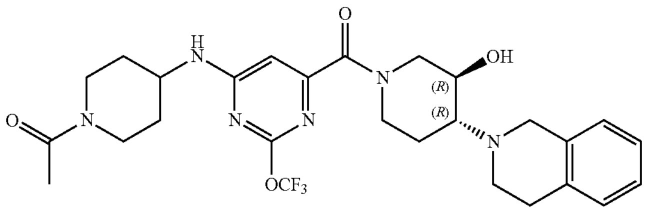 |
| 223 | 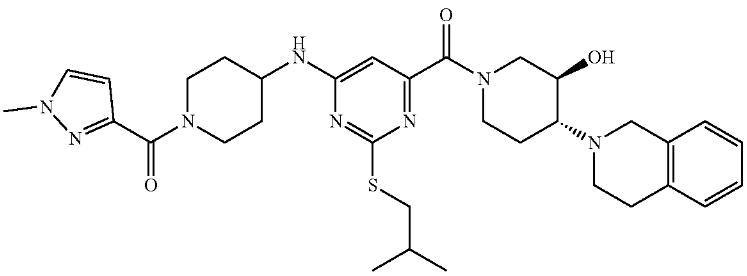 |

-continued
| No. | Structure |
| --- | --- |
| 224 | 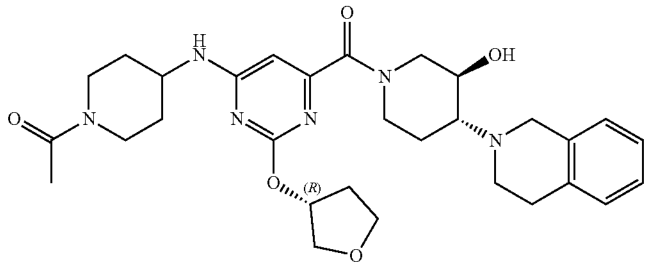 |
| 225 | 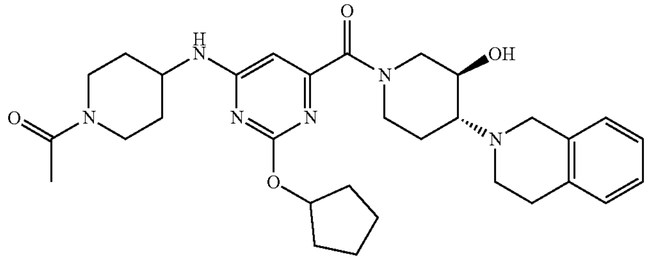 [SMILES: CC(=O)N1CCC(Nc2cc(C(=O)N3CC[C@@H](N4CCc5ccccc5C4)[C@H](O)C3)nc(OC3CCCC3)n2)CC1] |
| 226 | 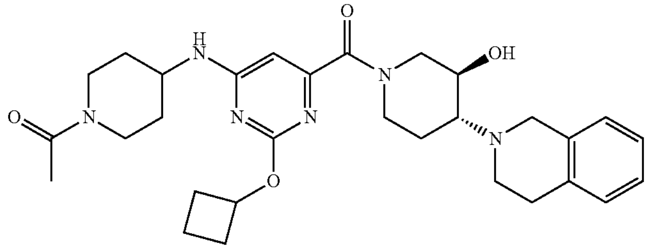 [SMILES: CC(=O)N1CCC(Nc2cc(C(=O)N3CC[C@@H](N4CCc5ccccc5C4)[C@H](O)C3)nc(OC3CCC3)n2)CC1] |
| 227 | 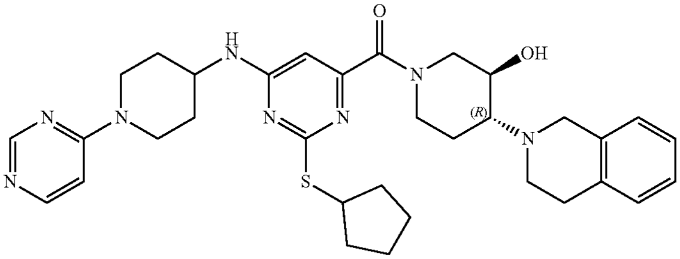 |
| 228 | 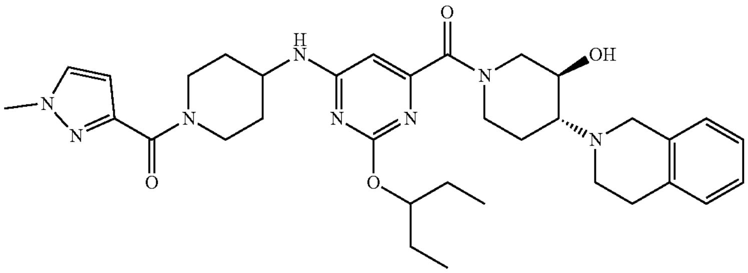 [SMILES: CCC(CC)Oc1nc(NC2CCN(C(=O)c3ccn(C)n3)CC2)cc(C(=O)N2CC[C@@H](N3CCc4ccccc4C3)[C@H](O)C2)n1] |

-continued
| No. | Structure |
|---|---|
| 229 | 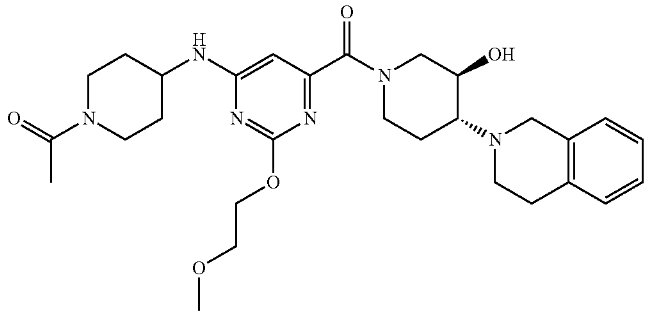 [SMILES: COCCOc1nc(NC2CCN(C(C)=O)CC2)cc(C(=O)N2CC[C@@H](N3CCc4ccccc4C3)[C@H](O)C2)n1] |
| 230 | 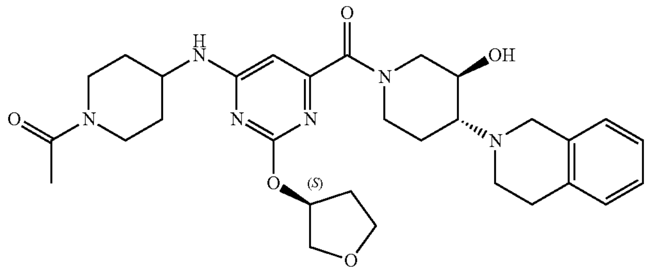 |
| 231 | 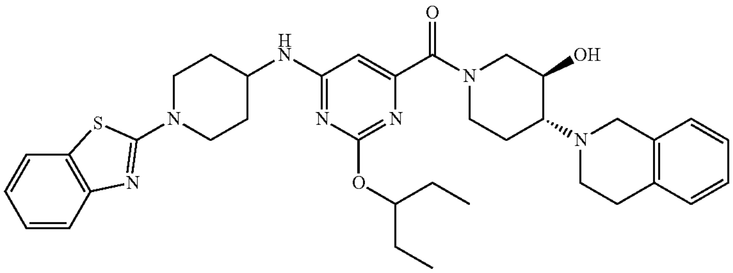 |
| 232 | 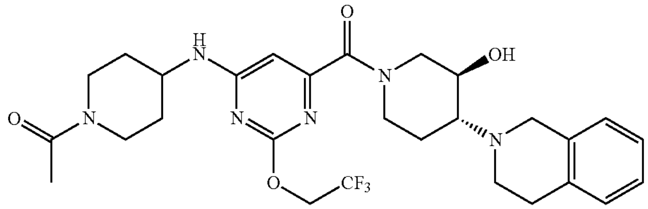 [SMILES: CC(=O)N1CCC(Nc2cc(C(=O)N3CC[C@@H](N4CCc5ccccc5C4)[C@H](O)C3)nc(OCC(F)(F)F)n2)CC1] |
| 233 | 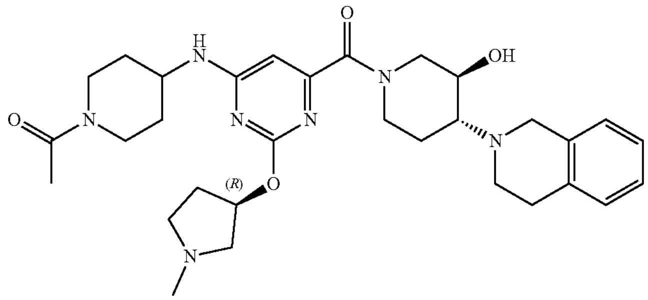 |

-continued
| No. | Structure |
|---|---|
| 234 | 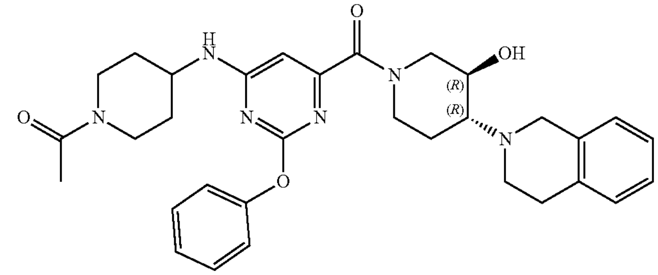 |
| 235 | 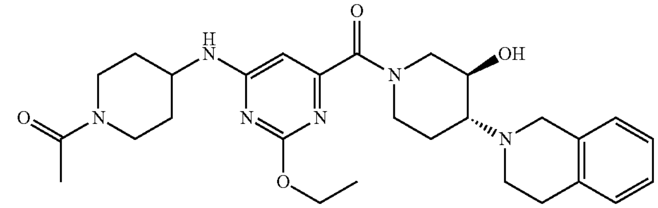 [SMILES: CCOc1nc(NC2CCN(C(C)=O)CC2)cc(C(=O)N2CC[C@@H](N3CCc4ccccc4C3)[C@H](O)C2)n1] |
| 236 | 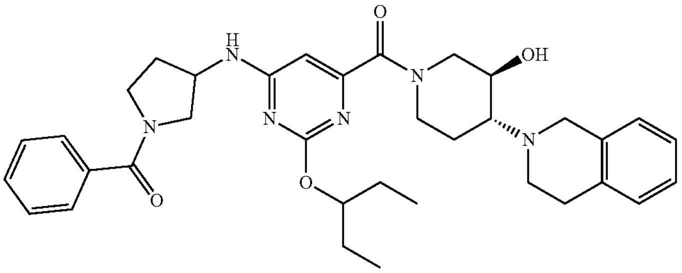 |
| 237 | 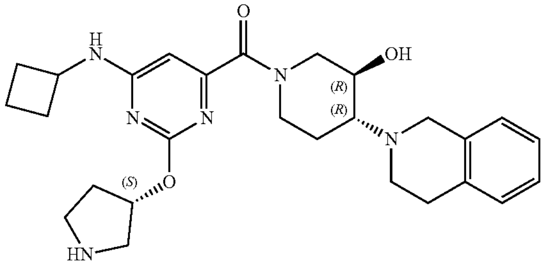 |
| 238 | 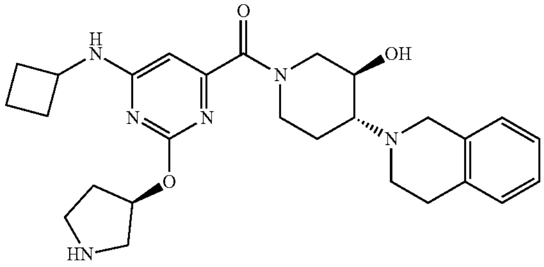 [SMILES: O=C(c1cc(NC2CCC2)nc(O[C@@H]2CCNC2)n1)N1CC[C@@H](N2CCc3ccccc3C2)[C@H](O)C1] |
| 239 | 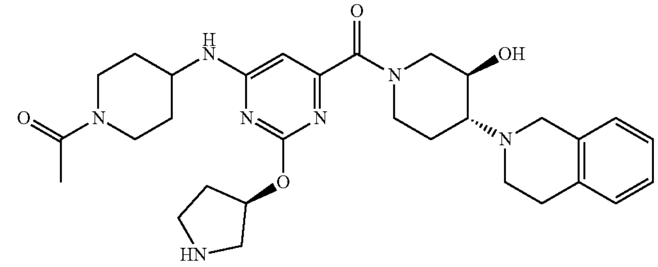 [SMILES: CC(=O)N1CCC(Nc2cc(C(=O)N3CC[C@@H](N4CCc5ccccc5C4)[C@H](O)C3)nc(O[C@@H]3CCNC3)n2)CC1] |

-continued
| No. | Structure |
|---|---|
| 240 | 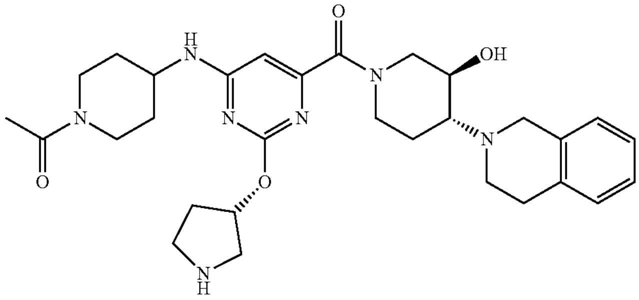 |
| 241 | 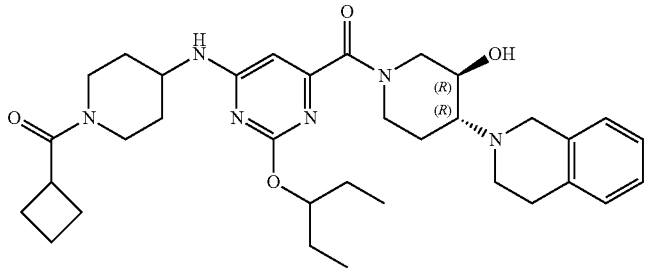 |
| 242 | 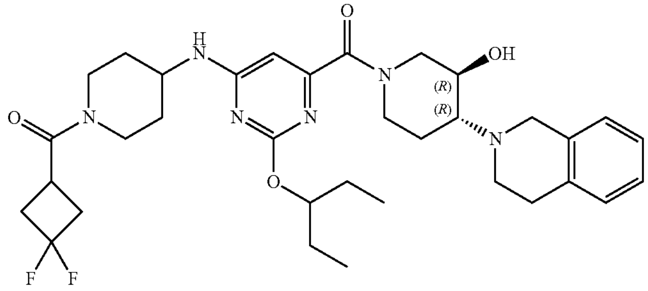 |
| 243 | 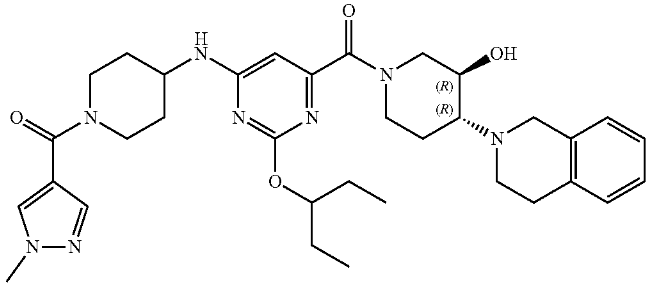 |
| 244 | 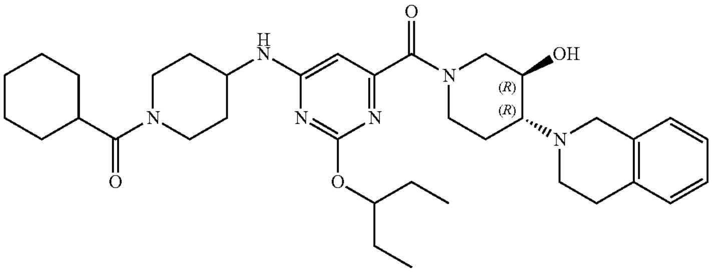 |

-continued
| No. | Structure |
|---|---|
| 245 | 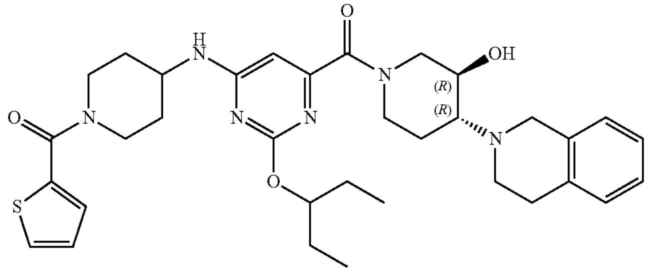 |
| 246 | 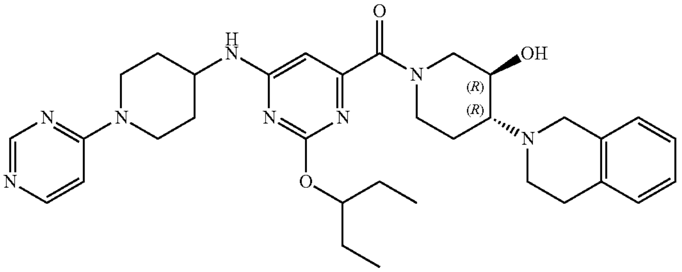 |
| 247 | 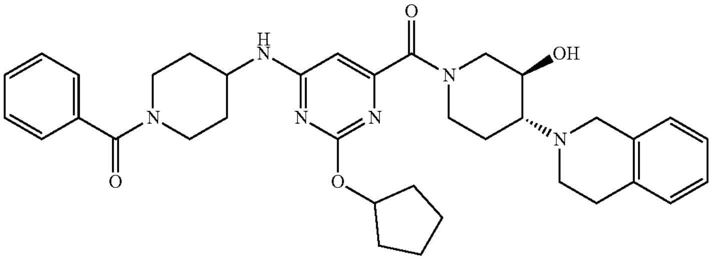 [SMILES: O=C(c1ccccc1)N1CCC(Nc2cc(C(=O)N3CC[C@@H](N4CCc5ccccc5C4)[C@H](O)C3)nc(OC3CCCC3)n2)CC1] |
| 248 | 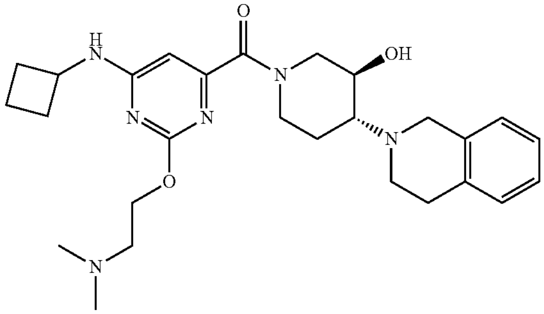 [SMILES: CN(C)CCOc1nc(NC2CCC2)cc(C(=O)N2CC[C@@H](N3CCc4ccccc4C3)[C@H](O)C2)n1] |
| 249 | 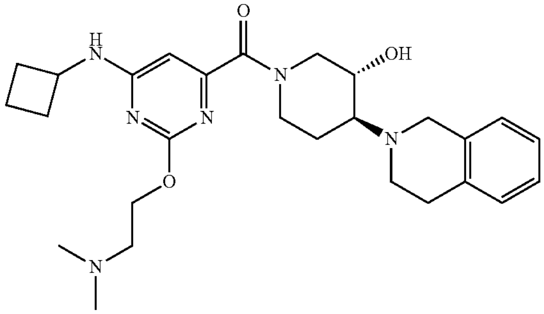 [SMILES: CN(C)CCOc1nc(NC2CCC2)cc(C(=O)N2CC[C@H](N3CCc4ccccc4C3)[C@@H](O)C2)n1] |

-continued
| No. | Structure |
| --- | --- |
| 250 | 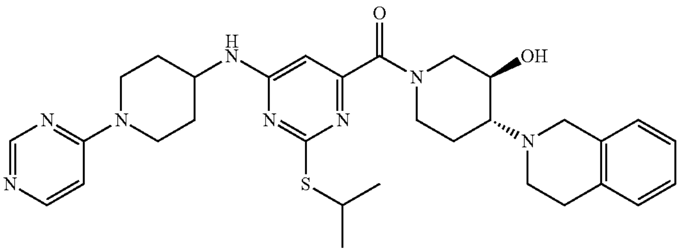 [SMILES: CC(C)Sc1nc(NC2CCN(c3ccncn3)CC2)cc(C(=O)N2CC[C@@H](N3CCc4ccccc4C3)[C@H](O)C2)n1] |
| 251 | 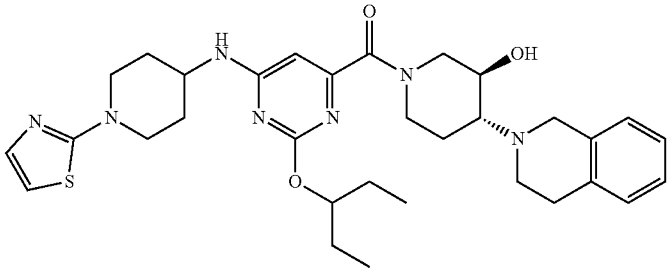 [SMILES: CCC(CC)Oc1nc(NC2CCN(c3nccs3)CC2)cc(C(=O)N2CC[C@@H](N3CCc4ccccc4C3)[C@H](O)C2)n1] |
| 252 | 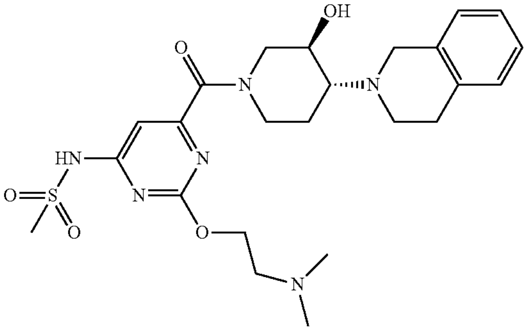 [SMILES: CN(C)CCOc1nc(NS(C)(=O)=O)cc(C(=O)N2CC[C@@H](N3CCc4ccccc4C3)[C@H](O)C2)n1] |
| 253 | 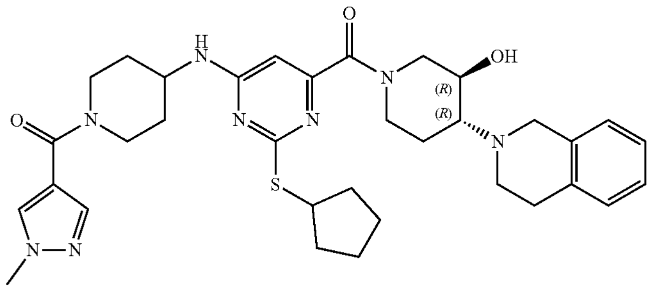 |
| 254 | 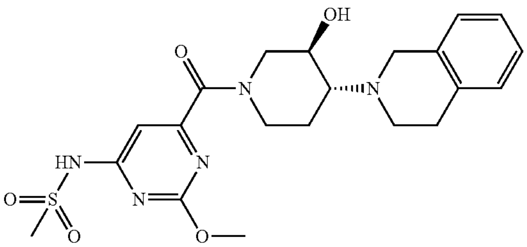 [SMILES: COc1nc(NS(C)(=O)=O)cc(C(=O)N2CC[C@@H](N3CCc4ccccc4C3)[C@H](O)C2)n1] |

-continued
| No. | Structure |
| --- | --- |
| 255 | 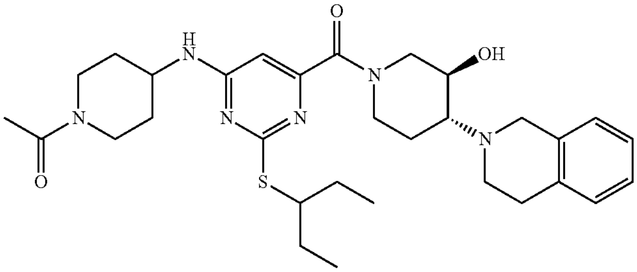 [SMILES: CCC(CC)Sc1nc(NC2CCN(C(C)=O)CC2)cc(C(=O)N2CC[C@@H](N3CCc4ccccc4C3)[C@H](O)C2)n1] |
| 256 | 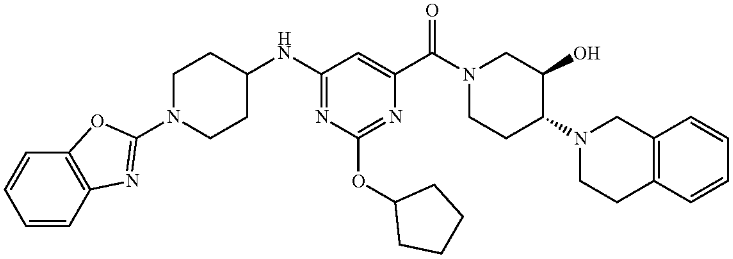 |
| 257 | 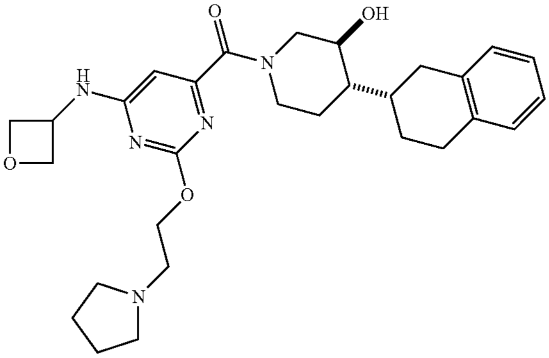 [SMILES: O=C(c1cc(NC2COC2)nc(OCCN2CCCC2)n1)N1CC[C@@H](C2CCc3ccccc3C2)[C@H](O)C1] |
| 258 | 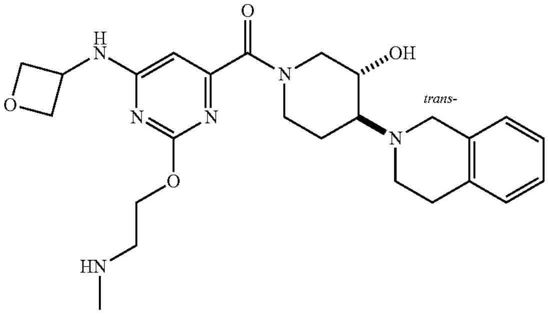 [SMILES: CNCCOc1nc(NC2COC2)cc(C(=O)N2CC[C@H](N3CCc4ccccc4C3)[C@@H](O)C2)n1] |
| 259 | 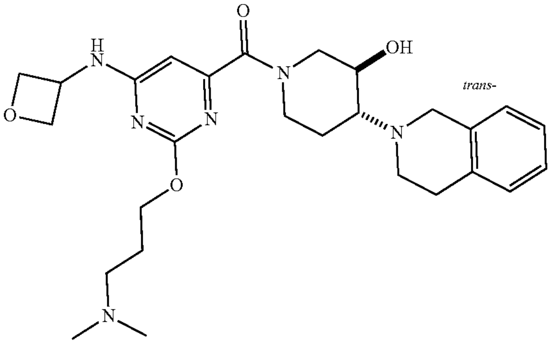 [SMILES: CN(C)CCCOc1nc(NC2COC2)cc(C(=O)N2CC[C@@H](N3CCc4ccccc4C3)[C@H](O)C2)n1] |

-continued
| No. | Structure |
| --- | --- |
| 260 | 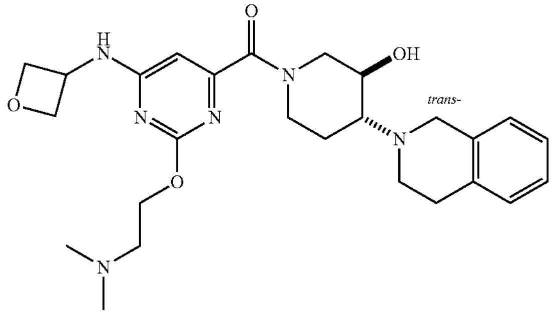 [SMILES: CN(C)CCOc1nc(NC2COC2)cc(C(=O)N2CC[C@@H](N3CCc4ccccc4C3)[C@H](O)C2)n1] |
| 261 | 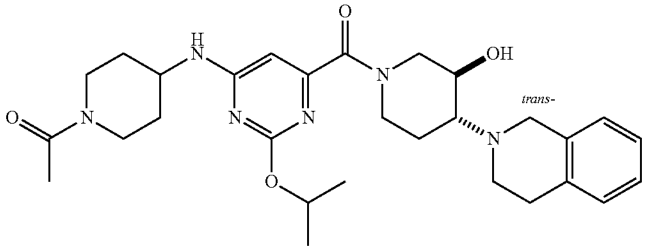 [SMILES: CC(=O)N1CCC(Nc2cc(C(=O)N3CC[C@@H](N4CCc5ccccc5C4)[C@H](O)C3)nc(OC(C)C)n2)CC1] |
| 262 | 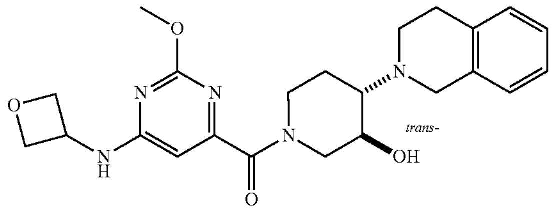 [SMILES: COc1nc(NC2COC2)cc(C(=O)N2CC[C@H](N3CCc4ccccc4C3)[C@@H](O)C2)n1] |
| 263 | 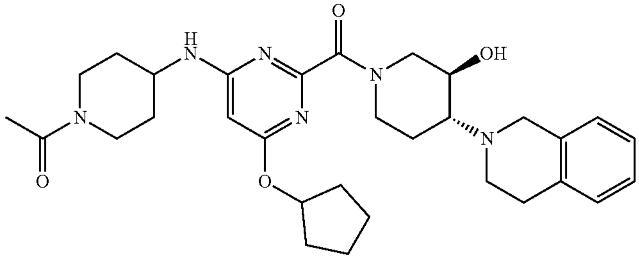 [SMILES: CC(=O)N1CCC(Nc2cc(OC3CCCC3)nc(C(=O)N3CC[C@@H](N4CCc5ccccc5C4)[C@H](O)C3)n2)CC1] |
| 264 | 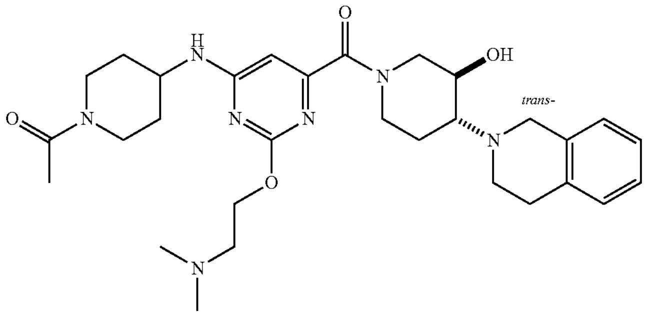 [SMILES: CC(=O)N1CCC(Nc2cc(C(=O)N3CC[C@@H](N4CCc5ccccc5C4)[C@H](O)C3)nc(OCCN(C)C)n2)CC1] |
| 265 | 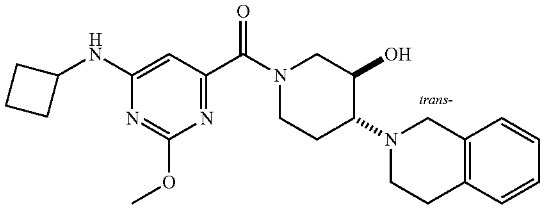 [SMILES: COc1nc(NC2CCC2)cc(C(=O)N2CC[C@@H](N3CCc4ccccc4C3)[C@H](O)C2)n1] |

-continued
| No. | Structure |
|---|---|
| 266 | 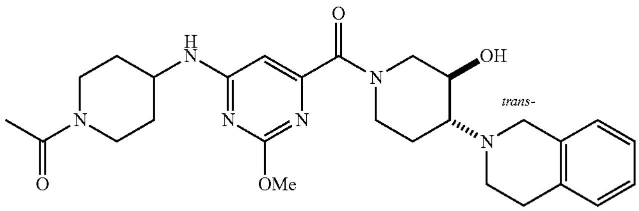 [SMILES: COc1nc(NC2CCN(C(C)=O)CC2)cc(C(=O)N2CC[C@@H](N3CCc4ccccc4C3)[C@H](O)C2)n1] |
| 267 | 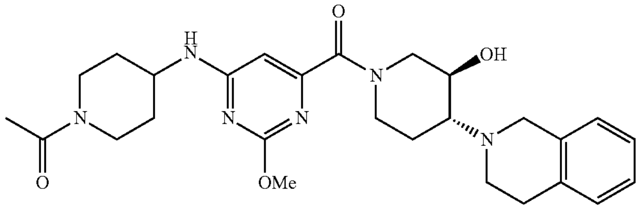 [SMILES: COc1nc(NC2CCN(C(C)=O)CC2)cc(C(=O)N2CC[C@@H](N3CCc4ccccc4C3)[C@H](O)C2)n1] |
| 268 | 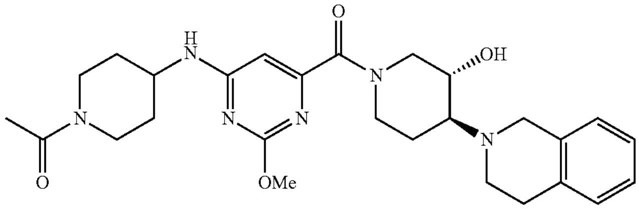 [SMILES: COc1nc(NC2CCN(C(C)=O)CC2)cc(C(=O)N2CC[C@H](N3CCc4ccccc4C3)[C@@H](O)C2)n1] |
| 269 | 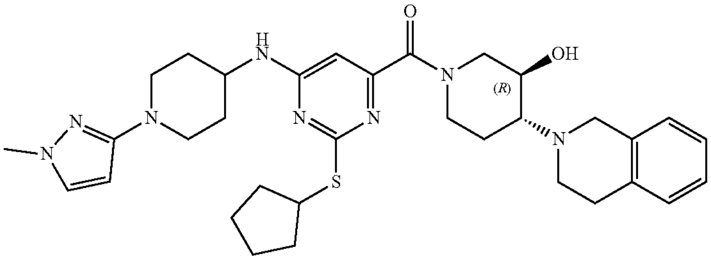 |
| 270 | 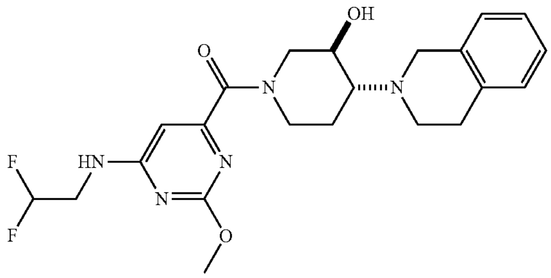 [SMILES: COc1nc(NCC(F)F)cc(C(=O)N2CC[C@@H](N3CCc4ccccc4C3)[C@H](O)C2)n1] |
| 271 | 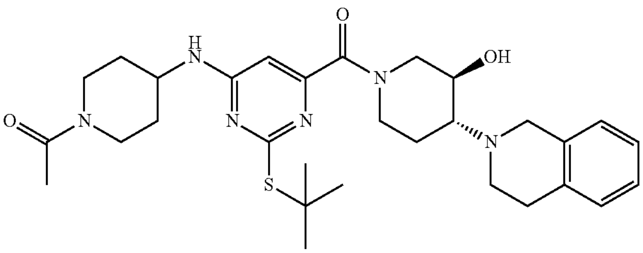 [SMILES: CC(=O)N1CCC(Nc2cc(C(=O)N3CC[C@@H](N4CCc5ccccc5C4)[C@H](O)C3)nc(SC(C)(C)C)n2)CC1] |

-continued
| No. | Structure |
|---|---|
| 272 | 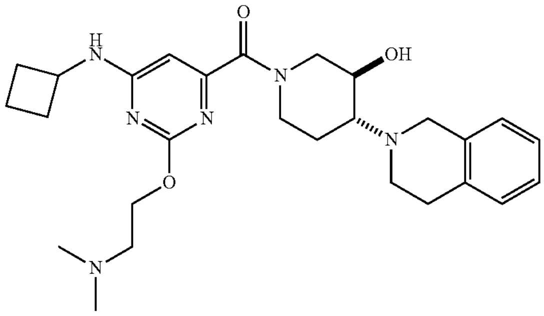 [SMILES: CN(C)CCOc1nc(NC2CCC2)cc(C(=O)N2CC[C@@H](N3CCc4ccccc4C3)[C@H](O)C2)n1] |
| 273 | 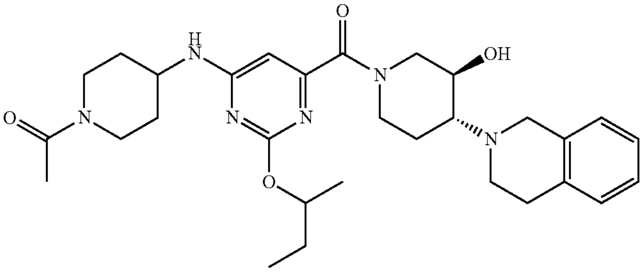 [SMILES: CCC(C)Oc1nc(NC2CCN(C(C)=O)CC2)cc(C(=O)N2CC[C@@H](N3CCc4ccccc4C3)[C@H](O)C2)n1] |
| 274 | 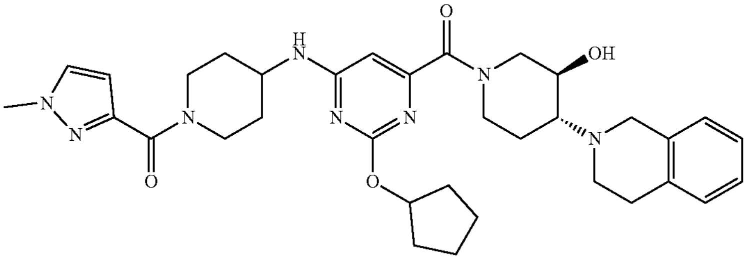 [SMILES: Cn1ccc(C(=O)N2CCC(Nc3cc(C(=O)N4CC[C@@H](N5CCc6ccccc6C5)[C@H](O)C4)nc(OC4CCCC4)n3)CC2)n1] |
| 275 | 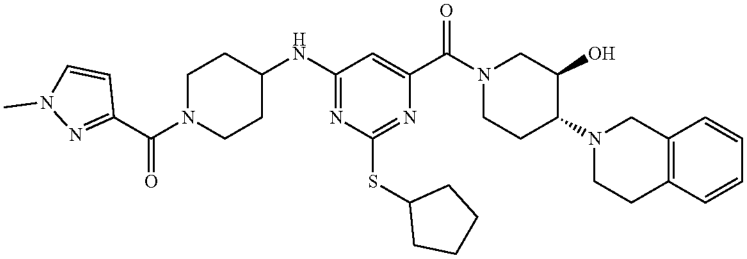 |
| 276 | 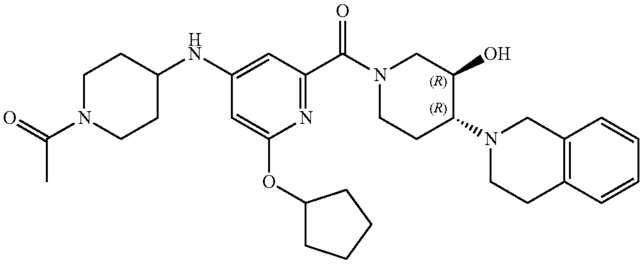 |

-continued
| No. | Structure |
| --- | --- |
| 277 | 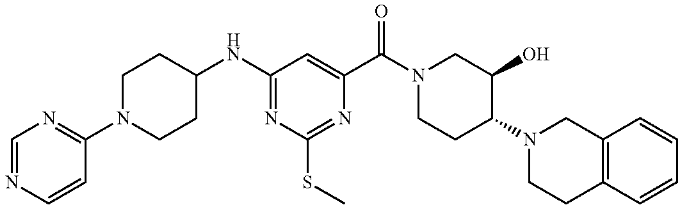 [SMILES: CSc1nc(NC2CCN(c3ccncn3)CC2)cc(C(=O)N2CC[C@@H](N3CCc4ccccc4C3)[C@H](O)C2)n1] |
| 278 | 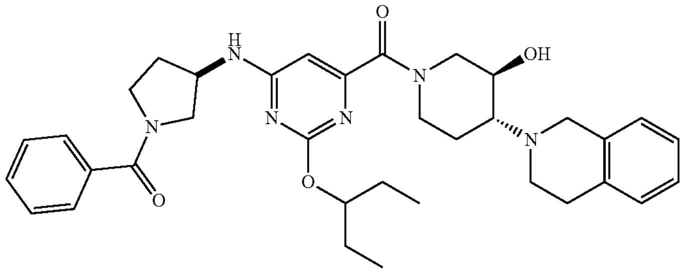 [SMILES: CCC(CC)Oc1nc(N[C@@H]2CCN(C(=O)c3ccccc3)C2)cc(C(=O)N2CC[C@@H](N3CCc4ccccc4C3)[C@H](O)C2)n1] |
| 279 | 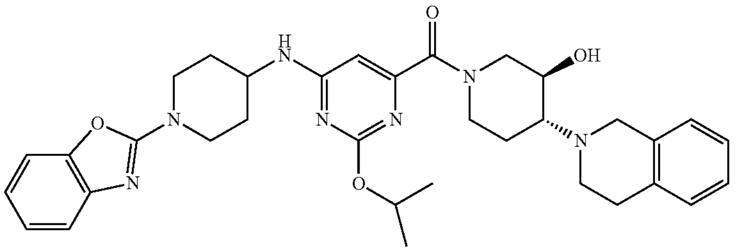 [SMILES: CC(C)Oc1nc(NC2CCN(c3nc4ccccc4o3)CC2)cc(C(=O)N2CC[C@@H](N3CCc4ccccc4C3)[C@H](O)C2)n1] |
| 280 | 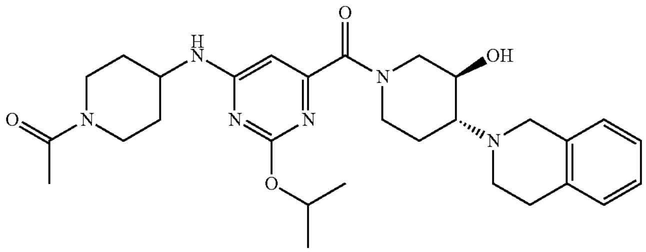 [SMILES: CC(=O)N1CCC(Nc2cc(C(=O)N3CC[C@@H](N4CCc5ccccc5C4)[C@H](O)C3)nc(OC(C)C)n2)CC1] |
| 281 | 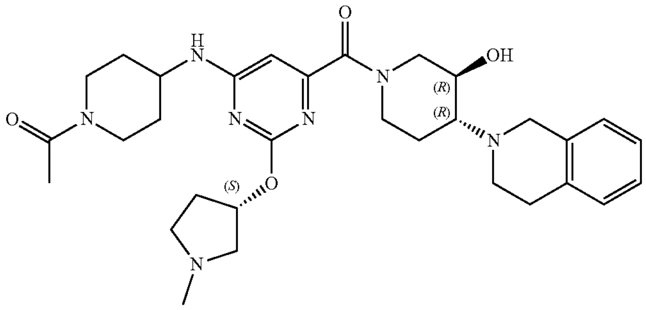 |
| 282 | 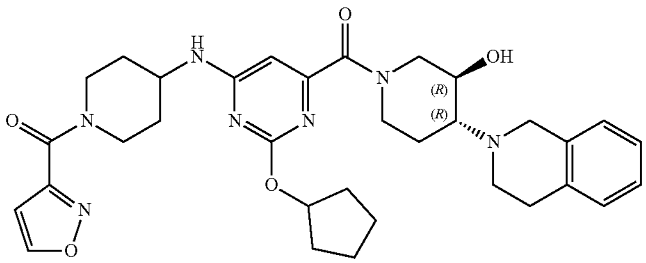 |

-continued
| No. | Structure |
| --- | --- |
| 283 | 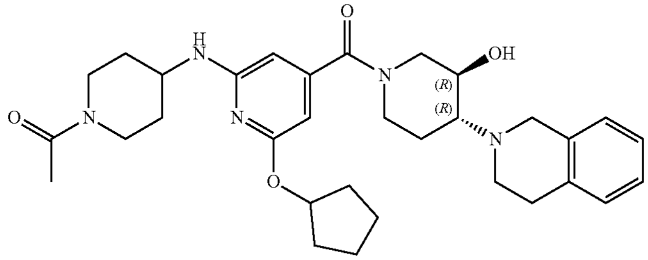 |
| 284 | 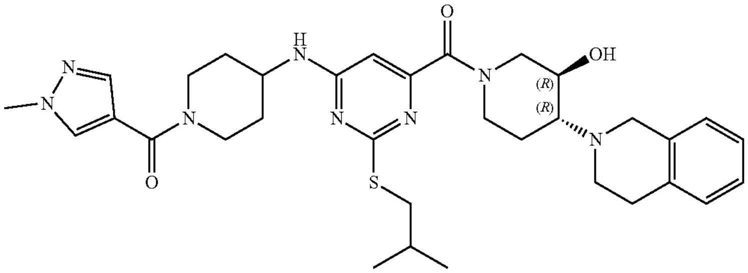 |
| 285 | 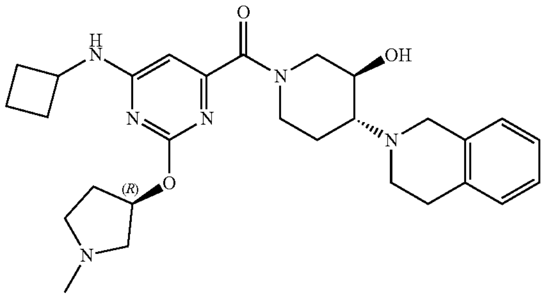 |
| 286 | 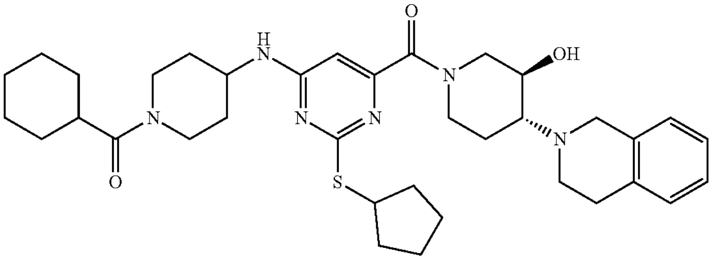 [SMILES: O=C(c1cc(NC2CCN(C(=O)C3CCCCC3)CC2)nc(SC2CCCC2)n1)N1CC[C@@H](N2CCc3ccccc3C2)[C@H](O)C1] |
| 287 | 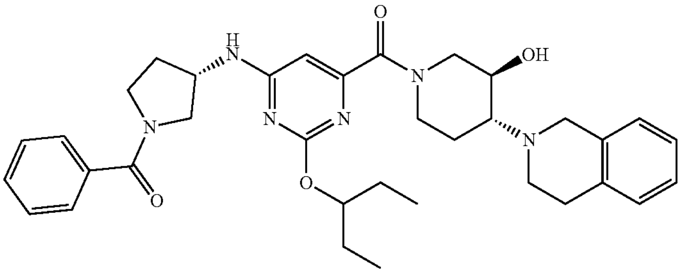 [SMILES: CCC(CC)Oc1nc(N[C@H]2CCN(C(=O)c3ccccc3)C2)cc(C(=O)N2CC[C@@H](N3CCc4ccccc4C3)[C@H](O)C2)n1] |

-continued
| No. | Structure |
|---|---|
| 288 | 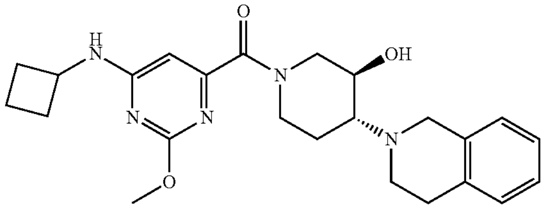 [SMILES: COc1nc(NC2CCC2)cc(C(=O)N2CC[C@@H](N3CCc4ccccc4C3)[C@H](O)C2)n1] |
| 289 | 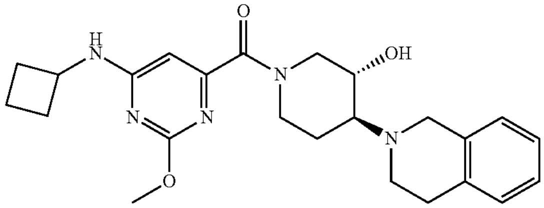 [SMILES: COc1nc(NC2CCC2)cc(C(=O)N2CC[C@H](N3CCc4ccccc4C3)[C@@H](O)C2)n1] |
| 290 | 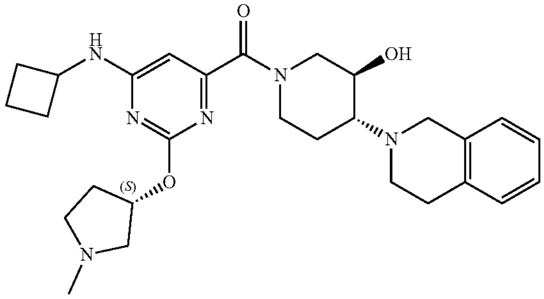 |
| 291 | 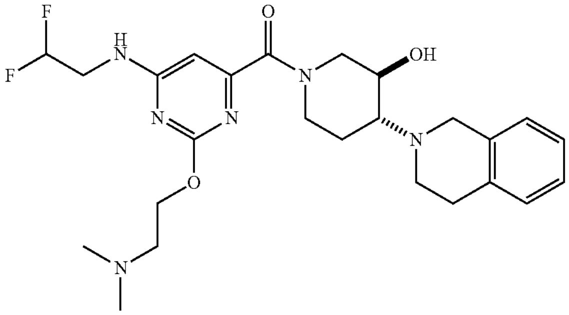 [SMILES: CN(C)CCOc1nc(NCC(F)F)cc(C(=O)N2CC[C@@H](N3CCc4ccccc4C3)[C@H](O)C2)n1] |
| 292 | 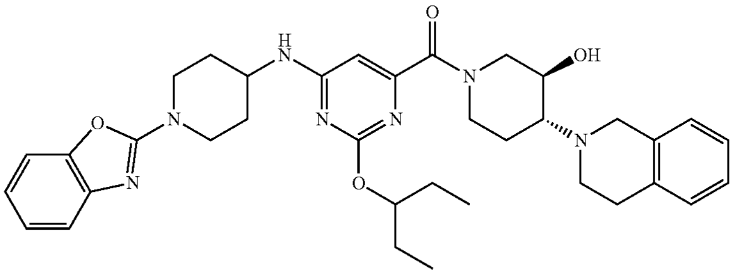 [SMILES: CCC(CC)Oc1nc(NC2CCN(c3nc4ccccc4o3)CC2)cc(C(=O)N2CC[C@@H](N3CCc4ccccc4C3)[C@H](O)C2)n1] |

-continued
| No. | Structure |
| --- | --- |
| 293 | 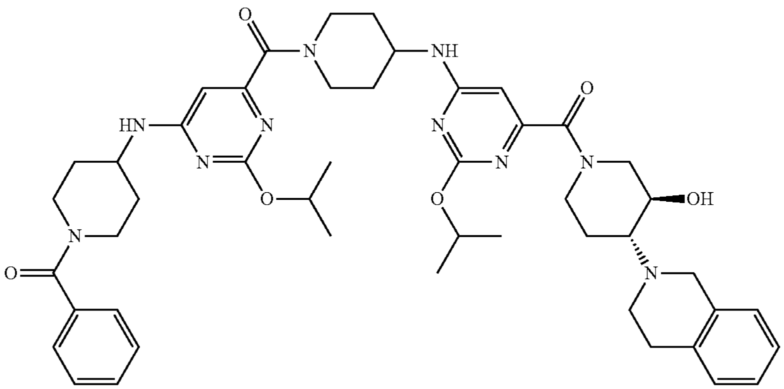 [SMILES: CC(C)Oc1nc(NC2CCN(C(=O)c3ccccc3)CC2)cc(C(=O)N2CCC(Nc3cc(C(=O)N4CC[C@@H](N5CCc6ccccc6C5)[C@H](O)C4)nc(OC(C)C)n3)CC2)n1] |
| 294 | 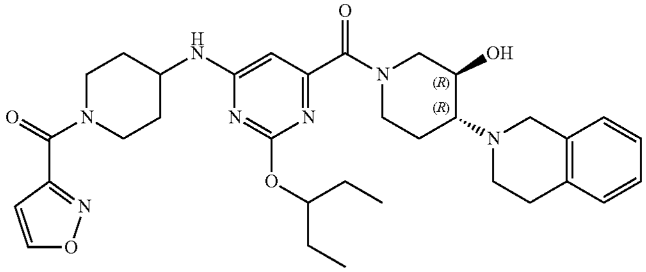 |
| 295 | 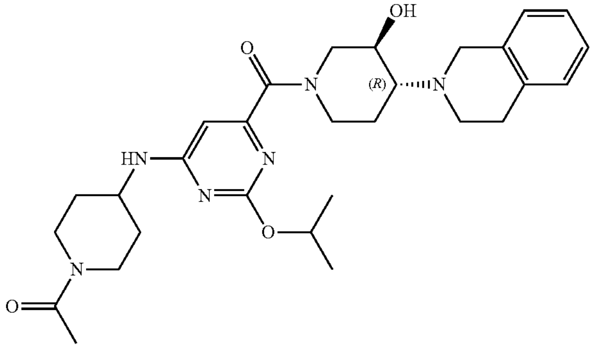 |
| 296 | 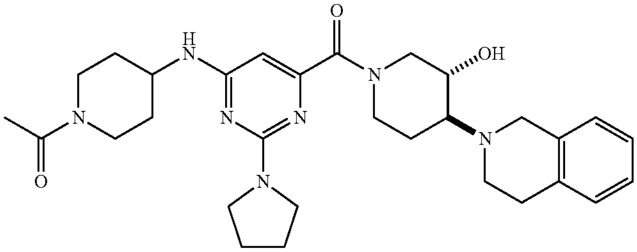 [SMILES: CC(=O)N1CCC(Nc2cc(C(=O)N3CC[C@H](N4CCc5ccccc5C4)[C@@H](O)C3)nc(N3CCCC3)n2)CC1] |
| 297 | 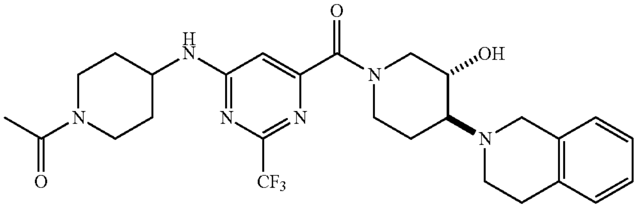 [SMILES: CC(=O)N1CCC(Nc2cc(C(=O)N3CC[C@H](N4CCc5ccccc5C4)[C@@H](O)C3)nc(C(F)(F)F)n2)CC1] |

-continued
| No. | Structure |
|---|---|
| 298 | 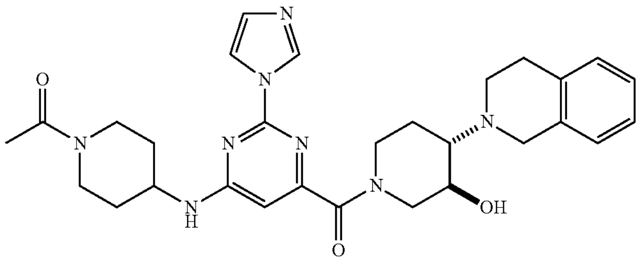 [SMILES: CC(=O)N1CCC(Nc2cc(C(=O)N3CC[C@H](N4CCc5ccccc5C4)[C@@H](O)C3)nc(-n3ccnc3)n2)CC1] |
| 299 | 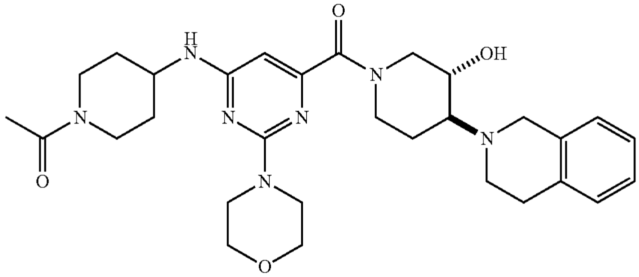 [SMILES: CC(=O)N1CCC(Nc2cc(C(=O)N3CC[C@H](N4CCc5ccccc5C4)[C@@H](O)C3)nc(N3CCOCC3)n2)CC1] |
| 300 | 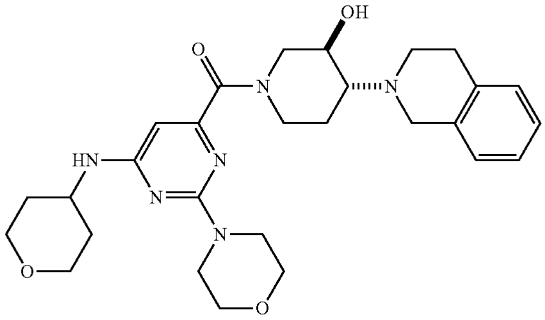 [SMILES: O=C(c1cc(NC2CCOCC2)nc(N2CCOCC2)n1)N1CC[C@@H](N2CCc3ccccc3C2)[C@H](O)C1] |
| 301 | 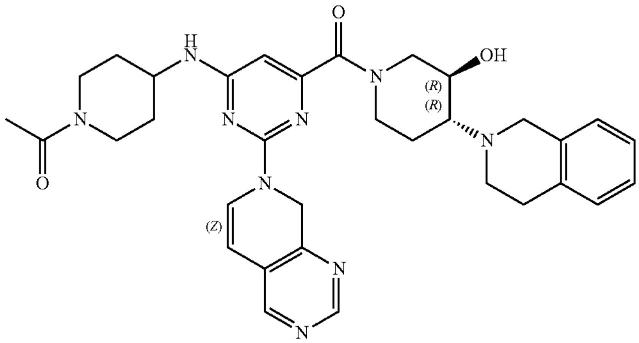 |
| 302 | 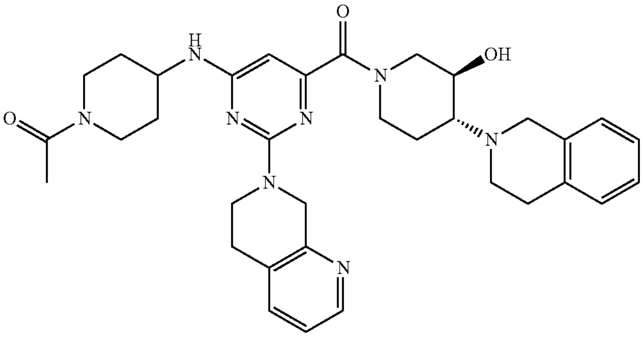 [SMILES: CC(=O)N1CCC(Nc2cc(C(=O)N3CC[C@@H](N4CCc5ccccc5C4)[C@H](O)C3)nc(N3CCc4cccnc4C3)n2)CC1] |

-continued
| No. | Structure |
| --- | --- |
| 303 | 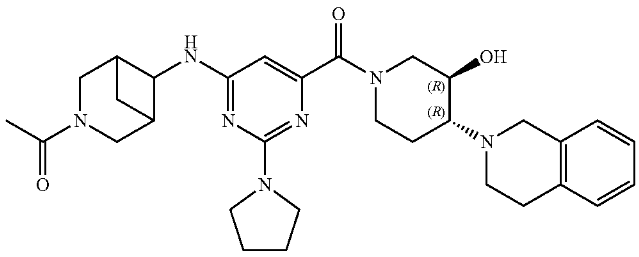 |
| 304 | 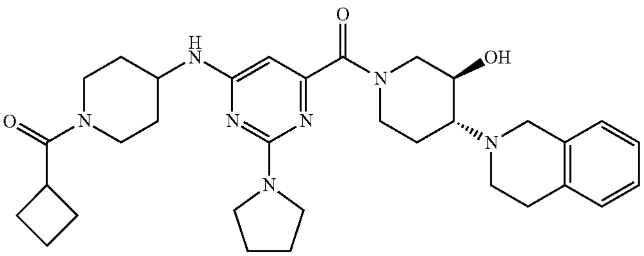 [SMILES: O=C(c1cc(NC2CCN(C(=O)C3CCC3)CC2)nc(N2CCCC2)n1)N1CC[C@@H](N2CCc3ccccc3C2)[C@H](O)C1] |
| 305 | 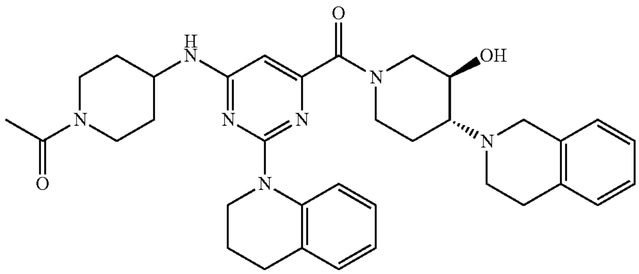 [SMILES: CC(=O)N1CCC(Nc2cc(C(=O)N3CC[C@@H](N4CCc5ccccc5C4)[C@H](O)C3)nc(N3CCCc4ccccc43)n2)CC1] |
| 306 | 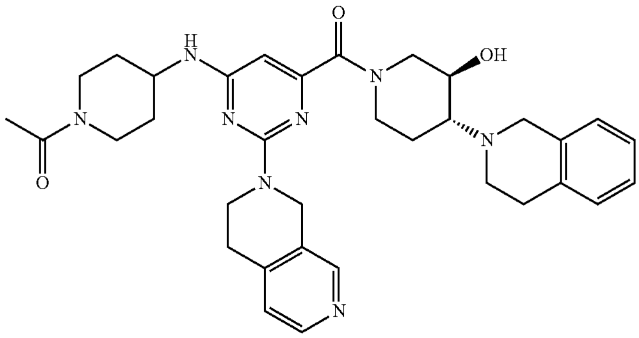 [SMILES: CC(=O)N1CCC(Nc2cc(C(=O)N3CC[C@@H](N4CCc5ccccc5C4)[C@H](O)C3)nc(N3CCc4ccncc4C3)n2)CC1] |
| 307 | 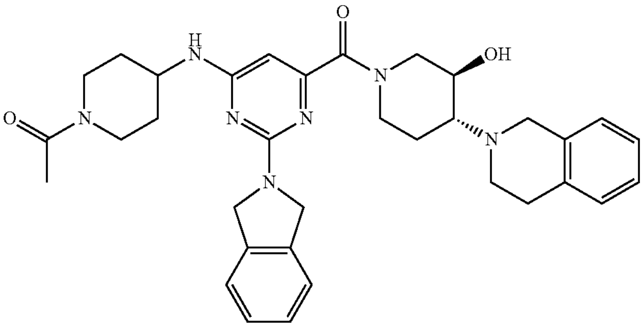 [SMILES: CC(=O)N1CCC(Nc2cc(C(=O)N3CC[C@@H](N4CCc5ccccc5C4)[C@H](O)C3)nc(N3Cc4ccccc4C3)n2)CC1] |

-continued
| No. | Structure |
| --- | --- |
| 308 | 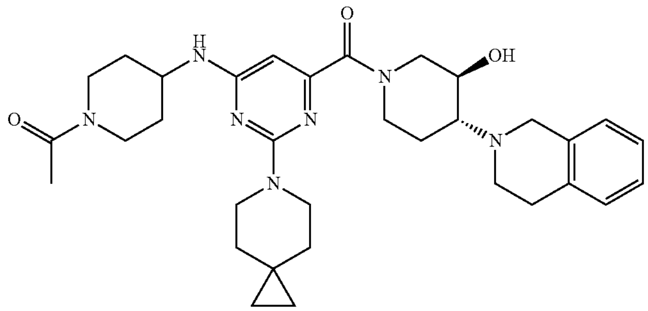 [SMILES: CC(=O)N1CCC(Nc2cc(C(=O)N3CC[C@@H](N4CCc5ccccc5C4)[C@H](O)C3)nc(N3CCC4(CC3)CC4)n2)CC1] |
| 309 | 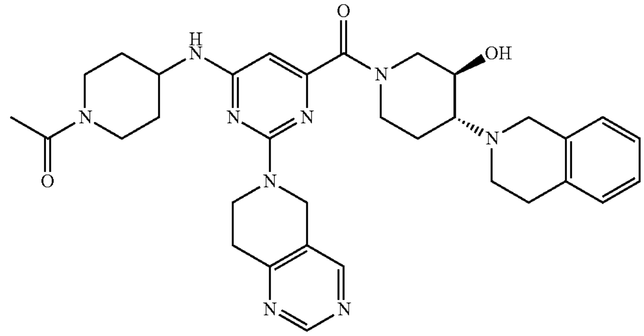 [SMILES: CC(=O)N1CCC(Nc2cc(C(=O)N3CC[C@@H](N4CCc5ccccc5C4)[C@H](O)C3)nc(N3CCc4ncncc4C3)n2)CC1] |
| 310 | 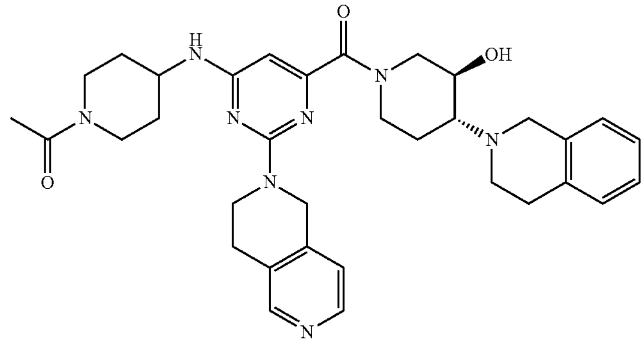 [SMILES: CC(=O)N1CCC(Nc2cc(C(=O)N3CC[C@@H](N4CCc5ccccc5C4)[C@H](O)C3)nc(N3CCc4cnccc4C3)n2)CC1] |
| 311 | 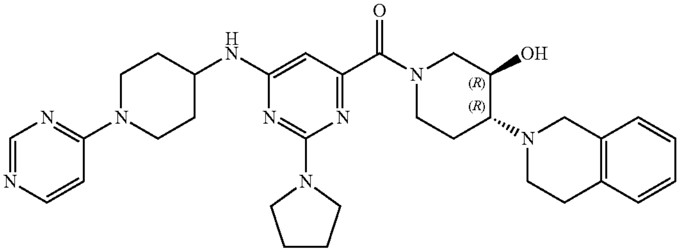 |

-continued
| No. | Structure |
| --- | --- |
| 312 | 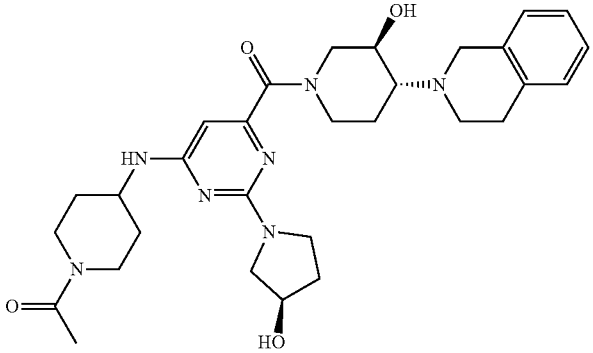 [SMILES: CC(=O)N1CCC(Nc2cc(C(=O)N3CC[C@@H](N4CCc5ccccc5C4)[C@H](O)C3)nc(N3CC[C@@H](O)C3)n2)CC1] |
| 313 | 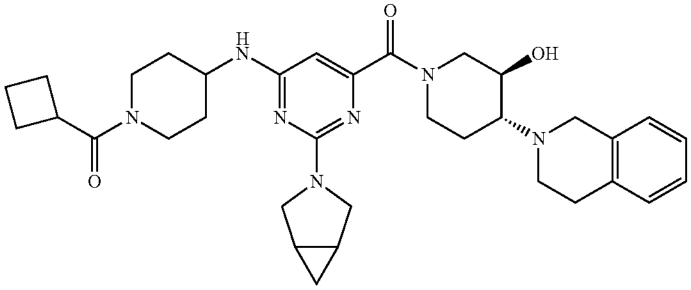 [SMILES: O=C(c1cc(NC2CCN(C(=O)C3CCC3)CC2)nc(N2CC3CC3C2)n1)N1CC[C@@H](N2CCc3ccccc3C2)[C@H](O)C1] |
| 314 | 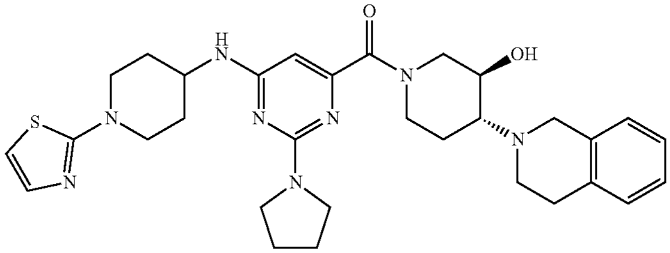 [SMILES: O=C(c1cc(NC2CCN(c3nccs3)CC2)nc(N2CCCC2)n1)N1CC[C@@H](N2CCc3ccccc3C2)[C@H](O)C1] |
| 315 | 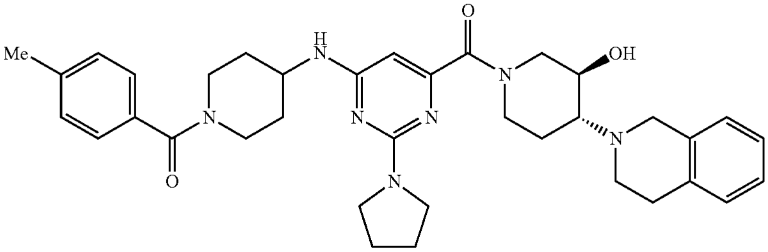 [SMILES: Cc1ccc(C(=O)N2CCC(Nc3cc(C(=O)N4CC[C@@H](N5CCc6ccccc6C5)[C@H](O)C4)nc(N4CCCC4)n3)CC2)cc1] |
| 316 | 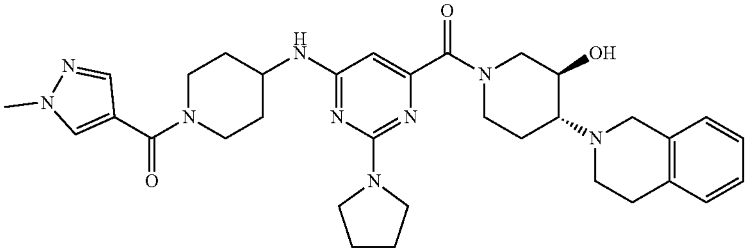 [SMILES: Cn1cc(C(=O)N2CCC(Nc3cc(C(=O)N4CC[C@@H](N5CCc6ccccc6C5)[C@H](O)C4)nc(N4CCCC4)n3)CC2)cn1] |

-continued
| No. | Structure |
| --- | --- |
| 317 | 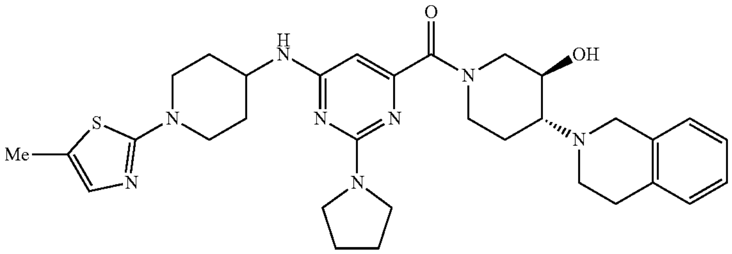 [SMILES: Cc1cnc(N2CCC(Nc3cc(C(=O)N4CC[C@@H](N5CCc6ccccc6C5)[C@H](O)C4)nc(N4CCCC4)n3)CC2)s1] |
| 318 | 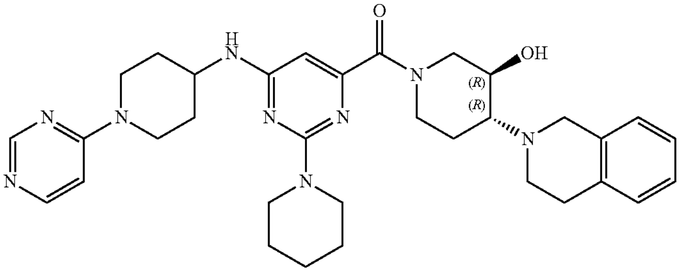 |
| 319 | 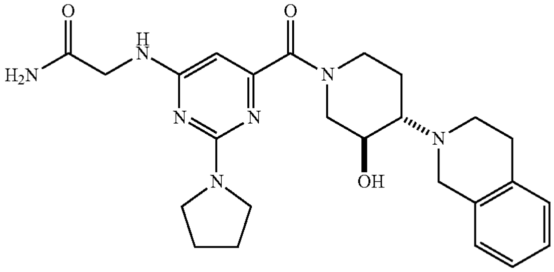 [SMILES: NC(=O)CNc1cc(C(=O)N2CC[C@H](N3CCc4ccccc4C3)[C@@H](O)C2)nc(N2CCCC2)n1] |
| 320 | 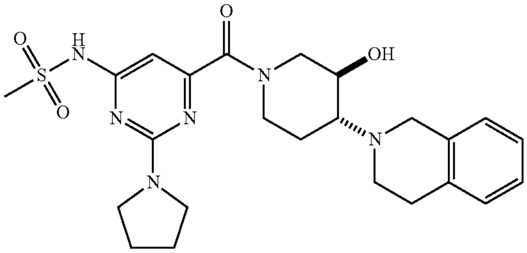 [SMILES: CS(=O)(=O)Nc1cc(C(=O)N2CC[C@@H](N3CCc4ccccc4C3)[C@H](O)C2)nc(N2CCCC2)n1] |
| 321 | 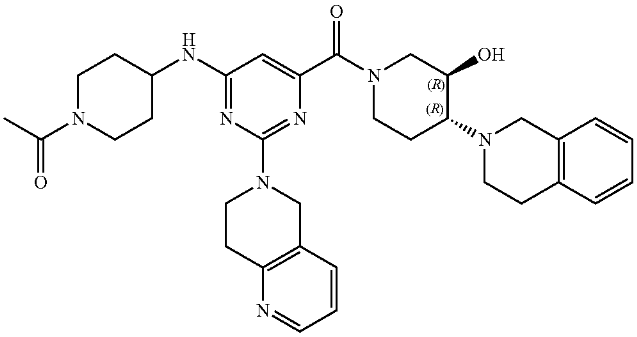 |

-continued
| No. | Structure |
|---|---|
| 322 | 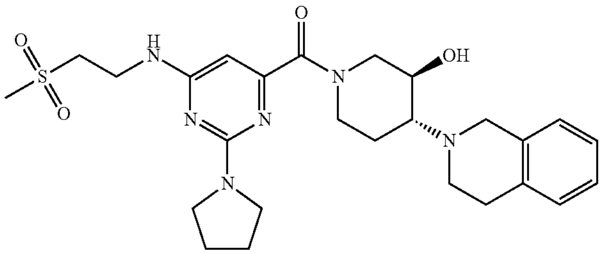 [SMILES: CS(=O)(=O)CCNc1cc(C(=O)N2CC[C@@H](N3CCc4ccccc4C3)[C@H](O)C2)nc(N2CCCC2)n1] |
| 323 | 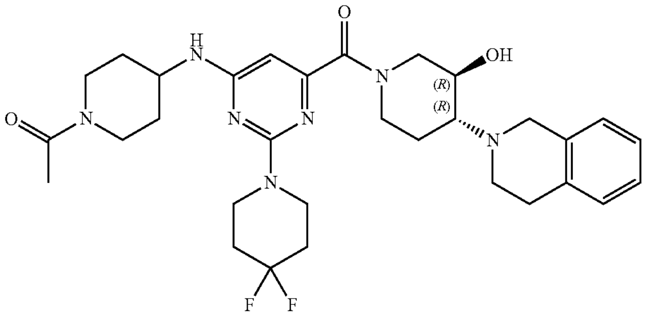 |
| 324 | 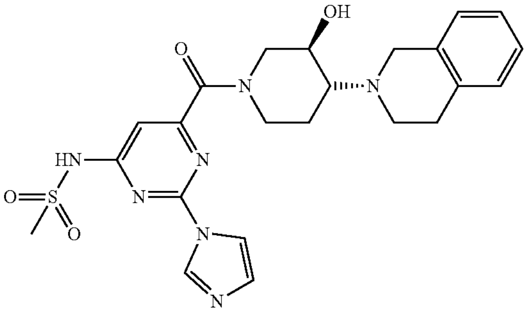 |
| 325 | 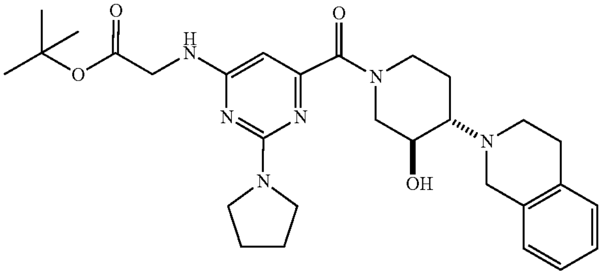 [SMILES: CC(C)(C)OC(=O)CNc1cc(C(=O)N2CC[C@H](N3CCc4ccccc4C3)[C@@H](O)C2)nc(N2CCCC2)n1] |
| 326 | 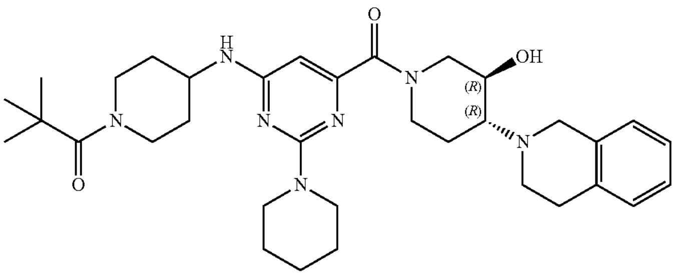 |

-continued
| No. | Structure |
|---|---|
| 327 | 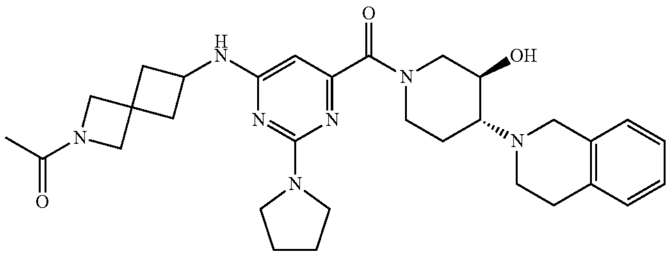 [SMILES: CC(=O)N1CC2(CC(Nc3cc(C(=O)N4CC[C@@H](N5CCc6ccccc6C5)[C@H](O)C4)nc(N4CCCC4)n3)C2)C1] |
| 328 | 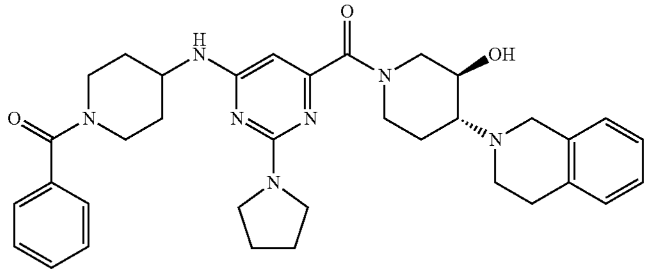 [SMILES: O=C(c1ccccc1)N1CCC(Nc2cc(C(=O)N3CC[C@@H](N4CCc5ccccc5C4)[C@H](O)C3)nc(N3CCCC3)n2)CC1] |
| 329 | 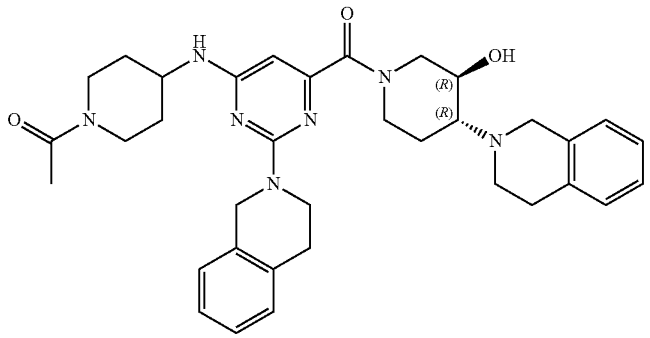 |
| 330 | 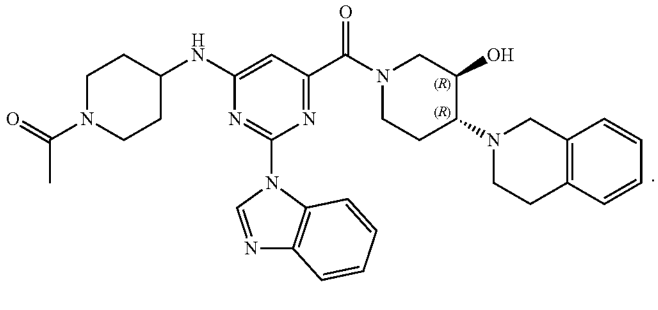 |
| 331 | 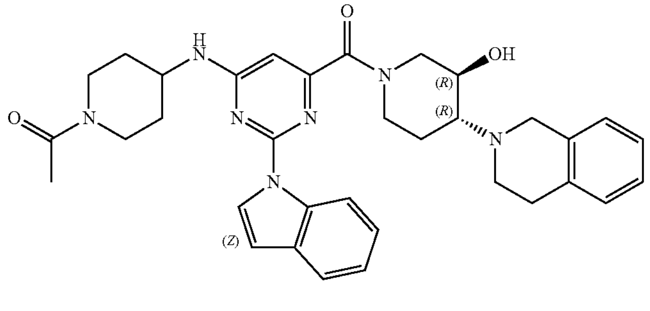 |

-continued
| No. | Structure |
|---|---|
| 332 | 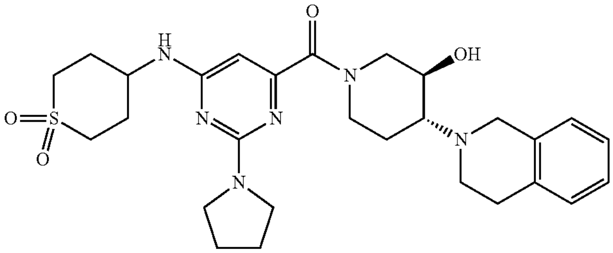 [SMILES: O=C(c1cc(NC2CCS(=O)(=O)CC2)nc(N2CCCC2)n1)N1CC[C@@H](N2CCc3ccccc3C2)[C@H](O)C1] |
| 333 | 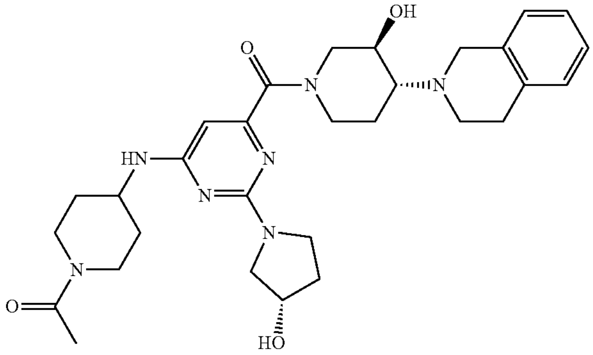 [SMILES: CC(=O)N1CCC(Nc2cc(C(=O)N3CC[C@@H](N4CCc5ccccc5C4)[C@H](O)C3)nc(N3CC[C@H](O)C3)n2)CC1] |
| 334 | 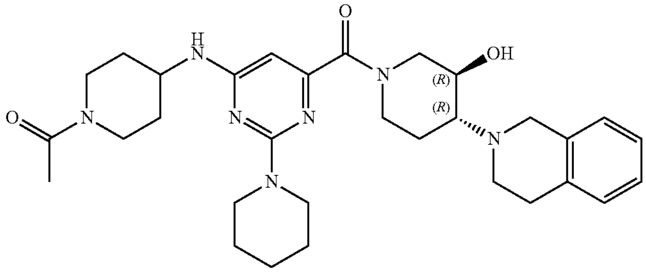 |
| 335 | 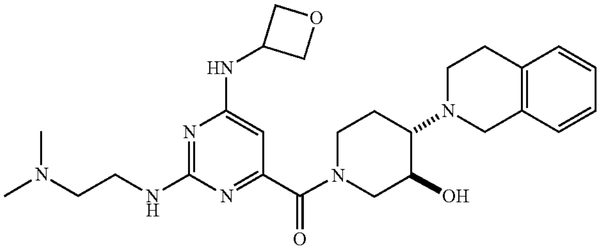 [SMILES: CN(C)CCNc1nc(NC2COC2)cc(C(=O)N2CC[C@H](N3CCc4ccccc4C3)[C@@H](O)C2)n1] |
| 336 | 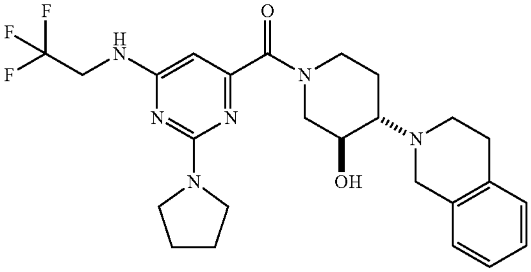 [SMILES: O=C(c1cc(NCC(F)(F)F)nc(N2CCCC2)n1)N1CC[C@H](N2CCc3ccccc3C2)[C@@H](O)C1] |

-continued
| No. | Structure |
| --- | --- |
| 337 | 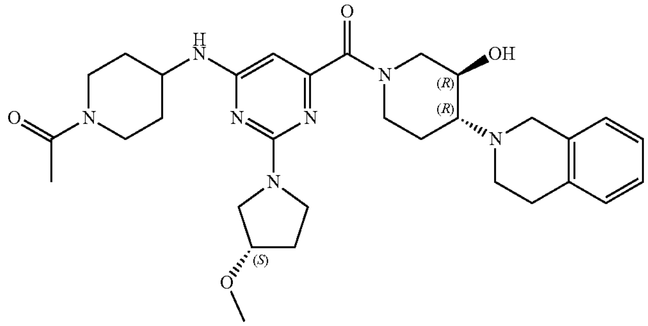 |
| 338 | 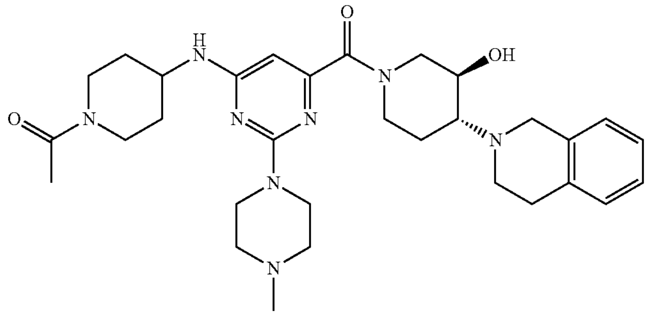 [SMILES: CC(=O)N1CCC(Nc2cc(C(=O)N3CC[C@@H](N4CCc5ccccc5C4)[C@H](O)C3)nc(N3CCN(C)CC3)n2)CC1] |
| 339 | 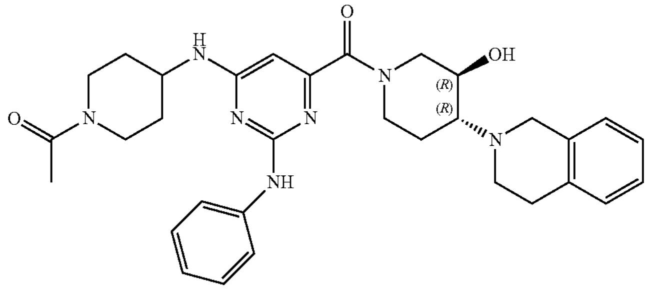 |
| 340 | 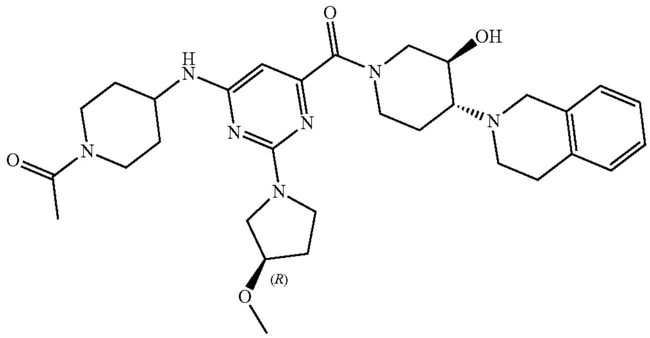 |

-continued
| No. | Structure |
| --- | --- |
| 341 | 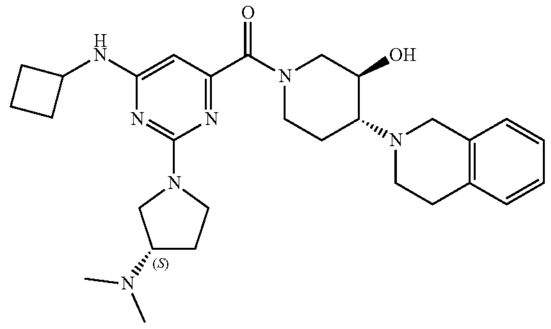 |
| 342 | 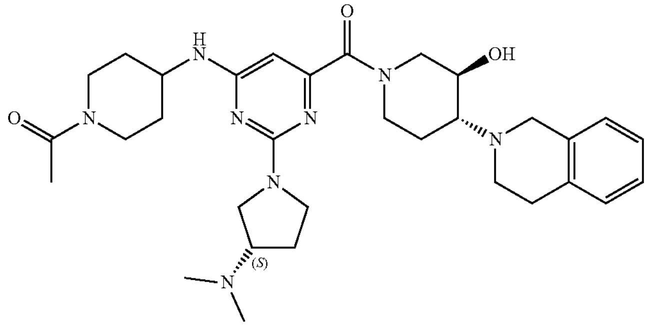 |
| 343 | 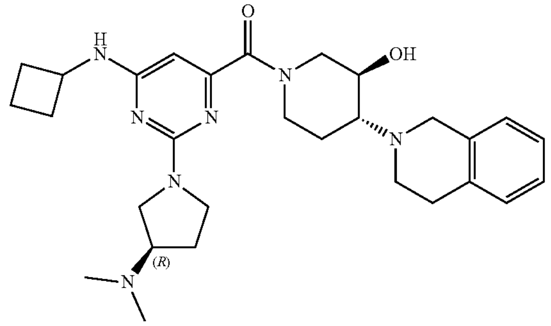 |
| 344 | 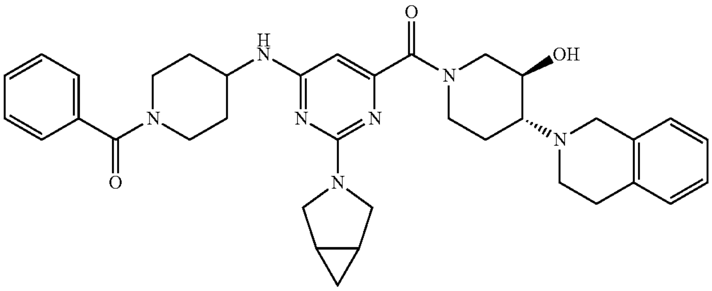 [SMILES: O=C(c1ccccc1)N1CCC(Nc2cc(C(=O)N3CC[C@@H](N4CCc5ccccc5C4)[C@H](O)C3)nc(N3CC4CC4C3)n2)CC1] |

-continued
| No. | Structure |
| --- | --- |
| 345 | 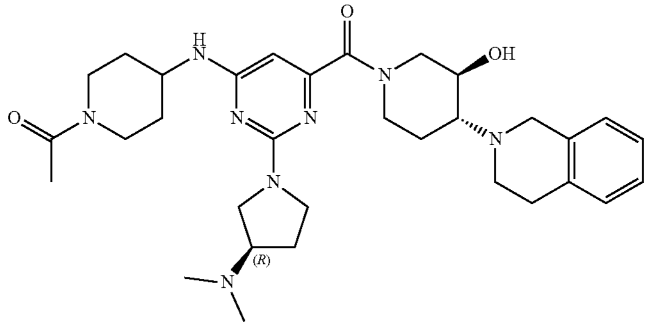 |
| 346 | 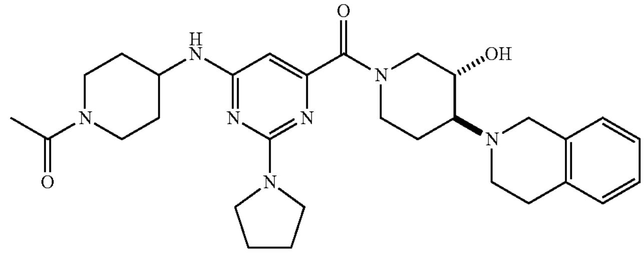 [SMILES: CC(=O)N1CCC(Nc2cc(C(=O)N3CC[C@H](N4CCc5ccccc5C4)[C@@H](O)C3)nc(N3CCCC3)n2)CC1] |
| 347 | 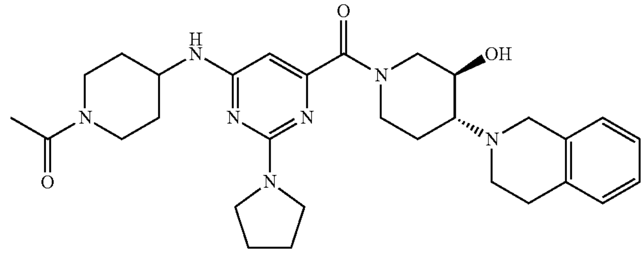 [SMILES: CC(=O)N1CCC(Nc2cc(C(=O)N3CC[C@@H](N4CCc5ccccc5C4)[C@H](O)C3)nc(N3CCCC3)n2)CC1] |
| 348 | 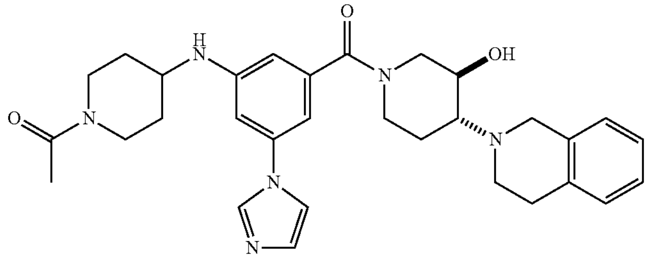 [SMILES: CC(=O)N1CCC(Nc2cc(C(=O)N3CC[C@@H](N4CCc5ccccc5C4)[C@H](O)C3)cc(-n3ccnc3)c2)CC1] |
| 349 | 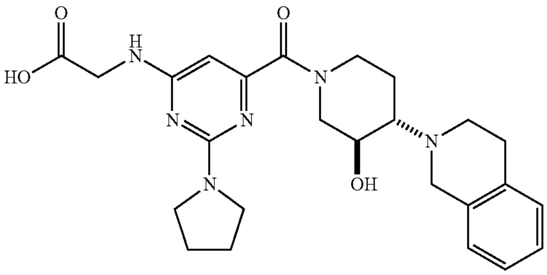 [SMILES: O=C(O)CNc1cc(C(=O)N2CC[C@H](N3CCc4ccccc4C3)[C@@H](O)C2)nc(N2CCCC2)n1] |

-continued
| No. | Structure |
| --- | --- |
| 350 | 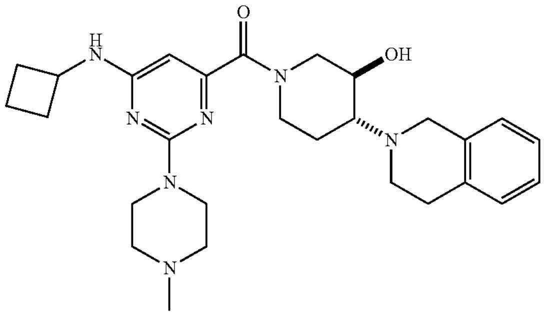 [SMILES: CN1CCN(c2nc(NC3CCC3)cc(C(=O)N3CC[C@@H](N4CCc5ccccc5C4)[C@H](O)C3)n2)CC1] |
| 351 | 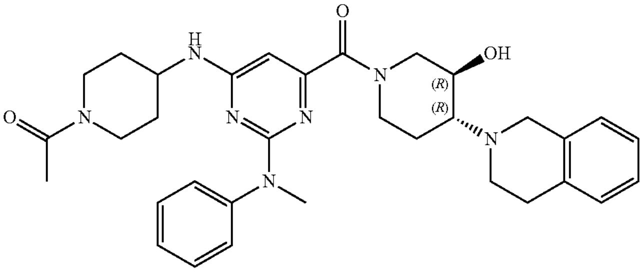 |
| 352 | 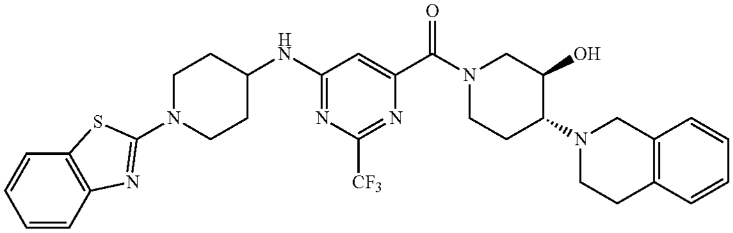 [SMILES: O=C(c1cc(NC2CCN(c3nc4ccccc4s3)CC2)nc(C(F)(F)F)n1)N1CC[C@@H](N2CCc3ccccc3C2)[C@H](O)C1] |
| 353 | 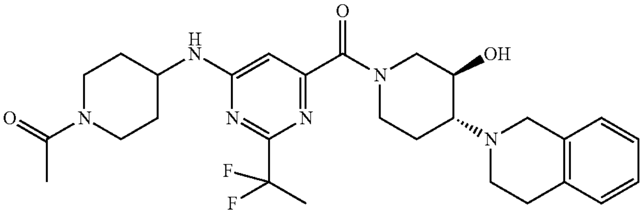 [SMILES: CC(=O)N1CCC(Nc2cc(C(=O)N3CC[C@@H](N4CCc5ccccc5C4)[C@H](O)C3)nc(C(C)(F)F)n2)CC1] |
| 354 | 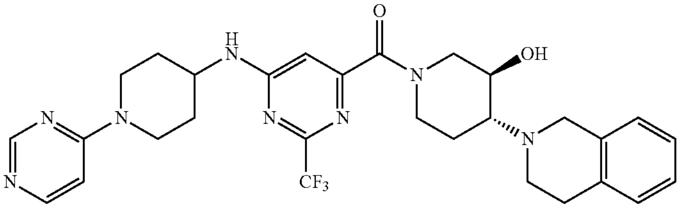 [SMILES: O=C(c1cc(NC2CCN(c3ccncn3)CC2)nc(C(F)(F)F)n1)N1CC[C@@H](N2CCc3ccccc3C2)[C@H](O)C1] |
| 355 | 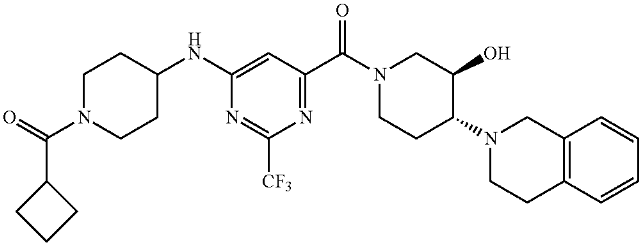 [SMILES: O=C(c1cc(NC2CCN(C(=O)C3CCC3)CC2)nc(C(F)(F)F)n1)N1CC[C@@H](N2CCc3ccccc3C2)[C@H](O)C1] |

-continued
| No. | Structure |
| --- | --- |
| 356 | 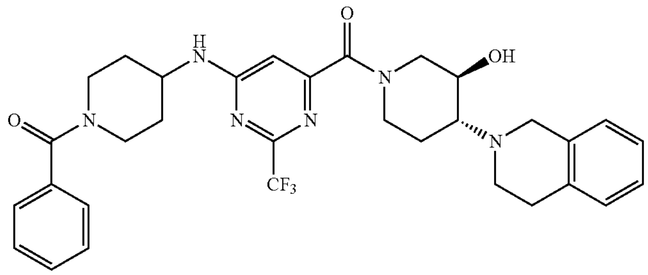 [SMILES: O=C(c1ccccc1)N1CCC(Nc2cc(C(=O)N3CC[C@@H](N4CCc5ccccc5C4)[C@H](O)C3)nc(C(F)(F)F)n2)CC1] |
| 357 | 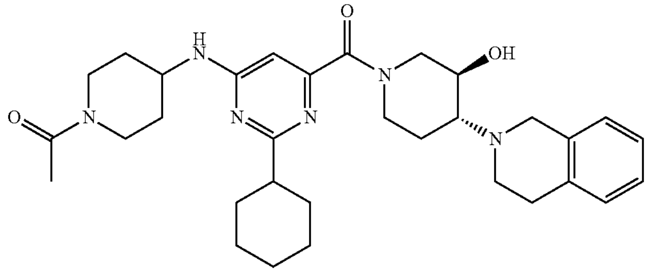 [SMILES: CC(=O)N1CCC(Nc2cc(C(=O)N3CC[C@@H](N4CCc5ccccc5C4)[C@H](O)C3)nc(C3CCCCC3)n2)CC1] |
| 358 | 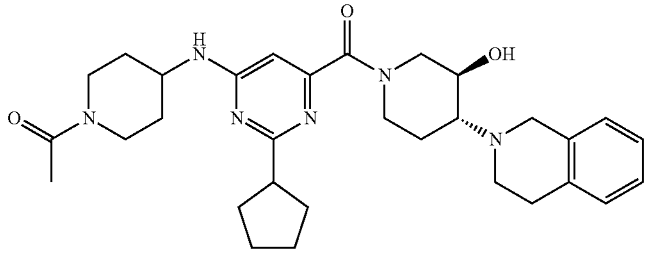 [SMILES: CC(=O)N1CCC(Nc2cc(C(=O)N3CC[C@@H](N4CCc5ccccc5C4)[C@H](O)C3)nc(C3CCCC3)n2)CC1] |
| 359 | 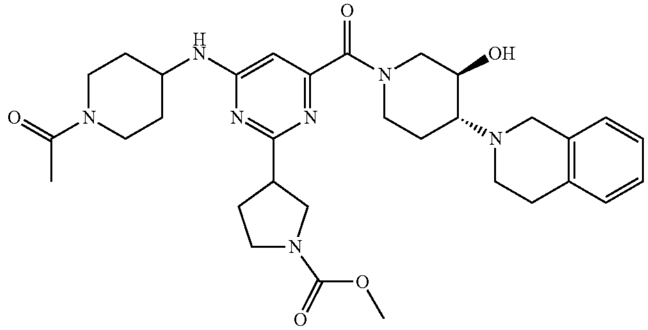 [SMILES: COC(=O)N1CCC(c2nc(NC3CCN(C(C)=O)CC3)cc(C(=O)N3CC[C@@H](N4CCc5ccccc5C4)[C@H](O)C3)n2)C1] |
| 360 | 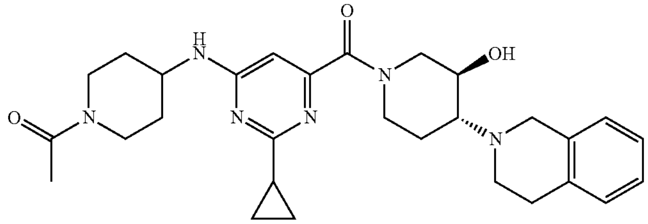 [SMILES: CC(=O)N1CCC(Nc2cc(C(=O)N3CC[C@@H](N4CCc5ccccc5C4)[C@H](O)C3)nc(C3CC3)n2)CC1] |

-continued
| No. | Structure |
| --- | --- |
| 361 | 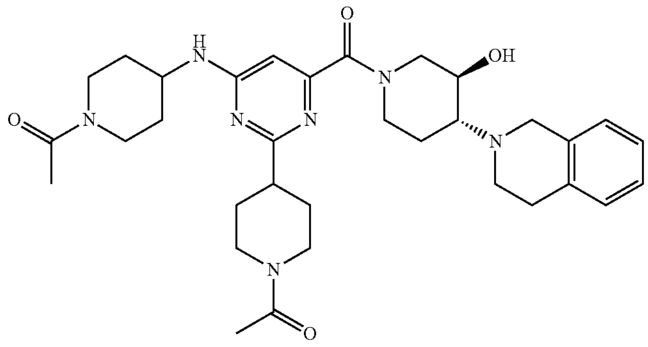 [SMILES: CC(=O)N1CCC(Nc2cc(C(=O)N3CC[C@@H](N4CCc5ccccc5C4)[C@H](O)C3)nc(C3CCN(C(C)=O)CC3)n2)CC1] |
| 362 | 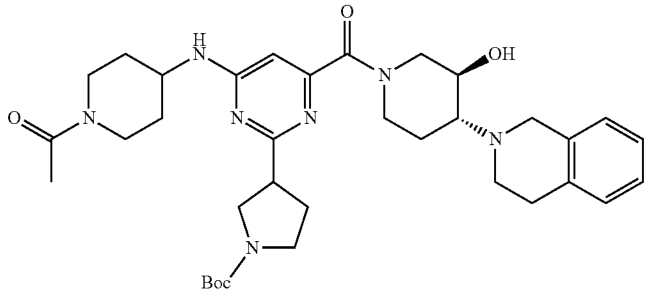 [SMILES: CC(=O)N1CCC(Nc2cc(C(=O)N3CC[C@@H](N4CCc5ccccc5C4)[C@H](O)C3)nc(C3CCN(C(=O)OC(C)(C)C)C3)n2)CC1] |
| 363 | 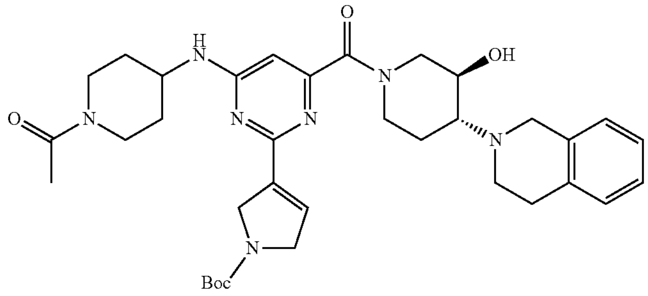 [SMILES: CC(=O)N1CCC(Nc2cc(C(=O)N3CC[C@@H](N4CCc5ccccc5C4)[C@H](O)C3)nc(C3=CCN(C(=O)OC(C)(C)C)C3)n2)CC1] |
| 364 | 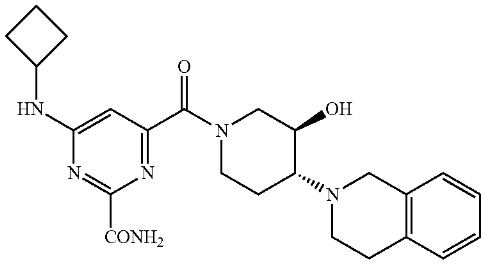 [SMILES: NC(=O)c1nc(NC2CCC2)cc(C(=O)N2CC[C@@H](N3CCc4ccccc4C3)[C@H](O)C2)n1] |
| 365 | 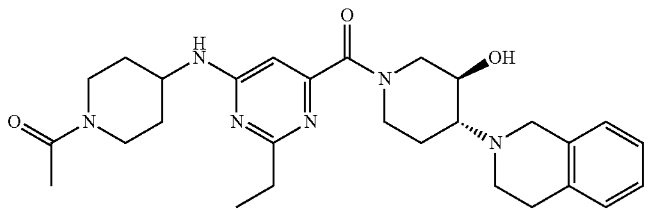 [SMILES: CCc1nc(NC2CCN(C(C)=O)CC2)cc(C(=O)N2CC[C@@H](N3CCc4ccccc4C3)[C@H](O)C2)n1] |

-continued
| No. | Structure |
|---|---|
| 366 | 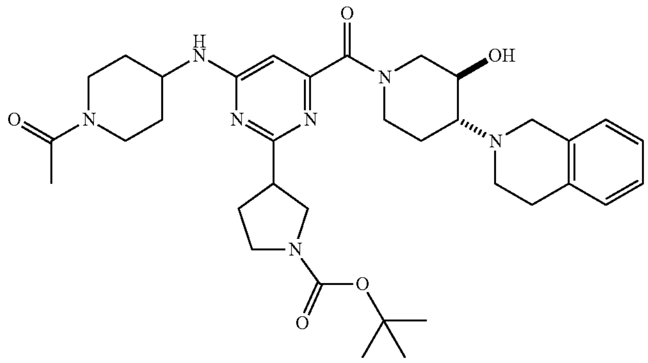 [SMILES: CC(=O)N1CCC(Nc2cc(C(=O)N3CC[C@@H](N4CCc5ccccc5C4)[C@H](O)C3)nc(C3CCN(C(=O)OC(C)(C)C)C3)n2)CC1] |
| 367 | 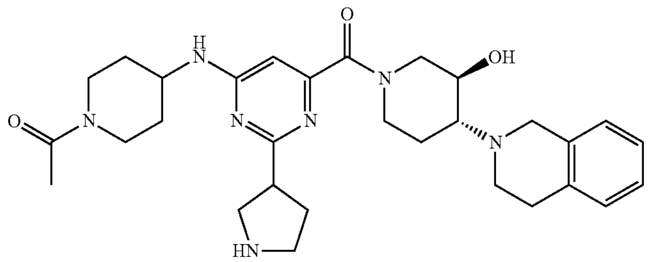 [SMILES: CC(=O)N1CCC(Nc2cc(C(=O)N3CC[C@@H](N4CCc5ccccc5C4)[C@H](O)C3)nc(C3CCNC3)n2)CC1] |
| 368 | 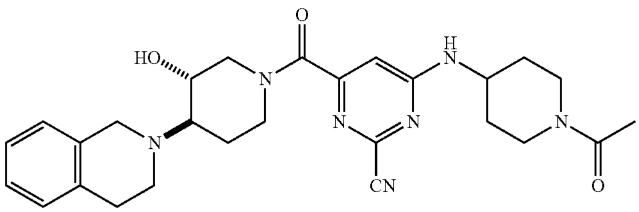 [SMILES: CC(=O)N1CCC(Nc2cc(C(=O)N3CC[C@@H](N4CCc5ccccc5C4)[C@H](O)C3)nc(C#N)n2)CC1] |
| 369 | 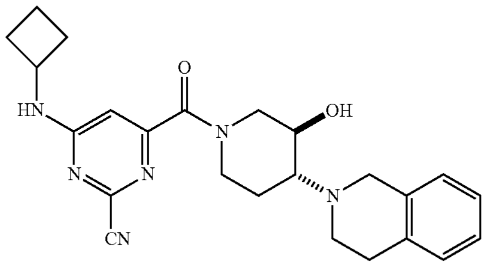 |
| 370 | 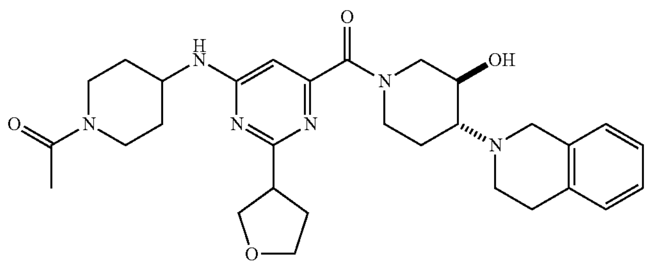 [SMILES: CC(=O)N1CCC(Nc2cc(C(=O)N3CC[C@@H](N4CCc5ccccc5C4)[C@H](O)C3)nc(C3CCOC3)n2)CC1] |

-continued
| No. | Structure |
|---|---|
| 371 | 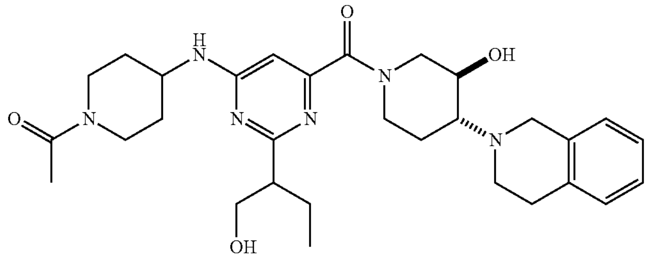 [SMILES: CCC(CO)c1nc(NC2CCN(C(C)=O)CC2)cc(C(=O)N2CC[C@@H](N3CCc4ccccc4C3)[C@H](O)C2)n1] |
| 372 | 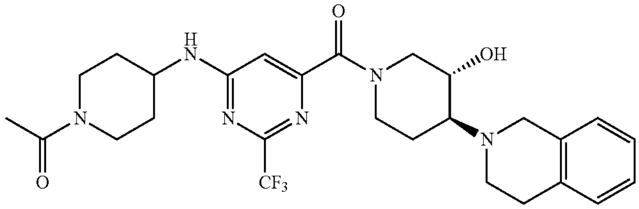 [SMILES: CC(=O)N1CCC(Nc2cc(C(=O)N3CC[C@H](N4CCc5ccccc5C4)[C@@H](O)C3)nc(C(F)(F)F)n2)CC1] |
| 373 | 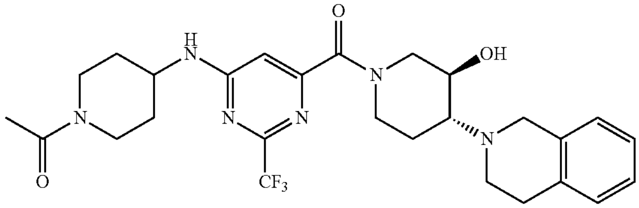 |
| 374 | 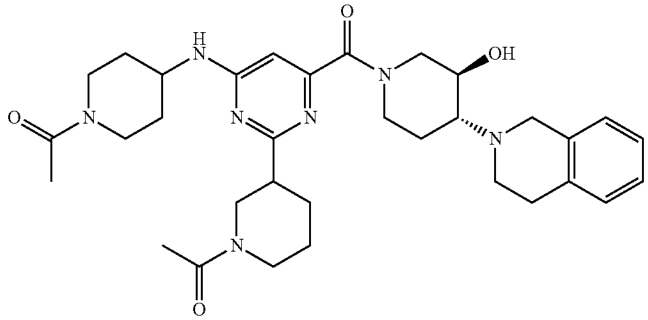 [SMILES: CC(=O)N1CCC(Nc2cc(C(=O)N3CC[C@@H](N4CCc5ccccc5C4)[C@H](O)C3)nc(C3CCCN(C(C)=O)C3)n2)CC1] |
| 375 | 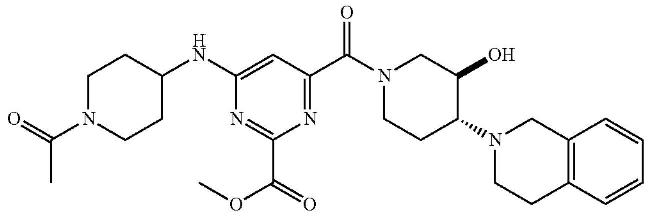 [SMILES: COC(=O)c1nc(NC2CCN(C(C)=O)CC2)cc(C(=O)N2CC[C@@H](N3CCc4ccccc4C3)[C@H](O)C2)n1] |
| 376 | 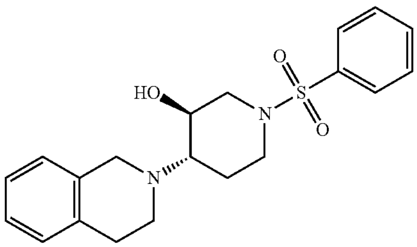 [SMILES: O=S(=O)(c1ccccc1)N1CC[C@H](N2CCc3ccccc3C2)[C@@H](O)C1] |

-continued
| No. | Structure |
|---|---|
| 377 | 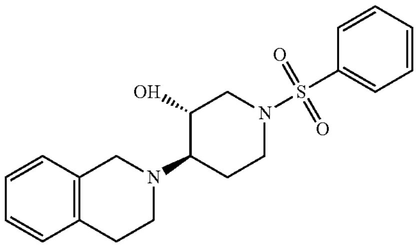 [SMILES: O=S(=O)(c1ccccc1)N1CC[C@@H](N2CCc3ccccc3C2)[C@H](O)C1] |
| 378 | 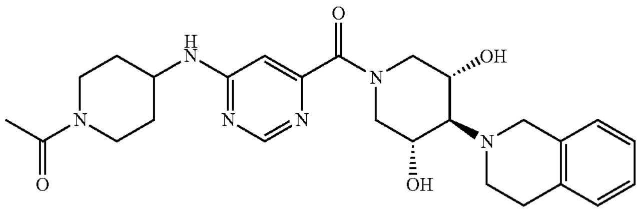 [SMILES: CC(=O)N1CCC(Nc2cc(C(=O)N3C[C@@H](O)[C@H](N4CCc5ccccc5C4)[C@@H](O)C3)ncn2)CC1] |
| 379 | 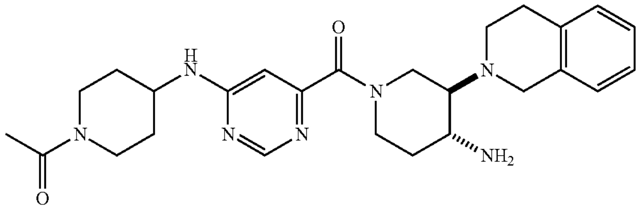 [SMILES: CC(=O)N1CCC(Nc2cc(C(=O)N3CC[C@@H](N)[C@H](N4CCc5ccccc5C4)C3)ncn2)CC1] |
| 380 | 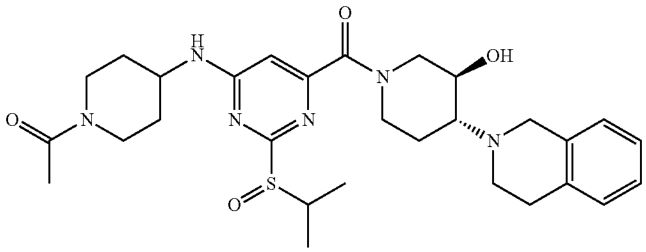 [SMILES: CC(=O)N1CCC(Nc2cc(C(=O)N3CC[C@@H](N4CCc5ccccc5C4)[C@H](O)C3)nc(S(=O)C(C)C)n2)CC1] |
| 381 | 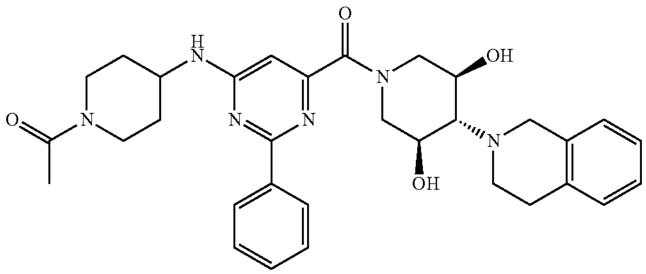 [SMILES: CC(=O)N1CCC(Nc2cc(C(=O)N3C[C@@H](O)[C@H](N4CCc5ccccc5C4)[C@@H](O)C3)nc(-c3ccccc3)n2)CC1] |
| 382 | 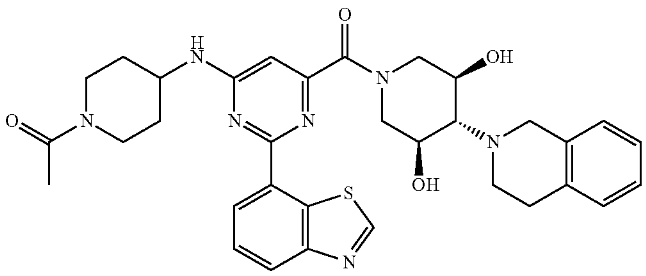 [SMILES: CC(=O)N1CCC(Nc2cc(C(=O)N3C[C@@H](O)[C@H](N4CCc5ccccc5C4)[C@@H](O)C3)nc(-c3cccc4ncsc34)n2)CC1] |

-continued
| No. | Structure |
| --- | --- |
| 383 | 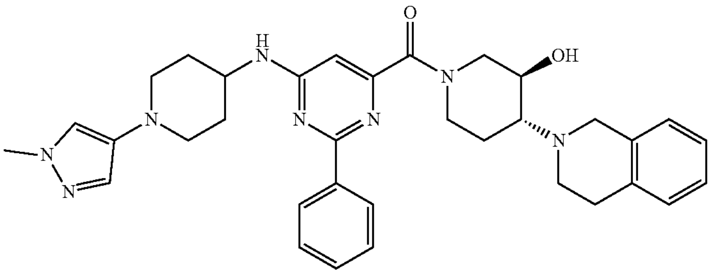 [SMILES: Cn1cc(N2CCC(Nc3cc(C(=O)N4CC[C@@H](N5CCc6ccccc6C5)[C@H](O)C4)nc(-c4ccccc4)n3)CC2)cn1] |
| 384 | 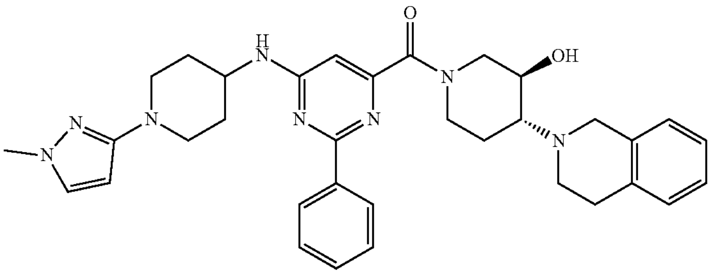 [SMILES: Cn1ccc(N2CCC(Nc3cc(C(=O)N4CC[C@@H](N5CCc6ccccc6C5)[C@H](O)C4)nc(-c4ccccc4)n3)CC2)n1] |
| 385 | 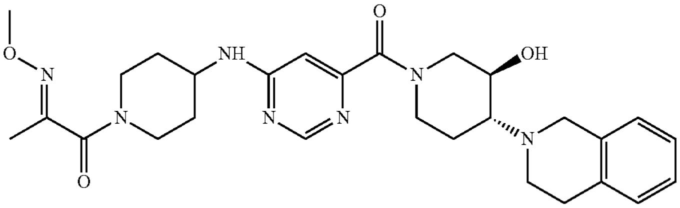 [SMILES: CO/N=C(\C)C(=O)N1CCC(Nc2cc(C(=O)N3CC[C@@H](N4CCc5ccccc5C4)[C@H](O)C3)ncn2)CC1] |
| 386 | 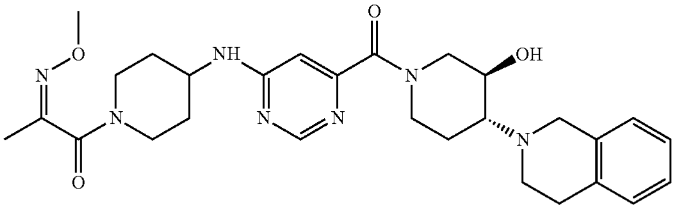 [SMILES: CO/N=C(/C)C(=O)N1CCC(Nc2cc(C(=O)N3CC[C@@H](N4CCc5ccccc5C4)[C@H](O)C3)ncn2)CC1] |
| 387 | 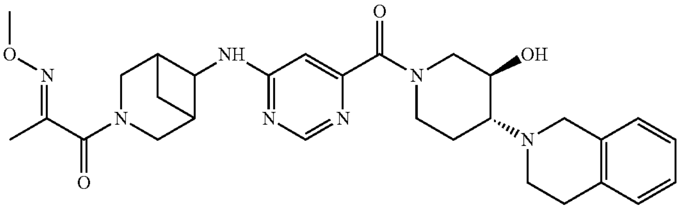 [SMILES: CO/N=C(\C)C(=O)N1CC2CC(C1)C2Nc1cc(C(=O)N2CC[C@@H](N3CCc4ccccc4C3)[C@H](O)C2)ncn1] |
| 388 | 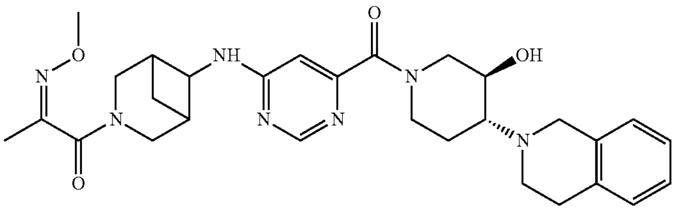 [SMILES: CO/N=C(/C)C(=O)N1CC2CC(C1)C2Nc1cc(C(=O)N2CC[C@@H](N3CCc4ccccc4C3)[C@H](O)C2)ncn1] |

-continued
| No. | Structure |
|---|---|
| 389 | 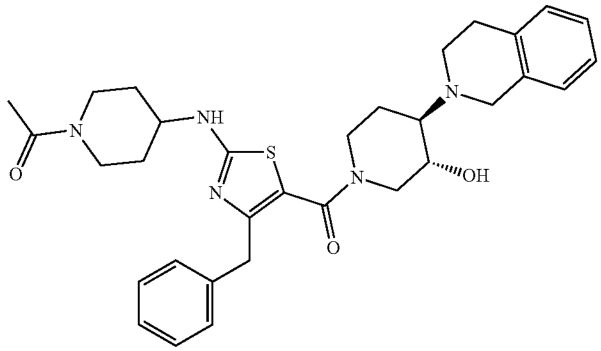 [SMILES: CC(=O)N1CCC(Nc2nc(Cc3ccccc3)c(C(=O)N3CC[C@@H](N4CCc5ccccc5C4)[C@H](O)C3)s2)CC1] |
| 390 | 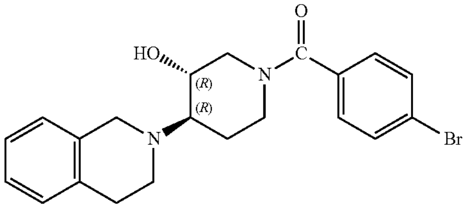 |
| 391 | 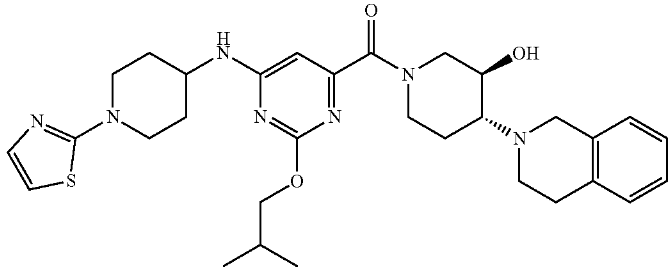 [SMILES: CC(C)COc1nc(NC2CCN(c3nccs3)CC2)cc(C(=O)N2CC[C@@H](N3CCc4ccccc4C3)[C@H](O)C2)n1] |
| 392 | 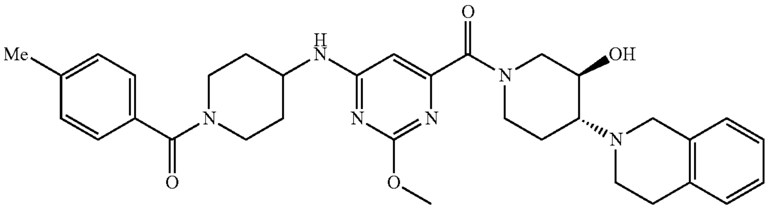 [SMILES: COc1nc(NC2CCN(C(=O)c3ccc(C)cc3)CC2)cc(C(=O)N2CC[C@@H](N3CCc4ccccc4C3)[C@H](O)C2)n1] |
| 393 | 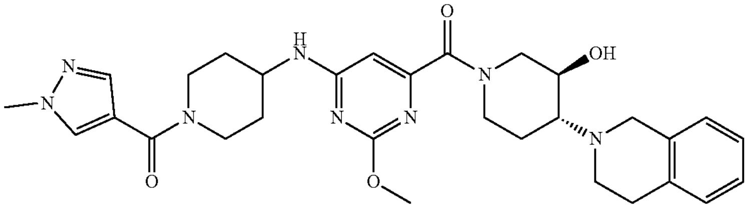 [SMILES: COc1nc(NC2CCN(C(=O)c3cnn(C)c3)CC2)cc(C(=O)N2CC[C@@H](N3CCc4ccccc4C3)[C@H](O)C2)n1] |
| 394 | 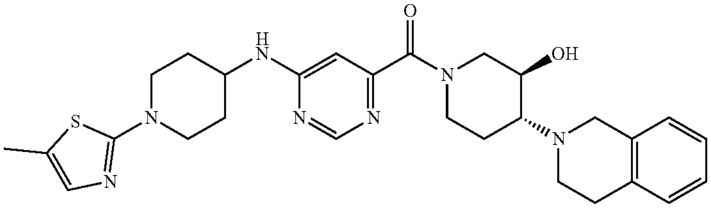 [SMILES: Cc1cnc(N2CCC(Nc3cc(C(=O)N4CC[C@@H](N5CCc6ccccc6C5)[C@H](O)C4)ncn3)CC2)s1] |

-continued
| No. | Structure |
|---|---|
| 395 | 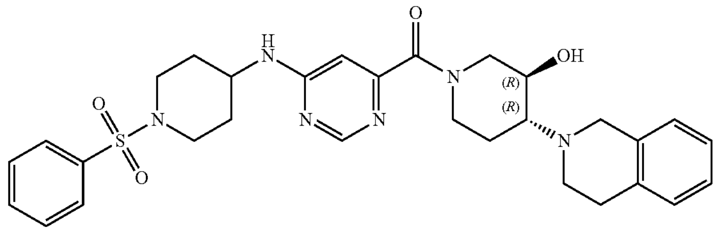 |
| 396 | 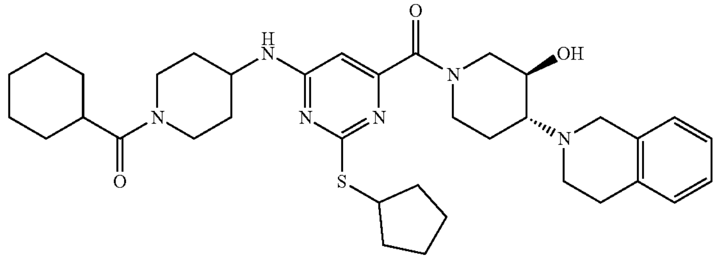 [SMILES: O=C(c1cc(NC2CCN(C(=O)C3CCCCC3)CC2)nc(SC2CCCC2)n1)N1CC[C@@H](N2CCc3ccccc3C2)[C@H](O)C1] |
| 397 | 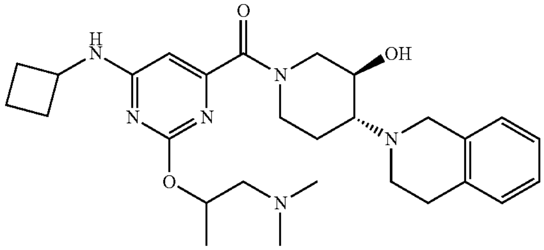 [SMILES: CC(CN(C)C)Oc1nc(NC2CCC2)cc(C(=O)N2CC[C@@H](N3CCc4ccccc4C3)[C@H](O)C2)n1] |
| 398 | 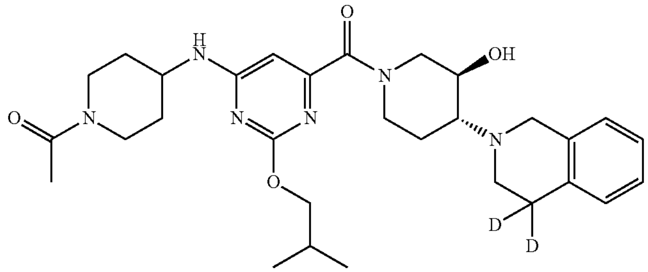 [SMILES: [2H]C1([2H])CN([C@@H]2CCN(C(=O)c3cc(NC4CCN(C(C)=O)CC4)nc(OCC(C)C)n3)C[C@H]2O)Cc2ccccc21] |
| 399 | 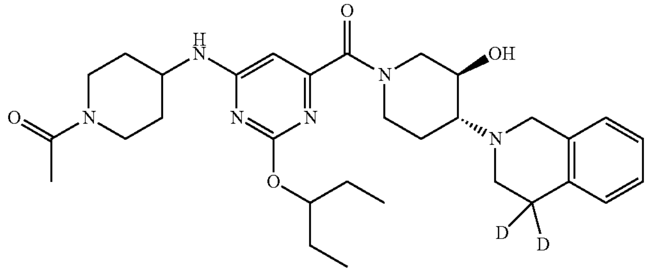 [SMILES: [2H]C1([2H])CN([C@@H]2CCN(C(=O)c3cc(NC4CCN(C(C)=O)CC4)nc(OC(CC)CC)n3)C[C@H]2O)Cc2ccccc21] |
| 400 | 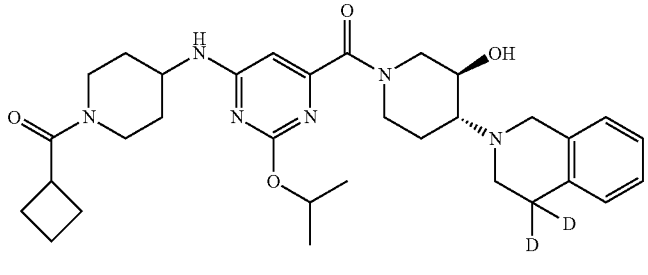 [SMILES: [2H]C1([2H])CN([C@@H]2CCN(C(=O)c3cc(NC4CCN(C(=O)C5CCC5)CC4)nc(OC(C)C)n3)C[C@H]2O)Cc2ccccc21] |

-continued
| No. | Structure |
| --- | --- |
| 401 | 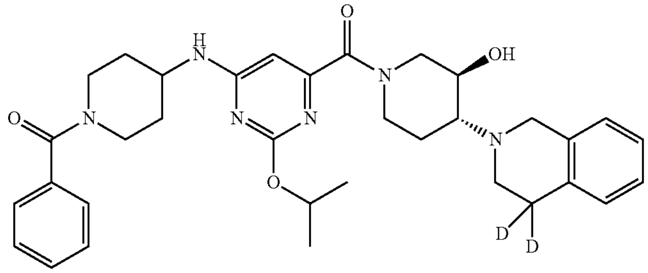 [SMILES: [2H]C1([2H])CN([C@@H]2CCN(C(=O)c3cc(NC4CCN(C(=O)c5ccccc5)CC4)nc(OC(C)C)n3)C[C@H]2O)Cc2ccccc21] |
| 402 | 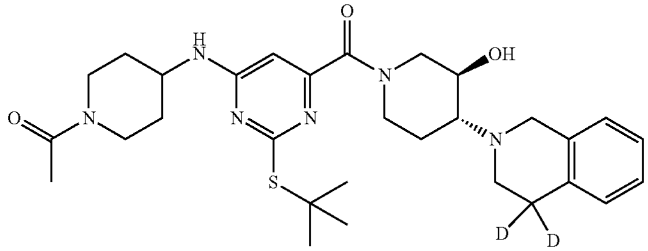 [SMILES: [2H]C1([2H])CN([C@@H]2CCN(C(=O)c3cc(NC4CCN(C(C)=O)CC4)nc(SC(C)(C)C)n3)C[C@H]2O)Cc2ccccc21] |
| 403 | 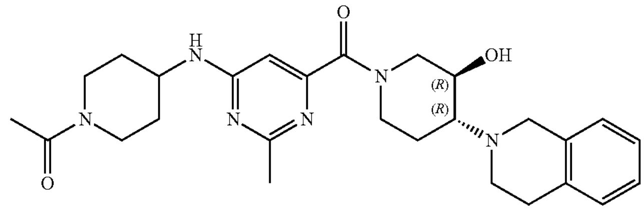 |
| 404 | 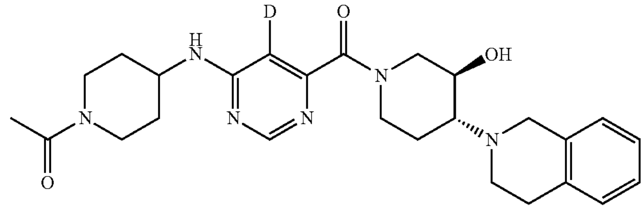 [SMILES: [2H]c1c(NC2CCN(C(C)=O)CC2)ncnc1C(=O)N1CC[C@@H](N2CCc3ccccc3C2)[C@H](O)C1] |
| 405 | 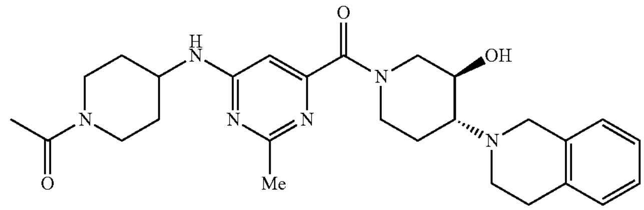 |
| 406 | 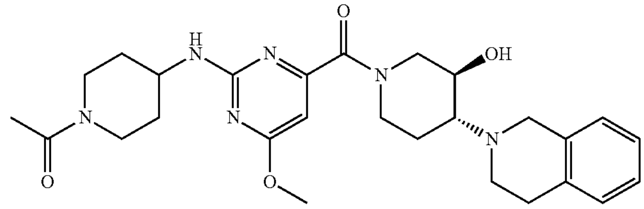 [SMILES: COc1cc(C(=O)N2CC[C@@H](N3CCc4ccccc4C3)[C@H](O)C2)nc(NC2CCN(C(C)=O)CC2)n1] |

-continued
| No. | Structure |
| --- | --- |
| 407 | 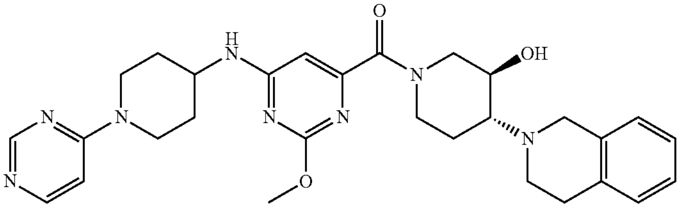 [SMILES: COc1nc(NC2CCN(c3ccncn3)CC2)cc(C(=O)N2CC[C@@H](N3CCc4ccccc4C3)[C@H](O)C2)n1] |
| 408 | 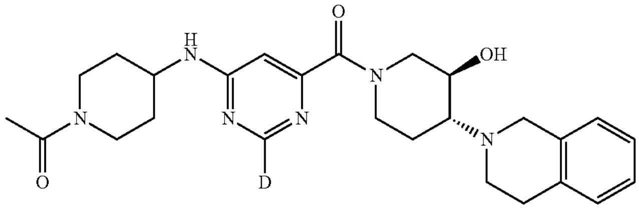 [SMILES: [2H]c1nc(NC2CCN(C(C)=O)CC2)cc(C(=O)N2CC[C@@H](N3CCc4ccccc4C3)[C@H](O)C2)n1] |
| 409 | 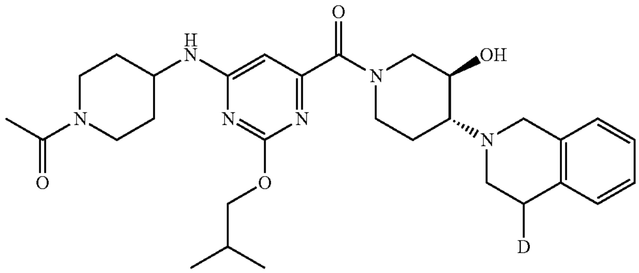 [SMILES: [2H]C1CN([C@@H]2CCN(C(=O)c3cc(NC4CCN(C(C)=O)CC4)nc(OCC(C)C)n3)C[C@H]2O)Cc2ccccc21] |
| 410 | 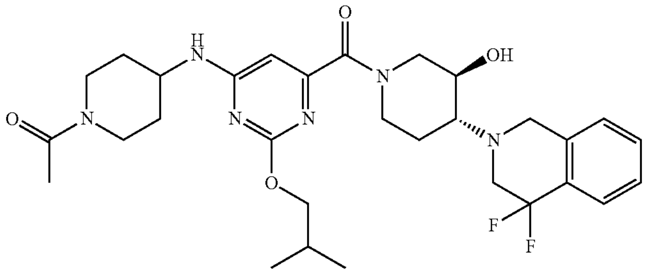 [SMILES: CC(=O)N1CCC(Nc2cc(C(=O)N3CC[C@@H](N4Cc5ccccc5C(F)(F)C4)[C@H](O)C3)nc(OCC(C)C)n2)CC1] |
| 411 | 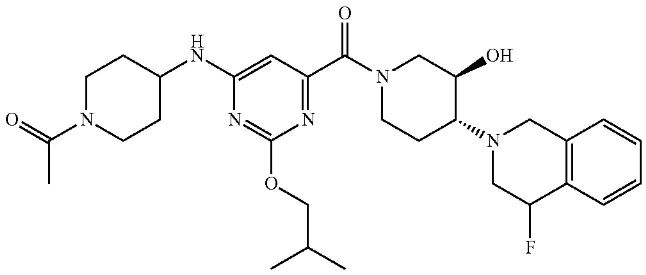 [SMILES: CC(=O)N1CCC(Nc2cc(C(=O)N3CC[C@@H](N4Cc5ccccc5C(F)C4)[C@H](O)C3)nc(OCC(C)C)n2)CC1] |
| 412 | 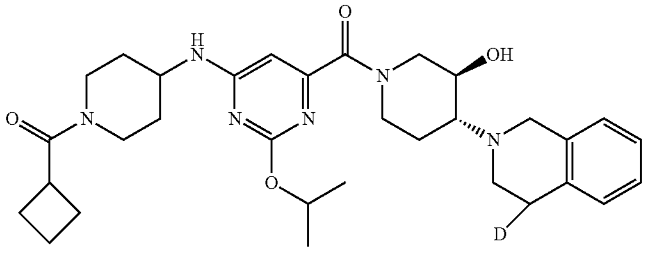 [SMILES: [2H]C1CN([C@@H]2CCN(C(=O)c3cc(NC4CCN(C(=O)C5CCC5)CC4)nc(OC(C)C)n3)C[C@H]2O)Cc2ccccc21] |

-continued
| No. | Structure |
| --- | --- |
| 413 | 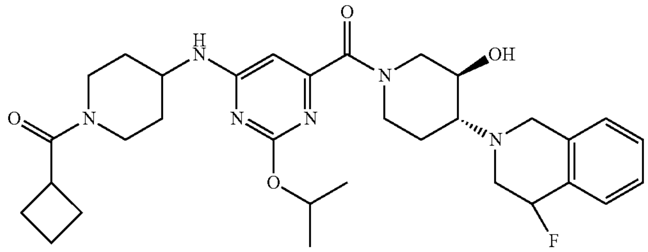 [SMILES: CC(C)Oc1nc(NC2CCN(C(=O)C3CCC3)CC2)cc(C(=O)N2CC[C@@H](N3Cc4ccccc4C(F)C3)[C@H](O)C2)n1] |
| 414 | 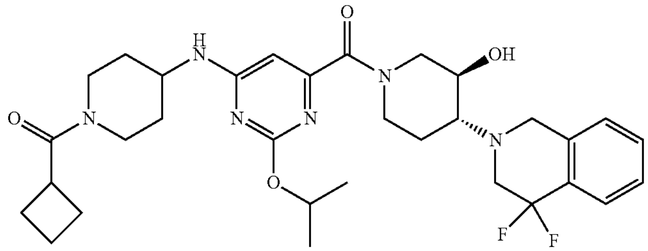 [SMILES: CC(C)Oc1nc(NC2CCN(C(=O)C3CCC3)CC2)cc(C(=O)N2CC[C@@H](N3Cc4ccccc4C(F)(F)C3)[C@H](O)C2)n1] |
| 415 | 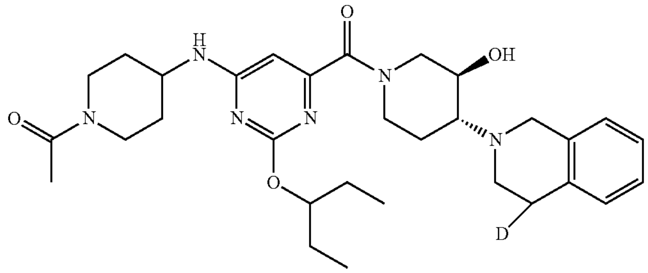 [SMILES: [2H]C1CN([C@@H]2CCN(C(=O)c3cc(NC4CCN(C(C)=O)CC4)nc(OC(CC)CC)n3)C[C@H]2O)Cc2ccccc21] |
| 416 | 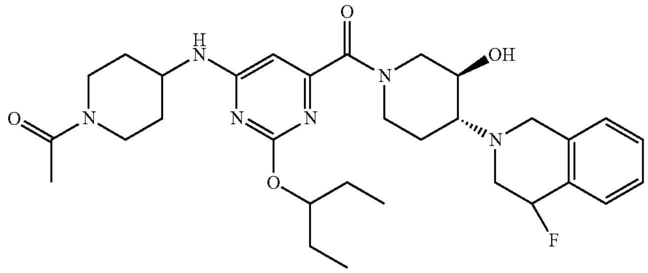 [SMILES: CCC(CC)Oc1nc(NC2CCN(C(C)=O)CC2)cc(C(=O)N2CC[C@@H](N3Cc4ccccc4C(F)C3)[C@H](O)C2)n1] |
| 417 | 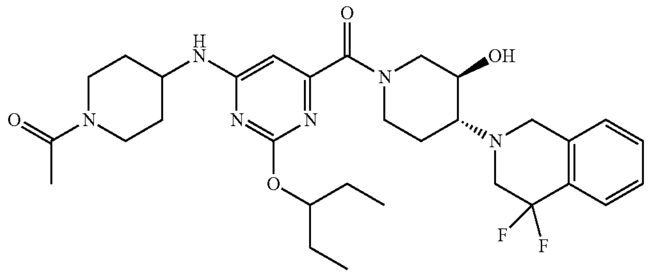 [SMILES: CCC(CC)Oc1nc(NC2CCN(C(C)=O)CC2)cc(C(=O)N2CC[C@@H](N3Cc4ccccc4C(F)(F)C3)[C@H](O)C2)n1] |

-continued
| No. | Structure |
|---|---|
| 418 | 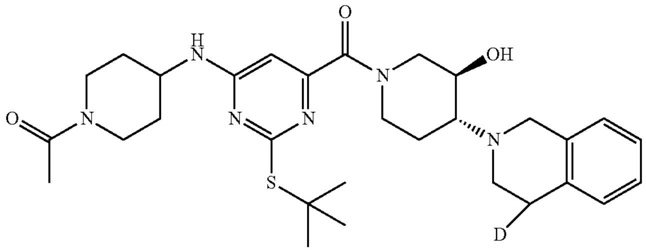 [SMILES: [2H]C1CN([C@@H]2CCN(C(=O)c3cc(NC4CCN(C(C)=O)CC4)nc(SC(C)(C)C)n3)C[C@H]2O)Cc2ccccc21] |
| 419 | 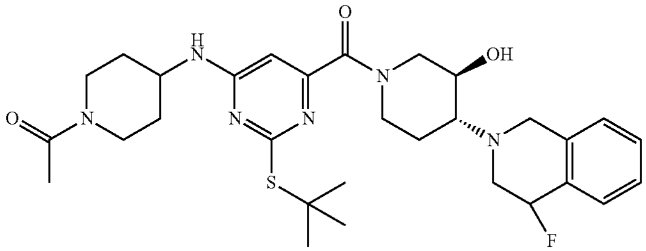 [SMILES: CC(=O)N1CCC(Nc2cc(C(=O)N3CC[C@@H](N4Cc5ccccc5C(F)C4)[C@H](O)C3)nc(SC(C)(C)C)n2)CC1] |
| 420 | 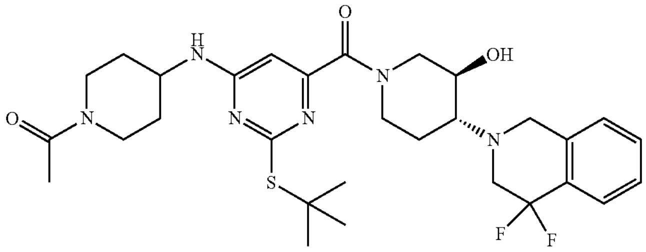 [SMILES: CC(=O)N1CCC(Nc2cc(C(=O)N3CC[C@@H](N4Cc5ccccc5C(F)(F)C4)[C@H](O)C3)nc(SC(C)(C)C)n2)CC1] |
| 421 | 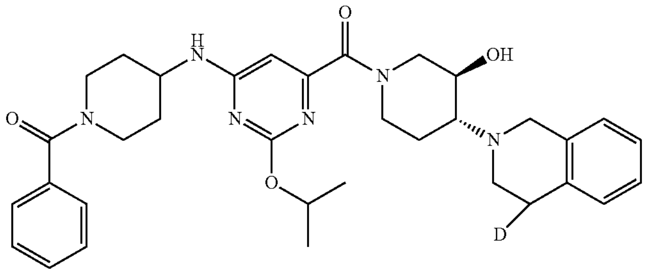 [SMILES: [2H]C1CN([C@@H]2CCN(C(=O)c3cc(NC4CCN(C(=O)c5ccccc5)CC4)nc(OC(C)C)n3)C[C@H]2O)Cc2ccccc21] |
| 422 | 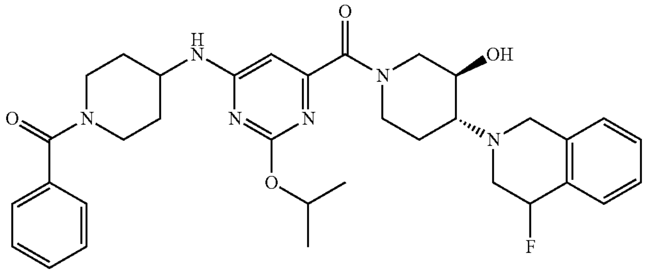 [SMILES: CC(C)Oc1nc(NC2CCN(C(=O)c3ccccc3)CC2)cc(C(=O)N2CC[C@@H](N3Cc4ccccc4C(F)C3)[C@H](O)C2)n1] |

-continued

| No. | Structure |
| --- | --- |
| 423 | 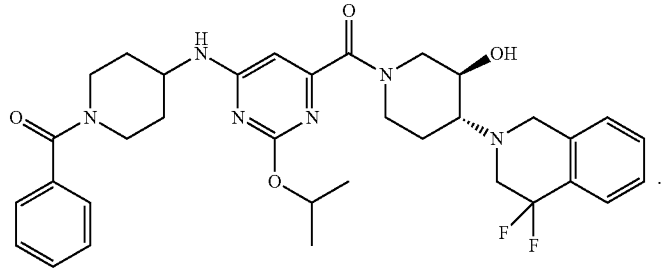 [SMILES: CC(C)Oc1nc(NC2CCN(C(=O)c3ccccc3)CC2)cc(C(=O)N2CC[C@@H](N3Cc4ccccc4C(F)(F)C3)[C@H](O)C2)n1] |

The object of the present invention also includes providing a process for preparing compounds represented by general formula (I), and stereoisomers, geometric isomers, tautomers, pharmaceutical salts, prodrugs, hydrates, solvates or isotope-labeled analogues thereof.

For example, said process can be performed according to the process shown in Scheme 1. The target compound can be synthesized by firstly connecting the $LG^a$ (leaving group a) of the left chain of the $G^3$-Z structure to $G^4$-YH, and then connecting the $LG^C$ (leaving group c) of the cyclic structure to the $LG^b$ (leaving group b) of the right chain of the $G^3$-Z structure. Scheme 1 is as follows:

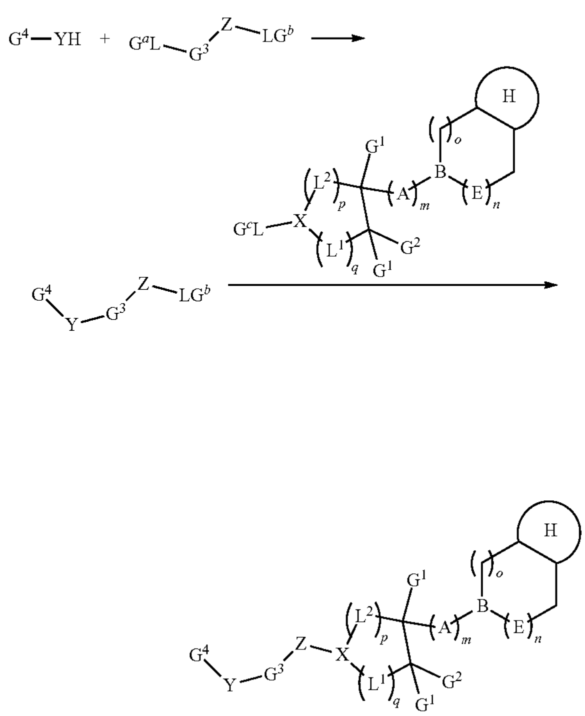

(I)

For example, said process can be performed according to the process shown in Scheme 2. The target compound can be synthesized by firstly connecting the $LG^C$ (leaving group c) of the cyclic structure to the $LG^b$ (leaving group b) of the right chain of the $G^3$-Z structure, and then connecting the $LG^a$ (leaving group a) of the left chain of the $G^3$-Z structure to $G^4$-YH. Scheme 2 is as follows:

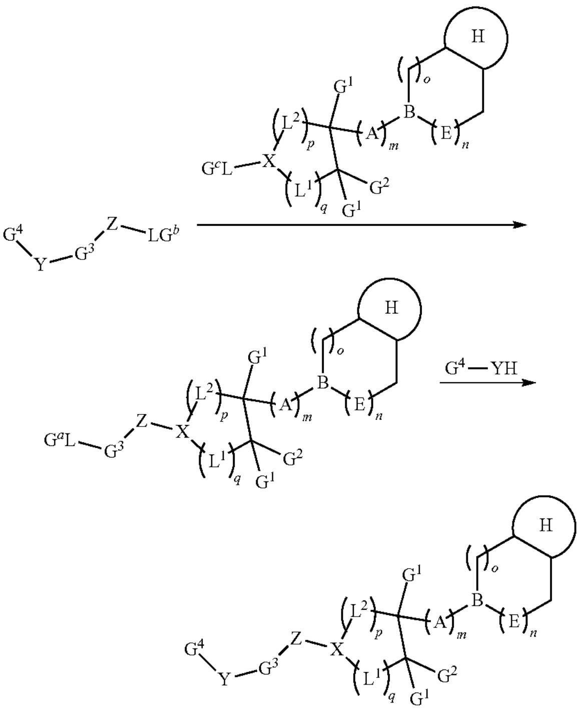

(I)

wherein, in the above preparation processes, each substituent in the compounds shown are defined as described above.

The present invention also provides a pharmaceutical composition, which contains the compound of the present invention, or stereoisomer, geometric isomer, tautomer, pharmaceutical salt, prodrug, hydrate, solvate, or isotope-labeled analogue thereof, and a pharmaceutically acceptable adjuvant.

The object of the present invention also includes providing the use of the compound of the present invention, or stereoisomer, geometric isomer, tautomer, pharmaceutical salt, prodrug, hydrate, solvate, or isotope-labeled analogue thereof in manufacture of a medicament for preventing and/or treating PRMT5-mediated diseases.

In some embodiments, the PRMT5-mediated disease is cancer or a tumor-related disease.

The object of the present invention also includes providing a method for preventing and/or treating PRMT5-mediated diseases, which includes administering a therapeutically effective dose of the compound of the present invention, or stereoisomer, geometric isomer, tautomer, pharmaceutical salt, prodrug, hydrate, solvate, or isotope-labeled analogue thereof, or the pharmaceutical composition of the present invention to a patient.

In some embodiments, the PRMT5-mediated disease is cancer or a tumor-related disease.

In some embodiments, the cancer or tumor-related disease is preferably lymphoma.

When the compound of the present invention or a pharmaceutically acceptable salt thereof is combined with another anticancer agent or immune checkpoint inhibitor for treating cancer or tumor, the compound of the present invention or a pharmaceutically acceptable salt thereof can provide enhanced anticancer effects.

Beneficial Effects of the Present Invention

The present invention designs a class of compounds with novel structures and provides a new direction for the development of PRMT5 inhibitor drugs. The activity study on in vitro enzyme activity inhibition shows that these compounds have strong inhibitory effects on the PRMT5 enzyme, and the assay on subcutaneous xenografts of human B-cell non-Hodgkin lymphoma Z-138 cell line in NOD/SCID female mice shows the compounds have excellent tumor inhibitory effect, and in vivo pharmacokinetic assays in mice show that the compounds have excellent metabolic properties, therefore these compounds can be used as promising compounds for the treatment of PRMT5-mediated diseases. In addition, the present invention discloses a specific synthesis process, which is simple and easy to operate and is conducive to large-scale industrial production and application.

DETAILED DESCRIPTION

Definitions

Unless specified otherwise, the term "alkyl" refers to a monovalent saturated aliphatic hydrocarbyl, including a linear or branched group containing 1 to 20 carbon atoms, preferably 1 to 10 carbon atoms (i.e. $C_{1-10}$ alkyl), further preferably 1 to 8 carbon atoms ($C_{1-3}$ alkyl), more preferably 1 to 6 carbon atoms (i.e. $C_{1-6}$ alkyl). For example "$C_{1-6}$ alkyl" means that the group is an alkyl group, and the number of carbon atoms in the carbon chain is between 1 and 6 (specifically 1, 2, 3, 4, 5 or 6). Examples include, but are not limited to methyl, ethyl, n-propyl, isopropyl, n-butyl, isobutyl, tert-butyl, sec-butyl, n-pentyl, neopentyl, 1,1-dimethylpropyl, 1,2-dimethylpropyl, 2,2-dimethylpropyl, 1-ethylpropyl, 2-methylbutyl, 3-methylbutyl, n-hexyl, n-heptyl, n-octyl, and the like.

Unless specified otherwise, the term "cycloalkyl" refers to a monocyclic saturated aliphatic hydrocarbyl having a specified number of carbon atoms, preferably containing 3 to 12 carbon atoms (i.e. $C_{3-12}$ cycloalkyl), more preferably 3 to 10 carbon atoms ($C_{3-10}$ cycloalkyl), further preferably 3 to 6 carbon atoms ($C_{3-6}$ cycloalkyl), 4 to 6 carbon atoms ($C_{4-6}$ cycloalkyl), or 5 to 6 carbon atoms ($C_{5-6}$ cycloalkyl). Examples include, but are not limited to cyclopropyl, cyclobutyl, cyclopentyl, cyclohexyl, methylcyclopropyl, 2-ethyl-cyclopentyl, dimethylcyclobutyl, and the like.

Unless specified otherwise, the term "alkoxy" refers to —O-alkyl where the alkyl is as defined above, that is, containing 1 to 20 carbon atoms, preferably 1 to 10 carbon atoms, further preferably 1 to 8 carbon atoms, still further preferably 1 to 6 carbon atoms (specifically 1, 2, 3, 4, 5 or 6). Representative examples include, but are not limited to methoxy, ethoxy, propoxy, isopropoxy, butoxy, 1-methylpropoxy, 2-methylpropoxy, t-butoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, and the like.

Unless specified otherwise, the term "halogen" or "halo" refers to F, Cl, Br, or I. The term "haloalkyl" refers to an alkyl group as defined above, in which one, two or more hydrogen atoms or all hydrogen atoms are substituted by halogen.

Representative examples of haloalkyl include $CCl_3$, $CF_3$, $CHCl_2$, $CH_2Cl$, $CH_2Br$, $CH_2I$, $CH_2CF_3$, $CF_2CF_3$ and the like.

Unless specified otherwise, the term "heterocyclyl" refers to a saturated or partially unsaturated monocyclic, bicyclic or polycyclic hydrocarbon substituent, which is in a non-aromatic structure and contains 3 to 20 ring atoms, of which 1, 2, 3 or more ring atoms are selected from N, O and S, and the remaining ring atoms are C. Preferably, it contains 3 to 12 ring atoms, more preferably 3 to 10 ring atoms, or 3 to 8 ring atoms, or 3 to 6 ring atoms, or 4 to 6 ring atoms, or 5 to 6 ring atoms. The number of heteroatoms is preferably 1 to 4, more preferably 1 to 3 (namely 1, 2 or 3). Examples of monocyclic heterocyclyl include pyrrolidinyl, imidazolidinyl, tetrahydrofuranyl, dihydropyrrolyl, piperidinyl, piperazinyl, pyranyl, and the like. Polycyclic heterocyclyls include spiro, fused and bridged heterocyclyls.

Unless specified otherwise, the term "carbocyclyl" or "carbocycle" refers to a non-aromatic cyclic hydrocarbyl having from 3 to 14 ring carbon atoms ("$C_{3-14}$ carbocyclyl") and having no heteroatom in the non-aromatic ring system. In some embodiments, the carbocyclyl has 3 to 12 ring carbon atoms ("$C_{3-12}$ carbocyclyl"), or 4 to 12 ring carbon atoms ("$C_{4-12}$ carbocyclyl"), or 3 to 10 ring carbon atoms ("$C_{3-10}$ carbocyclyl"). In some embodiments, the carbocyclyl group has 3 to 8 ring carbon atoms ("$C_{3-8}$ carbocyclyl"). In some embodiments, the carbocyclyl group has 3 to 7 ring carbon atoms ("$C_{3-7}$ carbocyclyl"). In some embodiments, the carbocyclyl group has 4 to 6 ring carbon atoms ("C4-6 carbocyclyl"). In some embodiments, the carbocyclyl group has 5 to 10 ring carbon atoms ("$C_{5-10}$ carbocyclyl") or 5 to 7 ring carbon atoms ("$C_{5-7}$ carbocyclyl"). Exemplary $C_{3-6}$ carbocyclyl groups include, but are not limited to cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$) and the like. Exemplary $C_{3-8}$ carbocyclyl groups include, but are not limited to the aforementioned $C_{3-6}$ carbocyclyl groups and cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptyl ($C_7$), bicyclo[2.2.2]octyl ($C_8$) and the like. Exemplary $C_{3-10}$ carbocyclyl groups include, but are not limited to, the aforementioned $C_{3-8}$ carbocyclyl groups and cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decyl ($C_{10}$) and the like. As in the above examples, in certain embodiments, the carbocyclyl group is monocyclic ("monocyclic carbocyclyl") or a fused (fused carbocyclyl), bridged (bridged carbocyclyl) or spiro-fused (spirocyclyl) ring system, such as a bicyclic ring system ("bicyclic carbocyclyl"), and may be saturated or partially unsaturated. The "carbocyclyl" also includes ring systems, in which the carbocyclyl ring as defined above is fused by one or more aryl or heteroaryl groups, wherein the attachment point is on the carbocyclyl ring and in such cases, the number of carbon still indicates the number of carbon in the carbocyclic ring system. In certain embodiments, each instance of the carbocyclyl group is independently optionally substituted, e.g., unsubstituted (an "unsubstituted carbocyclyl") or substituted with one or more substituents (a "substituted carbocyclyl"). In certain embodiments, the carbocyclyl group is anunsubstituted $C_{3-10}$ carbocyclyl. In certain embodiments, the carbocyclyl group is a substituted $C_{3-10}$ carbocyclyl.

Unless specified otherwise, the term "aryl" refers to monocyclic, bicyclic and tricyclic aromatic carbocyclic ring systems containing 6 to 16 carbon atoms, or 6 to 14 carbon atoms, or 6 to 12 carbon atoms, or 6 to 10 carbon atoms, preferably 6 to 10 carbon atoms. The term "aryl" may be used interchangeably with the term "aromatic ring". Examples of aryl groups may include, but are not limited to phenyl, naphthyl, anthracenyl, phenanthrenyl, pyrenyl, and the like.

Unless specified otherwise, the term "heteroaryl" refers to an aromatic monocyclic or polycyclic ring system having a 5-12 membered structure, or preferably a 5-10 membered structure, or a 5-8 membered structure, more preferably a 5-6 membered structure, in which 1, 2, 3 or more ring atoms are heteroatoms and the remaining atoms are carbon, the heteroatoms are independently selected from O, N and S, and the number of heteroatoms is preferably 1, 2 or 3. Examples of heteroaryl include, but are not limited to furyl, thienyl, oxazolyl, thiazolyl, isoxazolyl, oxadiazolyl, thiadiazolyl, pyrrolyl, pyrazolyl, imidazolyl, triazolyl, tetrazolyl, pyridyl, pyrimidinyl, pyrazinyl, pyridazinyl, thiodiazolyl, triazinyl, phthalazinyl, quinolinyl, isoquinolinyl, pteridyl, purinyl, indolyl, isoindolyl, indazolyl, benzofuryl, benzothienyl, benzopyridyl, benzopyrimidinyl, benzopyrazinyl, benzimidazolyl, benzophthalazinyl, pyrrolo[2,3-b]pyridyl, imidazo[1,2-a]pyridyl, pyrazolo[1,5-a]pyridyl, pyrazolo[1,5-a]pyrimidinyl, imidazo[1,2-b]pyridazinyl, [1,2,4]triazolo[4,3-b]pyridazinyl, [1,2,4]triazolo[1,5-a]pyrimidinyl, [1,2,4]triazolo[1,5-a]pyridyl, and the like.

Unless specified otherwise, the term "pharmaceutically acceptable salt", "pharmaceutical salt" or "officinal salt" refers to a salt that is suitable for use in contact with the tissues of mammals, especially humans, without undue toxicity, irritation, allergic response or the like, and commensurates with a reasonable benefit/risk ratio within the range of reasonable medical judgment. For example, the pharmaceutically acceptable salts of amines, carboxylic acids and other types of compounds are well known in the art. The salts can be prepared in situ during the final isolation and purification of the compounds according to the present invention, or separately by reacting the free base or acid with a suitable reagent, as outlined below.

For example, the functionality of the free base can be reacted with a suitable acid.

Unless specified otherwise, the term "solvate" refers to a physical association of a compound according to the present invention with one or more solvent molecules, regardless of organic or inorganic. This physical association includes hydrogen bond. In some cases, for example, when one or more solvent molecules are incorporated into the crystal lattice of a crystalline solid, the solvates can be isolated. Solvent molecules in the solvates may exist in regular and/or disordered arrangements. The solvates may contain stoichiometric or non-stoichiometric amounts of solvent molecules. The "solvate" encompasses both solution phase and isolatable solvate. Exemplary solvates include, but are not limited to hydrates, ethanolates, methanolates, and isopropanolates. Solvation methods are well known in the art.

Unless specified otherwise, the term "isotope-labeled analogue" refers to an isotope-labeled molecule in the compounds of formulae I and II, thereby providing isotope-labeled analogues that may have improved pharmacological activity. Isotopes commonly used as isotopic labels are: hydrogen isotopes: $^{2}H$ and $^{3}H$; carbon isotope: $^{11}C$, $^{13}C$ and $^{14}C$; chlorine isotopes: $^{35}Cl$ and $^{37}Cl$; fluorine isotopes: $^{18}F$; iodine isotopes: $^{123}I$ and $^{125}I$; nitrogen isotopes: $^{13}N$ and $^{15}N$; oxygen isotopes: $^{15}O$, $^{17}O$ and $^{18}O$; and sulfur isotope $^{35}S$. These isotope-labeled compounds can be used to study the distribution of pharmaceutical molecules in tissues. In particular, deuterium (D or $^{2}H$), $^{3}H$ and carbon $^{13}C$ are more widely used due to their ease of labeling and ease of detection. The substitution with certain heavy isotopes, such as deuterium ($^{2}H$), can enhance the stability of metabolism, and prolong the half-life, so as to achieve the purpose of reducing dosage and providing therapeutic advantages. Isotope labeled compounds are generally synthesized starting from labeled starting materials in the same way as non-isotope labeled compounds using known synthetic techniques.

Unless specified otherwise, the term "prodrug" refers to a drug that is converted into the parent drug in vivo. The prodrugs are often useful, because they may be more easily administered than the parent drug in some cases. For example, they are bioavailable via oral administration, whereas the parent drug cannot. The prodrugs also have improved solubility in pharmaceutical compositions compared to the parent drug. An example of the prodrug may be, but not limited to, any compound of formula (I) administered as an ester ("prodrug") to facilitate delivery across cell membranes where water solubility is detrimental to mobility, but once into the cells, the water solubility is beneficial, which is then metabolically hydrolyzed to carboxylic acids, i.e., active entities. Another example of the prodrug may be a short peptide (polyamino acid) bound to an acid group, where the peptide is metabolized to reveal the active moiety.

Unless otherwise specified, the term "stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc. Any resulting mixtures of stereoisomers can be separated on the basis of the physicochemical differences of the constituents, into the pure or substantially pure geometric isomers, enantiomers, diastereomers, for example, by chromatography and/or fractional crystallization.

Unless specified otherwise, the term "tautomer" refers to structural isomers of different energies which are interconvertible via a low energy barrier. If tautomerism is possible (for example, in solution), a chemical equilibrium of tautomers can be reached. For example, protontautomer (also known as prototropic tautomer) includes interconversion through proton migration, such as ketone-enol isomerization and imine-enamine isomerization. Valence tautomer includes interconversion through recombination of some bonding electrons.

Unless otherwise indicated, structure formulae depicted in the present invention include all isomeric forms (such as enantiomers, diastereomers, and geometric isomers (or conformational isomers)): for example, R and S configurations with asymmetric center, (Z) and (E) isomers of double bond, and (Z) and (E) conformational isomers. Therefore, individual stereochemical isomers or mixtures of enantiomers, diastereomers, or geometric isomers (or conformational isomers) of the compounds of the present invention are within the scope of the present invention.

Unless specified otherwise, the term “optionally substituted” means that the hydrogen at the substitutable site of the group is unsubstituted, or substituted by one or more substituents, which are preferably selected from the group consisting of halogen, hydroxy, mercapto, cyano, nitro, amino, azido, oxo, carboxyl, $C_{2-6}$ alkenyl, $C_{2-6}$ alkynyl, $C_{1-6}$ alkyl, $C_{1-6}$ alkoxy, $C_{3-10}$ cycloalkyl, $C_{3-10}$ cycloalkylsulfonyl, 3-10 membered heterocycloalkyl, $C_{6-14}$ aryl or 5-10 membered heteroaryl, wherein the $C_{2-6}$alkenyl, $C_{2-6}$alkynyl, $C_{1-6}$alkyl, $C_{1-6}$alkoxy, $C_{3-10}$cycloalkyl, $C_{3-10}$cycloalkylsulfonyl, 3-10 membered heterocycloalkyl, $C_{6-14}$aryl or 5-10 membered heteroaryl may be optionally substituted with one or more of halogen, hydroxy, amino, cyano, $C_{1-6}$alkyl and $C_{1-6}$alkoxy, and the oxo group means that two Hs in the same substitutable site are substituted by the single O to form a double bond.

The present invention is further described below in connection with specific examples. It should be understood that these examples are intended to illustrate the present invention only and are not intended to limit the scope of the present invention.

Experimental methods for which no specific conditions are indicated in the following examples are generally in accordance with conventional conditions or in accordance with the conditions recommended by the manufacturers. Unless otherwise defined, all professional and scientific terms used herein have the same meaning as those familiar to those skilled in the art. In addition, any methods and materials similar or equivalent to those described herein may be used in the methods of the present invention. The preferred embodiments and materials shown herein are illustrative only.

The structures of the compounds according to the present invention are determined by nuclear magnetic resonance (NMR) or/and liquid chromatograph mass spectrometry (LC-MS) or/and liquid chromatography (HPLC). The instrument used for NMR is Bruker AVANCE NEO 400 MHz; the instrument used for LC-MS is LCMS WATERS ACQUITY UPLCH-Class PLUS and/or SQD2; the instrument used for HPLC is WATERS ACQUITYUPLC or/and Agilent 1260.

The starting materials in the examples of the present invention are known and commercially available, or can be synthesised using or according to methods known in the art.

PREPARATION OF INTERMEDIATES

Preparation Example 1: Preparation of 6-((1-acetylpiperidin-4-yl)amino)-2-chloropyrimidine-4-carboxylic acid methyl ester

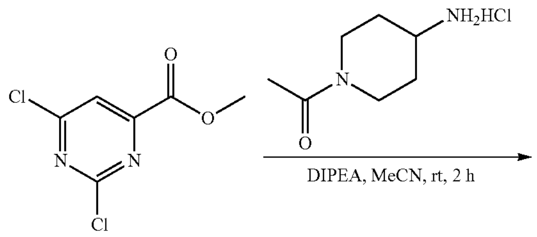

-continued

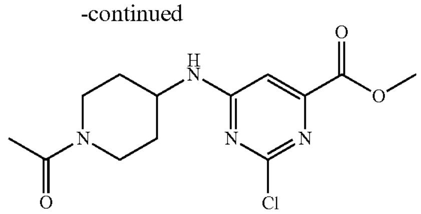

2,6-dichloro-pyrimidine-4-carboxylic acid methyl ester (6 g, 28.98 mmol), 1-acetylpiperidine-4-amine hydrochloride (5.7 g, 31.88 mmol) and DIPEA (14.98 g, 115.94 mmol) were dissolved in acetonitrile (50 mL). The resulting mixture was stirred at room temperature (25-30° C.) for 2 hours, and extracted with ethyl acetate three times (each 100 mL). Ethyl acetate phases were combined, washed with water (50 mL) once and washed with saturated brine (50 mL) once, dried over anhydrous sodium sulfate for 10 minutes, and filtered to give a crude product, which was separated and purified with a column chromatography (DCM:MeOH=100:1) to obtain a product (5.8 g, yield: 64%).

LC-MS (ESI) $[M+H]^+$=313.2.

Preparation Example 2: Preparation of trans-(6-chloropyrimidin-4-yl)(4-(3,4-dihydroisoquinolin-2(1H)-yl)-3-hydroxypiperidin-1-yl)methanone (for example this intermediate could be used as an intermediate for the compound of Example 1)

Step 1: Preparation of 6-chloropyrimidine-4-formyl chloride

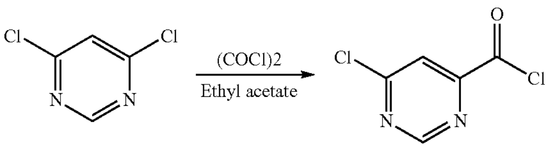

4,6-dichloropyrimidine (570 mg, 3.83 mmol, 1.0 eq) was dissolved in EA (18 mL), and oxalyl chloride (2.43 g, 19.13 mmol, 5.0 eq) and N,N-dimethyl formamide (1.8 mL) were added. The reaction was performed at 85° C. for 2 hours. After the completion of the reaction was monitored with the TLC plate and LC-MS, the reaction solution was quickly rotary dried using a rotary evaporator, sealed, and directly used for the next step.

Step 2: Preparation of trans-4-(3,4-dihydroisoquinolin-2(1H)-yl)-3-hydroxypiperidine-1-carboxylic acid tert-butyl ester

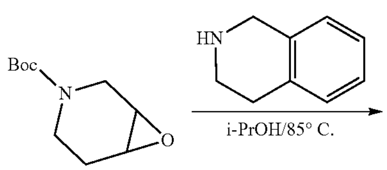

-continued

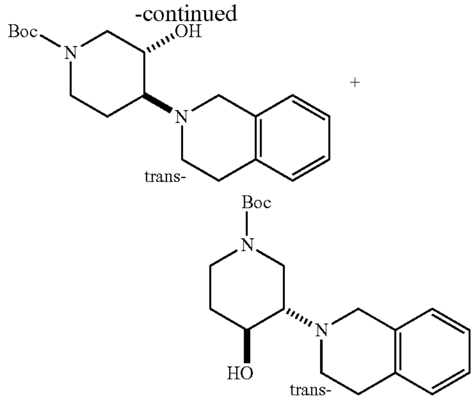

transtransby-product 7-oxa-3-azabicyclo[4.1.0]heptane-3-carboxylic acid tert-butyl ester (2.50 g, 12.56 mmol, 1.0 eq) was dissolved in i-PrOH (isopropanol, 63 mL), and 1, 2, 3,4-tetrahydroisoquinoline (1.67 g, 12.56 mmol, 1.0 eq) was added. The reaction was performed under the nitrogen protection at 85° C. for 18 hrs. After the completion of the reaction was monitored with the TLC plate and LC-MS, the reaction solvent was removed by rotary drying. Water (200 mL) was added. The mixture was extracted with dichloromethane (3 times in total, 200 mL, each time), dried over anhydrous sodium sulfate, filtered by suction, and rotary dried. Regional isomers were present in this step, including trans-4-(3,4-dihydroisoquinolin-2(1H)-yl)-3-hydroxypiperidine-1-carboxylic acid tert-butyl ester and trans-3-(3,4-dihydroisoquinolin-2(1H)-yl)-4-hydroxypiperidine-1-carboxylic acid tert-butyl ester. The crude mixture (3.40 g, yield: 81.5%) was separated and purified with chromatography (silica gel, ethyl acetate:petroleum ether=15:85) two or three times to produce the title compound (1.7 g, yield: 41%).

LC-MS (ESI) $[M+H]^+$=333.3; $^1H$ NMR (400 MHz, $CDCl_3$) δ 7.20-7.08 (m, 3H), 7.05-6.98 (m, 1H), 4.59-4.17 (m, 2H), 3.94 (d, J=14.6 Hz, 1H), 3.68 (d, J=14.5 Hz, 2H), 3.54 (td, J=10.0, 5.0 Hz, 1H), 3.03 (dt, J=10.9, 5.3 Hz, 1H), 2.91 (t, J=5.6 Hz, 2H), 2.80-2.47 (m, 4H), 1.82 (dd, J=12.7, 2.5 Hz, 1H), 1.59-1.38 (m, 10H).

Step 3: Preparation of trans-4-(3,4-dihydroisoquinolin-2(1H)-yl)piperidin-3-ol

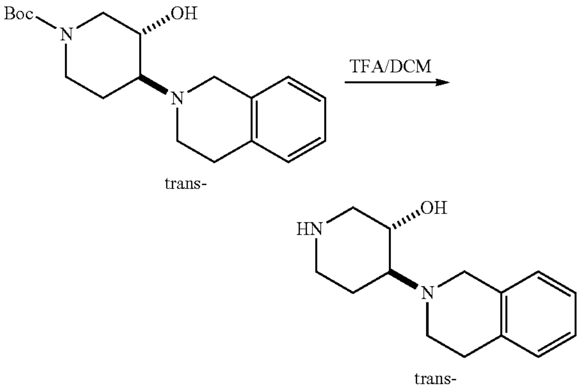

transtranstrans-4-(3,4-dihydroisoquinolin-2(1H)-yl)-3-hydroxypiperidine-1-carboxylic acid tert-butyl ester (1.00 g, 3.01 mmol, 1.0 eq) was dissolved in DCM (dichloromethane) (15 mL) and TFA (trifluoroacetic acid) (3.75 mL). The reaction was performed under stirring at room temperature (20-25° C.) for 2 hours. After the completion of the reaction was monitored with the TLC plate and LC-MS, the reaction solution was rotary-dried using a rotary evaporator. An addition of 1,2-dichloroethane to remove the redundant TFA was repeatedly performed three times. The reaction product was rotary-dried and sealed, and directly used for the next step.

LC-MS (ESI) $[M+H]^+$=233.2.

Step 4: Preparation of trans-(6-chloropyrimidin-4-yl)(4-(3,4-dihydroisoquinolin-2(1H)-yl)-3-hydroxypiperidin-1-yl)methanone

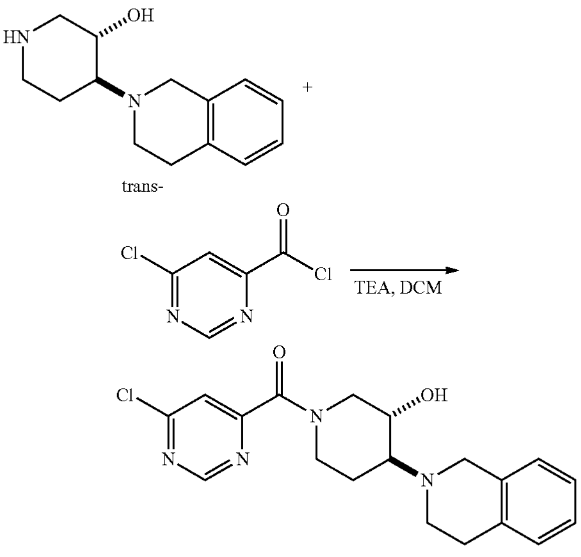

transtrans-

Trans-4-(3,4-dihydroisoquinolin-2(1H)-yl)piperidin-3-ol (570 mg, 3.23 mmol, 1.0 eq) was dissolved in DCM (dichloromethane) (8 mL) and TEA (triethylamine) (653 mg, 6.46 mmol, 2.0 eq). 6-chloropyrimidine-4-formyl chloride was dissolved in dichloromethane (8 mL), and was slowly added to the reaction solution of trans-4-(3,4-dihydroisoquinolin-2(1H)-yl)piperidin-3-ol under the nitrogen gas protection. The reaction solution was reacted under an ice bath condition for 2 hours, slowly warmed up to room temperature (20-25° C.) and reacted for 1 hour. After the completion of the reaction was monitored with the TLC plate and LC-MS, 100 mL water was added to the reaction solution. The resulting mixture was extracted with ethyl acetate, and dried over anhydrous sodium sulfate. The organic phase was concentrated, and separated and purified with the reverse phase HPLC (C18, 0.08% aqueous $NH_4HCO_3$ solution/acetonitrile) to produce the title compound (900 mg, yield: 56.3%).

LC-MS (ESI) $[M+H]^+$=373.

Preparation Example 3: Preparation of 6-((1-acetylpiperidin-4-yl)amino)-2-(benzo[d]thiazol-5-yl)pyrimidine-4-carboxylic acid (for example this intermediate could be used as an intermediate for the compound of Example 9)

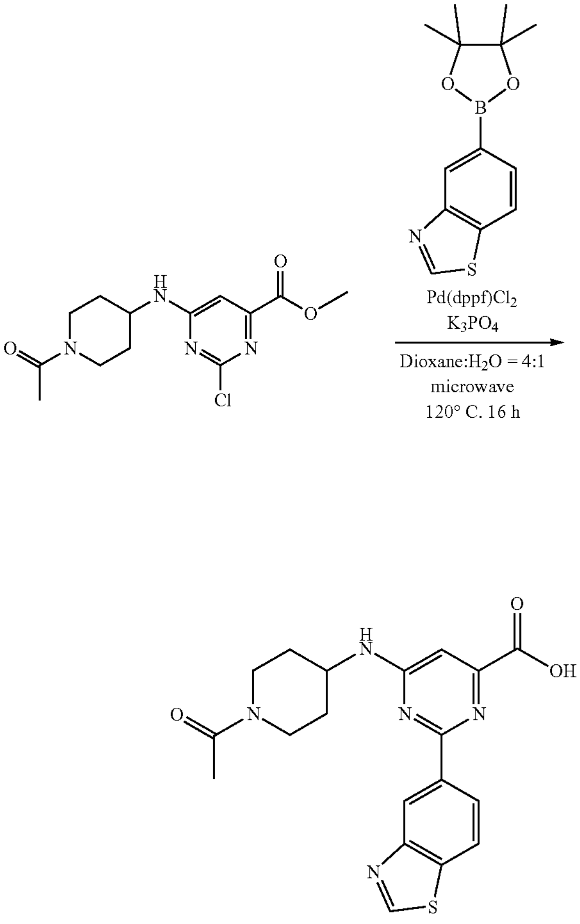 [SMILES: COC(=O)c1cc(NC2CCN(C(C)=O)CC2)nc(Cl)n1 ; CC1(C)OB(c2ccc3scnc3c2)OC1(C)C ; CC(=O)N1CCC(Nc2cc(C(=O)O)nc(-c3ccc4scnc4c3)n2)CC1]

6-((1-acetylpiperidin-4-yl)amino)-2-chloropyrimidine-4-carboxylic acid methyl ester (90 mg, 0.29 mmol, 1.0 equiv.), benzothiazole-5-boronic acid pinacol ester (113 mg, 0.43 mmol, 1.5 equiv.), (1,1-bis (diphenylphosphino)ferrocene) palladium dichloride (21 mg, 0.03 mmol, 0.1 equiv.) and potassium phosphate (183 mg, 0.86 mmol, 3.0 equiv.) were dissolved in dioxane (2 mL) and water (0.5 mL). The atmosphere was replaced with nitrogen gas three times. The reaction was performed at 120° C. for 16 hours. After the completion of the reaction was detected with LC-MS, the reaction mixture was extracted with dichloromethane (5 mL) three times. The aqueous phase was concentrated, and the solvent was removed by rotary drying to produce a crude product of the title compound (80 mg).

LC-MS (ESI) $[M+H]^+$=398.20.

Preparation Example 4: Preparation of 2-phenyl-6-((tetrahydro-2H-pyran-4-yl)amino)pyrimidine-4-carboxylic acid (for example this intermediate could be used as an intermediate for the compound of Example 10)

Step 1: Preparation of 2-chloro-6-((tetrahydro-2H-pyran-4-yl)amino)pyrimidine-4-carboxylic acid methyl ester

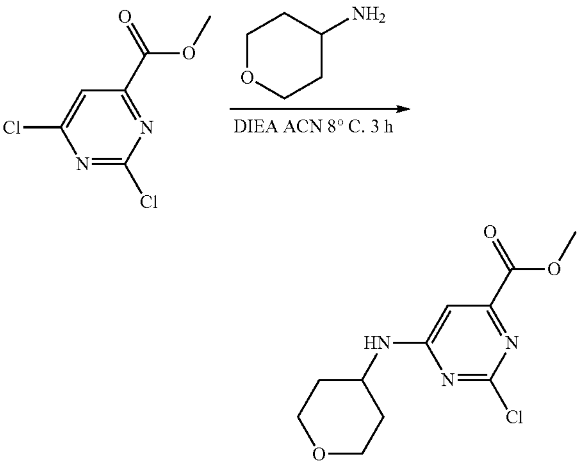

2,6-dichloropyrimidine-4-carboxylic acid methyl ester (500 mg, 2.41 mmol, 1.01 equiv.) and tetrahydro-2H-pyran-4-amine (240 mg, 2.37 mmol, 1 equiv.) were dissolved in acetonitrile (12 mL), and DIPEA (920 mg, 7.12 mmol, 3 equiv.) was added. The reaction was performed at 80° C. under stirring for 3 hours. The completion of the reaction was monitored with LC-MS. The reaction solution was quenched with water, and then extracted with ethyl acetate. The organic phases were combined, then washed with saturated sodium chloride, dried over anhydrous sodium sulfate, then filtered, and concentrated to produce a crude product, which was separated and purified with flash chromatography (silica gel, petroleum ether:ethyl acetate=0-15%) to produce the title compound (500 mg, yield: 82%).

LC-MS (ESI) $[M+H]^+$=272.1.

Step 2: Preparation of 2-phenyl-6-((tetrahydro-2H-pyran-4-yl)amino)pyrimidine-4-carboxylic acid

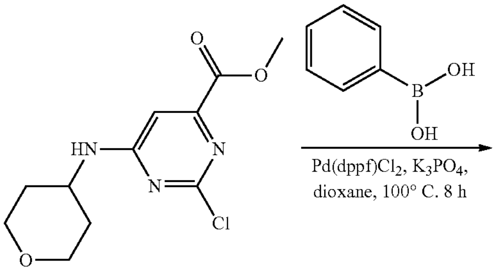

-continued

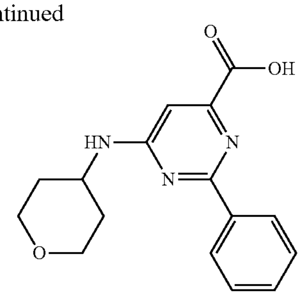

2-chloro-6-((tetrahydro-2H-pyran-4-yl)amino)pyrimidine-4-carboxylic acid methyl ester (200 mg, 0.737 mmol, 1.0 equiv.), and phenylboronic acid (140 mg, 1.106 mmol, 1.5 equiv.) were dissolved in 1,4-dioxane (2.5 mL) and water (0.5 mL), and $Pd(dppf)Cl_2$ (270 mg, 0.369 mmol, 0.5 equiv.) and potassium phosphate (470 mg, 2.211 mmol, 3 equiv.) were added. The reaction was performed at 100° C. under stirring for 8 hours. The completion of the reaction was monitored with LC-MS. The reaction solution was quenched with water, and then filtered with diatomite to remove an insoluble solid impurity. The filtrate was extracted with ethyl acetate. The aqueous phase was directly concentrated. The obtained solid was dissolved into dichloromethane and methanol. The resulting mixture was filtered. The filtrate was collected, and concentrated to produce a crude product of the title compound (98 mg), which was directly used in the next step.

LC-MS (ESI) $[M+H]^+$=300.2.

Preparation Example 5: Preparation of 6-((1-acetylpiperidin-4-yl)amino)-2-(benzo[d]oxazol-7-yl) pyrimidine-4-carboxylic acid (for example this intermediate could be used as an intermediate for the compound of Example 13)

Step 1: Preparation of 7-bromobenzo[d]oxazole

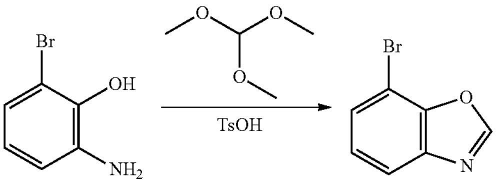

2-amino-6-bromophenol (1.0 g, 5.319 mmol, 1 equiv.) was dissolved in trimethyl orthoformate (10 mL), and p-toluenesulfonic acid (100 mg, 0.581 mmol, 0.11 equiv.) was added. The reaction was performed under nitrogen gas at 80° C. under stirring for 2 hours. The completion of the reaction was monitored with TLC. The reaction solution was rotary dried under a reduce pressure. The resulting crude product was separated and purified with flash chromatography (silica gel, EA:PE=1:20) to produce the title compound (1.12 g, yield: 98.9%).

LC-MS (ESI) $[M+H]^+$=180.0.

Step 2: Preparation of 7-(4,4,5,5-tetramethyl-1,3,2-dioxaborolane-2-yl)benzo[d]oxazole

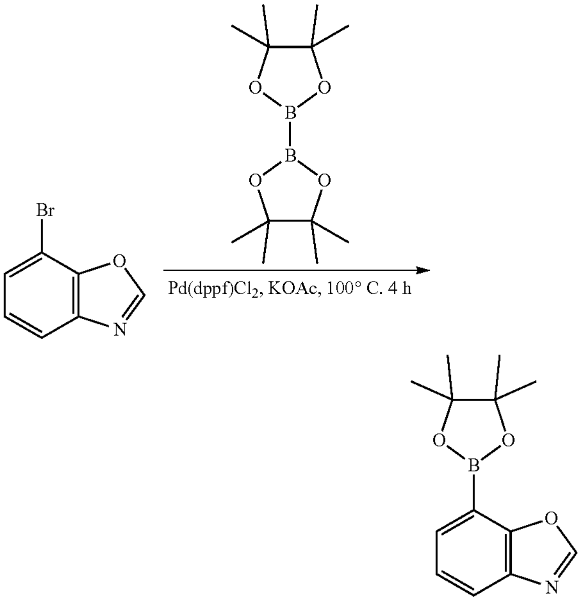

7-bromobenzo[d]oxazole (210 mg, 1.060 mmol, 1 equiv.), bis (pinacolato)diboron (645 mg, 2.540 mmol, 2.4 equiv.), $Pd(dppf)Cl_2$ (74 mg, 0.102 mmol, 0.1 equiv.) and potassium acetate (200 mg, 2.038 mmol, 1.92 equiv.) was weighed and placed in a microwave tube. The tube was capped, and the atmosphere was replaced with nitrogen gas. 1,4-dioxane (5 mL) was added. Under the protection of nitrogen gas, the resulting mixture was heated to 100° C. and reacted for 2 hours. The completion of the reaction was monitored with LC-MS. The reaction solution was filtered, and rotary dried. The resulting crude product was separated and purified with flash chromatography (silica gel, EA:PE=1:20) to produce the title compound (252 mg, yield: 97%).

LC-MS (ESI) $[M+H]^+$=246.2, 341.0; $^1H$ NMR (400 MHz, $CDCl_3$) δ 8.20 (s, 1H), 7.90 (d, J=7.9 Hz, 1H), 7.83 (d, J=7.4 Hz, 1H), 7.39 (t, J=7.6 Hz, 1H), 1.42 (s, 12H).

Step 3: Preparation of 6-((1-acetylpiperidin-4-yl) amino)-2-(benzo[d]oxazol-7-yl)pyrimidine-4-carboxylic acid methyl ester

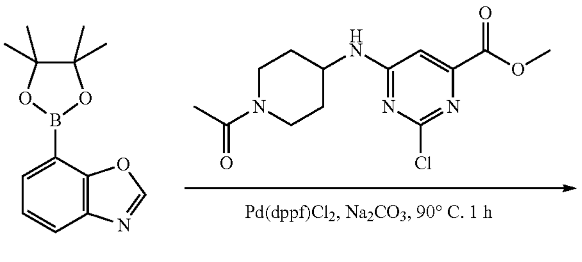

-continued

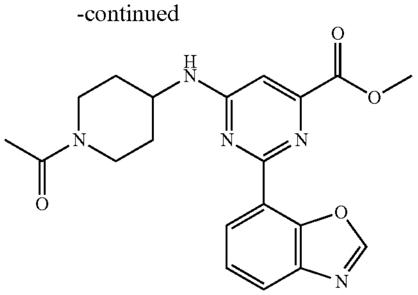

7-(4,4,5,5-tetramethyl-1,3,2-dioxaborolane-2-yl)benzo[d]oxazole (100 mg, 0.408 mmol, 1 equiv.), 6-((1-acetylpiperidin-4-yl)amino)-2-chloropyrimidine-4-carboxylic acid methyl ester (127 mg, 0.406 mmol, 1 equiv.), Pd(dppf)$Cl_2$ (30 mg, 0.0410 mmol, 0.1 equiv.) and sodium carbonate (80 mg, 0.755 mmol, 1.86 equiv.) were weighed and placed in a 50 mL single-neck flask, and 1,4-dioxane (2 mL) and water (0.5 mL) were added. The system atmosphere was replaced with nitrogen gas. The resulting mixture was heated to 90° C. and reacted for 1 hour. The completion of the reaction was monitored with LC-MS. To the reaction solution were added ethyl acetate and water, two phases were separated, and the aqueous phase was extracted with ethyl acetate (2×15 mL). The organic phases were combined, dried over anhydrous sodium sulfate, filtered, and rotary dried. The crude product was separated and purified with flash chromatography (silica gel, MeOH:DCM=1:25) to produce the title compound (66 mg, yield: 41.1%).

LC-MS (ESI) $[M+H]^+$=396.20.

Step 4: Preparation of 6-((1-acetylpiperidin-4-yl)amino)-2-(benzo[d]oxazol-7-yl)pyrimidine-4-carboxylic acid (Intermediate 3)

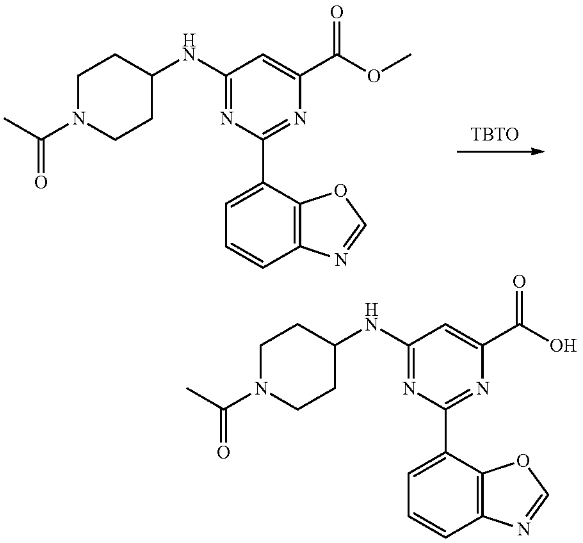

Tributyltin oxide (180 mg, 0.302 mmol, 1.99 equiv.) was added to a suspension of 6-((1-acetylpiperidin-4-yl)amino)-2-(benzo[d]oxazol-7-yl)pyrimidine-4-carboxylic acid methyl ester (60 mg, 0.152 mmol, 1 equiv.) in toluene (5 mL). Under the protection of nitrogen gas, the resulting mixture was heated at 110° C. and refluxed for 4 hours. The completion of the reaction was monitored with TLC. The toluene was removed by rotary drying, and then petroleum ether was added to form a slurry. The slurry was filtered, and the filter cake was rinsed with petroleum ether. The residual solvent was removed by suction with an oil pump to produce the title compound (75 mg), which was directly used in the next step.

LC-MS (ESI) $[M+H]^+$=382.0.

Preparation Example 6: Preparation of 4-((6-((3R,4R)-4-(3,4-dihydroisoquinoline-2(1H)-yl)-3-hydroxypiperidine-1-carbonyl)-2-phenylpyrimidine-4-yl)amino)piperidine-1-carboxylic acid tert-butyl ester (for example this intermediate could be used as an intermediate for the compound of Example 20)

Step 1: Preparation of 6-((1-(tert-butoxycarbonyl)piperidin-4-yl)amino)-2-chloropyrimidine-4-carboxylic acid methyl ester

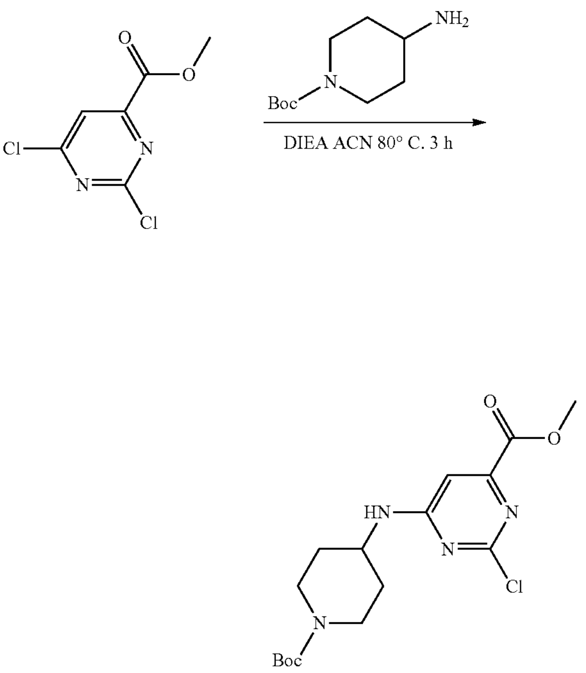

2,6-dichloropyrimidine-4-carboxylic acid methyl ester (1.086 g, 5.24 mmol, 1.05 equiv.) and 4-aminopiperidine-1-carboxylic acid tert-butyl ester (1 g, 4.99 mmol, 1.05 equiv.) were dissolved in acetonitrile (40 mL), and DIPEA (1.94 g, 14.97 mmol, 3 equiv.) was added. The reaction was performed at 80° C. under stirring for 3 hours. The completion of the reaction was monitored with LC-MS. The reaction solution was quenched with water, and then extracted with ethyl acetate. The organic phases were combined, then washed with saturated sodium chloride, dried over anhydrous sodium sulfate, then filtered, and concentrated to produce a crude product, which was separated and purified with flash chromatography (silica gel, petroleum ether:ethyl acetate=1:5) to produce the title compound (1.5 g, yield: 80%).

LC-MS (ESI) $[M+H]^+$=371.0.

Step 2: Preparation of 6-((1-(tert-butoxycarbonyl)piperidine-4-yl)amino)-2-phenylpyrimidine-4-carboxylic acid methyl ester

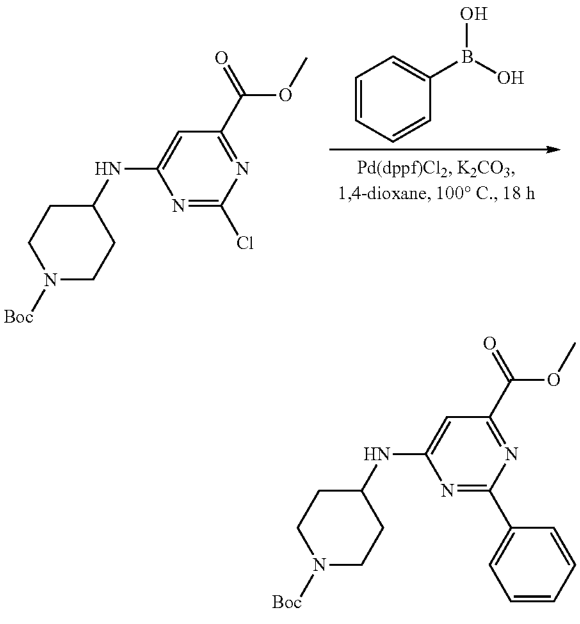

6-((1-(tert-butoxycarbonyl)piperidin-4-yl)amino)-2-chloropyrimidine-4-carboxylic acid methyl ester (300 mg, 0.809 mmol, 1.0 equiv.), phenylboronic acid (148 mg, 1.213 mmol, 1.5 equiv.) were dissolve in 1,4-dioxane (8 mL) and water (2 mL), and Pd(dppf)Cl$_2$ (118 mg, 0.162 mmol, 0.2 equiv.) and potassium phosphate (859 mg, 4.045 mmol, 5 equiv.) were added. The reaction was performed at 100° C. under stirring for 18 hours. The completion of the reaction was monitored with LC-MS. The reaction solution was filtered to remove an insoluble solid impurity. The filtrate was extracted with ethyl acetate. Then the aqueous phase was directly concentrated. The obtained solid was dissolved into dichloromethane and methanol. Then the resulting mixture was filtered. The filtrate was collected, and concentrated to produce the title compound (340 mg, crude product).

LC-MS (ESI) $[M+H]^+$=399.2.

Step 3: Preparation of 4-((6-((3R,4R)-4-(3,4-dihydroisoquinoline-2(1H)-yl)-3-hydroxypiperidine-1-carbonyl)-2-phenylpyrimidine-4-yl)amino)piperidine-1-carboxylic acid tert-butyl ester

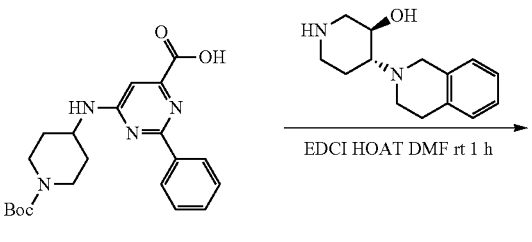

-continued

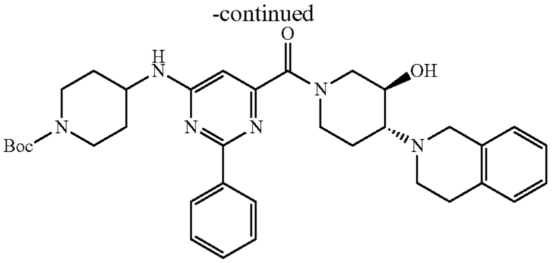

6-((1-(tert-butoxycarbonyl)piperidin-4-yl)amino)-2-phenylpyrimidine-4-carboxylic acid (340 mg crude product), (3R,4R)-4-(3,4-dihydroisoquinoline-2(1H)-yl)piperidine-3-ol (200 mg, 0.861 mmol, 1 equiv.), EDCI (198 mg, 1.033 mmol, 1.2 equiv.) and HOAt (140 mg, 1.033 mmol, 1.2 equiv.) were dissolved in DMF (2 mL). The reaction solution was stirred at 25° C. for 1 hour. LC-MS indicated the completion of the reaction. The reaction solution was quenched with water, and then extracted with dichloromethane and methanol. The organic phases were combined, dried over anhydrous sodium sulfate, filtered, and concentrated to produce the title compound (1 g).

LC-MS (ESI) $[M+H]^+$=613.4.

Preparation Example 7: Preparation of trans-(4-(3,4-dihydroisoquinoline-2(1H)-yl)-3-hydroxypiperidine-1-yl)(6-((2,4-dimethoxybenzyl)(4-methoxybutyl)amino)-2-phenylpyrimidine-4-yl)ketone (for example this intermediate could be used as an intermediate for the compound of Example 45)

Step 1: Preparation of N-(2,4-dimethoxybenzyl)-4-methoxybutyl-1-amine

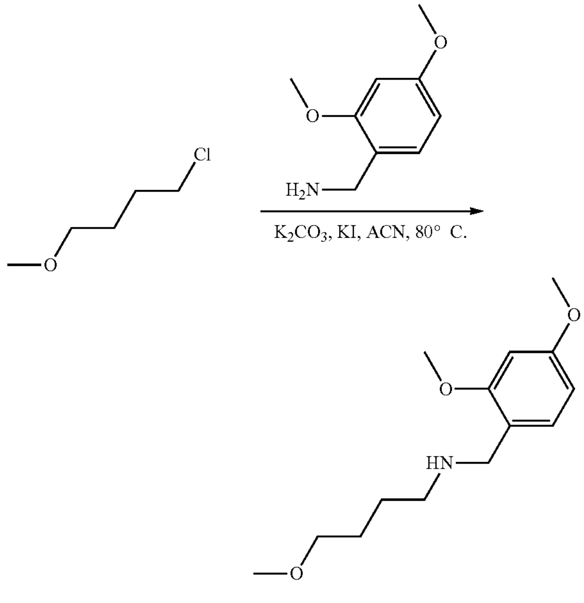

4-chlorobutyl methyl ether (300 mg, 2.45 mmol, 1 equiv.) and 2,4-dimethoxybenzylamine (1.64 g, 9.81 mmol, 4.01 equiv.) were dissolved in acetonitrile (9 mL), and potassium carbonate (676 mg, 4.89 mmol, 2 equiv.) and potassium iodide (812 mg, 4.89 mmol, 2 equiv.) were added. The resulting mixture was stirred overnight (16 hours) at 80° C.

LC-MS monitoring indicated a product was formed. The reaction solution was filtered. The filtrate was rotary dried. The crude product was separated and purified with flash chromatography (silica gel, MeOH:EA=1:50) to produce the title compound (90 mg, yield: 11.8%).

LC-MS (ESI) $[M+H]^+=254.2$.

Step 2: Preparation of 2-chloro-6-((2,4-dimethoxybenzyl)(4-methoxybutyl)amino)pyrimidine-4-carboxylic acid methyl ester

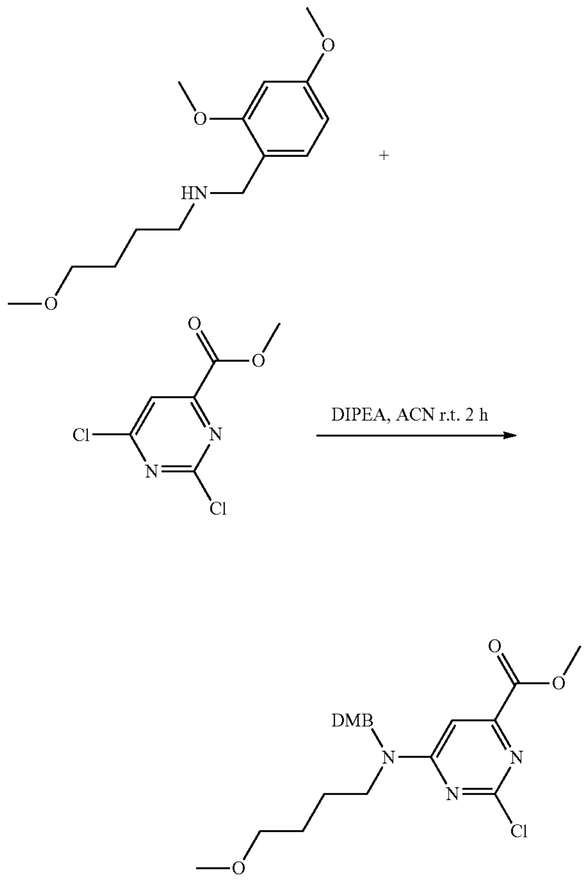

N-(2,4-dimethoxybenzyl)-4-methoxybutyl-1-amine (90 mg, 0.356 mmol, 1 equiv.) and 2,6-dichloropyrimidine-4-carboxylic acid methyl ester (220 mg, 1.063 mmol, 3 equiv.) were dissolved in acetonitrile (3 mL), and DIPEA (250 mg, 1.934 mmol, 5.4 equiv.) was added. The resulting mixture was stirred for 2 hours at room temperature (25° C.). After the completion of the reaction was monitored with TLC, the solvent was removed by rotary drying. The crude product was separated and purified with flash chromatography (silica gel, EA:PE=1:5) to produce the title compound (134 mg, yield: 75.5%).

LC-MS (ESI) $[M+H]^+=424.2$.

Step 3: Preparation of 6-((2,4-dimethoxybenzyl(4-methoxybutyl)amino)-2-phenylpyrimidine-4-carboxylic acid

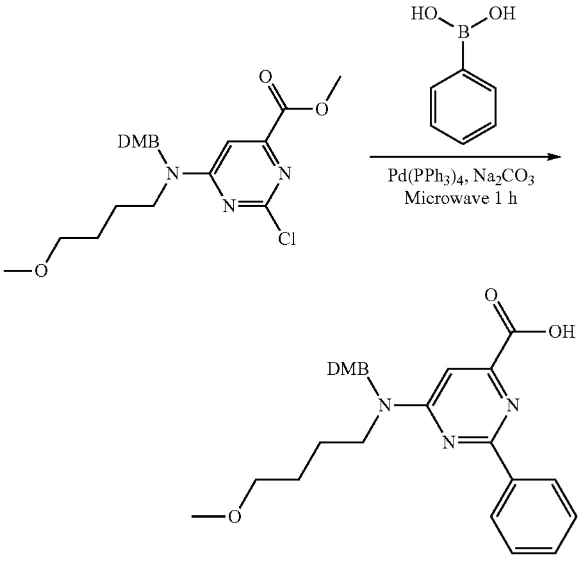

2-chloro-6-((2,4-dimethoxybenzyl)(4-methoxybutyl)amino)pyrimidine-4-carboxylic acid methyl ester (134 mg, 0.316 mmol, 1 equiv.), phenylboronic acid (77 mg, 0.632 mmol, 2 equiv.), tetrakis (triphenylphosphine)palladium (36 mg, 0.0312 mmol, 0.1 equiv.) and sodium carbonate (70 mg, 0.660 mmol, 2.09 equiv.) was weighed and placed in a microwave tube. The tube was capped, and the atmosphere was replaced with nitrogen gas. Dioxane (1.6 mL) and water (0.4 mL) were added. The reaction was performed under a nitrogen gas condition under microwave at 120° C. for 1 hour. The completion of the reaction was monitored with LC-MS. 1M (molar concentration) aqueous hydrochloric acid solution was added, and the pH was adjusted to 4-5. The resulting mixture was filtered and the solvent was removed by rotary drying to produce a crude product of the title compound, which was directly used in the next step.

LC-MS (ESI) $[M+H]^+=452.2$.

Step 4: Preparation of trans-(4-(3,4-dihydroisoquinolin-2(1H)-yl)-3-hydroxypiperidin-1-yl) (6-((2,4-dimethoxybenzyl)(4-methoxybutyl)amino)-2-phenylpyrimidin-4-yl) methanone

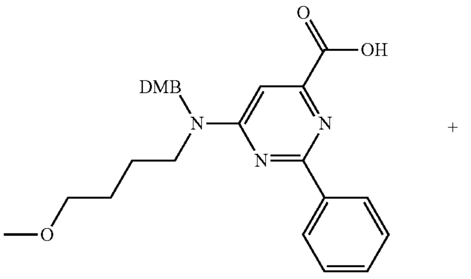

-continued

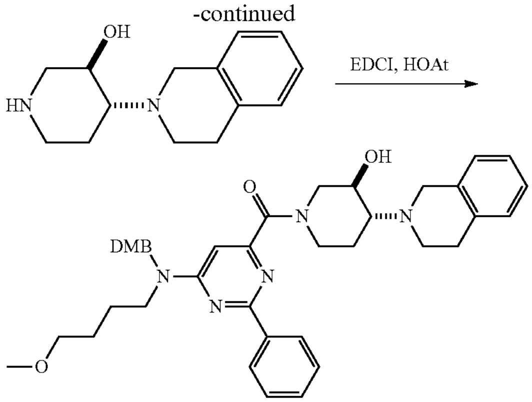

6-((2,4-dimethoxybenzyl)(4-methoxybutyl)amino)-2-phenylpyrimidine-4-carboxylic acid (180 mg, 0.315 mmol, 1 equiv.), EDCI (1-(3-dimethylaminopropyl)-3-ethylcarbodiimide hydrochloride) (91 mg, 0.475 mmol, 1.51 equiv.) and HOAt (N-hydroxy-7-azabenzotriazole) (65 mg, 0.478 mmol, 1.52 equiv.) were dissolved in DMF (1 mL), and the mixture was stirred for 5 minutes. Then a solution of trans-4-(3,4-dihydroisoquinoline-2(1H)-yl)piperidine-3-ol (88 mg, 0.379 mmol, 1.2 equiv.) in DMF (0.6 mL) was added. The reaction was performed at room temperature under stirring for 2 hours. The solvent was removed by rotary drying, and the resulting crude product was separated and purified with flash chromatography (silica gel, MeOH: DCM=1:20) to produce the title compound (51 mg, yield: 24.4%).

LC-MS (ESI) $[M+H]^+$=666.4.

Preparation Example 8: Preparation of 6-((1-acetylpiperidin-4-yl)amino)-2-vinylpyrimidine-4-carboxylic acid (for example this intermediate could be used as an intermediate for the compound of Example 46)

Step 1: Preparation of 6-((1-acetylpiperidin-4-yl)amino)-2-vinylpyrimidine-4-carboxylic acid methyl ester

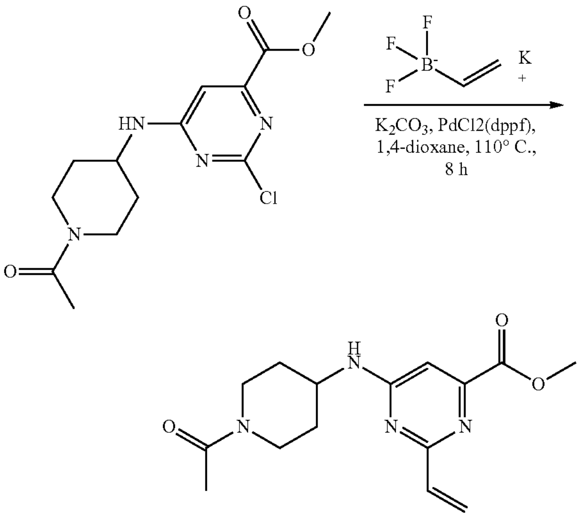

6-((1-acetylpiperidin-4-yl)amino)-2-chloropyrimidine-4-carboxylic acid methyl ester (0.90 g, 2.9 mmol, 1 equiv.), potassium vinyltrifluoroborate (0.46 g, 3.5 mmol, 1.2 equiv.), potassium carbonate (0.99 g, 7.2 mmol, 2.5 equiv.) and [1,1-bis(diphenylphosphino)ferrocene]palladium dichloride (90 mg, 0.1 equiv.) were dissolved in 1,4-dioxane (30 mL). The atmosphere was replaced with nitrogen gas for 2 minutes. The resulting mixture was heated to 110° C. and reacted for 8 hours. After the completion of the reaction was detected with LC-MS, the reaction mixture was filtered. The filter cake was washed twice with a mixed solvent (DCM: MeOH=10:1) (15 mL). The filtrate was concentrated. The crude product was firstly separated with a reverse phase column chromatography by using a mixed solvent (DCM: MeOH=10:1), and concentrated to produce the title compound (0.85 g, yield: 97%).

LC-MS (ESI) $[M+H]^+$=305.2.

Step 2: Preparation of 6-((1-acetylpiperidin-4-yl)amino)-2-vinylpyrimidine-4-carboxylic acid

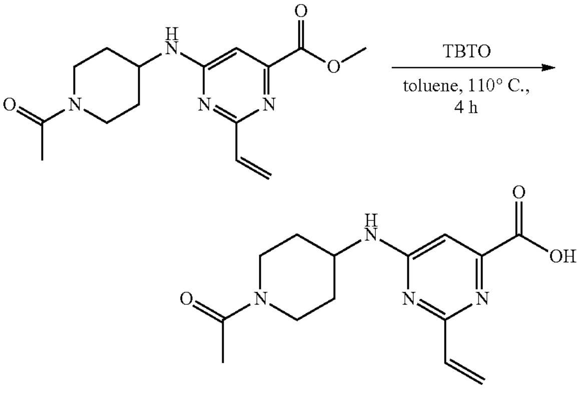

Tributyltin oxide (0.47 g, 0.79 mmol, 1.2 equiv.) was added to a mixed solution of 6-((1-acetylpiperidin-4-yl)amino)-2-vinylpyrimidine-4-carboxylic acid methyl ester (0.2 g, 0.66 mmol, 1 equiv.), acetonitrile (4 mL, 20%) and toluene (16 mL, 80%). The reaction was performed at 110° C. for 4 hours. After the completion of the reaction was detected with LC-MS, the crude product was quenched with an aqueous KF solution (2 mL), and the resulting mixture was concentrated. Then the crude product was slurrized with diethyl ether, and the resulting slurry was dried by suction to produce the title compound (0.15 g, yield: 78%).

LC-MS (ESI) $[M+H]^+$=291.1.

Preparation Example 9: Preparation of 6-((1-acetylpiperidin-4-yl)amino)-2-(thiazolo[4,5-c]pyridine-7-yl)pyrimidine-4-carboxylic acid (for example this intermediate could be used as an intermediate for the compound of Example 63)

Step 1: Preparation of 3-bromo-5-nitropyridine-4-thiol

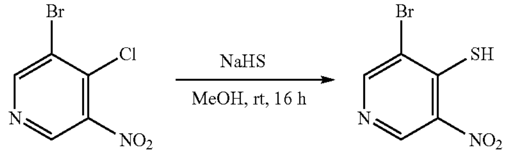 [SMILES: O=[N+]([O-])c1cncc(Br)c1Cl ; "NaHS" ; O=[N+]([O-])c1cncc(Br)c1S]

3-bromo-4-chloro-5-nitropyridine (10 g, 42.12 mmol, 1.0 equiv.) was dissolved in methanol (80 mL), and sodium hydrogensulfide (4.72 g, 84.23 mmol, 2.0 equiv., purity 70%) was added. The resulting mixture was stirred at 25° C. for 16 hours. After the completion of the reaction was detected with LC-MS, sodium hydroxide solution (100 mL, 20%) was added. Then the resulting mixture was filtered. The filtrate was acidified with HCl to pH=4, and then filtered. The filter cake was dried to produce the title compound (9 g, yield: 90.9%).

LC-MS (ESI) $[M-H]^-$=232.8.

Step 2: Preparation of 3-amino-5-bromopyridine-4-thiol

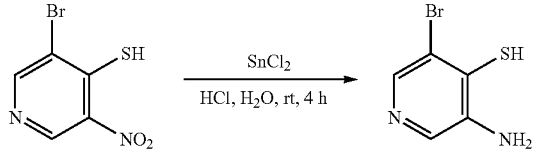 [SMILES: O=[N+]([O-])c1cncc(Br)c1S ; "SnCl2" ; Nc1cncc(Br)c1S]

3-bromo-5-nitropyridine-4-thiol (10 g, 42.5 mmol, 1.0 equiv.) was dissolved in water (60 mL) and HCl (12M, 25 mL). Stannous chloride (16.13 g, 85.1 mmol, 2.0 equiv.) was added. The resulting mixture was stirred for 4 hours. After the completion of the reaction was detected with LC-MS, the reaction mixture was filtered. The filtrate was concentrated to produce a crude product of the title compound (12 g), which was directly used in the next step.

LC-MS (ESI) $[M-H]^-$=202.8.

Step 3: Preparation of 7-bromothiazolo[4,5-c]pyridine

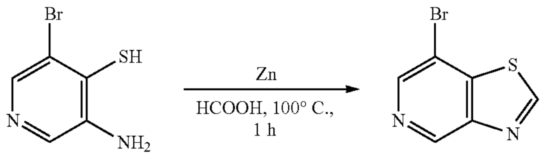

3-amino-5-bromopyridine-4-thiol (10 g, 48.76 mmol, 1.0 equiv.) was dissolved in formic acid (50 mL). Zinc powder (1.59 g, 24.38 mmol, 0.5 equiv.) was added. The resulting mixture was reacted at 100° C. for 1 hour. After the completion of the reaction was detected with LC-MS, the reaction mixture was concentrated. The crude product was separated and purified with flash chromatography (silica gel, 50% EA/PE solution) to produce the title product (2.7 g, yield: 25.7%).

LC-MS (ESI) $[M+H]^+$=215.8.

Step 4: Preparation of thiazolo[4,5-c]pyridine-7-yl boric acid

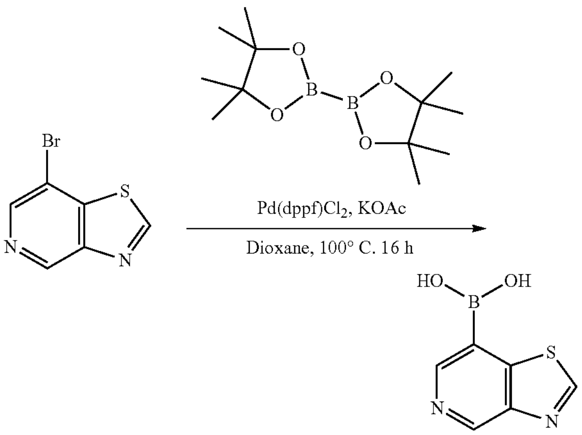

7-bromothiazolo[4,5-c]pyridine (300 mg, 1.39 mmol, 1.0 equiv.), bis (pinacolato)diboron (885 mg, 3.49 mmol, 2.5 equiv.), (1,1'-bis(diphenylphosphino)ferrocene)palladium dichloride (102 mg, 0.14 mmol, 0.1 equiv.) and potassium acetate (274 mg, 2.79 mmol, 2.0 equiv.) were dissolved in dioxane (7 mL). The atmosphere was replaced with nitrogen gas three times. The reaction was performed at 120° C. for 16 hours. After the completion of the reaction was detected with LC-MS, the reaction mixture was concentrated, to produce a crude product of the title compound (350 mg), which was directly used in the next step.

LC-MS (ESI) $[M+H]^+$=180.92.

Step 5: Preparation of 6-((1-acetylpiperidin-4-yl)amino)-2-(thiazolo[4,5-c]pyridine-7-yl)pyrimidine-4-carboxylic acid methyl ester

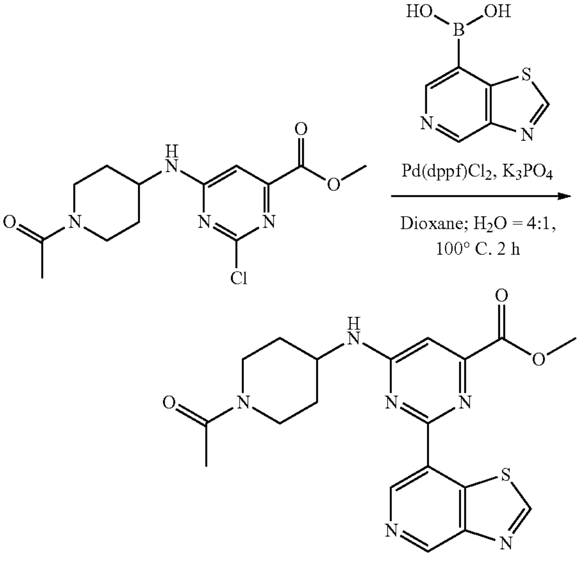

6-((1-acetylpiperidin-4-yl)amino)-2-chloropyrimidine-4-carboxylic acid methyl ester (300 mg, 0.96 mmol, 1.0 equiv.), thiazolo[4,5-c]pyridine-7-yl boric acid (259 mg, 1.44 mmol, 1.5 equiv.), (1,1'-bis(diphenylphosphino)ferrocene)palladium dichloride (76 mg, 0.09 mmol, 0.1 equiv.) and potassium phosphate (1.02 g, 4.80 mmol, 5.0 equiv.) were dissolved in dioxane (6 mL) and water (1.5 mL). The atmosphere was replaced with nitrogen gas three times. The reaction was performed at 100° C. for 2 hours. After the completion of the reaction was detected with LC-MS, the reaction mixture was concentrated. The crude product was separated and purified with flash chromatography (silica gel, 5% MeOH/DCM solution) to produce the title compound (390 mg, yield: 98.6%).

LC-MS (ESI) $[M+H]^+$=412.85.

Step 6: Preparation of 6-((1-acetypiperidin-4-yl) amino)-2-(thiazolo[4,5-c]pyridine-7-yl)pyrimidine-4-carboxylic acid

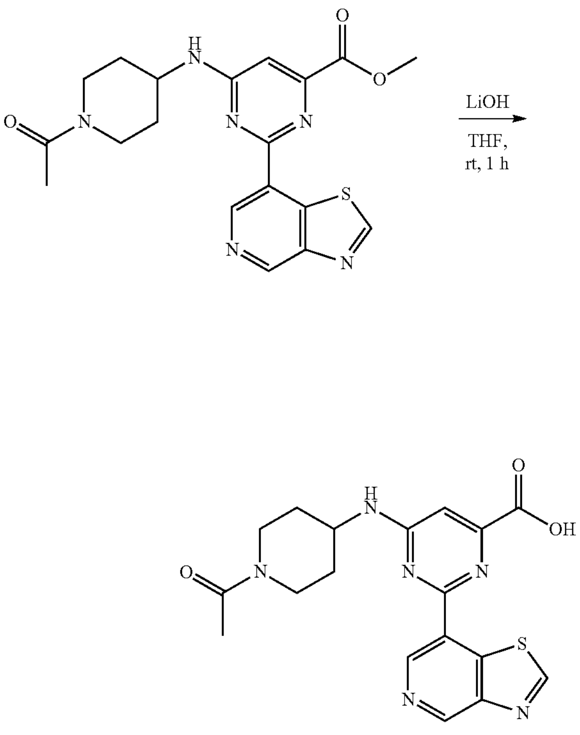

6-((1-acetylpiperidin-4-yl)amino)-2-(thiazo[4,5-c]pyridine-7-yl)pyrimidine-4-carboxylic acid methyl ester (350 mg, 0.85 mmol, 1.0 equiv.), was dissolved in tetrahydrofuran (5 mL), and an aqueous lithium hydroxide solution (2M) (24 mg, 1.02 mmol, 1.2 equiv.) was added. The resulting mixture was stirred at 25° C. for 1 hour. After the completion of the reaction was detected with LC-MS, the reaction mixture was concentrated to produce a crude product of the title compound (370 mg), which could be directly used in the next step.

LC-MS (ESI) $[M+H]^+$=399.0.

Preparation Example 10: Preparation of 4-((1-acetylpiperidin-4-yl)amino)-6-phenyl-1,3,5-triazine-2-carboxylic acid (for example this intermediate could be used as an intermediate for the compound of Example 70)

Step 1: Preparation of 1-(4-((4,6-dichloro-1,3,5-triazin-2-yl)amino)piperidine-1-yl)ethane-1-one

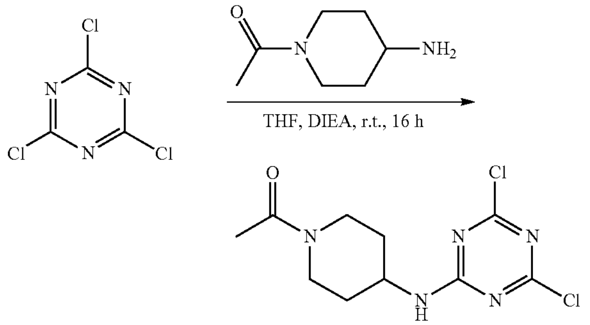

Cyanuric chloride (4.0 g, 0.0217 mol, 1 equiv.), 1-(4-aminopiperidine-1-yl)ethane-1-one (3.08 g, 0.0217 mol, 1 equiv.) was added to tetrahydrofuran (110 mL). Then N,N-diiso-propylethylamine (5.61 g, 0.0434 mol, 2 equiv.) was added. The mixture was stirred at 16° C. for 16 hours, and TLC detected the reaction of raw materials was completed. The solvent was removed by rotary drying. The crude product was purified with a column chromatography (DCM: MeOH=99:1) to produce the title compound (3.98 g, yield: 63.2%).

LC-MS (ESI) $[M+H]^+$=290.0.

Step 2: Preparation of 1-(4-((4-chloro-6-phenyl-1,3,5-triazine-2-yl)amino)piperidine-1-yl)ethane-1-one

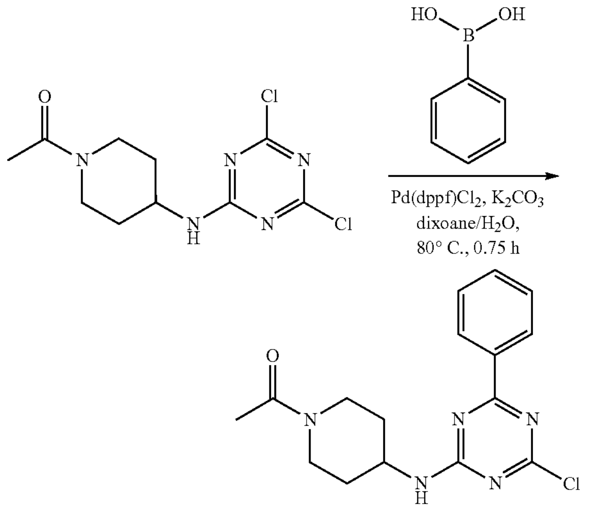

1-(4-((4,6-dichloro-1,3,5-triazine-2-yl)amino)piperidine-1-yl)ethane-1-one (2 g, 6.893 mmol, 1 equiv.), phenylboronic acid (0.84 g, 6.893 mmol, 1 equiv.), and potassium carbonate (2.86 g, 20.68 mmol, 3 equiv.) were added to 1,4-dioxane/water (45 mL, 4:1). Then [1,1'-bis(diphenylphosphino)ferrocene]palladium dichloride (252 mg, 0.345 mmol, 0.05 equiv.) was added. The mixture was stirred under nitrogen gas at 80° C. for 0.75 hours, and TLC detected the reaction of raw materials was completed. To the reaction system was added water, and the reaction system was extracted with ethyl acetate (50 mL) three times. The solvent was removed by rotary drying. The crude product was purified with a column chromatography (DCM: MeOH=99:1) to produce the title compound (0.498 g, yield: 21.8%).

LC-MS (ESI) $[M+H]^+$=332.0.

Step 3: Preparation of 4-((1-acetylpiperidin-4-yl)amino)-6-phenyl-1,3,5-triazine-2-carboxylic acid methyl ester

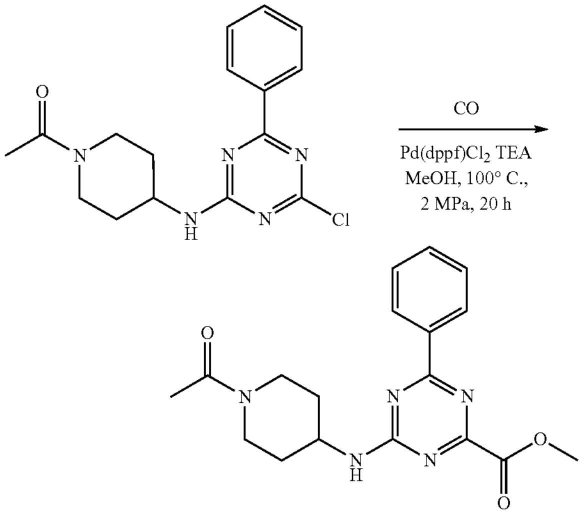

1-(4-((4-chloro-6-phenyl-1,3,5-triazine-2-yl)amino)piperidine-1-yl)ethane-1-one (0.44 g, 1.33 mmol, 1 equiv.), and triethylamine (0.671 g, 6.63 mmol, 5 equiv.) were added to methanol (30 mL). Then [1,1'-bis(diphenylphosphino)ferrocene]palladium dichloride (97 mg, 0.133 mmol, 0.1 equiv.) was added. The resulting mixture was stirred under carbon monoxide at 100° C. under 2 MPa for 20 hours, and TLC detected the reaction of raw materials was completed. The solvent was removed by rotary drying. The crude product was purified with a column chromatography (DCM: MeOH=98:2) to produce the title compound (0.21 g, yield: 44.6%).

LC-MS (ESI) $[M+H]^+$=356.2.

Step 4: Preparation of 4-((1-acetylpiperidine-4-yl)amino)-6-phenyl-1,3,5-triazine-2-carboxylic acid

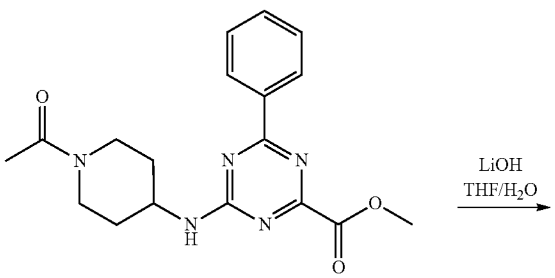

-continued

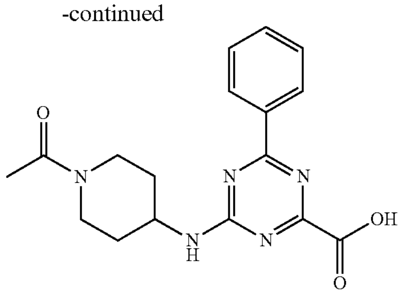

4-((1-acetylpiperidine-4-yl)amino)-6-phenyl-1,3,5-triazine-2-carboxylic acid methyl ester (150 mg, 0.422 mmol, 1 equiv.) was dissolved in tetrahydrofuran/water (5 mL, 4:1). Lithium hydroxide (20 mg, 0.844 mmol, 2 equiv.) was added. The resulting mixture was stirred at 16° C. for 2 hours. TLC detected the reaction of raw materials was completed. Water was added to the reaction system. The reaction system was extracted with ethyl acetate (15 mL) three times. The aqueous phase was adjusted with 1M HCl solution to pH=4-5, and lyophilized to produce a crude product of the title compound (0.13 g, yield: 90.2%).

LC-MS (ESI) $[M+H]^+$=342.2.

Preparation Example 11: Preparation of 6-((3-(N-methylacetylamido)propyl)amino)-2-phenylpyrimidine-4-carboxylic acid (for example this intermediate could be used as an intermediate for the compound of Example 74)

Step 1: Preparation of (3-(N-methylacetylamido)propyl)carbamic acid tert-butyl ester

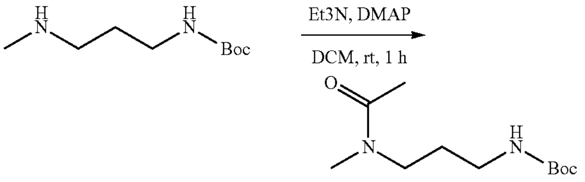

(3-(methylamino)propyl)carbamic acid tert-butyl ester (980 mg, 5.3 mmol), DMAP (68 mg, 0.06 mmol) and $Et_3N$ (1.07 g, 1.06 mmol) were dissolved in DCM (10 mL). The resulting mixture was cooled to 0° C., and then acetyl chloride (540 mg, 6.9 mmol) was added dropwise. The reaction solution was stirred at room temperature (25-30° C.) for 2 hours. The reaction was monitored with TLC until raw materials disappeared. The reaction mixture was extracted with ethyl acetate three times, each time 20 mL. The ethyl acetate phases were combined, washed with water (10 mL) once, washed with saturated brine (10 mL) once, dried over anhydrous sodium sulfate for 10 minutes, filtered, and concentrated by rotary drying to obtain a crude product, which was then purified with a column chromatography to produce the title compound (1.328 g).

$^1H$ NMR (400 MHz, $CDCl_3$) δ 5.39 (s, 1H), 3.50-3.27 (m, 2H), 3.20-3.03 (m, 2H), 3.01-2.87 (m, 3H), 2.09 (s, 3H), 1.84- 1.61 (m, 2H), 1.44 (d, J=4.6 Hz, 9H).

Step 2: Preparation of N-(3-aminopropyl)-N-methylacetamide trifluoroacetate

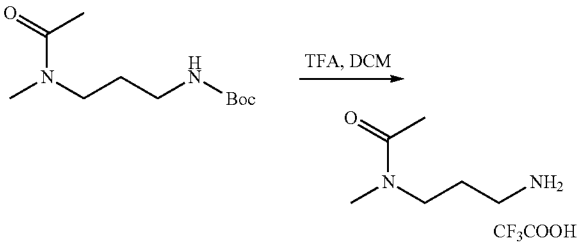

(3-(N-methylacetylamido)propyl)carbamic acid tert-butyl ester (700 mg, 3 mmol) was dissolved in DCM (5 mL). Trifluoroacetic acid (2 mL) was added. The reaction solution was stirred for 3 hours. The reaction was monitored with LC-MS until raw materials disappeared. The resulting mixture was concentrated by rotary drying to produce a crude product of the title compound (1.42 g).

LC-MS (ESI) $[M+H]^+$=131.2.

Step 3: Preparation of 2-chloro-6-((3-(N-methylacetylamido)propyl)amino)pyrimidine-4-carboxylic acid methyl ester

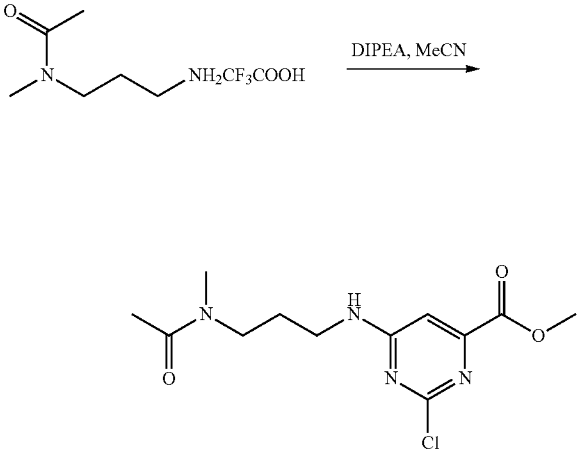

2,6-dichloropyrimidine-4-carboxylic acid methyl ester (300 mg, 0.467 mmol), N-(3-aminopropyl)-N-methylacetamide trifluoroacetate (crude, 600 mg, 1.46 mmol) and N,N-diisopropylethylamine (930 mg, 7.3 mmol) were dissolved in acetonitrile (6 mL). The resulting mixture was stirred at 25° C. for 2 hours, and extracted with ethyl acetate (50 mL*3). The ethyl acetate phases were combined, washed with water (20 mL), washed with saturated brine (20 mL), dried over anhydrous sodium sulfate for 10 minutes, and filtered to obtain a crude product, which was separated and purified with a column chromatography (DCM: MeOH=100:2) to produce the title compound (0.5 g, yield: 85%).

LC-MS (ESI) $[M+H]^+$=295.2.

Step 4: Preparation of 6-((3-(N-methylacetylamido)propyl)amino)-2-phenylpyrimidine-4-carboxylic acid

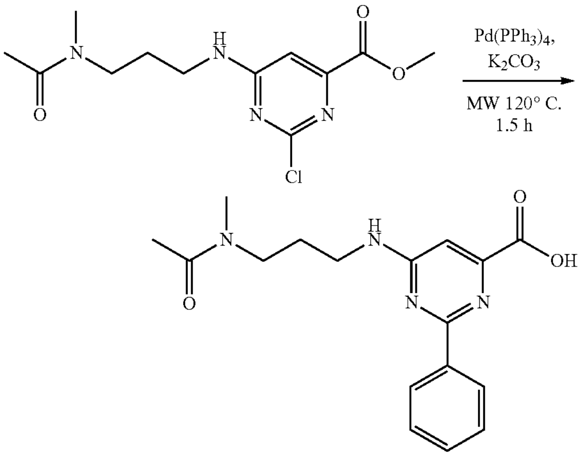

2-chloro-6-((3-(N-methylacetylamido)propyl)amino)pyrimidine-4-carboxylic acid methyl ester (500 mg, 1.67 mmol), phenylboronic acid (244 mg, 2.0 mmol), $K_2CO_3$ (460 mg, 3.34 mmol) and $Pd(PPh_3)_4$ (190 mg, 0.167 mmol) were dissolved in 1,4-dioxane (5 mL) and water (1 mL). The resulting mixture was stirred under microwave heating at 120° C. for 1.5 hours. The reaction was monitored with LC-MS, until the raw materials disappeared. The reaction mixture was extracted with ethyl acetate three times, each time 20 mL. The product was in the aqueous phase, which was concentrated by rotary drying, then washed with a mixed solvent of DCM:MeOH=10:1 (100 mL), and filtered. The filtrate was concentrated to produce a crude product of the title compound (500 mg).

LC-MS (ESI) $[M+H]^+$=343.2.

Preparation Example 12: Preparation of 4-amino-1-methylcyclohexane-1-ol (for example this intermediate could be used as an intermediate for the compound of Example 86)

Step 1: Preparation of 8-methyl-1,4-dioxaspiro[4.5]decane-8-ol

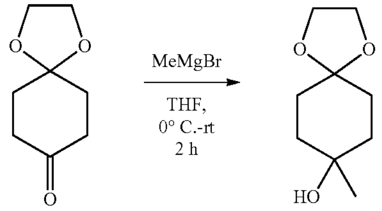

At 0° C., 1,4-dioxaspiro[4.5]decane-8-one (2.0 g, 12.8 mmol, 1 equiv.) was added to anhydrous tetrahydrofuran (40 mL). Then methyl magnesium bromide (3.0M, a solution in 2-methyltetrahydrofuran)(5.6 mL, 16.64 mmol, 1.3 equiv) was added. The resulting mixture was stirred at 28° C. for 2 hours. After the completion of the reaction was detected with TLC, a saturated aqueous ammonium chloride solution (15 mL) was added. The resulting mixture was extracted with ethyl acetate (15 mL×3) three times. The organic phases were combined, filtered, dried over anhydrous sodium sulfate, and concentrated to obtain a crude product, which was separated and purified with flash chromatography (silica gel, dichloromethane:methanol (V/V=10/1)) to produce the title compound (1 g, yield: 45%).

$^1$H NMR (400 MHz, $CDCl_3$) δ 3.99-3.94 (m, 4H), 1.91-1.87 (m, 2H), 1.73-1.68 (m, 4H), 1.64-1.59 (m, 2H), 1.28 (m, 3H).

Step 2: Preparation of 4-hydroxy-4-methylcyclohexane-1-one

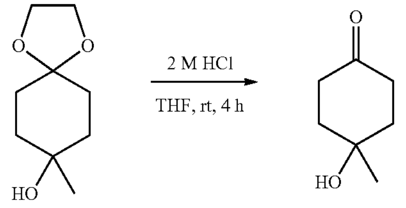

At 0° C., 8-methyl-1,4-dioxaspiro[4.5]decane-8-ol (1.0 g, 5.8 mmol, 1.0 equiv.) was added to water (5 mL) and tetrahydrofuran (20.0 mL). 2M HCl (10 mL) was added. The resulting mixture was stirred at room temperature for 4 hours. After the completion of the reaction was detected with TLC (dichloromethane:methanol (V/V=10/1)), the reaction solution was concentrated to 10 mL, washed with saturated sodium bicarbonate solution (30 mL), and extracted with ethyl acetate (30 mL×3) three times. The organic phases were combined, filtered, and concentrated to produce the title compound (526 mg, yield: 70%).

$^1$H NMR (400 MHz, $CDCl_3$) δ 2.77-2.69 (m, 4H), 2.28-2.22 (m, 2H), 2.02-1.96 (m, 4H), 1.90-1.82 (m, 2H), 1.38 (m, 3H).

Step 3: Preparation of (S)-N-(4-hydroxy-4-methylcyclohexylidene)-2-methylpropane-2-sulfinamide

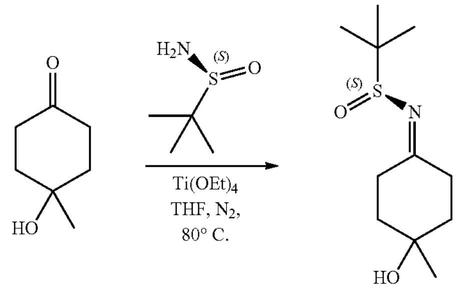

4-hydroxy-4-methylcyclohexane-1-one (350 mg, 2.73 mmol, 1.0 equiv) was added to THF (15 mL). Then (S)-2-methylpropane-2-sulfinamide (496 mg, 4.1 mmol, 1.5 equiv) and $Ti(OEt)_4$ (titanium ethoxide)(1.56 g, 6.83 mmol, 2.5 equiv) were added. Under the protection of nitrogen gas, the resulting mixture was stirred at 80° C. for 3 hours, and after the completion of the reaction was detected with LC-MC, added to water (100 mL). The resulting mixture was stirred for 15 minutes, and extracted with ethyl acetate (50 mL×3) three times. The organic phases were combined, filtered, dried over anhydrous sodium sulfate, and concentrated to obtain a crude product, which was separated and purified with flash chromatography (silica gel, petroleum ether:ethyl acetate (V/V=1/1) to produce the title compound (155 mg, yield: 45%).

LC-MS (ESI) $[M+H]^+$=232.1.

Step 4: Preparation of (S)-N-(4-hydroxy-4-methylcyclohexyl)-2-methylpropane-2-sulfinamide

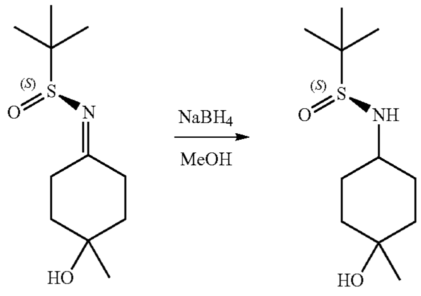

(S)-N-(4-hydroxy-4-methylcyclohexylidene)-2-methylpropane-2-sulfinamide (150 mg, 0.86 mmol, 1.0 equiv) was added to methanol (10 mL). Then $NaBH_4$ (66 mg, 1.73 mmol, 2.0 equiv) was added. The resulting mixture was stirred at 28° C. for 10 hours, and after the completion of the reaction was detected with LC-MC, concentrated to obtain a crude product, which was separated and purified with flash chromatography (silica gel, petroleum ether:ethyl acetate (V/V=1/1)) to produce the title compound (155 mg, yield: 45%).

LC-MS (ESI) $[M+H]^+$=234.2.

Step 5: Preparation of 4-amino-1-methylcyclohexane-1-ol

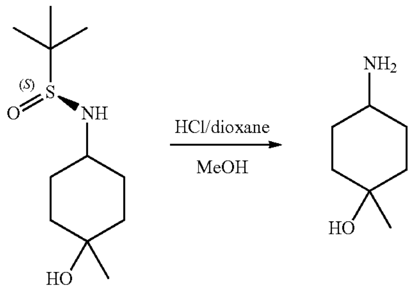

(S)-N-(4-hydroxy-4-methylcyclohexyl)-2-methylpropane-2-sulfinamide (200 mg, 0.86 mmol, 1.0 equiv) was added to methanol (10 mL). Then 4M HCl/dioxane (4 mL) was added. The resulting mixture was stirred at 28° C. for 2 hours, and after the completion of the reaction was detected with TLC, concentrated to obtain a crude product of the title compound (120 mg).

Preparation Example 13: Preparation of 6-((1-acetylpiperidine-4-yl)amino)-2-(cyclopropylethynyl)pyrimidine-4-carboxylic acid (for example this intermediate could be used as an intermediate for the compound of Example 92)

Step 1: Preparation of 6-((1-acetylpiperidine-4-yl)amino)-2-(cyclopropylethynyl)pyrimidine-4-carboxylic acid methyl ester

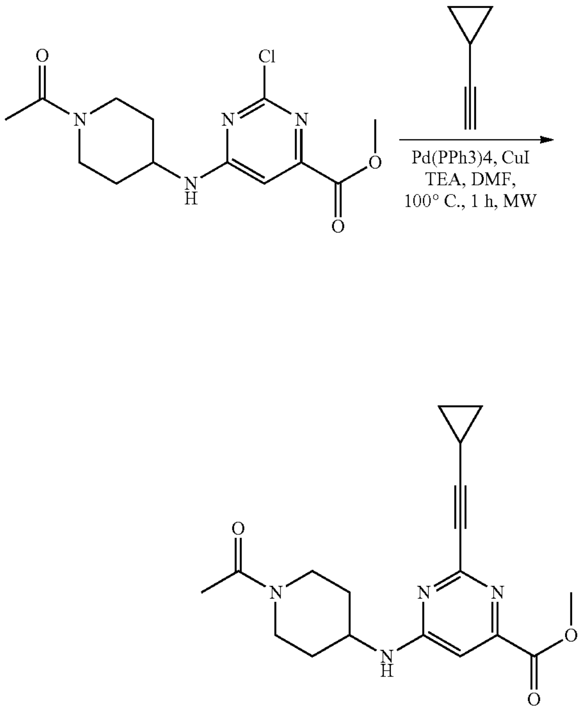

At 28° C., under the protection of nitrogen gas, 6-((1-acetylpiperidine-4-yl)amino)-2-chloropyrimidine-4-carboxylic acid methyl ester (180 mg, 1.31 mmol, 1.0 equiv.) was added to DMF (2 mL). Then ethynylcyclopropane (433 mg, 6.59 mmol, 5.0 equiv.), copper(I) iodide (51 mg, 0.26 mmol, 0.2 equiv.), and tetrakis(triphenylphosphine)palladium (151 mg, 0.131 mmol, 0.1 equiv.) were added. The resulting mixture was stirred at room temperature for 10 minutes, and stirred at 140° C. under microwave heating for 1 hour. After the completion of the reaction was detected with LC-MC, the reaction mixture was cooled to room temperature, and filtered to obtain a crude product, which was separated and purified with Prep-HPLC (C18, 10 mmol/L aqueous $NH_4HCO_3$ solution, MeCN) to produce the title compound (170 mg, yield: 82.98%).

LC-MS (ESI) $[M+H]^+$=343.3.

Step 2: Preparation of 6-((1-acetylpiperidine-4-yl)amino)-2-(cyclopropylethynyl)pyrimidine-4-carboxylic acid

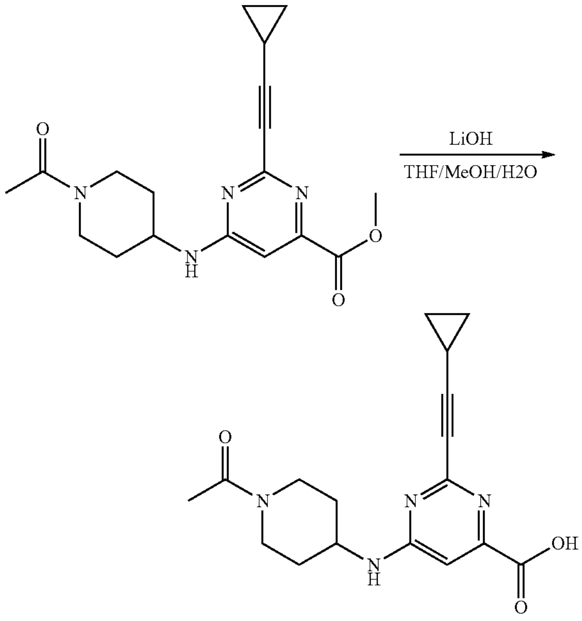

At 28° C., 6-((1-acetylpiperidine-4-yl)amino)-2-(cyclopropylethynyl)pyrimidine-4-carboxylic acid methyl ester (170 mg, 0.5 mmol, 1.0 equiv.) was added to water (1 mL), methanol (1.0 mL) and tetrahydrofuran (1.0 mL). Lithium hydroxide (36 mg, 1.5 mmol, 3.0 equiv.) was added. The resulting mixture was stirred at room temperature for 2 hours. After the completion of the reaction was detected with TLC (dichloromethane:methanol (V/V=10/1)), the reaction solution was concentrated to 1 mL, and adjusted with 1M hydrochloric acid to pH=1-2. The aqueous phase was lyophilized to produce the title compound (200 mg, yield: 90%).

LC-MS (ESI) $[M+H]^+$=330.2.

Preparation Example 14: Preparation of 6-((2-acetyl-2-azaspiro[3.3]heptan-6-yl)amino)-2-(pentan-3-yloxy)pyrimidine-4-carboxylic acid (for example this intermediate could be used as an intermediate for the compound of Example 197)

Step 1: Preparation of 6-((2-(benzyloxycarbonyl)-2-azaspiro[3.3]heptan-6-yl)amino)-2-chloropyrimidine-4-carboxylic acid

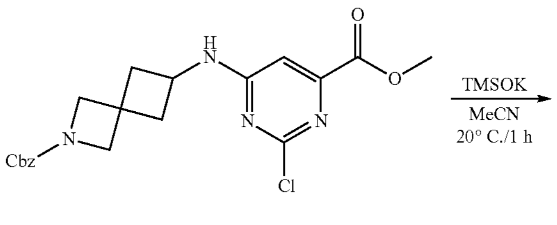

-continued

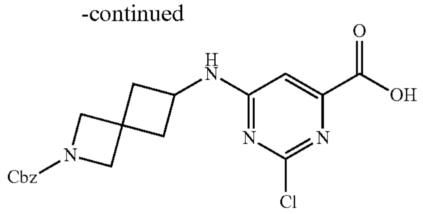

6-((2-chloro-6-(methoxycarbonyl)pyrimidine-4-yl)amino)-2-azaspiro[3.3]heptane-2-carboxylic acid benzyl ester (220 mg, 0.53 mmol, 1.0 equiv.) and TMSOK (74 mg, 0.58 mmol, 1.1 equiv.) were dissolved in MeCN (8 mL). The reaction was performed at 20° C. for 1 hour. The reaction solution was concentrated to produce the target compound (crude, 240 mg).

LC-MS (ESI) $[M+H]^+$=402.8.

Step 2: Preparation of 6-((2-azaspiro[3.3]heptan-6-yl)amino)-2-(pentan-3-yloxy)pyrimidine-4-carboxylic acid

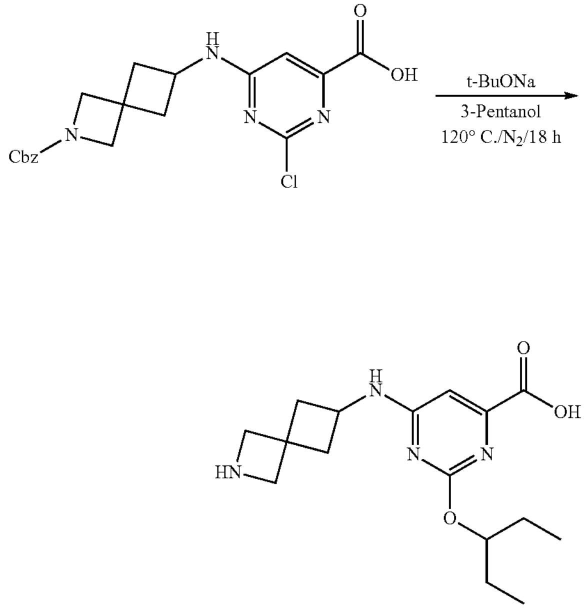

6-((2-(benzyloxycarbonyl)-2-azaspiro[3.3]heptan-6-yl)amino)-2-chloropyrimidine-4-carboxylic acid (210 mg, 0.52 mmol, 1.0 equiv.) and sodium tert-butoxide (200 mg, 2.09 mmol, 4.0 equiv.) were dissolved in 3-pentanol (10 mL). The reaction was performed in the protection of nitrogen gas at 120° C. for 18 hours. The reaction solution was concentrated to obtain a crude product, which was purified with reverse phase Prep-HPLC (C18, 10 mmol/L aqueous $NH_4HCO_3$ solution/acetonitrile) to produce the target compound (crude, 12 mg, yield: 7.2%).

LC-MS (ESI) $[M+H]^+$=321.0.

Step 3: Preparation of 6-((2-acetyl-2-azaspiro[3.3]heptan-6-yl)amino)-2-(pentan-3-yloxy)pyrimidine-4-carboxylic acid

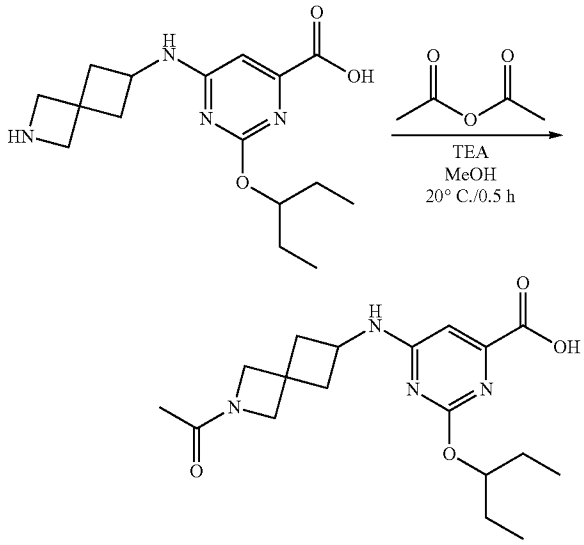

6-((2-azaspiro[3.3]heptan-6-yl)amino)-2-(pentan-3-yloxy)pyrimidine-4-carboxylic acid (12 mg, 0.04 mmol, 1.0 equiv.), acetic anhydride (4 mg, 0.04 mmol, 1.1 equiv.) and TEA (6 mg, 0.06 mmol, 1.5 equiv.) were dissolved in DMF (1 mL). The reaction was performed at 20° C. for 0.5 hours. The reaction solution was concentrated to produce the target compound (crude, 14 mg).

LC-MS (ESI) $[M+H]^+$=363.1.

Preparation Example 15: Preparation of trans-(1-(6-((1-acetylpiperidine-4-yl)amino)pyrimidine-4-carbonyl)-4-(3,4-dihydroisoquinoline-2(1H)-yl)piperidine-3-yl)carbamic acid tert-butyl ester (for example this intermediate could be used as an intermediate for the compound of Example 151)

Step 1: Preparation of trans-(4-(3,4-dihydroisoquinoline-2(1H)-yl)piperidine-3-yl)carbamic acid tert-butyl ester

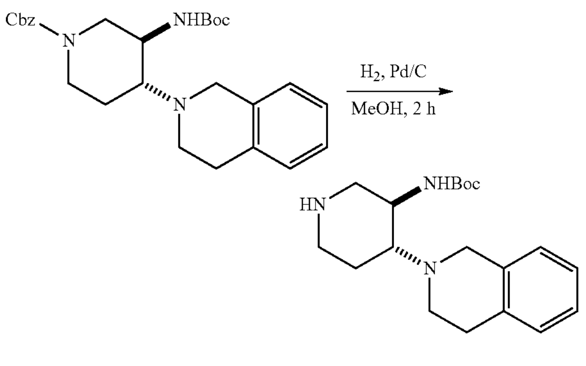

trans-3-((tert-butoxycarbonyl)amino)-4-(3,4-dihydroisoquinoline-2(1H)-yl)piperidine-1-carboxylic acid benzyl ester (68 mg, 0.186 mmol, 1 equiv.) was dissolved in methanol (chromatographic grade, 5 mL). Pd/C (10%, 70 mg) was added. The resulting mixture was stirred in the condition of hydrogen gas for 2 hours. The completion of the reaction was monitored with TLC. The reaction solution was filtered, and rotary dried to produce a crude product of the title compound (45 mg), which was directly used in the next step.

LC-MS (ESI) $[M+H]^+$=332.20.

Step 2: Preparation of trans-(1-(6-((1-acetylpiperidine-4-yl)amino)pyrimidine-4-carbonyl)-4-(3,4-dihydroisoquinoline-2(1H)-yl)piperidine-3-yl)carbamic acid tert-butyl ester

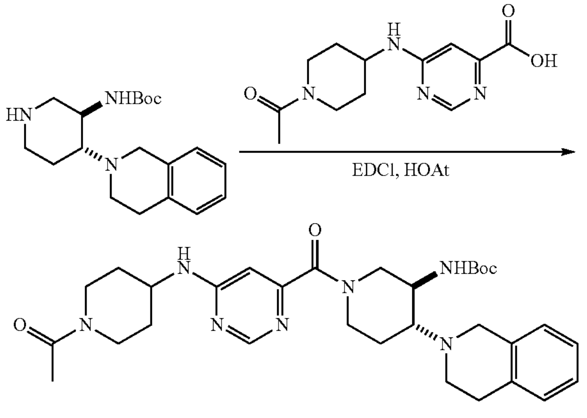

6-((1-acetylpiperidine-4-yl)amino)pyrimidine-4-carboxylic acid (36 mg, 0.136 mmol, 1 equiv.), EDCI (39 mg, 0.203 mmol, 1.49 equiv.) and HOAt (28 mg, 0.206 mmol, 1.51 equiv.) were dissolved in DMF (2 mL). The resulting mixture was stirred at room temperature (15-20° C.) for 5 minutes, and then a solution of trans-(4-(3,4-dihydroisoquinoline-2(1H)-yl)piperidine-3-yl)carbamic acid tert-butyl ester (45 mg, 0.174 mmol, 1.7 equiv.) in DMF (1 mL) was added. The resulting mixture was stirred at room temperature for 1.5 hours. The solvent was removed by rotary drying to obtain a crude product, which was separated and purified with flash chromatography (silica gel, 0-7% MeOH/DCM solution) to produce trans-(1-(6-((1-acetylpiperidine-4-yl)amino)pyrimidine-4-carbonyl)-4-(3,4-dihydroisoquinoline-2(1H)-yl)piperidine-3-yl)carbamic acid tert-butyl ester (53 mg, yield: 67.3%).

Preparation Example 16: Preparation of 2-(1-acetylpiperidine-4-yl)-1H-benzo[d]imidazole-6-carboxylic acid (for example this intermediate could be used as an intermediate for the compound of Example 155)

Step 1: Preparation of 4-(1-acetylpiperidine-4-carboxamido)-3-aminobenzoic acid methyl ester

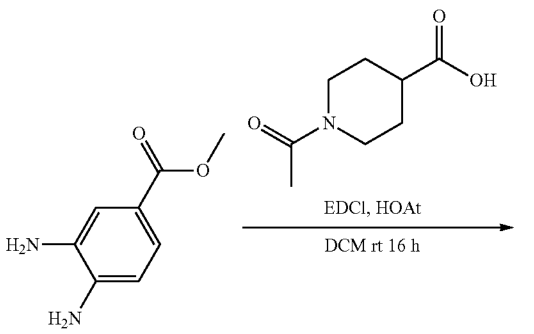

-continued

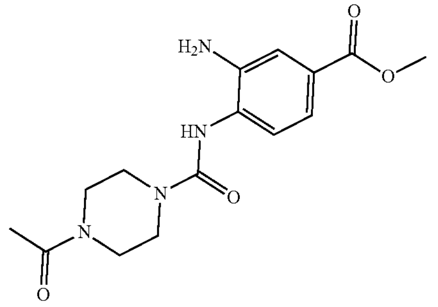

3,4-diaminobenzoic acid methyl ester (200 mg, 1.20 mmol, 1 equiv.), 1-acetyl-4-piperidine-carboxylic acid (206 mg, 1.20 mmol, 1.0 equiv.), EDCI (1-(3-dimethylaminopropyl)-3-ethylcarbodiimide hydrochloride) (277 mg, 1.44 mmol, 1.2 equiv.) and HOAt (N-hydroxy-7-aza-benzotriazole) (196 mg, 1.44 mmol, 1.2 equiv.) were dissolved in DCM (6 mL). The reaction was performed at 25° C. for 16 hours. The precipitate was collected by filtering, and the filter cake was dried to produce a crude product of the title compound (300 mg).

LC-MS (ESI) $[M+H]^+$=320.2.

Step 2: Preparation of 2-(1-acetylpiperidine-4-yl)-1H-benzo[d]imidazole-6-carboxylic acid methyl ester

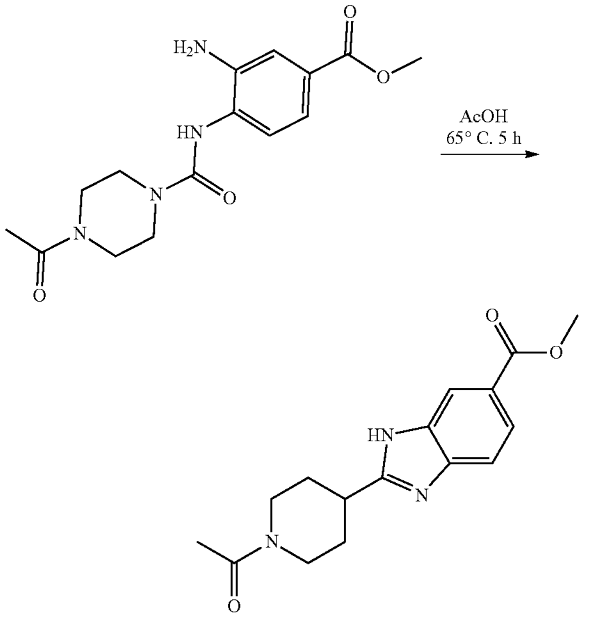

4-(1-acetylpiperidine-4-carboxamido)-3-aminobenzoic acid methyl ester (250 mg, 0.78 mmol, 1 equiv.) was dissolved in acetic acid (6 mL). The reaction was performed at 65° C. for 5 hours. The reaction mixture was neutralized with saturated aqueous $NaHCO_3$ solution to pH=6-7, and extracted with dichloromethane (3*10 mL). The combined organic phases were washed with brine, dried over Na2SO4, and concentrated to produce the title compound (170 mg, yield: 72.1%).

LC-MS (ESI) $[M+H]^+$=302.2.

Step 3: Preparation of 2-(1-acetylpiperidine-4-yl)-1H-benzo[d]imidazole-6-carboxylic acid

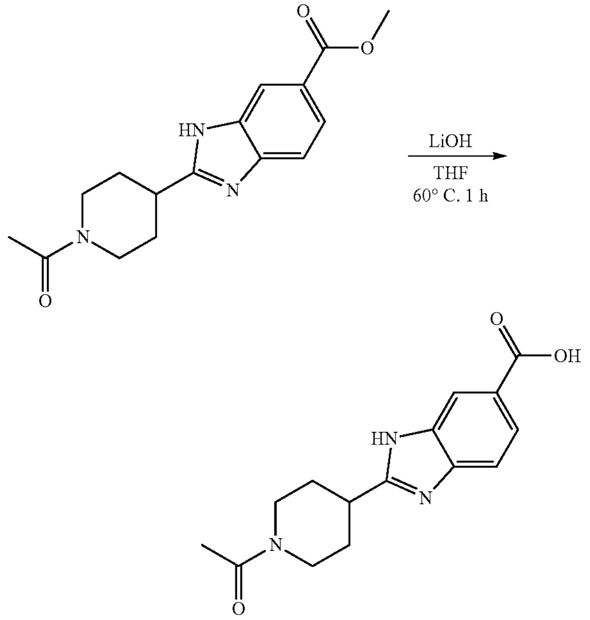

2-(1-acetylpiperidine-4-yl)-1H-benzo[d]imidazole-6-carboxylic acid methyl ester (80 mg, 0.27 mmol, 1.0 equiv.) was dissolved in tetrahydrofuran (1 mL). aqueous lithium hydroxide solution (2 M)(13 mg, 0.53 mmol, 2.0 equiv.) was added. The resulting mixture was stirred at 60° C. for 1 hour, and after the completion of the reaction was detected with LC-MC, concentrated to produce a crude product of the title compound (90 mg).

LC-MS (ESI) $[M+H]^+$=288.2.

Preparation Example 17: Preparation of 6-((1-(tetrahydro-2H-pyran-4-carbonyl)piperidine-4-yl)amino) pyrimidine-4-carboxylic acid (for example this intermediate could be used as an intermediate for the compound of Example 157)

Step 1: Preparation of 6-((1-(tert-butoxycarbonyl) piperidine-4-yl)amino)pyrimidine-4-carboxylic acid methyl ester

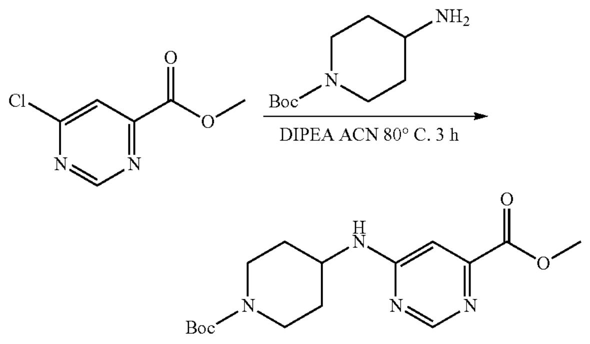

6-chloropyrimidine-4-carboxylic acid methyl ester (4 g, 23.17 mmol, 1 equiv.) and 4-aminopiperidine-1-carboxylic acid tert-butyl ester (4.9 g, 24.33 mmol, 1.05 equiv.) were dissolved in acetonitrile (40 mL). DIPEA (8.99 g, 69.51 mmol, 3 equiv.) was added. The reaction was performed at 80° C. under stirring for 3 hours. The completion of the reaction was monitored with LC-MS. The reaction solution was quenched with water, and then extracted with ethyl acetate. The organic phases were combined, then washed with saturated sodium chloride, dried over anhydrous sodium sulfate, then filtered, and concentrated to produce a crude product, which was separated and purified with flash chromatography (silica gel, petroleum ether:ethyl acetate=1:5) to produce the title compound (5.56 g, yield: 71%).

LC-MS (ESI) $[M+H]^+$=337.2.

Step 2: Preparation of 6-(piperidine-4-ylamino)pyrimidine-4-carboxylic acid methyl ester

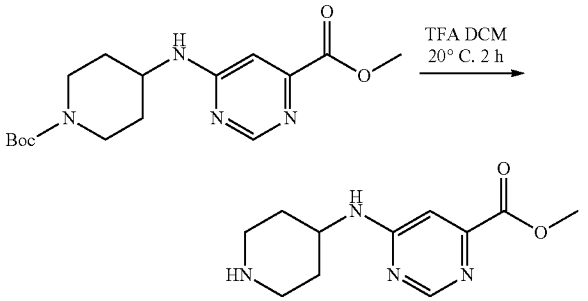

6-((1-(tert-butoxycarbonyl)piperidine-4-yl)amino)pyrimidine-4-carboxylic acid methyl ester (5.46 g, 16.2 mmol, 1 equiv.) was dissolved in dichloromethane (40 mL). Trifluoroacetic acid (10 mL) was added. The reaction was performed at 20° C. under stirring for 2 hours. The completion of the reaction was monitored with LC-MS. To the reaction solution was added water, and then the resulting mixture was adjusted with saturated sodium bicarbonate solution to pH=8-9, and extracted with ethyl acetate. The aqueous phase was concentrated to produce a crude product of the title compound (11 g).

LC-MS (ESI) $[M+H]^+$=237.1.

Step 3: Preparation of 6-((1-(tetrahydro-2H-pyran-4-carbonyl)piperidine-4-yl)amino)pyrimidine-4-carboxylic acid methyl ester

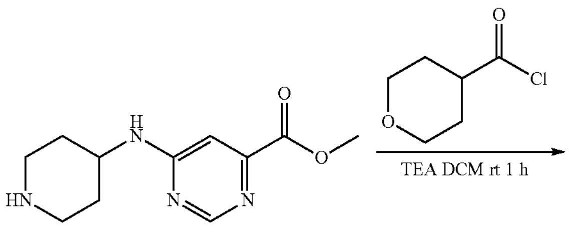

-continued

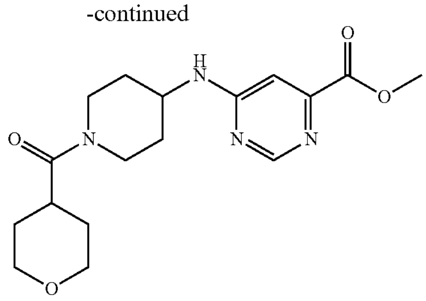

6-(piperidine-4-ylamino)pyrimidine-4-carboxylic acid methyl ester (923 mg, crude) was dissolved in dichloromethane (5 mL), and then triethylamine (195 mg, 1.907 mmol, 1.5 equiv.) was added. The reaction was cooled down to about −10° C. Then to the reaction solution was slowly added tetrahydropyran-4-carbonyl chloride (190 mg, 1.271 mmol, 1 equiv.), and the temperature of the reaction system was maintained at no more than 0° C. After the completion of the addition, the reaction was gradually warmed up to room temperature (20° C.). After stirring for 1 hour, LC-MS indicated the completion of the reaction. The reaction solution was quenched with water, and then extracted with dichloromethane. The organic phases were combined, then washed with saturated brine, dried over anhydrous sodium sulfate, then filtered, and concentrated to produce a crude product of the title compound (340 mg).

LC-MS (ESI) $[M+H]^+$=349.2.

Step 4: Preparation of 6-((1-(tetrahydro-2H-pyran-4-carbonyl)piperidine-4-yl)amino)pyrimidine-4-carboxylic acid

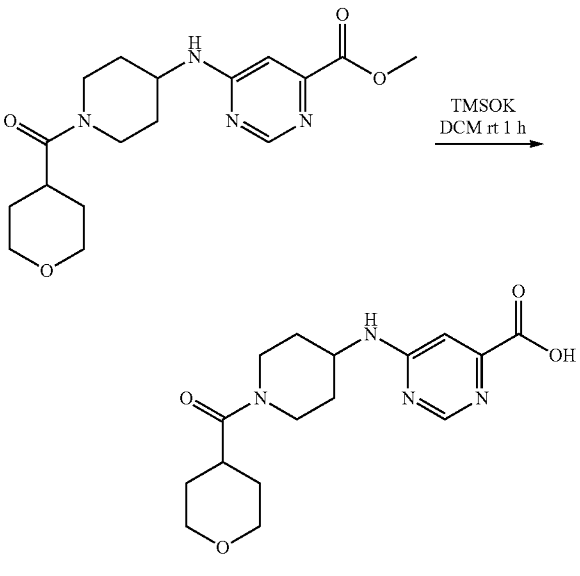

6-((1-(tetrahydro-2H-pyran-4-carbonyl)piperidine-4-yl)amino)pyrimidine-4-carboxylic acid methyl ester (340 mg, crude) was dissolved in dichloromethane (15 mL) and methanol (3 mL). TMSOK (potassium trimethylsilanol) (340 mg, 1.172 mmol, 1.2 equiv.) was added. The resulting mixture was stirred at room temperature (20° C.) for 1 hour. The completion of the reaction was monitored with TLC. The reaction solution was concentrated to produce a solid, which was dissolved in water. The resulting solution was adjusted with 1N hydrochloric acid to pH=5-6, and extracted with dichloromethane. Then the aqueous phase was concentrated to produce a solid, which was dissolved in dichloromethane and methanol. The solid impurity was removed by filtering, and the resulting filtrate was concentrated to produce a crude product of the title compound (300 mg), which could be directly used in the next step.

LC-MS (ESI) $[M+H]^+$=335.2.

Preparation Example 18: Preparation of 6-((1-(thiazole-5-carbonyl)piperidine-4-yl)amino)pyrimidine-4-carboxylic acid (for example this intermediate could be used as an intermediate for the compound of Example 167)

Step 1: Preparation of 6-((1-(thiazole-5-carbonyl)piperidine-4-yl)amino)pyrimidine-4-carboxylic acid methyl ester

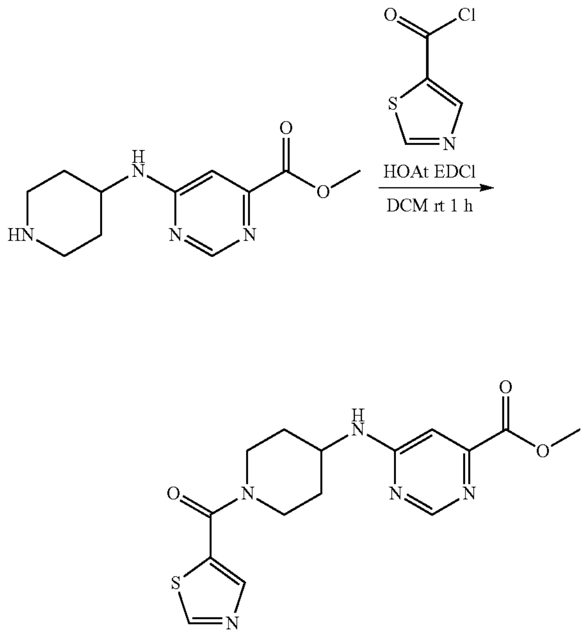

6-(piperidine-4-ylamino)pyrimidine-4-carboxylic acid methyl ester (100 mg, 0.42 mmol, 1.0 equiv.), thiazole-5-carboxylic acid (67 mg, 0.42 mmol, 1.0 equiv.), EDCI (1-(3-dimethylaminopropyl)-3-ethylcarbodiimide hydrochloride)(60 mg, 0.32 mmol, 1.5 equiv.) and HOAt (N-hydroxy-7-aza-benzotriazole)(43 mg, 0.32 mmol, 1.5 equiv.) were dissolved in DMF (N,N-dimethyl formamide)(1 mL). The reaction was performed at 25° C. for 1 hour. After the completion of the reaction was detected with LC-MC, the resulting mixture was concentrated to obtain a crude product, which was separated and purified with flash chromatography (silica gel, 5% MeOH/DCM solution) to produce the title product (90 mg, yield: 61.2%).

LC-MS (ESI) $[M+H]^+$=348.2.

Step 2: Preparation of 6-((1-(thiazole-5-carbonyl)piperidine-4-yl)amino)pyrimidine-4-carboxylic acid

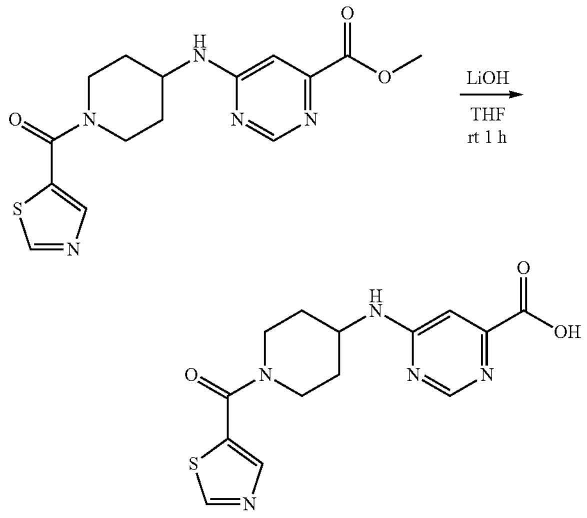

6-((1-(thiazole-5-carbonyl)piperidine-4-yl)amino)pyrimidine-4-carboxylic acid methyl ester (90 mg, 0.26 mmol, 1.0 equiv.) was dissolved in tetrahydrofuran (1 mL). aqueous lithium hydroxide solution (2 M)(12 mg, 0.52 mmol, 2.0 equiv.) was added. The resulting mixture was stirred at 25° C. for 1 hour. After the completion of the reaction was detected with LC-MC, the resulting mixture was concentrated to produce a crude product of the title compound (90 mg).

LC-MS (ESI) $[M+H]^+$=334.0.

Preparation Example 19: Preparation of 6-((1-acetylpiperidine-4-yl)amino)-2-(cyclopentylthio)pyrimidine-4-carboxylic acid (for example this intermediate could be used as an intermediate for the compound of Example 198)

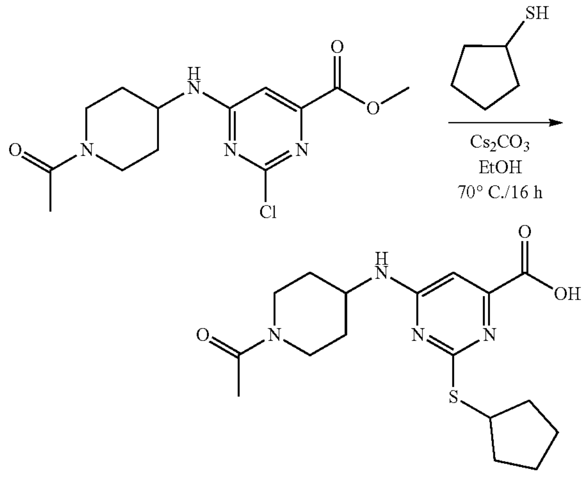

6-((1-acetylpiperidine-4-yl)amino)-2-chloropyrimidine-4-carboxylic acid methyl ester (100 mg, 0.32 mmol, 1.0 equiv.), cyclopentylthiol (163 mg, 1.60 mmol, 5.0 equiv.) and $Cs_2CO_3$ (208 mg, 0.64 mmol, 2.0 equiv.) were dissolved in EtOH (0.7 mL). The reaction was performed at 70° C. for 16 hours. The reaction solution was filtered by suction. The filtrate was adjusted with diluted hydrochloric acid to acidity, and concentrated to produce the target compound (crude, 340 mg).

LC-MS (ESI) $[M+H]^+$=365.2.

Preparation Example 20: Preparation of 6-((2-acetyl-2-azaspiro[3.3]heptan-6-yl)amino)-2-isopropoxypyrimidine-4-carboxylic acid (for example this intermediate could be used as an intermediate for the compound of Example 200)

Step 1: Preparation of 2-isopropoxy-6-((2-(isopropoxycarbonyl)-2-azaspiro[3.3]heptan-6-yl)amino)pyrimidine-4-carboxylic acid

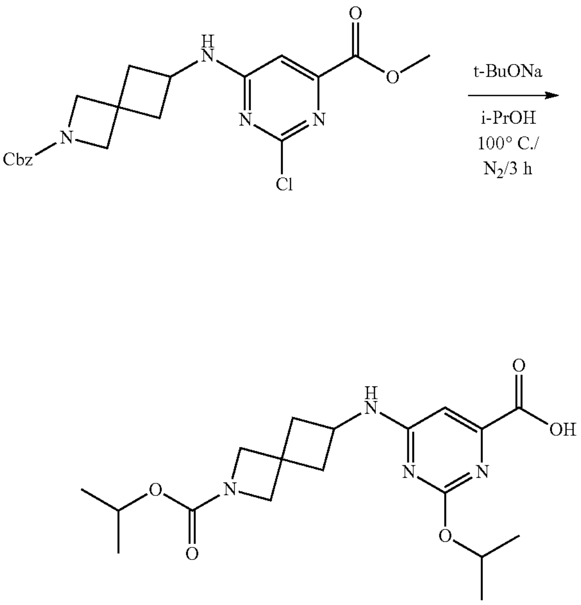

6-((2-chloro-6-(methoxycarbonyl)pyrimidine-4-yl)amino)-2-azaspiro[3.3]heptane-2-carboxylic acid benzyl ester (150 mg, 0.36 mmol, 1.0 equiv.) and sodium tert-butoxide (138 mg, 1.44 mmol, 4.0 equiv.) were dissolved in i-PrOH (15 mL). The reaction was performed in the protection of nitrogen gas at 100° C. for 3 hours. The reaction solution was adjusted with diluted hydrochloric acid to acidity, and concentrated to produce the target compound (crude, 270 mg).

LC-MS (ESI) $[M+H]^+$=379.2.

Step 2: Preparation of 6-((6-((3R,4R)-4-(3,4-dihydroisoquinoline-2(1H)-yl)-3-hydroxypiperidine-1-carbonyl)-2-isopropoxypyrimidine-4-yl)amino)-2-azaspiro[3.3]heptan-2-carboxylic acid isopropyl ester

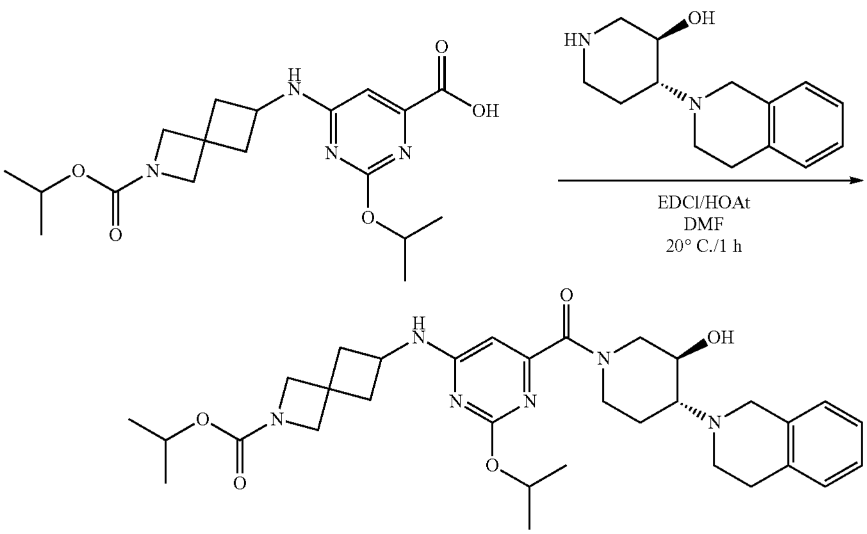

2-isopropoxy-6-((2-(isopropoxycarbonyl)-2-azaspiro[3.3]heptan-6-yl)amino)pyrimidine-4-carboxylic acid (250 mg, 0.33 mmol, 1.0 equiv.), (3R,4R)-4-(3,4-dihydroisoquinoline-2(1H)-yl)piperidine-3-ol (77 mg, 0.33 mmol, 1.0 equiv.), EDCI (95 mg, 0.50 mmol, 1.5 equiv.) and HOAt (67 mg, 0.50 mmol, 1.5 equiv.) were dissolved in DMF (3.7 mL). The reaction was performed at 20° C. for 1 hour. The reaction solution was quenched with saturated aqueous sodium bicarbonate solution, and extracted with ethyl acetate. The organic phase was concentrated to obtain a crude product, which was separated and purified with flash chromatography (silica gel, DCM:MeOH=30:1) to produce the target compound (70 mg, yield: 35.8%).

LC-MS (ESI) $[M+H]^+$=593.3.

Step 3: Preparation of 6-((2-azaspiro[3.3]heptan-6-yl)amino)-2-isopropoxypyrimidine-4-carboxylic acid

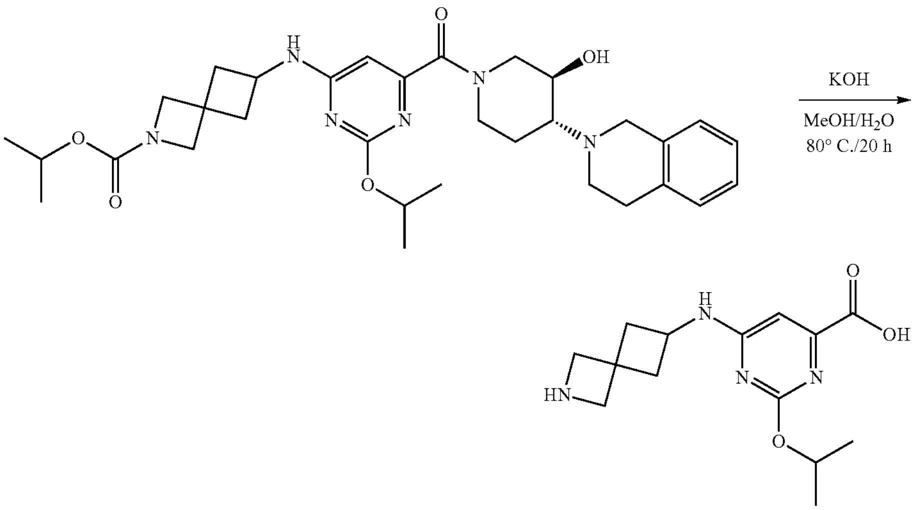

6-((6-((3R,4R)-4-(3,4-dihydroisoquinoline-2(1H)-yl)-3-hydroxypiperidine-1-carbonyl)-2-isopropoxypyrimidine-4-yl)amino)-2-azaspiro[3.3]heptane-2-carboxylic acid isopropyl ester (55 mg, 0.09 mmol, 1.0 equiv.) was dissolved in MeOH (3 mL) and aqueous potassium hydroxide solution (2 M)(3 mL). The reaction was performed at 80° C. for 20 hours. The reaction solution was adjusted to acidity, and filtered by suction. The filtrate was concentrated to produce the target compound (crude, 170 mg).

LC-MS (ESI) $[M+H]^+$=293.1.

Step 4: Preparation of 6-((2-acetyl-2-azaspiro[3.3]heptan-6-yl)amino)-2-isopropoxypyrimidine-4-carboxylic acid

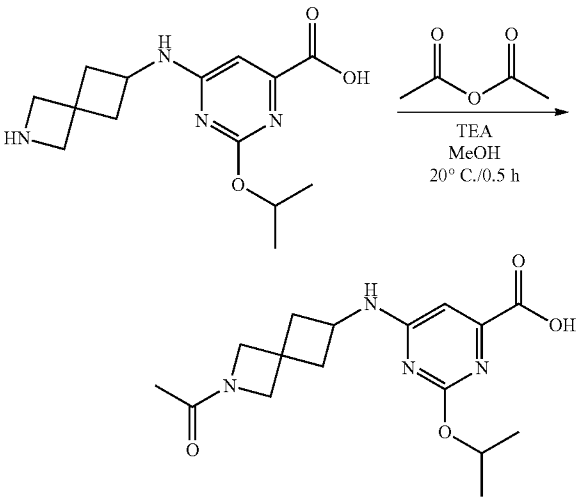

6-((2-azaspiro[3.3]heptan-6-yl)amino)-2-isopropoxypyrimidine-4-carboxylic acid (140 mg, 0.09 mmol, 1.0 equiv.), acetic anhydride (10 mg, 0.09 mmol, 1.0 equiv.) and TEA (15 mg, 0.14 mmol, 1.5 equiv.) were dissolved in MeOH (5 mL). The reaction was performed at 20° C. for 0.5 hours. The reaction solution was concentrated to produce the target compound (crude, 32 mg).

LC-MS (ESI) $[M+H]^+$=335.2.

Preparation Example 21: Preparation of 2-isopropoxy-6-((1-(pyrimidine-4-yl)piperidine-4-yl)amino)pyrimidine-4-carboxylic acid (for example this intermediate could be used as an intermediate for the compound of Example 204)

Step 1: Preparation of 2-isopropoxy-6-((1-(pyrimidine-4-yl)piperidine-4-yl)amino)pyrimidine-4-carboxylic acid

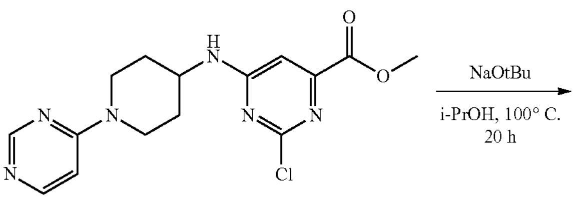

-continued

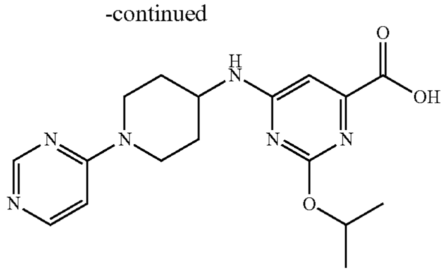

Sodium tert-butoxide (0.33 g, 3.44 mmol, 6 equiv.) was added to a solution of 2-chloro-6-((1-(pyrimidine-4-yl)piperidine-4-yl)amino)pyrimidine-4-carboxylic acid methyl ester (0.20 g, 0.57 mmol, 1 equiv.) in isopropanol (8 mL, 100%). The atmosphere was replaced with nitrogen gas twice. The reaction was performed at 100° C. for 20 hours, and after the completion of the reaction was detected with LC-MC, concentrated to obtain a crude product, which was adjusted with 1M hydrochloric acid to pH=5, and dried by suction to produce the title compound (0.1 g, yield: 48.7%).

LC-MS (ESI) $[M+H]^+$=359.1.

Preparation Example 22: Preparation of 6-((1-(tert-butoxycarbonyl)piperidine-4-yl)amino)-2-methoxypyrimidine-4-carboxylic acid (for example this intermediate could be used as an intermediate for the compound of Example 220)

Step 1: Preparation of 6-((1-(tert-butoxycarbonyl)piperidine-4-yl)amino)-2-chloropyrimidine-4-carboxylic acid methyl ester

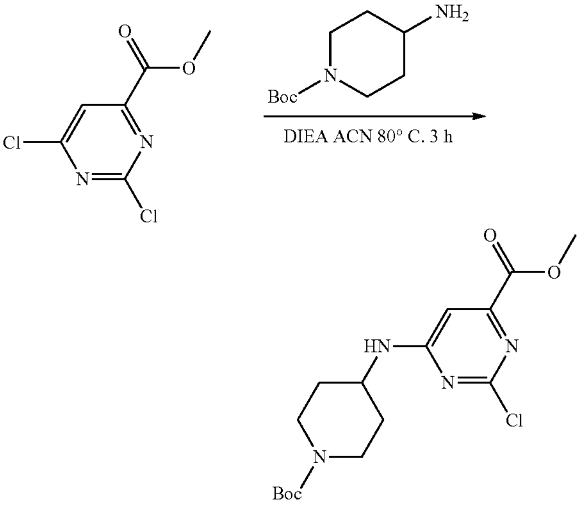

2,6-dichloropyrimidine-4-carboxylic acid methyl ester (1.086 g, 5.24 mmol, 1.05 equiv.) and 4-aminopiperidine-1-carboxylic acid tert-butyl ester (1 g, 4.99 mmol, 1.05 equiv.) were dissolved in acetonitrile (40 mL). DIPEA (1.94 g, 14.97 mmol, 3 equiv.) was added. The reaction was performed at 80° C. under stirring for 3 hours. The completion of the reaction was monitored with LC-MS. The reaction solution was quenched with water, and then extracted with ethyl acetate. The organic phases were combined, then washed with saturated sodium chloride, dried over anhydrous sodium sulfate, then filtered, and concentrated to produce a crude product, which was separated and purified with flash chromatography (silica gel, petroleum ether:ethyl acetate=0-20%) to produce the title compound (1.5 g, yield: 80%).

LC-MS (ESI) $[M+H]^+$=371.0.

Step 2: Preparation of 6-((1-(tert-butoxycarbonyl) piperidine-4-yl)amino)-2-methoxypyrimidine-4-carboxylic acid methyl ester

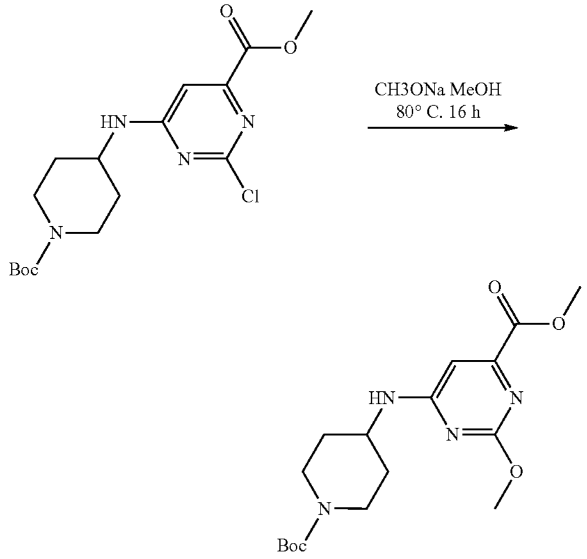

6-((1-(tert-butoxycarbonyl)piperidine-4-yl)amino)-2-chloropyrimidine-4-carboxylic acid methyl ester (500 mg, 1.348 mmol, 1.0 equiv.) and sodium methoxide (110 mg, 2.022 mmol, 2 equiv.) were dissolved in methanol (10 mL). The reaction was performed at 80° C. under stirring for 16 hours. The completion of the reaction was monitored with LC-MS. The reaction solution was quenched with water, and extracted with dichloromethane. The organic phases were combined, then washed with saturated NaCl solution, dried over anhydrous sodium sulfate, filtered, and concentrated to produce a crude product of the title compound (400 mg).

LC-MS (ESI) $[M+H]^+$=367.2.

Step 3: Preparation of 6-((1-(tert-butoxycarbonyl) piperidine-4-yl)amino)-2-methoxypyrimidine-4-carboxylic acid

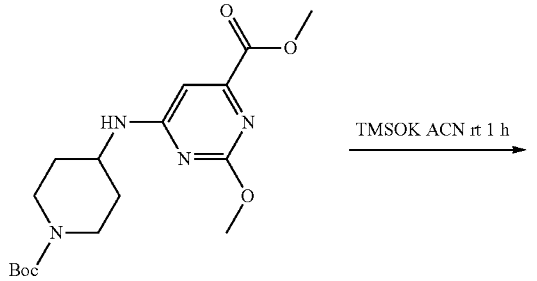

-continued

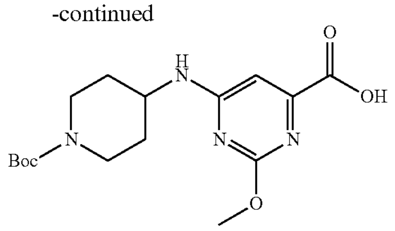

6-((1-(tert-butoxycarbonyl)piperidine-4-yl)amino)-2-methoxypyrimidine-4-carboxylic acid methyl ester (400 mg) was dissolved in acetonitrile (20 mL). TMSOK (potassium trimethylsilanol)(169 mg, 1.307 mmol, 1.2 equiv.) was added. The resulting mixture was stirred at room temperature (20° C.) for 1 hour. The completion of the reaction was monitored with TLC. The reaction solution was concentrated to produce a solid, which was dissolved in water. The resulting solution was adjusted with 1N hydrochloric acid to pH=5-6, and extracted with dichloromethane. Then the aqueous phase was concentrated to produce a solid, which was dissolved in dichloromethane and methanol. The solid impurity was removed by filtering, and the resulting filtrate was concentrated to produce a crude product of the title compound (350 mg), which could be directly used in the next step.

LC-MS (ESI) $[M+H]^+$=353.2.

Preparation Example 23: Preparation of 6-((1-acetylpiperidine-4-yl)amino)-2-(trifluoromethoxy) pyrimidine-4-carboxylic acid (for example this intermediate could be used as an intermediate for the compound of Example 222)

Step 1: Preparation of 6-((1-acetylpiperidine-4-yl) amino)-2-hydroxypyrimidine-4-carboxylic acid methyl ester

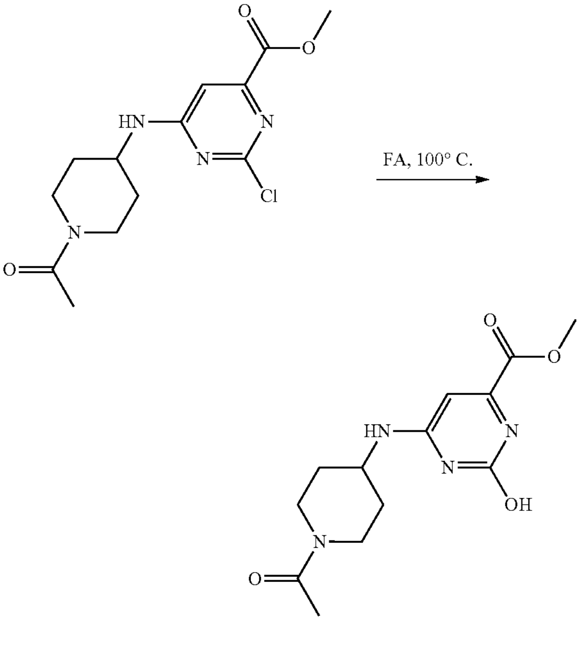

6-[(1-acetylpiperidine-4-yl)amino]-2-chloropyrimidine-4-carboxylic acid methyl ester (1 g, 3.2 mmol, 1 equiv.) was dissolved in formic acid (10 mL, 100%). The reaction was performed under heating at 100° C. for 12 hours. After the completion of the reaction was detected with LC-MC, the reaction mixture was concentrated to obtain a crude product, which was purified with column chromatography (C18, 5 mmol/L aqueous $NH_3$ solution/acetonitrile) to produce the title compound (200 mg, 21.3%).

LC-MS (ESI) $[M+H]^+=295.1$.

Step 2: Preparation of 6-((1-acetylpiperidine-4-yl) amino)-2-(trifluoromethoxy)pyrimidine-4-carboxylic acid methyl ester

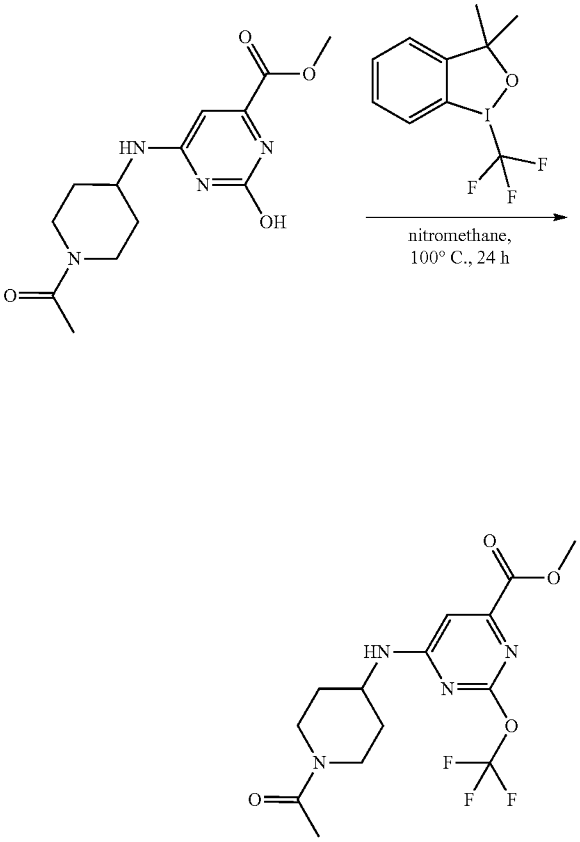

At room temperature, 3,3-dimethyl-1-(trifluoromethyl)-1,2-benziodoxole (0.22 g, 0.68 mmol, 1 equiv.) was added to a solution of 6-((1-acetylpiperidine-4-yl)amino)-2-hydroxy-pyrimidine-4-carboxylic acid methyl ester (200.13 mg, 0.68 mmol, 1 equiv.) in nitromethane (3 mL, 100%). The atmosphere was replaced with nitrogen gas. Then the reaction was performed under heating at 100° C. for 12 hours. 3,3-dimethyl-1-(trifluoromethyl)-1,2-benziodoxole (0.011 g, 0.034 mmol, 0.5 equiv.) was supplemented. The reaction was continuously performed under heating at 100° C. for 12 hours. After the completion of the reaction was detected with LC-MC, the resulting mixture was concentrated to dryness, and purified with a column chromatography (using with 10% DCM/MeOH) to produce 6-((1-acetylpiperidine-4-yl) amino)-2-(trifluoromethoxy)pyrimidine-4-carboxylic acid methyl ester (35 mg, 14.2%).

LC-MS (ESI) $[M+H]^+=363.1$.

Step 3: Preparation of 6-((1-acetylpiperidine-4-yl) amino)-2-(trifluoromethoxy)pyrimidine-4-carboxylic acid

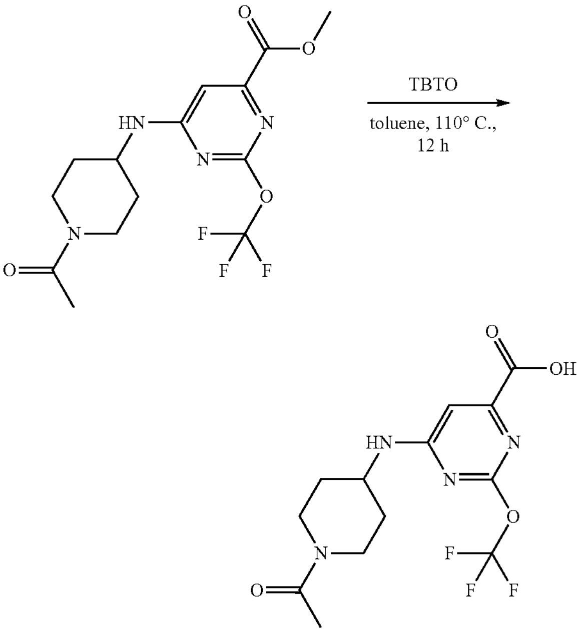

Tributyltin oxide (0.069 g, 0.12 mmol, 1.2 equiv.) was added to a mixed solution of 6-((1-acetylpiperidine-4-yl) amino)-2-(trifluoromethoxy)pyrimidine-4-carboxylic acid methyl ester (25 mg, 0.07 mmol, 1 equiv.) in acetonitrile (1 mL, 20%) and toluene (4 mL, 80%). The reaction was performed at 110° C. for 12 hours. After the completion of the reaction was detected with LC-MC, The crude product was quenched with 1 mL aqueous potassium fluoride solution, concentrated to obtain a crude product, which was slurrized with diethyl ether and dried by suction to produce 6-((1-acetylpiperidine-4-yl)amino)-2-(trifluoromethoxy)pyrimidine-4-carboxylic acid (25 mg, yield: 74.3%).

LC-MS (ESI) $[M+H]^+=349.0$.

Preparation Example 24: Preparation of 6-((1-acetylpiperidine-4-yl)amino)-2-ethoxypyrimidine-4-carboxylic acid (for Example this Intermediate could be Used as an Intermediate for the Compound of Example 235)

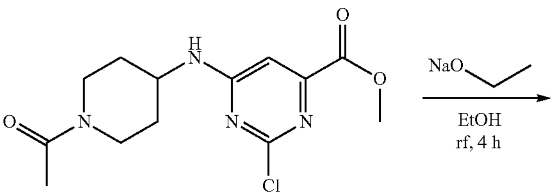

-continued

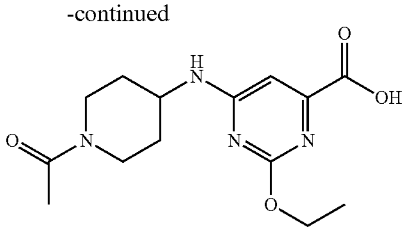

At 20° C., 6-((1-acetylpiperidine-4-yl)amino)-2-chloropyrimidine-4-carboxylic acid methyl ester (100 mg, 0.06 mmol, 1.0 equiv.) was dissolved in ethanol (3 mL). Sodium ethoxide was added. The resulting mixture was stirred at 80° C. for 10 hours. After the completion of the reaction was detected with LC-MC, the reaction product was concentrated to obtain a crude product, which was separated and purified with Prep-HPLC (C18, 10 mmol/L aqueous $NH_4HCO_3$ solution/acetonitrile), and lyophilized to produce the title compound (60 mg, yield: 61%).

LC-MS (ESI) $[M+H]^+$=309.3.

Preparation Example 25: Preparation of 2-(pentan-3-yloxy)-6-((1-(thiazole-2-yl)piperidine-4-yl)amino)pyrimidine-4-carboxylic acid (for example this intermediate could be used as an intermediate for the compound of Example 251)

Step 1: Preparation of (1-(thiazole-2-yl)piperidine-4-yl)carbamic acid tert-butyl ester

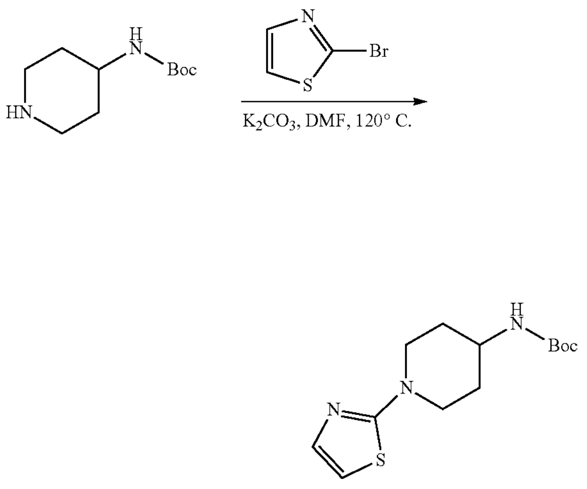

Piperidine-4-ylcarbamic acid tert-butyl ester (1 g, 4.993 mmol, 1.0 equiv.), was dissolved in DMF (10 mL). 2-bromothiazole (0.82 g, 4.993 mmol, 1.0 equiv) and potassium carbonate (3.45 g, 24.997 mmol, 5.0 equiv) were added. The resulting mixture was stirred at 120° C. for 16 hours After the completion of the reaction was detected with LC-MC, the resulting mixture was concentrated, and separated and purified with chromatography column (MeOH:DCM=50%) to produce the title compound (670 mg, yield: 47.4%).

LC-MS (ESI) $[M+H]^+$=284.0.

Step 2: Preparation of 1-(thiazole-2-yl)piperidine-4-amine

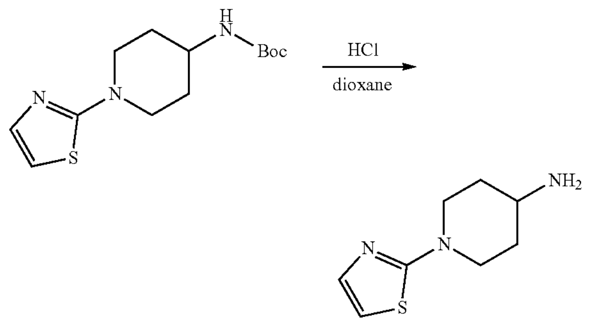

(1-(thiazole-2-yl)piperidine-4-yl)carbamic acid tert-butyl ester (660 mg, 2.329 mmol, 1.0 equiv.) was dissolved in dioxane (10 mL). Hydrochloric acid/dioxane solution (4 mL) was added. The resulting mixture was stirred at 25° C. for 2 hours, and after the completion of the reaction was detected with LC-MC, concentrated to produce a crude product of the title compound (569 mg).

LC-MS (ESI) $[M+H]^+$=183.9.

Step 3: Preparation of 2-chloro-6-((1-(thiazole-2-yl)piperidine-4-yl)amino)pyrimidine-4-carboxylic acid methyl ester

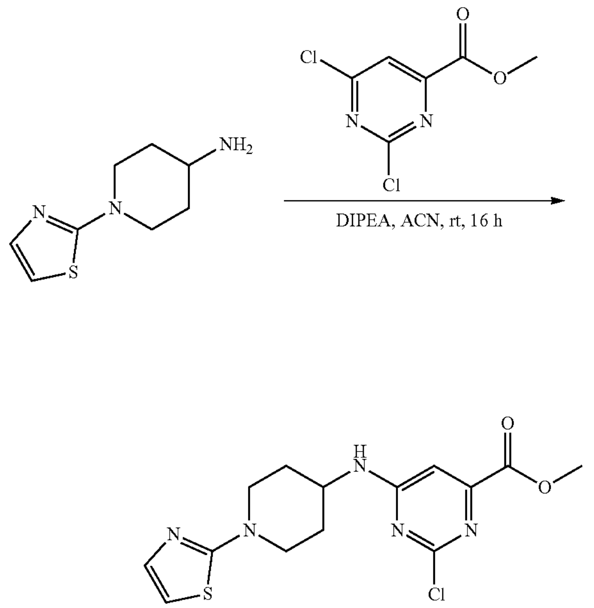

At 0° C., 2,6-dichloropyrimidine-4-carboxylic acid methyl ester (632 mg, 3.056 mmol, 1.0 equiv.) was added to acetonitrile (10 mL). 1-(thiazole-2-yl)piperidine-4-amine (560 mg, 3.056 mmol, 1.0 equiv.) and DIPEA (0.39 g, 6.111 mmol, 2.0 equiv.) were added. The resulting mixture was stirred at 0° C. for 16 hours, and after the completion of the reaction was detected with LC-MC, concentrated to produce the title compound (150 mg, yield: 13.9%).

LC-MS (ESI) $[M+H]^+$=353.9.

Step 4: Preparation of 2-(pentan-3-yloxy)-6-((1-(thiazole-2-yl)piperidine-4-yl)amino)pyrimidine-4-carboxylic acid

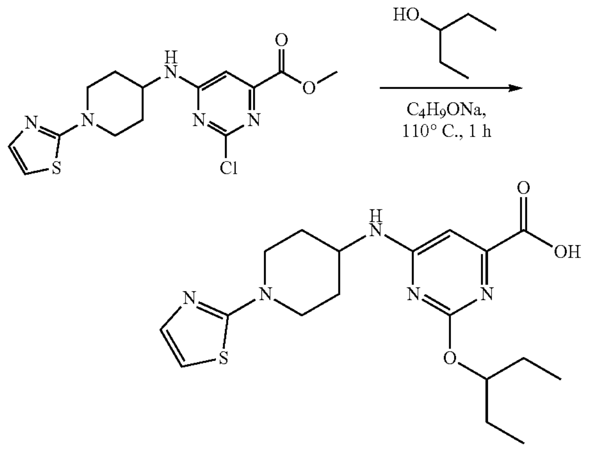

2-chloro-6-((1-(thiazole-2-yl)piperidine-4-yl)amino)pyrimidine-4-carboxylic acid methyl ester (135 mg, 0.381 mmol, 1.0 equiv.) was dissolved in 3-pentanol (2 mL). Sodium tert-butoxide (220 mg, 2.289 mmol, 6.0 equiv) was added. The resulting mixture was stirred at 110° C. for 1 hour, and after the completion of the reaction was detected with LC-MC, concentrated to produce the title compound (50 mg, yield: 33.5%).

LC-MS (ESI) $[M+H]^+$=392.2.

Preparation Example 26: Preparation of 2-((1-acetylpiperidine-4-yl)amino)-6-(cyclopentyloxy) isonicotinic acid (for example this intermediate could be used as an intermediate for the compound of Example 283)

Step 1: Preparation of 2,6-dichloroisonicotinic acid

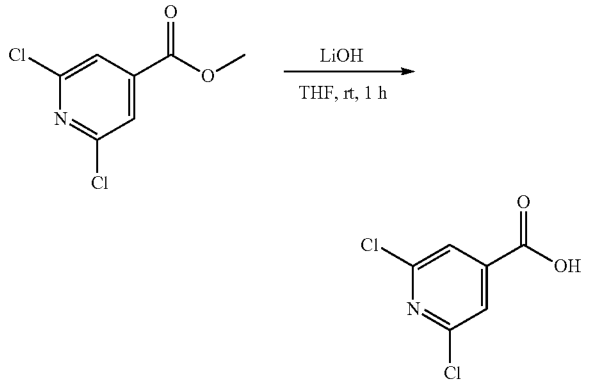

2,6-dichloroisonicotinic acid methyl ester (1.5 g, 7.28 mmol, 1.0 equiv.) was dissolved intetrahydrofuran (10 mL). aqueous lithium hydroxide solution (2 M)(209 mg, 8.73 mmol, 1.2 equiv.) was added. The resulting mixture was stirred at 25° C. for 1 hour, and after the completion of the reaction was detected with LC-MC, concentrated to produce a crude product of the title compound (1.7 g).

LC-MS (ESI) $[M+H]^+$=191.9.

Step 2: Preparation of 2-chloro-6-(cyclopentyloxy)isonicotinic acid

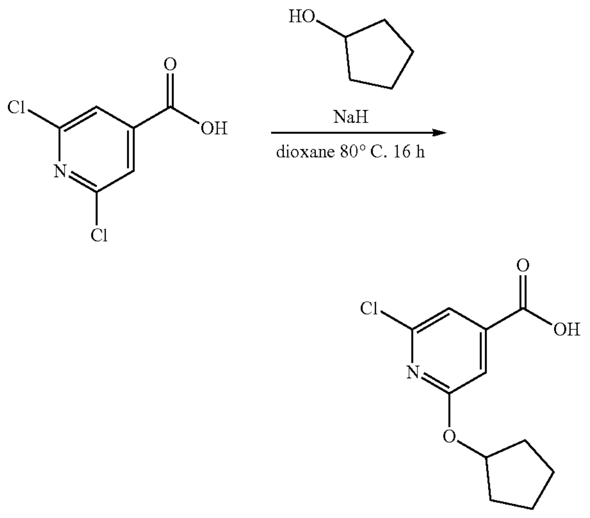

Sodium hydride (1.5 g, 37.5 mmol, 4.0 equiv., purity: 60%) was dissolved in dioxane (40 mL). Cyclopentanol (1.21 g, 14.1 mmol, 1.5 equiv.) was added dropwise at room temperature. The resulting mixture was stirred for 15 minutes. Then 2,6-dichloroisonicotinic acid (1.8 g, 9.38 mmol, 1.0 equiv.) was added. The atmosphere was replaced with nitrogen gas three times. The reaction was performed at 80° C. for 16 hours. After the completion of the reaction was detected with LC-MC, the reaction mixture was diluted with ethyl acetate (50 mL), and washed with 1M hydrochloric acid and saturated brine (50 mL) once. The organic phase was dried over anhydrous sodium sulfate, and concentrated to produce a crude product of the title compound (2.5 g).

LC-MS (ESI) $[M+H]^+$=242.0.

Step 3: Preparation of 2-chloro-6-(cyclopentyloxy)isonicotinic acid methyl ester

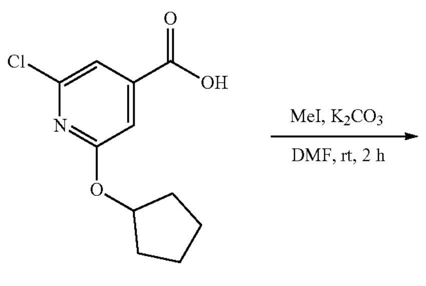

-continued

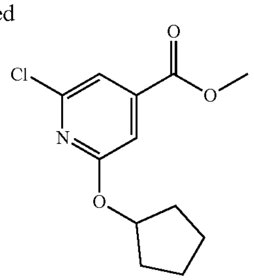

2-chloro-6-(cyclopentyloxy)isonicotinic acid (2.3 g, 9.52 mmol, 1.0 equiv.), iodomethane (1.62 g, 11.42 mmol, 1.2 equiv.) and potassium carbonate (5.26 g, 38.07 mmol, 4.0 equiv.) were dissolved in DMF (40 mL). The reaction was performed at 25° C. for 2 hours. After the completion of the reaction was detected with LC-MC, the resulting mixture was concentrated to obtain a crude product, which was separated and purified with flash chromatography (silica gel, 5% EA/PE solution) to produce the title compound (2 g, yield: 84.9%).

LC-MS (ESI) $[M+H]^+$=256.0.

Step 4: Preparation of 7-((1-acetylpiperidine-4-yl) amino)-6-(cyclopentyloxy)isonicotinic acid methyl ester

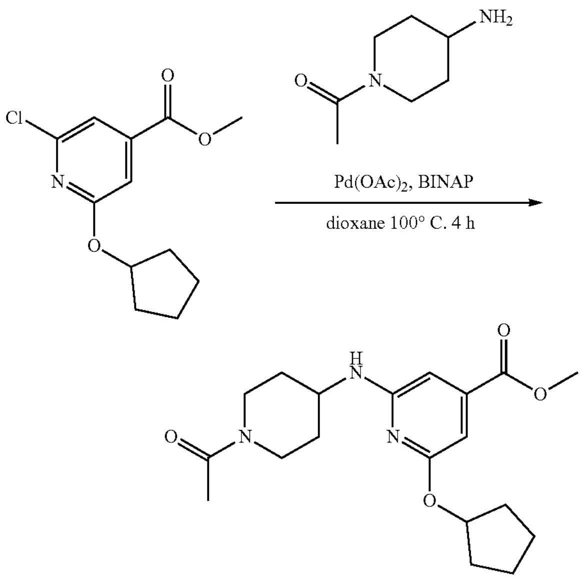

2-chloro-6-(cyclopentyloxy)isonicotinic acid methyl ester (1.4 g, 5.48 mmol, 1.0 equiv.), 1-acetylpiperidine-4-amine (1.17 g, 8.21 mmol, 1.5 equiv.), 2,2'-bis(diphenylphosphino)-1,1'-binaphthyl (1.37 g, 2.19 mmol, 0.4 equiv.), palladium acetate (246 mg, 1.10 mmol, 0.2 equiv.) and cesium carbonate (5.38 g, 16.42 mmol, 3.0 equiv.) were dissolved in dioxane (30 mL). The atmosphere was replaced with nitrogen gas for three times. The reaction was performed at 100° C. for 4 hours. After the completion of the reaction was detected with LC-MC, the resulting mixture was concentrated to obtain a crude product, which was separated and purified with reverse phase HPLC (C18, 10 mmol/L aqueous $NH_4HCO_3$ solution/acetonitrile) to produce the title compound (170 mg, yield: 8.6%).

LC-MS (ESI) $[M+H]^+$=362.0.

Step 5: Preparation of 2-((1-acetylpiperidine-4-yl amino)-6-(cyclopentyloxy)isonicotinic acid

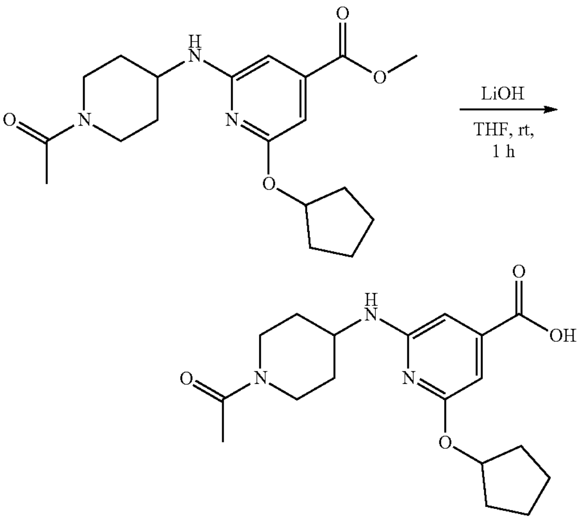

2-((1-acetylpiperidine-4-yl)amino)-6-(cyclopentyloxy) isonicotinic acid methyl ester (150 mg, 0.42 mmol, 1.0 equiv.) was dissolved in tetrahydrofuran (1 mL). aqueous lithium hydroxide solution (2 M)(12 mg, 0.50 mmol, 1.2 equiv.) was added. The resulting mixture was stirred at 25° C. for 1 hour, and after the completion of the reaction was detected with LC-MC, concentrated to produce a crude product of the title compound (150 mg).

LC-MS (ESI) $[M+H]^+$=348.0.

Preparation Example 27: Preparation of ((3R,4R)-4-(3,4-dihydroisoquinoline-2(1H)-yl)-3-hydroxypiperidine-1-yl)(2-isopropoxy-6-(piperidine-4-ylamino) pyrimidine-4-yl)methanone (for example this intermediate could be used as an intermediate for the compound of Example 293)

Step 1: Preparation of 6-((1-(tert-butoxycarbonyl) piperidine-4-yl)amino)-2-chloropyrimidine-4-carboxylic acid methyl ester

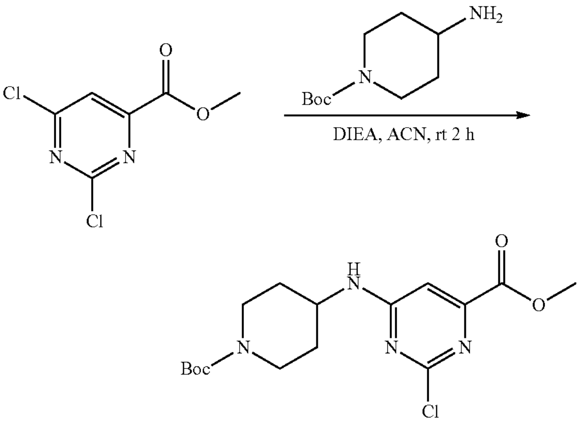

2,6-dichloropyrimidine-4-carboxylic acid methyl ester (1.0 g, 4.85 mmol, 1.0 equiv.) was dissolved in acetonitrile (10 mL). 4-aminopiperidine-1-carboxylic acid tert-butyl ester (873.79 mg, 4.37 mmol, 0.9 equiv.) and N,N-diisopropylethylamine (1.88 g, 14.55 mmol, 3.0 equiv) were added. The resulting mixture was stirred at 25° C. for 2 hours. The completion of the reaction was detected with TLC and LC-MS. The solvent was removed by rotary drying. The crude product was separated and purified with Prep-TLC (EA:PE=20%) to produce the title compound (1.5 g, yield: 83.7%).

LC-MS (ESI) $[M+H]^+$=371.3.

Step 2: Preparation of 6-((1-(tert-butoxycarbonyl)piperidine-4-yl)amino)-2-chloropyrimidine-4-carboxylic acid

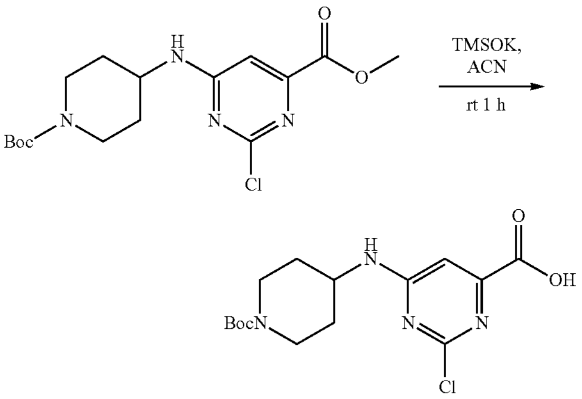

6-((1-(tert-butoxycarbonyl)piperidine-4-yl)amino)-2-chloropyrimidine-4-carboxylic acid methyl ester (500 mg, 1.347 mmol, 1.0 equiv.) was dissolved in acetonitrile (5 mL). Potassium trimethylsilanol (0.1729 g, 1.347 mmol, 1.0 equiv.) was added. The resulting mixture was stirred at 25° C. for 2 hours. After the completion of the reaction was detected with LC-MC, the resulting mixture was concentrated, dissolved in 10% dichloromethane/methanol solution, and filtered. The filtrate was concentrated to produce a crude product of the title compound (480 mg, yield: 99.8%).

LC-MS (ESI) $[M+H]^+$=357.2.

Step 3: Preparation of 6-((1-(tert-butoxycarbonyl)piperidine-4-yl)amino)-2-isopropoxypyrimidine-4-carboxylic acid

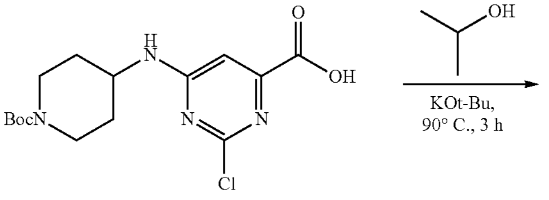

-continued

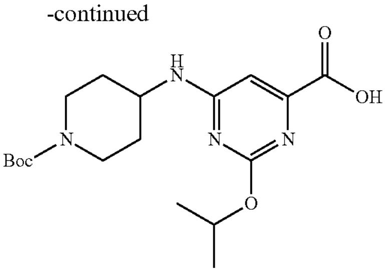

6-((1-(tert-butoxycarbonyl)piperidine-4-yl)amino)-2-chloropyrimidine-4-carboxylic acid (480 mg, 1.35 mmol, 1.0 equiv.) was dissolved in isopropanol (5 mL). Potassium tert-butoxide (628.8 mg, 5.4 mmol, 4.0 equiv) was added. The resulting mixture was stirred at 90° C. for 16 hours. After the completion of the reaction was detected with LC-MC, the resulting mixture was concentrated, and separated and purified with Prep-TLC (MeOH:DCM=10%) to produce the title compound (529 mg, yield: 99.3%).

LC-MS (ESI) $[M+H]^+$=381.3.

Step 4: Preparation of 4-((6-((3R,4R)-4-(3,4-dihydroisoquinoline-2(1H)-yl)-3-hydroxypiperidine-1-carbonyl)-2-isopropoxypyrimidine-4-yl)amino)piperidine-1-carboxylic acid tert-butyl ester

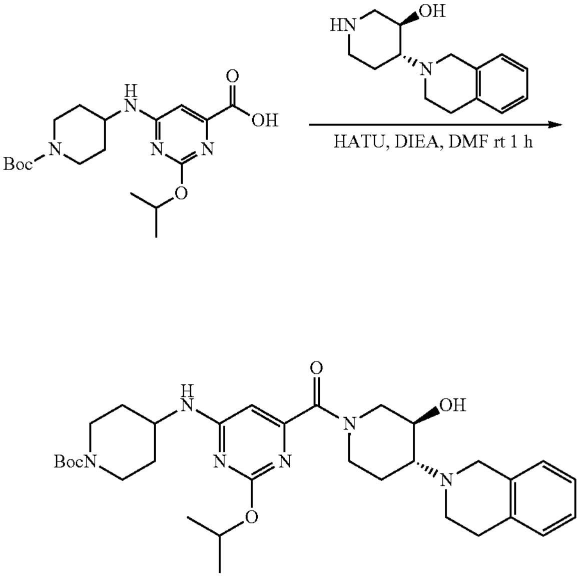

6-((1-(tert-butoxycarbonyl)piperidine-4-yl)amino)-2-isopropoxypyrimidine-4-carboxylic acid (200 mg, 0.526 mmol, 1.0 equiv.) was dissolved in N,N-dimethyl formamide (2 mL). (3R,4R)-4-(3,4-dihydroisoquinoline-2(1H)-yl)piperidine-3-ol (146.6 mg, 0.631 mmol, 1.2 equiv), HATU (299.8 mg, 0.789 mmol, 1.5 equiv) and N,N-diisopropylethylamine (203.8 mg, 1.577 mmol, 3.0 equiv) was added. The resulting mixture was stirred at room temperature for 2 hours. After the completion of the reaction was detected with LC-MC, the mixture was extracted, concentrated, and purified with reverse phase preparative chromatography to produce the title compound (80 mg, yield: 25.6%).

LC-MS (ESI) $[M+H]^+$=595.4.

Step 5: Preparation of ((3R,4R)-4-(3,4-dihydroisoquinoline-2(1H)-yl)-3-hydroxypiperidine-1-yl)(2-isopropoxy-6-(piperidine-4-ylamino)pyrimidine-4-yl)methanone

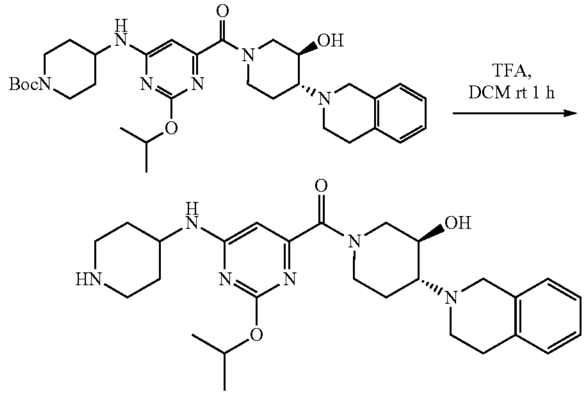

4-((6-((3R,4R)-4-(3,4-dihydroisoquinoline-2(1H)-yl)-3-hydroxypiperidine-1-carbonyl)-2-isopropoxypyrimidine-4-yl)amino)piperidine-1-carboxylic acid tert-butyl ester (80 mg, 0.134 mmol, 1.0 equiv.) was dissolved in dichloromethane (2 mL). trifluoroacetic acid (0.5 mL) was added. The resulting mixture was stirred at 25° C. for 2 hours, and after the completion of the reaction was detected with LC-MC, concentrated to produce a crude product of the title compound (70 mg).

LC-MS (ESI) $[M+H]^+$=495.3.

Preparation Example 28: Preparation of 6-((1-(cyclobutanecarbonyl)piperidine-4-yl)amino)-2-(pyrrolidin-1-yl)pyrimidine-4-carboxylic acid (for example this intermediate could be used as an intermediate for the compound of Example 304)

Step 1: Preparation of 6-((1-(tert-butoxycarbonyl)piperidine-4-yl)amino)-2-chloropyrimidine-4-carboxylic acid methyl ester

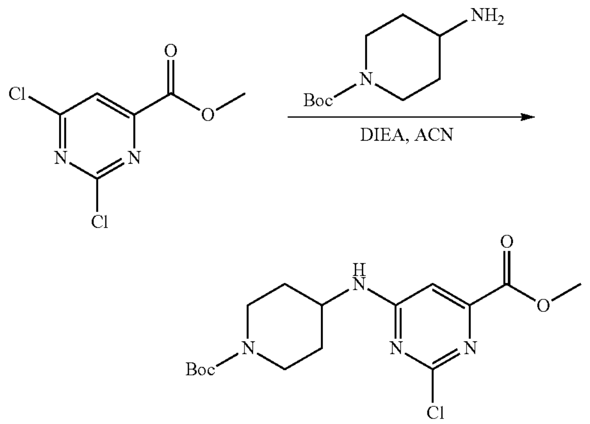

2,6-dichloropyrimidine-4-carboxylic acid methyl ester (1000 mg, 4.85 mmol, 1.0 equiv.) was dissolved in acetonitrile (10 mL). 4-aminopiperidine-1-carboxylic acid tert-butyl ester (873.79 mg, 4.37 mmol, 0.9 equiv.) and N,N-diisopropylethylamine (1876.95 mg, 14.55 mmol, 3.0 equiv) were added. The resulting mixture was stirred at 25° C. for 2 hours. The completion of the reaction was detected with TLC and LC-MS. The solvent was removed by rotary drying. The crude product was separated and purified with Prep-TLC (EA:PE=20%) to produce the title compound (1500 mg, yield: 83.7%).

LC-MS (ESI) $[M+H]^+$=371.3.

Step 2: Preparation of 6-((1-(tert-butoxycarbonyl)piperidine-4-yl)amino)-2-(pyrrolidin-1-yl)pyrimidine-4-carboxylic acid methyl ester

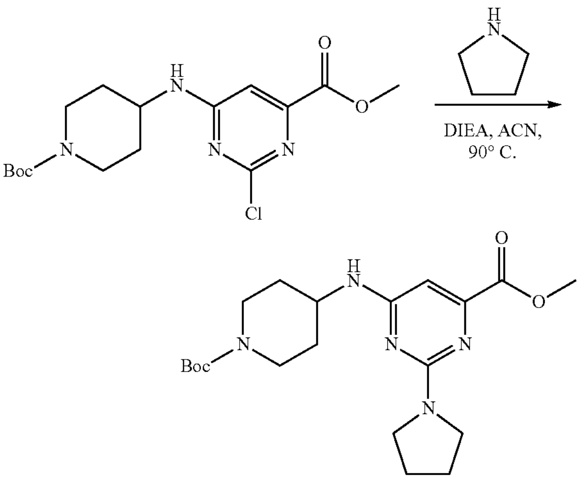

6-((1-(tert-butoxycarbonyl)piperidine-4-yl)amino)-2-chloropyrimidine-4-carboxylic acid methyl ester (500 mg, 1.35 mmol, 1.0 equiv.) was dissolved in acetonitrile (5 mL). Tetrahydropyrrole (105.72 mg, 1.49 mmol, 1.1 equiv) and N,N-diisopropylethylamine (348.3 mg, 2.7 mmol, 2.0 equiv) were added. The resulting mixture was stirred at 90° C. for 16 hours After the completion of the reaction was detected with LC-MC, the resulting mixture was concentrated, and separated and purified with Prep-TLC (EA:PE=30%) to produce the title compound (373 mg, yield: 68.2%).

LC-MS (ESI) $[M+H]^+$=406.4.

Step 3: Preparation of 6-(piperidine-4-ylamino)-2-(pyrrolidin-1-yl)pyrimidine-4-carboxylic acid methyl ester

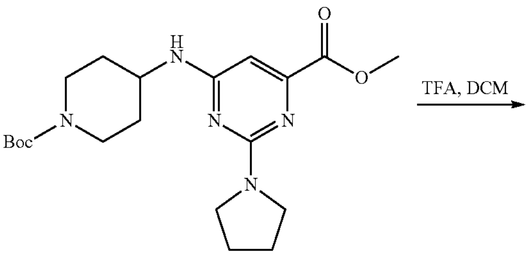

-continued

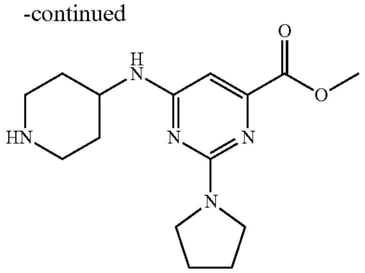

6-((1-(tert-butoxycarbonyl)piperidine-4-yl)amino)-2-(pyrrolidin-1-yl)pyrimidine-4-carboxylic acid methyl ester (50 mg, 0.123 mmol, 1.0 equiv.) was dissolved in dichloromethane (1 mL). Trifluoroacetic acid (0.25 mL) was added. The resulting mixture was stirred at 25° C. for 2 hours. After the completion of the reaction was detected with LC-MC, the mixture was extracted, and concentrated to produce a crude product of the title compound (50 mg, yield: 100%).

LC-MS (ESI) $[M+H]^+$=306.4.

Step 4: Preparation of 6-((1-(cyclobutanecarbonyl)piperidine-4-yl)amino)-2-(pyrrolidin-1-yl)pyrimidine-4-carboxylic acid methyl ester

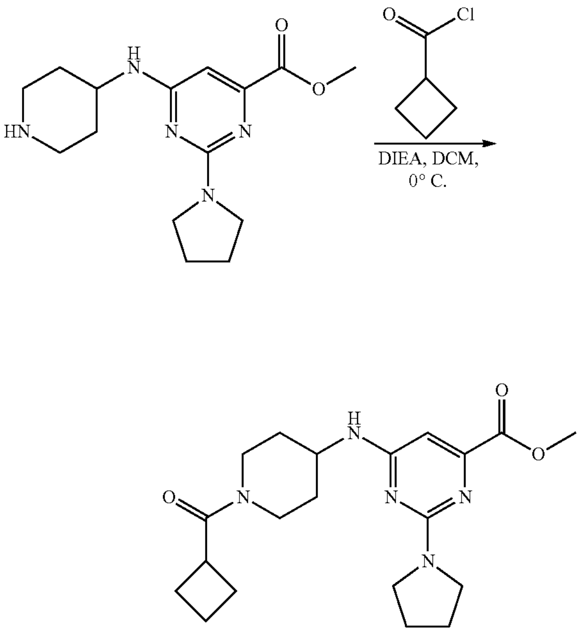

6-(piperidine-4-ylamino)-2-(pyrrolidin-1-yl)pyrimidine-4-carboxylic acid methyl ester (50 mg, 0.164 mmol, 1.0 equiv.) was dissolved in dichloromethane (1 mL). N,N-diisopropylethylamine (63.44 mg, 0.49 mmol, 3.0 equiv) was added. The resulting mixture was stirred at 0° C. for 15 minutes. Under an ice bath, cyclobutanecarbonyl chloride (21.29 mg, 0.18 mmol, 1.1 equiv) was added dropwise. The resulting mixture was stirred for 1 hour. After the completion of the reaction was detected with LC-MC, the mixture was extracted, and concentrated to produce a crude product of the title compound (62 mg, yield: 97.79%).

LC-MS (ESI) $[M+H]^+$=388.3.

Step 5: Preparation of 6-((1-(cyclobutanecarbonyl)piperidine-4-yl)amino)-2-(pyrrolidin-1-yl)pyrimidine-4-carboxylic acid

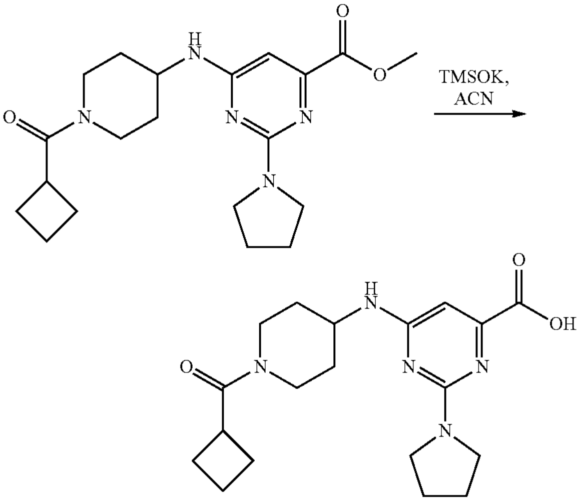

6-((1-(cyclobutanecarbonyl)piperidine-4-yl)amino)-2-(pyrrolidin-1-yl)pyrimidine-4-carboxylic acid methyl ester (62 mg, 0.16 mmol, 1.0 equiv.) was dissolved in acetonitrile (1 mL). Potassium trimethylsilanol (24.8 mg, 0.24 mmol, 1.5 equiv) was added. The resulting mixture was stirred at 25° C. for 2 hours. After the completion of the reaction was detected with LC-MC, the resulting mixture was concentrated, adjusted with diluted hydrochloric acid solution to a weak acidic pH to produce a crude product of the title compound (62 mg).

LC-MS (ESI) $[M+H]^+$=374.3.

Preparation Example 29: Preparation of 2-(piperidine-1-yl)-6-((1-(pyrimidine-4-yl)piperidine-4-yl)amino)pyrimidine-4-carboxylic acid (for example this intermediate could be used as an intermediate for the compound of Example 318)

Step 1: Preparation of 6-((1-(tert-butoxycarbonyl)piperidine-4-yl)amino)-2-chloropyrimidine-4-carboxylic acid methyl ester

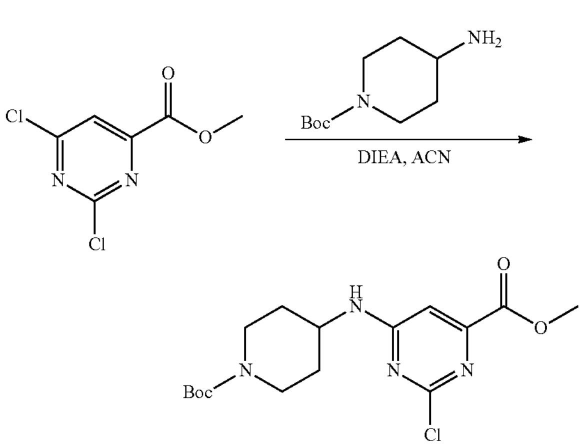

2,6-dichloropyrimidine-4-carboxylic acid methyl ester (1 g, 4.85 mmol, 1.0 equiv.) was dissolved in acetonitrile (10 mL). 4-aminopiperidine-1-carboxylic acid tert-butyl ester (873.79 mg, 4.37 mmol, 0.9 equiv.) and N,N-diisopropylethylamine (1.88 g, 14.55 mmol, 3.0 equiv) were added. The resulting mixture was stirred at 25° C. for 2 hours. The completion of the reaction was detected with TLC and LC-MS. The solvent was removed by rotary drying. The crude product was separated and purified flash silica gel column chromatography (EA:PE=1:5) to produce the title compound (1.5 g, yield: 83.7%).

LC-MS (ESI) $[M+H]^+$=371.3.

Step 2: Preparation of 6-((1-(tert-butoxycarbonyl)piperidine-4-yl)amino)-2-(piperidine-1-yl)pyrimidine-4-carboxylic acid methyl ester

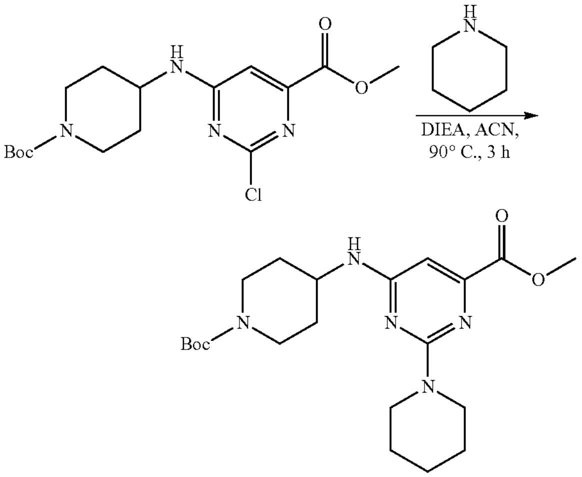

6-((1-(tert-butoxycarbonyl)piperidine-4-yl)amino)-2-chloropyrimidine-4-carboxylic acid methyl ester (500 mg, 1.35 mmol, 1.0 equiv.) was dissolved in acetonitrile (5 mL). hexahydropyridine (126.3 mg, 1.48 mmol, 1.1 equiv) and N,N-diisopropylethylamine (348.3 mg, 2.7 mmol, 2.0 equiv) were added. The resulting mixture was stirred at 90° C. for 16 hours After the completion of the reaction was detected with LC-MC, the resulting mixture was concentrated, and separated and purified flash silica gel column chromatography (EA:PE=1:3) to produce the title compound (300 mg, yield: 53%).

LC-MS (ESI) $[M+H]^+$=420.2.

Step 3: Preparation of 2-(piperidine-1-yl)-6-(piperidine-4-ylamino)pyrimidine-4-carboxylic acid methyl ester

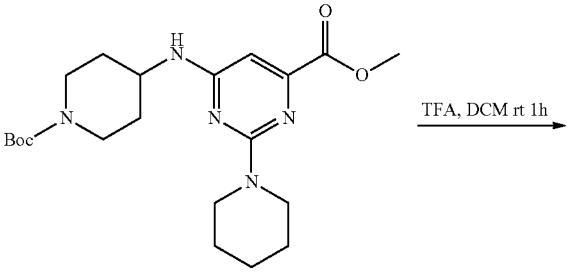

-continued

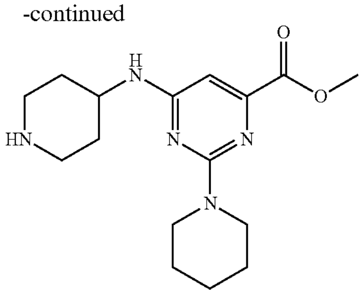

6-((1-(tert-butoxycarbonyl)piperidine-4-yl)amino)-2-(piperidine-1-yl)pyrimidine-4-carboxylic acid methyl ester (150 mg, 0.358 mmol, 1.0 equiv.) was dissolved in dichloromethane (2 mL). Trifluoroacetic acid (0.25 mL) was added. The resulting mixture was stirred at 25° C. for 2 hours. After the completion of the reaction was detected with LC-MC, water was added, and the reaction mixture was extracted with dichloromethane, and concentrated to produce a crude product of the title compound (140 mg).

LC-MS (ESI) $[M+H]^+$=320.2.

Step 4: Preparation of 2-(piperidine-1-yl)-6-((1-(pyrimidine-4-yl)piperidine-4-yl)amino)pyrimidine-4-carboxylic acid methyl ester

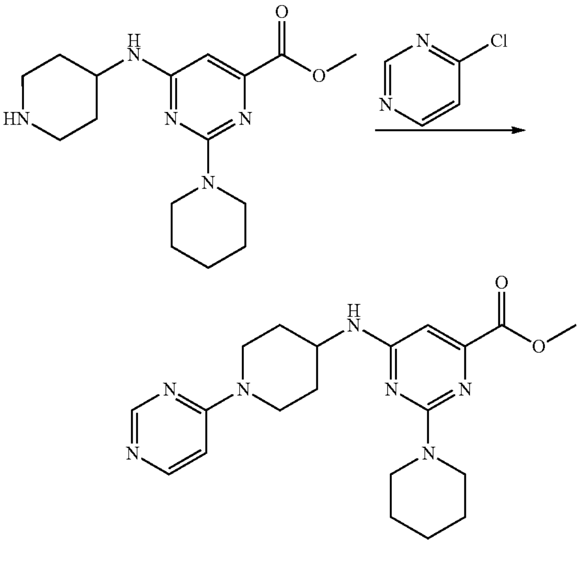

2-(piperidine-1-yl)-6-(piperidine-4-ylamino)pyrimidine-4-carboxylic acid methyl ester (100 mg, 0.31 mmol, 1.0 equiv.) was dissolved in dichloromethane (1 mL). DIPEA (121.40 mg, 0.94 mmol, 3.0 equiv) was added. The resulting mixture was stirred at 0° C. for 15 minutes. Under an ice bath, 4-chloropyrimidine (39.40 mg, 0.34 mmol, 1.1 equiv) was added dropwise. The resulting mixture was stirred for 1 hour. After the completion of the reaction was detected with LC-MC, water was added. The resulting mixture was extracted with dichloromethane, and concentrated to produce a crude product of the title compound (112 mg, yield: 90%).

LC-MS (ESI) $[M+H]^+$=398.2.

Step 5: Preparation of 2-piperidine-1-yl)-6-((1-(pyrimidine-4-yl)piperidine-4-yl)amino)pyrimidine-4-carboxylic acid

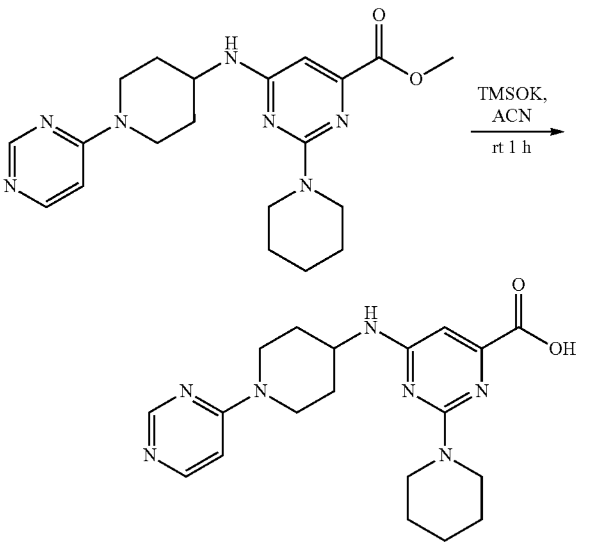

2-(piperidine-1-yl)-6-((1-(pyrimidine-4-yl)piperidine-4-yl)amino)pyrimidine-4-carboxylic acid methyl ester (112 mg, 0.28 mmol, 1.0 equiv.) was dissolved in acetonitrile (1 mL). Potassium trimethylsilanol (53.76 mg, 0.42 mmol, 1.5 equiv) was added. The resulting mixture was stirred at 25° C. for 2 hours. After the completion of the reaction was detected with LC-MC, the resulting mixture was concentrated, and adjusted with diluted hydrochloric acid solution to a weak acidic pH to produce a crude product of the title compound (62 mg, yield: 57.4%).

LC-MS (ESI) $[M+H]^+$=385.1.

Preparation Example 30: Preparation of 6-((2-(methylsulfonyl)ethyl)amino)-2-(pyrrolidin-1-yl) pyrimidine-4-carboxylic acid (for example this intermediate could be used as an intermediate for the compound of Example 322)

Step 1: Preparation of 2-(methylsulfonyl)ethane-1-amino

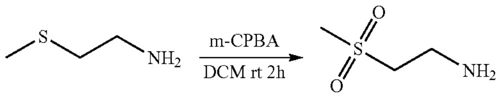

2-(methylthio)ethylamine (500 mg, 7.48 mmol, 1.0 equiv.) was dissolved in dichloromethane (30 mL). meta-chloroperoxybenzoic acid (2.08 g, 12.06 mmol, 2.2 equiv.) was added. The resulting mixture was stirred at room temperature (25° C.) for 3 hours, and quenched with saturated sodium sulfite solution. The solvent was removed by rotary drying to produce a crude product of the title compound (500 mg).

Step 2: Preparation of 2-chloro-6-((2-(methylsulfonyl)ethyl)amino)pyrimidine-4-carboxylic acid methyl ester

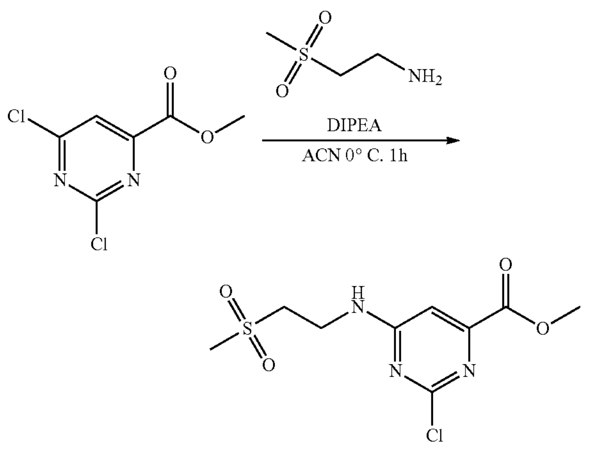

2,6-dichloropyrimidine-4-carboxylic acid methyl ester (1.2 g, 5.79 mmol, 1.0 equiv.) was dissolved in acetonitrile (25 mL). 2-(methylsulfonyl)ethane-1-amine (714 mg, 5.79 mmol, 1.0 equiv.) and N,N-diisopropylethylamine (2.25 g, 17.39 mmol, 3.0 equiv.) were added at 0° C. The resulting mixture was stirred at 0° C. under nitrogen gas for 1 hour. After the completion of the reaction was detected with TLC, the solvent was removed by rotary drying, and the residue was slurrized with ethyl acetate. The resulting slurry was filtered to collect a solid to produce the title compound (500 mg, yield: 29.4%).

LC-MS (ESI) $[M+H]^+$=294.0.

Step 3: Preparation of 6-((2-(methylsulfonyl)ethyl) amino)-2-(pyrrolidin-1-yl)pyrimidine-4-carboxylic acid methyl ester

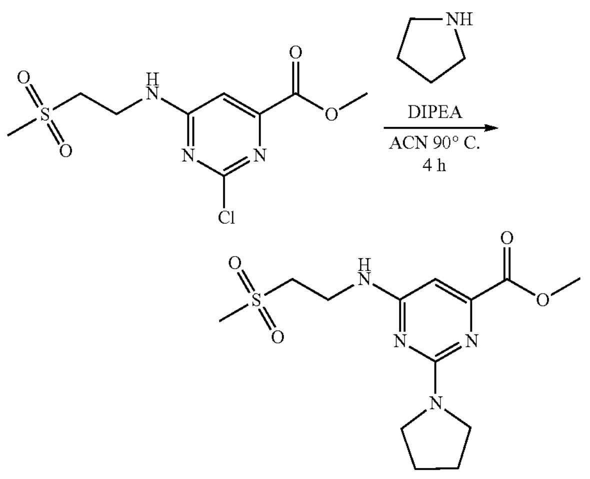

2-chloro-6-((2-(methylsulfonyl)ethyl)amino)pyrimidine-4-carboxylic acid methyl ester (250 mg, 0.85 mmol, 1.0 equiv.), and tetrahydropyrrole (67 mg, 0.94 mmol, 1.1 equiv.) were dissolved in acetonitrile (5 mL). N,N-diisopropylethylamine (165 mg, 1.28 mmol, 1.5 equiv.) was added.

The resulting mixture was stirred at 90° C. for 2 hours. After the completion of the reaction was detected with LC-MC, the reaction mixture was extracted with ethyl acetate (5 mL) three times, and separated and purified with flash chromatography (silica gel, DCM:MeOH=100:6) to produce the title compound (140 mg, yield: 50.1%).

LC-MS (ESI) $[M+H]^+$=329.2.

Step 4: Preparation of 6-((2-(methylsulfonyl)ethyl) amino)-2-(pyrrolidin-1-yl)pyrimidine-4-carboxylic acid

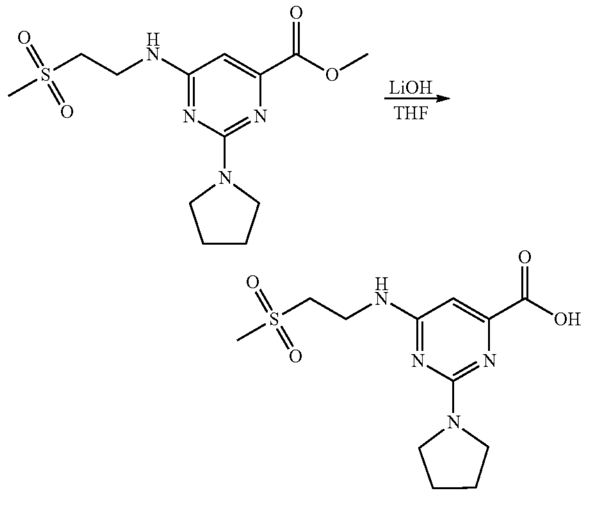

6-((2-(methylsulfonyl)ethyl)amino)-2-(pyrrolidin-1-yl) pyrimidine-4-carboxylic acid methyl ester (150 mg, 0.46 mmol, 1.0 equiv.) was dissolved in tetrahydrofuran (2 mL). aqueous lithium hydroxide solution (2 M)(21 mg, 0.91 mmol, 2.0 equiv.) was added. The resulting mixture was stirred at 25° C. for 2 hours, and after the completion of the reaction was detected with LC-MC, concentrated to produce a crude product of the title compound (170 mg).

LC-MS (ESI) $[M+H]^+$=315.2.

Preparation Example 31: Preparation of 6-((2-(benzyloxycarbonyl)-2-azaspiro[3.3]heptan-6-yl)amino)-2-(pyrrolidin-1-yl)pyrimidine-4-carboxylic acid (for example this intermediate could be used as an intermediate for the compound of Example 327)

Step 1: Preparation of 6-((tert-butoxycarbonyl) amino)-2-azaspiro[3.3]heptane-2-carboxylic acid benzyl ester

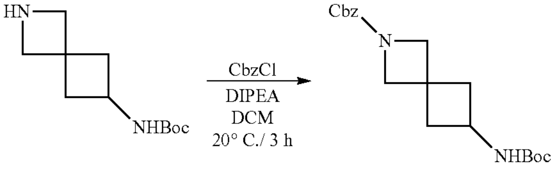 [SMILES: "CbzCl" ; CC(C)(C)OC(=O)NC1CC2(CNC2)C1 ; CC(C)(C)OC(=O)NC1CC2(C1)CN(C(=O)OCc1ccccc1)C2]

(2-azaspiro[3.3]heptan-6-yl)carbamic acid tert-butyl ester (550 mg, 2.59 mmol, 1.0 equiv.), CbzCl (486 mg, 2.85 mmol, 1.1 equiv.) and DIPEA (670 mg, 5.18 mmol, 2.0 equiv.) were dissolved in DCM (13 mL). The reaction was performed at 20° C. for 3 hours. The reaction solution was concentrated. The resulting crude product was separated and purified with flash chromatography (silica gel, DCM: MeOH=49:1) to produce the target compound (658 mg, yield: 73.3%).

LC-MS (ESI) $[M+H]^+$=347.2.

Step 2: Preparation of 6-amino-2-azaspiro[3.3]heptane-2-carboxylic acid benzyl ester

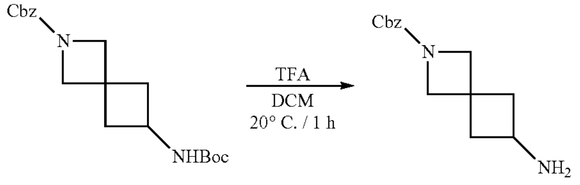 [SMILES: CC(C)(C)OC(=O)NC1CC2(C1)CN(C(=O)OCc1ccccc1)C2 ; NC1CC2(C1)CN(C(=O)OCc1ccccc1)C2 ; "TFA"]

6-((tert-butoxycarbonyl)amino)-2-azaspiro[3.3]heptane-2-carboxylic acid benzyl ester (658 mg, 1.90 mmol, 1.0 equiv.) and TFA (2.5 mL) were dissolved in dichloromethane (10 mL). The reaction was performed at 20° C. for 1 hour. The reaction solution was quenched with saturated aqueous sodium bicarbonate solution, and extracted with dichloromethane. The organic phase was concentrated to produce the target compound (crude, 468 mg, yield: 100%).

LC-MS (ESI) $[M+H]^+$=247.2.

Step 3: Preparation of 6-((2-chloro-6-(methoxycarbonyl)pyrimidine-4-yl)amino)-2-azaspiro[3.3]heptane-2-carboxylic acid benzyl ester

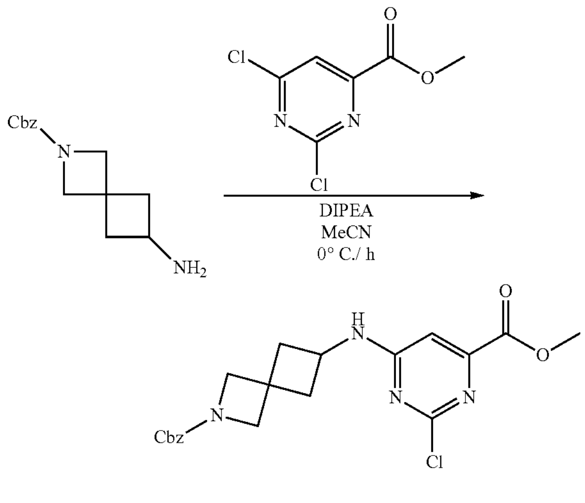

6-amino-2-azaspiro[3.3]heptane-2-carboxylic acid benzyl ester (468 mg, 1.90 mmol, 1.0 equiv.), 2,6-dichloropyrimidine-4-carboxylic acid methyl ester (393 mg, 1.90 mmol, 1.0 equiv.) and DIPEA (491 mg, 3.80 mmol, 2.0 equiv.) were dissolved in acetonitrile (20 mL). The reaction was performed for 0° C. for 1 hours. The reaction solution was concentrated. The crude product was separated and purified with flash chromatography (silica gel, DCM:MeOH=49:1) to produce the title compound (754 mg, yield: 95.3%).

LC-MS (ESI) $[M+H]^+$=417.2.

Step 4: Preparation of 6-((6-(methoxycarbonyl)-2-(pyrrolidin-1-yl)pyrimidine-4-yl)amino)-2-azaspiro[3.3]heptane-2-carboxylic acid benzyl ester

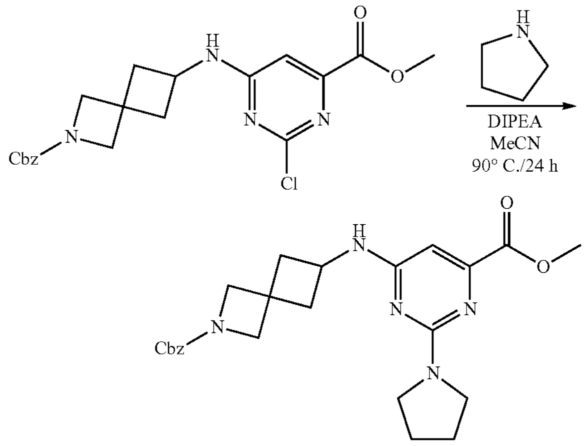

6-((2-chloro-6-(methoxycarbonyl)pyrimidine-4-yl)amino)-2-azaspiro[3.3]heptane-2-carboxylic acid benzyl ester (120 mg, 0.29 mmol, 1.0 equiv.), tetrahydropyrrole (23 mg, 0.32 mmol, 1.1 equiv.) and DIPEA (74 mg, 0.58 mmol, 2.0 equiv.) were dissolved in acetonitrile (4 mL). The reaction was performed at 90° C. for 24 hours. The reaction solution was concentrated. The crude product was separated and purified with flash chromatography (silica gel, DCM:MeOH=49:1) to produce the title compound (120 mg, yield: 92.3%).

LC-MS (ESI) $[M+H]^+$=452.2.

Step 5: Preparation of 6-((2-(benzyloxycarbonyl)-2-azaspiro[3.3]heptan-6-yl)amino)-2-(pyrrolidin-1-yl)pyrimidine-4-carboxylic acid

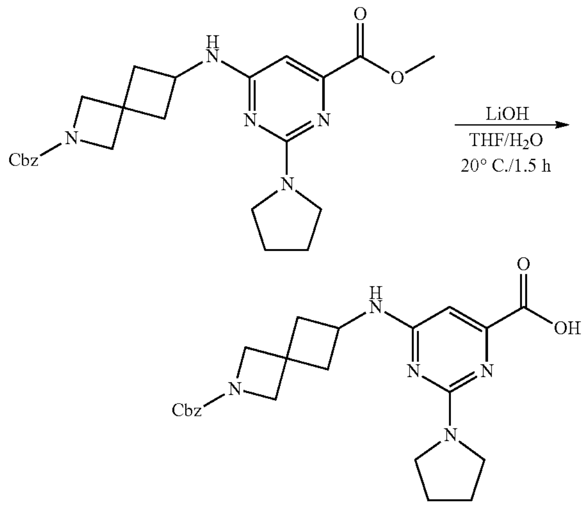

6-((6-(methoxycarbonyl)-2-(pyrrolidin-1-yl)pyrimidine-4-yl)amino)-2-azaspiro[3.3]heptane-2-carboxylic acid benzyl ester (120 mg, 0.27 mmol, 1.0 equiv.) and LiOH (13 mg, 0.53 mmol, 2.0 equiv.) were dissolved in THF (4 mL) and water (0.4 mL). The reaction was performed at 20° C. for 1.5 hours. The reaction solution was adjusted with diluted hydrochloric acid to acidity, and concentrated to produce the target compound (crude, 197 mg).

LC-MS (ESI) $[M+H]^+$=438.2.

Preparation Example 32: Preparation of 6-((1-(tert-butoxycarbonyl)piperidine-4-yl)amino)-2-(trifluoromethyl)pyrimidine-4-carboxylic acid (for example this intermediate could be used as an intermediate for the compound of Example 356)

Step 1: Preparation of 4-((6-chloro-2-(trifluoromethyl)pyrimidine-4-yl)amino)piperidine-1-carboxylic acid tert-butyl ester

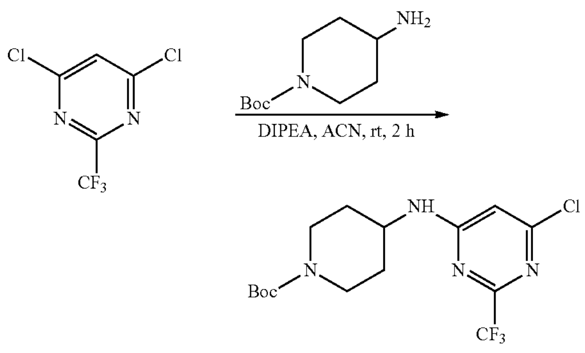

4,6-dichloro-2-(trifluoromethyl)pyrimidine (2 g, 9.2 mmol), 4-aminopiperidine-1-carboxylic acid tert-butyl ester (1.846 g, 9.2 mmol) and DIPEA (1.78 g, 13.82 mmol) were dissolved in acetonitrile (20 mL). The resulting mixture was stirred at room temperature (25-30° C.) for 2 hours. The reaction was monitored with LC-MS, until the raw materials disappeared. The resulting mixture was extracted with ethyl acetate three times, each time 40 mL. The ethyl acetate phases were combined, washed with water (40 mL) once, washed with saturated brine (40 mL) once, dried over anhydrous sodium sulfate for 10 minutes, and filtered. The crude product was separated and purified with a column chromatography (DCM:MeOH=50:1) to produce a product (3.47 g, yield: 96.9%).

LC-MS (ESI) $[M+H]^+$=381.2.

Step 2: Preparation of 6-((1-(tert-butoxycarbonyl)piperidine-4-yl)amino)-2-(trifluoromethyl)pyrimidine-4-carboxylic acid methyl ester

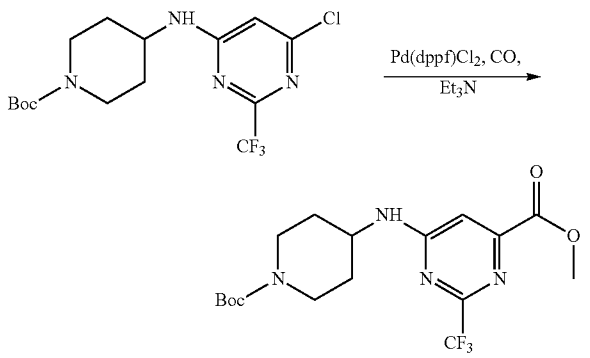

4-((6-chloro-2-(trifluoromethyl)pyrimidine-4-yl)amino) piperidine-1-carboxylic acid tert-butyl ester (3.47 g, 9.1 mmol), $Et_3N$ (2.76 g, 27.3 mmol) and Pd(dppf)$Cl_2$ (0.66 g, 0.91 mmol) were dissolved in a mixed solution of methanol (50 mL) and DMF (50 mL). The reaction was performed in a CO atmosphere of 4 atm under heating at 100° C. for 72 hours. LC-MS detection indicated all raw materials were converted to the product. The reaction solvent was removed by rotary drying. The reaction mixture were extracted with ethyl acetate three times, each time 40 mL. The ethyl acetate phases were combined, washed with water (40 mL) once, washed with saturated brine (40 mL) once, dried over anhydrous sodium sulfate for 10 minutes, and filtered. The crude product was separated and purified with a column chromatography (DCM:MeOH=30:1) to obtain a crude product (3 g, yield: 81.6%).

LC-MS (ESI) $[M+H]^+$=405.2.

Step 3: Preparation of 6-((1-(tert-butoxycarbonyl) piperidine-4-yl)amino)-2-(trifluoromethyl)pyrimidine-4-carboxylic acid

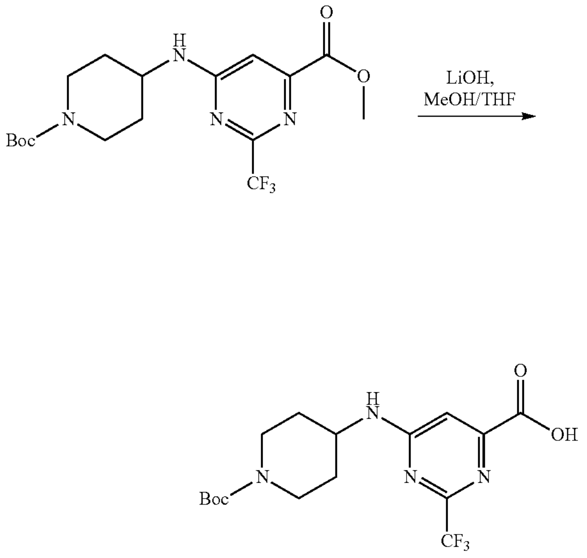

6-((1-(tert-butoxycarbonyl)piperidine-4-yl)amino)-2-(trifluoromethyl)pyrimidine-4-carboxylic acid methyl ester (2 g, 4.95 mmol) was dissolved in THF (10 mL) and methanol (10 mL). Then aqueous lithium hydroxide solution (5 mL, 10 mmol, 2M) was added. The reaction solution was stirred at room temperature for 1 hour. LC-MS indicated the completion of the reaction. The reaction solution was extracted with ethyl acetate three times, each time 10 mL. The aqueous phase was retained, adjusted with 1 M (molar concentration) hydrochloric acid to pH=6-7, and directly rotary dried to produce a crude product of the title compound (2.18 g).

LC-MS (ESI) $[M+H]^+$=391.2.

Preparation Example 33: Preparation of 6-((1-acetylpiperidine-4-yl)amino)-2-cyclohexylpyrimidine-4-carboxylic acid (for example this intermediate could be used as an intermediate for the compound of Example 357)

Step 1: Preparation of 6-((1-acetylpiperidine-4-yl) amino)-2-(cyclohex-1-en-1-yl)pyrimidine-4-carboxylic acid methyl ester

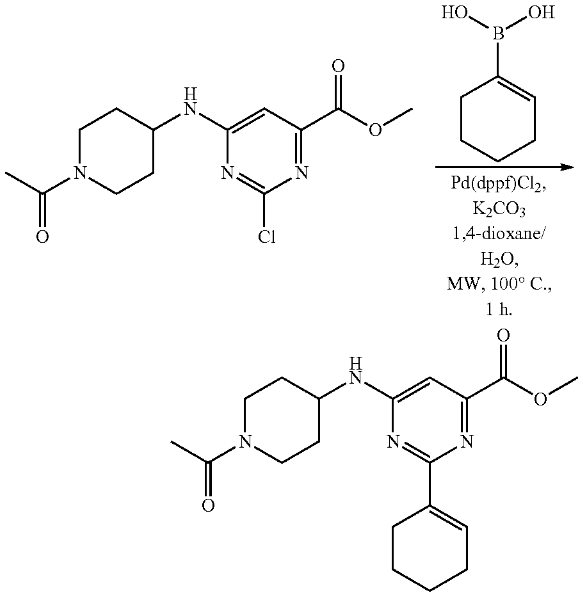

6-((1-acetylpiperidine-4-yl)amino)-2-chloropyrimidine-4-carboxylic acid methyl ester (300 mg, 0.959 mmol, 1 equiv.), cyclohex-1-en-1-ylboronic acid (241.6 mg, 1.918 mmol, 2.0 equiv.), [1,1'-bis(diphenylphosphino)ferrocene] palladium dichloride (70.24 mg, 0.096 mmol, 0.1 equiv.) and potassium carbonate (397.7 mg, 2.978 mmol, 3 equiv.) were mixed in dioxane (80 mL) and water (20 mL, deoxygenated with nitrogen in advance), The reaction was performed under heating in an oil bath at 100° C. for 1 hour. LC-MS monitored the complete consumption of raw materials. The reaction solution was filtered, and rotary dried to produce a crude product of the title compound (343 mg).

LC-MS (ESI) $[M+H]^+$=359.2.

Step 2: Preparation of 6-((1-acetylpiperidine-4-yl) amino)-2-(cyclohex 1-en-1-yl)pyrimidine-4-carboxylic acid

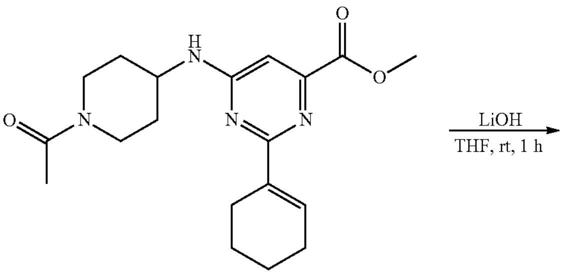

-continued

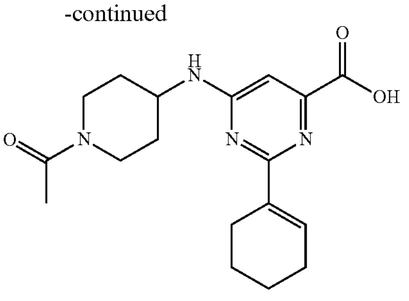

At room temperature (25° C.), 6-((1-acetylpiperidine-4-yl)amino)-2-(cyclohex-1-en-1-yl)pyrimidine-4-carboxylic acid methyl ester (343 mg, 0.957 mmol, 1.0 equiv.) was added to water (1 mL) and tetrahydrofuran (4.0 mL). lithium hydroxide (45.8 mg, 1.914 mmol, 2.0 equiv.) was added. The resulting mixture was stirred at room temperature for 1 hour. After the completion of the reaction was detected with LC-MC, the reaction solution was concentrated, and the organic solvent was removed. The system was adjusted with 1M hydrochloric acid to pH=3, and extracted with dichloromethane:methanol (V/V=10/1)(30 mL×5). The organic phases were combined, dried, filtered, and concentrated to produce a crude product of the title compound (1.1 g).

LC-MS (ESI) $[M+H]^+$=345.2.

Step 3: Preparation of 6-((1-acetylpiperidine-4-yl)amino)-2-cyclohexylpyrimidine-4-carboxylic acid

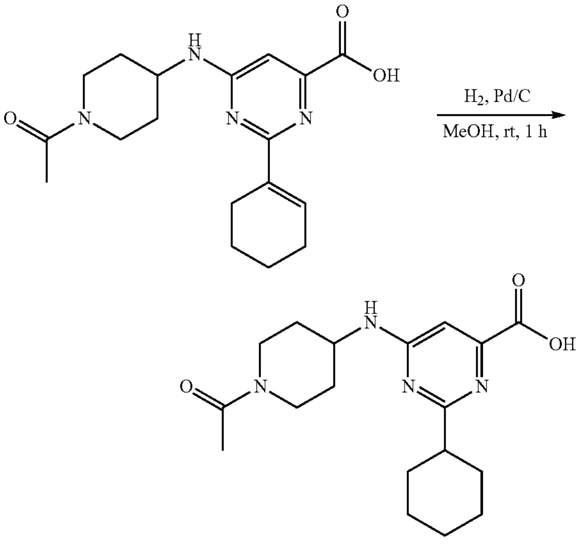

6-((1-acetylpiperidine-4-yl)amino)-2-(cyclohex-1-en-1-yl)pyrimidine-4-carboxylic acid (1.05 g, 3.049 mmol, 1.0 equiv.) was added to methanol (10 mL). Then palladium/carbon (324 mg, 0.305 mmol, 0.1 equiv, 10%.) was added. Under the condition of hydrogen gas, the resulting mixture was stirred at room temperature for 2 hours. After the completion of the reaction was detected with LC-MC, the system was filtered, and concentrated to obtain a crude product, which was separated and purified with Prep-HPLC (C18, 10 mmol/L aqueous $NH_4HCO_3$ solution, MeCN), lyophilized to produce the title compound (148 mg, yield: 14%).

LC-MS (ESI) $[M+H]^+$=347.3.

Preparation Example 34: Preparation of 6-((1-acetylpiperidine-4-yl)amino)-2-ethylpyrimidine-4-carboxylic acid (for example this intermediate could be used as an intermediate for the compound of Example 365)

Step 1: Preparation of 6-((1-acetylpiperidine-4-yl)amino)-2-((trimethylsilyl)ethynyl)pyrimidine-4-carboxylic acid methyl ester

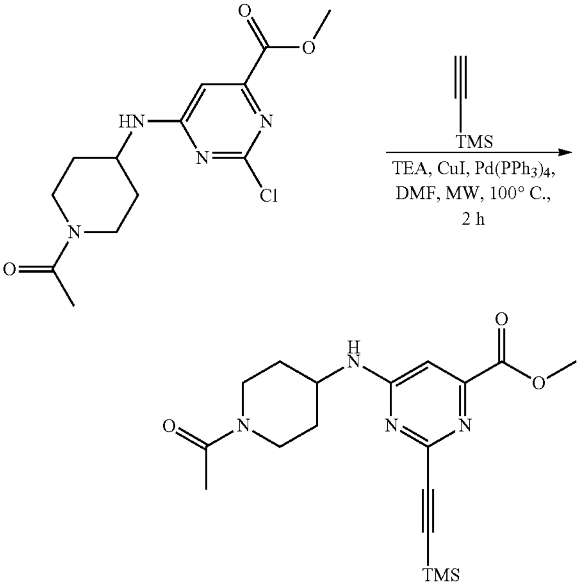

6-((1-acetylpiperidine-4-yl)amino)-2-chloropyrimidine-4-carboxylic acid methyl ester (999.86 mg, 3.2 mmol, 1 equiv.), ethynyltrimethylsilane (1.88 g, 0.019 mol, 6 equiv.), copper(I) iodide (0.091 g, 0.48 mmol, 0.15 equiv.), triethylamine (0.97 g, 9.6 mmol, 3 equiv.) and tetrakis(triphenylphosphine)palladium (0.55 g, 0.48 mmol, 0.15 equiv.) were dissolved in DMF (N,N-dimethyl formamide)(8 mL). The atmosphere was replaced with nitrogen gas for 2 minutes. The reaction was performed under microwave heating at 100° C. for 2 hours. After the completion of the reaction was detected with TLC, the reaction system was filtered. The filter cake was washed with a mixed solvent (DCM:MeOH=10:1, 15 mL) two times. The filtrate was concentrated to obtain a crude product, which was firstly separated with column chromatography (DCM:MeOH=10:1), and concentrated to produce the title compound (0.5 g, yield: 41.8%).

$^1H$ NMR (400 MHz, DMSO) δ 7.95 (d, J=7.4 Hz, 1H), 7.06 (s, 1H), 4.17 (d, J=14.0 Hz, 2H), 3.84 (s, 3H), 3.75 (s, 1H), 3.22 (t, J=11.7 Hz, 1H), 2.86 (t, J=10.9 Hz, 1H), 2.01 (s, 3H), 1.87 (dd, J=23.0 Hz, 12.0 Hz, 2H), 1.42-1.33 (m, 1H), 1.33- 1.25 (m, 1H), 0.26 (s, 9H).

Step 2: Preparation of 6-((1-acetylpiperidine-4-yl) amino)-2-ethynylpyrimidine-4-carboxylic acid methyl ester

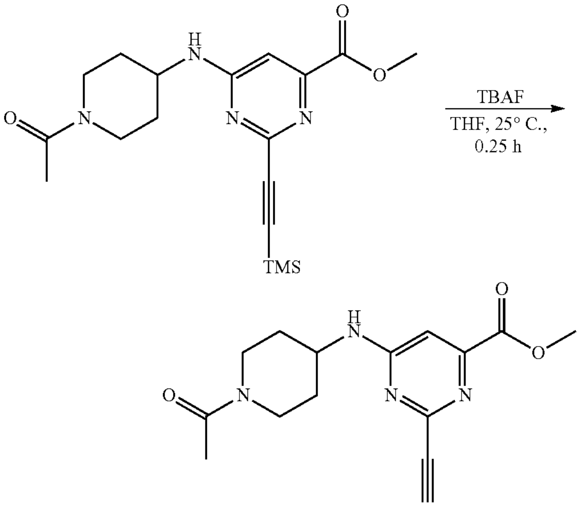

A solution of tetrabutylammonium fluoride in tetrahydrofuran (0.21 mL, 0.80 mmol, 1.5 equiv.) was added to a solution of 6-((1-acetylpiperidine-4-yl)amino)-2-((trimethylsilyl)ethynyl)pyrimidine-4-carboxylic acid methyl ester (0.2 g, 0.53 mmol, 1 equiv.) in tetrahydrofuran (10 mL). The reaction was performed at 25° C. for half an hour. After the completion of the reaction was detected with LC-MC, the system was concentrated to produce a crude product (161.44 mg, 0.534 mmol), which was used directly in the next reaction without purification.

LC-MS (ESI) $[M+H]^+$=303.1.

Step 3: Preparation of 6-((1-acetylpiperidine-4-yl) amino)-2-ethylpyrimidine-4-carboxylic acid methyl ester

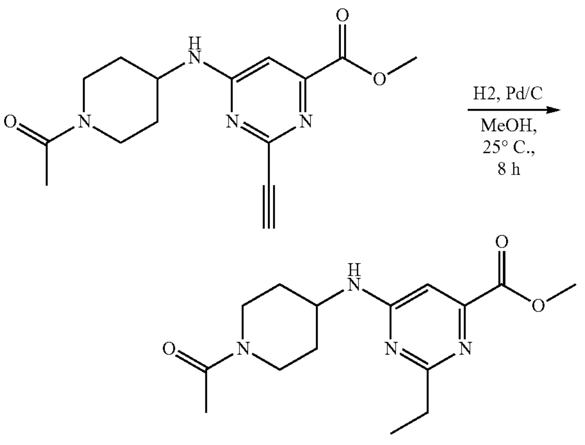

Under the atmosphere of nitrogen gas, Pd/C (0.0227 g, 0.11 mmol, 0.2 equiv.) was added to a solution of 6-((1-acetylpiperidine-4-yl)amino)-2-ethynylpyrimidine-4-carboxylic acid methyl ester (161.44 mg, 0.53 mmol, 1 equiv.) in methanol (10 mL). The atmosphere was replaced with hydrogen gas four times. The reaction was performed at 25° C. for 8 hours. After the completion of the reaction was detected with LC-MC, the system was filtered. The filter cake was washed with methanol (10 mL) three times. The filtrate was concentrated to obtain a crude product, which was purified with reverse phase column chromatography (C18, 10 mmol/L aqueous $NH_4HCO_3$ solution/acetonitrile) to produce the title compound (60 mg, yield: 36.7%).

LC-MS (ESI) $[M+H]^+$=307.2.

Step 4: Preparation of 6-((1-acetylpiperidine-4-yl) amino)-2-ethylpyrimidine-4-carboxylic acid

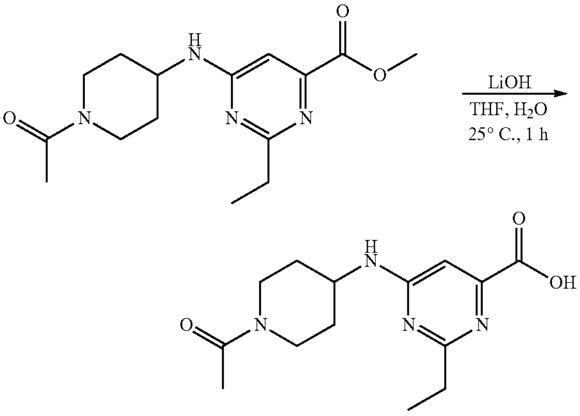

A solution of lithium hydroxide (20.54 mg, 0.49 mmol, 2.5 equiv.) in water (3 mL, 33.33%) was added to a mixed solution of 6-((1-acetylpiperidine-4-yl)amino)-2-ethylpyrimidine-4-carboxylic acid methyl ester (60 mg, 0.20 mmol, 1 equiv.) in tetrahydrofuran (3 mL, 33.33%) and methanol (3 mL, 33.33%). The reaction was performed at 25° C. for 1 hour. After the completion of the reaction was detected with LC-MC, the system was concentrated to obtain a crude product, which was dissolved in acetonitrile (2 mL), adjusted with 1M aqueous HCl solution to pH=5, and lyophilized to produce the title compound (50 mg, yield: 87.3%).

LC-MS (ESI) $[M+H]^+$=293.2.

Preparation Example 35: Preparation of trans-(4-(3,4-dihydroisoquinoline-2(1H)-yl)-3-hydroxypiperidine-1-yl)(6-(piperidine-4-ylamino)pyrimidine-4-yl) methanone Step 1: Preparation of 6-((1-(tert-butoxycarbonyl) piperidine-4-yl)amino)pyrimidine-4-carboxylic acid methyl ester

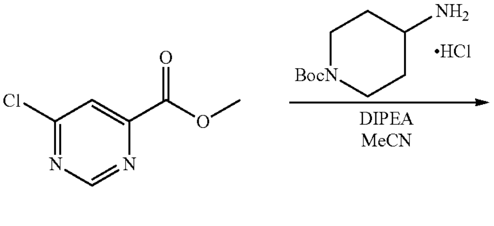

-continued

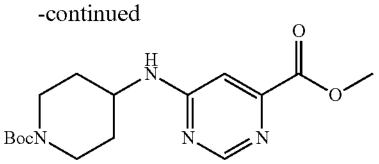

6-chloropyrimidine-4-carboxylic acid methyl ester (1 g, 5.80 mmol, 1.0 equiv.), 4-aminopiperidine-1-carboxylic acid tert-butyl ester hydrochloride (1.65 g, 6.95 mmol, 1.2 equiv.) and DIPEA (N,N-diisopropylethylamine)(3.00 g, 23.18 mmol, 4.0 equiv.) were dissolved in MeCN (acetonitrile)(30 mL). The reaction was performed at 90° C. for 15 hours. The reaction solution was concentrated. The crude product was separated and purified with flash chromatography (silica gel, PE:EA=3:2) to produce the target compound (1.82 g, 93.4%).

LC-MS (ESI) $[M+H]^+$=337.3.

Step-2: Preparation of 6-((1-(tert-butoxycarbonyl) piperidine-4-yl)amino)pyrimidine-4-carboxylic acid

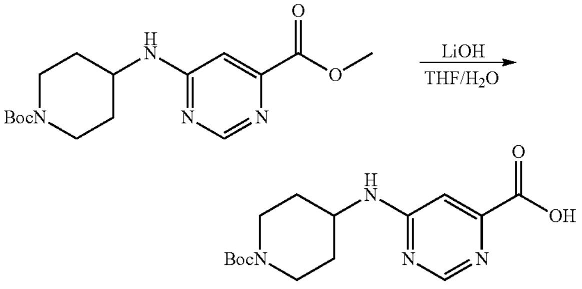

6-((1-(tert-butoxycarbonyl)piperidine-4-yl)amino)pyrimidine-4-carboxylic acid methyl ester (1.8 g, 5.35 mmol, 1.0 equiv.) and LiOH (lithium hydroxide)(0.26 g, 10.70 mmol, 2.0 equiv.) were dissolved in THF (tetrahydrofuran) (27 mL) and $H_2O$ (water)(9 mL). The reaction was performed at 20° C. for 1 hour. The reaction solution was concentrated, diluted with dichloromethane/methanol (3:1), and filtered by suction. The filtrate was concentrated to produce the target compound (crude, 2.14 g, yield: not determined).

LC-MS (ESI) $[M+H]^+$=323.2.

Step 3: Preparation of trans-4-((6-(4-(3,4-dihydroisoquinoline-2(1H)-yl)-3-hydroxypiperidine-1-carbonyl)pyrimidine-4-yl)amino)piperidine-1-carboxylic acid tert-butyl ester

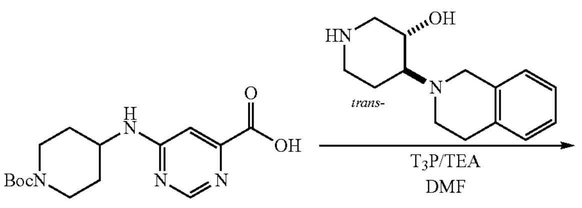

-continued

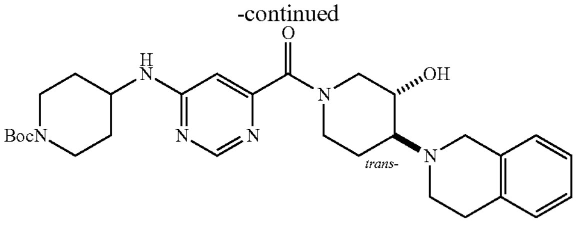

6-((1-(tert-butoxycarbonyl)piperidine-4-yl)amino)pyrimidine-4-carboxylic acid (2.1 g, 6.51 mmol, 1.0 equiv.), trans-4-(3,4-dihydroisoquinoline-2(1H)-yl)piperidine-3-ol (2.09 g, 8.99 mmol, 1.38 equiv.), a solution of $T_3P$ (1-n-propylphosphonic anhydride) in ethyl acetate (mass fraction: 50%)(8.29 g, 13.03 mmol, 2.0 equiv.) and TEA (triethylamine)(3.30 g, 32.57 mmol, 5.0 equiv.) were dissolved in DMF (N,N-dimethyl formamide)(30 mL). The reaction was performed at 20° C. for 17 hours. The reaction solution was extracted with ethyl acetate. The organic phase was concentrated to obtain a crude product, which was separated and purified with flash chromatography (silica gel, DCM: MeOH=20:1) to produce a crude product of the title compound (0.98 g, 28.0%). 30 mg of the crude product of the title compound was separated and purified with Prep-HPLC (C18, 10 mmol/L aqueous $NH_4HCO_3$ solution/acetonitrile) to produce the target compound (19.4 mg).

LC-MS (ESI) $[M+H]^+$=537.6; $^1H$ NMR (400 MHz, $CDCl_3$) δ 8.57-8.51 (m, 1H), 7.19-7.08 (m, 3H), 7.06-6.99 (m, 1H), 6.63-6.54 (m, 1H), 5.17-4.66 (m, 2H), 4.32-3.84 (m, 6H), 3.77-3.62 (m, 2H), 3.17-2.80 (m, 7H), 2.79-2.54 (m, 2H), 2.08-1.81 (m, 3H), 1.76-1.65 (m, 1H), 1.47 (s, 9H), 1.44-1.35 (m, 2H).

Step 4: Preparation of trans-(4-(3,4-dihydroisoquinoline-2(1H)-yl)-3-hydroxypiperidine-1-yl)(6-(piperidine-4-ylamino)pyrimidine-4-yl)methanone

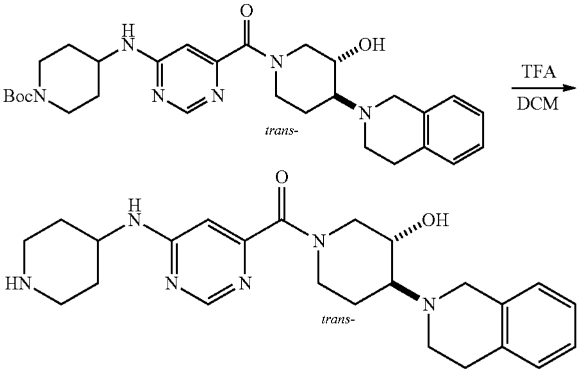

trans-4-((6-(4-(3,4-dihydroisoquinoline-2(1H)-yl)-3-hydroxypiperidine-1-carbonyl)pyrimidine-4-yl)amino)piperidine-1-carboxylic acid tert-butyl ester (30 mg, 0.06 mmol, 1.0 equiv.) was dissolved in DCM (dichloromethane)(0.4 mL). Then TFA (trifluoroacetic acid)(0.1 mL) was added. The reaction was performed at 20° C. for 0.5 hours. The reaction solution was quenched with saturated aqueous sodium bicarbonate solution, and concentrated to obtain a crude product, which was separated and purified with preparative HPLC (C18, 10 mmol/L aqueous $NH_4HCO_3$ solution/acetonitrile) to produce the title compound (17.42 mg, 71.4%).

LC-MS (ESI) $[M+H]^+$=437.5; $^1H$ NMR (400 MHz, DMSO-$d_6$) δ 8.46-8.32 (m, 1H), 7.61 (t, J=7.7 Hz, 1H), 7.13-7.01 (m, 4H), 6.51 (s, 1H), 4.79 (dd, J=35.1, 3.9 Hz, 1H), 4.40 (dd, J=56.4, 12.7 Hz, 1H), 3.93 (m, 1H), 3.87-3.56 (m, 5H), 2.98 (d, J=12.5 Hz, 2H), 2.93-2.87 (m, 1H), 2.85-2.75 (m, 4H), 2.69-2.53 (m, 4H), 1.92-1.69 (m, 3H), 1.57-1.43 (m, 1H), 1.41-1.27 (m, 2H).

Preparation Example 36: Preparation of (3R,4R)-4-(3,4-dihydroisoquinoline-2(1H)-yl-4,4-$d_2$)piperidine-3-ol Step 1: Preparation of (3R,4R)-3-((tert-butoxycarbonyl)oxy)-4-(3,4-dihydroisoquinoline-2(1H)-yl)piperidine-1-carboxylic acid tert-butyl ester

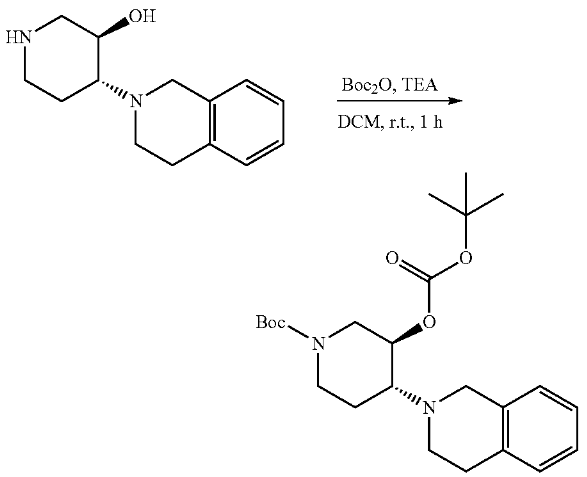

(3R,4R)-4-(3,4-dihydroisoquinoline-2(1H)-yl)piperidine-3-ol (1 g, 4.3 mmol, 1.0 equiv.), TEA (1.3 g, 12.9 mmol, 3.0 equiv.) and DMAP (105 mg, 0.86 mmol, 0.2 equiv.) were dissolved in THF (20 mL). Under stirring, $Boc_2O$ (1.88 g, 8.6 mmol, 2.0 equiv.) was added. The reaction was performed at 20° C. for 1 hour. The reaction solution was concentrated to obtain a crude product, which was separated and purified with column chromatography (silica gel, PE:EA=20:1) to produce the target compound (1.12 g, yield: 60%).

LC-MS (ESI) $[M+H]^+$=433.3.

Step 2: Preparation of (3R,4R)-3-((tert-butoxycarbonyl)oxy)-4-(4-oxo-3,4-dihydroisoquinoline-2(1H)-yl)piperidine-1-carboxylic acid tert-butyl ester

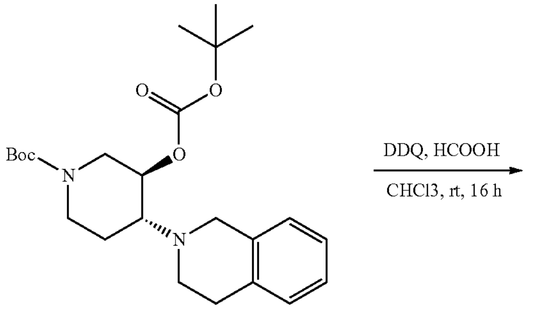

-continued

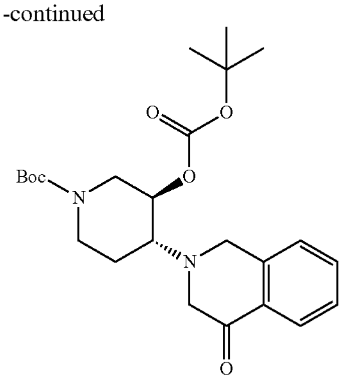

(3R,4R)-3-((tert-butoxycarbonyl)oxy)-4-(3,4-dihydroisoquinoline-2(1H)-yl)piperidine-1-carboxylic acid tert-butyl ester (300 mg, 0.49 mmol, 1.0 equiv.) was dissolved in $CHCl_3$ (10 mL). Formic acid (451 mg, 9.8 mmol, 20.0 equiv.) and DDQ (473 mg, 2.08 mmol, 3.0 equiv.) were added. The reaction was performed at 20° C. for 16 hours. To the reaction solution was added aqueous saturated sodium carbonate solution (5 mL). The resulting mixture was extracted with water and DCM. The organic phase was concentrated to obtain a crude product, which was separated and purified with column chromatography (silica gel, DCM: MeOH=50:1) to produce the target compound (46 mg, yield: 18%).

LC-MS (ESI) $[M+Na]^+$=469.3.

Step 3: Preparation of 2-((3R,4R)-3-hydroxypiperidine-4-yl)-2,3-dihydroisoquinoline-4(1H)-one

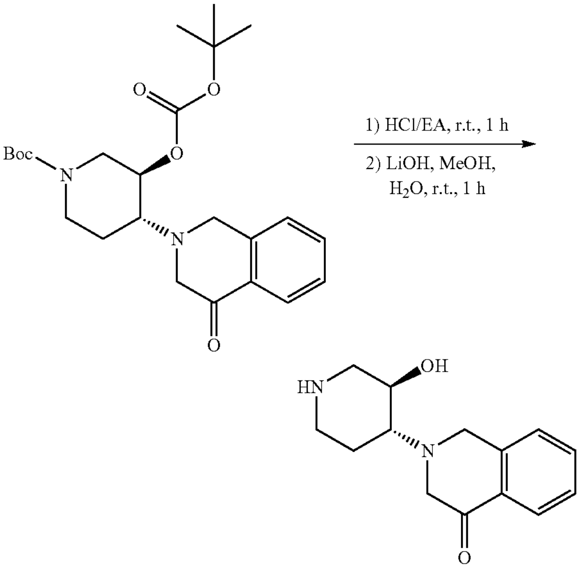

(3R,4R)-3-((tert-butoxycarbonyl)oxy)-4-(4-oxo-3,4-dihydroisoquinoline-2(1H)-yl)piperidine-1-carboxylic acid tert-butyl ester (46 mg, 0.1 mmol, 1.0 equiv.) was dissolved in EA (0.5 mL). Ethyl acetate-hydrochloric acid gas (5 mL, 4M) was added. The reaction was performed at 20° C. for 1 hour. The reaction solution was concentrated to obtain a crude product, which was dissolved in MeOH:$H_2O$ (1 mL:1 mL). Lithium hydroxide (7 mg, 0.3 mmol, 3.0 equiv.) was added. The reaction was performed at 20° C. for 1 hour. The reaction solution was concentrated, and purified with pre-TL (silica gel, DCM:MeOH=5:1) to produce the target compound (12 mg, yield: 48%).

LC-MS (ESI) $[M+H]^+$=247.3.

Step 4: Preparation of (3R,4R)-4-(3,4-dihydroisoquinoline-2(1H)-yl-4,4-$d_2$)piperidine-3-ol

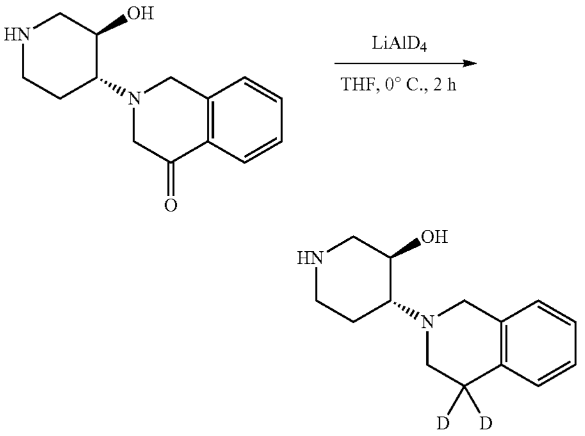

2-((3R,4R)-3-hydroxypiperidine-4-yl)-2,3-dihydroisoquinoline-4(1H)-one (4 mg, 0.016 mmol, 1.0 equiv.) was dissolved in dry THF (1 mL). $LiAlD_4$ (1.3 mg, 0.032 mmol, 2.0 equiv.) was added. The reaction was performed at 0° C. for hours. The reaction solution was quenched with heavy water, and concentrated to produce the target compound (6 mg, crude).

LC-MS (ESI) $[M+H]^+$=235.1.

Preparation Example 37: Preparation of 2-((3R,4R)-3-hydroxypiperidine-4-yl)-1,2,3,4-tetrahydroisoquinoline-4-ol Step 1: Preparation of (3R,4R)-3-((tert-butoxycarbonyl)oxy)-4-(4-hydroxy-3,4-dihydroisoquinoline-2(1H)-yl)piperidine-1-carboxylic acid tert-butyl ester

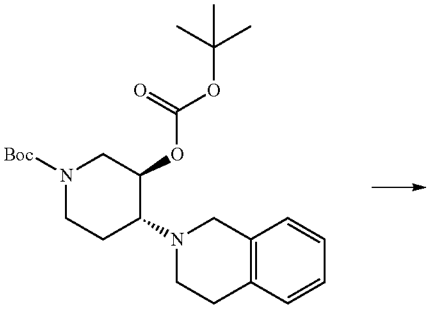

-continued

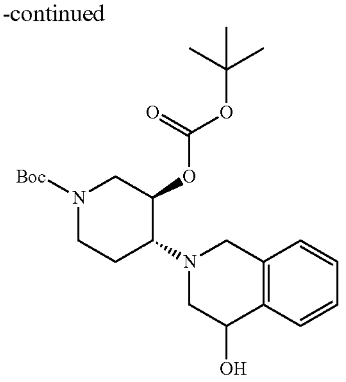

(3R,4R)-3-((tert-butoxycarbonyl)oxy)-4-(3,4-dihydroisoquinoline-2(1H)-yl)piperidine-1-carboxylic acid tert-butyl ester (500 mg, 1.16 mmol, 1.0 equiv.) was dissolved in a mixed solution of THF:H2O (10 mL:10 mL). Under stirring, Oxone (1.42 g, 2.31 mmol, 2.0 equiv.) was added. The reaction was performed at 20° C. for 16 hours. To the reaction solution was added water (20 mL). The resulting mixture was extracted with ethyl acetate (20 mL*3). The organic phases were combined, dried, concentrated to obtain a crude product, which was separated and purified with column chromatography (silica gel, DCM:MeOH=50:1) to produce the title compound (120 mg, yield: 23%).

LC-MS (ESI) $[M+H]^+$=449.3.

Step 2: Preparation of 2-((3R,4R)-3-hydroxypiperidine-4-yl)-1,2,3,4-tetrahydroisoquinoline-4-ol

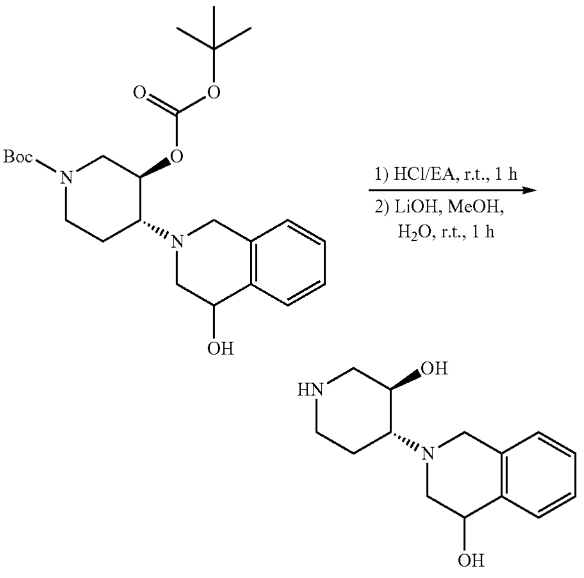

(3R,4R)-3-((tert-butoxycarbonyl)oxy)-4-(4-hydroxy-3,4-dihydroisoquinoline-2(1H)-yl)piperidine-1-carboxylic acid tert-butyl ester (100 mg, 0.223 mmol, 1.0 equiv.) was dissolved in EA (0.5 mL). Ethyl acetate hydrochloric acid gas (5 mL, 4M) was added. The reaction was performed at 20° C. for 1 hour. The reaction solution was concentrated to obtain a crude product, which was dissolved in $MeOH:H_2O$ (1 mL:1 mL). Lithium hydroxide monohydrate (29 mg, 0.669 mmol, 3.0 equiv.) was added. The reaction was performed at 20° C. for 1 hour. The reaction solution was concentrated, and purified with pre-TL (silica gel, DCM: MeOH=5:1) to produce the target compound (35 mg, yield: 64%).

LC-MS (ESI) $[M+H]^+$=249.2.

Preparation Example 38: Preparation of 6-((1-acetylpiperidine-4-yl)amino)-2-(tert-butylthio)pyrimidine-4-carboxylic acid

Step 1: Preparation of 6-((1-acetylpiperidine-4-yl) amino)-2-(tert-butylthio)pyrimidine-4-carboxylic acid methyl ester

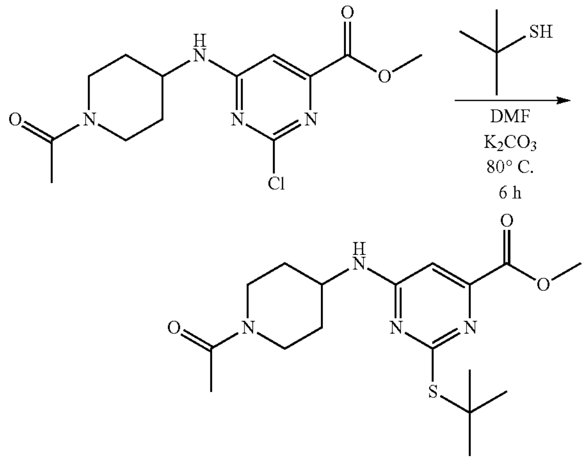

6-((1-acetylpiperidine-4-yl)amino)-2-chloropyrimidine-4-carboxylic acid methyl ester (1 g, 3.20 mmol, 1 equiv.), and potassium carbonate (0.884 g, 6.40 mmol, 2 equiv.) were added to N,N-dimethyl formamide (16 mL). Then tert-butylthiol (1.45 g, 16.0 mmol, 5 equiv.) was added. The resulting mixture was stirred at 80° C. for 6 hours. TLC detected the reaction of raw materials was completed. To the reaction system was added water (160 mL). The resulting mixture was extracted with ethyl acetate three times (3×50 mL). The organic phases were combined, washed with saturated sodium chloride solution (50 mL) once, dried over anhydrous sodium sulfate, and filtered by suction. The solvent was concentrated, and the crude product was purified with a column chromatography (DCM:MeOH=98:2) to produce the title compound (0.49 g, yield: 41.8%).

LC-MS (ESI) $[M+H]^+$=367.2.

Step 2: Preparation of 6-((1-acetylpiperidine-4-yl) amino)-2-(tert-butylthio)pyrimidine-4-carboxylic acid

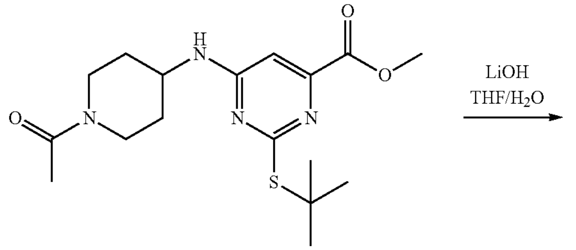

-continued

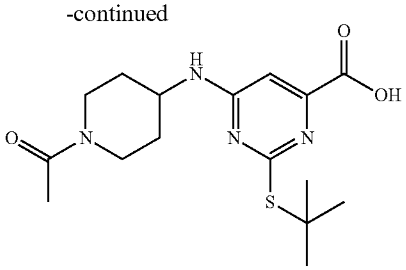

6-((1-acetylpiperidine-4-yl)amino)-2-(tert-butylthio)pyrimidine-4-carboxylic acid methyl ester (0.29 g, 0.791 mmol, 1 equiv.) was dissolved in tetrahydrofuran/water (25 mL, 4:1). lithium hydroxide (38 mg, 1.582 mmol, 2 equiv.) was added. The resulting mixture was stirred at 16° C. for 2 hours. TLC detected the reaction of raw materials was completed. Water was added to the reaction system, and the reaction system was extracted with ethyl acetate three times. The aqueous phase was adjusted with 1M HCl solution to pH=4-5, and lyophilized to produce a crude product of the title compound (0.25 g, yield: 89.7%).

LC-MS (ESI) $[M+H]^+$=353.2.

Preparation Example 39: Preparation of 6-((1-acetylazacyclobutane-3-yl)amino)-2-chloropyrimidine-4-carboxylic acid methyl ester

Step 1: Preparation of 6-((1-acetylazacyclobutane-3-yl)amino)-2-chloropyrimidine-4-carboxylic acid methyl ester

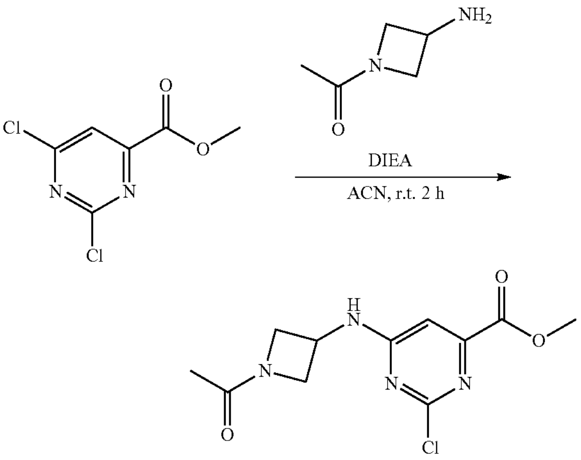

2,6-dichloropyridimine-4-carboxylic acid methyl ester (500 mg, 2.42 mmol, 1.2 equiv.), and 1-(3-aminoazacyclobutane-1-yl)ethane-1-one (230 mg, 2.02 mmol, 1.0 equiv.) were dissolved in acetonitrile (5 mL). N,N-diisopropylethylamine (521 mg, 4.04 mmol, 2.0 equiv.) was added. The reaction was performed at room temperature for 2 hours. After the completion of the reaction was detected with LC-MC, the solvent was removed by rotary drying to obtain a crude product, which was separated and purified with flash chromatography (silica gel, DCM:MeOH=5%) to produce the title compound (530 mg, yield: 92%).

LC-MS (ESI) $[M+H]^+$=285.1.

Example 1: Preparation of trans-1-(4-((6-(4-(3,4-dihydroisoquinoline-2(1H)-yl)-3-hydroxypiperidine-1-carbonyl)pyrimidine-4-yl)oxy)piperidine-1-yl) ethane-1-one

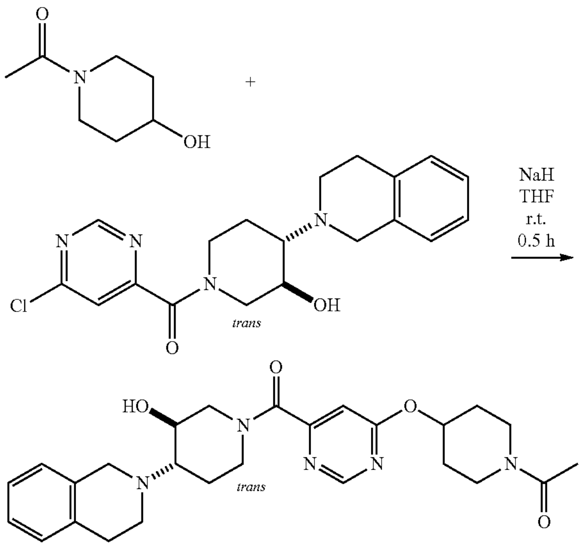

1-(4-hydroxypiperidine-1-yl)ethane-1-one (77 mg, 0.536 mmol, 2.0 equiv.) was added to a solution in NaH (mass fraction: 60%) (35.7 mg, 0.536 mmol, 2.0 equiv.) in THF (1.4 mL). The resulting mixture was stirred at 0° C. under the protection of nitrogen gas for 0.5 hours. Then trans-(6-chloropyrimidin-4-yl)(4-(3,4-dihydroisoquinolin-2(1H)-yl)-3-hydroxypiperidin-1-yl)methanone (100 mg, 0.268 mmol, 1.0 equiv.) was added, and the stirring was continued at 16° C. for 0.5 hours. The completion of the reaction was monitored with LC-MS. At 0° C., saturated ammonium chloride solution (10 mL) was added dropwise. The resulting mixture was extracted with EA (20 mL) once. The organic phase was washed with saturated sodium chloride solution (20 mL) once, dried over anhydrous sodium sulfate, and filtered by suction. The mother liquor was concentrated to obtain a crude product, which was separated and purified with reverse phase column chromatography (C18, 10 mmol/L aqueous ammonium bicarbonate solution/acetonitrile) to produce the title compound (2.32 mg, yield: 1.5%).

LC-MS (ESI): m/z=480.5; $^1$H NMR (400 MHz, $CDCl_3$) δ 8.76-8.74 (m, 1H), 7.21-7.10 (m, 3H), 7.06-7.01 (m, 1H), 7.00-6.93 (m, 1H), 5.49-5.37 (m, 1H), 5.09-4.76 (m, 1H), 4.18-4.06 (m, 1H), 4.03-3.92 (m, 2H), 3.79-3.68 (m, 3H), 3.56-3.39 (m, 2H), 3.13-2.92 (m, 4H), 2.83-2.72 (m, 2H), 2.14 (s, 3H), 2.10-2.02 (m, 2H), 1.86-1.67 (m, 6H).

Example 2 and Example 3: Preparation of (Z)-2-(4-((6-(trans-4-(3,4-dihydroisoquinoline-2(1H)-yl)-3-hydroxypiperidine-1-carbonyl)pyrimidine-4-yl) amino)piperidine-1-carbonyl)-3-(dimethylamino) acrylonitrile (the compound of Example 2) and 3-(4-((6-(trans-4-(3,4-dihydroisoquinoline-2(1H)-yl)-3-hydroxypiperidine-1-carbonyl)pyrimidine-4-yl) amino)piperidine-1-yl)-3-oxopropanenitrile (the compound of Example 3)

Step 1: Preparation of (Z)-2-cyano-3-(dimethylamino)acryloyl chloride and 2-cyanoacetyl chloride

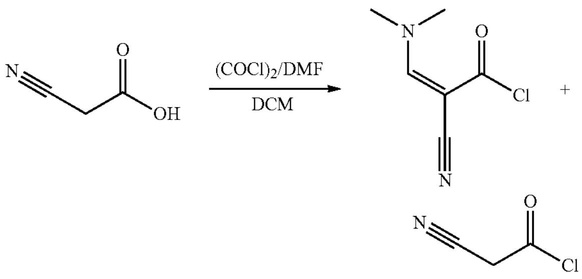

Cyanoacetic acid (1 g, 11.8 mmol, 1.0 equiv.) was dissolved in DCM (100 mL). $(COCl)_2$ (1.64 g, 12.9 mmol, 1.1 equiv.) and DMF (8 mg, 0.1 mmol, 0.01 equiv.) were added at 0° C. The resulting mixture was stirred at 25° C. for 1 hour under nitrogen gas. After the completion of the reaction was detected with TLC, the reaction was rotary dried to produce a mixture of (Z)-2-cyano-3-(dimethylamino)acryloyl chloride and 2-cyanoacetyl chloride (1.1 g, crude).

Step 2: Preparation of (Z)-2-(4-((6-(trans-4-(3,4-dihydroisoquinoline-2(1H)-yl)-3-hydroxypiperidine-1-carbonyl)pyrimidine-4-yl)amino)piperidine-1-carbonyl)-3-(dimethylamino)acrylonitrile (Example 2) and 3-(4-((6-(trans-4-(3,4-dihydroisoquinoline-2(1H)-yl)-3-hydroxypiperidine-1-carbonyl)pyrimidine-4-yl)amino)piperidine-1-yl)-3-oxopropanenitrile (Example 3)

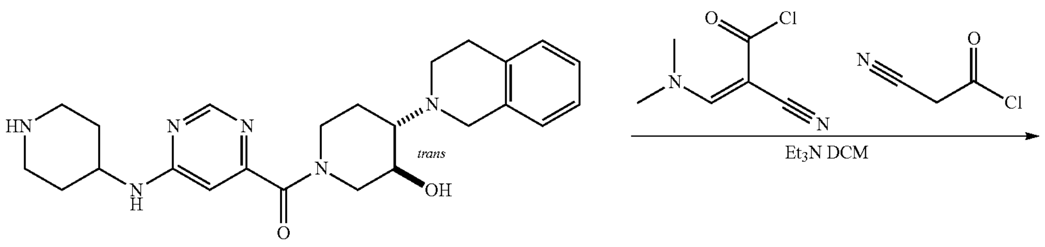

-continued

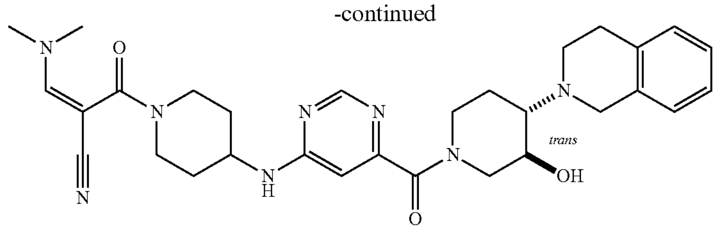

+

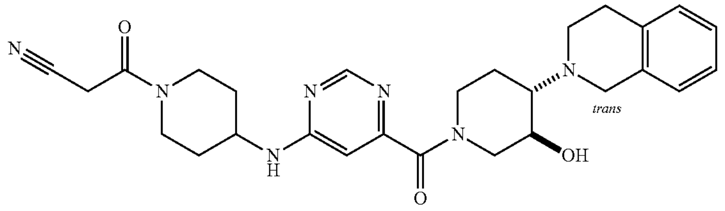

The mixture of (Z)-2-cyano-3-(dimethylamino)acryloyl chloride and 2-cyanoacetyl chloride (5 mg, 0.046 mmol, 1.0 equiv.) was dissolved in DCM (2 mL). At 0° C., the resulting mixture was added dropwise to a solution of (trans-4-(3,4-dihydroisoquinoline-2(1H)-yl)-3-hydroxypiperidine-1-yl)(6-(piperidine-4-ylamino)pyrimidine-4-yl)methanone (20 mg, 0.046 mmol, 1.0 equiv.) in DCM (1.5 mL). Triethylamine (9 mg, 0.09 mmol, 2.0 equiv.) was added. The resulting mixture was stirred at 0° C. for 1 hour, and after the completion of the reaction was detected with LC-MC, concentrated to obtain a crude product, which was separated and purified with reverse phase column chromatography (C18, 10 mmol/L aqueous ammonium bicarbonate solution/acetonitrile) to produce two title compounds:

Compound of Example 2 (14.5 mg, yield: 56.7%)

LC-MS (ESI) $[M+H]^+$=559.56; $^1$H NMR (400 MHz, $CDCl_3$) δ 8.60-8.48 (m, 1H), 7.54 (s, 1H), 7.19-7.09 (m, 3H), 7.08-6.98 (m, 1H), 6.67-6.55 (m, 1H), 5.47-5.27 (m, 1H), 5.07-4.63 (m, 1H), 4.31-4.23 (m, 2H), 4.22-4.12 (m, 1H), 4.04-3.91 (m, 2H), 3.79-3.68 (m, 2H), 3.35 (s, 3H), 3.17 (s, 3H), 3.12-2.98 (m, 4H), 2.97-2.83 (m, 3H), 2.76-2.65 (m, 2H), 2.13-2.05 (m, 2H), 2.03-1.89 (m, 1H), 1.71-1.64 (m, 1H), 1.60-1.43 (m, 2H).

Compound of Example 3 (5.8 mg, yield: 25.4%)

LC-MS (ESI) $[M+H]^+$=504.56; $^1$H NMR (400 MHz, $CDCl_3$) δ 8.60-8.45 (m, 1H), 7.20-7.09 (m, 3H), 7.08-6.99 (m, 1H), 6.71-6.58 (m, 1H), 6.02-5.60 (m, 1H), 5.07-4.65 (m, 1H), 4.47 (d, J=13.3 Hz, 1H), 4.23-4.10 (m, 2H), 4.01-3.93 (m, 1H), 3.79-3.69 (m, 3H), 3.63-3.46 (m, 2H), 3.37-3.26 (m, 1H), 3.11-2.99 (m, 2H), 2.97-2.88 (m, 3H), 2.80-2.66 (m, 2H), 2.20-2.04 (m, 2H), 2.01-1.78 (m, 3H), 1.76-1.63 (m, 1H), 1.61-1.41 (m, 2H).

Example 4: Preparation of trans-1-(6-((6-(4-(3,4-dihydroisoquinoline-2(1H)-yl)-3-hydroxypiperidine-1-carbonyl)pyrimidine-4-yl)amino)-2-azaspiro[3.3]heptan-2-yl)ethane-1-one

Step 1: Preparation of (2-acetyl-2-azaspiro[3.3]heptan-6-yl)carbamic acid tert-butyl ester

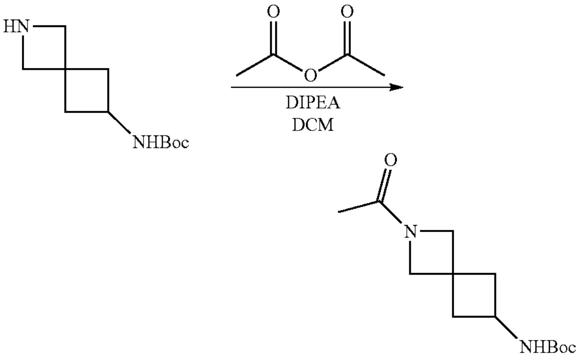

(2-azaspiro[3.3]heptan-6-yl)carbamic acid tert-butyl ester (300 mg, 1.41 mmol, 1.0 equiv.) and DIPEA (N,N-diisopropylethylamine)(365 mg, 2.83 mmol, 2.0 equiv.) were dissolved in DCM (dichloromethane)(7 mL). Then at 0° C., acetic anhydride (159 mg, 1.55 mmol, 1.1 equiv.) was added. The reaction was performed at 20° C. for 0.5 hours. The reaction solution was concentrated. The crude product was separated and purified with flash chromatography (silica gel, DCM:MeOH=30:1) to produce the target compound (336 mg, yield: 93.5%).

LC-MS (ESI) $[M+H]^+$=255.2.

Step 2: Preparation of 1-(6-amino-2-azaspiro[3.3]heptan-2-yl)ethane-1-one

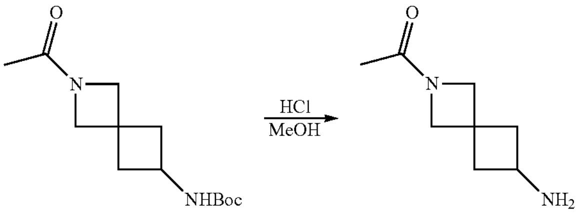 [SMILES: "MeOH" ; CC(=O)N1CC2(CC(NC(=O)OC(C)(C)C)C2)C1 ; Cl ; CC(=O)N1CC2(CC(N)C2)C1]

(2-acetyl-2-azaspiro[3.3]heptan-6-yl)carbamic acid tert-butyl ester (310 mg, 1.22 mmol, 1.0 equiv.) was dissolved in MeOH (methanol)(1 mL). Then a solution of hydrochloric acid in 1,4-dioxane (3 mL, 4 M) was added. The reaction was performed at 20° C. for 1 hour. The reaction solution was concentrated to produce the target compound (crude, 290 mg).

LC-MS (ESI) $[M+H]^+$=155.1.

Step 3: Preparation of trans-1-(6-((6-(4-(3,4-dihydroisoquinoline-2(1H)-yl)-3-hydroxypiperidine-1-carbonyl)pyrimidine-4-yl)amino)-2-azaspiro[3.3]heptan-2-yl)ethane-1-one

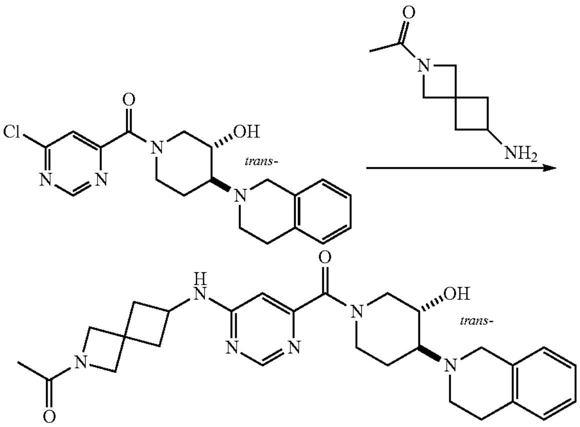

(6-chloropyrimidine-4-yl)(trans-4-(3,4-dihydroisoquinoline-2(1H)-yl)-3-hydroxypiperidine-1-yl)methanone (60 mg, 0.16 mmol, 1.0 equiv.), 1-(6-amino-2-azaspiro[3.3]heptan-2-yl)ethane-1-one (50 mg, 0.32 mmol, 2.0 equiv.), $Pd(OAc)_2$ (palladium acetate)(7 mg, 0.03 mmol, 0.2 equiv.), BINAP (2,2'-bis(diphenylphosphino)-1,1'-binaphthyl)(40 mg, 0.06 mmol, 0.4 equiv.) and $Cs_2CO_3$ (cesium carbonate) (262 mg, 0.80 mmol, 5.0 equiv.) were dissolved in 1,4-dioxane (1,4-dioxane)(1 mL). The reaction was performed in the protection of nitrogen gas at 80° C. for 16 hours. The reaction solution was filtered. The filtrate was concentrated to obtain a crude product, which was separated and purified with Prep-HPLC (C18, 10 mmol/L aqueous $NH_4HCO_3$ solution, MeCN) to produce the title compound (2.04 mg, yield: 2.6%).

LC-MS (ESI) $[M+H]^+$=491.5; $^1$H NMR (400 MHz, $CDCl_3$) δ 8.57-8.51 (m, 1H), 7.20-7.09 (m, 3H), 7.07-7.00 (m, 1H), 6.61-6.50 (m, 1H), 5.52-5.32 (m, 1H), 5.07-4.66 (m, 1H), 4.26-4.05 (m, 5H), 4.04-3.95 (m, 2H), 3.81-3.67 (m, 2H), 3.16-2.58 (m, 10H), 2.22-2.09 (m, 2H), 2.05-1.98 (m, 1H), 1.92-1.83 (m, 4H).

Example 5: Preparation of 1-(4-((2-(benzo[d]thiazole-7-yl)-6-((3R,4R)-4-(3,4-dihydroisoquinoline-2(1H)-yl)-3-hydroxypiperidine-1-carbonyl)pyrimidine4-yl)amino)piperidine-1-yl)ethane-1-one Step 1: Preparation of 6-((1-acetylpiperidine-4-yl)amino)-2-(benzo[d]thiazole-7-yl)pyrimidine-4-carboxylic acid

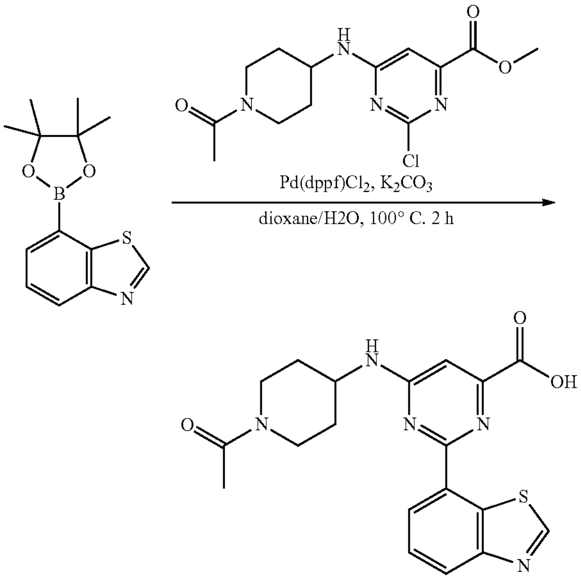

7-(4,4,5,5-tetramethyl-1,3,2-dioxaborolane-2-yl)benzo[d]thiazole (190 mg. 0.728 mmol, 1.0 equiv.), 6-((1-acetylpiperidine-4-yl)amino)-2-chloropyrimidine-4-carboxylic acid methyl ester (249 mg. 0.8 mmol, 1.1 equiv.). $Pd(dppf)Cl_2$ (53 mg. 0.0728 mmol, 0.1 equiv.) and potassium carbonate (301 mg. 2.18 mmol, 3.0 equiv.) were dissolved in dioxane (3 mL) and water (1 mL). The reaction was performed at 100° C. for 1 hour. The completion of the reaction was detected with LC-MS. The system was diluted with water, and extracted with EA. The aqueous phase was adjusted with 1M hydrochloric acid to pH=4, and then the aqueous phase was lyophilized to produce a crude product (300 mg).

LC-MS (ESI) $[M+H]^+$=398.3.

Step 2: Preparation of 1-(4-((2-(benzo[d]thiazole-7-yl)-6-((3R,4R)-4-(3,4-dihydroisoquinoline-2 (1H)-yl)-3-hydroxypiperidine-1-carbonyl)pyrimidine4-yl)amino)piperidine-1-yl)ethane-1-one

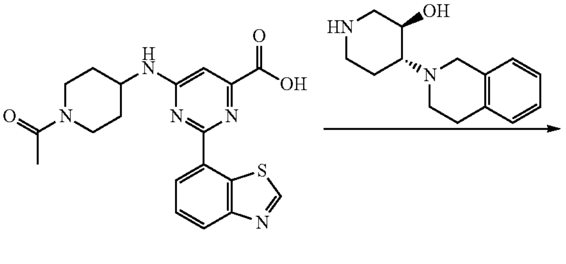

-continued

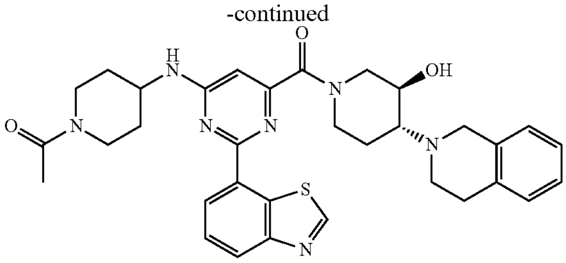

6-((1-acetylpiperidine-4-yl)amino)-2-(benzo[d]thiazole-7-yl)pyrimidine-4-carboxylic acid (85 mg, 0.215 mmol, 1.0 equiv.), (3R,4R)-4-(3,4-dihydroisoquinoline-2(1H)-yl)piperidine-3-ol (50 mg, 0.215 mmol, 1.0 equiv.), EDCI (62 mg, 0.32 mmol, 1.5 equiv.), and HOAt (44 mg, 0.32 mmol, 1.5 equiv.) were dissolved in DMF (2 mL). The reaction was performed at 25° C. for 1 hour. The completion of the reaction was detected with LC-MS. The reaction system was concentrated, and separated with reverse phase HPLC (C18, 10 mmol/L aqueous $NH_4HCO_3$ solution/acetonitrile) to produce the title compound (26.28 mg, yield: 20%).

LC-MS (ESI) $[M+H]^+$=612.2; $^1H$ NMR (400 MHz, $CDCl_3$) δ 9.10 (s, 1H), 8.72-8.57 (m, 1H), 8.28-8.25 (m, 1H), 7.68-7.63 (m, 1H), 7.20-7.10 (m, 3H), 7.08-7.02 (m, 1H), 6.66-6.55 (m, 1H), 5.49-5.30 (m, 1H), 5.11-4.86 (m, 1H), 4.68-4.26 (m, 3H), 4.07-4.04 (m, 1H), 3.80-3.85 (m, 3H), 3.34-3.32 (m, 1H), 3.20-2.70 (m, 8H), 2.32-2.03 (m, 6H), 1.88-1.75 (m, 1H), 1.55-1.50 (m, 2H).

Example 6: Preparation of 1-(3-((6-((3R,4R)-4-(3,4-dihydroisoquinoline-2(1H)-yl)-3-hydroxypiperidine-1-carbonyl)-2-(thiazole-5-yl)pyrimidine-4-yl)amino)azetidin-1-yl)ethane-1-one

Step 1: Preparation of 6-((1-acetylazetidine-3-yl)amino)-2-(thiazole-5-yl)pyrimidine-4-carboxylic acid methyl ester

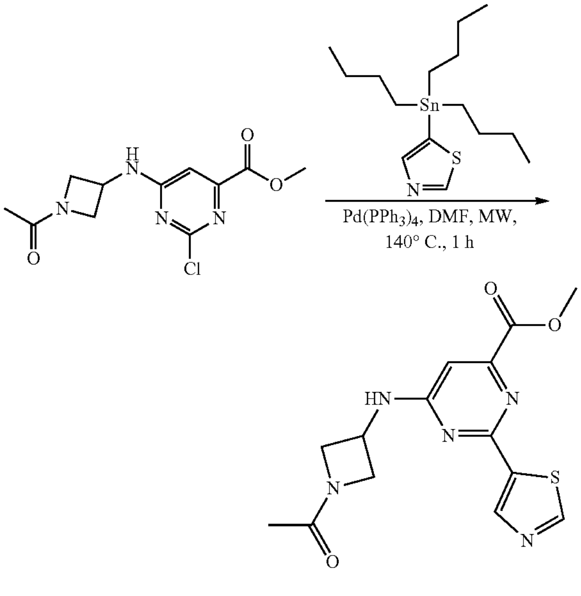

At room temperature (25° C.), 6-((1-acetylazetidine-3-yl)amino)-2-chloropyrimidine-4-carboxylic acid methyl ester (50 mg, 0.176 mmol, 1.0 equiv.) was added to DMF (2.0 mL). Under the protection of nitrogen gas, 5-(tributylstannanyl)thiazole (1.503 g, 0.351 mmol, 2.0 equiv.) and tetrakis (triphenylphosphine)palladium (20.3 mg, 0.018 mmol, 0.1 equiv.) were added. The resulting mixture was stirred in microwave at 140° C. for 1 hour. The completion of the reaction was detected with LC-MS. The reaction system was filtered, and the resulting mother liquor was concentrated to produce a crude product, which was Separated and purified with column chromatography (DCM:MeOH=0-10%) to produce the title compound (35 mg, yield: 59.7%).

LC-MS (ESI) $[M+H]^+$=334.1.

Step 2: Preparation of 6-((1-acetylazetidine-3-yl)amino)-2-(thiazole-5-yl)pyrimidine-4-carboxylic acid

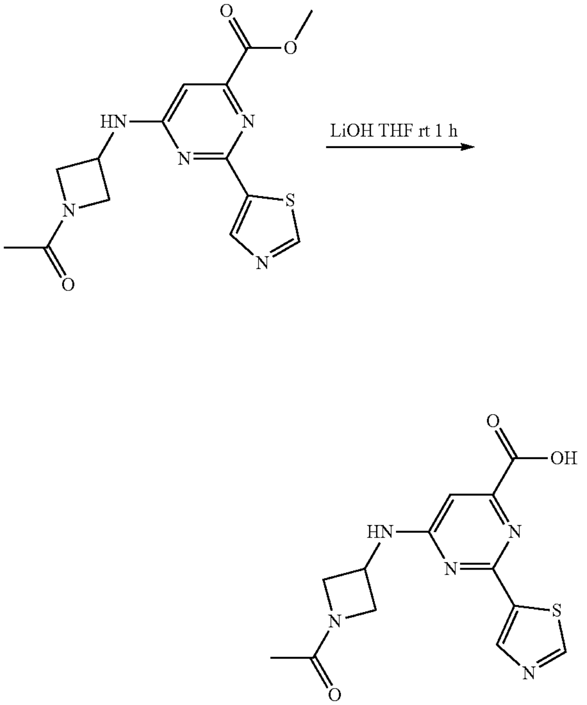

At room temperature, 6-((1-acetylazetidine-3-yl)amino)-2-(thiazole-5-yl)pyrimidine-4-carboxylic acid methyl ester (30 mg, 0.09 mmol, 1.0 equiv.) was added to water (1 mL) and tetrahydrofuran (2.0 mL). Lithium hydroxide (4.3 mg, 0.18 mmol, 2.0 equiv.) was added. The resulting mixture was stirred at room temperature for 1 hour. The completion of the reaction was detected with LC-MS, the system was concentrated to remove the organic solvent, adjusted with 1M hydrochloric acid to pH=3, and extracted with dichloromethane:methanol (V/V=10/1)(30 mL×5) three times. The organic phases were combined, dried, filtered, and concentrated to produce the title compound (20 mg, crude).

LC-MS (ESI) $[M+H]^+$=320.3.

Step 3: Preparation of 1-(3-((6-((3R,4R)-4-(3,4-dihydroisoquinoline-2(1H)-yl)-3-hydroxypiperidine-1-carbonyl)-2-(thiazole-5-yl)pyrimidine-4-yl)amino)azetidin-1-yl)ethane-1-one

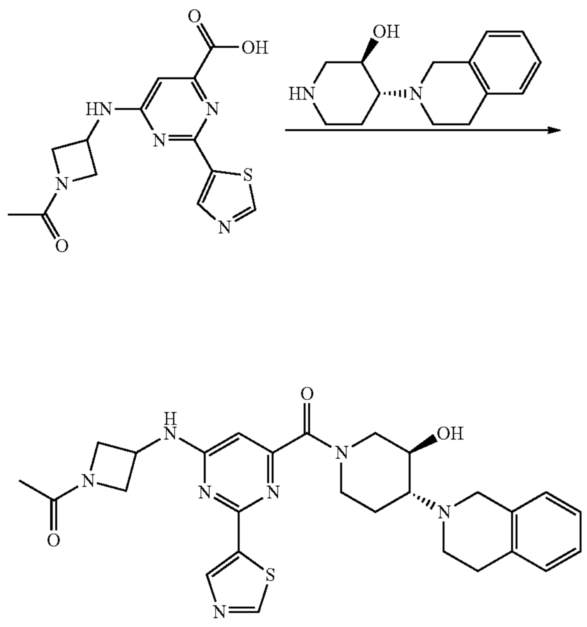

According to the process in step 2 of Example 5, the synthesis was performed to produce the title compound (4.96 mg, yield: 14.8%).

LC-MS (ESI) $[M+H]^+$=534.4; $^1H$ NMR (400 MHz, $CD_3OD$) δ 9.06 (d, J=6.0 Hz, 1H), 8.59 (d, J=11.2 Hz, 1H), 7.10-7.06 (m, 4H), 6.58 (d, J=8.0 Hz, 1H), 4.76-3.68 (m, 9H), 3.07-2.70 (m, 10H), 1.92 (s, 3H).

Example 7: Preparation of trans-1-(4-((6-(4-(3,4-dihydroisoquinoline-2(1H)-yl)-3-hydroxypiperidine-1-carbonyl)-2-(thiazole-2-yl)pyrimidine-4-yl)amino)piperidine-1-yl)ethane-1-one Step 1: Preparation of 6-((1-acetylpiperidine-4-yl)amino)-2-(thiazole-2-yl)pyrimidine-4-carboxylic acid methyl ester

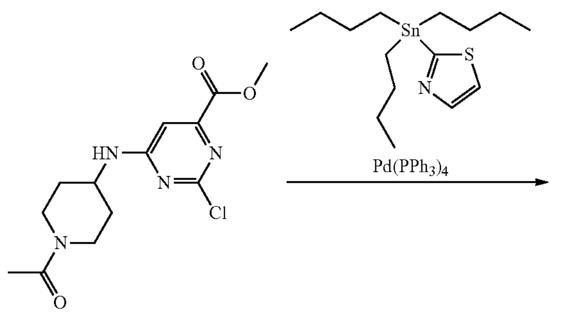

-continued

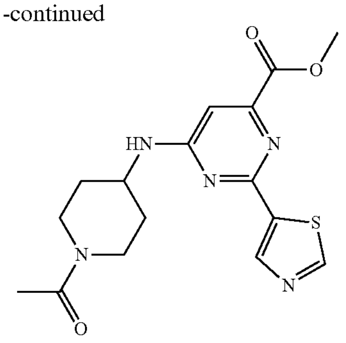

6-((1-acetylpiperidine-4-yl)amino)-2-chloropyrimidine-4-carboxylic acid methyl ester (4.50 g, 1.44 mmol, 1 equiv.) and $Pd(PPh_3)_4$ (1.68 g, 0.144 mmol, 0.1 equiv.) were replaced in a reaction container. Dioxane (72 mL) and 2-(tributylstannanyl)thiazole (9 mL, 2.88 mmol, 1.99 equiv.) were added. Under the protection of nitrogen gas, the resulting mixture was stirred at 110° C. for 14 hours. The formation of the product was monitored with LC-MS. The system was concentrated to remove the solvent to obtain a crude produce, which was separated and purified with flash chromatography (silica gel, MeOH:EA=0-5%) to produce the title compound (1.11 g, yield: 21.3%).

LC-MS (ESI) $[M+H]^+$=362.2.

Step 2: Preparation of 6-((1-acetylpiperidine-4-yl)amino)-2-(thiazole-2-yl)pyrimidine-4-carboxylic acid

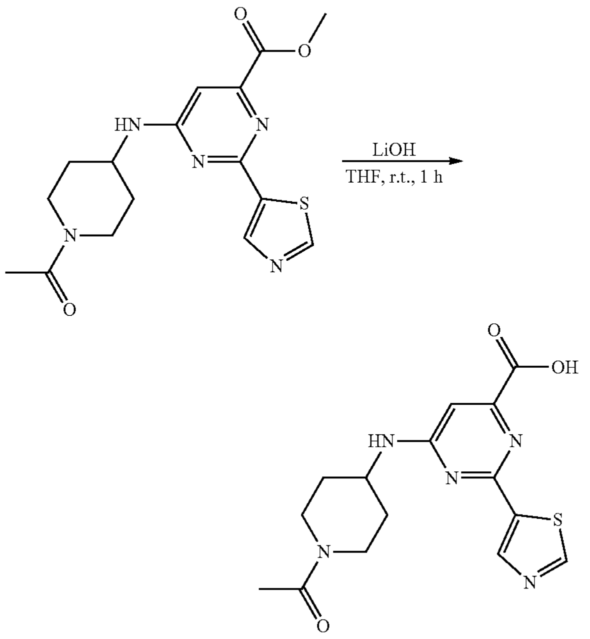

6-((1-acetylpiperidine-4-yl)amino)-2-(thiazole-2-yl)pyrimidine-4-carboxylic acid methyl ester (1.11 g, 3.06 mmol, 1 equiv.) was dissolved in THF (24 mL). Water (6 mL) and LiOH (180 mg, 7.5 mmol, 2.45 equiv.) were added. The resulting mixture was stirred at room temperature for 1 hour. The completion of the reaction was monitored with TLC. The system was adjusted with 1M (molar concentration)

HCl to pH=3-4. The resulting aqueous solution was lyophilized to obtain a crude product (1.0 g), which was directly used in the next step.

LC-MS (ESI) $[M+H]^+$=348.0.

Step 3: Preparation of trans-1-(4-((6-(4-(3,4-dihydroisoquinoline-2(1H)-yl)-3-hydroxypiperidine-1-carbonyl)-2-(thiazole-2-yl)pyrimidine-4-yl)amino) piperidine-1-yl)ethane-1-one

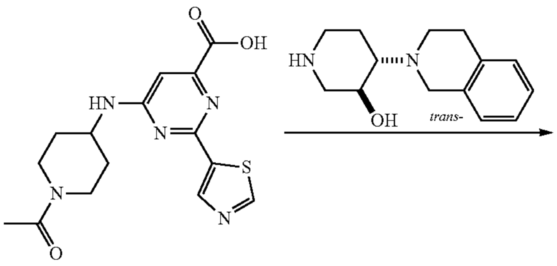

-continued

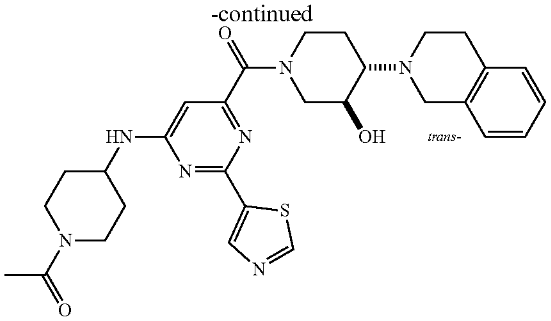

According to the process in step 2 of Example 5, the synthesis was performed to produce the title compound (555 mg, yield: 32%).

LC-MS (ESI) $[M+H]^+$=562.5; $^1H$ NMR (400 MHz, $CDCl_3$) δ 8.04-7.95 (m, 1H), 7.52-7.46 (m, 1H), 7.20-7.10 (m, 3H), 7.07-7.01 (m, 1H), 6.75-6.62 (m, 1H), 5.81-5.54 (m, 1H), 5.13-4.66 (m, 1H), 4.49 (d, J=13.6 Hz, 1H), 4.43-4.25 (m, 1H), 4.05-3.96 (m, 1H), 3.94-3.70 (m, 4H), 3.33-3.21 (m, 1H), 3.17-2.55 (m, 8H), 2.23-1.99 (m, 6H), 1.98-1.82 (m, 1H), 1.54-1.41 (m, 2H).

Example 8-138

Using the same processes as in Examples 5, 6 and 7, the compounds of Examples 8-138 were synthesized. The compound structures and specific characterization data (LC-MS and $^1H$ NMR) were as follows:

| Ex. | Structure | $^1H$ NMR | LC-MS (ESI) $[M + H]^+$ |
|---|---|---|---|
| 8 | 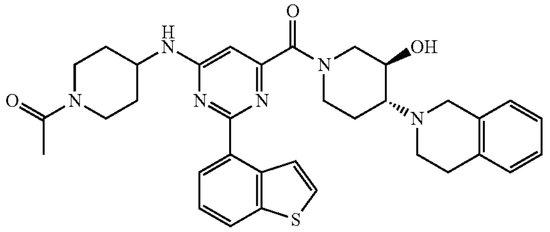 [SMILES: CC(=O)N1CCC(Nc2cc(C(=O)N3CC[C@@H](N4CCc5ccccc5C4)[C@H](O)C3)nc(-c3cccc4sccc34)n2)CC1] | (400 MHz, $CDCl_3$) δ 8.53-8.34 (m, 1H), 8.31-8.20 (m, 1H), 8.05-7.93 (m, 1H), 7.58-7.49 (m, 1H), 7.49-7.41 (m, 1H), 7.20-7.09 (m, 3H), 7.07-7.00 (m, 1H), 6.67-6.51 (m, 1H), 5.26-5.05 (m, 1H), 4.90-4.50 (m, 2H), 4.47-4.32 (m, 1H), 4.01-3.90 (s, 1H), 3.91-3.42 (m, 4H), 3.33-3.17 (m, 1H), 3.15-3.02 (m, 2H), 3.00-2.54 (m, 6H), 2.21-2.12 (m, 1H), 2.15-1.94 (m, 5H), 1.86-1.72 (m, 1H), 1.54-1.44 (m, 2H). | 611.0 |
| 9 | 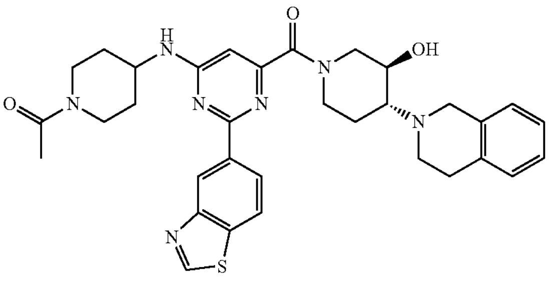 [SMILES: CC(=O)N1CCC(Nc2cc(C(=O)N3CC[C@@H](N4CCc5ccccc5C4)[C@H](O)C3)nc(-c3ccc4scnc4c3)n2)CC1] | (400 MHz, $CDCl_3$) δ 9.18-9.08 (m, 1H), 9.04 (s, 1H), 8.54-8.44 (m, 1H), 8.10-7.96 (m, 1H), 7.18-7.10 (m, 3H), 7.08-7.01 (m, 1H), 6.65-6.51 (m, 1H), 5.45-4.75 (m, 2H), 4.62-4.40 (m, 2H), 4.10-3.71 (m, 5H), 3.38-3.22 (m, 1H), 3.21-3.01 (m, 2H), 3.01-2.68 (m, 6H), 2.29-2.16 (m, 1H), 2.16-2.02 (m, 5H), 1.98-1.77 (m, 1H), 1.55-1.43 (m, 2H). | 612.31 |

-continued
| Ex. | Structure | $^1$H NMR | LC-MS (ESI) [M + H]$^+$ |
|---|---|---|---|
| 10 | 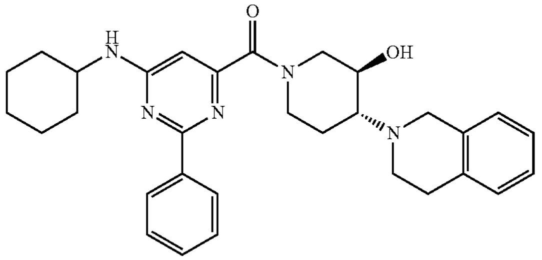 [SMILES: O=C(c1cc(NC2CCCCC2)nc(-c2ccccc2)n1)N1CC[C@@H](N2CCc3ccccc3C2)[C@H](O)C1] | (400 MHz, DMSO-$d_6$) δ 8.35-8.26 (m, 2H), 7.72-7.64 (m, 1H), 7.54-7.45 (m, 3H), 7.14-7.00 (m, 4H), 6.50 (s, 1H), 4.78 (dd, J = 5.2, 3.8 Hz, 1H), 4.58-4.33 (m, 1H), 4.32-4.15 (m, 1H), 3.96-3.77 (m, 5H), 3.74-3.63 (m, 1H), 3.56-3.41 (m, 2H), 3.12-2.90 (m, 2H), 2.89-2.78 (m, 3H), 2.76-2.60 (m, 2H), 2.05-1.73 (m, 3H), 1.66-1.43 (m, 3H). | 514.3 |
| 11 | 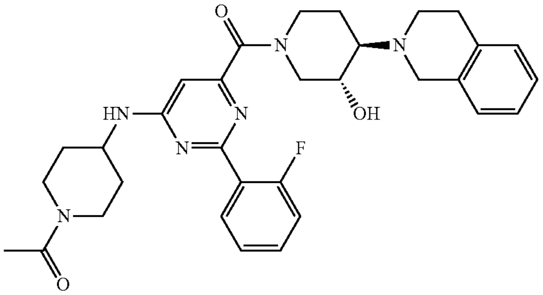 [SMILES: CC(=O)N1CCC(Nc2cc(C(=O)N3CC[C@@H](N4CCc5ccccc5C4)[C@H](O)C3)nc(-c3ccccc3F)n2)CC1] | (400 MHz, DMSO-$d_6$) δ 8.01-7.85 (m, 1H), 7.78-7.70 (m, 1H), 7.58-7.45 (m, 1H), 7.34-7.23 (m, 2H), 7.13-6.99 (m, 4H), 6.54 (s, 1H), 4.77 (dd, J = 4.9, 3.9 Hz, 1H), 4.56-4.07 (m, 3H), 3.94-3.73 (m, 4H), 3.69-3.58 (m, 1H), 3.25-2.98 (m, 2H), 2.96-2.75 (m, 5H), 2.71-2.58 (m, 2H), 2.01 (s, 4H), 1.95-1.71 (m, 2H), 1.62-1.50 (m, 1H), 1.48-1.29 (m 2H). | 573.3 |
| 12 | 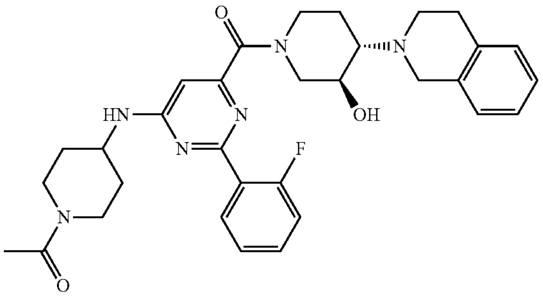 [SMILES: CC(=O)N1CCC(Nc2cc(C(=O)N3CC[C@H](N4CCc5ccccc5C4)[C@@H](O)C3)nc(-c3ccccc3F)n2)CC1] | (400 MHz, DMSO-$d_6$) δ 8.02-7.88 (m, 1H), 7.78-7.71 (m, 1H), 7.56-7.45 (m, 1H), 7.34-7.24 (m, 2H), 7.13-7.00 (m, 4H), 6.54 (s, 1H), 4.77 (dd, J = 4.9, 3.2 Hz, 1H), 4.56-4.07 (m, 3H), 3.90-3.74 (m, 4H), 3.72-3.59 (m, 1H), 3.25-2.97 (m, 2H), 2.95-2.78 (m, 5H), 2.74-2.58 (m, 2H), 2.01 (s, 4H), 1.96-1.71 (m, 2H), 1.63-1.50 (m, 1H), 1.48-1.27 (m, 2H). | 573.3 |
| 13 | 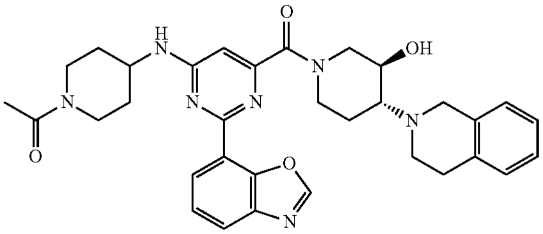 | (400 MHz, $CDCl_3$) δ 8.33-8.13 (m, 2H), 7.94-7.88 (m, 1H), 7.51-7.45 (m, 1H), 7.21-7.10 (m, 3H), 7.08-7.01 (m, 1H), 6.71 (s, 1H), 5.47-5.16 (m, 1H), 5.13-4.91 (m, 1H), 4.89-4.55 (m, 2H), 4.42-3.70 (m, 5H), 3.33-3.23 (m, 1H), 3.19-2.65 (m, 8H), 2.31-2.00 (m, 6H), 1.77-7.69 (m, 1H), 1.59-1.45 (m, 2H). | 596.0 |
| 14 | 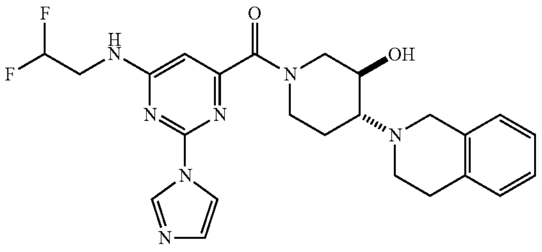 | (400 MHz, DMSO-$d_6$) δ 8.54 (d, J = 8.4 Hz, 1H), 8.48-8.39 (m, 1H), 7.88 (d, J = 10.7 Hz, 1H), 7.12-7.06 (m, 4H), 7.05-7.02 (m, 1H), 6.62 (d, J = 9.5 Hz, 1H), 6.40-6.05 (m, 1H), 4.79-4.72 (m, c1H), 4.51-4.29 (m, 1H), 4.03-3.87 (m, 2H), 3.85-3.81 (m, 2H), 3.77-3.62 (m, 2H), 3.11-2.97 (m, 5H), 2.77-2.60 (m, 2H), 1.90-1.71 (m, 1H), 1.62-1.49 (m, 1H). | 484.4 |

-continued

| Ex. | Structure | $^1$H NMR | LC-MS (ESI) [M + H]$^+$ |
|---|---|---|---|
| 15 | 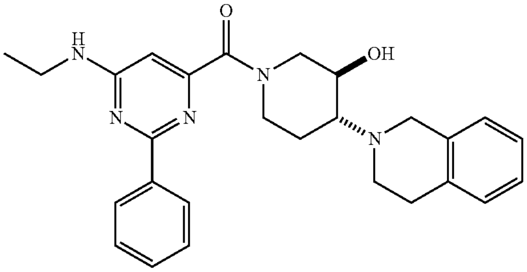 [SMILES: CCNc1cc(C(=O)N2CC[C@@H](N3CCc4ccccc4C3)[C@H](O)C2)nc(-c2ccccc2)n1] | (400 MHz, DMSO-$d_6$) δ 8.32 (s, 2H), 7.69 (d, J = 5.6 Hz, 1H), 7.51-7.47 (m, 3H), 7.11-7.03 (m, 4H), 6.49 (d, J = 4.0 Hz, 1H), 4.84-4.70 (m, 1H), 4.54-4.36 (m, 1H), 3.89-3.79 (m, 3H), 3.83-3.75 (m, 1H), 3.72-3.63 (m, 2H), 3.09-2.75 (m, 6H), 2.70-2.61 (m, 1H), 1.89-1.75 (m, 1H), 1.62-1.52 (m, 1H), 1.24-1.16 (m, 3H). | 458.4 |
| 16 | 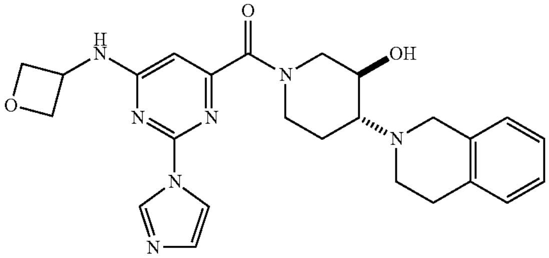 [SMILES: O=C(c1cc(NC2COC2)nc(-n2ccnc2)n1)N1CC[C@@H](N2CCc3ccccc3C2)[C@H](O)C1] | (400 MHz, $CD_3OD$) δ 8.60 (d, J = 8.8 Hz, 1H), 7.93 (d, J = 10.4 Hz, 1H), 7.12-7.07 (m, 5H), 6.62 (d, J = 11.6 Hz, 1H), 5.27 (s, 1H), 5.06-5.03 (m, 2H), 4.71-4.53 (m, 3H), 4.07-3.85 (m, 4H), 3.18-2.76 (m, 7H), 2.09-1.93 (m, 1H), 1.77-1.67 (m, 1H). | 476.2 |
| 17 | 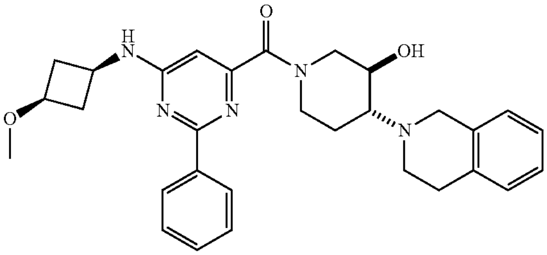 [SMILES: CO[C@H]1C[C@@H](Nc2cc(C(=O)N3CC[C@@H](N4CCc5ccccc5C4)[C@H](O)C3)nc(-c3ccccc3)n2)C1] | (400 MHz, $CDCl_3$) δ 8.39-8.31 (m, 2H), 7.48-7.41 (m, 3H), 7.19-7.08 (m, 3H), 7.07-7.01 (m, 1H), 6.56-6.47 (m, 1H), 5.35 (s, 1H), 5.13-4.70 (m, 1H), 4.51-4.34 (m, 1H), 4.03-3.68 (m, 5H), 3.31-3.25 (m, 3H), 3.14-2.98 (m, 2H), 2.98-2.84 (m, 4H), 2.79-2.61 (m, 2H), 2.08-1.84 (m, 3H), 1.86-1.67 (m, 3H). | 514.7 |
| 18 | 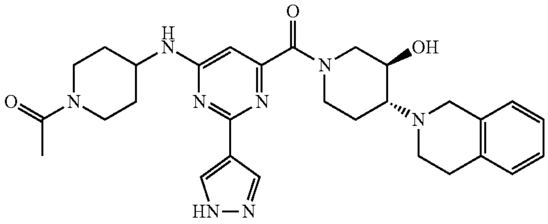 [SMILES: CC(=O)N1CCC(Nc2cc(C(=O)N3CC[C@@H](N4CCc5ccccc5C4)[C@H](O)C3)nc(-c3cn[nH]c3)n2)CC1] | (400 MHz, DMSO-$d_6$) δ 13.08 (s, 1H), 8.21-8.01 (m, 2H), 7.53-7.49 (m, 1H), 7.11-7.04 (m, 4H), 6.34-6.32 (m, 1H), 4.83-4.76 (m, 1H), 4.51-4.15 (m, 3H), 3.88-3.79 (m, 4H), 3.71-3.65 (m, 1H), 3.28-3.21 (m, 1H), 3.15-2.75 (m, 7H), 2.68-2.57 (m, 1H), 2.07-1.74 (m, 6H), 1.61-1.17 (m, 3H). | 545.7 |
| 19 | 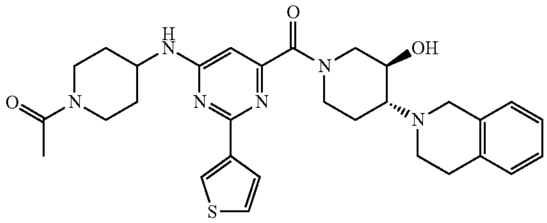 [SMILES: CC(=O)N1CCC(Nc2cc(C(=O)N3CC[C@@H](N4CCc5ccccc5C4)[C@H](O)C3)nc(-c3ccsc3)n2)CC1] | (400 MHz, DMSO-$d_6$) δ 8.26-8.24 (m, 1H), 7.75-7.70 (m, 1H), 7.64-7.58 (m, 2H), 7.10-7.03 (m, 4H), 6.44-6.43 (m, 1H), 4.83-4.73 (m, 1H), 4.52-4.35 (m, 1H), 4.37-4.35 (m, 2H), 3.91-3.79 (m, 4H), 3.71-3.63 (m, 1H), 3.27-3.21 (m, 1H), 3.07-3.01 (m, 0.5H), 2.94-2.74 (m, 6H), 2.69-2.59 (m, 1.5H), 2.02-1.91 (m, 5H), 1.86-1.75 (m, 1H), 1.58-1.30 (m, 3H). | 561.2 |
| 20 | 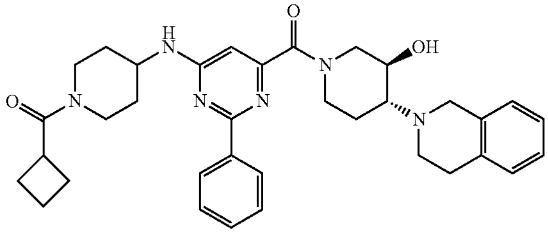 [SMILES: O=C(c1cc(NC2CCN(C(=O)C3CCC3)CC2)nc(-c2ccccc2)n1)N1CC[C@@H](N2CCc3ccccc3C2)[C@H](O)C1] | (400 MHz, DMSO-$d_6$ $(CD_3)_2SO$) δ 8.40-8.25 (m, 2H), 7.73-7.62 (m, 1H), 7.54-7.41 (m, 3H), 7.13-7.00 (m, 4H), 6.67-6.45 (m, 1H), 4.88-4.68 (m, 1H), 4.58-4.20 (m, 3H), 3.94-3.78 (m, 3H), 3.76-3.64 (m, 2H), 3.24-3.02 (m, 2H), 2.96-2.76 (m, 6H), 2.75-2.58 (m, 2H), 2.25-2.06 (m, 4H), 2.03-1.70 (m, 5H), 1.65-1.47 (m, 1H), 1.45-1.28 (m, 2H). | 595.4 |

-continued

| Ex. | Structure | $^1$H NMR | LC-MS (ESI) [M + H]$^+$ |
| --- | --- | --- | --- |
| 21 | 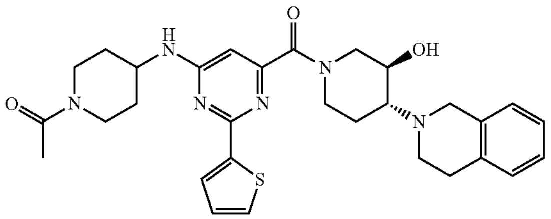 [SMILES: CC(=O)N1CCC(Nc2cc(C(=O)N3CC[C@@H](N4CCc5ccccc5C4)[C@H](O)C3)nc(-c3cccs3)n2)CC1] | (400 MHz, $CDCl_3$) δ 7.95-7.83 (m, 1H), 7.48-7.40 (m, 1H), 7.19-7.09 (m, 4H), 7.08-7.00 (m, 1H), 6.55-6.43 (m, 1H), 5.15-4.98 (m, 1H), 4.80-4.30 (m, 3H), 4.03-3.71 (m, 5H), 3.33-3.18 (m, 1H), 3.15-2.98 (m, 2H), 2.98-2.63 (m 6H), 2.25-2.15 (m, 1H), 2.13-2.01 (m, 4H), 1.96-1.84 (m, 1H), 1.77-1.67 (m, 1H), 1.49-1.39 (m, 2H). | 561.20 |
| 22 | 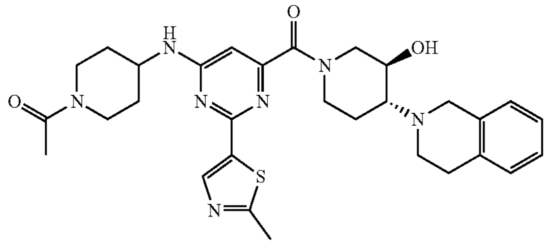 [SMILES: CC(=O)N1CCC(Nc2cc(C(=O)N3CC[C@@H](N4CCc5ccccc5C4)[C@H](O)C3)nc(-c3cnc(C)s3)n2)CC1] | (400 MHz, $CD_3OD$) δ 8.33 (d, J = 10.0 Hz, 1H), 7.13-7.08 (m, 4H), 6.51-6.44 (m, 1H), 4.77-4.57 (m, 1H), 4.61-4.40 (m, 1H), 4.31 (m, 1H), 4.05-3.83 (m, 5H), 3.40-3.33 (m, 1H), 3.18-3.12 (m, 1H), 3.08-3.01 (m, 2H), 2.95-2.91 (m, 3H), 2.90-2.73 (m, 5H), 2.20-2.14 (s, 4H), 2.09-1.92 (m, 2H), 1.78-1.71 (m, 1H), 1.57-1.47 (m, 2H). | 576.2 |
| 23 | 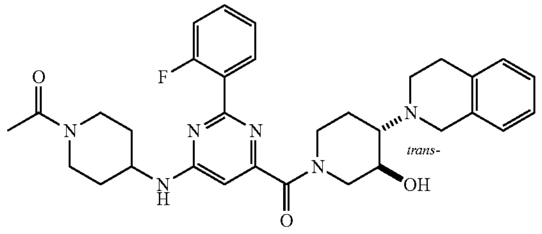 [SMILES: CC(=O)N1CCC(Nc2cc(C(=O)N3CC[C@H](N4CCc5ccccc5C4)[C@@H](O)C3)nc(-c3ccccc3F)n2)CC1] | (400 MHz, DMSO-$d_6$) δ 8.05-7.85 (m, 1H), 7.80-7.68 (m, 1H), 7.55-7.45 (m, 1H), 7.32-7.21 (m, 2H), 7.13-7.06 (m, 3H), 7.05-7.01 (m, 1H), 6.54 (s, 1H), 4.89-4.68 (m, 1H), 4.55-4.30 (m, 1H), 4.22-4.10 (m, 1H), 3.96-3.78 (m, 4H), 3.70-3.60 (m, 1H), 3.25-3.01 (m, 2H), 2.96-2.74 (m, 6H), 2.72-2.56 (m, 2H), 2.10-1.95 (m, 4H), 1.94-1.69 (m, 2H), 1.62-1.50 (m, 1H), 1.46-1.27 (m, 2H). | 573.3 |
| 24 | 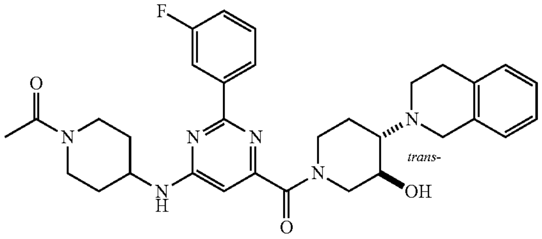 [SMILES: CC(=O)N1CCC(Nc2cc(C(=O)N3CC[C@H](N4CCc5ccccc5C4)[C@@H](O)C3)nc(-c3cccc(F)c3)n2)CC1] | (400 MHz, DMSO-$d_6$) δ 8.21-8.12 (m, 1H), 8.04-7.95 (m, 1H), 7.80-7.71 (m, 1H), 7.59-7.50 (m, 1H), 7.38-7.30 (m, 1H), 7.15-7.01 (m, 4H), 6.54 (s, 1H), 4.90-4.68 (m, 1H), 4.57-4.35 (m, 1H), 4.28-4.23 (m, 2H), 3.92-3.78 (m, 4H), 3.71-3.62 (m, 1H), 3.20-3.01 (m, 1H), 2.96-2.77 (m, 6H), 2.71-2.61 (m, 2H), 2.03 (s, 4H), 1.91-7.70 (m, 2H), 1.65-1.51 (m, 1H), 1.50-1.29 (m, 2H). | 573.3 |
| 25 | 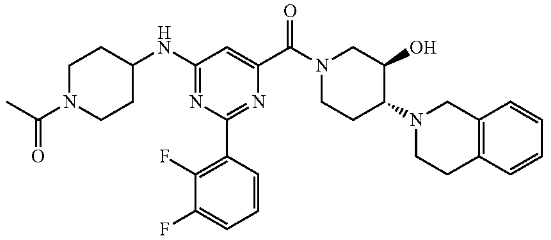 [SMILES: CC(=O)N1CCC(Nc2cc(C(=O)N3CC[C@@H](N4CCc5ccccc5C4)[C@H](O)C3)nc(-c3cccc(F)c3F)n2)CC1] | (400 MHz, $CD_3OD$) δ 7.74 (dd, J = 16.4, 8.0 Hz, 1H), 7.41-7.32 (m, 1H), 7.28-7.19 (m, 1H), 7.11-7.00 (m, 4H), 6.57 (s, 1H), 4.76-4.52 (m, 1H), 4.42 (d, J = 13.2 Hz, 1H), 4.31 (s, 1H), 4.04-3.78 (m, 5H), 3.20-3.01 (m, 2H), 3.01-2.91 (m, 2H), 2.91-2.84 (m, 3H), 2.84-2.69 (m, 2H), 2.21-2.14 (m, 1H), 2.12 (d, J = 0.8 Hz, 3H), 2.09-1.87 (m, 2H), 1.83-1.65 (m, 1H), 1.59-1.40 (m, 2H). | 591.3 |
| 26 | 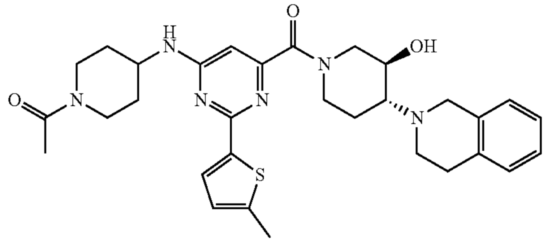 | (400 MHz, DMSO-$d_6$) δ 10.51-10.32 (m, 1H), 8.14-8.13 (m, 1H), 7.83-7.79 (m, 1H), 7.30-7.19 (m, 4H), 6.89 (s, 1H), 6.51 (s, 1H), 4.74-4.43 (m, 3H), 4.25-4.15 (m, 2H), 4.06-4.04 (m, 2H), 3.93-3.72 (m, 5H), 3.45-3.10 (m, 5H), 3.00-2.84 (m, 3H), 2.74-2.67 (m, 1H), 2.37-2.14 (m, 1H), 2.01-1.86 (m, 6H), 1.47-1.23 (m, 2H). | 575.3 |

-continued

| Ex. | Structure | $^1$H NMR | LC-MS (ESI) $[M + H]^+$ |
| --- | --- | --- | --- |
| 27 | 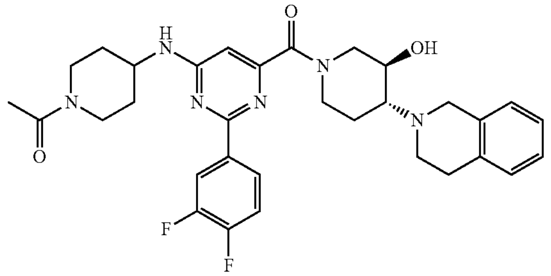 [SMILES: CC(=O)N1CCC(Nc2cc(C(=O)N3CC[C@@H](N4CCc5ccccc5C4)[C@H](O)C3)nc(-c3ccc(F)c(F)c3)n2)CC1] | (400 MHz, $CD_3OD$) δ 8.26-8.14 (m, 2H), 7.41-7.29 (m, 1H), 7.12-7.00 (m, 4H), 6.53 (d, J = 6.8 Hz, 1H), 4.79-4.55 (m, 1H), 4.47-4.31 (m, 2H), 4.07-3.79 (m, 5H), 3.36 (dd, J = 20.4, 8.4 Hz, 1H), 3.22-2.96 (m, 3H), 2.96-2.71 (m, 5H), 2.23-2.14 (m, 1H), 2.13 (s, 3H), 2.11-1.88 (m, 2H), 1.81-1.65 (m, 1H), 1.62-1.42 (m, 2H). | 591.3 |
| 28 | 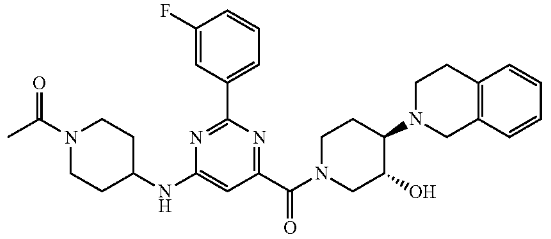 [SMILES: CC(=O)N1CCC(Nc2cc(C(=O)N3CC[C@@H](N4CCc5ccccc5C4)[C@H](O)C3)nc(-c3cccc(F)c3)n2)CC1] | (400 MHz, DMSO-$d_6$) δ 8.16 (t, J = 7.9 Hz, 1H), 8.01 (t, J = 9.1 Hz, 1H), 7.77 (t, J = 6.4 Hz, 1H), 7.61-7.49 (m, 1H), 7.40-7.29 (m, 1H), 7.15-6.99 (m, 4H), 6.54 (s, 1H), 4.78 (dd, J = 56.0, 3.9 Hz, 1H), 4.58-4.14 (m, 3H), 3.91-3.76 (m, 4H), 3.74-3.63 (m, 1H), 3.27-2.94 (m, 2H), 2.94-2.77 (m, 5H), 2.75-2.59 (m, 2H), 2.03 (s, 4H), 1.96-1.73 (m, 2H), 1.64-1.53 (m, 1H), 1.49-1.30 (m, 2H). | 573.3 |
| 29 | 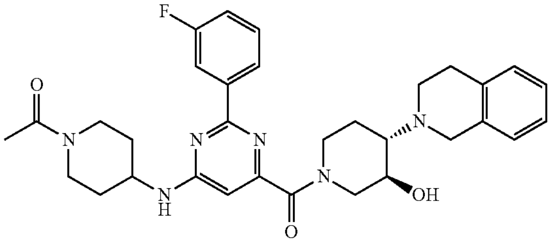 [SMILES: CC(=O)N1CCC(Nc2cc(C(=O)N3CC[C@H](N4CCc5ccccc5C4)[C@@H](O)C3)nc(-c3cccc(F)c3)n2)CC1] | (400 MHz, DMSO-$d_6$) δ 8.16 (t, J = 7.9 Hz, 1H), 8.01 (t, J = 8.9 Hz, 1H), 7.78 (d, J = 6.5 Hz, 1H), 7.59-7.49 (m, 1H), 7.39-7.30 (m, 1H), 7.14-7.01 (m, 4H), 6.54 (s, 1H), 4.78 (dd, J = 56.0, 3.8 Hz, 1H), 4.57-4.09 (m, 1H), 3.93-3.77 (m, 4H), 3.73-3.63 (m, 1H), 3.25-2.99 (m, 2H), 2.93-2.78 (m, 5H), 2.76-2.57 (m, 2H), 2.03 (s, 4H), 1.97-1.74 (m, 2H), 1.66-1.52 (m, 1H), 1.48-1.30 (m, 2H). | 573.3 |
| 30 | 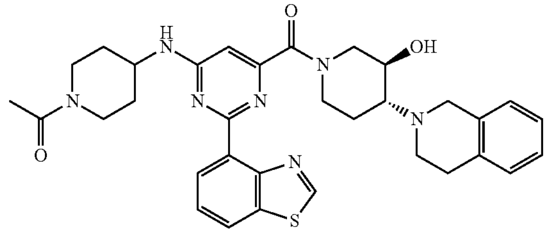 [SMILES: CC(=O)N1CCC(Nc2cc(C(=O)N3CC[C@@H](N4CCc5ccccc5C4)[C@H](O)C3)nc(-c3cccc4scnc34)n2)CC1] | (400 MHz, $CDCl_3$) δ 9.20-8.93 (m, 1H), 8.14-7.95 (m, 2H), 7.61-7.49 (m, 2H), 7.22-7.07 (m, 3H), 7.07-6.98 (m, 1H), 6.76-6.60 (m, 1H), 5.44-4.99 (m, 1H), 4.85-4.46 (m, 3H), 4.13-3.64 (m, 5H), 3.29-2.82 (m, 7H), 2.80-2.58 (m, 2H), 2.29-1.87 (m, 7H), 1.83-1.58 (m, 2H). | 613.3 |
| 31 | 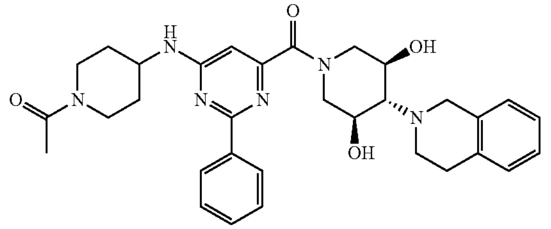 [SMILES: CC(=O)N1CCC(Nc2cc(C(=O)N3C[C@@H](O)[C@H](N4CCc5ccccc5C4)[C@@H](O)C3)nc(-c3ccccc3)n2)CC1] | (400 MHz, $CDCl_3$) δ 8.36-8.27 (m, 2H), 7.50-7.43 (m, 3H), 7.18-7.09 (m, 3H), 7.05-6.99 (m, 1H), 6.61 (s, 1H), 5.39 (s, 1H), 4.78-4.64 (m, 1H), 4.59-4.50 (m, 1H), 4.48-4.39 (m, 1H), 4.17-3.57 (m, 6H), 3.30-3.08 (m, 4H), 3.04-2.82 (m, 4H), 2.77-2.56 (m, 1H), 2.25-2.15 (m, 1H), 2.12 (s, 3H), 2.11-2.03 (m, 1H), 1.54-1.42 (m, 2H). | 571.4 |
| 32 | 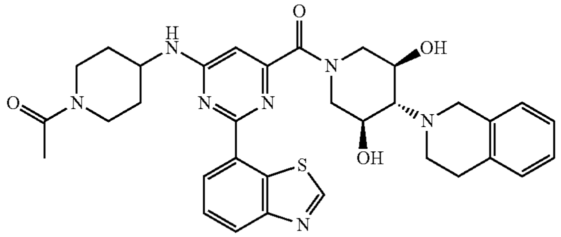 [SMILES: CC(=O)N1CCC(Nc2cc(C(=O)N3C[C@@H](O)[C@H](N4CCc5ccccc5C4)[C@@H](O)C3)nc(-c3cccc4ncsc34)n2)CC1] | (400 MHz, DMSO-$d_6$) δ 9.48 (s, 1H), 8.63 (d, J = 7.6 Hz, 1H), 8.25 (d, J = 7.9 Hz, 1H), 7.96 (d, J = 7.3 Hz, 1H), 7.71 (t, J = 7.8 Hz, 1H), 7.12-7.07 (m, 3H), 7.06-7.02 (m, 1H), 6.57 (s, 1H), 4.86 (d, J = 3.5 Hz, 1H), 4.69-4.62 (m, 1H), 4.60-4.30 (m, 3H), 4.10-3.96 (m, 2H), 3.94-3.81 (m, 2H), 3.76-3.61 (m, 2H), 3.41-3.33 (m, 1H), 3.13-3.02 (m, 2H), 3.01-2.89 (m, 2H), 2.86-2.76 (m, 2H), 2.69-2.61 (m, 1H), 2.46 (s, 1H), 2.18-2.06 (m, 2H), 2.05 (s, 3H), 1.57-1.45 (m, 1H), 1.43-1.32 (m, 1H). | 628.4 |

-continued

| Ex. | Structure | $^1$H NMR | LC-MS (ESI) [M + H]$^+$ |
|---|---|---|---|
| 33 | 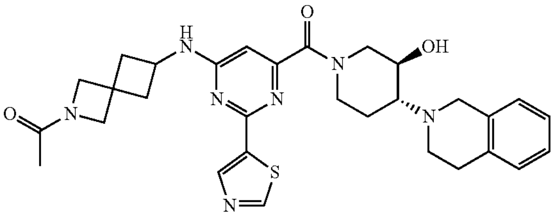 [SMILES: CC(=O)N1CC2(CC(Nc3cc(C(=O)N4CC[C@@H](N5CCc6ccccc6C5)[C@H](O)C4)nc(-c4cncs4)n3)C2)C1] | (400 MHz, $CDCl_3$) δ 8.89-8.81 (m, 1H), 8.65-8.54 (m, 1H), 7.19-7.12 (m, 3H), 7.08-7.03 (m, 1H), 6.56-6.41 (m, 1H), 5.34 (s, 1H), 5.13-4.73 (m, 1H), 4.48-4.29 (m, 1H), 4.27-4.20 (m, 1H), 4.16-4.07 (m, 2H), 4.07-3.93 (m, 2H), 3.88-3.68 (m, 2H), 3.16-3.05 (m, 1H), 3.07-2.93 (m, 3H), 2.91-2.82 (m, 1H), 2.82-2.63 (m, 3H), 2.29-2.15 (m, 2H), 2.08-1.98 (m, 1H), 1.96-1.81 (m, 4H), 1.81-1.66 (m, 1H), 1.37-1.23 (m, 1H). | 574.2 |
| 34 | 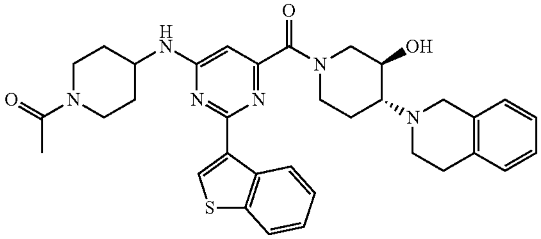 [SMILES: CC(=O)N1CCC(Nc2cc(C(=O)N3CC[C@@H](N4CCc5ccccc5C4)[C@H](O)C3)nc(-c3csc4ccccc34)n2)CC1] | (400 MHz, $CDCl_3$) δ 9.13-8.91 (m, 1H), 8.59-8.39 (m, 1H), 7.97-7.82 (m, 1H), 7.54-7.34 (m, 2H), 7.21-7.10 (m, 3H), 7.10-6.99 (m, 1H), 6.64-6.47 (m, 1H), 5.27-4.78 (m, 2H), 4.65-4.34 (m, 2H), 4.07-3.94 (m, 1H), 3.91-3.52 (m, 4H), 3.35-3.21 (m, 1H), 3.19-3.03 (m, 2H), 3.03-2.85 (m, 4H), 2.83-2.68 (m, 2H), 2.28-2.19 (m, 1H), 2.20-1.98 (m, 5H), 1.92-1.77 (m, 1H), 1.53-1.43 (m, 2H). | 611.00 |
| 35 | 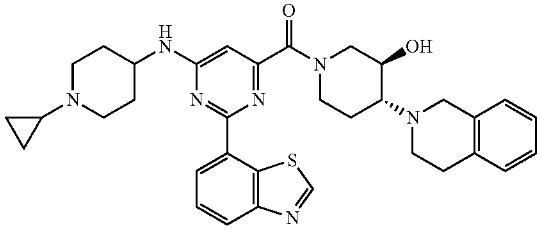 [SMILES: O=C(c1cc(NC2CCN(C3CC3)CC2)nc(-c2cccc3ncsc23)n1)N1CC[C@@H](N2CCc3ccccc3C2)[C@H](O)C1] | (400 MHz, DMSO-$d_6$) δ 9.51 (m, 1H), 8.62-8.58 (m, 1H), 8.26-8.22 (m, 1H), 7.87-7.83 (m, 1H), 7.87-7.83 (m, 1H), 7.10-7.04 (m, 4H), 6.68-6.50 (m, 1H), 4.86-4.67 (m, 1H), 4.56-4.38 (m, 1H), 4.25-4.16 (m, 1H), 3.89-3.78 (m, 3H), 3.73-3.69 (m, 1H), 3.14-3.08 (m, 0.5H), 3.00-2.91 (m, 4H), 2.84-2.80 (m, 3H), 2.67-2.64 (m, 1.5H), 2.45-2.42 (m, 3H), 2.05-2.03 (m, 2H), 1.90-1.72 (m, 1H), 1.69-1.62 (m, 1H), 1.50-1.45 (m, 2H), 0.45-0.32 (m, 4H). | 609.79 |
| 36 | 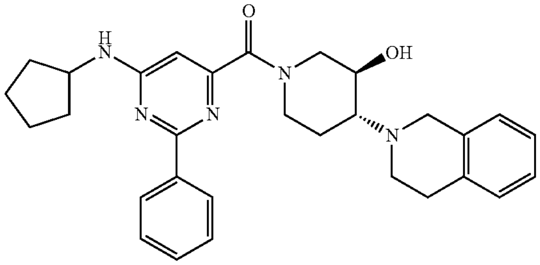 [SMILES: O=C(c1cc(NC2CCCC2)nc(-c2ccccc2)n1)N1CC[C@@H](N2CCc3ccccc3C2)[C@H](O)C1] | (400 MHz, $CDCl_3$) δ 8.44-8.21 (m, 2H), 7.45-7.43 (m, 3H), 7.17-7.10 (m, 3H), 7.05-7.03 (m, 1H), 6.56-6.52 (m, 1H), 5.22-5.07 (m, 1H), 4.77-4.74 (m, 1H), 4.49-4.44 (m, 1H), 3.99-3.88 (m, 2H), 3.78-3.71 (m, 2H), 3.07-3.00 (m, 2H), 2.95-2.92 (m, 3H), 2.74-2.66 (m, 2H), 2.12-2.00 (m, 3H), 1.89-1.67 (m, 5H), 1.57-1.55 (m, 2H). | 498.2 |
| 37 | 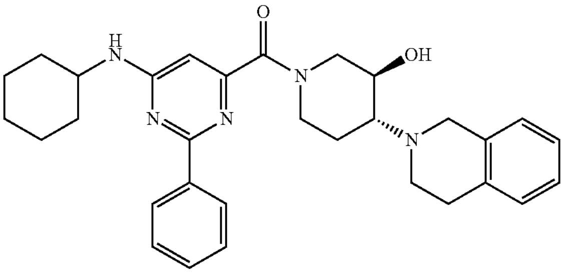 [SMILES: O=C(c1cc(NC2CCCCC2)nc(-c2ccccc2)n1)N1CC[C@@H](N2CCc3ccccc3C2)[C@H](O)C1] | (400 MHz, $CD_3OD$) δ 8.36-8.32 (m, 2H), 7.48-7.45 (m, 3H), 7.11-7.04 (m, 4H), 6.51-6.42 (m, 1H), 4.79-4.57 (m, 1H), 4.14-3.82 (m, 5H), 3.17-3.00 (m, 2H), 2.95-2.72 (m, 5H), 2.10-2.05 (m, 3H), 1.91-1.69 (m, 4H), 1.53-1.44 (m, 2H), 1.39-1.28 (m, 3H). | 512.2 |
| 38 | 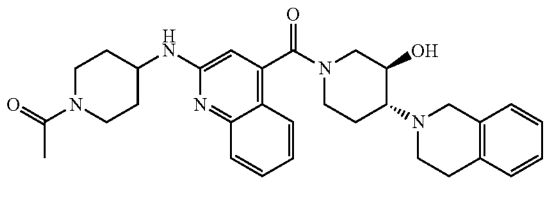 [SMILES: CC(=O)N1CCC(Nc2cc(C(=O)N3CC[C@@H](N4CCc5ccccc5C4)[C@H](O)C3)c3ccccc3n2)CC1] | (400 MHz, DMSO-$d_6$) δ 7.57-7.39 (m, 3H), 7.25-7.18 (m, 1H), 7.13-7.03 (m, 5H), 6.73-6.62 (m, 1H), 7.05-7.03 (m, 1H), 6.81-6.78 (m, 1H), 4.91-4.69 (m, 1H), 4.61-4.45 (m, 1H), 4.22-4.21 (m, 2H), 3.85-3.81 (m, 3.5H), 3.55-3.40 (m, 1H), 3.29-3.21 (m, 1.5H), 3.02-2.78 (m, 7H), 2.71-2.54 (m, 1H), 2.02-1.89 (m, 5.5H), 1.69-1.54 (m, 1H), 1.42-1.31 (m, 2.5H). | 528.3 |

-continued
| Ex. | Structure | $^1$H NMR | LC-MS (ESI) [M + H]$^+$ |
| --- | --- | --- | --- |
| 39 | 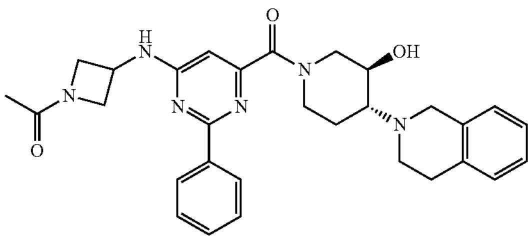 [SMILES: CC(=O)N1CC(Nc2cc(C(=O)N3CC[C@@H](N4CCc5ccccc5C4)[C@H](O)C3)nc(-c3ccccc3)n2)C1] | (400 MHz, $CDCl_3$) δ 8.35-8.33 (m, 2H), 7.46-7.44 (m, 3H), 7.16-7.04 (m, 4H), 6.66-6.63 (m, 1H), 6.31-6.14 (m, 1H), 5.07-4.80 (m, 2H), 4.56-4.33 (m, 3H), 4.01-3.95 (m, 3H), 3.77-3.70 (m, 2H), 3.08-2.86 (m, 5H), 2.74-2.70 (m, 2H), 2.06-2.02 (m, 1H), 1.88 (s, 3H), 1.78-1.71 (m, 1H). | 527.2 |
| 40 | 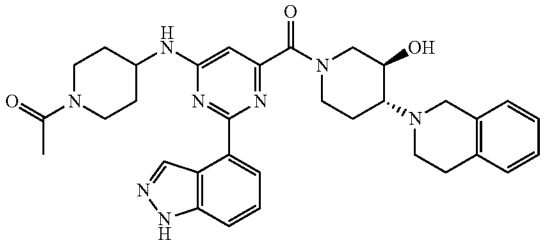 [SMILES: CC(=O)N1CCC(Nc2cc(C(=O)N3CC[C@@H](N4CCc5ccccc5C4)[C@H](O)C3)nc(-c3cccc4[nH]ncc34)n2)CC1] | (400 MHz, $CDCl_3$) δ 10.64 (s, 1H), 8.93-8.88 (m, 1H), 8.31-8.19 (m, 1H), 7.62-7.57 (m, 1H), 7.50-7.43 (m, 1H), 7.17-7.09 (m, 3H), 7.07-7.03 (m, 1H), 6.66-6.55 (m, 1H), 5.66-5.47 (m, 1H), 5.15-4.79 (m, 1H), 4.59-4.50 (m, 1H), 4.48-4.11 (m, 2H), 4.02-3.91 (m, 1H), 3.91-3.67 (m, 4H), 3.30-3.19 (m, 1H), 3.17-3.01 (m, 2H), 2.98-2.66 (m, 6H), 2.22-2.14 (m, 1H), 2.12-1.96 (m, 4H), 1.90-1.64 (m, 2H), 1.55-1.37 (m, 2H). | 595.32 |
| 41 | 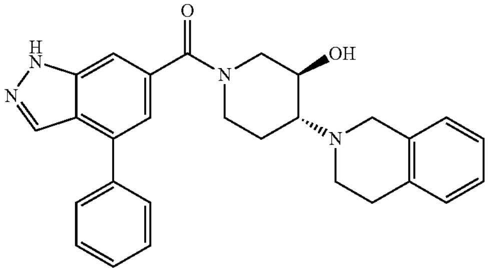 [SMILES: O=C(c1cc(-c2ccccc2)c2cn[nH]c2c1)N1CC[C@@H](N2CCc3ccccc3C2)[C@H](O)C1] | (400 MHz, $CDCl_3$) δ 10.52 (s, 1H), 8.31-8.08 (m, 1H), 7.73-7.66 (m, 2H), 7.61-7.50 (m, 3H), 7.49-7.43 (m, 1H), 7.26 (s, 1H), 7.17-7.09 (m, 3H), 7.05-7.00 (m, 1H), 5.19-4.87 (m, 1H), 4.20 (s, 1H), 4.06-3.94 (m, 1H), 3.85-3.52 (m, 3H), 3.15-3.03 (m, 1H), 3.05-2.88 (m, 2H), 2.85-2.64 (m, 3H), 2.06-1.94 (m, 2H). | 453.18 |
| 42 | 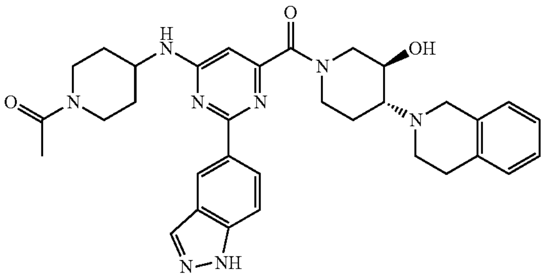 [SMILES: CC(=O)N1CCC(Nc2cc(C(=O)N3CC[C@@H](N4CCc5ccccc5C4)[C@H](O)C3)nc(-c3ccc4[nH]ncc4c3)n2)CC1] | (400 MHz, $CDCl_3$) δ 10.21 (s, 1H), 8.81 (s, 1H), 8.53-8.39 (m, 1H), 8.30-8.07 (m, 1H), 7.62-7.47 (m, 1H), 7.19-7.12 (m, 3H), 7.10-6.98 (m, 1H), 6.64-6.44 (m, 1H), 5.19-5.04 (m, 1H), 4.84-4.34 (m, 3H), 4.05-3.96 (m, 1H), 3.94-3.66 (m, 4H), 3.37-3.23 (m, 1H), 3.19-3.02 (m, 2H), 3.02-2.86 (m, 4H), 2.85-2.66 (m, 2H), 2.28-2.18 (m, 1H), 2.15-2.13 (m, 3H), 2.12-1.86 (m, 2H), 1.85-1.69 (m, 1H), 1.56-1.44 (m, 3H). | 595.32 |
| 43 | 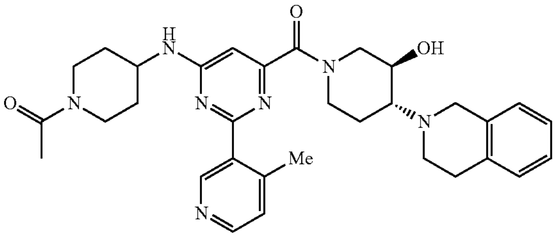 [SMILES: CC(=O)N1CCC(Nc2cc(C(=O)N3CC[C@@H](N4CCc5ccccc5C4)[C@H](O)C3)nc(-c3cnccc3C)n2)CC1] | (400 MHz, $CDCl_3$) δ 9.005-8.982 (m, 1H), 8.498-8.481 (m, 1H), 7.162-7.019 (m, 5H), 6.629-6.550 (m, 1H), 5.30-5.040 (m, 1H), 4.805-4.741 (m, 1H), 4.582-4.550 (m, 1H), 4.370-4.329 (m, 1H), 4.399-3.860 (m, 1H), 3.824-3.758 (m, 1H), 3.719-3.489 (m, 2H), 3.252-3.189 (m, 1H), 3.077-2.824 (m, 8H), 2.736-2.597 (m, 3H), 2.172-1.996 (m, 3H), 1.733-1.563 (m, 4H), 1.473-1.443 (m, 2H). | 570.4 |

-continued

| Ex. | Structure | $^1$H NMR | LC-MS (ESI) [M + H]$^+$ |
|---|---|---|---|
| 44 | 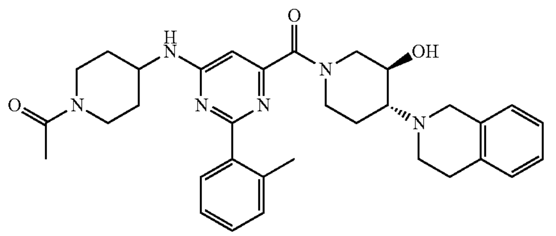 [SMILES: CC(=O)N1CCC(Nc2cc(C(=O)N3CC[C@@H](N4CCc5ccccc5C4)[C@H](O)C3)nc(-c3ccccc3C)n2)CC1] | (400 MHz, $CDCl_3$) δ 7.738-7.723 (m, 1H), 7.341-7.292 (m, 4H), 7.164-7.106 (m, 3H), 7.037-7.016 (m, 1H), 6.575-6.513 (m, 1H), 5.3-5.031 (m, 1H), 4.567-4.535 (m, 1H), 4.355-4.325 (m, 1H), 3.990-3.955 (m, 1H), 3.848-3.814 (m, 1H), 3.758-3.729 (m, 3H), 3.084-3.210 (m, 1H), 3.056-3.027 (m, 2H), 2.939-2.901 (m, 2H), 2.866-2.673 (m, 3H), 2.546 (s, 3H), 2.045 (s, 3H), 2.034-2.000 (m, 6H). | 569.4 |
| 45 | 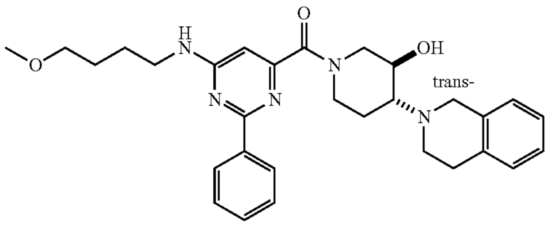 [SMILES: COCCCCNc1cc(C(=O)N2CC[C@@H](N3CCc4ccccc4C3)[C@H](O)C2)nc(-c2ccccc2)n1] | (400 MHz, $CD_3Cl$) δ 8.43-8.29 (m, 2H), 7.49-7.39 (m, 3H), 7.20-7.09 (m, 3H), 7.08-7.01 (m, 1H), 6.60-6.47 (m, 1H), 5.39 (brs, 1H), 5.15-5.05 (m, 0.4H), 4.81-4.70 (m, 0.6H), 4.52-4.43 (m, 0.6H), 4.43-4.35 (m, 0.4H), 4.02-3.94 (m, 1H), 3.93-3.65 (m, 3H), 3.58-3.40 (m, 3H), 3.39-3.30 (m, 3H), 3.07 (ddd, J = 13.1, 9.2, 4.1 Hz, 2H), 2.98-2.60 (m, 5H), 2.07-1.65 (m, 6H). | 516.2 |
| 46 | 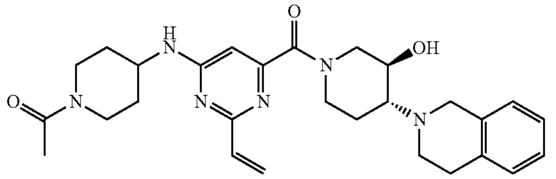 [SMILES: C=Cc1nc(NC2CCN(C(C)=O)CC2)cc(C(=O)N2CC[C@@H](N3CCc4ccccc4C3)[C@H](O)C2)n1] | (400 MHz, $CD_3OD$) δ 7.13-7.01 (m, 4H), 6.70-6.59 (m, 1H), 6.57-6.48 (m, 1H), 6.47-6.35 (m, 1H), 5.73-5.61 (m, 1H), 4.76-4.49 (m, 2H), 4.41 (d, J = 13.2 Hz, 1H), 4.31-4.20 (m, 1H), 4.02-3.87 (m, 3H), 3.86-3.73 (m, 2H), 3.16-3.00 (m, 2H), 2.99-2.83 (m, 5H), 2.83-2.67 (m, 1H), 2.12 (s, 3H), 2.10-1.84 (m, 3H), 1.76-1.63 (m, 1H), 1.58-1.38 (m, 2H). | 505.3 |
| 47 | 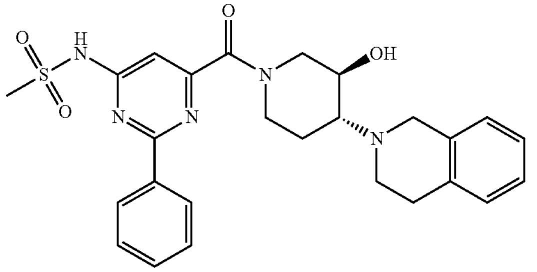 [SMILES: CS(=O)(=O)Nc1cc(C(=O)N2CC[C@@H](N3CCc4ccccc4C3)[C@H](O)C2)nc(-c2ccccc2)n1] | (400 MHz, $CD_3OD$) δ 8.44-8.39 (m, 2H), 7.52-7.48 (m, 3H), 7.19-7.11 (m, 4H), 6.90 (d, J = 5.2 Hz, 1H), 4.84-4.66 (m, 1H), 4.20-4.05 (m, 3H), 4.02-3.92 (m, 1H), 3.38 (d, J = 2.4 Hz, 3H), 3.30-3.13 (m, 3H), 3.09-3.00 (m, 4H), 2.16-2.00 (m, 1H), 1.88-1.81 (m, 1H). | 508.2 |
| 48 | 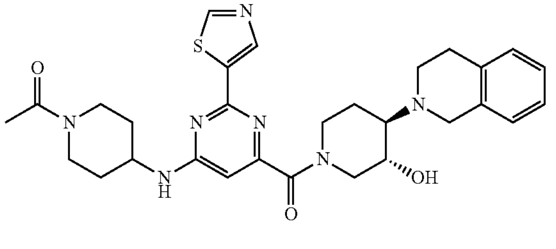 [SMILES: CC(=O)N1CCC(Nc2cc(C(=O)N3CC[C@@H](N4CCc5ccccc5C4)[C@H](O)C3)nc(-c3cncs3)n2)CC1] | (400 MHz, $CD_3OD$) δ 9.05-9.04 (m, 1H), 8.59-8.57 (m, 1H), 7.11-7.04 (m, 4H), 6.51-6.49 (m, 1H), 4.75-4.56 (m, 2H), 4.45-4.31 (m, 2H), 4.04-3.80 (m, 5H), 3.17-2.71 (m, 8H), 2.13-1.90 (m, 6H), 1.79-1.69 (m, 1H) 1.59-1.43 (m, 2H). | 562.4 |
| 49 | 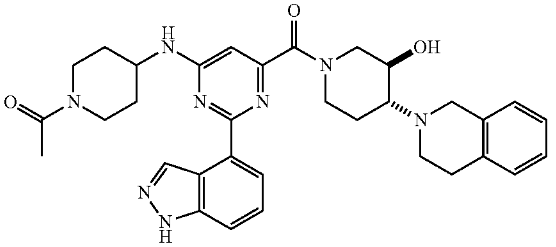 [SMILES: CC(=O)N1CCC(Nc2cc(C(=O)N3CC[C@@H](N4CCc5ccccc5C4)[C@H](O)C3)nc(-c3cccc4[nH]ncc34)n2)CC1] | (400 MHz, $CDCl_3$) δ 10.52 (s, 1H), 8.99-8.84 (m, 1H), 8.27-8.19 (m, 1H), 7.64-7.57 (m, 1H), 7.51-7.43 (m, 1H), 7.17-7.09 (m, 3H), 7.07-7.03 (m, 1H), 6.65-6.54 (m, 1H), 5.57-5.33 (m, 1H), 5.16-4.77 (m, 1H), 4.61-4.12 (m, 3H), 4.02-3.92 (m, 1H), 3.87-3.65 (m, 4H), 3.31-3.21 (m, 1H), 3.18-3.00 (m, 2H), 2.98-2.65 (m, 6H), 2.26-2.15 (m, 1H), 2.14-1.98 (m, 5H), 1.89-1.75 (m, 1H), 1.55-1.40 (m, 2H). | 595.6 |

-continued
| Ex. | Structure | $^{1}$H NMR | LC-MS (ESI) [M + H]$^{+}$ |
|---|---|---|---|
| 50 | 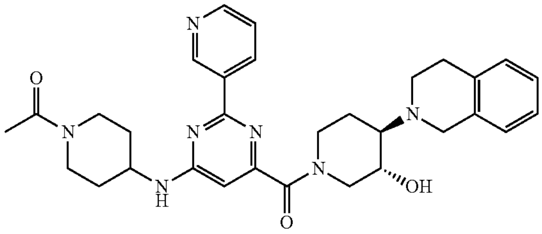 [SMILES: CC(=O)N1CCC(Nc2cc(C(=O)N3CC[C@@H](N4CCc5ccccc5C4)[C@H](O)C3)nc(-c3cccnc3)n2)CC1] | (400 MHz, $CD_3OD$) δ 9.48-9.45 (m, 1H), 8.76-8.71 (m, 1H), 8.63-8.61 (m, 1H), 7.57-7.53 (m, 1H), 7.10-7.05 (m, 4H), 6.59-6.57 (m, 1H), 4.78-4.59 (m, 1H), 4.45-4.42 (m, 2H), 4.10-3.81 (m, 5H), 3.40-3.33 (m, 1H) 3.20-2.73 (m, 8H), 2.19-1.91 (m, 6H), 1.77-1.70 (m, 1H), 1.60-1.45 (m, 2H). | 556.5 |
| 51 | 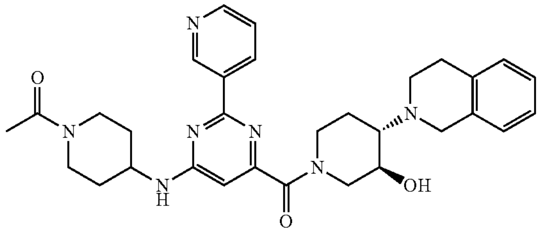 [SMILES: CC(=O)N1CCC(Nc2cc(C(=O)N3CC[C@H](N4CCc5ccccc5C4)[C@@H](O)C3)nc(-c3cccnc3)n2)CC1] | (400 MHz, $CD_3OD$) δ 9.48-9.45 (m, 1H), 8.76-8.71 (m, 1H), 8.64-8.61 (m, 1H), 7.57-7.53 (m, 1H), 7.11-7.05 (m, 4H), 6.59-6.57 (m, 1H), 4.77-4.59 (m, 1H), 4.45-4.42 (m, 2H), 4.10-3.82 (m, 5H), 3.41-3.32 (m, 1H), 3.20-2.73 (m, 8H), 2.19-1.91 (m, 6H), 1.77-1.70 (m, 1H), 1.61-1.45 (m, 2H). | 556.5 |
| 52 | 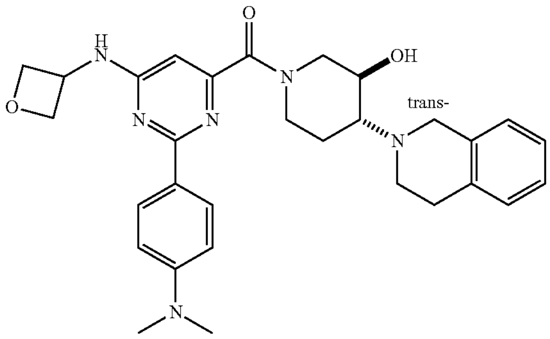 [SMILES: CN(C)c1ccc(-c2nc(NC3COC3)cc(C(=O)N3CC[C@@H](N4CCc5ccccc5C4)[C@H](O)C3)n2)cc1] | (400 MHz, $CDCl_3$) δ 8.30-8.18 (m, 2H), 7.18-7.09 (m, 3H), 7.08-6.99 (m, 1H), 6.80-6.66 (m, 2H), 6.52-6.36 (m, 1H), 5.67-5.47 (m, 1H), 5.26-5.09 (m, 1H), 5.07-4.97 (m, 2H), 4.88-4.17 (m, 4H), 4.03-3.62 (m, 4H), 3.14-2.91 (m, 10H), 2.81-2.63 (m, 2H), 2.10-1.82 (m, 1H), 1.81-1.68 (m, 1H). | 529.34 |
| 53 | 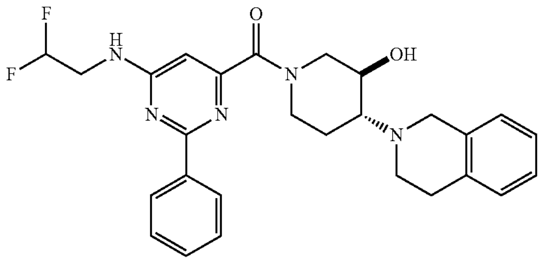 [SMILES: O=C(c1cc(NCC(F)F)nc(-c2ccccc2)n1)N1CC[C@@H](N2CCc3ccccc3C2)[C@H](O)C1] | (400 MHz, DMSO-$d_6$) δ 8.33 (s, 2H), 8.07 (s, 1H), 7.50 (s, 3H), 7.13-6.96 (m, 4H), 6.65 (s, 1H), 6.25 (t, J = 56.5 Hz, 1H), 4.90-4.66 (m, 1H), 4.57-4.32 (m, 1H), 4.05-3.61 (m, 6H), 3.14-2.78 (m, 5H), 2.75-2.60 (m, 2H), 1.92-1.71 (m, 1H), 1.67-1.49 (m, 1H). | 494.5 |
| 54 | 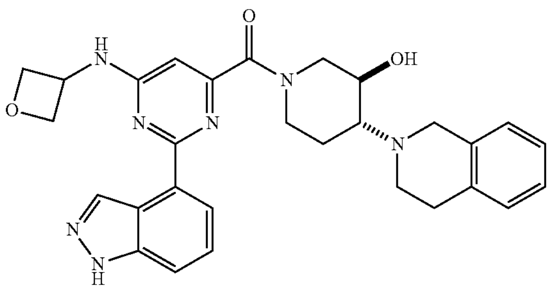 [SMILES: O=C(c1cc(NC2COC2)nc(-c2cccc3[nH]ncc23)n1)N1CC[C@@H](N2CCc3ccccc3C2)[C@H](O)C1] | (400 MHz, $CDCl_3$) δ 10.31 (s, 1H), 9.02-8.84 (m, 1H), 8.28-8.20 (m, 1H), 7.65-7.58 (m, 1H), 7.53-7.42 (m, 1H), 7.17-7.09 (m, 3H), 7.08-7.03 (m, 1H), 6.69-6.57 (m, 1H), 5.96-5.72 (m, 1H), 5.27 (s, 1H), 5.16-4.82 (m, 3H), 4.71-4.61 (m, 2H), 4.50-4.29 (m, 1H), 4.07-3.91 (m, 1H), 3.84-3.62 (m, 3H), 3.18-3.00 (m, 2H), 2.97-2.57 (m, 5H), 2.11-1.82 (m, 1H), 1.80-1.68 (m, 1H). | 526.5 |

-continued

| Ex. | Structure | $^1$H NMR | LC-MS (ESI) [M + H]$^+$ |
|---|---|---|---|
| 55 | 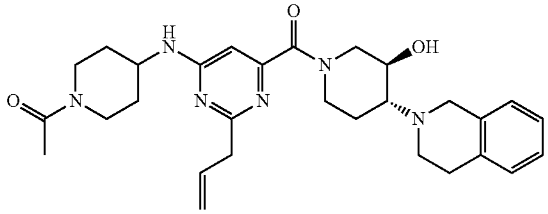 [SMILES: C=CCc1nc(NC2CCN(C(C)=O)CC2)cc(C(=O)N2CC[C@@H](N3CCc4ccccc4C3)[C@H](O)C2)n1] | (400 MHz, $CDCl_3$) δ 7.17-7.10 (m, 3H), 7.03-6.99 (m, 1H), 6.45-6.40 (m, 1H), 6.16-6.06 (m, 1H), 5.20-5.09 (m, 2H), 5.03-4.62 (m, 1H), 4.62-4.58 (m, 1H), 4.54-4.51 (m, 1H), 4.19-4.17 (m, 1H), 4.00-3.91 (m, 2H), 3.84-3.77 (m, 2H), 3.73-3.66 (m, 2H), 3.54-3.50 (m, 2H), 3.25-3.19 (m, 1H), 3.05-2.84 (m, 6H), 2.72-2.62 (m, 2H), 2.12-2.09 (m, 4H), 2.05-1.92 (m, 3H), 1.45-1.37 (m, 2H). | 519.3 |
| 56 | 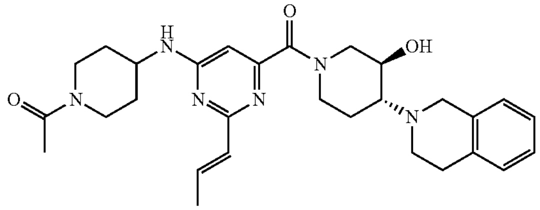 [SMILES: C/C=C/c1nc(NC2CCN(C(C)=O)CC2)cc(C(=O)N2CC[C@@H](N3CCc4ccccc4C3)[C@H](O)C2)n1] | (400 MHz, $CDCl_3$) δ 7.17-7.12 (m, 3H), 7.07-7.01 (m, 2H), 6.42-6.37 (m, 2H), 5.18-5.00 (m, 1H), 4.64-4.50 (m, 2H), 4.28-4.19 (m, 1H), 4.07-4.05 (m, 1H), 3.95-3.92 (m, 1H), 3.83-3.80 (m, 1H), 3.74-3.67 (m, 2H), 3.25-3.18 (m, 1H), 3.07-2.82 (m, 6H), 2.73-2.61 (m, 2H), 2.14-2.10 (m, 5H), 2.02-1.99 (m, 2H), 1.93 (d, J = 6.9 Hz, 3H), 1.42-1.39 (m, 2H). | 519.3 |
| 57 | 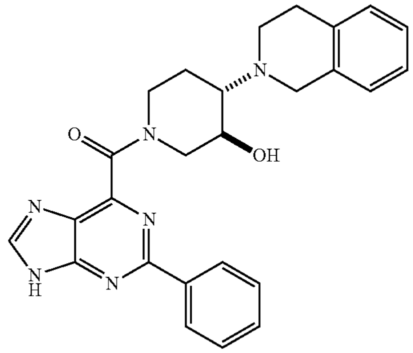 [SMILES: O=C(c1nc(-c2ccccc2)nc2[nH]cnc12)N1CC[C@H](N2CCc3ccccc3C2)[C@@H](O)C1] | (400 MHz, $CDCl_3$) δ 8.56-8.26 (m, 3H), 7.54-7.40 (m, 3H), 7.16-7.13 (m, J = 6.6, 2.8 Hz, 3H), 7.07-7.00 (m, 1H), 5.48-4.87 (m, 2H), 4.07-3.71 (m, 3.4H), 3.24 (t, J = 12.7 Hz, 0.6H), 3.18-3.05 (m, 2H), 3.03-2.70 (m, 5H), 2.14-1.96 (m, 1H), 1.94-1.71 (m, 1H). | 455.6 |
| 58 | 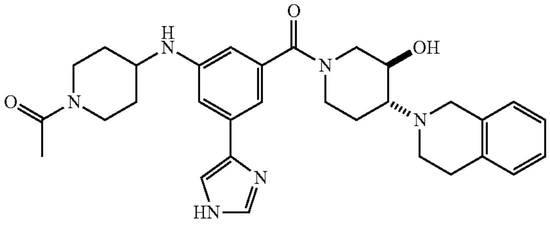 [SMILES: CC(=O)N1CCC(Nc2cc(C(=O)N3CC[C@@H](N4CCc5ccccc5C4)[C@H](O)C3)cc(-c3c[nH]cn3)c2)CC1] | (400 MHz, $CDCl_3$) δ 7.59 (d, J = 2.2 Hz, 1H), 7.20-6.96 (m, 6H), 6.64-6.50 (m, 2H), 5.14-4.80 (m, 1H), 4.53-4.39 (m, 1H), 4.24 (s, 1H), 4.02-3.88 (m, 2H), 3.84-3.63 (m, 3H), 3.55 (t, J = 8.4 Hz, 2H), 3.24-3.11 (m, 1H), 3.10-2.96 (m, 1H), 2.96-2.77 (m, 4H), 2.77-2.47 (m, 3H), 2.19-1.91 (m, 6H), 1.56-1.17 (m, 3H). | 543.4 |
| 59 | 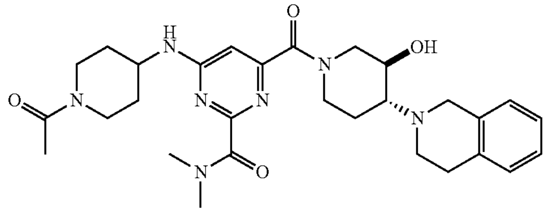 [SMILES: CC(=O)N1CCC(Nc2cc(C(=O)N3CC[C@@H](N4CCc5ccccc5C4)[C@H](O)C3)nc(C(=O)N(C)C)n2)CC1] | (400 MHz, $CD_3OD$) δ 7.12-6.99 (m, 4H), 6.56 (d, J = 8.4 Hz, 1H), 4.71-4.48 (m, 1H), 4.43 (d, J = 13.6 Hz, 1H), 4.24 (s, 1H), 3.97-3.89 (m, 2H), 3.89-3.75 (m, 3H), 3.29-3.11 (m, 2H), 3.09 (d, J = 5.2 Hz, 3H), 3.04-2.99 (m, 1H), 2.97 (d, J = 8.0 Hz, 3H), 2.94-2.67 (m, 6H), 2.11 (s, 3H), 2.09-1.83 (m, 3H), 1.75-1.59 (m, 1H), 1.55-1.36 (m, 2H). | 550.4 |
| 60 | 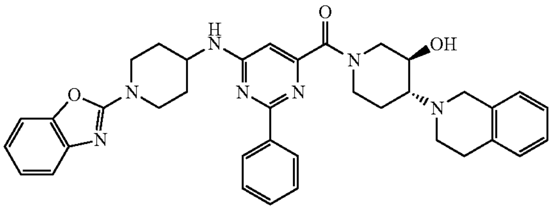 [SMILES: O=C(c1cc(NC2CCN(c3nc4ccccc4o3)CC2)nc(-c2ccccc2)n1)N1CC[C@@H](N2CCc3ccccc3C2)[C@H](O)C1] | (400 MHz, DMSO-$d_6$) δ 8.45-8.09 (m, 2H), 7.83-7.65 (m, 1H), 7.55-7.36 (m, 4H), 7.30 (d, J = 7.7 Hz, 1H), 7.16 (t, J = 7.6 Hz, 1H), 7.12-6.98 (m, 5H), 6.79-6.42 (m, 1H), 4.88-4.65 (m, 1H), 4.58-4.27 (m, 2H), 4.23-4.05 (m, 2H), 3.94-3.77 (m, 3H), 3.75-3.60 (m, 1H), 3.52-3.36 (m, 2H), 3.12-2.79 (m, 5H), 2.76-2.58 (m, 2H), 2.22-1.96 (m, 2H), 1.92-1.72 (m, 1H), 1.69-1.52 (m, 3H). | 630.0 |

-continued

| Ex. | Structure | $^1$H NMR | LC-MS (ESI) [M + H]$^+$ |
|---|---|---|---|
| 61 | 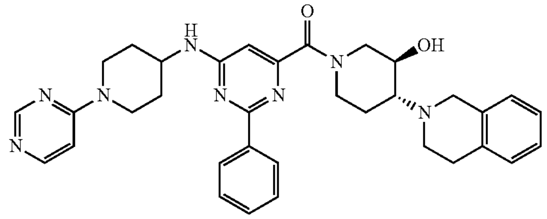 [SMILES: O=C(c1cc(NC2CCN(c3ccncn3)CC2)nc(-c2ccccc2)n1)N1CC[C@@H](N2CCc3ccccc3C2)[C@H](O)C1] | (400 MHz, DMSO-$d_6$) δ 8.50 (s, 1H), 8.37-8.26 (m, 2H), 8.17 (d, J = 6.4 Hz, 1H), 7.75-7.70 (m, 1H), 7.50-7.48 (m, 3H), 7.11-7.05 (m, 4H), 6.88 (d, J = 6.4 Hz, 1H), 6.52-6.49 (m, 1H), 4.85-4.72 (m, 1H), 4.54-4.36 (m, 4H), 3.89-3.68 (m, 5H), 3.28-3.21 (m, 2H), 3.10-2.81 (m, 3H), 2.83-2.81 (m, 2H), 2.67-2.62 (m, 1H), 2.14-2.05 (m, 2H), 1.76-1.46 (m, 4H). | 591.0 |
| 62 | 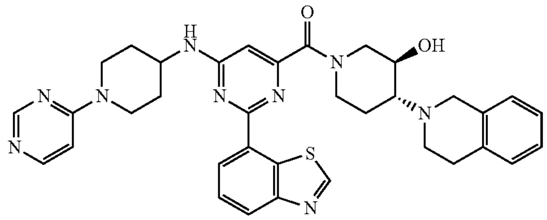 [SMILES: O=C(c1cc(NC2CCN(c3ccncn3)CC2)nc(-c2cccc3ncsc23)n1)N1CC[C@@H](N2CCc3ccccc3C2)[C@H](O)C1] | (400 MHz, DMSO-$d_6$) δ 9.48 (d, J = 2.4 Hz, 1H), 8.63 (t, J = 8.4 Hz, 1H), 8.52 (s, 1H), 8.25 (t, J = 7.6 Hz, 1H), 8.19 (d, J = 6.0 Hz, 1H), 7.96-7.93 (m, 1H), 7.74-7.69 (m, 1H), 7.11-7.06 (m, 4 H), 6.92 (d, J = 6.0 Hz, 1H), 6.54 (d, J = 6.0 Hz, 1H), 4.87-4.68 (m, 1H), 4.55-4.41 (m, 4H), 3.84-3.78 (m, 3H), 3.73-3.70 (m, 1H), 3.32-3.29 (m, 1H), 3.14-3.09 (m, 1H), 2.94-2.81 (m, 5H), 2.71-2.68 (m, 2H), 2.18-2.15 (m, 2H), 1.91-1.73 (m, 1H), 1.62-1.49 (m, 3H). | 648.0 |
| 63 | 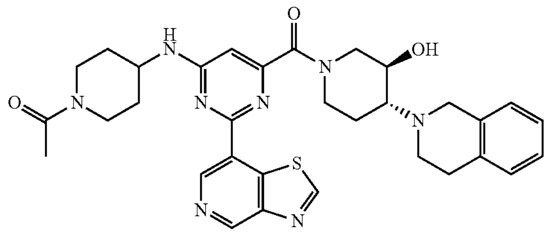 [SMILES: CC(=O)N1CCC(Nc2cc(C(=O)N3CC[C@@H](N4CCc5ccccc5C4)[C@H](O)C3)nc(-c3cncc4ncsc34)n2)CC1] | (400 MHz, $CDCl_3$) δ 9.75-9.60 (m, 1H), 9.51 (s, 1H), 9.21-9.09 (m, 1H), 7.20-7.10 (m, 3H), 7.09-6.97 (m, 1H), 6.75-6.48 (m, 1H), 5.82-5.48 (m, 1H), 5.15-4.87 (m, 1H), 4.68-4.55 (m, 1H), 4.43-4.31 (m, 1H), 4.08-3.98 (m, 1H), 3.93-3.61 (m, 4H), 3.41-3.25 (m, 1H), 3.17-3.00 (m, 2H), 2.99-2.70 (m, 6H), 2.30-2.20 (m, 1H), 2.19-2.11 (m, 4H), 2.09-1.99 (m, 1H), 1.93-1.80 (m, 1H), 1.56-1.47 (m, 2H). | 613.0 |
| 64 | 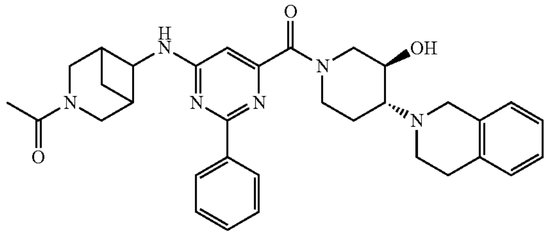 [SMILES: CC(=O)N1CC2CC(C1)C2Nc1cc(C(=O)N2CC[C@@H](N3CCc4ccccc4C3)[C@H](O)C2)nc(-c2ccccc2)n1] | (400 MHz, $CDCl_3$) δ 8.57-8.03 (m, 2H), 7.55-7.40 (m, 3H), 7.21-7.10 (m, 3H), 7.08-6.99 (m, 1H), 6.79-6.51 (m, 1H), 5.71-5.52 (m, 1H), 5.14-4.73 (m, 1H), 4.48-4.34 (m, 1H), 4.06-3.95 (m, 1H), 3.83-3.60 (m, 6H), 3.16-2.99 (m, 2H), 2.97-2.83 (m, 4H), 2.78-2.64 (m, 2H), 2.15-2.10 (m, 3H), 2.09-1.90 (m, 2H), 1.90-1.53 (m, 3H), 1.51-1.46 (m, 1H). | 567.00 |
| 65 | 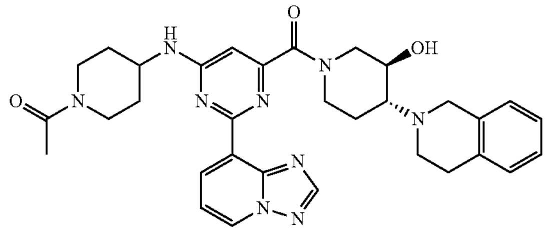 [SMILES: CC(=O)N1CCC(Nc2cc(C(=O)N3CC[C@@H](N4CCc5ccccc5C4)[C@H](O)C3)nc(-c3cccn4ncnc34)n2)CC1] | (400 MHz, $CDCl_3$) δ 8.76-8.68 (m, 1H), 8.48-8.30 (m, 2H), 7.22-7.09 (m, 4H), 7.07-7.00 (m, 1H), 6.76-6.68 (m, 1H), 5.58 (s, 1H), 5.11-4.42 (m, 3H), 4.13-3.68 (m, 5H), 3.36-2.58 (m, 9H), 2.32-2.04 (m, 6H), 1.96-1.82 (m, 1H), 1.58-1.41 (m, 2H). | 596.0 |
| 66 | 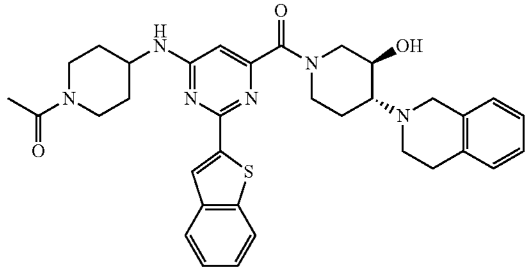 [SMILES: CC(=O)N1CCC(Nc2cc(C(=O)N3CC[C@@H](N4CCc5ccccc5C4)[C@H](O)C3)nc(-c3cc4ccccc4s3)n2)CC1] | (400 MHz, DMSO-$d_6$) δ 8.21 (d, J = 8.1 Hz, 1H), 8.00-7.93 (m, 2H), 7.85-7.76 (m, 1H), 7.44-7.38 (m, 2H), 7.11-7.06 (m, 4H), 6.70-6.50 (m, 1H), 4.76-4.72 (m, 1H), 4.52-4.35 (m, 1H), 4.28-4.25 (m, 2H), 3.89-3.81 (m, 4H), 3.75-3.69 (m, 1H), 3.28-3.05 (m, 1H), 2.96-2.82 (m, 6H), 2.71-2.63 (m, 2H), 2.08-1.98 (m, 5H), 1.89-1.77 (m, 1H), 1.67-1.54 (m, 1H), 1.51-1.35 (m, 2H). | 611.0 |

-continued

| Ex. | Structure | $^1$H NMR | LC-MS (ESI) [M + H]$^+$ |
|---|---|---|---|
| 67 | 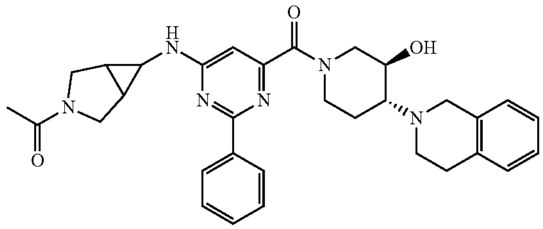 [SMILES: CC(=O)N1CC2C(C1)C2Nc1cc(C(=O)N2CC[C@@H](N3CCc4ccccc4C3)[C@H](O)C2)nc(-c2ccccc2)n1] | (400 MHz, DMSO-$d_6$) δ 8.36-8.28 (m, 2H), 8.05-7.94 (m, 1H), 7.49 (s, 3H), 7.11-7.09 (m, 4H), 6.73-6.49 (m, 1H), 4.85-4.70 (m, 1H), 4.53-4.36 (m, 1H), 3.89-3.60 (m, 7H), 3.42-3.37 (m, 1H), 3.10-2.75 (m, 6H), 2.68-2.62 (m, 1H), 2.59-2.52 (m, 0.5H), 2.39-2.35 (m, 0.5H), 1.95 (s, 3H), 1.89-1.75 (m, 3H), 1.69-1.50 (m, 1H). | 553.0 |
| 68 | 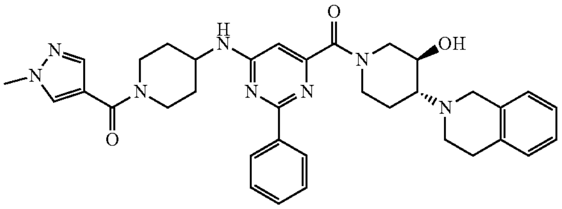 [SMILES: Cn1cc(C(=O)N2CCC(Nc3cc(C(=O)N4CC[C@@H](N5CCc6ccccc6C5)[C@H](O)C4)nc(-c4ccccc4)n3)CC2)cn1] | 400 MHz, DMSO-$d_6$) δ 8.44-8.25 (m, 2H), 8.06 (s, 1H), 7.76-7.64 (m, 2H), 7.52-7.45 (m, 3H), 7.11-7.02 (m, 4H), 6.71-6.43 (m, 1H), 4.88-4.66 (m, 1H), 4.60-4.07 (m, 4H), 3.91-3.79 (m, 6H), 3.74-3.62 (m, 1H), 3.30-2.78 (m, 7H), 2.77-2.57 (m, 2H), 2.15-1.93 (m, 2H), 1.91-1.71 (m, 1H), 1.63-1.41 (m, 3H). | 621.3 |
| 69 | 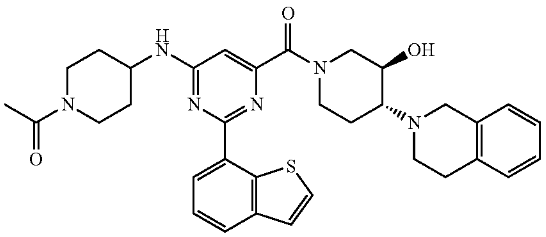 [SMILES: CC(=O)N1CCC(Nc2cc(C(=O)N3CC[C@@H](N4CCc5ccccc5C4)[C@H](O)C3)nc(-c3cccc4ccsc34)n2)CC1] | (400 MHz, $CDCl_3$) δ 8.62-8.64 (m, 1H), 7.99-7.92 (m, 1H), 7.55-7.45 (m, 2H), 7.45-7.39 (m, 1H), 7.19-7.08 (m, 3H), 7.09-7.01 (m, 1H), 6.64-6.54 (m, 1H), 5.78-5.54 (m, 1H), 5.15-4.79 (m, 1H), 4.63-4.54 (m, 1H), 4.48-4.23 (m, 1H), 4.03-3.93 (m, 1H), 3.87-3.65 (m, 4H), 3.31-3.16 (m, 1H), 3.18-2.99 (m, 2H), 2.98-2.66 (m, 6H), 2.27-2.08 (m, 2H), 2.09-1.98 (m, 3H), 1.92-1.70 (m, 2H), 1.54-1.31 (m, 2H). | 611.0 |
| 70 | 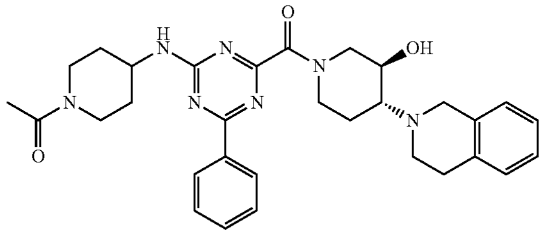 [SMILES: CC(=O)N1CCC(Nc2nc(C(=O)N3CC[C@@H](N4CCc5ccccc5C4)[C@H](O)C3)nc(-c3ccccc3)n2)CC1] | (400 MHz, $CDCl_3$) δ 8.47-8.35 (m, 2H), 7.60-7.43 (m, 3H), 7.21-7.09 (m, 3H), 7.07-7.01 (m, 1H), 5.61-5.50 (m, 1H), 5.14-4.82 (m, 1H), 4.62-4.49 (m, 1H), 4.38-4.18 (m, 1H), 4.13-3.54 (m, 6H), 3.37-3.19 (m, 1H), 3.11-2.90 (m, 4H), 2.88-2.66 (m, 3H), 2.13 (s, 3H), 2.07-1.37 (m, 6H). | 556.3 |
| 71 | 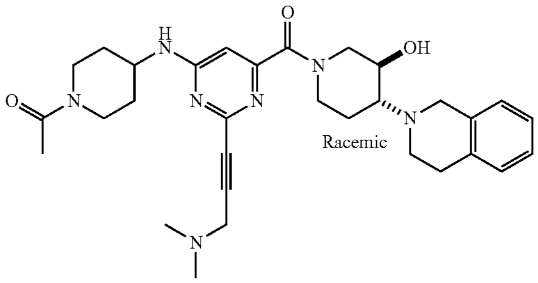 [SMILES: CC(=O)N1CCC(Nc2cc(C(=O)N3CC[C@@H](N4CCc5ccccc5C4)[C@H](O)C3)nc(C#CCN(C)C)n2)CC1] Racemic | (400 MHz, $CD_3OD$) δ 7.11-6.97 (m, 4H), 6.49 (s, 1H), 4.73-4.38 (m, 3H), 4.23 (s, 1H), 3.98-3.68 (m, 6H), 3.52 (d, J = 3.6 Hz, 1H), 3.15-2.97 (m, 2H), 2.91-2.83 (m, 4H), 2.79-2.68 (m, 2H), 2.39 (d, J = 4.8 Hz, 6H), 2.12 (s, 3H), 2.07-1.96 (m, 3H), 1.74-1.62 (m, 1H), 1.54-1.37 (m, 2H). | 560.5 |
| 72 | 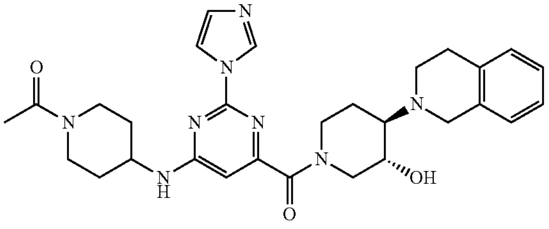 [SMILES: CC(=O)N1CCC(Nc2cc(C(=O)N3CC[C@@H](N4CCc5ccccc5C4)[C@H](O)C3)nc(-n3ccnc3)n2)CC1] | (400 MHz, DMSO-$d_6$) δ 8.55-8.35 (m, 1H), 8.14-8.03 (m, 1H), 7.90-7.75 (m, 1H), 7.17-6.98 (m, 5H), 6.76-6.43 (m, 1H), 4.53-4.42 (m, 1H), 4.38-4.08 (m, 3H), 3.95-3.85 (s, 4H), 3.82-7.75 (m, 1H), 3.11-3.01 (m, 1H), 3.01-2.77 (m, 6H), 2.74-2.58 (m, 2H), 2.02 (s, 3H), 1.93-1.82 (m, 2H), 1.81-1.48 (m, 2H), 1.50-1.24 (m, 2H). | 545.2 |

-continued
| Ex. | Structure | $^1$H NMR | LC-MS (ESI) [M + H]$^+$ |
|---|---|---|---|
| 73 | 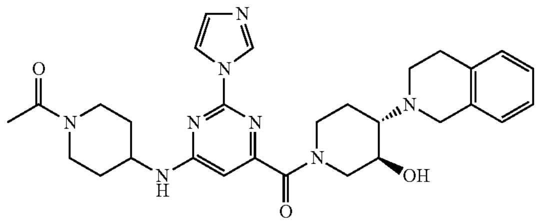 [SMILES: CC(=O)N1CCC(Nc2cc(C(=O)N3CC[C@H](N4CCc5ccccc5C4)[C@@H](O)C3)nc(-n3ccnc3)n2)CC1] | (400 MHz, DMSO-$d_6$) δ 8.56-8.38 (m, 1H), 8.15-8.02 (m, 1H), 7.90-7.75 (m, 1H), 7.20-6.93 (m, 5H), 6.76-6.42 (m, 1H), 4.79 (dd, J = 42.8, 3.8 Hz, 1H), 4.58-4.17 (m, 3H), 3.88-3.76 (m, 4H), 3.73-3.60 (m, 1H), 3.29-3.15 (m, 1H), 3.11-2.77 (m, 6H), 2.75-2.66 (m, 2H), 2.02 (s, 3H), 1.93-1.73 (m, 2H), 1.62-1.41 (m, 2H), 1.40-1.15 (m, 1H). | 545.7 |
| 74 | 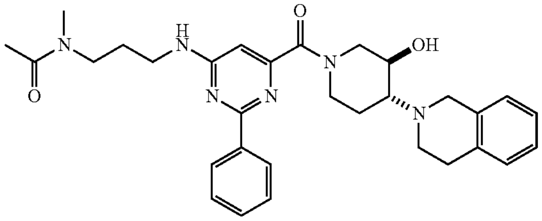 [SMILES: CC(=O)N(C)CCCNc1cc(C(=O)N2CC[C@@H](N3CCc4ccccc4C3)[C@H](O)C2)nc(-c2ccccc2)n1] | (400 MHz, DMSO-$d_6$) δ 8.41-8.26 (m, 2H), 7.85-7.63 (m, 1H), 7.55-7.43 (m, 3H), 7.14-6.99 (m, 4H), 6.61-6.45 (m, 1H), 4.89-4.64 (m, 1H), 4.59-4.30 (m, 1H), 3.93-3.76 (m, 3H), 3.74-3.62 (m, 1H), 3.57-3.36 (m, 4H), 3.13-3.01 (m, 0.6H), 3.00-2.86 (m, 3.4H), 2.87-2.72 (m, 4.4H), 2.72-2.58 (m, 1.6H), 2.03-1.96 (m, 3H), 1.94-1.71 (m, 3H), 1.68-1.49 (m, 1H). | 543.3 |
| 75 | 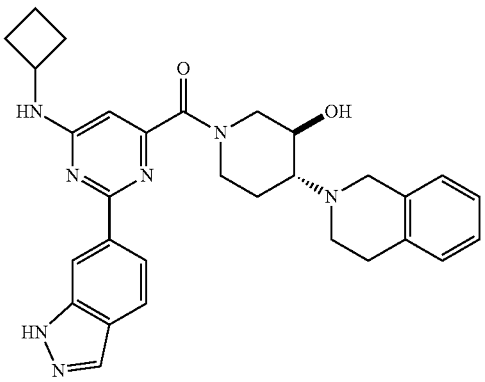 [SMILES: O=C(c1cc(NC2CCC2)nc(-c2ccc3cn[nH]c3c2)n1)N1CC[C@@H](N2CCc3ccccc3C2)[C@H](O)C1] | (400 MHz, DMSO-$d_6$) δ 13.23 (s, 1H), 8.51 (d, J = 10.1 Hz, 1H), 8.21-8.07 (m, 2H), 8.07-7.93 (m, 1H), 7.89-7.73 (m, 1H), 7.16-6.96 (m, 4H), 6.57-6.36 (m, 1H), 4.89-4.70 (m, 1H), 4.65 (s, 1H), 4.58-4.33 (m, 1H), 3.96-3.76 (m, 3H), 3.76-3.62 (m, 1H), 3.16-2.89 (m, 2.5H), 2.89-2.73 (m, 3H), 2.73-2.61 (m, 1.5H), 2.40 (s, 2H), 2.12-1.94 (m, 2H), 1.94-1.67 (m, 3H), 1.67-1.51 (m, 1H). | 524.3 |
| 76 | 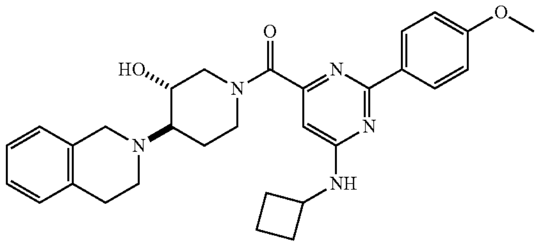 [SMILES: COc1ccc(-c2nc(NC3CCC3)cc(C(=O)N3CC[C@@H](N4CCc5ccccc5C4)[C@H](O)C3)n2)cc1] | (400 MHz, DMSO-$d_6$) δ 8.26 (t, J = 8.3 Hz, 2H), 7.88 (t, J = 6.5 Hz, 1H), 7.13-6.98 (m, 6H), 6.37 (d, J = 4.3 Hz, 1H), 4.76 (dd, J = 52.3, 3.8 Hz, 1H), 4.64-4.31 (m, 2H), 3.92-3.75 (m, 6H), 3.73-3.61 (m, 1H), 3.10-2.79 (m, 5H), 2.77-2.58 (m, 2H), 2.41-2.26 (m, 2H), 2.05-1.89 (m, 2H), 1.89-1.68 (m, 3H), 1.63-1.46 (m, 1H). | 514.26 |
| 77 | 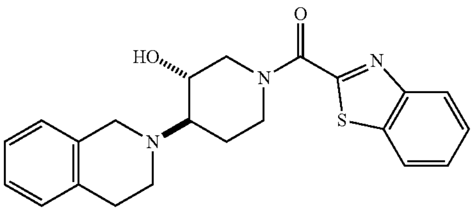 [SMILES: O=C(c1nc2ccccc2s1)N1CC[C@@H](N2CCc3ccccc3C2)[C@H](O)C1] | (400 MHz, DMSO-$d_6$) δ 8.42-8.02 (m, 2H), 7.77-7.47 (m, 2H), 7.25-6.87 (m, 4H), 5.20-5.06 (m, 1H), 4.88 (dd, J = 36.2, 4.1 Hz, 1H), 4.64-4.28 (m, 1H), 4.07-3.64 (m, 3H), 3.30-3.03 (m, 1H), 2.97-2.63 (m, 6H), 1.96-1.85 (m, 1H), 1.74-1.54 (m, 1H). | 394.2 |

-continued
| Ex. | Structure | $^1$H NMR | LC-MS (ESI) [M + H]$^+$ |
| --- | --- | --- | --- |
| 78 | 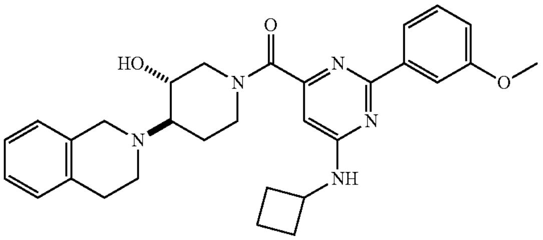 [SMILES: COc1cccc(-c2nc(NC3CCC3)cc(C(=O)N3CC[C@@H](N4CCc5ccccc5C4)[C@H](O)C3)n2)c1] | (400 MHz, DMSO-$d_6$) δ 8.05-7.77 (m, 3H), 7.42-7.37 (m, 1H), 7.14-6.97 (m, 5H), 6.46 (d, J = 3.8 Hz, 1H), 4.76 (dd, J = 63.8, 3.8 Hz, 1H), 4.63-4.31 (m, 2H), 3.92-3.79 (m, 6H), 3.77-3.60 (m, 1H), 3.11-2.93 (m, 1H), 2.92-2.78 (m, 4H), 2.70-2.58 (m, 2H), 2.42-2.30 (m, 2H), 2.05-1.91 (m, 2H), 1.91-1.71 (m, 3H), 1.69-1.50 (m, 1H). | 514.27 |
| 79 | 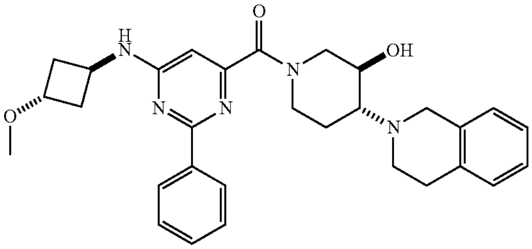 | (400 MHz, $CDCl_3$) δ 8.40-8.28 (m, 2H), 7.49-7.39 (m, 3H), 7.21-7.09 (m, 3H), 7.09-7.01 (m, 1H), 6.55-6.41 (m, 1H), 5.44 (brs, 1H), 5.15-5.05 (m, 0.5 H), 4.84-4.73 (m, 0.5H), 4.49-4.41 (m, 2H), 4.40-4.32 (m, 1H), 4.14-4.05 (m, 1H), 3.77-3.73 (m, 2H), 3.32-3.24 (m, 3H), 3.13-2.99 (m, 2H), 2.98-2.63 (m, 5H), 2.58-2.47 (m, 2H), 2.30-2.19 (m, 2H), 2.07-1.85 (m, 1H), 1.84-1.67 (m, 1H). | 514.25 |
| 80 | 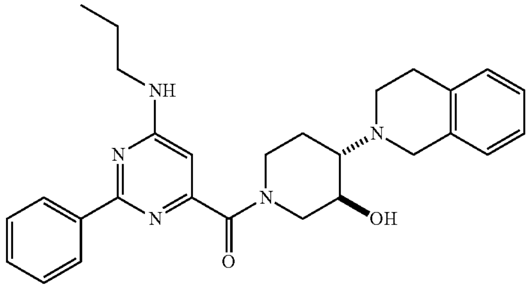 [SMILES: CCCNc1cc(C(=O)N2CC[C@H](N3CCc4ccccc4C3)[C@@H](O)C2)nc(-c2ccccc2)n1] | (400 MHz, $CDCl_3$) δ 8.55-8.17 (m, 2H), 7.51-7.38 (m, 3H), 7.21-7.10 (m, 3H), 7.08-7.01 (m, 1H), 6.60-6.47 (m, 1H), 5.36-4.65 (m, 2H), 4.60-4.31 (m, 1H), 4.10-3.65 (m, 4H), 3.40 (s, 2H), 3.15-2.60 (m, 7H), 2.08-1.87 (m, 1H), 1.85-1.67 (m, 3H), 1.08-0.90 (m, 3H). | 472.54 |
| 81 | 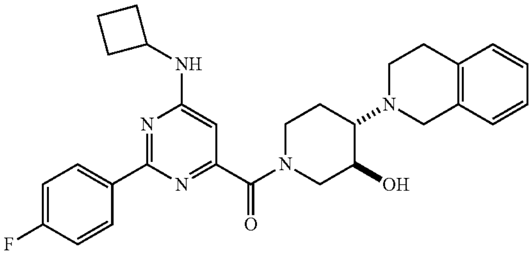 [SMILES: O=C(c1cc(NC2CCC2)nc(-c2ccc(F)cc2)n1)N1CC[C@H](N2CCc3ccccc3C2)[C@@H](O)C1] | (400 MHz, $CDCl_3$) δ 8.41-8.29 (m, 2H), 7.18-7.08 (m, 5H), 7.06-7.02 (m, 1H), 6.53-6.42 (m, 1H), 5.39 (s, 1H), 5.15-4.72 (m, 1H), 4.47-4.28 (m, 1H), 4.02-3.68 (m, 4H), 3.12-2.84 (m, 5H), 2.79-2.63 (m, 2H), 2.54-2.42 (m, 2H), 2.06-1.92 (m, 3H), 1.91-1.71 (m, 3H). | 502.35 |
| 82 | 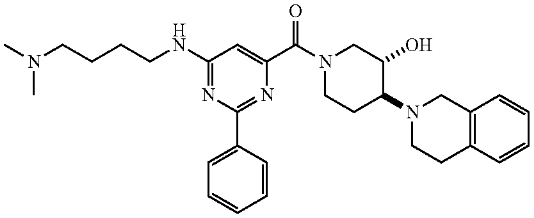 [SMILES: CN(C)CCCCNc1cc(C(=O)N2CC[C@H](N3CCc4ccccc4C3)[C@@H](O)C2)nc(-c2ccccc2)n1] | (400 MHz, $CDCl_3$) δ 8.42-8.29 (m, 2H), 7.47-7.41 (m, 3H), 7.97-7.09 (m, 3H), 7.07-7.01 (m, 1H), 6.55-6.46 (m, 1H), 6.37-6.27 (m, 1H), 5.18-4.68 (m, 1H), 4.55-4.31 (m, 1H), 4.08-3.65 (m, 4H), 3.63-3.31 (m, 2H), 3.13-2.87 (m, 5H), 2.80-2.60 (m, 2H), 2.42-2.31 (m, 2H), 2.30-2.22 (m, 6H), 2.07-1.77 (m, 2H), 1.80-1.70 (m, 2H), 1.68-1.58 (m, 2H). | 529.6 |

-continued
| Ex. | Structure | $^1$H NMR | LC-MS (ESI) [M + H]$^+$ |
|---|---|---|---|
| 83 | 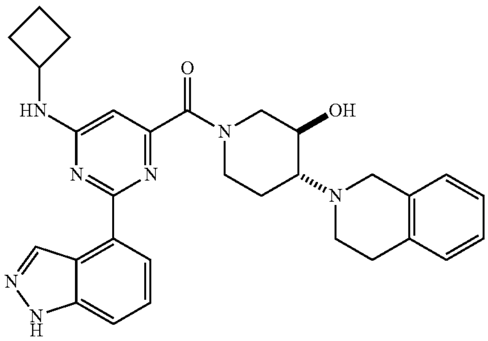 [SMILES: O=C(c1cc(NC2CCC2)nc(-c2cccc3[nH]ncc23)n1)N1CC[C@@H](N2CCc3ccccc3C2)[C@H](O)C1] | (400 MHz, DMSO-$d_6$) δ 13.21 (s, 1H), 8.82 (s, 1H), 8.18 (t, J = 8.2 Hz, 1H), 8.02 (s, 1H), 7.80-7.63 (m, 1H), 7.56-7.40 (m, 1H), 7.15-7.02 (m, 4H), 6.48 (s, 1H), 4.87 (d, J = 3.9 Hz, 0.5H), 4.67 (m, 0.5H), 4.59-4.36 (m, 1H), 3.95-3.75 (m, 3H), 3.74-3.63 (m, 1H), 3.17-2.61 (m, 8H), 2.45-2.34 (m, 2H), 2.08-1.98 (m, 2H), 1.92-1.56 (m, 4H). | 524.7 |
| 84 | 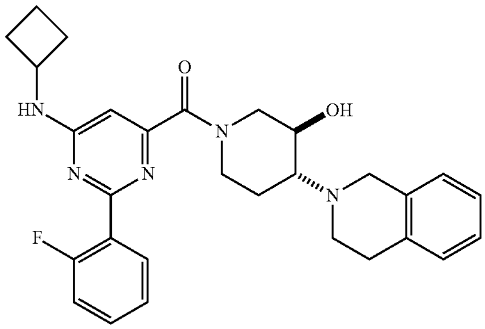 [SMILES: O=C(c1cc(NC2CCC2)nc(-c2ccccc2F)n1)N1CC[C@@H](N2CCc3ccccc3C2)[C@H](O)C1] | (400 MHz, DMSO-$d_6$) δ 8.02-7.93 (m, 2H), 7.54-7.48 (m, 1H), 7.32-7.25 (m, 2H), 7.11-7.04 (m, 4H), 6.48 (s, 1H), 4.83-4.69 (m, 1H), 4.52-4.32 (m, 1H), 3.87-3.77 (m, 3H), 3.65 (brs, 1H), 3.07-2.59 (m, 7H), 2.33-2.31 (m, 2H), 1.97 (brs, 2H), 1.88-1.67 (m, 3H), 1.58-1.52 (m, 1H). | 502.2 |
| 85 | 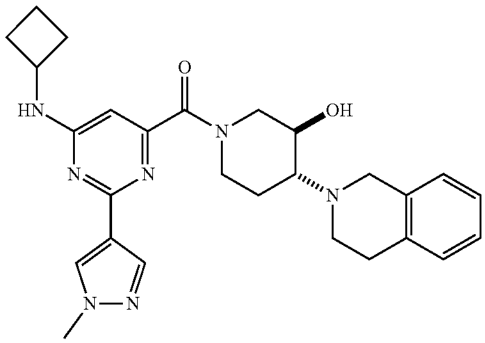 [SMILES: Cn1cc(-c2nc(NC3CCC3)cc(C(=O)N3CC[C@@H](N4CCc5ccccc5C4)[C@H](O)C3)n2)cn1] | (400 MHz, DMSO-$d_6$) δ 8.21 (d, J = 6.0 Hz, 1H), 7.89 (d, J = 11.6 Hz, 1H), 7.79 (t, J = 8.0 Hz, 1H), 7.10-7.03 (m, 4H), 6.26 (d, J = 7.6 Hz, 1H), 4.82-4.74 (m, 1H), 4.56-4.32 (m, 2H), 3.88-3.87 (m, 3H), 3.83-3.75 (m, 2H), 3.72-3.62 (m, 1H), 3.04-2.74 (m, 6H), 2.68-2.56 (m, 1H), 2.34-2.32 (m, 2H), 1.99-1.84 (m, 3H), 1.72-1.49 (m, 4H). | 488.5 |
| 86 | 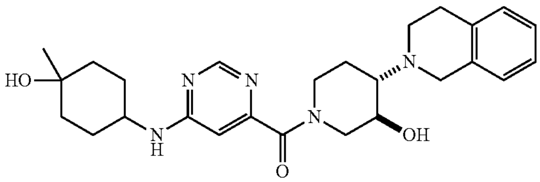 [SMILES: CC1(O)CCC(Nc2cc(C(=O)N3CC[C@H](N4CCc5ccccc5C4)[C@@H](O)C3)ncn2)CC1] | (400 MHz, $CD_3OD$) δ 8.42 (d, J = 8.0 Hz, 1H), 7.12-7.06 (m, 4H), 6.55 (d, J = 8.8 Hz, 1H), 4.73-4.53 (m, 1H), 3.97-3.82 (m, 5H), 3.12-2.98 (m, 3H), 2.92-2.87 (m, 3H), 2.78-2.73 (m, 1H), 2.05-2.01 (m, 1H), 1.91-1.55 (m, 6H), 1.58-1.52 (m, 2H), 1.35-1.31 (m, 1H), 1.24 (s, 3H). | 466.2 |
| 87 | 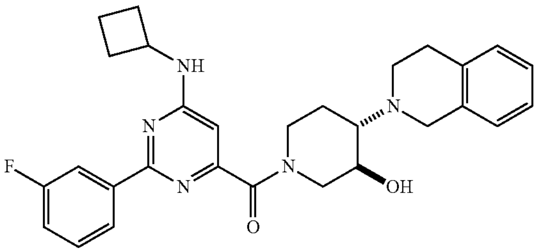 [SMILES: O=C(c1cc(NC2CCC2)nc(-c2cccc(F)c2)n1)N1CC[C@H](N2CCc3ccccc3C2)[C@@H](O)C1] | (400 MHz, $CDCl_3$) δ 8.27-7.96 (m, 2H), 7.46-7.34 (m, 1H), 7.19-7.10 (m, 4H), 7.07-7.01 (m, 1H), 6.57-6.44 (m, 1H), 5.38 (s, 1H), 5.14-4.74 (m, 1H), 4.45-4.30 (m, 1H), 4.08-3.91 (m, 1H), 3.90-3.61 (m, 3H), 3.16-2.60 (m, 7H), 2.55-2.43 (m, 2H), 2.05-1.68 (m, 6H). | 502.52 |

-continued
| Ex. | Structure | $^1$H NMR | LC-MS (ESI) [M + H]$^+$ |
|---|---|---|---|
| 88 | 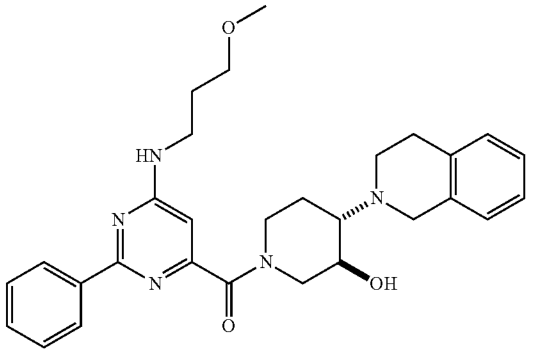 [SMILES: COCCCNc1cc(C(=O)N2CC[C@H](N3CCc4ccccc4C3)[C@@H](O)C2)nc(-c2ccccc2)n1] | (400 MHz, $CDCl_3$) δ 8.41-8.27 (m, 2H), 7.49-7.37 (m, 3H), 7.21-7.10 (m, 3H), 7.09-6.98 (m, 1H), 6.62-6.47 (m, 1H), 5.56 (s, 1H), 5.23-4.68 (m, 1H), 4.56-4.34 (m, 1H), 4.04-3.94 (m, 1H), 3.93-3.47 (m, 7H), 3.44-3.34 (m, 3H), 3.15-3.01 (m, 2H), 2.99-2.60 (m, 5H), 2.07-1.71 (m, 4H). | 502.52 |
| 89 | 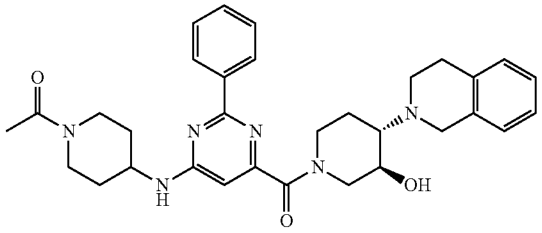 | (400 MHz, $CDCl_3$) δ 8.37-8.29 (m, 2H), 7.49-7.41 (m, 3H), 7.19-7.10 (m, 3H), 7.08-7.01 (m, 1H), 6.63-6.51 (m, 1H), 5.56-5.43 (m, 0.4H), 5.43-5.34 (m, 0.6H), 5.13-5.02 (m, 0.4H), 4.83-4.71 (m, 0.6H), 4.59-4.49 (m, 1H), 4.49-4.41 (m, 0.6H), 4.41-4.31 (m, 0.4H), 4.17 (brs, 1H), 4.04-3.91 (m, 1H), 3.86-3.68 (m, 3H), 3.31-3.17 (m, 1H), 3.16-2.99 (m, 2H), 2.98-2.61 (m, 6H), 2.23-1.98 (m, 6H), 1.95-1.65 (m, 1H), 1.54-1.36 (m, 2H). | 555.4 |
| 90 | 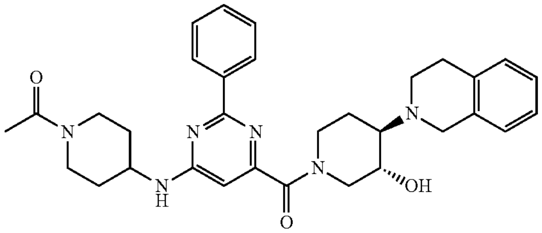 [SMILES: CC(=O)N1CCC(Nc2cc(C(=O)N3CC[C@@H](N4CCc5ccccc5C4)[C@H](O)C3)nc(-c3ccccc3)n2)CC1] | (400 MHz, $CDCl_3$) δ 8.38-8.29 (m, 2H), 7.50-7.40 (m, 3H), 7.20-7.09 (m, 3H), 7.08-7.01 (m, 1H), 6.64-6.51 (m, 1H), 5.51-5.42 (m, 0.4H), 5.40-5.33 (m, 0.6H), 5.13-5.03 (m, 0.4H), 4.83-4.71 (m, 0.6H), 4.59-4.50 (m, 1H), 4.49-4.41 (m, 0.6H), 4.40-4.34 (m, 0.4H), 4.17 (brs, 1H), 4.03-3.92 (m, 1H), 3.91-3.66 (m, 3H), 3.31-3.18 (m, 1H), 3.16-2.99 (m, 2H), 2.98-2.63 (m, 6H), 2.22-1.98 (m, 6H), 1.94-1.65 (m, 1H), 1.53-1.35 (m, 2H). | 555.4 |
| 91 | 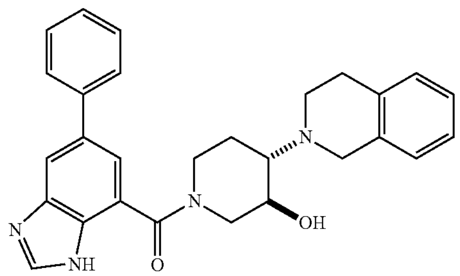 [SMILES: O=C(c1cc(-c2ccccc2)cc2nc[nH]c12)N1CC[C@H](N2CCc3ccccc3C2)[C@@H](O)C1] | (400 MHz, $CDCl_3$) δ 7.98 (s, 1H), 7.63-7.31 (m, 7H), 7.16-7.08 (m, 3H), 7.03-6.99 (m, 1H), 4.83 (s, 1H), 4.18-3.54 (m, 4H), 3.17-2.59 (m, 8H), 2.06-1.89 (m, 2H). | 453.43 |
| 92 | 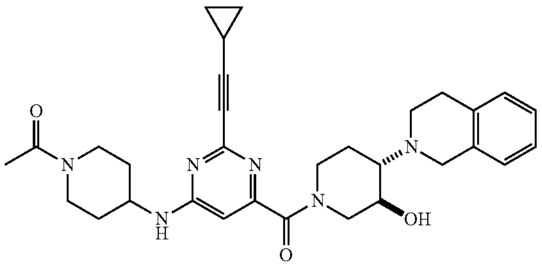 [SMILES: CC(=O)N1CCC(Nc2cc(C(=O)N3CC[C@H](N4CCc5ccccc5C4)[C@@H](O)C3)nc(C#CC3CC3)n2)CC1] | (400 MHz, DMSO-$d_6$) δ 7.78-7.63 (m, 1H), 7.11-7.00 (m, 4H), 6.63-6.41 (m, 1H), 4.83-4.74 (m, 1H), 4.45-4.22 (m, 1H), 4.10 (s, 1H), 3.86-3.72 (m, 3H), 3.61-3.57 (m, 2H), 3.20 (t, J = 11.2 Hz, 1H), 3.04-2.74 (m, 7H), 2.66-2.56 (m, 2H), 2.01 (s, 3H), 1.85-1.72 (m, 3H), 1.58-1.21 (m, 4H), 0.95-0.90 (m, 2H), 0.79 (s, 2H). | 543.6 |

-continued

| Ex. | Structure | $^1$H NMR | LC-MS (ESI) [M + H]$^+$ |
|---|---|---|---|
| 93 | 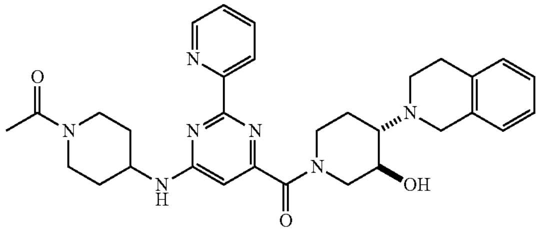 [SMILES: CC(=O)N1CCC(Nc2cc(C(=O)N3CC[C@H](N4CCc5ccccc5C4)[C@@H](O)C3)nc(-c3ccccn3)n2)CC1] | (400 MHz, DMSO-$d_6$) δ 8.71 (s, 1H), 8.27 (t, J = 8.8 Hz, 1H), 7.96-7.91 (m, 1H), 7.94 (brs, 1H), 7.51-7.47 (m, 1H), 7.11-7.03 (m, 4H), 6.75-6.58 (m, 1H), 4.86-4.78 (m, 1H), 4.51 (d, J = 5.6 Hz, 0.5H), 4.29-4.23 (m, 2H), 3.84-3.78 (m, 4H), 3.67 (brs, 1H), 3.28-3.25 (m, 1H), 3.07 (t, J = 19.6 Hz, 0.5H), 2.93-2.74 (m, 6H), 2.70-2.62 (m, 2H), 2.03 (s, 3.5H), 1.95-1.87 (m, 2H), 1.74 (d, J = 10.0 Hz, 0.5H), 1.62-1.44 (m, 2H), 1.36-1.33 (m, 1H). | 556.6 |
| 94 | 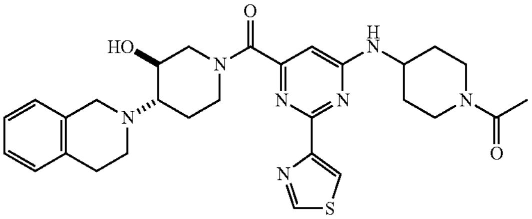 [SMILES: CC(=O)N1CCC(Nc2cc(C(=O)N3CC[C@H](N4CCc5ccccc5C4)[C@@H](O)C3)nc(-c3cscn3)n2)CC1] | (400 MHz, DMSO-$d_6$) δ 9.16 (dd, J = 6.1, 2.0 Hz, 1H), 8.42 (d, J = 9.8 Hz, 1H), 7.75 (m, 1H), 7.13-7.01 (m, 4H), 6.67-6.49 (m, 1H), 4.84-4.75 (m, 1H), 4.51-4.49 (m, 0.5H), 4.26-4.26 (m, 2.5H), 3.87-3.75 (m, 4H), 3.66 (s, 1H), 3.23 (s, 1H), 3.05 (t, J = 12.4 Hz, 0.5H), 2.96-2.75 (m, 6H), 2.69-2.60 (m, 1.5H), 2.02-1.90 (m, 5H), 1.81-1.73 (m, 1H), 1.60-1.28 (m, 3H). | 562.2 |
| 95 | 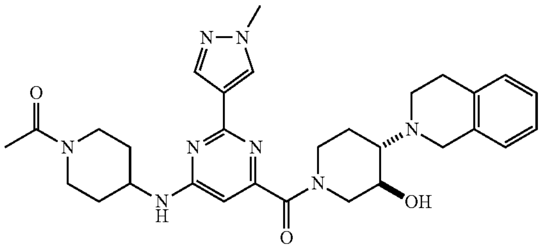 [SMILES: CC(=O)N1CCC(Nc2cc(C(=O)N3CC[C@H](N4CCc5ccccc5C4)[C@@H](O)C3)nc(-c3cnn(C)c3)n2)CC1] | (400 MHz, $CD_3OD$) δ 8.21-8.19 (m, 1H), 8.07-8.05 (m, 1H), 7.10-7.04 (m, 4H), 6.38-6.35 (m, 1H), 4.75-4.52 (m, 1H), 4.44-4.30 (m, 2H), 3.99-3.80 (m, 8H), 3.38-3.35 (m, 1H), 3.17-2.97 (m, 3H), 2.94-2.70 (m, 5H), 2.15-1.87 (m, 6H), 1.76-1.67 (m, 1H), 1.57-1.40 (m, 2H). | 559.6 |
| 96 | 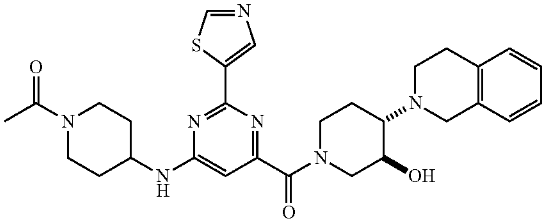 [SMILES: CC(=O)N1CCC(Nc2cc(C(=O)N3CC[C@H](N4CCc5ccccc5C4)[C@@H](O)C3)nc(-c3cncs3)n2)CC1] | (400 MHz, $CD_3OD$) δ 9.06-9.03 (m, 1H), 8.59-8.57 (m, 1H), 7.11-7.05 (m, 4H), 6.50-6.49 (m, 1H), 4.75-4.56 (m, 1H), 4.45-4.31 (m, 2H), 4.04-3.80 (m, 5H), 3.39-3.33 (m, 1H), 3.17-2.97 (m, 3H), 2.95-2.71 (m, 5H), 2.17-1.90 (m, 6H), 1.82-1.69 (m, 1H), 1.60-1.34 (m, 2H). | 562.6 |
| 97 | 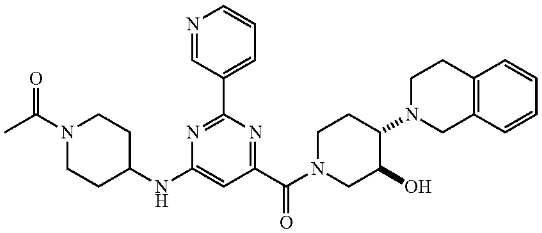 [SMILES: CC(=O)N1CCC(Nc2cc(C(=O)N3CC[C@H](N4CCc5ccccc5C4)[C@@H](O)C3)nc(-c3cccnc3)n2)CC1] | 1(400 MHz, $CD_3OD$) δ 9.48-9.45 (m, 1H), 8.76-8.71 (m, 1H), 8.64-8.61 (m, 1H), 7.60-7.51 (m, 1H), 7.11-7.06 (m, 4H), 6.59-6.55 (m, 1H), 4.78-4.52 (m, 0.5H), 4.63-4.58 (m, 1H), 4.48-4.36 (m, 2H), 4.11-4.05 (m, 0.5H), 4.02-3.79 (m, 4H), 3.40-3.31 (m, 1H) 3.20-2.95 (m, 3H), 2.87-2.69 (m, 5H), 2.19-1.93 (m, 6H), 1.81-1.66 (m, 1H), 1.61-1.43 (m, 2H). | 556.6 |
| 98 | 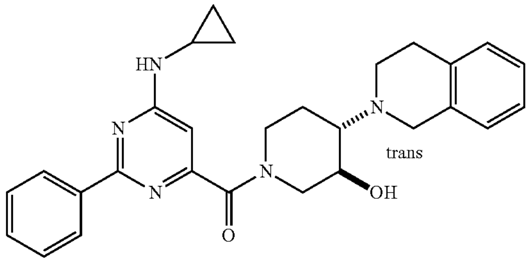 [SMILES: O=C(c1cc(NC2CC2)nc(-c2ccccc2)n1)N1CC[C@H](N2CCc3ccccc3C2)[C@@H](O)C1] | (400 MHz, $CDCl_3$) δ 8.38-8.26 (m, 2H), 7.48-7.39 (m, 3H), 7.21-7.10 (m, 3H), 7.09-7.01 (m, 1H), 6.96-6.85 (m, 1H), 5.63-5.52 (m, 1H), 5.19-4.74 (m, 1H), 4.54-4.32 (m, 1H), 4.06-3.95 (m, 1H), 3.85-3.72 (m, 2H), 3.18-3.02 (m, 2H), 2.99-2.57 (m, 6H), 2.10-1.70 (m, 2H), 0.95-0.84 (m, 2H), 0.69-0.59 (m, 2H). | 470.60 |

-continued
| Ex. | Structure | $^1H$ NMR | LC-MS (ESI) $[M + H]^+$ |
|---|---|---|---|
| 99 | 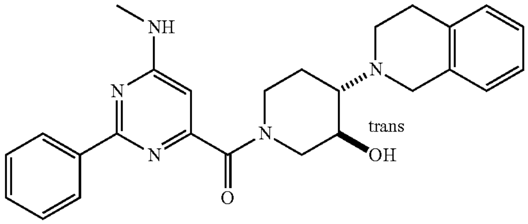 [SMILES: CNc1cc(C(=O)N2CC[C@H](N3CCc4ccccc4C3)[C@@H](O)C2)nc(-c2ccccc2)n1] | (400 MHz, $CDCl_3$) δ 8.44-8.25 (m, 2H), 7.53-7.38 (m, 3H), 7.22-7.09 (m, 3H), 7.08-7.02 (m, 1H), 6.96-6.49 (m, 1H), 5.31-4.70 (m, 2H), 4.57-4.35 (m, 1H), 4.11-4.00 (m, 1H), 3.91-3.76 (m, 2H), 3.18-3.11 (m, 1H), 3.08-3.04 (m, 3H), 3.02-2.90 (m, 3H), 2.89-2.63 (m, 2H), 2.17-1.24 (m, 4H). | 444.50 |
| 100 | 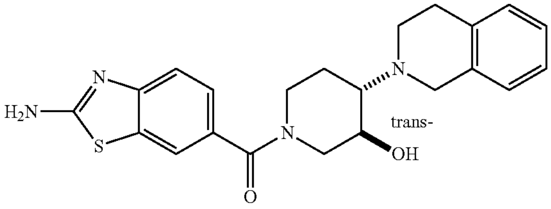 [SMILES: Nc1nc2ccc(C(=O)N3CC[C@H](N4CCc5ccccc5C4)[C@@H](O)C3)cc2s1] | (400 MHz, DMSO-$d_6$) δ 7.72 (d, 1H), 7.54 (d, J = 8.3 Hz, 1H), 7.38 (dd, J = 8.3, 1.7 Hz, 1H), 7.18-7.11 (m, 3H), 7.04-7.02 (m, 1H), 5.33 (s, 2H), 4.86-4.79 (m, 0.5H), 4.30-4.24 (m, 0.5H), 3.97 (d, J = 14.5 Hz, 1H), 3.72 (d, J = 14.1 Hz, 2H), 3.62 (s, 1H), 3.0.0-3.04 (m, 1H), 2.99-2.75 (m, 4H), 2.75-2.63 (m, 2H), 1.94-1.92 (m, 1H), 1.62 (m, 1H). | 409.4 |
| 101 | 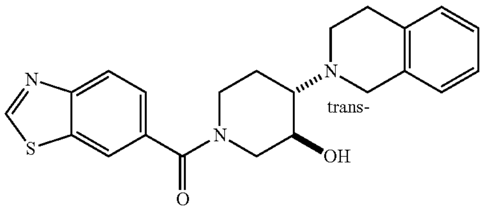 [SMILES: O=C(c1ccc2ncsc2c1)N1CC[C@H](N2CCc3ccccc3C2)[C@@H](O)C1] | (400 MHz, $CDCl_3$) δ 9.09 (s, 1H), 8.18 (d, J = 8.3 Hz, 1H), 8.08 (d, J = 1.5 Hz, 1H), 7.57 (dd, J = 8.4, 1.6 Hz, 1H), 7.19-7.10 (m, 3H), 7.06-7.01 (m, 1H), 5.21-4.85 (m, 1H), 4.22-3.89 (m, 2H), 3.80-3.50 (m, 3H), 3.12-3.02 (m, 1H), 3.01-2.62 (m, 6H), 2.13-1.79 (m, 2H). | 394.4 |
| 102 | 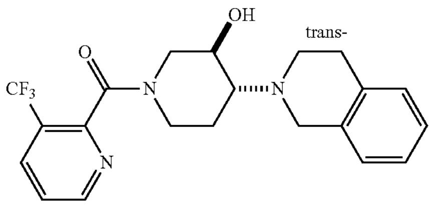 [SMILES: O=C(c1ncccc1C(F)(F)F)N1CC[C@@H](N2CCc3ccccc3C2)[C@H](O)C1] | (400 MHz, DMSO-$d_6$) δ 8.91-8.87 (m, 1H), 8.37-8.32 (m, 1H), 7.76-7.70 (m, 1H), 7.10-7.03 (m, 4H), 4.91-4.69 (m, 1H), 4.56-4.47 (m, 1H), 3.86-3.76 (m, 2H), 3.66-3.51 (m, 1H), 3.21-3.13 (m, 1H), 3.05-2.64 (m, 7H), 1.90-1.65 (m, 1H), 1.52-1.40 (m, 1H). | 406.4 |
| 103 | 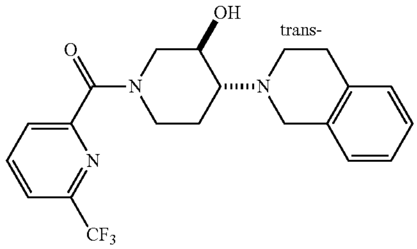 [SMILES: O=C(c1cccc(C(F)(F)F)n1)N1CC[C@@H](N2CCc3ccccc3C2)[C@H](O)C1] | (400 MHz, DMSO-$d_6$) δ 8.28-8.22 (m, 1H), 8.01 (d, J = 7.2 Hz, 1H), 7.94-7.91 (m, 1H), 7.10-7.02 (m, 4H), 4.87-4.65 (m, 1H), 4.56-4.37 (m, 1H), 3.87-3.77 (m, 2H), 3.73-3.53 (m, 2H), 3.11-2.61 (m, 7H), 1.91-1.69 (m, 1H), 1.63-1.52 (m, 1H). | 406.4 |
| 104 | 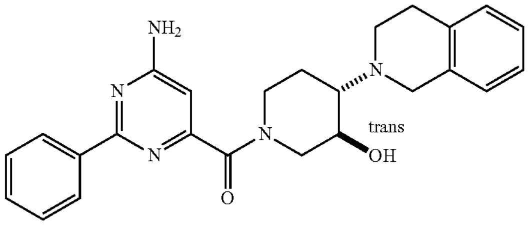 [SMILES: Nc1cc(C(=O)N2CC[C@H](N3CCc4ccccc4C3)[C@@H](O)C2)nc(-c2ccccc2)n1] | (400 MHz, $CDCl_3$) δ 8.45-8.26 (m, 2H), 7.49-7.39 (m, 3H), 7.20-7.10 (m, 3H), 7.07-7.01 (m, 1H), 6.74-6.56 (m, 1H), 5.18-4.72 (m, 3H), 4.57-4.32 (m, 1H), 4.09-3.96 (m, 1H), 3.89-3.75 (m, 2H), 3.17-3.03 (m, 2H), 3.03-2.91 (m, 2H), 2.86-2.62 (m, 2H), 2.09-1.48 (m, 4H). | 509.62 |

-continued

| Ex. | Structure | $^1$H NMR | LC-MS (ESI) [M + H]$^+$ |
|---|---|---|---|
| 105 | 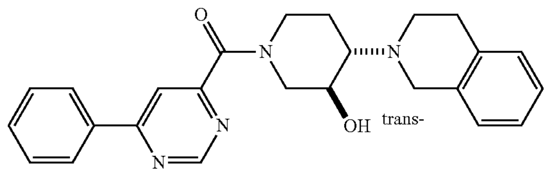 HCOOH trans- | (400 MHz, DMSO-$d_6$) δ 9.33-9.30 (m, 1H), 8.36-8.19 (m, 3H), 8.13 (s, 1H), 7.75-7.52 (m, 3H), 7.32-7.02 (m, 4H), 4.62-4.54 (m, 2H), 3.83-3.71 (m, 4H), 2.83 (m, 8H), 1.63-1.45 (m, 2H). | 415.4 |
| 106 | 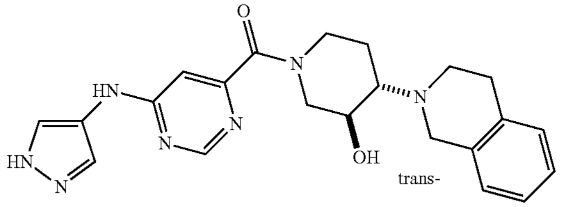 [SMILES: O=C(c1cc(Nc2cn[nH]c2)ncn1)N1CC[C@H](N2CCc3ccccc3C2)[C@@H](O)C1] trans- | (400 MHz, $CD_3OD$) δ 8.61-8.59 (m, 1H), 8.04-7.22 (m, 2H), 7.08-7.03 (m, 4H), 6.75-6.73 (m, 1H), 4.72-4.51 (m, 1H), 3.95-3.75 (m, 4H), 3.15-2.70 (m, 7H), 2.03-1.86 (m, 1H), 1.72-1.63 (m, 1H). | 420.4 |
| 107 | 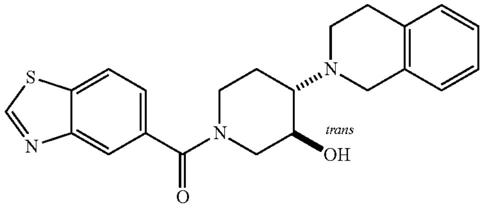 [SMILES: O=C(c1ccc2scnc2c1)N1CC[C@H](N2CCc3ccccc3C2)[C@@H](O)C1] *trans* | (400 MHz, $CDCl_3$) δ 9.08 (s, 1H), 8.19 (s, 1H), 8.08-7.99 (m, 1H), 7.59-7.48 (m, 1H), 7.19-7.11 (m, 3H), 7.09-7.02 (m, 1H), 5.27-4.75 (m, 1H), 4.21-3.95 (m, 2H), 3.82-3.57 (m, 3H), 3.13-3.05 (m, 1H), 3.01-2.89 (m, 3H), 2.85-2.65 (m, 3H), 2.16-1.76 (m, 2H). | 394.35 |
| 108 | 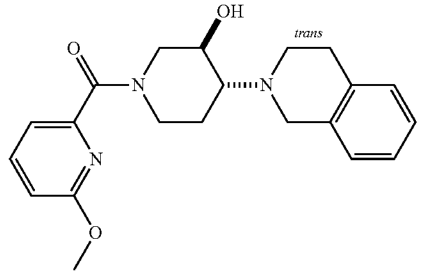 [SMILES: COc1cccc(C(=O)N2CC[C@@H](N3CCc4ccccc4C3)[C@H](O)C2)n1] *trans* | (400 MHz, DMSO-$d_6$) δ 7.85-7.80 (m, 1H), 7.19-7.16 (m, 1H), 7.10-7.03 (m, 4H), 6.92 (t, J = 8.0 Hz, 1H), 4.83-4.68 (m, 1H), 4.57-4.41 (m, 1H), 3.87 (d, J = 12.4 Hz, 3H), 3.84-3.82 (m, 2H), 3.75-3.64 (m, 1H), 3.06-2.77 (m, 6H), 2.69-2.59 (m, 2H), 1.88-1.73 (m, 1H), 1.59-1.52 (m, 1H). | 368.2 |
| 109 | 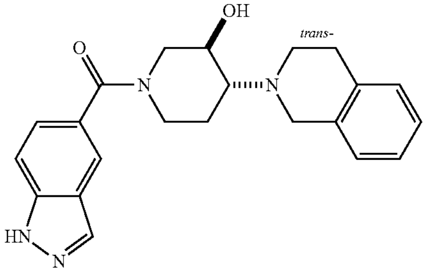 [SMILES: O=C(c1ccc2[nH]ncc2c1)N1CC[C@@H](N2CCc3ccccc3C2)[C@H](O)C1] *trans-* | (400 MHz, DMSO-$d_6$) δ 13.24 (s, 1H), 8.16 (s, 1H), 7.87 (s, 1H), 7.59 (d, J = 8.4 Hz, 1H), 7.40 (dd, J = 8.4 Hz, 1.2 Hz, 1H), 8.28-8.12 (m, 1H), 7.10-7.02 (m, 4H), 4.78-4.31 (m, 2H), 3.88-3.79 (m, 2H), 3.71-3.61 (m, 1H), 2.94-2.92 (m, 2H), 2.85-2.75 (m, 4H), 2.68-2.60 (m, 2H), 1.91-1.70 (m, 1H), 1.59-1.47 (m, 1H). | 377.4 |
| 110 | 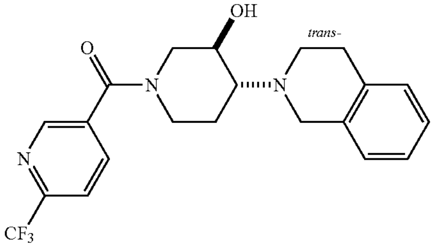 [SMILES: O=C(c1ccc(C(F)(F)F)nc1)N1CC[C@@H](N2CCc3ccccc3C2)[C@H](O)C1] *trans-* | (400 MHz, DMSO-$d_6$) δ 8.84 (d, J = 6.8 Hz, 1H), 8.19-8.16 (m, 1H), 8.01 (t, J = 8.4 Hz, 1H), 7.10-7.02 (m, 4H), 4.87-4.74 (m, 1H), 4.54-4.28 (m, 1H), 3.83 (s, 2H), 3.75-3.70 (m, 1H), 3.51-3.43 (m, 1H), 3.13-2.63 (m, 7H), 1.89-1.56 (m, 2H). | 406.3 |

-continued

| Ex. | Structure | $^1$H NMR | LC-MS (ESI) $[M + H]^+$ |
|---|---|---|---|
| 111 | 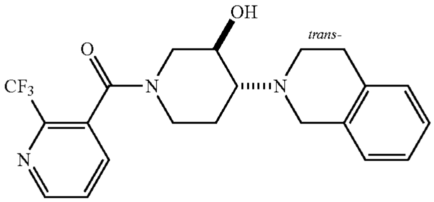 [SMILES: O=C(c1cccnc1C(F)(F)F)N1CC[C@@H](N2CCc3ccccc3C2)[C@H](O)C1] | (400 MHz, DMSO-$d_6$) δ 8.85-8.81 (m, 1H), 8.19-8.00 (m, 1H), 7.87-7.79 (m, 1H), 7.10-7.01 (m, 4H), 4.93-4.65 (m, 1H), 4.56-4.30 (m, 1H), 3.88-3.80 (m, 2H), 3.75-3.50 (m, 1H), 3.28-2.58 (m, 8H), 1.91-1.32 (m, 2H). | 406.3 |
| 112 | 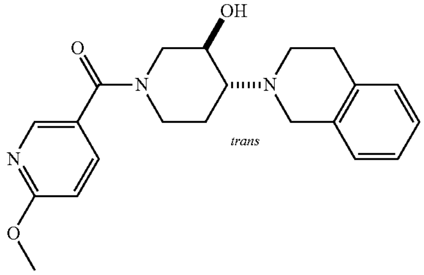 [SMILES: COc1ccc(C(=O)N2CC[C@@H](N3CCc4ccccc4C3)[C@H](O)C2)cn1] | (400 MHz, DMSO-$d_6$) δ 8.28 (d, J = 1.6 Hz, 1H), 7.78 (dd, J = 2.4 Hz, 8.8 Hz, 1H), 7.11-7.02 (m, 4H), 6.88 (d, J = 8.8 Hz, 1H), 4.76 (brs, 1H), 4.55-4.29 (m, 1H), 3.91 (s, 3H), 3.87-3.79 (m, 2H), 3.71-3.64 (m, 2H), 3.09-2.76 (m, 6H), 2.66-2.60 (m, 1H), 1.80 (s, 1H), 1.59-1.54 (m, 1H). | 368.2 |
| 113 | 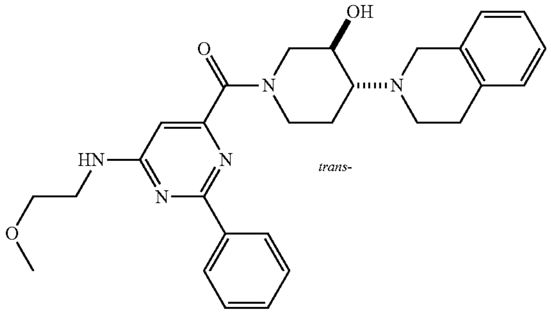 [SMILES: COCCNc1cc(C(=O)N2CC[C@@H](N3CCc4ccccc4C3)[C@H](O)C2)nc(-c2ccccc2)n1] | (400 MHz, DMSO-$d_6$) δ 8.34 8.31 (m, 2H), 7.80 (s, 1H), 7.50-7.48 (m, 3H), 7.11-7.06 (m, 4H), 6.55 (d, J = 4 Hz, 1H), 4.85-4.71 (m, 1H), 4.54-4.37 (m, 1H), 3.89-3.79 (m, 3H), 3.67 (brs, 3H), 3.56 (d, J = 4.4 Hz, 2H), 3.31 (d, J = 4.4 Hz, 3H), 3.07 (t, J = 12.4 Hz, 0.5H), 2.95-2.78 (m, 5H), 2.71-2.62 (m, 1.5H), 1.89-1.75 (m, 1H), 1.60-1.54 (m, 1H). | 488.7 |
| 114 | 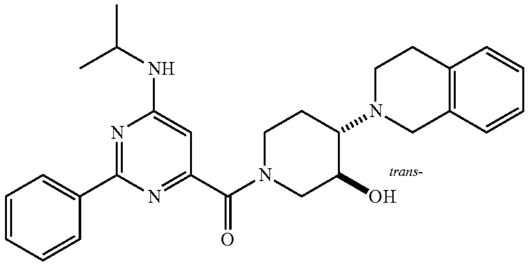 [SMILES: CC(C)Nc1cc(C(=O)N2CC[C@H](N3CCc4ccccc4C3)[C@@H](O)C2)nc(-c2ccccc2)n1] | (400 MHz, $CDCl_3$) δ 8.39-8.29 (m, 2H), 7.48-7.40 (m, 3H), 7.18-7.09 (m, 3H), 7.07-7.01 (m, 1H), 6.57-6.49 (m, 1H), 5.22-5.03 (m, 1H), 4.81-4.33 (m, 2H), 3.99-3.93 (m, 1H), 3.91-3.68 (m, 3H), 3.12-3.00 (m, 2H), 2.97-2.85 (m, 2H), 2.76-2.64 (m, 2H), 2.08-1.66 (m, 3H), 1.35-1.24 (m 6H). | 472.5 |
| 115 | 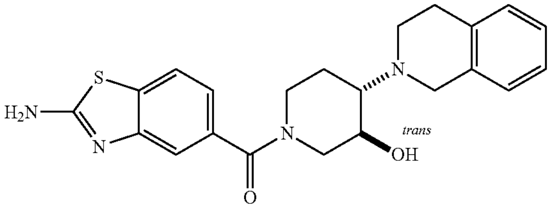 [SMILES: Nc1nc2cc(C(=O)N3CC[C@H](N4CCc5ccccc5C4)[C@@H](O)C3)ccc2s1] | (400 MHz, DMSO-$d_6$) δ 7.72 (d, J = 7.7 Hz, 1H), 7.60 (s, 2H), 7.32 (s, 1H), 7.14-7.06 (m, 3H), 7.06-6.98 (m, 2H), 4.70 (s, 1H), 4.62-4.26 (m, 1H), 3.91-3.78 (m, 2H), 3.77-3.51 (m, 2H), 2.98-2.56 (m, 7H), 1.92-1.62 (m, 1H), 1.62-1.39 (m, 1H). | 409.4 |
| 116 | 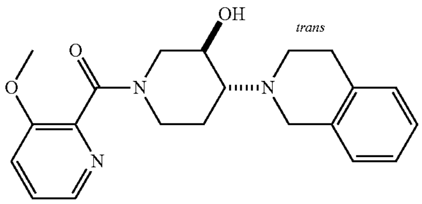 [SMILES: COc1cccnc1C(=O)N1CC[C@@H](N2CCc3ccccc3C2)[C@H](O)C1] | (400 MHz, DMSO-$d_6$) δ 8.18-8.14 (m, 1H), 7.58 (t, J = 8.8 Hz, 1H), 7.47-7.42 (m, 1H), 7.11-7.05 (m, 4H), 4.84-4.65 (m, 1H), 4.59-4.48 (m, 1H), 3.86-3.78 (m, 5H), 3.63-3.52 (m, 1H), 3.26-3.14 (m, 1H), 3.0-2.91 (m, 1H), 2.82-2.55 (m, 6H), 1.87-1.65 (m, 1H), 1.50-1.41 (m, 1H). | 368.5 |

-continued
| Ex. | Structure | $^1$H NMR | LC-MS (ESI) [M + H]$^+$ |
| --- | --- | --- | --- |
| 117 | 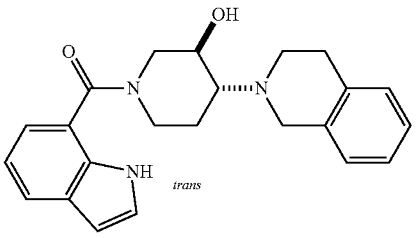 [SMILES: O=C(c1cccc2cc[nH]c12)N1CC[C@@H](N2CCc3ccccc3C2)[C@H](O)C1] | (400 MHz, DMSO-$d_6$) δ 11.09 (s, 1H), 7.64 (d, J = 7.6 Hz, 1H), 7.37 (t, J = 2.8 Hz, 1H), 7.12-7.02 (m, 6H), 6.50 (t, J = 2.0 Hz, 1H), 4.70-4.50 (m, 2H), 3.87-3.64 (m, 4H), 2.95-2.88 (m, 2H), 2.83-2.74 (m, 4H), 2.66-2.60 (m, 1H), 1.77-1.59 (m, 2H). | 376.2 |
| 118 | 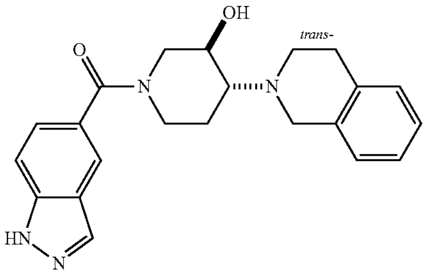 [SMILES: O=C(c1ccc2[nH]ncc2c1)N1CC[C@@H](N2CCc3ccccc3C2)[C@H](O)C1] | (400 MHz, DMSO-$d_6$) δ 12.61 (s, 1H), 8.31 (s, 1H), 7.74-7.56 (m, 2H), 7.33-7.22 (m, 1H), 7.15-6.98 (m, 4H), 4.84-4.35 (m, 2H), 3.89-3.78 (m, 2H), 3.66 (s, 2H), 3.05-2.89 (m, 2H), 2.88-2.71 (m, 4H), 2.69-2.59 (m, 1H), 1.92-1.65 (m, 1H), 1.64-1.42 (m, 1H). | 377.2 |
| 119 | 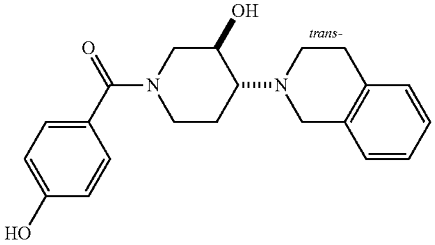 [SMILES: O=C(c1ccc(O)cc1)N1CC[C@@H](N2CCc3ccccc3C2)[C@H](O)C1] | (400 MHz, DMSO-$d_6$) δ 9.84 (s, 1H), 7.34-7.23 (m, 2H), 7.14-6.94 (m, 4H), 6.88-6.69 (m, 2H), 4.70 (s, 1H), 3.90-3.73 (m, 2.4H), 3.68-3.51 (m, 1H), 3.40-3.351 (m, 2H), 3.01-2.84 (m, 2.6H), 2.84-2.68 (m, 3.7H), 2.68-2.54 (m, 1.3H), 1.87-1.67 (m, 1H), 1.59-1.42 (m, 1H). | 353.2 |
| 120 | 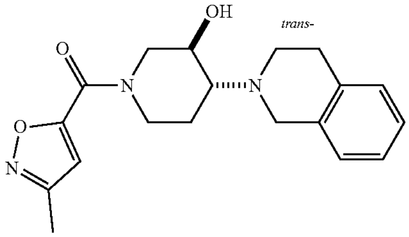 [SMILES: Cc1cc(C(=O)N2CC[C@@H](N3CCc4ccccc4C3)[C@H](O)C2)on1] | (400 MHz, DMSO-$d_6$) δ 7.14-7.06 (m, 3H), 7.06-6.98 (m, 1H), 6.79 (s, 1H), 4.96-4.80 (m, 1H), 4.47-4.16 (m, 1H), 3.91-3.76 (m, 3H), 3.76-3.57 (m, 1H), 3.24-3.01 (m, 1H), 3.00-2.86 (m, 1.5H), 2.86-2.74 (m, 3H), 2.74-2.58 (m, 1.5H), 2.36-2.25 (m, 3H), 1.95-1.72 (m, 1H), 1.63-1.45 (m, 1H). | 342.2 |
| 121 | 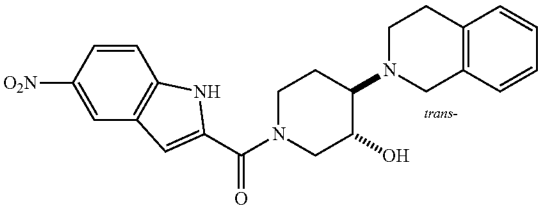 [SMILES: O=C(c1cc2cc([N+](=O)[O-])ccc2[nH]1)N1CC[C@@H](N2CCc3ccccc3C2)[C@H](O)C1] | (400 MHz, DMSO-$d_6$) δ 12.33 (s, 1H), 8.66 (d, J = 2.3 Hz, 1H), 8.13-7.96 (m, 1H), 7.59 (d, J = 9.1 Hz, 1H), 7.21-6.96 (m, 5H), 4.87 (s, 1H), 4.63-4.22 (m, 2H), 3.92-3.78 (m, 2H), 3.72 (s, 1H), 3.16 (s, 1H), 2.97-2.89 (m, 1.5H), 2.89-2.77 (m, 3H), 2.77-2.62 (m, 1.5H), 1.96-1.81 (m, 1H), 1.72-1.51 (m, 1H). | 421.2 |
| 122 | 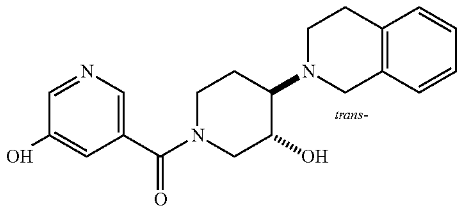 [SMILES: O=C(c1cncc(O)c1)N1CC[C@@H](N2CCc3ccccc3C2)[C@H](O)C1] | (400 MHz, DMSO-$d_6$) δ 10.20 (s, 1H), 8.19 (d, J = 2.8 Hz, 1H), 8.07 (s, 1H), 7.16 (s, 1H), 7.14-6.97 (m, 4H), 4.94-4.63 (m, 1H), 4.62-4.23 (m, 1H), 3.92-3.74 (m, 2H), 3.73-3.52 (m, 2H), 2.98-2.85 (m, 2H), 2.86-2.71 (m, 3.5H), 2.70-2.55 (m, 1.5H), 1.92-1.64 (m, 1H), 1.63-1.41 (m, 1H). | 354.2 |

-continued
| Ex. | Structure | $^1$H NMR | LC-MS (ESI) [M + H]$^+$ |
|---|---|---|---|
| 123 | 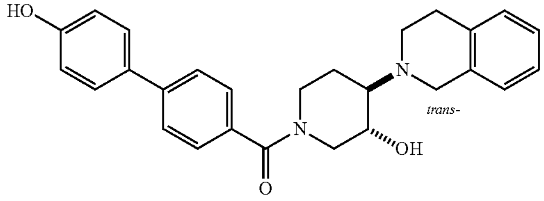 [SMILES: O=C(c1ccc(-c2ccc(O)cc2)cc1)N1CC[C@@H](N2CCc3ccccc3C2)[C@H](O)C1] | (400 MHz, DMSO-$d_6$) δ 9.64 (s, 1H), 7.70-7.59 (m, 2H), 7.59-7.49 (m, 2H), 7.49-7.40 (m, 2H), 7.14-6.97 (m, 4H), 6.92-6.81 (m, 2H), 4.90-4.64 (m, 1H), 4.64-4.27 (m, 1H), 3.93-3.76 (m, 2H), 3.76-3.54 (m, 2H), 3.13-2.88 (m, 2H), 2.87-2.72 (m, 3.5H), 2.72-2.56 (m, 1.5H), 1.96-1.65 (m, 1H), 1.64-1.39 (m, 1H). | 429.2 |
| 124 | 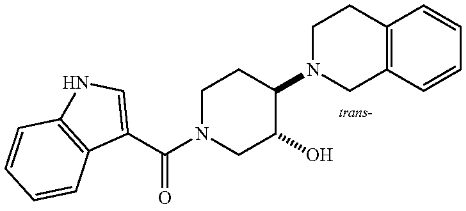 [SMILES: O=C(c1c[nH]c2ccccc12)N1CC[C@@H](N2CCc3ccccc3C2)[C@H](O)C1] | (400 MHz, DMSO-$d_6$) δ 11.51 (s, 1H), 7.79-7.70 (m, 1H), 7.68-7.59 (m, 1H), 7.52-7.38 (m, 1H), 7.22-6.97 (m, 6H), 4.75-4.62 (m, 1H), 4.45-4.16 (m, 2H), 3.90-3.73 (m, 2H), 3.71-3.55 (m, 1H), 3.07-2.88 (m, 2H), 2.88-2.69 (m, 4H), 2.69-2.59 (m, 1H), 1.87-1.72 (m, 1H), 1.62-1.42 (m, 1H). | 376.2 |
| 125 | 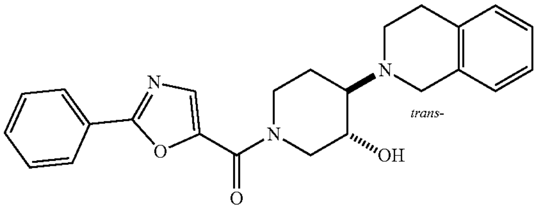 [SMILES: O=C(c1cnc(-c2ccccc2)o1)N1CC[C@@H](N2CCc3ccccc3C2)[C@H](O)C1] | (400 MHz, DMSO-$d_6$) δ 8.07-8.01 (m, 2H), 7.85 (s, 1H), 7.69-7.50 (m, 3H), 7.19-6.99 (m, 4H), 4.89 (d, J = 3.8 Hz, 1H), 4.50-4.22 (m, 2H), 4.00-3.58 (m, 3H), 3.18-2.94 (m, 1H), 2.92-2.61 (m, 6H), 1.92-1.78 (m, 1H), 1.69-1.55 (m, 1H). | 404.2 |
| 126 | 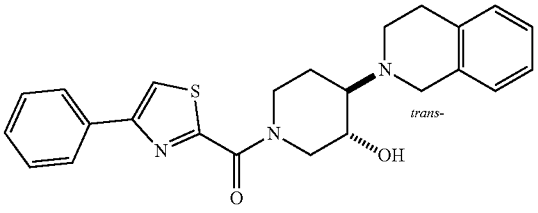 [SMILES: O=C(c1nc(-c2ccccc2)cs1)N1CC[C@@H](N2CCc3ccccc3C2)[C@H](O)C1] | (400 MHz, DMSO-$d_6$) δ 8.42 (s, 1H), 8.01-7.95 (m, 2H), 7.60-7.47 (m, 2H), 7.45-7.39 (m, 1H), 7.22-6.97 (m, 4H), 5.40-5.34 (m, 1H), 4.87 (dd, J = 17.0, 3.8 Hz, 1H), 4.53-4.38 (m, 1H), 4.01-3.60 (m, 3H), 3.27-2.99 (m, 1H), 2.98-2.64 (m, 6H), 1.92-1.89 (m, 1H), 1.73-1.44 (m, 1H). | 420.2 |
| 127 | 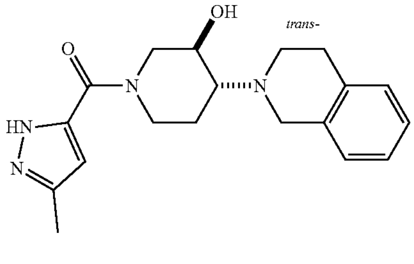 [SMILES: Cc1cc(C(=O)N2CC[C@@H](N3CCc4ccccc4C3)[C@H](O)C2)[nH]n1] | (400 MHz, DMSO-$d_6$) δ 12.82 (s, 1H), 7.10-7.02 (m, 4H), 6.29 (s, 1H), 4.74-4.65 (m, 2H), 4.57-4.44 (m, 1H), 3.86-3.76 (m, 2H), 3.58 (s, 1H), 3.05-2.74 (m, 6H), 2.68-2.63 (m, 1H), 2.25 (s, 3H), 1.84-1.75 (m, 1H), 1.50-1.45 (m, 1H). | 341.2 |
| 128 | 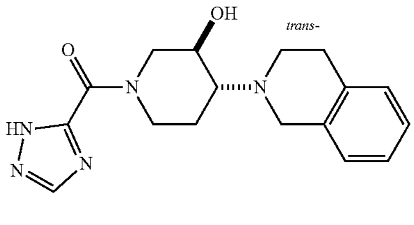 [SMILES: O=C(c1ncn[nH]1)N1CC[C@@H](N2CCc3ccccc3C2)[C@H](O)C1] | (400 MHz, DMSO-$d_6$) δ 8.47 (d, J = 8.4 Hz, 1H), 7.11-7.07 (m, 4H), 4.83-4.65 (m, 1H), 4.59-4.50 (m, 1H), 4.00-3.81 (m, 3H), 3.21-2.80 (m, 6H), 2.80-2.74 (m, 1H), 2.08-1.94 (m, 1H), 1.73-1.67 (m, 1H). | 329.4 |

-continued
| Ex. | Structure | $^1$H NMR | LC-MS (ESI) [M + H]$^+$ |
|---|---|---|---|
| 129 | 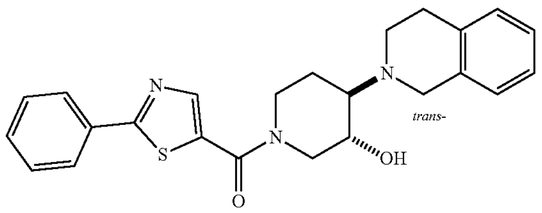 [SMILES: O=C(c1cnc(-c2ccccc2)s1)N1CC[C@@H](N2CCc3ccccc3C2)[C@H](O)C1] | (400 MHz, DMSO-$d_6$) δ 8.20 (s, 1H), 8.03-7.95 (m, 2H), 7.62-7.47 (m, 3H), 7.19-6.94 (m, 4H), 4.87 (d, J = 3.9 Hz, 1H), 4.47-4.05 (m, 2H), 3.97-3.80 (m, 2H), 3.76-3.65 (m, 1H), 3.15-3.02 (m, 1H), 3.01-2.77 (m, 5H), 2.72-2.61 (m, 1H), 1.84 (d, J = 11.3 Hz, 1H), 1.90-1.54 (m, 1H). | 420.2 |
| 130 | 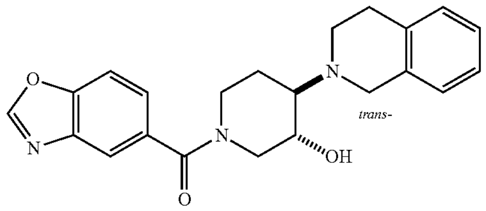 [SMILES: O=C(c1ccc2ocnc2c1)N1CC[C@@H](N2CCc3ccccc3C2)[C@H](O)C1] | (400MHz, DMSO-$d_6$) δ 8.85 (s, 1H), 8.07-7.71 (m, 2H), 7.50 (d, J = 8.4 Hz, 1H), 7.26-6.94 (m, 4H), 4.85-4.32 (m, 2H), 3.93-3.77 (m, 2H), 3.75-3.48 (m, 2H), 3.15-2.71 (m, 6H), 2.68-2.58 (m, 1H), 1.91-1.26 (m, 2H). | 378.4 |
| 131 | 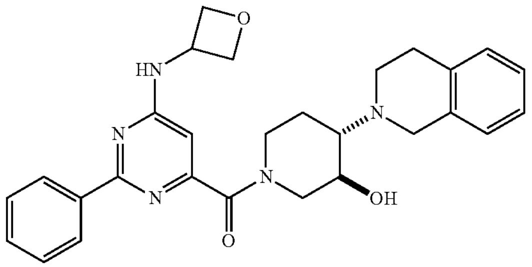 [SMILES: O=C(c1cc(NC2COC2)nc(-c2ccccc2)n1)N1CC[C@H](N2CCc3ccccc3C2)[C@@H](O)C1] | (400 MHz, $CDCl_3$) δ 8.39-8.29 (m, 2H), 7.56-7.38 (m, 3H), 7.20-7.10 (m, 3H), 7.08-6.99 (m, 1H), 6.66-6.53 (m, 1H), 5.67-5.49 (m, 1H), 5.21 (s, 1H), 5.10-5.02 (m, 2H), 4.84-4.56 (m, 3H), 4.52-4.34 (m, 1H), 4.09-3.96 (m, 1H), 3.81 (s, 2H), 3.24-2.63 (m, 7H), 2.08-1.88 (m, 1H), 1.85-1.70 (m, 1H). | 486.50 |
| 132 | 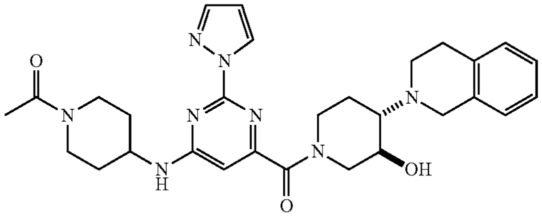 [SMILES: CC(=O)N1CCC(Nc2cc(C(=O)N3CC[C@H](N4CCc5ccccc5C4)[C@@H](O)C3)nc(-n3cccn3)n2)CC1] | (400 MHz, DMSO-$d_6$) δ 8.58-8.56 (m, 1H), 8.02-7.99 (m, 1H), 7.95-7.78 (m, 1H), 7.75-6.89 (m, 4H), 6.82-6.36 (m, 2H), 4.85-4.73 (m, 1H), 4.50-5.23 (m, 3H), 3.97-3.73 (m, 4H), 3.66-3.63 (m, 1H), 3.30-3.19 (m, 1H), 3.12-2.89 (m, 3H), 2.87-2.78 (m, 3H), 2.75-2.58 (m, 2H), 2.02 (s, 3H), 1.96-1.82 (m, 2H), 1.57-1.23 (m, 4H). | 545.3 |
| 133 | 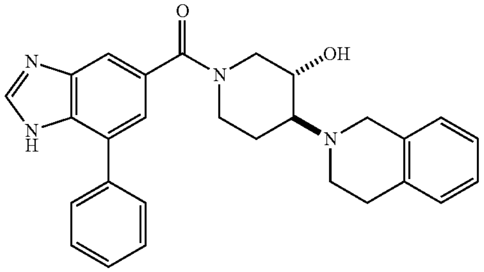 [SMILES: O=C(c1cc(-c2ccccc2)c2[nH]cnc2c1)N1CC[C@H](N2CCc3ccccc3C2)[C@@H](O)C1] | (400 MHz, $CD_3OD$) δ 9.06 (s, 1H), 7.91 (d, J = 1.4 Hz, 1H), 7.77-7.70 (m, 2H), 7.64 (d, J = 1.4 Hz, 1H), 7.63-7.55 (m, 2H), 7.56-7.48 (m, 1H), 7.34-7.23 (m, 3H), 7.25-7.18 (m, 1H), 4.72-4.46 (m, 3H), 4.21-3.93 (m, 2H), 3.85-3.52 (m, 3H), 3.26-2.79 (m, 4H), 2.33-2.09 (m, 1H), 1.94 (s, 1H). | 453.6 |

-continued
| Ex. | Structure | $^1H$ NMR | LC-MS (ESI) [M + H]$^+$ |
| --- | --- | --- | --- |
| 134 | 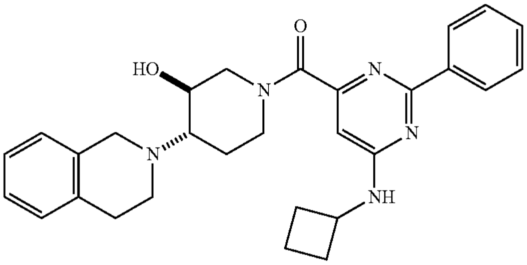 [SMILES: O=C(c1cc(NC2CCC2)nc(-c2ccccc2)n1)N1CC[C@H](N2CCc3ccccc3C2)[C@@H](O)C1] | (400 MHz, $CDCl_3$) δ 8.41-8.28 (m, 2H), 7.47-7.42 (m, 3H), 7.17-7.09 (m, 3H), 7.06-7.01 (m, 1H), 6.54-6.43 (m, 1H), 5.50 (s, 1H), 5.16-4.69 (m, 1H), 4.50-4.32 (m, 1H), 4.04-3.66 (m, 4H), 3.19-2.99 (m, 2H), 2.97-2.84 (m, 2H), 2.78-2.62 (m, 2H), 2.53-2.37 (m, 2H), 2.08-1.90 (m, 3H), 1.88-1.65 (m, 5H). | 484.5 |
| 135 | 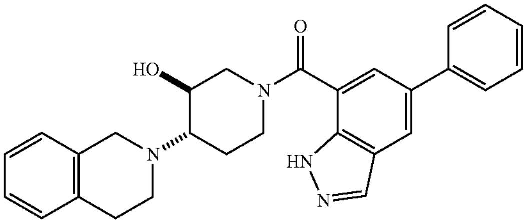 [SMILES: O=C(c1cc(-c2ccccc2)cc2cn[nH]c12)N1CC[C@H](N2CCc3ccccc3C2)[C@@H](O)C1] | (400 MHz, DMSO-$d_6$) δ 13.32 (s, 1H), 8.22 (s, 1H), 8.13 (s, 1H), 7.74 (d, J = 7.2 Hz, 2H), 7.68 (s, 1H), 7.49 (t, J = 7.6 Hz, 2H), 7.37 (t, J = 7.2 Hz, 1H), 7.10-7.08 (m, 3H), 7.05-7.01 (m, 1H), 4.81-4.45 (m, 2H), 3.83 (s, 3H), 3.60-3.57 (m, 1H), 2.95-2.60 (m, 7H), 1.87-1.45 (m, 2H). | 453.5 |
| 136 | 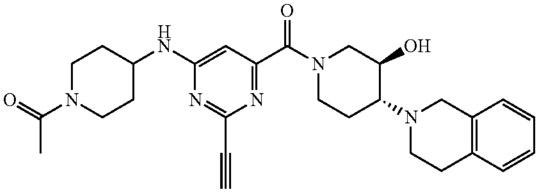 [SMILES: C#Cc1nc(NC2CCN(C(C)=O)CC2)cc(C(=O)N2CC[C@@H](N3CCc4ccccc4C3)[C@H](O)C2)n1] | (400 MHz, DMSO-$d_6$) δ 7.97-7.72 (m, 1H), 7.12-6.99 (m, 4H), 6.75-6.47 (m, 1H), 4.79 (d, J = 35.6 Hz, 1H), 4.50-4.17 (m, 2H), 4.16-4.01 (m, 2H), 3.90-3.73 (m, 3H), 3.72-3.53 (m, 2H), 3.70-3.51 (m, 1H), 3.07-2.85 (m, 2H), 2.85-2.73 (m, 4H), 2.68-2.55 (m, 2H), 2.01 (s, 3H), 1.95-1.70 (m, 3H), 1.57-1.32 (m, 2H), 1.28-1.17 (m, 1H). | 504.4 |
| 137 | 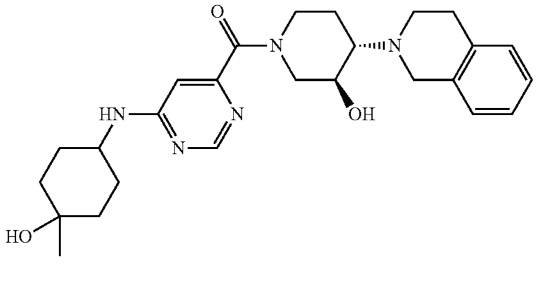 [SMILES: CC1(O)CCC(Nc2cc(C(=O)N3CC[C@H](N4CCc5ccccc5C4)[C@@H](O)C3)ncn2)CC1] | (400 MHz, MeOD-$d_4$) δ 8.44 (d, J = 8.8 Hz, 1H), 7.12-7.06 (m, 4H), 6.58 (d, J = 9.3 Hz, 1H), 4.72-4.51 (m, 1H), 3.94-3.80 (m, 5H), 3.06-2.98 (m, 3H), 2.96-2.88 (m, 3H), 2.78-2.73 (m, 1H), 2.03-1.98 (m, 3H), 1.75-1.71 (m, 5H), 1.53-1.50 (m, 2H), 1.28 (s, 3H). | 466.5 |
| 138 | 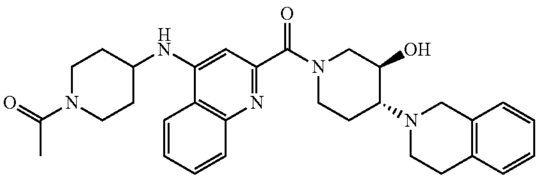 [SMILES: CC(=O)N1CCC(Nc2cc(C(=O)N3CC[C@@H](N4CCc5ccccc5C4)[C@H](O)C3)nc3ccccc23)CC1] | (400 MHz, DMSO-$d_6$) δ 8.01-7.93 (m, 1H), 7.74-7.66 (m, 2H), 7.52-7.47 (m, 1H), 7.16-7.10 (m, 3H), 7.05-7.03 (m, 1H), 6.81-6.78 (m, 1H), 5.16-5.12 (m, 0.3H), 5.06-5.01 (m, 1H), 4.67-4.61 (m, 1.7H), 4.39-4.32 (m, 1H), 3.98-3.72 (m, 5H), 3.29-3.02 (m, 4H), 2.93-2.83 (m, 3H), 2.76-2.67 (m, 2H), 2.280-2.25 (m, 1H), 2.20-2.17 (m, 1H), 2.14 (s, 3H), 2.11-2.0.6 (m, 1H), 2.83-1.74 (m, 1H), 1.58-1.49 (m, 2H). | 528.2 |

Example 139: Preparation of trans-1-(3-((6-((3S,4S)-4-(3,4-dihydroisoquinoline-2(1H)-yl)-3-hydroxypiperidine-1-carbonyl)pyrimidine-4-yl)amino)phenyl)pyrrolidine-2-one Step 1: Preparation of 1-(3-nitrophenyl)pyrrolidine-2-one

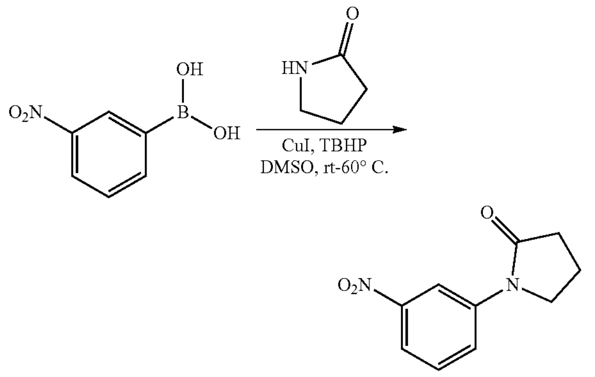

(3-nitrophenyl)boronic acid (2.0 g, 18.6 mmol, 1.0 equiv) was added to dimethyl sulfoxide (20 mL). Then 2-pyrrolidinone (4.74 g, 55.8 mmol, 3 equiv), and copper(I) iodide (178 mg, 0.93 mmol, 0.05 equiv) were added. The resulting mixture was stirred at room temperature for 10 minutes. Then 70% aqueous tert-butyl hydroperoxide solution (2.63 g, 20.46 mmol, 1.1 equiv) was added. The resulting mixture was stirred at room temperature for 10 minutes. Then the reaction solution was stirred at 60° C. for 4 hours. After the completion of the reaction was detected with LC-MC, the reaction system was cooled to room temperature 28° C. Water (100 mL) was added. The resulting mixture was extracted with ethyl acetate (40 mL×3) three times. The organic phases were combined, washed with saturated brine (50 mL), dried over anhydrous sodium sulfate for 10 minutes, filtered, and concentrated to obtain a crude product, which was separated and purified with flash chromatography (silica gel, petroleum ether/ethyl acetate (V/V=4/1) to produce the title compound (800 mg, yield: 20.87%).

LC-MS (ESI) $[M+H]^+$=207.1; $^1$H NMR (400 MHz, MeOD) δ 8.72 (t, J=2.4 Hz, 1H), 7.97 (t, J=8.0 Hz, 2H), 7.68 (t, J=8.0 Hz, 1H), 3.92 (t, J=6.8 Hz, 2H), 2.57 (t, J=8 Hz, 2H), 2.12-2.08 (m, 2H).

Step 2: Preparation of 1-(3-aminophenyl)pyrrolidine-2-one

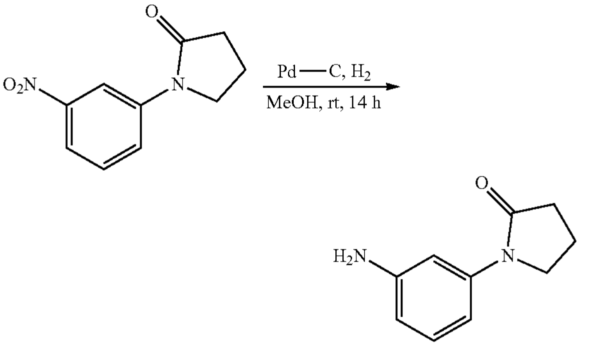

At 28° C., 1-(3-nitrophenyl)pyrrolidine-2-one (600 mg, 2.91 mmol, 1.0 equiv.) was added to methanol (20 mL). Then Pd/C (10%)(50 mg) was added. The resulting mixture was stirred at room temperature in an atmosphere of hydrogen gas for 14 hours. After the completion of the reaction was detected with LC-MC, the reaction system was filtered by suction to remove Pd—C. The reaction solution was concentrated to produce the title compound (400 mg, yield: 78%).

LC-MS (ESI) $[M+H]^+$=177.1.

Step 3: Preparation of 1-(3-((6-((3S,4S)-4-(3,4-dihydroisoquinoline-2(1H)-yl)-3-hydroxypiperidine-1-carbonyl)pyrimidine-4-yl)amino)phenyl)pyrrolidine-2-one

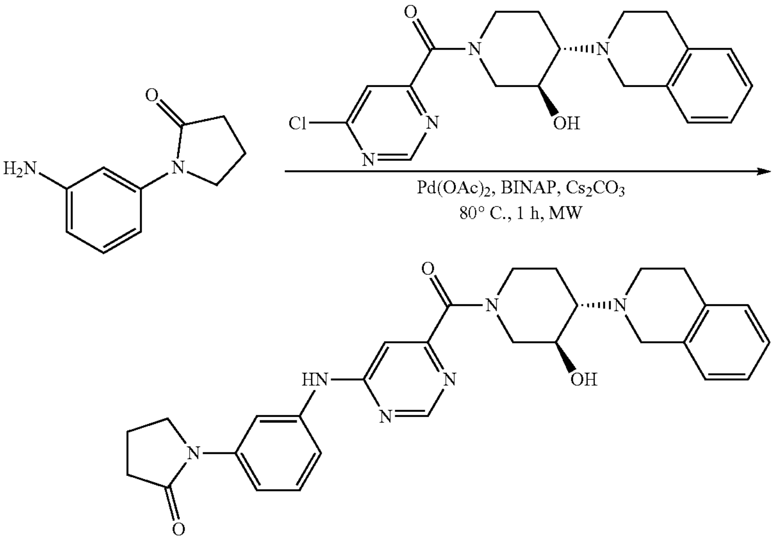

At 28° C., under the protection of nitrogen gas, (6-chloropyrimidine-4-yl)((3 S,4S)-4-(3,4-dihydroisoquinoline-2

(1H)-yl)-3-hydroxypiperidine-1-yl)methanone (67 mg, 0.18 mmol, 1.0 equiv) was dissolved in 1,4-dioxane (3 mL). 1-(3-aminophenyl)pyrrolidine-2-one (38 mg, 0.22 mmol, 1.2 equiv), palladium acetate (6 mg, 0.027 mmol, 0.15 equiv), BINAP (2,2'-bis(diphenylphosphino)-1,1'-binaphthyl)(33 mg, 0.054 mol, 0.3 equiv), and cesium carbonate (146 mg, 0.45 mmol, 2.5 equiv) were added. The resulting mixture was stirred at 80° C. under microwave heating for 1 hour. After the completion of the reaction was detected with LC-MC, the reaction system was cooled to room temperature, and filtered to obtain a crude product, which was separated and purified with Prep-HPLC (C18, 10 mmol/L aqueous $NH_4HCO_3$ solution, MeCN) to produce the title compound (20 mg, purity: 95.44%, yield: 21.65%).

LC-MS (ESI) [M+H](=513.5; $^1$H NMR (400 MHz, MeOD-$d_4$) δ 9.87 (d, J=8.0 Hz, 1H), 8.65 (d, J=8.4 Hz, 1H), 8.03 (s, 1H), 7.58 (t, J=5.6 Hz, 1H), 7.35 (td, J=8.0 Hz, 2.4 Hz, 1H), 7.28-7.26 (mi, 1H), 7.11-7.03 (m, 4H), 6.88 (dd, J=6.4 Hz, 0.8 Hz, 1H), 4.85-4.74 (m, 1H), 4.52-4.33 (m, 1H), 3.87-3.81 (m, 4H), 3.78-3.75 (d, 1H), 3.69-3.62 (m, 1H), 3.31-3.30 (m, 1H), 3.07-3.01 (m, 0.5H), 2.92-2.74 (m, 5H), 2.69-2.60 (m, 1.5H), 2.54-2.53 (m, 1H), 2.11-2.04 (m, 2H), 1.88-1.74 (m, 1H, 1.58-1.50 (m, 1H).

Examples 140-190

Using the same process as in Example 139, the compounds of Examples 140-190 were synthesized. The compound structures and specific characterization data (LC-MS and $^1$H NMR) were as follows:

| Ex. | Structure | $^1$H NMR | LC-MS (ESI) [M + H]$^+$ |
|---|---|---|---|
| 140 | 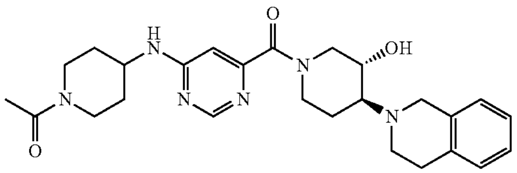 [SMILES: CC(=O)N1CCC(Nc2cc(C(=O)N3CC[C@H](N4CCc5ccccc5C4)[C@@H](O)C3)ncn2)CC1] | (400 MHz, $CDCl_3$) δ 8.54 (d, J = 6.8 Hz, 1H), 7.20-7.08 (m, 3H), 7.06-6.99 (m, 1H), 6.68-6.56 (m, 1H), 5.69-5.37 (m, 1H), 5.07-4.64 (m, 1H), 4.54 (d, J = 13.4 Hz, 1H), 4.19 (m, 1H), 3.95 (d, J = 14.5 Hz, 1H), 3.82 (d, J = 13.6 Hz, 1H), 3.76-3.60 (m, 2H), 3.22 (m, 1H), 3.11-2.75 (m, 6H), 2.76-2.59 (m, 2H), 2.12 (s, 4H), 2.07-1.96 (m, 2H), 1.93-1.76 (m, 2H), 1.75-1.59 (m, 1H), 1.49-1.34 (m, 2H). | 479.27 |
| 141 | 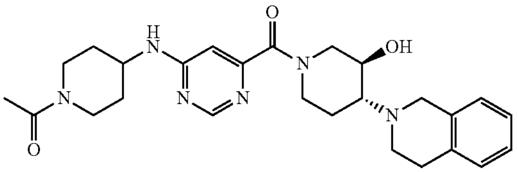 [SMILES: CC(=O)N1CCC(Nc2cc(C(=O)N3CC[C@@H](N4CCc5ccccc5C4)[C@H](O)C3)ncn2)CC1] | (400 MHz, $CDCl_3$) δ 8.53 (d, J = 6.3 Hz, 1H), 7.19-7.08 (m, 3H), 7.08-6.98 (m, 1H), 6.67-6.56 (m, 1H), 5.80-5.47 (m, 1H), 5.08-4.64 (m, 1H), 4.53 (d, J = 13.6 Hz, 1H), 4.29-4.08 (m, 1H), 3.95 (d, J = 14.6 Hz, 1H), 3.82 (d, J = 13.9 Hz, 1H), 3.70 (d, J = 14.2 Hz, 2H), 3.31-3.13 (m, 1H), 3.10-2.76 (m, 6H), 2.76-2.58 (m, 2H), 2.12 (m, 4H), 2.07-1.77 (m, 4H), 1.77-1.56 (m, 1H), 1.54-1.29 (m, 2H). | 479.31 |
| 142 | 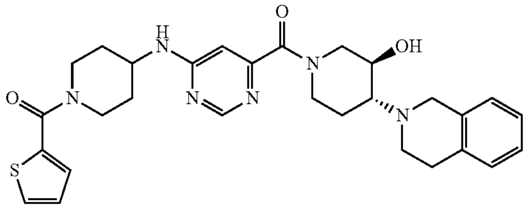 [SMILES: O=C(c1cc(NC2CCN(C(=O)c3cccs3)CC2)ncn1)N1CC[C@@H](N2CCc3ccccc3C2)[C@H](O)C1] | (400 MHz, $CDCl_3$) δ 8.56-8.52 (m, 1H), 7.48-7.44 (m, 1H), 7.32-7.29 (m, 1H), 7.17-7.10 (m, 3H), 7.07-7.00 (m, 2H), 6.65-6.58 (m, 1H), 5.48-5.31 (m, 1H), 5.04-4.68 (m, 1H), 4.54-4.33 (m, 2H), 4.24-4.15 (m, 1H), 3.98-3.94 (m, 1H), 3.75-3.69 (m, 2H), 3.30-3.13 (m, 2H), 3.09-2.97 (m, 2H), 2.94-2.88 (m, 2H), 2.75-2.64 (m, 2H), 2.16-2.07 (m, 2H), 1.99-1.62 (m, 4H), 1.58-1.45 (m, 2H). | 547.3 |
| 143 | 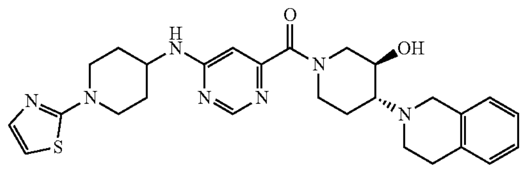 [SMILES: O=C(c1cc(NC2CCN(c3nccs3)CC2)ncn1)N1CC[C@@H](N2CCc3ccccc3C2)[C@H](O)C1] | (400 MHz, $CDCl_3$) δ 8.58-8.52 (m, 1H), 7.20-7.11 (m, 4H), 7.07-7.00 (m, 1H), 6.67-6.65 (m, 2H), 5.20-4.66 (m, 2H), 4.29-4.18 (m, 1H), 4.05-3.98 (m, 3H), 3.82-3.72 (m, 2H), 3.28-3.15 (m, 2H), 3.13-3.00 (m, 2H), 2.97-2.89 (m, 2H), 2.81-2.62 (m, 2H), 2.19-2.10 (m, 2H), 2.05-1.81 (m, 2H), 1.73-1.60 (m, 4H). | 520.3 |
| 144 | 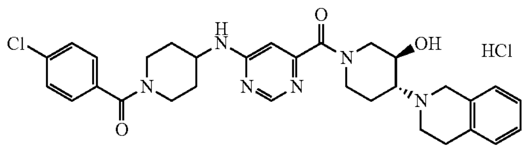 [SMILES: O=C(c1ccc(Cl)cc1)N1CCC(Nc2cc(C(=O)N3CC[C@@H](N4CCc5ccccc5C4)[C@H](O)C3)ncn2)CC1 ; Cl] | (400 MHz, $(CD_3)_2SO$) δ 10.64-10.34 (m, 1H), 8.59-8.38 (m, 2H), 7.57-7.49 (m, 2H), 7.46-7.39 (m, 2H), 7.31-7.17 (m, 4H), 6.77 (s, 1H), 6.44-6.04 (m, 1H), 4.76-4.41 (m, 3H), 4.37-4.15 (m, 2H), 4.05-3.67 (m, 6H), 3.26-2.93 (m, 5H), 2.91-2.66 (m, 1H), 2.41-2.12 (m, 1H), 2.05-1.75 (m, 3H), 1.60-1.28 (m, 2H). | 575.2 |
| 145 | 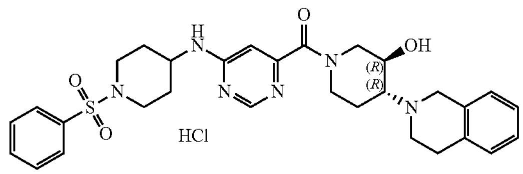 | (400 MHz, $(CD_3)_2SO$) δ 10.47-10.00 (m, 1H), 8.61-8.02 (m, 2H), 7.82-7.72 (m, 3H), 7.71-7.60 (m, 2H), 7.34-7.13 (m, 4H), 6.89-6.59 (m, 1H), 6.48-5.83 (m, 1H), 4.75-4.34 (m, 4H), 4.21-3.82 (m, 5H), 3.81-3.67 (m, 2H), 3.45-3.19 (m, 2H), 3.16-2.78 (m, 3H), 2.74-2.62 (m, 1H), 2.31-2.05 (m, 1H), 2.01-1.71 (m, 3H), 1.63-1.46 (m, 2H). | 577.2 |

-continued

| Ex. | Structure | $^1$H NMR | LC-MS (ESI) [M + H]$^+$ |
|---|---|---|---|
| 146 | 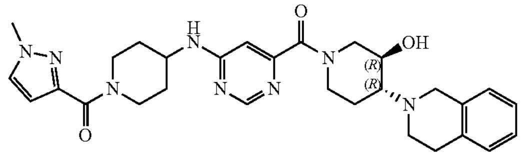 | (400 MHz, $CDCl_3$) δ 8.60-8.50 (m, 1H), 7.38-7.32 (m, 1H), 7.18-7.10 (m, 3H), 7.07-6.98 (m, 1H), 6.69-6.55 (m, 2H), 5.18-4.98 (m, 1H), 4.85-4.56 (m, 3H), 4.32-4.03 (m, 2H), 4.02-3.85 (m, 5H), 3.77-3.67 (m, 2H), 3.40-3.27 (m, 1H), 3.10-3.05 (m, 1H), 3.04-2.99 (m, 1H), 2.97-2.92 (m, 2H), 2.91-2.81 (m, 1H), 2.79-2.64 (m, 2H), 2.20-2.08 (m, 2H), 2.04-1.91 (m, 1H), 1.77-1.61 (m, 2H), 1.50-1.43 (m, 1H). | 545.0 |
| 147 | HCl 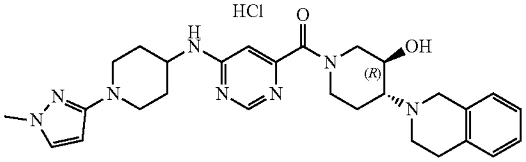 | (400 MHz, $(CD_3)_2SO$) δ 10.49-10.30 (m, 1H), 8.48-8.46 (d, J = 8, 1H), 8.02 (s, 1H), 7.39 (s, 1H), 7.29-7.19 (m, 5H), 6.66 (s, 1H), 6.32-6.07 (m, 1H), 4.72-4.42 (m, 3H), 4.03-3.95 (m, 3H), 3.74 (s, 4H), 3.38-2.94 (m, 7H), 2.89-2.65 (m, 3H), 2.26-2.13 (m, 1H), 1.97-1.97 (m, 2H), 1.82-1.65 (m, 3H). | 517.2 |
| 148 | HCl 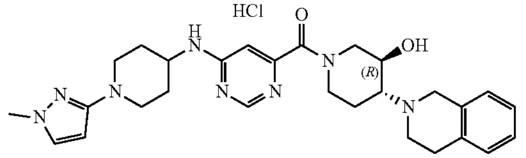 | (400 MHz, $(CD_3)_2SO$) δ 10.51-10.31 (m, 1H), 8.55-8.33 (m, 2H), 7.45-7.44 (m, 1H), 7.29-7.20 (m, 4H), 6.72 (s, 1H), 6.33-6.11 (m, 1H), 5.71 (s, 1H), 4.73-4.42 (m, 3H), 4.04-3.74 (m, 5H), 3.65-3.62 (m, 4H), 3.39-3.10 (m, 3H), 3.02-2.26 (m, 5H), 2.33-2.13 (m, 1H), 1.90-1.80 (m, 3H), 1.60-1.53 (m, 2H). | 517.2 |
| 149 | 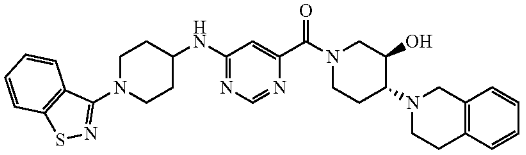 [SMILES: O=C(c1cc(NC2CCN(c3nsc4ccccc34)CC2)ncn1)N1CC[C@@H](N2CCc3ccccc3C2)[C@H](O)C1] | (400 MHz, $CDCl_3$) δ 8.56-8.50 (m, 1H), 7.66 (t, J = 8.8 Hz, 2H), 7.58 (t, J = 7.7 Hz, 1H), 7.30 (t, J = 7.6 Hz, 1H), 7.18-7.09 (m, 3H), 7.06-6.99 (m, 1H), 6.61-6.52 (m, 1H), 5.10-4.99 (m, 1H), 4.71 (d, J = 13.3 Hz, 1H), 4.27-4.15 (m, 1H), 4.01-3.95 (m, 1H), 3.77-3.69 (m, 2H), 3.35-3.27 (m, 2H), 3.13-2.83 (m, 7H), 2.76-2.59 (m, 2H), 2.11-2.04 (m, 2H), 2.01-1.84 (m, 1H), 1.75-1.65 (m, 3H). | 570.3 |
| 150 | 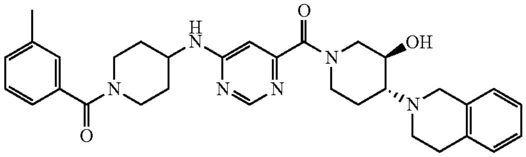 [SMILES: Cc1cccc(C(=O)N2CCC(Nc3cc(C(=O)N4CC[C@@H](N5CCc6ccccc6C5)[C@H](O)C4)ncn3)CC2)c1] | (400 MHz, $CDCl_3$) δ 8.55-8.52 (m, 1H), 7.31-7.27 (m, 1H), 7.32-7.21 (m, 2H), 7.18-7.11 (m, 4H), 7.04-7.02 (m, 1H), 6.66-6.60 (m, 1H), 5.29-4.99 (m, 1H), 4.71-4.68 (m, 1H), 4.26-3.78 (m, 7H), 3.10-2.60 (m, 9H), 2.37 (s, 3H), 2.04-1.52 (m, 6H). | 555.4 |
| 151 | 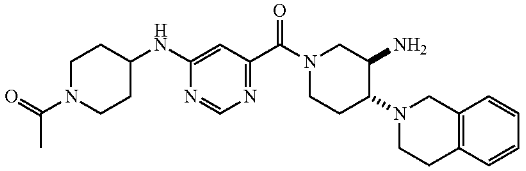 [SMILES: CC(=O)N1CCC(Nc2cc(C(=O)N3CC[C@@H](N4CCc5ccccc5C4)[C@H](N)C3)ncn2)CC1] | (400 MHz, $CDCl_3$) δ 8.55 (dd, J = 7.6, 1.1 Hz, 1H), 7.18-7.07 (m, 3H), 7.05-6.98 (m, 1H), 6.66-6.57 (m, 1H), 5.37-5.05 (m, 1H), 4.87-4.76 (m, 1H), 4.61-4.50 (m, 1H), 4.19-4.09 (m, 1H), 3.94-3.78 (m, 2H), 3.74-3.65 (m, 1H), 3.28-3.18 (m, 1H), 3.15-2.54 (m, 9H), 2.17-2.09 (m, 3H), 2.08-1.94 (m, 2.4H), 1.89-1.82 (m, 0.6H), 1.73-1.60 (m, 1H), 1.49-1.36 (m, 2H). | 478.2 |
| 152 | 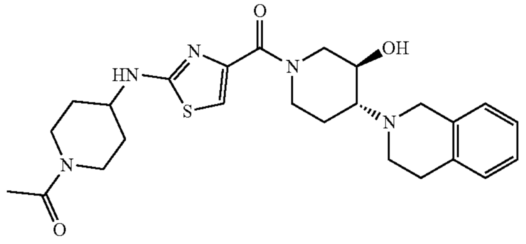 [SMILES: CC(=O)N1CCC(Nc2nc(C(=O)N3CC[C@@H](N4CCc5ccccc5C4)[C@H](O)C3)cs2)CC1] | (400 MHz, $CDCl_3$) δ 7.20-7.10 (m, 3H), 7.09-7.07 (m, 1H), 7.06-7.00 (m, 1H), 5.09-5.01 (m, 1H), 4.86 (s, 1H), 4.80-4.67 (m, 1H), 4.58-4.40 (m, 1H), 4.02-3.93 (m, 1H), 3.86-3.78 (m, 1H), 3.77-3.66 (m, 3H), 3.29-3.16 (m, 1H), 3.12-3.03 (m, 1H), 3.01-2.82 (m, 4H), 2.78-2.67 (m, 2H), 2.22 (s, 1H), 2.17-2.05 (m, 4H), 1.99-1.39 (m, 6H). | 484.25 |
| 153 | 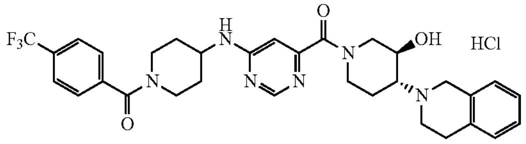 [SMILES: O=C(c1ccc(C(F)(F)F)cc1)N1CCC(Nc2cc(C(=O)N3CC[C@@H](N4CCc5ccccc5C4)[C@H](O)C3)ncn2)CC1 ; Cl] HCl | (400 MHz, $(CD_3)_2SO$) δ 10.55-10.26 (m, 1H), 8.61-8.26 (m, 2H), 7.87-7.80 (m, 2H), 7.66-7.57 (m, 2H), 7.31-7.17 (m, 4H), 6.75 (s, 1H), 6.46-5.92 (m, 1H), 4.74-4.33 (m, 4H), 4.26-4.16 (m, 1H), 4.03-3.70 (m, 4H), 3.46-2.95 (m, 7H), 2.92-2.64 (m, 1H), 2.38-2.09 (m, 1H), 2.07-1.73 (m, 3H), 1.64-1.34 (m, 2H). | 609.2 |

-continued

| Ex. | Structure | $^1$H NMR | LC-MS (ESI) [M + H]$^+$ |
| --- | --- | --- | --- |
| 154 | 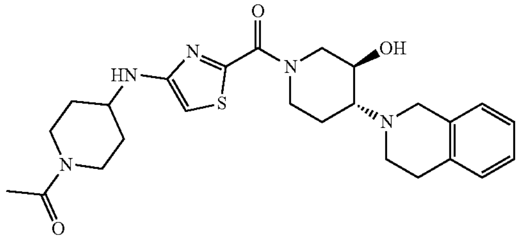 [SMILES: CC(=O)N1CCC(Nc2csc(C(=O)N3CC[C@@H](N4CCc5ccccc5C4)[C@H](O)C3)n2)CC1] | (400 MHz, $CDCl_3$) δ 7.19-7.10 (m, 3H), 7.06-7.01 (m, 1H), 5.97 (s, 1H), 5.80 (bs, 1H), 4.90-4.78 (m, 1H), 4.49-4.39 (m, 1H), 4.37-4.18 (m, 1H), 4.09-3.95 (m, 1H), 3.87-3.64 (m, 3H), 3.48 (bs, 1H), 3.29-3.18 (m, 1H), 3.15-3.05 (m, 1H), 3.01-2.72 (m, 6H), 2.19-2.04 (m, 5H), 2.04-1.93 (m, 1H), 1.72-1.64 (m, 1H), 1.37 (m, 2H). | 484.20 |
| 155 | 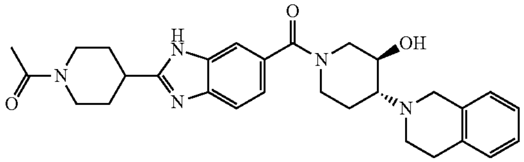 [SMILES: CC(=O)N1CCC(c2nc3ccc(C(=O)N4CC[C@@H](N5CCc6ccccc6C5)[C@H](O)C4)cc3[nH]2)CC1] | (400 MHz, $CDCl_3$) δ 7.65 (brs, 1H), 7.30-7.26 (m, 2H), 7.18-7.09 (m, 3H), 7.06-7.01 (m, 1H), 4.88 (brs, 1H), 4.69-4.60 (m, 1H), 4.04-3.60 (m, 5H), 3.30-3.04 (m, 3H), 3.01-2.65 (m, 7H), 2.22-2.15 (m, 1H), 2.14 (s, 3H), 2.11-2.02 (m, 1H), 2.02-1.71 (m, 4H). | 502.21 |
| 156 | 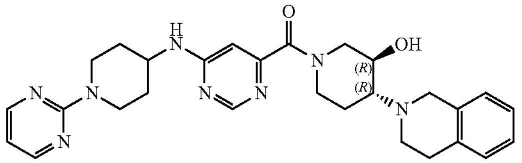 | (400 MHz, $CDCl_3$) δ 8.59-8.48 (m, 1H), 8.35-8.26 (m, 2H), 7.19-7.09 (m, 3H), 7.07-6.97 (m, 1H), 6.67-6.54 (m, 1H), 6.53-6.44 (m, 1H), 5.19-4.89 (m, 1H), 4.84-4.61 (m, 3H), 4.28-4.16 (m 1H), 4.04-3.80 (m, 2H), 3.77-3.62 (m, 2H), 3.20-2.78 (m, 7H), 2.78-2.61 (m, 2H), 2.17-2.07 (m, 2H), 2.04-1.80 (m, 1H), 1.74-1.66 (m, 1H), 1.54-1.41 (m, 2H). | 515.30 |
| 157 | 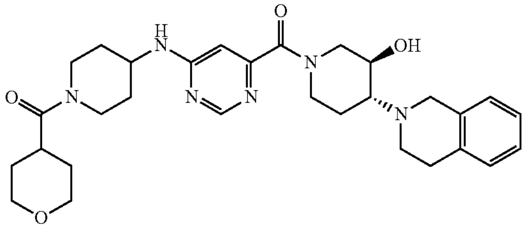 [SMILES: O=C(c1cc(NC2CCN(C(=O)C3CCOCC3)CC2)ncn1)N1CC[C@@H](N2CCc3ccccc3C2)[C@H](O)C1] | (400 MHz, DMSO-$d_6$) δ 8.44 (d, J = 9.1 Hz, 1H), 7.63 (t, J = 7.6 Hz, 1H), 7.11-6.99 (m, 4H), 6.52 (s, 1H), 4.82-4.72 (m, 1H), 4.52-4.23 (m, 2H), 4.19-3.91 (m, 2H), 3.89-3.75 (m, 4H), 3.74-3.56 (m, 2H), 3.39 (t, J = 11.7 Hz, 2H), 3.24-3.12 (m, 1H), 3.06-2.87 (m, 2H), 2.87-2.74 (m, 5H), 2.68-2.55 (m, 2H), 2.02-1.84 (m, 2H), 1.83-1.58 (m, 2H), 1.57-1.45 (m, 4H), 1.41-1.21 (m, 2H). | 549.3 |
| 158 | 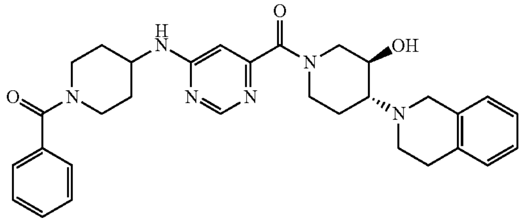 [SMILES: O=C(c1ccccc1)N1CCC(Nc2cc(C(=O)N3CC[C@@H](N4CCc5ccccc5C4)[C@H](O)C3)ncn2)CC1] | (400 MHz, DMSO-$d_6$) δ 8.44 (d, J = 8.8 Hz, 1H), 7.66 (t, J = 6.9 Hz, 1H), 7.50-7.42 (m, 3H), 7.41-7.35 (m, 2H), 7.18-7.07 (m, 3H), 7.05-7.01 (m, 1H), 6.54 (s, 1H), 4.82-4.72 (m, 1H), 4.44-4.25 (m, 2H), 4.16 (s, 1H), 3.85-3.76 (m, 2H), 3.75-3.67 (m, 1H), 3.65-3.55 (m, 2H), 3.25-3.14 (m, 1H), 3.10-2.96 (m, 1H), 2.93-2.76 (m, 5H), 2.72-2.53 (m, 2H), 2.04-1.84 (m, 2H), 1.83-1.66 (m, 1H), 1.57-1.32 (m, 3H). | 541.5 |
| 159 | 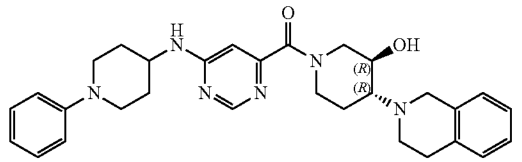 | (400 MHz, DMSO-$d_6$) δ 8.45 (d, J = 9.2 Hz, 1H), 7.65 (t, J = 7.6 Hz, 1H), 7.25-7.16 (m, 2H), 7.11-7.01 (m, 4H), 6.99-6.92 (m, 2H), 6.75 (t, J = 7.2 Hz, 1H), 6.53 (s, 1H), 4.87-4.68 (m, 1H), 4.52-4.27 (m, 1H), 4.15-3.94 (m, 1H), 3.88-3.76 (m, 2H), 3.75-3.55 (m, 4H), 3.08-2.95 (m, 1H), 2.93-2.75 (m, 6H), 2.69-2.55 (m, 2H), 2.04-1.93 (m, 2H), 1.87-1.69 (m, 1H), 1.63-1.44 (m, 3H). | 513.4 |
| 160 | 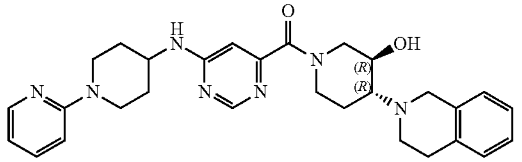 | (400 MHz, DMSO-$d_6$) δ 8.45 (d, J = 8.9 Hz, 1H), 8.10 (d, J = 4.8 Hz, 1H), 7.63 (t, J = 7.4 Hz, 1H), 7.55-7.46 (m, 1H), 7.12-7.01 (m, 4H), 6.86 (d, J = 8.6 Hz, 1H), 6.64-6.44 (m, 2H), 4.85-4.71 (m, 1H), 4.52-4.30 (m, 1H), 4.29-4.07 (m, 3H), 3.89-3.69 (m, 3H), 3.66-3.56 (m, 1H), 3.08-2.87 (m, 4H), 2.85-2.77 (m, 3H), 2.73-2.54 (m, 2H), 1.99-1.89 (m, 2H), 1.87-1.68 (m, 1H), 1.58-1.35 (m, 3H). | 515.4 |

-continued

| Ex. | Structure | $^1$H NMR | LC-MS (ESI) [M + H]$^+$ |
|---|---|---|---|
| 161 | 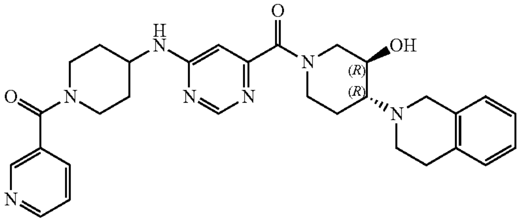 | (400 MHz, $CDCl_3$) δ 8.77-8.62 (m, 2H), 8.62-8.50 (m, 1H), 7.82-7.72 (m, 1H), 7.50-7.32 (m, 1H), 7.20-7.08 (m, 3H), 7.07-6.98 (m, 1H), 6.72-6.54 (m, 1H), 5.30-5.07 (m, 1H), 5.05-4.56 (m, 2H), 4.33-4.07 (m, 2H), 4.06-3.64 (m, 5H), 3.25 (s, 1H), 3.13-2.89 (m, 5H), 2.85-2.66 (m, 2H), 2.25-2.03 (m, 2H), 2.01-1.76 (m, 1H), 1.75-1.55 (m, 3H). | 542.17 |
| 162 | 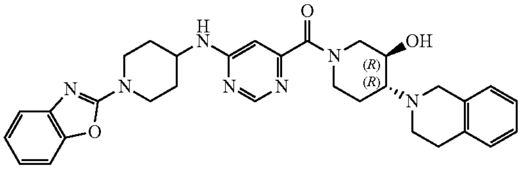 | (400 MHz, $CDCl_3$) δ 8.63-8.50 (m, 1H), 7.39-7.33 (m, 1H), 7.28-7.26 (m, 1H), 7.20-7.10 (m, 4H), 7.07-6.99 (m, 2H), 6.70-6.54 (m, 1H), 5.23-4.65 (m, 2H), 4.41-4.09 (m, 4H), 4.08-3.66 (m, 4H), 3.38-3.23 (m, 2H), 3.15-2.91 (m, 4H), 2.87-2.67 (m, 2H), 2.25-2.11 (m, 2H), 2.09-1.87 (m, 1H), 1.70-1.59 (m, 3H). | 554.16 |
| 163 | 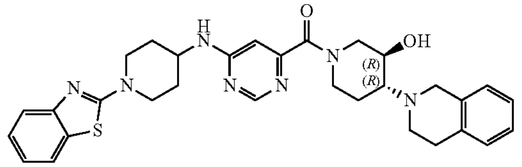 | (400 MHz, $CDCl_3$) δ 8.61-8.51 (m, 1H), 7.64-7.52 (m, 2H), 7.34-7.27 (m, 1H), 7.20-7.11 (m, 3H), 7.11-7.01 (m, 2H), 6.68-6.56 (m, 1H), 5.22-4.64 (m, 2H), 4.29-4.07 (m, 4H), 4.07-3.60 (m, 4H), 3.38-3.26 (m, 2H), 3.17-2.92 (m, 4H), 2.91-2.82 (m, 1H), 2.79-2.68 (m, 1H), 2.26-2.13 (m, 2H), 2.06-1.86 (m, 1H), 1.70-1.59 (m, 3H). | 570.14 |
| 164 | 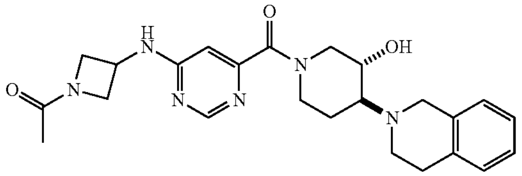 [SMILES: CC(=O)N1CC(Nc2cc(C(=O)N3CC[C@H](N4CCc5ccccc5C4)[C@@H](O)C3)ncn2)C1] | (400 MHz, DMSO-$d_6$) δ 8.48 (d, J = 9.2 Hz, 1H), 8.30 (m, 1H), 7.11-7.01 (m, 4H), 6.63-6.52 (m, 1H), 4.90-4.54 (m, 2H), 4.51-4.30 (m, 2H), 4.20-4.11 (m, 1H), 3.99-3.91 (m, 1H), 3.85-3.58 (m, 5H), 3.05-2.72 (m, 6H), 2.56-2.64 (m, 1H), 1.84 (m, 0.5H), 1.77 (s, 3H), 1.71 (m, 0.5 H), 1.51 (m, 1H). | 451.4 |
| 165 | 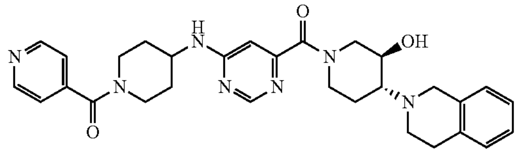 [SMILES: O=C(c1ccncc1)N1CCC(Nc2cc(C(=O)N3CC[C@@H](N4CCc5ccccc5C4)[C@H](O)C3)ncn2)CC1] | (400 MHz, $CDCl_3$) δ 8.72-8.69 (m, 2H), 8.57-8.54 (m, 1H), 7.30-7.26 (m, 2H), 7.15-7.12 (m, 3H), 7.03-7.01 (m, 1H), 6.64-6.58 (m, 1H), 5.20-5.00 (m, 1H), 4.74-4.66 (m, 1H), 4.26-4.16 (m, 2H), 3.96-3.80 (m, 2H), 3.72-3.67 (m, 3H), 3.24-2.89 (m, 7H), 2.68-2.65 (m, 2H), 2.17-1.84 (m, 4H), 1.69-1.65 (m, 1H), 1.41-1.37 (m, 1H). | 542.2 |
| 166 | 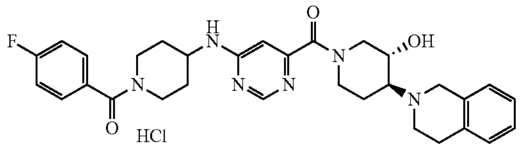 [SMILES: O=C(c1ccc(F)cc1)N1CCC(Nc2cc(C(=O)N3CC[C@H](N4CCc5ccccc5C4)[C@@H](O)C3)ncn2)CC1 ; Cl] | (400 MHz, DMSO-$d_6$) δ 10.30-10.13 (m, 1H), 8.53-8.51 (m, 1H), 8.17 (s, 1H), 7.48-7.45 (m, 2H), 7.31-7.21 (m, 6H), 6.70 (s, 1H), 6.29-6.09 (m, 1H), 4.67-4.41 (m, 4H), 4.19-4.16 (m, 1H), 4.03-3.96 (m, 2H), 3.76-3.73 (m, 1H), 3.43-2.99 (m, 8H), 2.87-2.66 (m, 1H), 2.29-2.08 (m, 1H), 1.98-1.83 (m, 3H), 1.46-1.42 (m, 2H). | 559.2 |
| 167 | 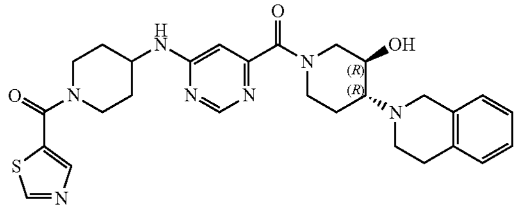 | (400 MHz, $CDCl_3$) δ 8.89 (s, 1H), 8.62-8.50 (m, 1H), 8.12-8.02 (m, 1H), 7.21-7.11 (m, 3H), 7.06-7.00 (m, 1H), 6.74-6.54 (m, 1H), 5.22-4.99 (m, 1H), 4.87-4.63 (m, 1H), 4.56-4.09 (m, 4H), 4.09-3.71 (m, 4H), 3.31-3.06 (m, 3H), 3.05-2.85 (m, 4H), 2.84-2.74 (m, 1H), 2.22-2.09 (m, 2H), 2.08-1.75 (m, 2H), 1.72-1.58 (m, 2H). | 548.20 |

-continued

| Ex. | Structure | $^1$H NMR | LC-MS (ESI) [M + H]$^+$ |
| --- | --- | --- | --- |
| 168 | 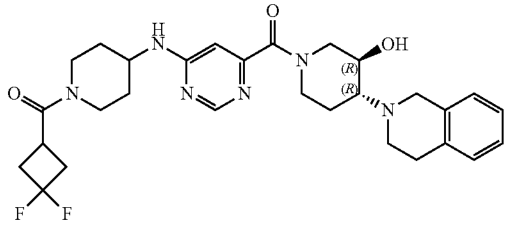 | (400 MHz, DMSO-$d_6$) δ 8.44 (d, J = 8.8 Hz, 1H), 8.44 (t, J = 7.2 Hz, 1H), 7.10-7.03 (m, 4H), 6.53 (s, 1H), 4.81-4.73 (m, 1H), 4.48-4.26 (m, 2H), 4.21-4.05 (m, 1H), 3.82-3.73 (m, 4H), 3.63-3.59 (m, 1H), 3.02-2.92 (m, 1H), 3.21-3.09 (m, 2H), 2.91-2.75 (m, 10H), 2.67-2.58 (m, 1H), 1.90-1.71 (m, 3H), 1.51-1.31 (m, 3H). | 555.3 |
| 169 | 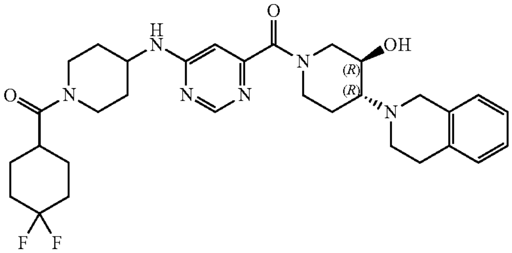 | $^1$H NMR (400 MHz, DMSO-$d_6$) δ 8.44 (d, J = 8.8 Hz, 1H), 8.44 (t, J = 7.6 Hz, 1H), 7.10-7.03 (m, 4H), 6.53 (s, 1H), 4.82-4.81 (m, 1H), 4.48-4.26 (m, 2H), 4.21-4.02 (m, 1H), 4.02-3.90 (m, 1H), 3.86-3.80 (m, 2H), 3.76-3.61 (m, 2H), 3.21 (t, J = 10.8 Hz, 1H), 3.03-2.88 (m, 2H), 2.86-2.73 (m, 6H), 2.67-2.61 (m, 1H), 2.08-1.83 (m, 7H), 1.74-1.71 (m, 2H), 1.64-1.46 (m, 3H), 1.38-1.25 (m, 2H). | 583.3 |
| 170 | 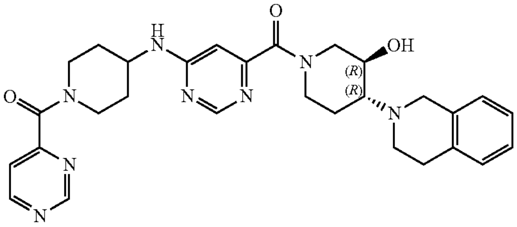 | (400 MHz, DMSO-$d_6$) δ 9.25 (s, 1H), 8.96 (d, J = 4.8 Hz, 1H), 8.44 (d, J = 8.8 Hz, 1H), 7.71-7.66 (m, 2H), 7.10-7.02 (m, 4H), 6.54 (s, 1H), 4.82-4.82 (m, 1H), 4.48-4.32 (m, 2H), 4.27-4.12 (m, 1H), 3.86-3.75 (m, 2H), 3.72-3.55 (m, 3H), 3.25-3.21 (m, 1H), 3.18-2.99 (m, 2H), 2.91-2.76 (m, 5H), 2.61-2.51 (m, 1H), 2.12-1.98 (m, 1H), 1.89-1.72 (m, 2H), 1.51-1.41 (m, 3H). | 543.3 |
| 171 | 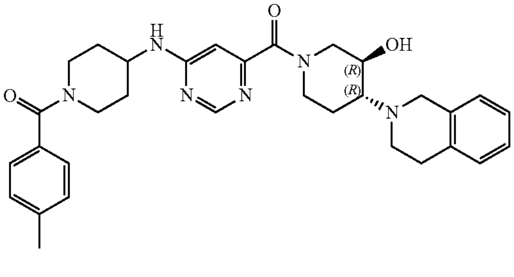 | (400 MHz, DMSO-$d_6$) δ 10.18-10.03 (m, 1H), 8.46 (d, J = 12.4 Hz, 1H), 7.83 (s, 1H), 7.29-7.20 (m, 8H), 6.63 (s, 1H), 6.26-6.01 (m, 1H), 4.64-4.39 (m, 4H), 4.25-4.10 (m, 1H), 4.05-3.81 (m, 2H), 3.77-3.70 (m, 1H), 3.59-3.47 (m, 2H), 3.17-2.99 (m, 5H), 2.93-2.65 (m, 2H), 2.34 (s, 3H), 2.04-1.80 (m, 4H), 1.51-1.27 (m, 2H). | 555.2 |
| 172 | 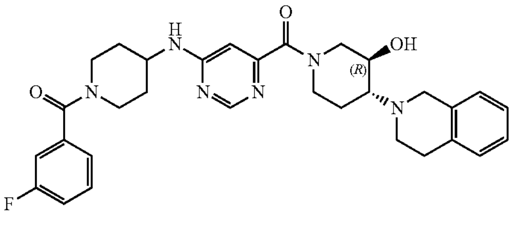 | (400 MHz, DMSO-$d_6$) δ 8.44 (d, J = 8.8 Hz, 1H), 7.66 (t, J = 6.4 Hz, 1H), 7.29-7.24 (m, 4H), 7.09-7.03 (m, 4H), 6.54 (s, 1H), 4.81-4.73 (m, 1H), 4.48-4.32 (m, 2H), 4.23-4.11 (m, 1H), 3.85-3.71 (m, 3H), 3.68-3.61 (m, 2H), 3.21-2.96 (m, 3H), 2.90-2.73 (m, 5H), 2.63-2.58 (m, 1H), 2.34 (s, 3H), 1.94-1.71 (m, 3H), 1.51-1.39 (m, 3H). | 559.2 |
| 173 | 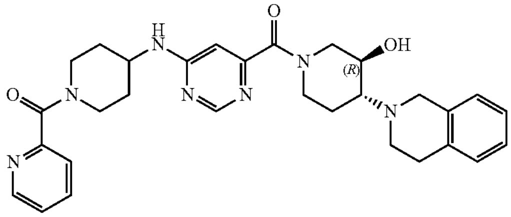 | $^1$H NMR (400 MHz, DMSO-$d_6$) δ 8.59 (d, J = 4.1 Hz, 1H), 8.44 (d, J = 8.8 Hz, 1H), 7.96-7.86 (m, 1H), 7.56-7.54 (m, 2 H), 7.49-7.46 (m, 1H), 7.09-7.03 (m, 4H), 6.53 (s, 1H), 4.81-4.73 (m, 1H), 4.48-4.31 (m, 2H), 4.26-4.13 (m, 1H), 3.86-3.76 (m, 2H), 3.68-3.61 (m, 3H), 3.22-3.16 (m, 1H), 3.09-2.97 (m, 2H), 2.91-2.73 (m, 5H), 2.67-2.55 (m, 1H), 2.05-1.94 (m, 1H), 1.85-1.72 (m, 2H), 1.51-1.43 (m, 3H). | 542.2 |

-continued

| Ex. | Structure | $^1$H NMR | LC-MS (ESI) [M + H]$^+$ |
|---|---|---|---|
| 174 | 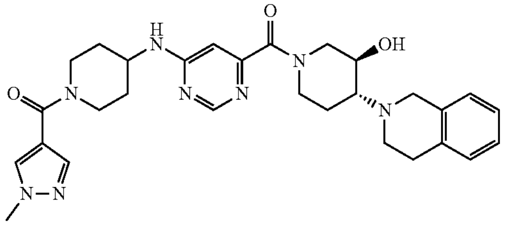 [SMILES: Cn1cc(C(=O)N2CCC(Nc3cc(C(=O)N4CC[C@@H](N5CCc6ccccc6C5)[C@H](O)C4)ncn3)CC2)cn1] | (400 MHz, DMSO-$d_6$) δ 8.45 (d, J = 8.6 Hz, 1H), 8.04 (s, 1H), 7.73-7.60 (m, 2H), 7.14-6.99 (m, 5H), 6.54 (s, 1H), 4.77 (dd, J = 32.7, 3.8 Hz, 1H), 4.54-4.32 (m, 1H), 4.32-4.01 (m, 2H), 3.85 (s, 3H), 3.83-3.67 (m, 3H), 3.65-3.55 (m, 1H), 3.06-2.96 (m, 1H), 2.93-2.75 (m, 6H), 2.68-2.55 (m, 2H), 2.04-1.89 (m, 2H), 1.88-1.70 (m, 1H), 1.57-1.30 (m, 3H). | 545.7 |
| 175 | 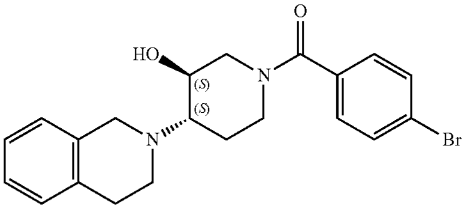 | (400 MHz, $CDCl_3$) δ 7.58-7.53 (m, 2H), 7.34-7.28 (m, 2H), 7.18-7.10 (m, 3H), 7.05-7.01 (m, 1H), 5.05-4.78 (m, 1H), 4.22-3.82 (m, 2H), 3.80-3.62 (m, 2H), 3.62-3.45 (m, 1H), 3.12-3.00 (m, 1H), 3.00-2.84 (m, 3H), 2.82-2.59 (m, 3H), 2.06-1.77 (m, 1H), 1.74-1.41 (m, 1H). | 417.0 |
| 176 | 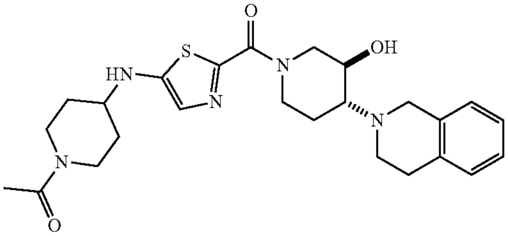 [SMILES: CC(=O)N1CCC(Nc2cnc(C(=O)N3CC[C@@H](N4CCc5ccccc5C4)[C@H](O)C3)s2)CC1] | (400 MHz, $CDCl_3$) δ 7.18-7.08 (m, 3H), 7.05-6.99 (m, 1H), 6.94 (s, 1H), 6.07-5.75 (m, 1H), 5.13-4.71 (m, 1H), 4.57-4.43 (m, 1H), 4.19 (d, J = 7.4 Hz, 1H), 3.98-3.64 (m, 5H), 3.42-3.32 (m, 1H), 3.25-3.15 (m, 1H), 3.08-2.88 (m, 4H), 2.88-2.81 (m, 1H), 2.73-2.63 (m, 2H), 2.23-2.06 (m, 5H), 2.01-1.91 (m, 1H), 1.69-1.65 (m, 1H), 1.48-1.36 (m, 2H). | 484.20 |
| 177 | 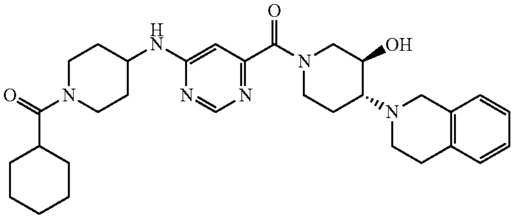 [SMILES: O=C(c1cc(NC2CCN(C(=O)C3CCCCC3)CC2)ncn1)N1CC[C@@H](N2CCc3ccccc3C2)[C@H](O)C1] | (400 MHz, DMSO-$d_6$) δ 8.44 (d, J = 8.8 Hz, 1H), 7.62 (t, J = 7.4 Hz, 1H), 7.12-7.00 (m, 4H), 6.52 (s, 1H), 4.77 (dd, J = 33.1, 3.8 Hz, 1H), 4.53-4.22 (m, 2H), 4.20-4.03 (m, 1H), 3.97-3.87 (m, 1H), 3.87-3.78 (m, 2H), 3.77-3.68 (m, 1H), 3.65-3.55 (m, 1H), 3.24-3.11 (m, 1H), 3.04-2.91 (m, 1H), 2.90-2.70 (m, 6H), 2.69-2.54 (m, 2H), 2.01-1.74 (m, 3H), 1.73-1.58 (m, 5H), 1.56-1.43 (m, 1H), 1.41-1.24 (m, 6H), 1.21-1.09 (m, 1H). | 547.7 |
| 178 | 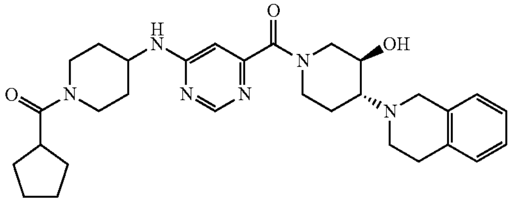 [SMILES: O=C(c1cc(NC2CCN(C(=O)C3CCCC3)CC2)ncn1)N1CC[C@@H](N2CCc3ccccc3C2)[C@H](O)C1] | (400 MHz, DMSO-$d_6$) δ 8.44 (d, J = 9.0 Hz, 1H), 7.63 (t, J = 7.4 Hz, 1H), 7.16-7.00 (m, 4H), 6.52 (s, 1H), 4.77 (dd, J = 33.4, 1.7 Hz, 1H), 4.54-4.22 (m, 2H), 4.20-4.03 (m, 1H), 4.01-3.89 (m, 1H), 3.87-3.67 (m, 3H), 3.66-3.55 (m, 1H), 3.24-3.10 (m, 1H), 3.06-2.94 (m, 2H), 2.91-2.74 (m, 5H), 2.71-2.55 (m, 2H), 1.99-1.84 (m, 2H), 1.83-1.69 (m, 3H), 1.69-1.56 (m, 4H), 1.57-1.43 (m, 3H), 1.41-1.18 (m, 2H). | 533.7 |
| 179 | 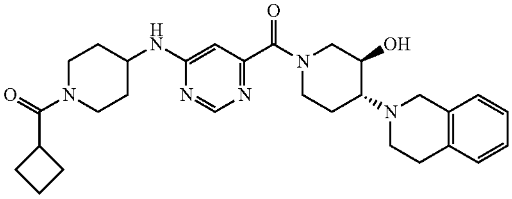 [SMILES: O=C(c1cc(NC2CCN(C(=O)C3CCC3)CC2)ncn1)N1CC[C@@H](N2CCc3ccccc3C2)[C@H](O)C1] | (400 MHz, DMSO-$d_6$) δ 8.44 (d, J = 8.8 Hz, 1H), 7.63 (t, J = 7.6 Hz, 1H), 7.15-7.00 (m, 4H), 6.52 (s, 1H), 4.77 (dd, J = 33.3, 3.8 Hz, 1H), 4.52-4.33 (m, 1H), 4.28-4.21 (m, 1H), 4.15-4.03 (m, 1H), 3.89-3.78 (m, 2H), 3.77-3.57 (m, 3H), 3.17-2.95 (m, 2H), 2.93-2.76 (m, 6H), 2.68-2.56 (m, 2H), 2.23-2.04 (m, 4H), 1.98-1.83 (m, 3H), 1.82-1.68 (m, 2H), 1.57-1.41 (m, 1H), 1.36-1.19 (m, 2H). | 518.7 |
| 180 | 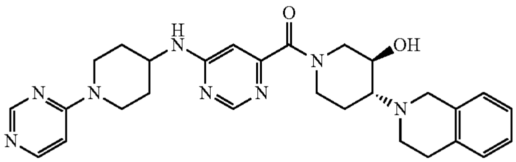 [SMILES: O=C(c1cc(NC2CCN(c3ccncn3)CC2)ncn1)N1CC[C@@H](N2CCc3ccccc3C2)[C@H](O)C1] | (400 MHz, DMSO-$d_6$) δ 8.55-8.38 (m, 2H), 8.21-8.13 (m, 1H), 7.64 (t, J = 7.5 Hz, 1H), 7.12-6.99 (m, 4H), 6.91-6.81 (m, 1H), 4.87-4.67 (m, 1H), 4.53-4.27 (m, 3H), 4.20 (s, 1H), 3.89-3.66 (m, 3H), 3.66-3.52 (m, 1H), 3.21-3.06 (m, 2H), 3.06-2.73 (m, 5H), 2.69-2.54 (m, 1H), 2.06-1.90 (m, 2H), 1.78 (dd, J = 42.7, 12.6 Hz, 1H), 1.57-1.28 (m, 3H). | 515.4 |

-continued

| Ex. | Structure | $^1$H NMR | LC-MS (ESI) [M + H]$^+$ |
|---|---|---|---|
| 181 | 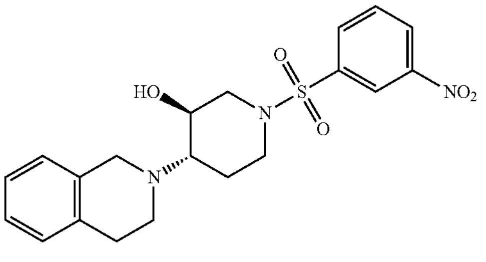 [SMILES: O=[N+]([O-])c1cccc(S(=O)(=O)N2CC[C@H](N3CCc4ccccc4C3)[C@@H](O)C2)c1] | (400 MHz, $CDCl_3$) δ 8.62 (t, J = 1.8 Hz, 1H), 8.50-8.45 (m, 1H), 8.14-8.09 (m, 1H), 7.78 (t, J = 8.0 Hz, 1H), 7.19-7.08 (m, 3H), 7.04-6.98 (m, 1H), 4.23-4.15 (m, 1H), 4.05-4.01 (m, 1H), 3.94 (d, J = 14.4 Hz, 1H), 3.84-3.63 (m, 3H), 3.10-2.99 (m, 1H), 2.96-2.87 (m, 2H), 2.74-2.62 (m, 1H), 2.52-2.37 (m, 2H), 2.30-2.20 (m, 1H), 2.02-1.91 (m, 1H), 1.87-1.77 (m, 1H). | 418.2 |
| 182 | 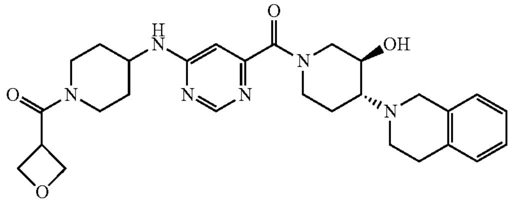 [SMILES: O=C(c1cc(NC2CCN(C(=O)C3COC3)CC2)ncn1)N1CC[C@@H](N2CCc3ccccc3C2)[C@H](O)C1] | (400 MHz, DMSO-$d_6$) δ 8.44 (d, J = 9.2 Hz, 1H), 7.62 (t, J = 7.3 Hz, 1H), 7.15-7.06 (m, 3H), 7.05-7.00 (m, 1H), 6.52 (s, 1H), 4.84-4.60 (m, 5H), 4.51-4.23 (m, 2H), 4.19-4.02 (m, 2H), 3.88-3.78 (m, 2H), 3.77-3.66 (m, 1H), 3.67-3.57 (m, 1H), 3.41-3.32 (m, 1H), 3.12-2.96 (m, 2H), 2.92-2.75 (m, 5H), 2.69-2.56 (m, 2H), 1.95-1.84 (m, 2H), 1.82-1.68 (m, 1H), 1.57-1.42 (m, 1H), 1.36-1.22 (m, 2H). | 521.4 |

Example 183: Preparation of (6-((1-benzoylpiperidine-4-yl)amino)-2-isopropoxypyrimidine-4-yl)((3R, 4R)-4-(3,4-dihydroisoquinoline-2(1H)-yl)-3-hydroxypiperidine-1-yl)methanone Step 1: Preparation of 6-((1-(tert-butoxycarbonyl) piperidine-4-yl)amino)-2-chloropyrimidine-4-carboxylic acid

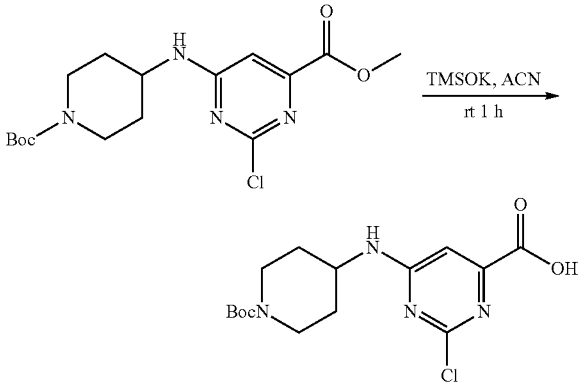

6-((1-(tert-butoxycarbonyl)piperidine-4-yl)amino)-2-chloropyrimidine-4-carboxylic acid methyl ester (500 mg, 1.347 mmol, 1.0 equiv.) was dissolved in acetonitrile (5 mL). Potassium trimethylsilanol (0.1729 g, 1.347 mmol, 1.0 equiv.) was added. The resulting mixture was stirred at 25° C. for 2 hours. After the completion of the reaction was detected with LC-MC, the resulting mixture was concentrated, and dissolved in 10% dichloromethane-methanol solution. The resulting mixture was filtered. The filtrate was concentrated to produce the title compound (480 mg, yield: 99.8%).

LC-MS (ESI) [M+H]$^+$=357.2.

Step 2: Preparation of 6-((1-(tert-butoxycarbonyl) piperdine-4-yl)amino-2-isopropoxypyrimidine-4-carboxylic acid

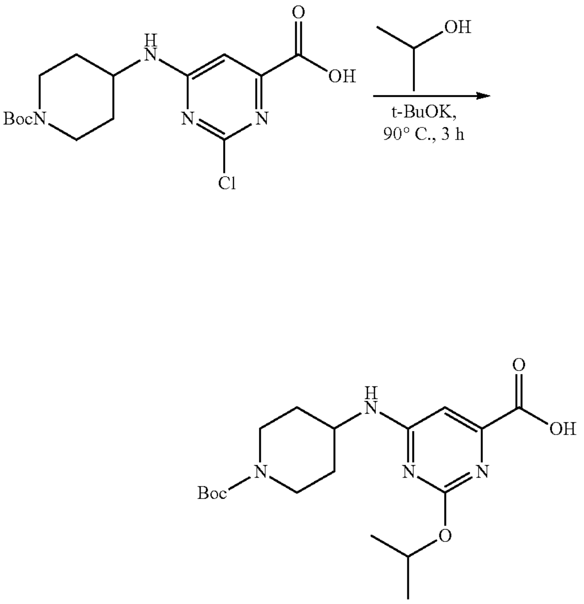

6-((1-(tert-butoxycarbonyl)piperidine-4-yl)amino)-2-chloropyrimidine-4-carboxylic acid (480 mg, 1.35 mmol, 1.0 equiv.) was dissolved in isopropanol (5 mL). Potassium tert-butoxide (628.8 mg, 5.4 mmol, 4.0 equiv) was added. The resulting mixture was stirred at 90° C. for 3 hours. The completion of the reaction was detected with LC-MS, the reaction system was concentrated, and separated and purified with Prep-TLC (MeOH:DCM=10%) to produce the title compound (529 mg, yield: 99.3%).

LC-MS (ESI) [M+H]$^+$=381.3.

Step 3: Preparation of 4-((6-((3R,4R)-4-(3,4-dihydroisoquinoline-2(1H)-yl)-3-hydroxypiperidine-1-carbonyl)-2-isopropoxypyrimidine-4-yl)amino)piperidine-1-carboxylic acid tert-butyl ester

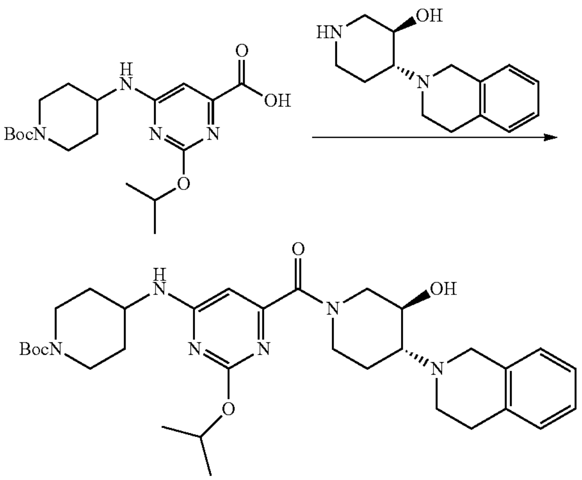

6-((1-(tert-butoxycarbonyl)piperidine-4-yl)amino)-2-isopropoxypyrimidine-4-carboxylic acid (200 mg, 0.526 mmol, 1.0 equiv.) was dissolved in N,N-dimethyl formamide (2 mL). (3R,4R)-4-(3,4-dihydroisoquinoline-2(1H)-yl)piperidine-3-ol (146.6 mg, 0.631 mmol, 1.2 equiv), HATU (299.8 mg, 0.789 mmol, 1.5 equiv) and N,N-diisopropylethylamine (203.8 mg, 1.577 mmol, 3.0 equiv) were added. The resulting mixture was stirred at room temperature for 2 hours. After the completion of the reaction was detected with LC-MC, the reaction system was extracted, concentrated, and purified with reverse phase preparative chromatography to produce the title compound (80 mg, yield: 25.6%).

LC-MS (ESI) $[M+H]^+$=595.4.

Step 4: Preparation of ((3R,4R)-4-(3,4-dihydroisoquinoline-2(1H)-yl)-3-hydroxypiperidine-1-yl)(2-isopropoxy-6-(piperidine-4-ylamino)pyrimidine-4-yl)methanone

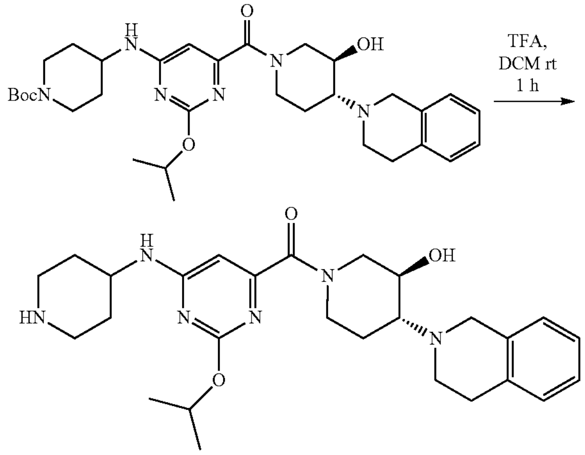

4-((6-((3R,4R)-4-(3,4-dihydroisoquinoline-2(1H)-yl)-3-hydroxypiperidine-1-carbonyl)-2-isopropoxypyrimidine-4-yl)amino)piperidine-1-carboxylic acid tert-butyl ester (80 mg, 0.134 mmol, 1.0 equiv.) was dissolved in dichloromethane (2 mL). Trifluoroacetic acid (0.5 mL) was added. The resulting mixture was stirred at 25° C. for 1 hour. After the completion of the reaction was detected with LC-MC, the reaction system was concentrated to produce the title compound (70 mg, crude).

LC-MS (ESI) $[M+H]^+$=495.3.

Step 5: Preparation of (6-((1-benzoylpiperidine-4-yl)amino)-2-isopropoxypyrimidine-4-yl)((3R,4R)-4-(3,4-dihydroisoquinoline-2(1H)-yl)-3-hydroxypiperidine-1-yl)methanone

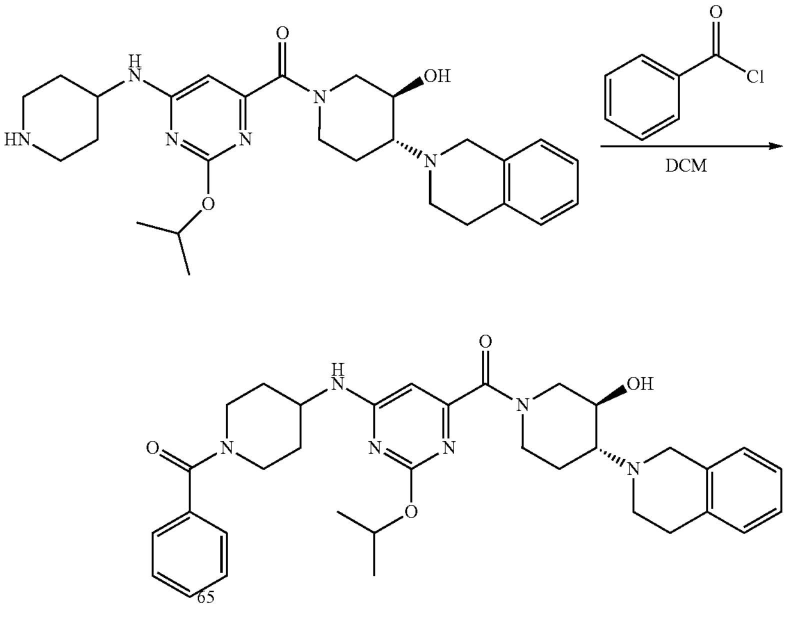

((3R,4R)-4-(3,4-dihydroisoquinoline-2(1H)-yl)-3-hydroxypiperidine-1-yl)(2-isopropoxy-6-(piperidine-4-ylamino)pyrimidine-4-yl)methanone (70 mg, 0.142 mmol, 1.0 equiv.) was dissolved in dichloromethane (1 mL). N,N-diisopropylethylamine (54.77 mg, 0.425 mmol, 3.0 equiv) was added. The resulting mixture was stirred under an ice bath for 15 minutes. Then benzoyl chloride (21.96 mg, 0.156 mmol, 1.1 equiv) was added. The resulting mixture was gradually warmed up to room temperature and stirred for 2 hours. After the completion of the reaction was detected with LC-MC, the reaction system was concentrated to produce a crude product, which was purified with reverse phase preparative chromatography to produce the title compound (37 mg, yield: 43.7%).

LC-MS (ESI) $[M+H]^+$=599.3; $^1H$ NMR (400 MHz, $CDCl_3$) δ 7.49-7.36 (m, 5H), 7.14 (m, 3H), 7.07-6.95 (m, 1H), 6.21 (d, J=22.4 Hz, 1H), 5.32-5.12 (m, 1H), 5.09-4.55 (m, 3H), 4.29 (m, 1H), 3.97 (m, 1H), 3.85-3.59 (m, 3H), 3.27-2.87 (m, 6H), 2.85-2.53 (m, 3H), 2.07-2.01 (m, 3H), 1.77-1.51 (m, 3H), 1.41-1.28 (m, 6H).

Example 184: Preparation of (2-chloro-6-(cyclobutylamino)pyrimidine-4-yl)(trans-4-(3,4-dihydroisoquinoline-2(1H)-yl)-3-hydroxypiperidine-1-yl) methanone

Step 1: Preparation of 2-chloro-6-(cyclobutylamino) pyrimidine-4-carboxylic acid

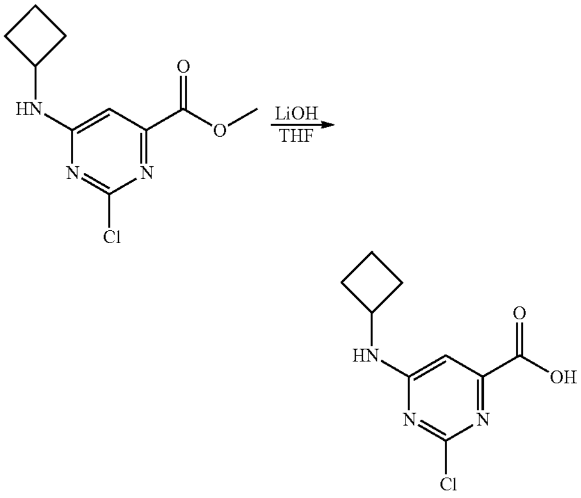

At room temperature, 2-chloro-6-(cyclobutylamino)pyrimidine-4-carboxylic acid methyl ester (1.5 g, 6.207 mmol, 1.0 equiv.) was added to water (5 mL) and THF (20 mL). Lithium hydroxide (297.3 mg, 12.414 mmol, 2.0 equiv.) was added. The resulting mixture was stirred at room temperature for 1 hour. After the completion of the reaction was detected with LC-MC, the reaction solution was concentrated to remove the organic solvent, and adjusted with 1M (molar concentration) hydrochloric acid to pH=3. The system was extracted with dichloromethane:methanol (V/V=10/1)(30 mL×5) three times. The organic phases were combined, dried, filtered, and concentrated to produce the title compound (1.5 g, crude).

LC-MS (ESI) $[M+H]^+$=442.4.

Step 2: Preparation of (2-chloro-6-(cyclobutylamino)pyrimidine-4-yl)(trans-4-(3,4-dihydroisoquinoline-2(1H)-yl)-3-hydroxypiperidine-1-yl) methanone

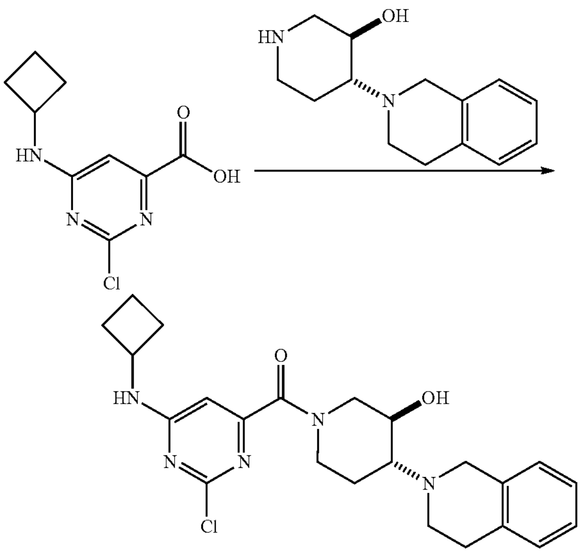

According to the process in step 2 of Example 5, the synthesis was performed to produce the title compound (1.14 g, yield: 39.7%).

LC-MS (ESI) $[M+H]^+$=442.3; $^1H$ NMR (400 MHz, DMSO-$d_6$) δ 8.58-8.35 (m, 1H), 7.10-6.88 (m, 4H), 6.52-6.45 (m, 1H), 4.83-4.73 (m, 1H), 4.42-4.03 (m, 2H), 3.86-3.76 (m, 2H), 3.70-3.53 (m, 2H), 3.05-2.73 (m, 5H), 2.69-2.57 (m, 1H), 2.33-2.28 (m, 2H), 2.03-1.82 (m, 3H), 1.73-1.61 (m, 2H), 1.56-1.40 (m, 1H), 1.23-1.21 (m, 1H).

Example 185: Preparation of trans-(6-(cyclobutylamino)-2-(2-(dimethylamino)ethoxy)pyrimidine-4-yl)(4-(3,4-dihydroisoquinoline-2(1H)-yl)-3-hydroxypiperidine-1-yl)methanone

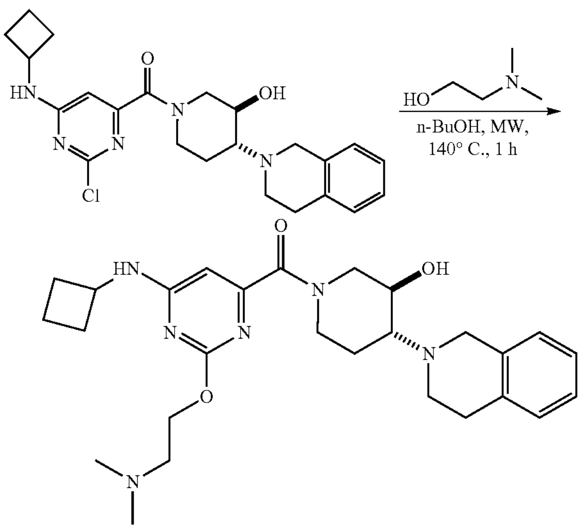

The compound of Example 184 (0.1 g, 0.226 mmol, 1.0 equiv.) was added to n-butanol (2 mL). Then 2-(dimethylamino)ethane-1-ol (201.7 mg, 2.263 mmol, 1.0 equiv.) was added. The resulting mixture was stirred under microwave at 140° C. for 1 hour. The completion of the reaction was detected with LC-MS. The system was separated and purified with reverse phase preparative HPLC (C18, 10 mmol/L aqueous $NH_4HCO_3$ solution, MeCN), and lyophilized to produce the title compound (27.36 mg, yield: 24.4%).

LC-MS (ESI) $[M+H]^+$=495.4; $^1H$ NMR (400 MHz, DMSO-$d_6$) δ 7.93-7.90 (m, 1H), 7.10-7.02 (m, 4H), 6.13 (d, J=5.2 Hz, 1H), 4.81-4.71 (m, 1H), 4.46-4.24 (m, 4H), 3.95-3.86 (m, 4H), 3.01-2.86 (m, 1H), 2.84-2.75 (m, 4H), 2.67-2.53 (m, 4H), 2.36-2.25 (m, 2H), 2.20 (s, 3H), 2.18 (s, 3H), 1.91-1.63 (m, 5H), 1.52-1.43 (m, 1H).

Example 186: Preparation of trans-(6-(cyclobutylamino)-2-phenyloxypyrimidine-4-yl)(4-(3,4-dihydroisoquinoline-2(1H)-yl)-3-hydroxypiperidine-1-yl) methanone

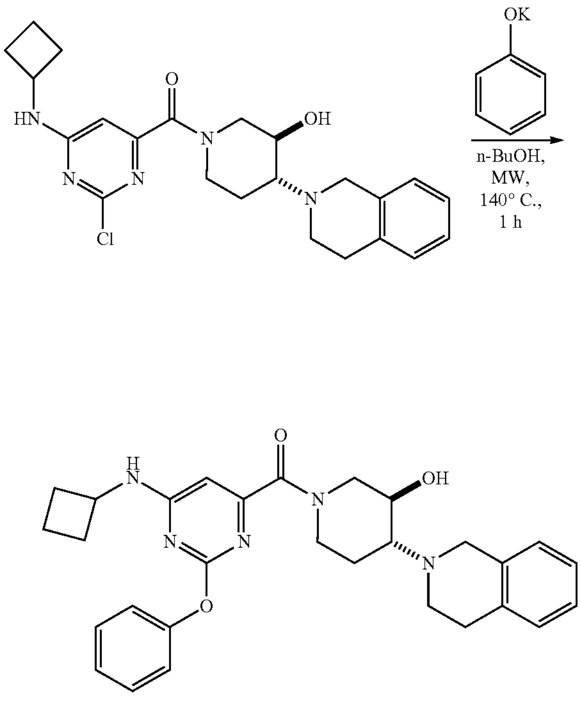

The compound of Example 184 (0.1 g, 0.226 mmol, 1.0 equiv.) was added to n-butanol (2 mL). Potassium phenolate (89.7 mg, 0.679 mmol, 3.0 equiv.) was added. The resulting mixture was stirred under microwave at 140° C. for 1 hour. The completion of the reaction was detected with LC-MS. The system was separated with reverse phase preparative HPLC (C18, 10 mmol/L aqueous $NH_4HCO_3$ solution, MeCN), and lyophilized to produce the title compound (4.21 mg, yield: 3.7%).

LC-MS (ESI) $[M+H]^+$=500.5; $^1H$ NMR (400 MHz, $CD_3OD$) δ 7.44-7.37 (m, 2H), 7.25-7.10 (m, 6H), 7.05-7.01 (m, 1H), 6.27-6.24 (m, 1H), 4.70-4.49 (m, 1H), 4.29-4.23 (m, 1H), 3.91-3.77 (m, 3H), 3.71-3.61 (m, 1H), 3.02-2.59 (m, 8H), 2.23-1.71 (m, 7H).

Example 187: Preparation of 1-(4-((6-((3R,4R)-4-(3,4-dihydroisoquinoline-2(1H)-yl)-3-hydroxypiperidine-1-carbonyl)-2-isobutoxypyrimidine-4-yl)amino) piperidine-1-yl)ethane-1-one Step-1: Preparation of 6-((1-acetylpiperidine-4-yl) amino)=2-chloropyrimidine-4-carboxylic acid methyl ester

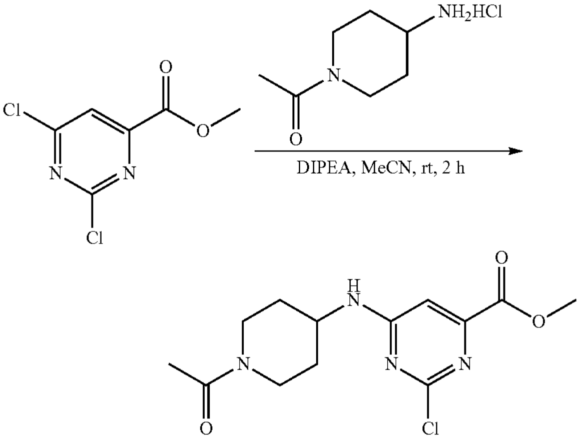

2,6-dichloropyridimine-4-carboxylic acid methyl ester (6 g, 28.98 mmol), 1-acetylpiperidine-4-amine hydrochloride (5.7 g, 31.88 mmol) and DIPEA (14.98 g, 115.94 mmol) were dissolved in acetonitrile (50 mL). The resulting mixture was stirred at room temperature (25-30° C.) for 2 hours, and extracted with ethyl acetate three times, each time 100 mL. The ethyl acetate phases were combined, washed with water (50 mL) once, washed with saturated brine (50 mL) once, dried over anhydrous sodium sulfate for 10 minutes, and filtered to obtain a crude product, which was separated and purified with a column chromatography (DCM: MeOH=100:1) to produce a product (5.8 g, yield: 64%).

LC-MS (ESI) $[M+H]^+$=313.2.

Step 2: Preparation of 6-((1-acetylpiperidine-4-yl) amino)-2-isobutoxypyrimidine-4-carboxylic acid

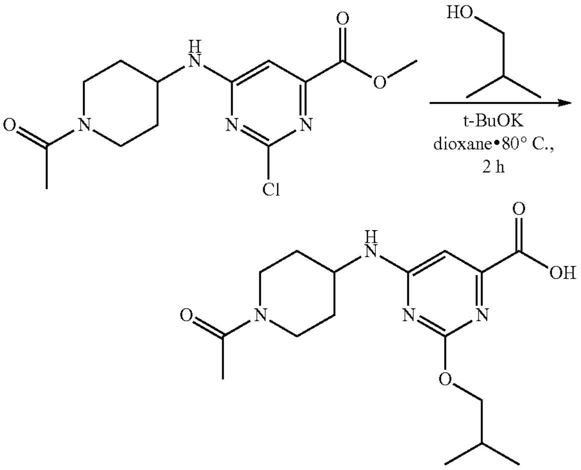

At 20° C., 6-((1-acetylpiperidine-4-yl)amino)-2-chloropyrimidine-4-carboxylic acid methyl ester (250 mg, 0.80 mmol, 1.0 equiv.) was dissolved in anhydrous dioxane (3 mL). 2-methylpropane-1-ol (178 mg, 2.4 mmol, 1.1 equiv.), and potassium tert-butoxide (180 mg, 1.6 mmol, 2 equiv.) were added. The resulting mixture was stirred at 80° C. for 2 hours. After the completion of the reaction was detected with LC-MC, the reaction system was concentrated to obtain a crude product, which was separated and purified with preparative HPLC (C18, 10 mmol/L aqueous $NH_4HCO_3$ solution/acetonitrile) and lyophilized to produce the title compound (35 mg, yield: 13%).

LC-MS (ESI) $[M+H]^+$=337.2.

Step 3: Preparation of 1-(4-((6-((3R,4R)-4-(3,4-dihydroisoquinoline-2(1H)-yl)-3-hydroxypiperidine-1-carbonyl)-2-isobutoxypyrimidine-4-yl)amino)piperidine-1-yl)ethane-1-one

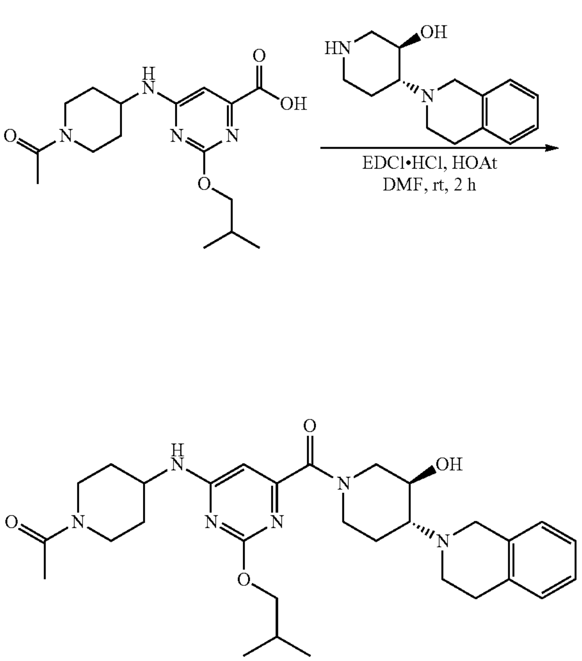 [SMILES: CC(=O)N1CCC(Nc2cc(C(=O)O)nc(OCC(C)C)n2)CC1 ; O[C@@H]1CNCC[C@H]1N1CCc2ccccc2C1 ; CC(=O)N1CCC(Nc2cc(C(=O)N3CC[C@@H](N4CCc5ccccc5C4)[C@H](O)C3)nc(OCC(C)C)n2)CC1]

At 20° C., the carboxylic acid intermediate (35 mg, 0.1 mmol, 1.0 equiv.) was added to DMF (2 mL). Then 1-(3-dimethylaminopropyl)-3-ethylcarbodiimide hydrochloride (28 mg, 0.12 mmol, 1.2 equiv.), HOAt (N-hydroxy-7-azabenzotriazole)(16 mg, 0.12 mmol, 2 equiv.), and (3R,4R)-4-(3,4-dihydroisoquinoline-2(1H)-yl)piperidine-3-ol (23 mg, 0.22 mmol, 1.0 equiv.) were added. The resulting mixture was stirred at room temperature 20° C. for 2 hours. After the completion of the reaction was detected with LC-MC, the crude product was separated and purified with preparative HPLC (C18, 10 mmol/L aqueous $NH_4HCO_3$ solution/acetonitrile) and lyophilized to produce the title compound (15 mg, yield: 27.3%).

LC-MS (ESI) $[M+H]^+$=551.4; $^1$H NMR (400 MHz, $CD_3OD$) δ 7.13-7.05 (m, 4H), 6.21 (d, J=7.6 Hz, 1H), 4.72-4.55 (m, 1H), 4.43 (d, J=13.2 Hz, 1H), 4.20-4.11 (m, 3H), 4.01-3.79 (m, 5H), 3.28-3.06 (m, 2H), 3.00-2.87 (m, 5H), 2.82-2.68 (m, 2H), 2.13-2.05 (m, 5H), 2.02-1.89 (m, 2H), 1.73-1.67 (m, 1H), 1.53-1.43 (m, 2H), 1.04 (t, J=6.4 Hz, 6H).

Example 188: Preparation of 1-(4-((6-((3R,4R)-4-(3,4-dihydroisoquinoline-2(1H)-yl)-3-hydroxypiperidine-1-carbonyl)-2-(pent-3-yloxy)pyrimidine-4-yl)amino)piperidine-1-yl)ethane-1-one Step 1: Preparation of 6-((1-acetylpiperidine-4-yl)amino)-2-(pent-3-yloxy)pyrimidine-4-carboxylic acid

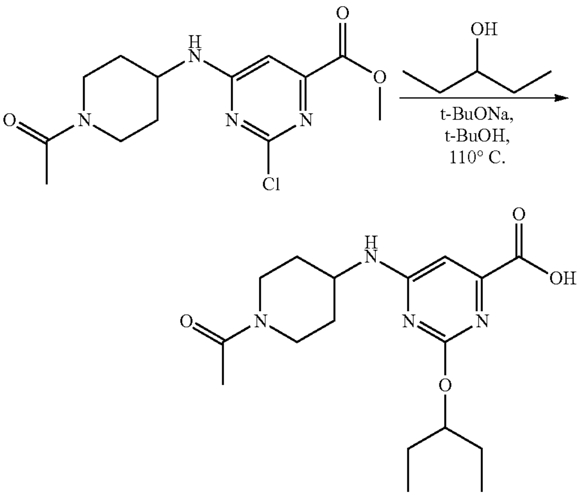

6-((1-acetylpiperidine-4-yl)amino)-2-chloropyrimidine-4-carboxylic acid methyl ester (300 mg, 0.96 mmol, 1.0 equiv.), and 3-pentanol (845 mg, 9.6 mmol, 10 equiv.) were dissolved in anhydrous tert-butyl alcohol (5 mL). Sodium tert-butoxide (369 mg, 3.84 mmol, 4.0 equiv.) was added. The reaction was performed at 100° C. for 16 hours. After the completion of the reaction was detected with LC-MC, the reaction solution was adjusted with 1M hydrochloric acid to pH=4, and the solvent was removed by rotary drying to obtain a crude product (700 mg).

LC-MS (ESI) $[M+H]^+$=351.2.

Step 2: Preparation of 1-(4-((6-((3R,4R)-4-(3,4-dihydroisoquinoline-2(1H)-yl)-3-hydroxypiperidine-1-carbonyl)-2-(pent-3-yloxy)pyrimidine-4-yl)amino)piperidine-1-yl)ethane-1-one

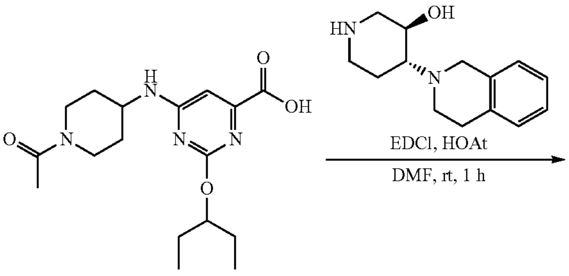

-continued

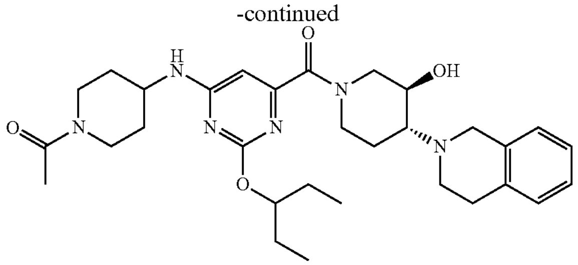

6-((1-acetylpiperidine-4-yl)amino)-2-(pent-3-yloxy)pyrimidine-4-carboxylic acid (90 mg, 0.26 mmol, 1.0 equiv.), (3R,4R)-4-(3,4-dihydroisoquinoline-2(1H)-yl)piperidine-3-ol (60 mg, 0.26 mmol, 1.0 equiv.), EDCI (74 mg, 0.38 mmol, 1.5 equiv.) and HOAt (52 mg, 0.38 mmol, 1.5 equiv.) were dissolved in DMF (N,N-dimethyl formamide)(2 mL). The reaction was performed at 25° C. for 1 hour. After the completion of the reaction was detected with LC-MC, the reaction system was concentrated to obtain a crude product, which was separated and purified with reverse phase HPLC (C18, 10 mmol/L aqueous $NH_4HCO_3$ solution/acetonitrile) to produce the title compound (26.33 mg, yield: 18%).

LC-MS (ESI) $[M+H]^+$=565.4; $^1$H NMR (400 MHz, $CDCl_3$) δ 7.17-7.10 (m, 3H), 7.03-7.01 (m, 1H), 6.22-6.17 (m, 1H), 5.29-5.17 (m, 1H), 5.00-4.90 (m, 1H), 4.77-4.74 (m, 1H), 4.51-4.47 (m, 1H), 4.24-4.12 (m, 1H), 3.96-3.92 (m, 1H), 3.81-3.78 (m, 1H), 3.72-3.62 (m, 2H), 3.24-3.21 (m, 1H), 3.06-2.64 (m, 9H), 2.11-2.10 (m, 4H), 2.02-1.94 (m, 2H), 1.70-1.60 (m, 5H), 1.41-1.38 (m, 2H), 0.96-0.89 (m, 6H).

Example 189: Preparation of (6-((1-(cyclobutanecarbonyl)piperidine-4-yl)amino)-2-isopropoxypyrimidine-4-yl)((3R,4R)-4-(3,4-dihydroisoquinoline-2(1H)-yl)-3-hydroxypiperidine-1-yl)methanone ((3R,4R)-4-(3,4-dihydroisoquinoline-2(1H)-yl)-3-hydroxypiperidine-1-yl) (2-isopropoxy-6-(piperidine-4-ylamino)pyrimidine-4-yl)methanone (70 mg, 0.142 mol, 1.0 equiv.) was dissolved in dichloromethane (1 m). N,N-diisopropylethylamine (54.77 mg, 0.425 mmol, 3.0 equiv) was added. The resulting mixture was stirred under an ice bath for 15 minutes. Then cyclobutanecarbonyl chloride (21.96 mg, 0.156 mmol, 1.1 equiv) was added. The resulting mixture was gradually warmed up to room temperature and stiffed for 2 hours. After the completion of the reaction was detected with LC-MC, the reaction system was concentrated to produce a crude product, which was purified with reverse phase preparative chromatography to produce the title compound (54 mg, yield: 66.2%).

LC-MS (ESI) [M+H]=577.4; $^1$H NMR (400 MHz, $CDCl_3$) δ 7.17-7.11 (m, 3H), 7.04-7.02 (m, 11H), 6.23-6.17 (m, 12), 5.22-5.17 (m, 1H), 5.02-4.74 (m, 2H), 4.52-4.49 (m, 1H), 4.30-4.27 (n, 1H)), 4.00-3.96 (4, 1H), 3.76-3.68 (m, 3H), 3.31-3.20 (m, 1H), 3.19-2.78 (m, 5H), 2.75-2.53 (2, 4H), 2.37-2.33 (m, 2H), 2.16-1.95 (m, 7H), 1.66-1.65 (m, 1H), 1.38-1.33 (m, 8H).

Examples 190-294

Using the same processes as in Examples 183, 185 and 186, the compounds of Examples 190-294 were synthesized. The compound structures and specific characterization data (LC-MS and $^1$H NMR) were as follows:

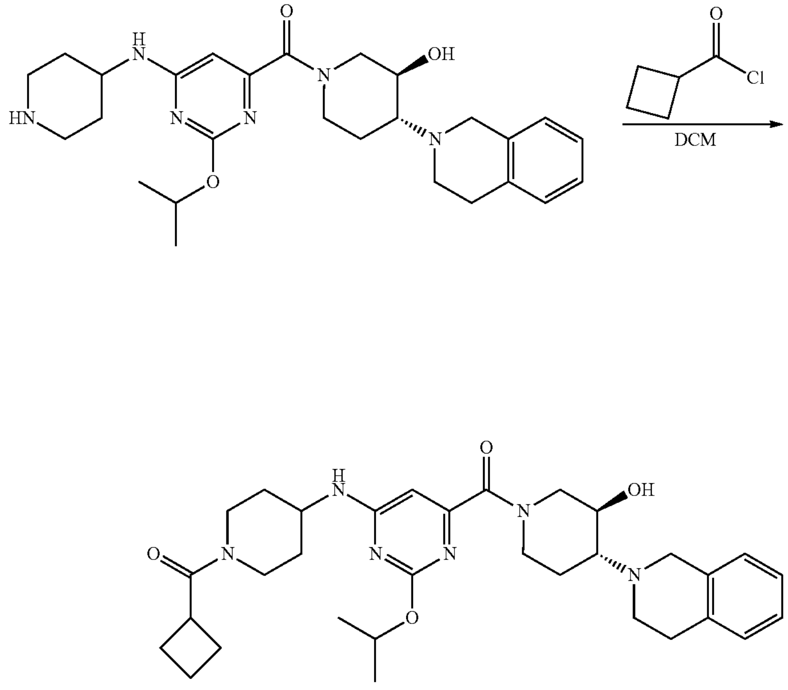

| Ex. | Structure | $^1$H NMR | LC-MS (ESI) [M + H]$^+$ |
|---|---|---|---|
| 190 | 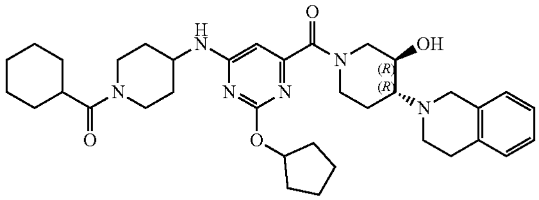 | (400 MHz, DMSO-$d_6$) δ 7.67-7.47 (m, 1H), 7.14-6.99 (m, 4H), 6.37-6.08 (m, 1H), 5.33-5.13 (m, 1H), 4.88-4.60 (m, 1H), 4.51-4.21 (m, 2H), 4.14-3.99 (m, 1H), 3.97-3.86 (m, 1H), 3.85-3.71 (m, 3H), 3.68-3.50 (m, 1H), 3.25-3.10 (m, 1H), 3.07-2.76 (m, 6H), 2.71-2.54 (m, 3H), 2.02-1.80 (m, 5H), 1.77-1.67 (m, 6H), 1.64-1.45 (m, 6H), 1.40-1.27 (m, 2H), 1.24-1.10 (m, 2H). | 631.0 |
| 191 | 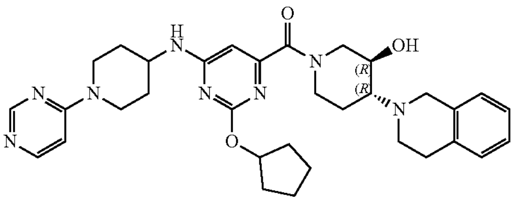 | (400 MHz, DMSO-$d_6$) δ 8.49 (s, 1H), 8.16 (d, J = 6.0Hz, 1H), 7.62-7.58 (m, 1H), 7.10-7.02 (m, 4H), 6.86 (d, J = 6.4Hz, 1H), 6.36-6.15 (m, 1H), 5.25-5.20 (m, 1H), 4.80-4.71 (m, 1H), 4.46-4.30 (m, 3H), 4.15 (s, 1H), 3.86-3.75 (m, 3H), 3.69-3.53 (m, 1H), 3.22-3.04 (m, 2H), 3.0-2.86 (m, 2H), 2.83-2.67 (m, 4H), 2.64-2.54 (m, 1H), 1.94-1.85 (m, 4H), 1.81-1.70 (m, 5H), 1.57-1.47 (m, 3H), 1.42-1.34 (m, 2H). | 599.0 |
| 192 | 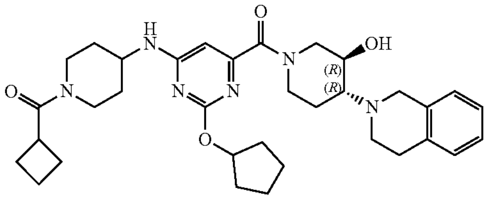 | (400 MHz, DMSO-$d_6$) δ 7.59-7.56 (m, 1H), 7.09-7.02 (m, 4H), 6.32-6.15 (m, 1H), 5.24-5.20 (m, 1H), 4.81-4.69 (m, 1H), 4.47-4.30 (m, 1H), 4.23-4.21 (m, 1H), 4.04 (s, 1H), 3.86-3.73 (m, 3H), 3.68-3.60 (m, 2H), 3.39-3.32 (m, 1H), 3.11-3.02 (m, 1H), 2.91-2.74 (m, 6H), 2.72-2.54 (m, 2H), 2.20-2.07 (m, 4H), 1.92-1.85 (m, 5H), 1.76-1.69 (m, 6H), 1.57-1.44 (m, 3H), 1.29-1.24 (m, 2H). | 603.0 |
| 193 | 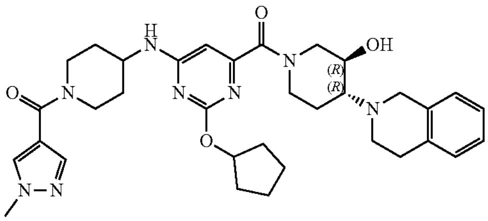 | (400 MHz, DMSO-$d_6$) δ 8.04 (s, 1H), 7.68-7.55 (m, 2H), 7.10-7.00 (m, 4H), 6.16 (s, 1H), 5.31-5.13 (m, 1H), 4.85-4.66 (m, 1H), 4.51-4.31 (m, 1H), 4.25-4.04 (m, 3H), 3.85 (s, 3H), 3.83-3.71 (m, 3H), 3.65-3.50 (m, 1H), 3.04-2.75 (m, 7H), 2.69-2.55 (m, 2H), 2.01-1.84 (m, 4H), 1.76-1.64 (m, 5H), 1.61-1.50 (m, 2H), 1.44-1.32 (m, 3H). | 629.0 |
| 194 | 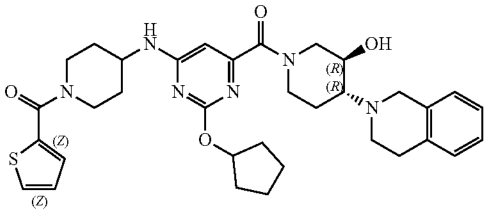 | (400 MHz, DMSO-$d_6$) δ 7.75 (d, J = 5.0 Hz, 1H), 7.69-7.60 (m, 1H), 7.43-7.35 (m, 1H), 7.13 (t, J = 4.1 Hz, 1H), 7.10-7.07 (m, 3H), 7.06-6.99 (m, 1H), 6.23-6.08 (m, 1H), 5.31-5.15 (m, 1H), 4.84-4.65 (m, 1H), 4.50-4.30 (m, 1H), 4.25-4.09 (m, 3H), 3.88-3.71 (m, 3H), 3.68-3.54 (m, 1H), 3.04-2.75 (m, 7H), 2.69-2.55 (m, 2H), 2.06-1.85 (m, 4H), 1.81-1.68 (m, 5H), 1.62-1.54 (m, 2H), 1.50-1.37 (m, 3H). | 631.0 |
| 195 | 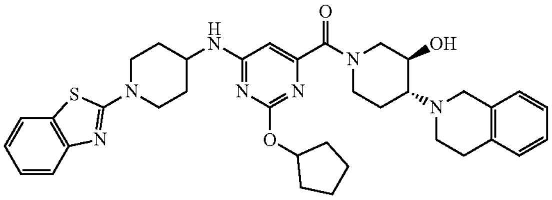 | (400 MHz, $CDCl_3$) δ 7.63-7.58 (m, 1H), 7.58-7.53 (m, 1H), 7.33-7.28 (m, 1H), 7.18-7.06 (m, 4H), 7.06-7.01 (m, 1H), 6.26-6.18 (m, 1H), 5.38-5.28 (m, 1H), 5.07-4.72 (m, 2H), 4.33-4.20 (m, 1H), 4.19-4.12 (m, 2H), 4.00-3.90 (m, 1H), 3.75-3.65 (m, 2H), 3.38-3.23 (m, 2H), 3.09-2.99 (m, 1H), 2.96-2.89 (m, 2H), 2.83-2.56 (m, 3H), 2.23-2.11 (m, 2H), 2.00-1.78 (m, 7H), 1.68-1.53 (m, 7H). | 654.3 |
| 196 | 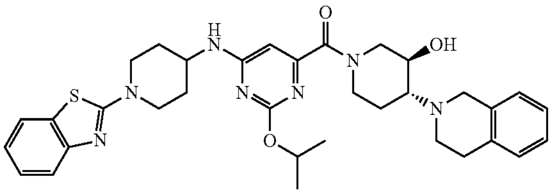 [SMILES: CC(C)Oc1nc(NC2CCN(c3nc4ccccc4s3)CC2)cc(C(=O)N2CC[C@@H](N3CCc4ccccc4C3)[C@H](O)C2)n1] | (400 MHz, DMSO-$d_6$) δ 10.29-9.97 (m, 1H), 7.99 (s, 1H), 7.80-7.74 (m, 1H), 7.49-7.43 (m, 1H), 7.32-7.18 (m, 5H), 7.11-7.04 (m, 1H), 6.36-5.96 (m, 2H), 5.21-5.05 (m, 1H), 4.74-4.34 (m, 3H), 4.24-4.12 (m, 1H), 4.10-3.84 (m, 4H), 3.81-3.67 (m, 1H), 3.61-3.48 (m, 3H), 3.26-2.61 (m, 5H), 2.35-2.15 (m, 1H), 2.13-1.94 (m, 2H), 1.87-1.69 (m, 1H), 1.66-1.49 (m, 2H), 1.36-1.20 (m, 6H). | 628.0 |

-continued

| Ex. | Structure | $^1$H NMR | LC-MS (ESI) [M + H]$^+$ |
| --- | --- | --- | --- |
| 197 | 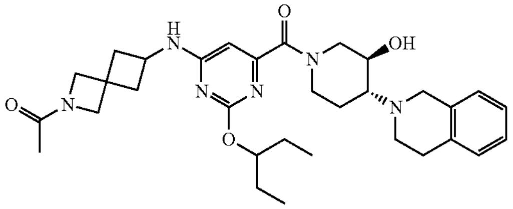 [SMILES: CCC(CC)Oc1nc(NC2CC3(C2)CN(C(C)=O)C3)cc(C(=O)N2CC[C@@H](N3CCc4ccccc4C3)[C@H](O)C2)n1] | (400 MHz, $CDCl_3$) δ 7.18-7.10 (m, 3H), 7.06-7.01 (m, 1H), 6.19-6.08 (m, 1H), 5.27-5.11 (m, 1H), 5.04-4.66 (m, 2H), 4.28-4.12 (m, 2H), 4.10-4.04 (m, 2H), 4.03-3.92 (m, 2H), 3.80-3.63 (m, 2H), 3.11-3.00 (m, 1H), 2.99-2.87 (m, 2H), 2.84-2.55 (m, 5H), 2.18-2.06 (m, 2H), 2.03-1.94 (m, 1H), 1.88-1.82 (m, 3H), 1.77-1.52 (m, 7H), 1.06-0.75 (m, 6H). | 577.1 |
| 198 | 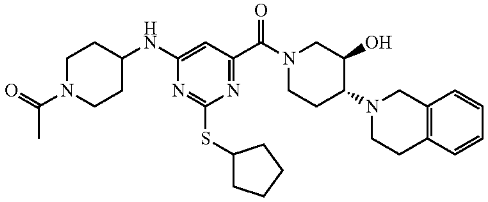 [SMILES: CC(=O)N1CCC(Nc2cc(C(=O)N3CC[C@@H](N4CCc5ccccc5C4)[C@H](O)C3)nc(SC3CCCC3)n2)CC1] | (400 MHz, DMSO-$d_6$) δ 10.64-10.02 (m, 1H), 8.10-7.70 (m, 1H), 7.31-7.14 (m, 4H), 6.57-5.84 (m, 2H), 4.75-4.37 (m, 3H), 4.30-4.18 (m, 1H), 4.14-3.64 (m, 7H), 3.41-3.22 (m, 2H), 3.22-2.93 (m, 3H), 2.89-2.63 (m, 2H), 2.34-2.08 (m, 3H), 2.04-1.98 (m, 3H), 1.96-1.50 (m, 9H), 1.47-1.23 (m, 2H). | 579.4 |
| 199 | 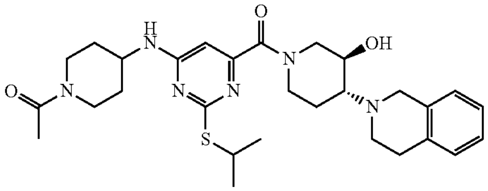 [SMILES: CC(=O)N1CCC(Nc2cc(C(=O)N3CC[C@@H](N4CCc5ccccc5C4)[C@H](O)C3)nc(SC(C)C)n2)CC1] | (400 MHz, DMSO-$d_6$) δ 10.50-10.00 (m, 1H), 8.13-7.70 (m, 1H), 7.40-7.01 (m, 4H), 6.57-5.89 (m, 2H), 4.77-4.35 (m, 3H), 4.30-4.01 (m, 2H), 3.99-3.74 (m, 6H), 3.45-3.24 (m, 2H), 3.23-2.93 (m, 3H), 2.89-2.62 (m, 2H), 2.38-2.08 (m, 1H), 2.06-1.98 (m, 3H), 1.95-1.68 (m, 3H), 1.47-1.24 (m, 8H). | 553.14 |
| 200 | 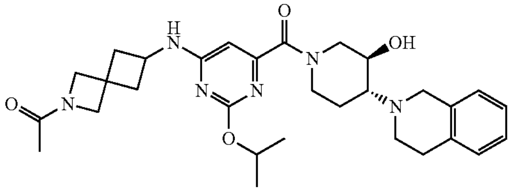 [SMILES: CC(=O)N1CC2(CC(Nc3cc(C(=O)N4CC[C@@H](N5CCc6ccccc6C5)[C@H](O)C4)nc(OC(C)C)n3)C2)C1] | (400 MHz, $CDCl_3$) δ 7.19-7.10 (m, 3H), 7.07-6.99 (m, 1H), 6.22-6.12 (m, 1H), 5.30-5.12 (m, 2H), 5.05-4.71 (m, 1H), 4.31-4.13 (m, 2H), 4.10-4.04 (m, 2H), 4.03-3.92 (m, 2H), 3.81-3.66 (m, 2H), 3.12-3.01 (m, 1H), 3.00-2.89 (m, 2H), 2.84-2.56 (m, 5H), 2.19-2.07 (m, 2H), 2.05-1.95 (m, 1H), 1.91-1.82 (m, 4H), 1.74-1.59 (m, 2H), 1.40-1.29 (m, 6H). | 549.21 |
| 201 | 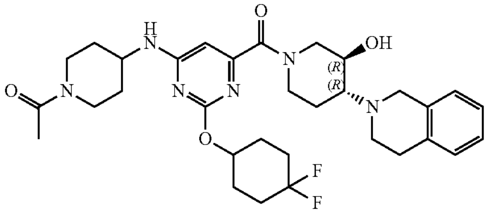 | (400 MHz, DMSO-$d_6$) δ 7.71-7.57 (m, 1H), 7.14-6.96 (m, 4H), 6.42-6.10 (m, 1H), 5.09-4.97 (m, 1H), 4.82-4.67 (m, 1H), 4.51-4.18 (m, 2H), 4.12-3.99 (m, 1H), 3.89-3.70 (m, 4H), 3.66-3.56 (m, 1H), 3.27-3.09 (m, 1H), 3.05-2.76 (m, 6H), 2.70-2.54 (m, 2H), 2.10-1.97 (m, 8H), 1.94-1.71 (m, 6H), 1.57-1.44 (m, 1H), 1.40-1.18 (m, 2H). | 613.4 |
| 202 | 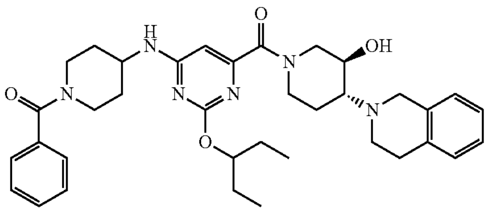 [SMILES: CCC(CC)Oc1nc(NC2CCN(C(=O)c3ccccc3)CC2)cc(C(=O)N2CC[C@@H](N3CCc4ccccc4C3)[C@H](O)C2)n1] | (400 MHz, DMSO-$d_6$) δ 10.23-10.02 (m, 1H), 8.06-7.02 (s, 0.6H), 7.46-7.38 (m, 5H), 7.34-7.15 (m, 4H), 6.28 (s, 1H), 6.05-5.94 (m, 0.6H), 4.88-4.83 (m, 1H), 4.71-4.20 (m, 4H), 4.12-3.69 (m, 6H), 3.46-2.95 (m, 7H), 1.85-1.64 (m, 1H), 2.33-1.72 (m, 4H), 1.63 (d, J = 6.4 Hz, 4H), 1.44-1.27 (m, 2H), 0.91-0.80 (m, 6H). | 627.3 |
| 203 | 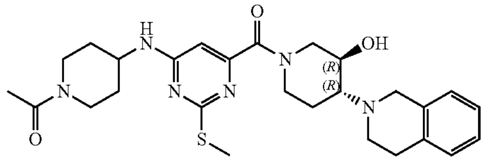 | (400 MHz, DMSO-$d_6$) δ 7.70-7.67 (m, 1H), 7.09-7.01 (m, 4H), 6.25-6.24 (m, 1H), 4.82-4.72 (m, 1H), 4.45-4.30 (m, 1H), 4.07-4.04 (m, 1H), 3.86-3.70 (m, 4H), 3.61-3.60 (m, 1H), 3.18-3.15 (m, 1H), 3.03-2.78 (m, 6H), 2.73-2.58 (m, 2H), 2.43-2.41 (m, 3H), 2.01-2.00 (m, 3H), 1.95-1.73 (m, 3H), 1.50-1.25 (m, 3H). | 525.2 |

-continued

| Ex. | Structure | $^1$H NMR | LC-MS (ESI) [M + H]$^+$ |
| --- | --- | --- | --- |
| 204 | 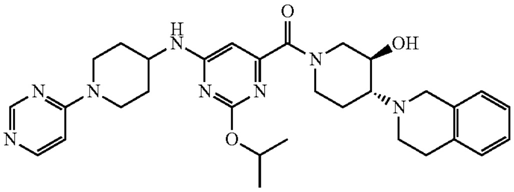 [SMILES: CC(C)Oc1nc(NC2CCN(c3ccncn3)CC2)cc(C(=O)N2CC[C@@H](N3CCc4ccccc4C3)[C@H](O)C2)n1] | (400 MHz, $CD_3OD$) δ 8.47-8.41 (m, 1H), 8.10 (d, J = 6.4 Hz, 1H), 7.13-6.99 (m, 4H), 6.81 (d, J = 6.4 Hz, 1H), 6.17 (d, J = 6.4 Hz, 1H), 5.31-5.18 (m, 1H), 4.71-4.50 (m, 1H), 4.44 (d, J = 12.0 Hz, 2H), 4.24 (s, 1H), 3.94 (d, J = 14.8 Hz, 1H), 3.91-3.73 (m, 3H), 3.19 (t, J = 12.4 Hz, 2H), 3.14-2.94 (m, 2H), 2.93-2.77 (m, 4H), 2.77-2.64 (m, 1H), 2.10 (d, J = 12.8 Hz, 2H), 2.04-1.85 (m, 1H), 1.74-1.59 (m, 1H), 1.58-1.45 (m, 2H), 1.41-1.30 (m, 6H). | 573.4 |
| 205 | 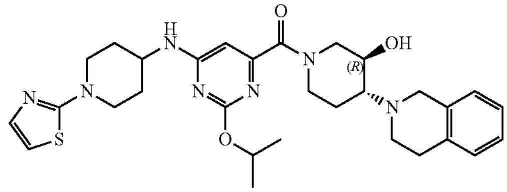 | (400 MHz, $CDCl_3$) δ 7.21-7.09 (m, 4H), 7.07-7.00 (m, 1H), 6.57 (d, J = 3.6 Hz, 1H), 6.24-6.19 (m, 1H), 5.24-5.11 (m, 1H), 5.09-4.97 (m, 1H), 4.77-4.74 (m, 1H), 4.31-4.15 (m, 1H), 4.00-3.94 (m, 3H), 3.84-3.63 (m, 3H), 3.27-3.14 (m, 2H), 3.09-2.90 (m, 4H), 2.81-2.57 (m, 3H), 2.13-2.11 (m, 2H), 2.00-1.86 (m, 1H), 1.67-1.54 (m, 3H), 1.40-1.30 (m, 6H). | 578.3 |
| 206 | 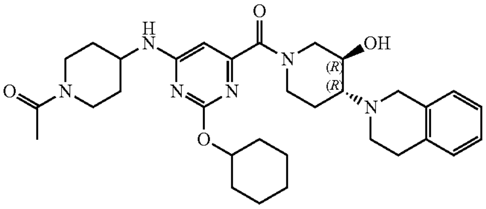 | (400 MHz, $CDCl_3$) δ 7.18-7.10 (m, 3H), 7.05-6.99 (m, 1H), 6.30-6.15 (m, 1H), 5.07-4.75 (m, 3H), 4.52 (d, J = 13.7 Hz, 1H), 4.34-4.20 (m, 1H), 4.03-3.92 (m, 1H), 3.85-3.63 (m, 4H), 3.28-3.14 (m, 1H), 3.12-2.89 (m, 4H), 2.86-2.59 (m, 4H), 2.15-2.09 (m, 4H), 2.09-1.92 (m, 4H), 1.91-1.70 (m, 3H), 1.69-1.60 (m, 2H), 1.51-1.19 (m, 6H). | 577.40 |
| 207 | 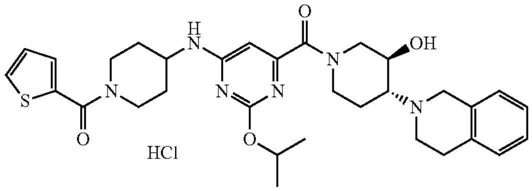 [SMILES: CC(C)Oc1nc(NC2CCN(C(=O)c3cccs3)CC2)cc(C(=O)N2CC[C@@H](N3CCc4ccccc4C3)[C@H](O)C2)n1 ; Cl] HCl | (400 MHz, $CDCl_3$) δ 7.46-7.44 (m, 1H), 7.31-7.28 (m, 1H), 7.19-7.09 (m, 3H), 7.08-7.00 (m, 2H), 6.25-6.20 (m, 1H), 5.38-5.15 (m, 2H), 5.04-4.72 (m, 1H), 4.46-4.14 (m, 4H), 3.96-3.92 (m, 1H), 3.74-3.62 (m, 2H), 3.28-3.11 (m, 2H), 3.08-3.00 (m, 1H), 2.97-2.86 (m, 3H), 2.82-2.57 (m, 3H), 2.14-2.05 (m, 2H), 2.00-1.95 (m, 1H), 1.87-1.84 (m, 1H), 1.73-1.59 (m, 2H), 1.41-1.30 (m, 6H). | 605.2 |
| 208 | 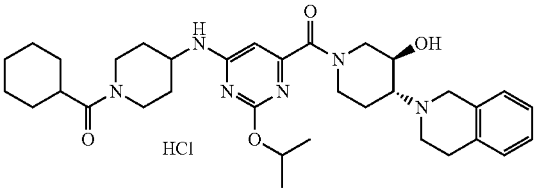 [SMILES: CC(C)Oc1nc(NC2CCN(C(=O)C3CCCCC3)CC2)cc(C(=O)N2CC[C@@H](N3CCc4ccccc4C3)[C@H](O)C2)n1 ; Cl] HCl | (400 MHz, $CDCl_3$) δ 7.19-7.09 (m, 3H), 7.05-6.97 (m, 1H), 6.23-6.18 (m, 1H), 5.32-5.14 (m, 2H), 5.02-4.72 (m, 1H), 4.53-4.50 (m, 1H), 4.30-4.14 (m, 1H), 3.96-3.92 (m, 2H), 3.74-3.62 (m, 2H), 3.20-3.14 (m, 1H), 3.06-3.02 (m, 1H), 2.98-2.88 (m, 3H), 2.84-2.42 (m, 6H), 2.17-2.10 (m, 1H), 2.04-1.93 (m, 2H), 1.89-1.80 (m, 4H), 1.77-1.72 (m, 1H), 1.66-1.61 (m, 1H), 1.57-1.47 (m, 2H), 1.42-1.31 (m, 8H), 1.29-1.24 (m, 3H). | 605.4 |
| 209 | 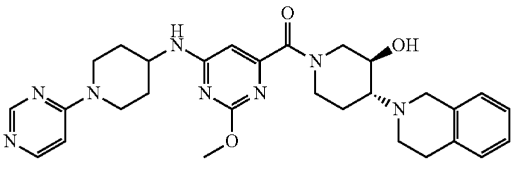 [SMILES: COc1nc(NC2CCN(c3ccncn3)CC2)cc(C(=O)N2CC[C@@H](N3CCc4ccccc4C3)[C@H](O)C2)n1] | (400 MHz, $CD_3OD$) δ 8.44 (s, 1H), 8.10 (d, J = 6.4 Hz, 1H), 7.13-7.00 (m, 4H), 6.81 (d, J = 6.4 Hz, 1H), 6.31-6.14 (m, 1H), 4.72-4.51 (m, 1H), 4.44 (d, J = 11.2 Hz, 2H), 4.32-4.20 (m, 1H), 4.02-3.96 (m, 1H), 3.94 (d, J = 8.0 Hz, 3H), 3.91-3.76 (m, 2H), 3.20 (t, J = 12.4 Hz, 2H), 3.15-2.97 (m, 2H), 2.96-2.84 (m, 4H), 2.83-2.65 (m, 2H), 2.16-2.06 (m, 2H), 2.05-1.86 (m, 1H), 1.76-1.62 (m, 1H), 1.57-1.44 (m, 2H). | 545.4 |
| 210 | 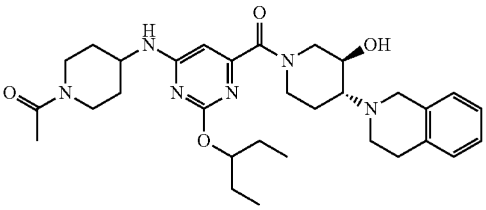 [SMILES: CCC(CC)Oc1nc(NC2CCN(C(C)=O)CC2)cc(C(=O)N2CC[C@@H](N3CCc4ccccc4C3)[C@H](O)C2)n1] | (400 MHz, $CDCl_3$) δ 7.17-7.10 (m, 3H), 7.03-7.01 (m, 1H), 6.22-6.17 (m, 1H), 5.29-5.17 (m, 1H), 5.00-4.90 (m, 1H), 4.77-4.74 (m, 1H), 4.51-4.47 (m, 1H), 4.24-4.12 (m, 1H), 3.96-3.92 (m, 1H), 3.81-3.78 (m, 1H), 3.72-3.62 (m, 2H), 3.24-3.21 (m, 1H), 3.06-2.64 (m, 9H), 2.11-2.10 (m, 4H), 2.02-1.94 (m, 2H), 1.70-1.60 (m, 5H), 1.41-1.38 (m, 2H), 0.96-0.89 (m, 6H). | 565.4 |

-continued

| Ex. | Structure | $^1$H NMR | LC-MS (ESI) [M + H]$^+$ |
|---|---|---|---|
| 211 | 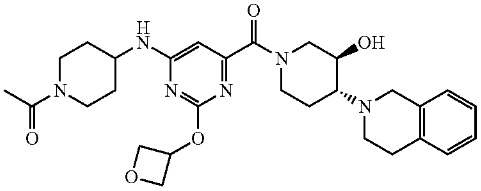 [SMILES: CC(=O)N1CCC(Nc2cc(C(=O)N3CC[C@@H](N4CCc5ccccc5C4)[C@H](O)C3)nc(OC3COC3)n2)CC1] | (400 MHz, $(CD_3)_2SO$) δ 7.84-7.69 (m, 1H), 7.16-6.97 (m, 4H), 6.30-6.13 (m, 1H), 5.52-5.35 (m, 1H), 4.91-4.67 (m, 3H), 4.65-4.51 (m, 2H), 4.49-4.17 (m, 2H), 4.06-3.92 (m, 1H), 3.88-3.65 (m, 4H), 3.64-3.52 (m, 1H), 3.26-3.10 (m, 1H), 3.04-2.71 (m, 7H), 2.69-2.58 (m, 1H), 2.06-1.96 (m, 3H), 1.97-1.67 (m, 3H), 1.60-1.15 (m, 3H). | 551.5 |
| 212 | 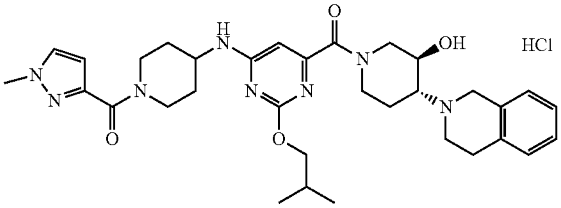 [SMILES: CC(C)COc1nc(NC2CCN(C(=O)c3ccn(C)n3)CC2)cc(C(=O)N2CC[C@@H](N3CCc4ccccc4C3)[C@H](O)C2)n1 ; Cl] HCl | (400 MHz, $(CD_3)_2SO$) δ 10.48-10.17 (m, 1H), 8.31-7.83 (m, 1H), 7.79-7.73 (m, 1H), 7.33-7.16 (m, 4H), 6.55-6.48 (m, 1H), 6.37-5.99 (m, 2H), 4.78-4.31 (m, 5H), 4.24-4.10 (m, 1H), 4.07-3.92 (m, 4H), 3.88 (s, 3H), 3.81-3.68 (m, 1H), 3.62-3.51 (m, 2H), 3.37-3.19 (m, 1H), 3.17-2.64 (m, 5H), 2.32-2.10 (m, 1H), 2.07-1.73 (m, 4H), 1.53-1.34 (m, 2H), 1.02-0.91 (m, 6H). | 617.2 |
| 213 | HCl 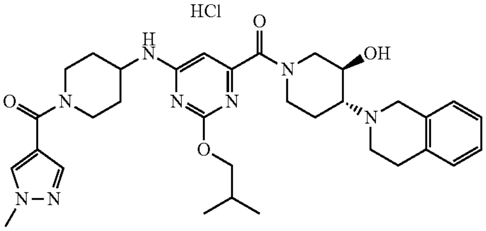 [SMILES: Cl ; CC(C)COc1nc(NC2CCN(C(=O)c3cnn(C)c3)CC2)cc(C(=O)N2CC[C@@H](N3CCc4ccccc4C3)[C@H](O)C2)n1] | (400 MHz, $(CD_3)_2SO$) δ 10.64-10.08 (m, 1H), 8.26-8.05 (m, 2H), 7.64 (s, 1H), 7.30-7.18 (m, 4H), 6.48-6.04 (m, 2H), 4.68-4.45 (m, 3H), 4.15-4.02 (m, 5H), 3.85 (s, 3H), 3.78-3.75 (m, 2H), 3.56-2.66 (m, 9H), 2.33-2.15 (m, 1H), 2.01-1.75 (m, 4H), 1.49-1.39 (m, 2H), 0.97-0.94 (m, 6H). | 617.2 |
| 214 | HCl 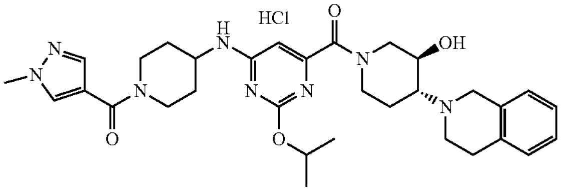 [SMILES: CC(C)Oc1nc(NC2CCN(C(=O)c3cnn(C)c3)CC2)cc(C(=O)N2CC[C@@H](N3CCc4ccccc4C3)[C@H](O)C2)n1 ; Cl] | (400 MHz, $(CD_3)_2SO$) δ 10.64-10.44 (m, 1H), 8.18 (s, 1H), 8.05 (s, 1H), 7.64 (s, 1H), 7.29-7.18 (m, 4H), 6.49-6.11 (m, 2H), 5.17-5.11 (m, 1H), 4.72-4.42 (m, 3H), 4.31-4.11 (m, 3H), 4.02-3.96 (m, 2H), 3.85 (s, 3H), 3.78-3.55 (m, 3H), 3.40-2.99 (m, 5H), 2.89-2.65 (m, 1H), 2.38-2.07 (m, 1H), 1.94-1.77 (m, 3H), 1.45-1.38 (m, 2H), 1.30-1.27 (m, 6H). | 603.2 |
| 215 | 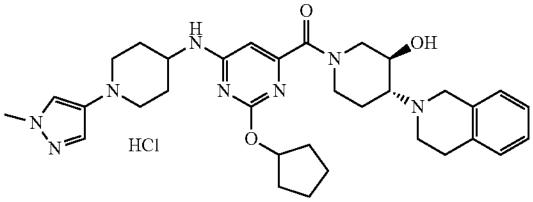 [SMILES: Cn1cc(N2CCC(Nc3cc(C(=O)N4CC[C@@H](N5CCc6ccccc6C5)[C@H](O)C4)nc(OC4CCCC4)n3)CC2)cn1 ; Cl] HCl | (400 MHz, $(CD_3)_2SO$) δ 10.09-9.98 (m, 1H), 7.87 (s, 1H), 7.30-7.18 (m, 4H), 6.27-5.81 (m, 2H), 5.24 (s, 1H), 4.63-4.39 (m, 3H), 4.01-3.92 (m, 3H), 3.79-3.71 (m, 4H), 3.53-3.46 (m, 6H), 3.23-3.17 (m, 2H), 3.04-2.95 (m, 2H), 2.84-2.65 (m, 2H), 2.26-1.91 (m, 6H), 1.71-1.69 (s, 6H), 1.57-1.58 (m, 2H). | 601.2 |
| 216 | HCl 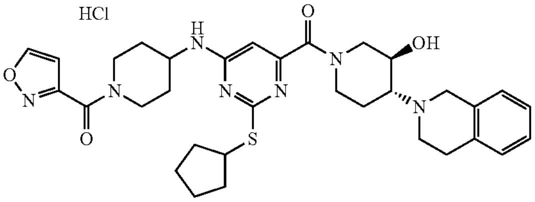 [SMILES: O=C(c1ccon1)N1CCC(Nc2cc(C(=O)N3CC[C@@H](N4CCc5ccccc5C4)[C@H](O)C3)nc(SC3CCCC3)n2)CC1 ; Cl] | (400 MHz, $(CD_3)_2SO$) δ 10.45-10.07 (m, 1H), 9.10-9.09 (m, 1H), 8.15-7.83 (m, 1H), 7.27-7.17 (m, 4H), 6.82-6.81 (m, 1H), 6.51-6.07 (m, 2H), 4.66-4.34 (m, 5H), 4.20-4.13 (m, 1H), 3.78-3.68 (m, 3H), 3.54-2.65 (m, 9H), 2.33-2.17 (m, 2H), 2.03-2.00 (m, 2H), 1.83-1.46 (m, 10H). | 632.2 |
| 217 | 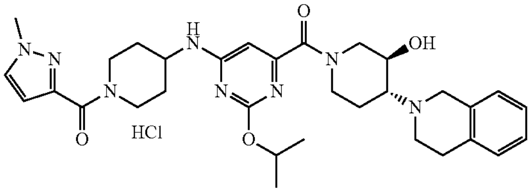 [SMILES: CC(C)Oc1nc(NC2CCN(C(=O)c3ccn(C)n3)CC2)cc(C(=O)N2CC[C@@H](N3CCc4ccccc4C3)[C@H](O)C2)n1 ; Cl] HCl | (400 MHz, $(CD_3)_2SO$) δ 10.52-10.00 (m, 1H), 7.96-7.75 (m, 2H), 7.27-7.18 (m, 4H), 6.52-6.51 (m, 1H), 6.28-6.00 (m, 2H), 5.16-5.08 (m, 1H), 4.65-4.39 (m, 5H), 4.19-4.11 (m, 1H), 3.99-3.87 (m, 5H), 3.76-3.70 (m, 1H), 3.40-3.09 (m, 4H), 3.03-2.64 (m, 4H), 2.33-2.14 (m, 1H), 1.97-1.72 (m, 3H), 1.45-1.38 (m, 2H), 1.29-1.26 (m, 6H). | 603.2 |

-continued

| Ex. | Structure | $^1$H NMR | LC-MS (ESI) [M + H]$^+$ |
| --- | --- | --- | --- |
| 218 | 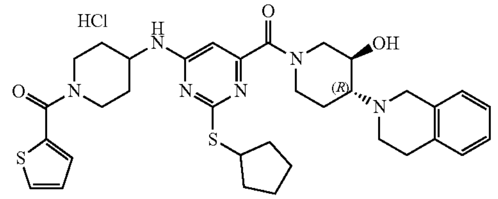 | (400 MHz, $(CD_3)_2SO$) δ 10.50-10.10 (m, 1H), 8.05-7.86 (m, 1H), 7.76 (dd, J = 5.0, 1.3 Hz, 1H), 7.40 (t, J = 2.8 Hz, 1H), 7.31-7.11 (m, 5H), 6.60-5.87 (m, 2H), 4.74-4.36 (m, 3H), 4.32-4.04 (m, 3H), 4.02-3.66 (m, 4H), 3.61-3.52 (m, 1H), 3.39-2.94 (m, 6H), 2.91-2.61 (m, 1H), 2.25-2.05 (m, 3H), 2.04-1.88 (m, 2H), 1.85-1.39 (m, 9H). | 647.0 |
| 219 | 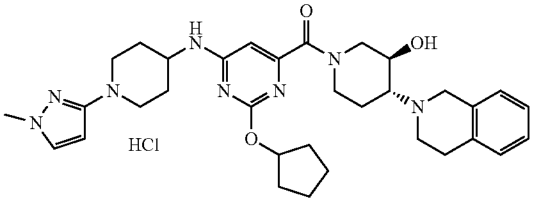 [SMILES: Cn1ccc(N2CCC(Nc3cc(C(=O)N4CC[C@@H](N5CCc6ccccc6C5)[C@H](O)C4)nc(OC4CCCC4)n3)CC2)n1 ; Cl] | (400 MHz, $(CD_3)_2SO$) δ 10.39-10.04 (m, 1H), 7.47 (s, 1H), 7.34-7.16 (m, 4H), 6.29 (s, 1H), 5.75 (s, 1H), 5.28 (s, 1H), 4.69-4.42 (m, 3H), 4.26-3.86 (m, 6H), 3.80-3.72 (m, 1H), 3.68-3.54 (m, 6H), 3.52-3.23 (m, 2H), 3.05-2.99 (m, 1H), 2.94-2.63 (m, 3H), 2.22-2.08 (m, 1H), 2.00-1.85 (m, 4H), 1.82-1.66 (m, 5H), 1.63-1.50 (m, 4H). | 601.3 |
| 220 | 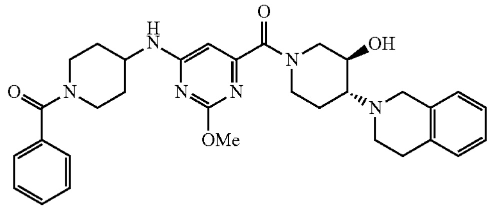 [SMILES: COc1nc(NC2CCN(C(=O)c3ccccc3)CC2)cc(C(=O)N2CC[C@@H](N3CCc4ccccc4C3)[C@H](O)C2)n1] | (400 MHz, $CDCl_3$) δ 7.48-7.37 (m, 5H), 7.19-7.09 (m, 3H), 7.05-6.98 (m, 1H), 6.31-6.22 (m, 1H), 5.42-5.29 (m, 1H), 5.22-4.98 (m, 1H), 4.81-4.68 (m, 1H), 4.32-4.14 (m, 2H), 3.94 (s, 3H), 3.92-3.88 (m, 1H), 3.83-3.65 (m, 3H), 3.25-3.05 (m, 3H), 3.01-2.88 (m, 3H), 2.85-2.76 (m, 1H), 2.76-2.58 (m, 2H), 1.97-1.82 (m, 4H), 1.75-1.60 (m, 2H). | 571.3 |
| 221 | 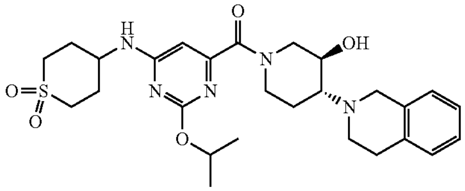 [SMILES: CC(C)Oc1nc(NC2CCS(=O)(=O)CC2)cc(C(=O)N2CC[C@@H](N3CCc4ccccc4C3)[C@H](O)C2)n1] | (400 MHz, $CDCl_3$) δ 7.19-7.09 (m, 3H), 7.07-7.00 (m, 1H), 6.34-6.21 (m, 1H), 5.89-5.57 (m, 1H), 5.28-5.13 (m, 1H), 5.03-4.70 (m, 1H), 4.36-4.13 (m, 2H), 4.04-3.91 (m, 1H), 3.86-3.57 (m, 3H), 3.22-2.89 (m, 8H), 2.86-2.53 (m, 3H), 2.44-2.29 (m, 2H), 2.25-2.12 (m, 2H), 2.06-1.93 (m, 1H), 1.91-1.70 (m, 1H), 1.40-1.32 (m, 6H). | 544.38 |
| 222 | 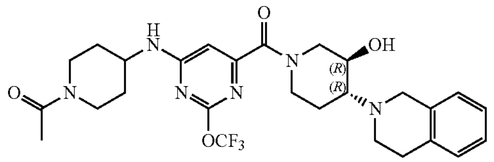 | (400 MHz, $CD_3OD$) δ 7.12-7.06 (m, 3H), 7.05-7.00 (m, 1H), 6.51-6.48 (m, 1H), 4.72-4.49 (m, 1H), 4.42 (d, J = 13.2 Hz, 1H), 4.18-4.07 (m, 1H), 4.00-3.84 (m, 4H), 3.83-3.73 (m, 1H), 3.63-3.43 (m, 1H), 3.15-2.96 (m, 2H), 2.95-2.88 (m, 4H), 2.87-2.67 (m, 2H), 2.12 (s, 3H), 2.10-1.87 (m, 3H), 1.74-1.63 (m, 1H), 1.56-1.37 (m, 2H). | 563.3 |
| 223 | 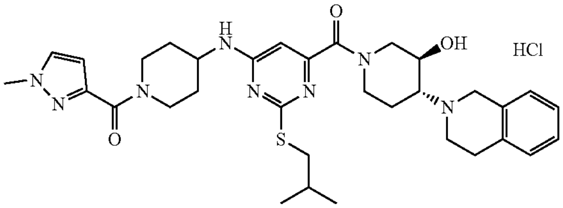 [SMILES: CC(C)CSc1nc(NC2CCN(C(=O)c3ccn(C)n3)CC2)cc(C(=O)N2CC[C@@H](N3CCc4ccccc4C3)[C@H](O)C2)n1 ; Cl] | (400 MHz, $(CD_3)_2SO$) δ 10.40-9.95 (m, 1H), 7.97-7.90 (m, 1H), 7.79-7.72 (m, 1H), 7.32-7.15 (m, 4H), 6.54-6.50 (m, 1H), 6.35-5.93 (m, 2H), 4.71-4.33 (m, 5H), 4.21-4.08 (m, 1H), 4.01-3.83 (m, 5H), 3.80-3.68 (m, 1H), 3.60-3.51 (m, 1H), 3.36-3.17 (m, 3H), 3.16-2.89 (m, 5H), 2.88-2.64 (m, 1H), 2.32-2.08 (m, 1H), 2.02-1.68 (m, 4H), 1.52-1.34 (m, 2H), 1.06-0.95 (m, 6H). | 633.2 |
| 224 | 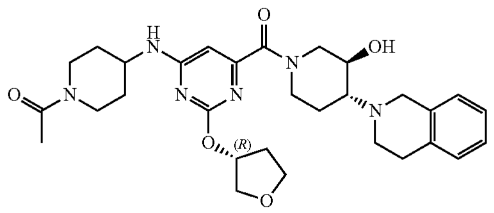 | (400MHz, $CDCl_3$) δ 7.17-7.13 (m, 3H), 7.04-7.02 (m, 1H), 6.29-6.24 (m, 1H), 5.47-5.41 (m, 1H), 5.18-4.75 (m, 2H), 4.79-4.51 (m, 2H), 4.1-4.06 (m, 1H), 4.02-3.99 (m, 3H), 3.98-3.95 (m, 2H), 3.93-3.90 (m, 2H), 3.87-3.80 (m, 1H), 3.25-3.18 (m, 1H), 3.07-2.91 (m, 4H), 2.85-2.60 (m, 4H), 2.24-1.89 (m, 9H), 1.42-1.39 (m, 2H). | 565.4 |

-continued

| Ex. | Structure | $^1$H NMR | LC-MS (ESI) [M + H]$^+$ |
| --- | --- | --- | --- |
| 225 | 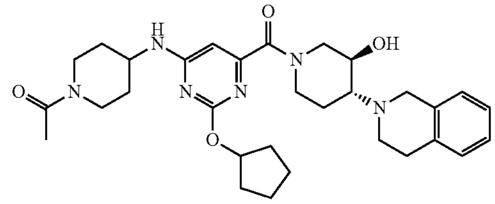 [SMILES: CC(=O)N1CCC(Nc2cc(C(=O)N3CC[C@@H](N4CCc5ccccc5C4)[C@H](O)C3)nc(OC3CCCC3)n2)CC1] | (400 MHz, $CDCl_3$) δ 7.21-7.10 (m, 3H), 7.08-7.01 (m, 1H), 6.22 (s, 1H), 5.37-5.26 (m, 1H), 5.06-4.71 (m, 2H), 4.57-4.46 (m, 1H), 4.32-4.18 (m, 1H), 4.05-3.96 (m, 1H), 3.85-3.70 (m, 3H), 3.26-3.17 (m, 1H), 3.14-2.55 (m, 8H), 2.11 (s, 3H), 2.08-1.78 (m, 8H), 1.71-1.53 (m, 6H), 1.45-1.36 (m, 2H). | 563.5 |
| 226 | 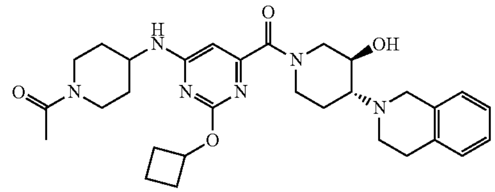 [SMILES: CC(=O)N1CCC(Nc2cc(C(=O)N3CC[C@@H](N4CCc5ccccc5C4)[C@H](O)C3)nc(OC3CCC3)n2)CC1] | (400 MHz, $CDCl_3$) δ 7.20-7.10 (m, 3H), 7.07-7.00 (m, 1H), 6.24 (s, 1H), 5.18-5.06 (m, 1H), 5.03-4.48 (m, 3H), 4.32-4.16 (m, 1H), 4.06-3.94 (m, 1H), 3.84-3.68 (m, 3H), 3.25-2.73 (m, 8H), 2.46-2.31 (m, 2H), 2.29-2.18 (m, 2H), 2.11 (s, 3H), 2.07-1.82 (m, 3H), 1.73-1.33 (m, 8H). | 549.4 |
| 227 | 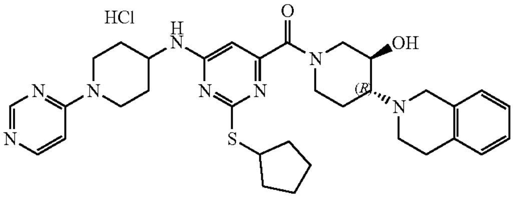 | (400 MHz, $(CD_3)_2SO$) δ 8.56 (s, 1H), 8.21 (d, J = 6.5 Hz, 1H), 8.00-7.64 (m, 1H), 7.30-7.13 (m, 4H), 6.96 (d, J = 6.6 Hz, 1H), 6.56-6.27 (m, 1H), 6.25-5.80 (m, 1H), 4.67-4.26 (m, 5H), 4.15 (s, 1H), 4.01-3.79 (m, 3H), 3.67-3.42 (m, 4H), 3.26-2.93 (m, 5H), 2.88-2.62 (m, 1H), 2.24-2.07 (m, 3H), 2.04-1.88 (m, 2H), 1.81-1.37 (m, 9H). | 615.0 |
| 228 | 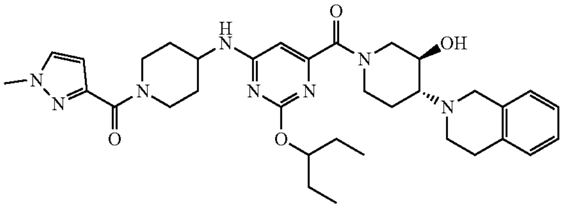 [SMILES: CCC(CC)Oc1nc(NC2CCN(C(=O)c3ccn(C)n3)CC2)cc(C(=O)N2CC[C@@H](N3CCc4ccccc4C3)[C@H](O)C2)n1] | (400 MHz, $CD_3OD$) δ 7.76-7.73 (m, 1H), 7.63-7.58 (m, 1H), 7.10-7.02 (m, 4H), 6.52 (t, J = 2.0 Hz, 1H), 6.16-6.11 (m, 1H), 4.88-4.67 (m, 2H), 4.56-4.32 (m, 3H), 4.13 (s, 1H), 3.88-3.70 (m, 6H), 3.61-3.57 (m, 1H), 3.02-2.73 (m, 6H), 2.67-2.52 (m, 3H), 1.97-1.73 (m, 3H), 1.60-1.39 (m, 7H), 0.90-0.84 (m, 6H). | 631.5 |
| 229 | 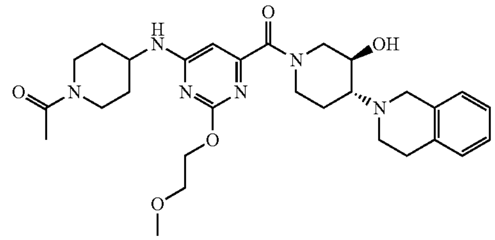 [SMILES: COCCOc1nc(NC2CCN(C(C)=O)CC2)cc(C(=O)N2CC[C@@H](N3CCc4ccccc4C3)[C@H](O)C2)n1] | (400 MHz, DMSO-$d_6$) δ 8.16 (s, 1H), 7.68-7.64 (m, 1H), 7.10-7.02 (m, 1H), 6.19 (d, J = 4.0 Hz, 1H), 4.82-4.73 (m, 1H), 4.46-4.22 (m, 4H), 4.05 (s, 1H), 3.86-3.71 (m, 4H), 3.64-3.54 (m, 4H), 3.21-2.96 (m, 3H), 2.92-2.79 (m, 6H), 2.68-2.60 (m, 1H), 2.01 (d, J = 1.2 Hz, 3H), 1.91-1.73 (m, 3H), 1.53-1.20 (m, 3H). | 553.4 |
| 230 | 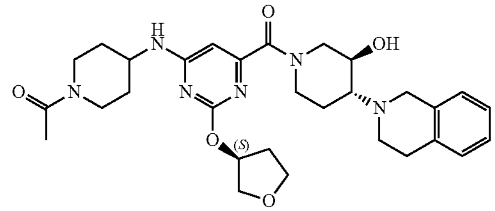 | (400 MHz, $CD_3OD$) δ 7.10-6.97 (m, 4H), 6.23-6.18 (m, 1H), 5.54-5.48 (m, 1H), 4.72-4.35 (m, 3H), 4.23-4.08 (m, 1H), 4.06-3.69 (m, 9H), 3.11-2.64 (m, 9H), 2.32-2.16 (m, 1H), 2.13-1.85 (m, 6H), 1.70-1.60 (m, 1H), 1.56-1.29 (m, 2H). | 565.4 |
| 231 | 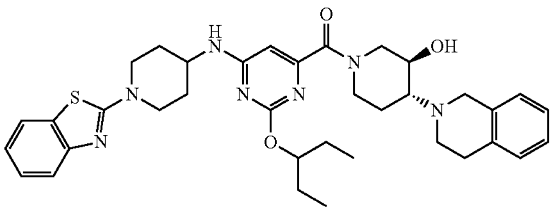 | (400 MHz, $CD_3OD$) δ 7.65 (d, J = 8.0 Hz, 1H), 7.47 (d, J = 8.0 Hz, 1H), 7.29 (t, J = 8.0 Hz, 1H), 7.11-7.03 (m, 5H), 6.22-6.12 (m, 1H), 5.02-4.98 (m, 1H), 4.70-4.53 (m, 1H), 4.25-4.11 (m, 3H), 3.96-3.78 (m, 4H), 3.48-3.36 (m, 2H), 3.13-2.85 (m, 6H), 2.77-2.66 (m, 1H), 2.20-2.08 (m, 2H), 2.03-1.86 (m, 1H), 1.73-1.61 (m, 7H), 0.99-0.94 (m, 6H). | 656.4 |

-continued
| Ex. | Structure | $^1$H NMR | LC-MS (ESI) [M + H]$^+$ |
| --- | --- | --- | --- |
| 232 | 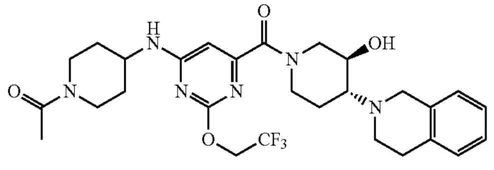 [SMILES: CC(=O)N1CCC(Nc2cc(C(=O)N3CC[C@@H](N4CCc5ccccc5C4)[C@H](O)C3)nc(OCC(F)(F)F)n2)CC1] | (400 MHz, $CD_3OD$) δ 7.11-7.05 (m, 4H), 6.31 (d, J = 8.8 Hz, 1H), 4.93-4.90 (m, 2H), 4.71-4.53 (m, 1H), 4.44 (d, J = 13.2 Hz, 1H), 4.24 (s, 1H), 3.97-3.80 (m, 5H), 3.06-2.88 (m, 7H), 2.77-2.75 (m, 2H), 2.14-1.89 (m, 6H), 1.73-1.67 (m, 1H), 1.53-1.43 (m, 2H). | 577.3 |
| 233 | 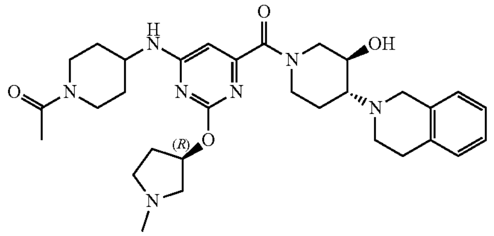 | (400 MHz, $CDCl_3$) δ 7.18-7.13 (m, 3H), 7.04-7.00 (m, 1H), 6.27-6.22 (m, 1H), 5.37-5.25 (m, 1H), 5.15-4.98 (m, 1H), 4.78-4.51 (m, 2H), 4.30-4.15 (m, 1H), 3.96-3.92 (m, 1H), 3.83-3.79 (m, 1H), 3.72-3.65 (m, 2H), 3.05-3.03 (m, 1H), 2.93-2.77 (m, 5H), 2.71-2.63 (m, 7H), 2.41-2.30 (m, 4H), 2.12-1.95 (m, 8H), 1.67-1.63 (m, 1H), 1.48-1.38 (m, 2H). | 578.4 |
| 234 | 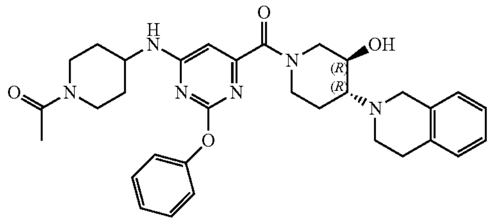 | (400 MHz, $CD_3OD$) δ 7.46-7.40 (m, 2H), 7.26-7.16 (m, 3H), 7.12-7.05 (m, 4H), 6.32 (d, J = 6.0 Hz, 1H), 4.68-4.51 (m, 1H), 4.40 (d, J = 13.2 Hz, 1H), 3.93-3.80 (m, 5H), 3.69 (brs, 1H), 3.15-2.91 (m, 5H), 2.85-2.62 (m, 4H), 2.11 (s, 3H), 2.02-1.75 (m, 3H), 1.60-1.34 (m, 3H). | 571.4 |
| 235 | 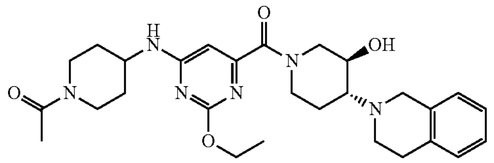 [SMILES: CCOc1nc(NC2CCN(C(C)=O)CC2)cc(C(=O)N2CC[C@@H](N3CCc4ccccc4C3)[C@H](O)C2)n1] | (400 MHz, $CD_3OD$) δ 7.12-7.05 (m, 4H), 6.20 (d, J = 7.6Hz, 1H), 4.77-4.67 (m, 2H), 4.45-4.36 (m, 3H), 4.21 (s, 1H), 4.97-4.80 (m, 5H), 3.09-2.87 (m, 6H), 2.80-2.68 (m, 2H), 2.14-2.10 (m, 4H), 2.05-1.89 (m, 2H), 1.70-1.66 (m, 1H), 1.53-1.35 (m, 5H). | 523.3 |
| 236 | 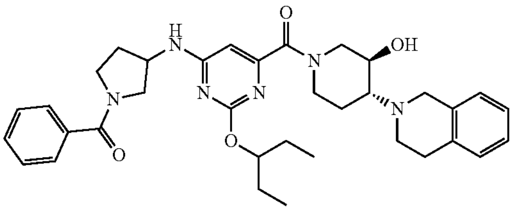 [SMILES: CCC(CC)Oc1nc(NC2CCN(C(=O)c3ccccc3)C2)cc(C(=O)N2CC[C@@H](N3CCc4ccccc4C3)[C@H](O)C2)n1] | (400 MHz, $(CD_3)_2SO$) δ 10.59-9.65 (m, 1H), 8.55-7.84 (m, 1H), 7.52-7.38 (m, 5H), 7.31-7.18 (m, 4H), 6.30-6.23 (m, 1H), 6.17-5.95 (m, 1H), 4.93-4.32 (m, 5H), 4.04-3.64 (m, 7H), 3.25-2.52 (m, 5H), 2.41-1.43 (m, 10H), 0.91-0.73 (m, 6H). | 613.4 |
| 237 | 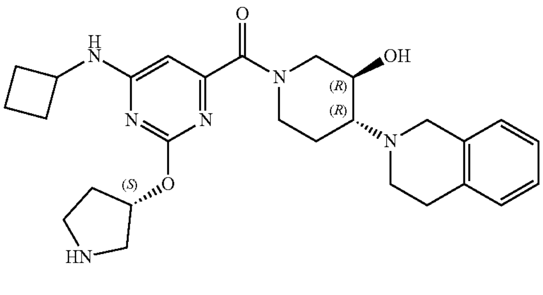 | (400 MHz, $CD_3OD$) δ 7.12-7.05 (m, 4H), 6.18 (d, J = 10 Hz, 1H), 5.49-5.47 (m, 1H), 4.71-4.57 (m, 2H), 3.98-3.77 (m, 4H), 3.22-2.96 (m, 6H), 2.90-2.68 (m, 5H), 2.42-2.41 (m, 2H), 2.21-1.79 (m, 7H), 1.73-1.66 (m, 1H). | 493.3 |

-continued
| Ex. | Structure | $^1$H NMR | LC-MS (ESI) [M + H]$^+$ |
| --- | --- | --- | --- |
| 238 | 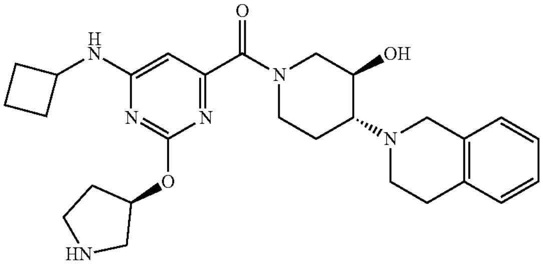 [SMILES: O=C(c1cc(NC2CCC2)nc(O[C@@H]2CCNC2)n1)N1CC[C@@H](N2CCc3ccccc3C2)[C@H](O)C1] | (400 MHz, $CDCl_3$) δ 8.03-7.81 (m, 1H), 7.13-6.97 (m, 4H), 6.20-6.08 (m, 1H), 5.39-5.15 (m, 1H), 4.84-4.65 (m, 1H), 4.50-4.24 (m, 2H), 3.88-3.67 (m, 3H), 3.64-3.51 (m, 1.5H), 3.13-2.94 (m, 1.5H), 2.93-2.71 (m, 7.5H), 2.70-2.55 (m, 1.5H), 2.37-2.22 (m, 2H), 2.05-1.84 (m, 3H), 1.84-1.59 (m, 4H), 1.58-1.38 (m, 1H). | 493.3 |
| 239 | 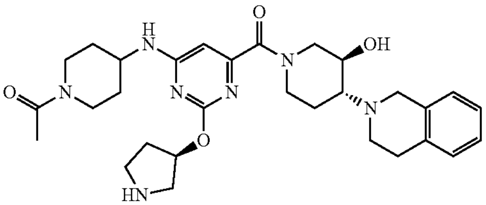 [SMILES: CC(=O)N1CCC(Nc2cc(C(=O)N3CC[C@@H](N4CCc5ccccc5C4)[C@H](O)C3)nc(O[C@@H]3CCNC3)n2)CC1] | (400 MHz, $CDCl_3$) δ 7.18-7.09 (m, 3H), 7.06-7.00 (m, 1H), 6.31-6.19 (m, 1H), 5.50-5.34 (m, 1H), 5.28-5.04 (m, 1H), 5.04-4.70 (m, 1H), 4.60-4.42 (m, 1H), 4.28-4.11 (m, 1H), 3.95-3.91 (m, 1H), 3.87-3.57 (m, 4H), 3.31-3.16 (m, 3H), 3.16-3.09 (m, 1H), 3.09-2.85 (m, 6H), 2.85-2.59 (m, 4H), 2.20-1.96 (m, 8H), 1.73-1.58 (m, 1H), 1.47-1.34 (m, 2H) | 564.4 |
| 240 | 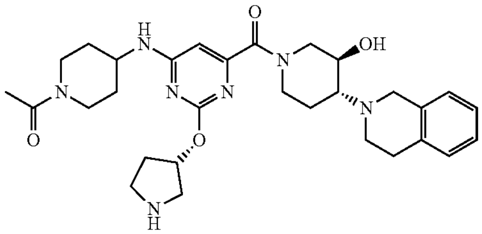 | (400 MHz, $CD_3OD$) δ 7.12-7.05 (m, 4H), 6.23 (d, J = 10 Hz, 1H), 5.51 (s, 1H), 4.71-4.57 (m, 1H), 4.20 (s, 1H), 3.98-3.77 (m, 6H), 3.28-3.00 (m, 6H), 2.97-2.88 (m, 5H), 2.88-2.69 (m, 2H), 2.20-2.10 (m, 6H), 2.05-1.92 (m, 2H), 1.70-1.66 (m, 1H), 1.54-1.43 (m, 2H). | 565.3 |
| 241 | 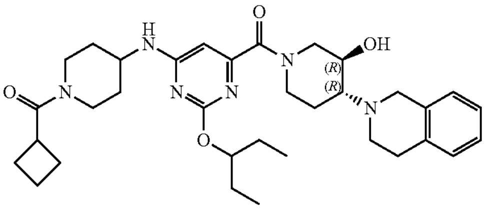 | (400 MHz, DMSO-$d_6$) δ 10.24-9.94 (m, 1H), 7.84-7.72 (m, 1H), 7.31-7.16 (m, 4H), 6.23 (s, 1H), 6.04-5.95 (m, 0.5H), 4.89-4.86 (m, 1H), 4.71-4.38 (m, 3H), 4.25-4.22 (m, 1H), 4.06-3.85 (m, 3H), 3.74-3.62 (m, 2H), 3.38-2.64 (m, 9H), 2.33-2.08 (m, 2H), 1.99-1.61 (m, 9H), 1.28-1.24 (m, 2H), 0.91-0.85 (m, 6H). | 605.0 |
| 242 | 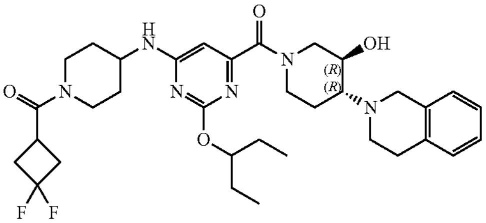 | (400 MHz, DMSO-$d_6$) δ 10.25-9.92 (m, 1H), 7.86-7.56 (m, 1H), 7.31-7.14 (m, 4H), 6.24 (s, 1H), 6.08-5.94 (m, 0.5H), 4.89-4.82 (m, 1H), 4.71-4.34 (m, 3H), 4.25-4.22 (m, 1H), 4.05-3.74 (m, 5H), 3.58-3.50 (m, 1H), 3.30-2.64 (m, 12H), 2.28-2.01 (m, 1H), 1.99-1.59 (m, 7H), 1.43-1.26 (m, 2H), 0.91-0.85 (m, 6H). | 641.5 |
| 243 | 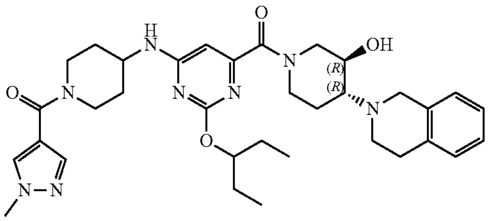 | (400 MHz, DMSO-$d_6$) δ 10.32-9.87 (m, 1H), 8.05 (s, 1H), 7.91-7.67 (m, 1H), 7.65 (s, 1H), 7.31-7.11 (m, 4H), 6.24 (s, 1H), 6.08-5.94 (m, 0.5H), 4.92-4.86 (m, 1H), 4.71-4.32 (m, 3H), 4.29-3.85 (m, 8H), 3.74-3.51 (m, 3H), 3.25-2.64 (m, 6H), 2.31-2.01 (m, 1H), 1.96-1.70 (m, 3H), 1.65-1.61 (m, 4H), 1.47-1.31 (m, 2H), 0.91-0.85 (m, 6H). | 631.5 |

-continued

| Ex. | Structure | $^1H$ NMR | LC-MS (ESI) [M + H]$^+$ |
|---|---|---|---|
| 244 | 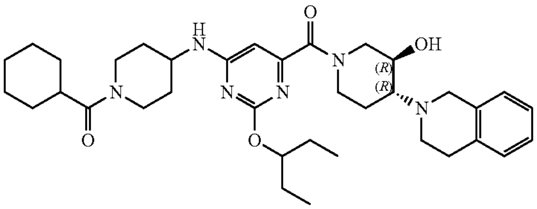 | (400 MHz, DMSO-$d_6$) δ 10.23-9.95 (m, 1H), 7.72 (s, 1H), 7.28-7.18 (m, 4H), 6.26-6.16 (m, 1H), 6.05-5.96 (m, 0.5H), 4.88-4.85 (m, 1H), 4.71-4.20 (m, 4H), 4.06-3.61 (m, 5H), 3.55-3.37 (m, 2H), 3.21-2.95 (m, 3H), 2.84-2.59 (m, 3H), 2.34-1.58 (m, 14H), 1.44-1.14 (m, 8H), 0.91-0.84 (m, 6H). | 633.5 |
| 245 | 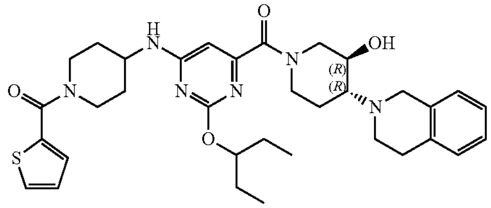 | (400 MHz, DMSO-$d_6$) δ 10.31-10.12 (m, 1H), 7.99-7.81 (m, 0.65H), 7.76 (d, J = 4.8 Hz, 1H), 7.40 (s, 1H), 7.30-7.18 (m, 4H), 7.15-7.10 (m, 1H), 6.27 (s, 1H), 6.06-6.00 (m, 0.5H), 4.90-4.87 (m, 1H), 4.72-4.36 (m, 3H), 4.18-3.76 (m, 6H), 3.66-3.51 (m, 2H), 3.34-2.96 (m, 5H), 2.85-2.62 (m, 1H), 2.33-2.10 (m, 1H), 2.03-1.96 (m, 2H), 1.87-1.61 (m, 5H), 1.49-1.41 (m, 2H), 1.31-1.20 (m, 1H), 0.91-0.85 (m, 6H). | 633.4 |
| 246 | 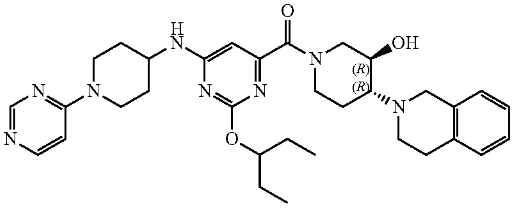 | (400 MHz, $CD_3OD$) δ 8.44 (s, 1H), 8.10 (d, J = 6.0 Hz, 1H), 7.08-7.03 (m, 4H), 6.81 (d, J = 6.0 Hz, 1H), 6.17 (d, J = 5.2 Hz, 1H), 7.10-7.02 (m, 4H), 5.02-4.97 (m, 1H), 4.69-4.52 (m, 2H), 4.45-4.23 (m, 3H), 3.95-3.77 (m, 4H), 3.22-3.13 (m, 2H), 3.10-2.95 (m, 2H), 2.93-2.84 (m, 3H), 2.75-2.65 (m, 1H), 2.10 (d, J = 12.4 Hz, 2H), 2.03-1.86 (m, 1H), 1.74-1.63 (m, 4H), 1.56-1.47 (m, 2H), 1.33-1.28 (m, 1H), 0.99-0.96 (m, 6H). | 601.5 |
| 247 | 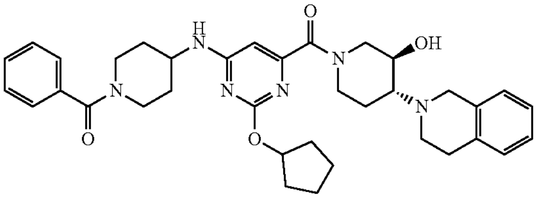 [SMILES: O=C(c1ccccc1)N1CCC(Nc2cc(C(=O)N3CC[C@@H](N4CCc5ccccc5C4)[C@H](O)C3)nc(OC3CCCC3)n2)CC1] | (400 MHz, $CDCl_3$) δ 7.42-7.40 (m, 5H), 7.17-7.13 (m, 3H), 7.12-7.02 (m, 1H), 6.25-6.20 (m, 1H), 5.34-5.30 (m, 1H), 5.02-5.00 (m, 1H), 4.77-4.74 (m, 2H), 4.31-4.28 (m, 1H), 3.99-3.72 (m, 5H), 3.06-3.03 (m, 3H), 2.97-2.94 (m, 3H), 2.78-2.60 (m, 3H), 2.07-1.81 (m, 10H), 1.66-1.57 (m, 4H). | 625.5 |
| 248 | 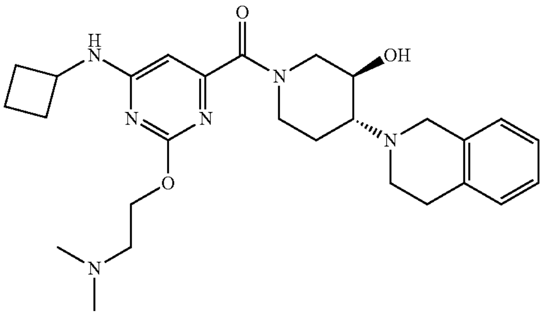 [SMILES: CN(C)CCOc1nc(NC2CCC2)cc(C(=O)N2CC[C@@H](N3CCc4ccccc4C3)[C@H](O)C2)n1] | (400 MHz, $CD_3OD$) δ 7.10-7.02 (m, 4H), 6.16 (d, J = 11.6 Hz, 1H), 4.69-4.43 (m, 4H), 3.95-3.76 (m, 4H), 3.12-2.65 (m, 9H), 2.39-2.37 (m, 8H), 2.01-1.64 (m, 6H). | 495.3 |
| 249 | 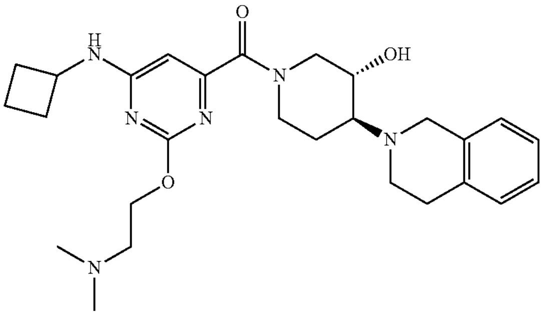 [SMILES: CN(C)CCOc1nc(NC2CCC2)cc(C(=O)N2CC[C@H](N3CCc4ccccc4C3)[C@@H](O)C2)n1] | (400 MHz, DMSO-$d_6$) δ 13.23 (s, 1H), 8.51 (d, J = 10.1 Hz, 1H), 8.21-8.07 (m, 2H), 8.07-7.93 (m, 1H), 7.89-7.73 (m, 1H), 7.16-6.96 (m, 4H), 6.57-6.36 (m, 1H), 4.89-4.70 (m, 1H), 4.65 (s, 1H), 4.58-4.33 (m, 1H), 3.96-3.76 (m, 3H), 3.76-3.62 (m, 1H), 3.16-2.89 (m, 2.5H), 2.89-2.73 (m, 3H), 2.73-2.61 (m, 1.5H), 2.40 (s, 2H), 2.12-1.94 (m, 2H), 1.94-1.67 (m, 3H), 1.67-1.51 (m, 1H). | 524.3 |

-continued
| Ex. | Structure | $^1$H NMR | LC-MS (ESI) [M + H]$^+$ |
| --- | --- | --- | --- |
| 250 | 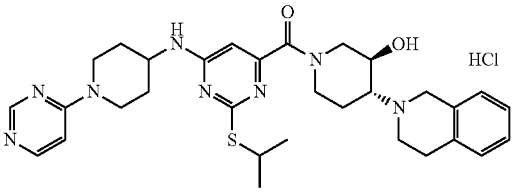 [SMILES: CC(C)Sc1nc(NC2CCN(c3ccncn3)CC2)cc(C(=O)N2CC[C@@H](N3CCc4ccccc4C3)[C@H](O)C2)n1 ; Cl] HCl | (400 MHz, $CDCl_3$) δ 8.61 (s, 1H), 8.21 (d, J = 6.2 Hz, 1H), 7.18-7.10 (m, 3H), 7.05-7.01 (m, 1H), 6.58-6.52 (m, 1H), 6.36-6.23 (m, 1H), 5.16-4.66 (m, 2H), 4.42-4.18 (m, 3H), 4.02-3.94 (m, 1H), 3.93-3.64 (m, 4H), 3.17-2.90 (m, 6H), 2.87-2.55 (m, 3H), 2.22-2.08 (m, 2H), 2.03-1.83 (m, 1H), 1.75-1.60 (m, 1H), 1.56-1.46 (m, 2H), 1.45-1.37 (m, 6H). | 589.0 |
| 251 | 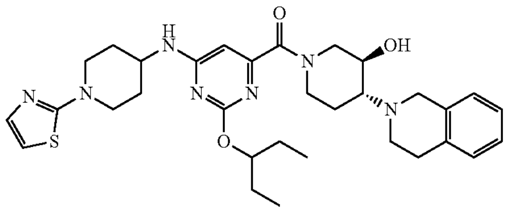 [SMILES: CCC(CC)Oc1nc(NC2CCN(c3nccs3)CC2)cc(C(=O)N2CC[C@@H](N3CCc4ccccc4C3)[C@H](O)C2)n1] | (400 MHz, $CD_3OD$) δ 7.13-7.03 (m, 5H), 6.72-6.71 (m, 1H), 6.21-6.13 (m, 1H), 5.01-4.97 (m, 1H), 4.70-4.52 (m, 1H), 4.17-4.13 (m, 1H), 3.98-3.75 (m, 6H), 3.28-3.21 (m, 2H), 3.14-2.65 (m, 7H), 2.17-2.07 (m, 2H), 2.03-1.87 (m, 1H), 1.76-1.61 (m, 7H), 0.99-0.94 (m, 6H). | 606.3 |
| 252 | 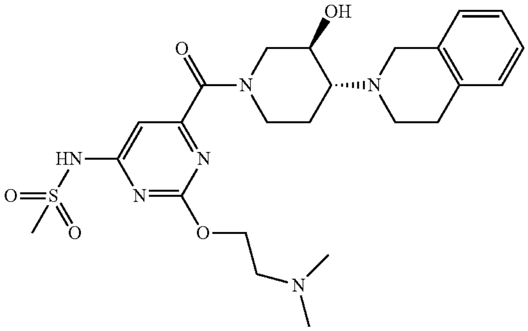 [SMILES: CN(C)CCOc1nc(NS(C)(=O)=O)cc(C(=O)N2CC[C@@H](N3CCc4ccccc4C3)[C@H](O)C2)n1] | (400 MHz, $CD_3OD$) δ 7.13-7.08 (m, 4H), 6.35 (d, J = 12 Hz, 1H), 4.73-4.56 (m, 3H), 4.05-4.00 (m, 2H), 3.85-3.80 (m, 2H), 3.50-3.46 (m, 2H), 3.16-3.06 (m, 4H), 3.0-2.96 (m, 4H), 2.89-2.70 (m, 8H), 2.07-1.90 (m, 1H), 1.75-1.65 (m, 1H). | 519.2 |
| 253 | 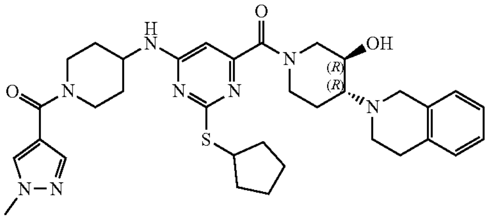 | (400 MHz, $CDCl_3$) δ 7.71 (s, 1H), 7.64-7.58 (m, 1H), 7.18-7.09 (m, 3H), 7.06-6.99 (m, 1H), 6.34-6.22 (m, 1H), 5.88-5.39 (m, 1H), 5.05-4.66 (m, 1H), 4.55-4.04 (m, 3H), 3.99-3.86 (m, 5H), 3.83-3.62 (m, 3H), 3.34-2.87 (m, 6H), 2.85-2.56 (m, 3H), 2.23-1.93 (m, 5H), 1.89-1.71 (m, 4H), 1.69-1.56 (m, 4H), 1.51-1.38 (m, 1H). | 645.0 |
| 254 | 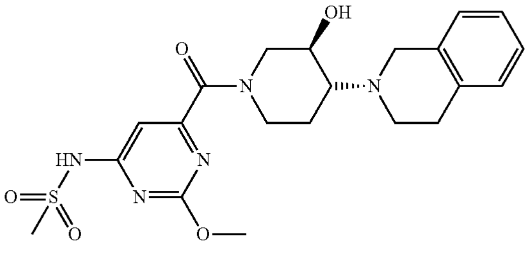 | (400 MHz, $CD_3OD$) δ 7.24-7.15 (m, 4H), 6.52 (d, J = 5.2 Hz, 1H), 4.84-4.64 (m, 1H), 4.33-4.24 (m, 2H), 3.00 (d, J = 7.6 Hz, 3H), 3.96-3.84 (m, 2H), 3.42-3.38 (m, 1H), 3.28-3.21 (m, 5H), 3.17-3.09 (m, 2H), 3.03-2.72 (m, 2H), 2.18-2.00 (m, 1H), 1.85-1.79 (m, 1H). | 462.3 |
| 255 | 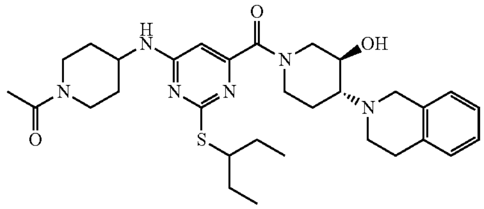 [SMILES: CCC(CC)Sc1nc(NC2CCN(C(C)=O)CC2)cc(C(=O)N2CC[C@@H](N3CCc4ccccc4C3)[C@H](O)C2)n1] | (400 MHz, $CDCl_3$) δ 7.20-7.09 (m, 3H), 7.07-6.99 (m, 1H), 6.35-6.18 (m, 1H), 5.38-5.12 (m, 1H), 5.03-4.67 (m, 1H), 4.57-4.46 (m, 1H), 4.31-4.17 (m, 1H), 4.01-3.94 (m, 1H), 3.91-3.61 (m, 5H), 3.25-3.14 (m, 1H), 3.11-2.90 (m, 4H), 2.87-2.56 (m, 4H), 2.16-1.95 (m, 5H), 1.82-1.60 (m, 6H), 1.47-1.34 (m, 2H), 1.05-0.97 (m, 6H). | 581.0 |

-continued
| Ex. | Structure | ¹H NMR | LC-MS (ESI) [M + H]⁺ |
|---|---|---|---|
| 256 | 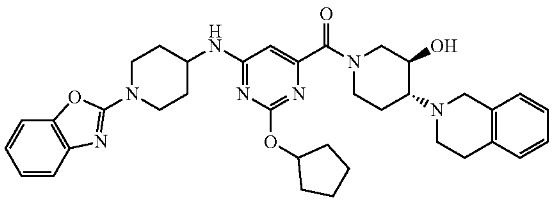 [SMILES: O=C(c1cc(NC2CCN(c3nc4ccccc4o3)CC2)nc(OC2CCCC2)n1)N1CC[C@@H](N2CCc3ccccc3C2)[C@H](O)C1] | (400MHz, DMSO-$d_6$) δ 7.69-7.58 (m, 1H), 7.40 (d, J = 8.0 Hz, 1H), 7.29 (d, J = 7.8 Hz, 1H), 7.15 (t, J = 7.6 Hz, 1H), 7.11-7.06 (m, 3H), 7.06-6.97 (m, 2H), 6.42-6.12 (m, 1H), 5.35-5.18 (m, 1H), 4.86-4.64 (m, 1H), 4.53-4.28 (m, 1H), 4.21-4.04 (m, 3H), 3.92-3.71 (m, 3H), 3.67-3.52 (m, 1H), 3.39-3.34 (m, 1H), 3.07-2.73 (m, 6H), 2.69-2.57 (m, 2H), 2.10-1.97 (m, 2H), 1.95-1.85 (m, 2H), 1.83-1.65 (m, 5H), 1.61-1.43 (m, 5H). | 638.0 |
| 257 | 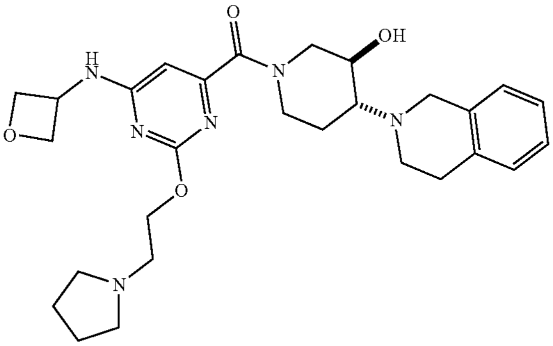 [SMILES: O=C(c1cc(NC2COC2)nc(OCCN2CCCC2)n1)N1CC[C@@H](N2CCc3ccccc3C2)[C@H](O)C1] | (400 MHz, $CDCl_3$) δ 7.18-7.08 (m, 3H), 7.06-6.99 (m, 1H), 6.32-6.19 (m, 1H), 5.72-5.59 (m, 1H), 5.20-4.71 (m, 4H), 4.59-4.53 (m, 2H), 4.52-4.40 (m, 2H), 4.30-4.09 (m, 1H), 3.98-3.90 (m, 1H), 3.76-3.63 (m, 2H), 3.07-2.87 (m, 6H), 2.84-2.55 (m, 7H), 2.01-1.84 (m, 1H), 1.83-1.76 (m, 4H), 1.73-1.57 (m, 1H). | 523.5 |
| 258 | 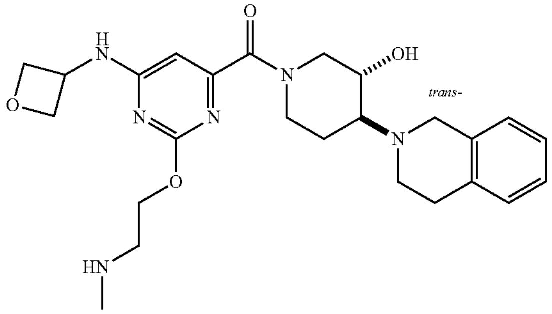 [SMILES: CNCCOc1nc(NC2COC2)cc(C(=O)N2CC[C@H](N3CCc4ccccc4C3)[C@@H](O)C2)n1] | (400 MHz, $CDCl_3$) δ 7.20-7.08 (m, 3H), 7.07-6.99 (m, 1H), 5.97-5.88 (m, 1H), 5.48-5.21 (m, 1H), 5.12-4.89 (m, 3H), 4.79-4.47 (m, 3H), 4.17-3.49 (m, 9H), 3.15 (s, 3H), 3.11-3.00 (m, 1H), 2.98-2.53 (m, 6H), 2.06-1.90 (m, 1H), 1.86-1.71 (m, 1H). | 483.52 |
| 259 | 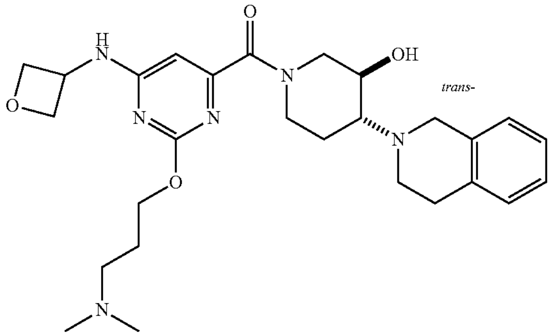 [SMILES: CN(C)CCCOc1nc(NC2COC2)cc(C(=O)N2CC[C@@H](N3CCc4ccccc4C3)[C@H](O)C2)n1] | (400 MHz, $CDCl_3$) δ 7.18-7.09 (m, 3H), 7.05-6.99 (m, 1H), 6.33-6.18 (m, 1H), 5.70-5.55 (m, 1H), 5.21-4.92 (m, 3H), 4.86-4.68 (m, 1H), 4.63-4.52 (m, 2H), 4.46-4.20 (m, 3H), 4.16-3.88 (m, 2H), 3.79-3.62 (m, 2H), 3.12-2.87 (m, 4H), 2.82-2.56 (m, 3H), 2.53-2.39 (m, 2H), 2.25 (s, 6H), 2.04-1.82 (m, 3H), 1.72-1.66 (m, 1H). | |

-continued
| Ex. | Structure | $^1$H NMR | LC-MS (ESI) [M + H]$^+$ |
|---|---|---|---|
| 260 | 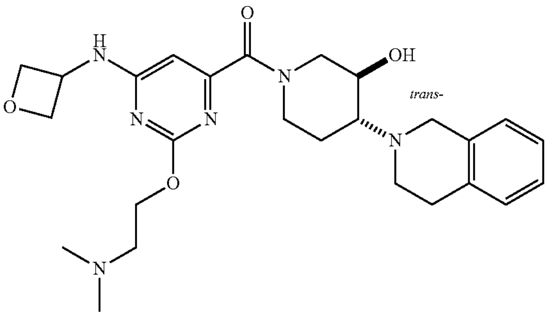 [SMILES: CN(C)CCOc1nc(NC2COC2)cc(C(=O)N2CC[C@@H](N3CCc4ccccc4C3)[C@H](O)C2)n1] | (400 MHz, $CDCl_3$) δ 7.17-7.09 (m, 3H), 7.06-7.00 (m, 1H), 6.35-6.25 (m, 1H), 6.05-5.87 (m, 1H), 5.17-4.71 (m, 4H), 4.61-4.53 (m, 2H), 4.48-4.34 (m, 2H), 4.31-4.09 (m, 1H), 3.99-3.85 (m, 1H), 3.77-3.62 (m, 2H), 3.09-2.86 (m, 4H), 2.83-2.55 (m, 5H), 2.37-2.29 (m, 6H), 2.03-1.80 (m, 1H), 1.73-1.57 (m, 1H). | 497.34 |
| 261 | 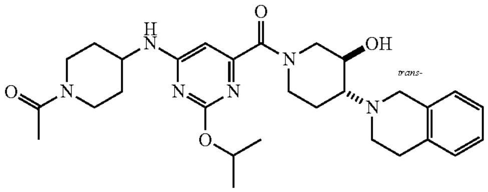 [SMILES: CC(=O)N1CCC(Nc2cc(C(=O)N3CC[C@@H](N4CCc5ccccc5C4)[C@H](O)C3)nc(OC(C)C)n2)CC1] | (400 MHz, $CDCl_3$) δ 7.20-7.09 (m, 3H), 7.07-6.99 (m, 1H), 6.30-6.14 (m, 1H), 5.60-5.28 (m, 1H), 5.26-5.15 (m, 1H), 5.04-4.95 (m, 0.4H), 4.80-4.71 (m, 0.6H), 4.55-4.45 (m, 1H), 4.31-4.24 (m, 1H), 4.21-4.13 (m, 1H), 4.01-3.91 (m, 1H), 3.87-3.62 (m, 4H), 3.28-3.15 (m, 1H), 3.11-2.56 (m, 8H), 2.21-1.93 (m, 6H), 1.92-1.74 (m, 2H), 1.72-1.59 (m, 1H), 1.40-1.34 (m, 6H). | 537.3 |
| 262 | 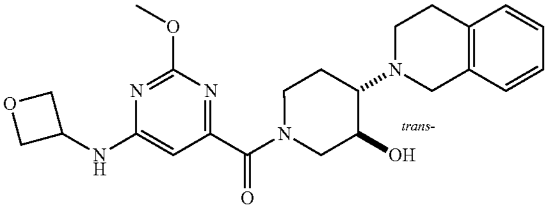 [SMILES: COc1nc(NC2COC2)cc(C(=O)N2CC[C@H](N3CCc4ccccc4C3)[C@@H](O)C2)n1] | (400 MHz, $CDCl_3$) δ 7.20-7.09 (m, 3H), 7.07-7.00 (m, 1H), 6.43-6.13 (m, 1H), 5.87-5.50 (m, 1H), 5.17-4.71 (m, 4H), 4.64-4.52 (m, 2H), 4.35-4.13 (m, 1H), 4.09-3.98 (m, 1H), 3.96-3.88 (m, 3H), 3.84-3.68 (m, 2H), 3.18-2.57 (m, 7H), 2.05-1.88 (m, 1H), 1.75-1.67 (m, 1H). | 440.46 |
| 263 | 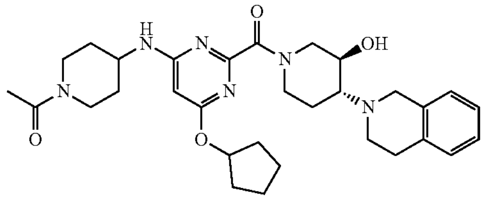 [SMILES: CC(=O)N1CCC(Nc2cc(OC3CCCC3)nc(C(=O)N3CC[C@@H](N4CCc5ccccc5C4)[C@H](O)C3)n2)CC1] | (400 MHz, $CDCl_3$) δ 7.18-7.11 (m, 3H), 7.04-7.01 (m, 1H), 5.58 (s, 1H), 5.41-5.37 (m, 1H), 5.08-4.83 (m, 2H), 4.47-4.43 (m, 1H), 4.00-3.95 (m, 2H), 3.81-3.72 (m, 4H), 3.24-2.58 (m, 9H), 2.11-1.90 (m, 8H), 1.83-1.74 (m, 4H), 1.71-1.61 (m, 3H), 1.45-1.40 (m, 2H). | 563.0 |
| 264 | 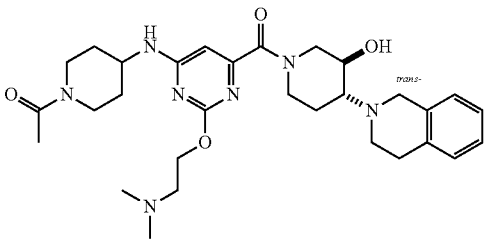 [SMILES: CC(=O)N1CCC(Nc2cc(C(=O)N3CC[C@@H](N4CCc5ccccc5C4)[C@H](O)C3)nc(OCCN(C)C)n2)CC1] | (400 MHz, $CDCl_3$) δ 7.17-7.09 (m, 3H), 7.05-7.00 (m, 1H), 6.30-6.20 (m, 1H), 5.23-5.09 (m, 1H), 5.04-4.71 (m, 1H), 4.57-4.37 (m, 3H), 4.32-3.90 (m, 3H), 3.85-3.77 (m, 1H), 3.77-3.62 (m, 2H), 3.26-3.15 (m, 1H), 3.10-2.57 (m, 11H), 2.36-2.32 (m, 6H), 2.13-2.09 (m, 3H), 2.05-1.95 (m, 2H), 1.88-1.80 (m, 1H), 1.73-1.58 (m, 1H), 1.46-1.33 (m, 2H). | 566.51 |
| 265 | 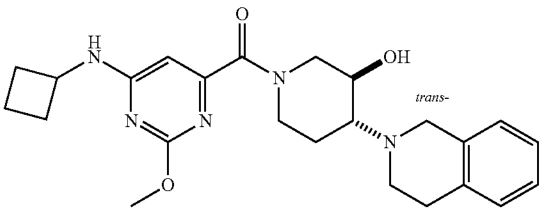 [SMILES: COc1nc(NC2CCC2)cc(C(=O)N2CC[C@@H](N3CCc4ccccc4C3)[C@H](O)C2)n1] | (400 MHz, DMSO-$d_6$) δ 7.94-7.91 (m, 1H), 7.10-7.02 (m, 4H), 6.14 (d, J = 5.2 Hz, 1H), 4.81-4.72 (m, 1H), 4.46-4.31 (m, 2H), 3.86-3.70 (m, 6H), 3.66-3.59 (m, 1H), 3.01-2.54 (m, 7H), 2.33-2.24 (m, 2H), 1.99-1.67 (m, 5H), 1.54-1.44 (m, 1H). | 438.5 |

-continued

| Ex. | Structure | $^1$H NMR | LC-MS (ESI) [M + H]$^+$ |
|---|---|---|---|
| 266 | 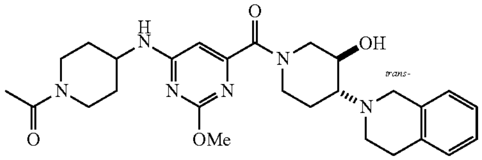 [SMILES: COc1nc(NC2CCN(C(C)=O)CC2)cc(C(=O)N2CC[C@@H](N3CCc4ccccc4C3)[C@H](O)C2)n1] | (400 MHz, $CDCl_3$) δ 7.16-7.11 (m, 3H), 7.04-7.02 (m, 1H), 6.28 (d, J = 18.1 Hz, 1H), 5.10 (d, J = 13.1 Hz, 0.3H), 5.03-4.99 (m, 1H), 4.77 (d, J = 13.2 Hz, 0.7H), 4.56 (d, J = 13.7 Hz, 1H), 4.33-4.18 (m, 1H), 3.95 (d, J = 10.5 Hz, 4H), 3.92-3.71 (m, 4H), 3.25 (t, J = 12.9 Hz, 1H), 3.07-3.05 (m, 1H), 2.97-2.93 (m, 3H), 2.84 (t, J = 12.7 Hz, 2H), 2.72-2.58 (m, 2H), 2.11-2.08 (d, 4H), 2.05-1.85 (m, 2H), 1.79-1.73 (m, 1H), 1.44-1.34 (m, 2H). | 509.3 |
| 267 | 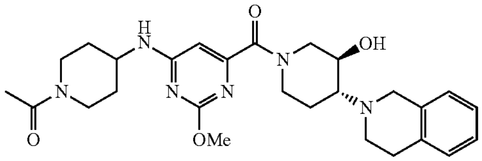 [SMILES: COc1nc(NC2CCN(C(C)=O)CC2)cc(C(=O)N2CC[C@@H](N3CCc4ccccc4C3)[C@H](O)C2)n1] | (400 MHz, DMSO-$d_6$) δ 7.74-7.58 (m, 1H), 7.15-6.97 (m, 4H), 6.30-6.13 (m, 1H), 4.88-4.68 (m, 1H), 4.50-4.29 (m, 1H), 4.29-4.15 (m, 1H), 4.15-3.96 (m, 1H), 3.89-3.69 (m, 6H), 3.67-3.52 (m, 1H), 3.26-3.11 (m, 1H), 3.05-2.86 (m, 2H), 2.86-2.71 (m, 5H), 2.69-2.57 (m, 2H), 2.06-1.98 (m, 3H), 1.98-1.71 (m, 3H), 1.58-1.45 (m, 1H), 1.45-1.33 (m, 1H), 1.33-1.18 (m, 1H). | 509.3 |
| 268 | 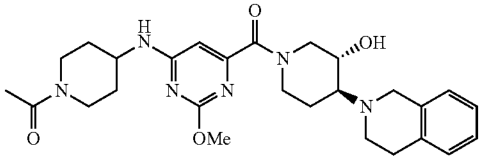 [SMILES: COc1nc(NC2CCN(C(C)=O)CC2)cc(C(=O)N2CC[C@H](N3CCc4ccccc4C3)[C@@H](O)C2)n1] | (400 MHz, DMSO-$d_6$) δ 7.74-7.58 (m, 1H), 7.15-6.97 (m, 4H), 6.30-6.13 (m, 1H), 4.88-4.68 (m, 1H), 4.50-4.29 (m, 1H), 4.29-4.15 (m, 1H), 4.15-3.96 (m, 1H), 3.89-3.69 (m, 6H), 3.67-3.52 (m, 1H), 3.26-3.11 (m, 1H), 3.05-2.86 (m, 2H), 2.86-2.71 (m, 5H), 2.69-2.57 (m, 2H), 2.06-1.98 (m, 3H), 1.98-1.71 (m, 3H), 1.58-1.45 (m, 1H), 1.45-1.33 (m, 1H), 1.33-1.18 (m, 1H). | 509.2 |
| 269 | 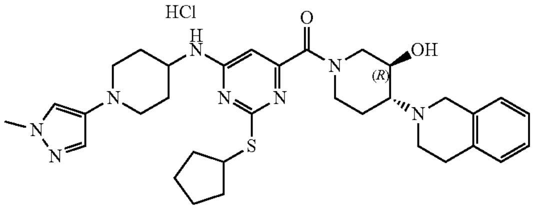 | (400 MHz, $(CD_3)_2SO$) δ 10.50-10.02 (m, 1H), 8.02-7.66 (m, 1H), 7.47 (s, 1H), 7.32-7.16 (m, 4H), 6.49-5.93 (m, 2H), 5.87-5.64 (m, 1H), 4.76-4.31 (m, 4H), 4.02-3.85 (m, 4H), 3.80-3.71 (m, 1H), 3.68-3.59 (m, 5H), 3.57-3.50 (m, 1H), 3.42-3.29 (m, 1H), 3.04-2.74 (m, 4H), 2.71-2.60 (m, 1H), 2.32-2.07 (m, 3H), 1.99-1.65 (m, 5H), 1.64-1.43 (m, 6H). | 617.2 |
| 270 | 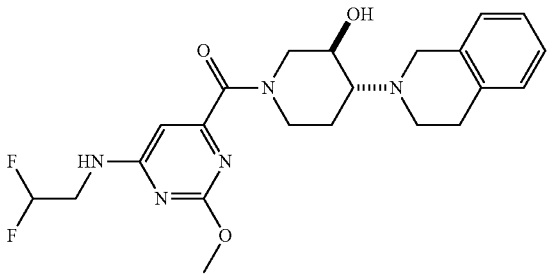 [SMILES: COc1nc(NCC(F)F)cc(C(=O)N2CC[C@@H](N3CCc4ccccc4C3)[C@H](O)C2)n1] | (400 MHz, DMSO-$d_6$) δ 8.05 (s, 1H), 7.15-6.98 (m, 4H), 6.38-5.98 (m, 2H), 4.77 (dd, J = 36.7, 3.9 Hz, 1H), 4.49-4.25 (m, 1H), 3.95-3.75 (m, 6H), 3.77-3.45 (m, 3H), 3.04-2.76 (m, 5H), 2.70-2.55 (m, 2H), 1.87-1.68 (m, 1H), 1.57-1.40 (m, 1H). | 448.4 |
| 271 | 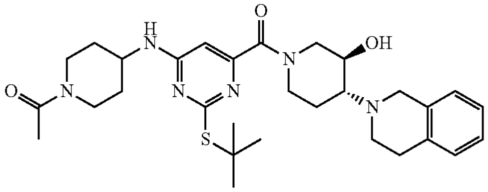 [SMILES: CC(=O)N1CCC(Nc2cc(C(=O)N3CC[C@@H](N4CCc5ccccc5C4)[C@H](O)C3)nc(SC(C)(C)C)n2)CC1] | (400 MHz, $CDCl_3$) δ 7.20-7.09 (m, 3H), 7.07-6.99 (m, 1H), 6.26 (s, 1H), 5.21-4.48 (m, 3H), 4.25-3.68 (m, 6H), 3.23-2.58 (m, 9H), 2.12 (s, 3H), 2.07-1.62 (m, 4H), 1.61 (s, 9H), 1.47-1.36 (m, 2H). | 567.3 |

-continued

| Ex. | Structure | $^1$H NMR | LC-MS (ESI) [M + H]$^+$ |
|---|---|---|---|
| 272 | 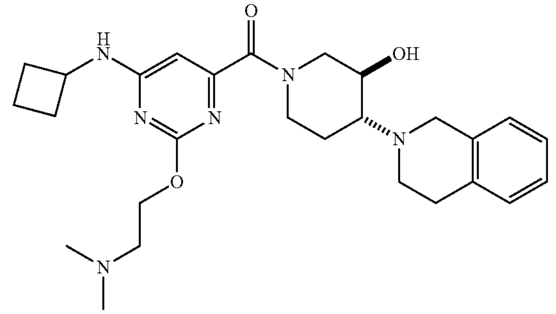 [SMILES: CN(C)CCOc1nc(NC2CCC2)cc(C(=O)N2CC[C@@H](N3CCc4ccccc4C3)[C@H](O)C2)n1] | (400 MHz, DMSO-$d_6$) δ 7.93-7.90 (m, 1H), 7.10-7.02 (m, 4H), 6.13 (d, J = 5.2 Hz, 1H), 4.81-4.71 (m, 1H), 4.46-4.24 (m, 4H), 3.95-3.86 (m, 4H), 3.01-2.86 (m, 1H), 2.84-2.75 (m, 4H), 2.67-2.53 (m, 4H), 2.36-2.25 (m, 2H), 2.20 (s, 3H), 2.18 (s, 3H), 1.91-1.63 (m, 5H), 1.52-1.43 (m, 1H). | 495.4 |
| 273 | 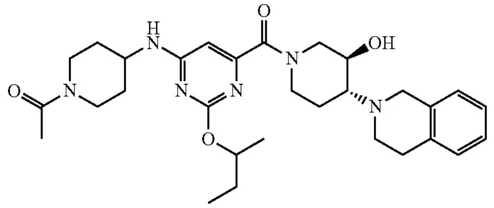 [SMILES: CCC(C)Oc1nc(NC2CCN(C(C)=O)CC2)cc(C(=O)N2CC[C@@H](N3CCc4ccccc4C3)[C@H](O)C2)n1] | (400 MHz, $CDCl_3$) δ 7.19-7.10 (m, 3H), 7.07-6.98 (m, 1H), 6.26-6.15 (m, 1H), 5.10-4.71 (m, 3H), 4.62-4.45 (m, 1H), 4.36-4.13 (m, 1H), 4.03-3.91 (m, 1H), 3.88-3.61 (m, 4H), 3.28-3.17 (m, 1H), 3.12-2.90 (m, 4H), 2.88-2.51 (m, 4H), 2.17-1.93 (m, 6H), 1.90-1.72 (m, 1H), 1.72-1.52 (m, 2H), 1.49-1.22 (m, 5H), 1.03-0.82 (m, 3H). | 551.2 |
| 274 | 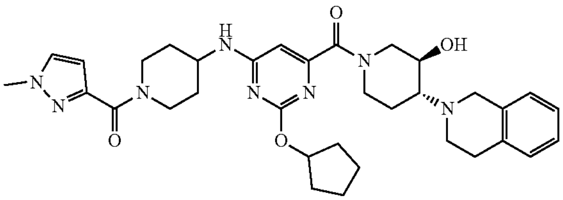 [SMILES: Cn1ccc(C(=O)N2CCC(Nc3cc(C(=O)N4CC[C@@H](N5CCc6ccccc6C5)[C@H](O)C4)nc(OC4CCCC4)n3)CC2)n1] | (400 MHz, $CD_3OD$) δ 7.76-7.73 (m, 1H), 7.63-7.59 (m, 1H), 7.10-7.02 (m, 4H), 6.52 (t, J = 2.0 Hz, 1H), 6.16-6.11 (m, 1H), 5.23-5.22 (m, 1H), 4.80-4.71 (m, 1H), 4.57-4.31 (m, 3H), 4.13 (s, 1H), 3.88-3.70 (m, 6H), 3.64-3.60 (m, 1H), 3.03-2.73 (m, 6H), 2.67-2.52 (m, 3H), 1.93-1.63 (m, 9H), 1.56-1.39 (m, 5H). | 629.4 |
| 275 | 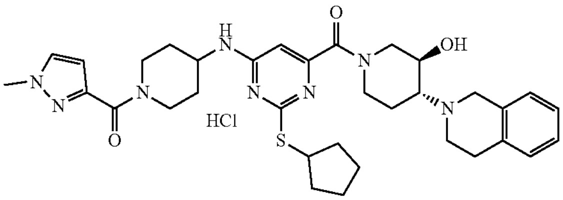 [SMILES: Cn1ccc(C(=O)N2CCC(Nc3cc(C(=O)N4CC[C@@H](N5CCc6ccccc6C5)[C@H](O)C4)nc(SC4CCCC4)n3)CC2)n1 ; Cl] HCl | (400 MHz, $(CD_3)_2SO$) δ 10.69-10.13 (m, 1H), 8.36-7.99 (m, 1H), 7.97-7.67 (m, 1H), 7.32-7.15 (m, 4H), 6.52 (s, 1H), 6.42-5.94 (m, 2H), 4.78-4.35 (m, 5H), 4.14 (s, 1H), 4.04-3.83 (m, 6H), 3.81-3.67 (m, 1H), 3.62-3.25 (m, 4H), 3.18-2.93 (m, 3H), 2.89-2.62 (m, 1H), 2.31-2.07 (m, 3H), 2.03-1.86 (m, 2H), 1.83-1.53 (m, 7H), 1.50-1.30 (m, 2H). | 645.2 |
| 276 | 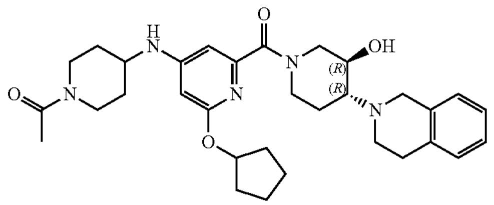 | (400 MHz, $CDCl_3$) δ 7.20-7.11 (m, 3H), 7.04-6.99 (m, 1H), 6.50-6.45 (m, 1H), 5.83-5.81 (m, 1H), 5.35-5.31 (m, 1H), 5.06-4.77 (m, 1H), 4.53-4.37 (m, 2H), 4.15-4.09 (m, 1H), 3.40-3.98 (m, 1H), 3.83-3.74 (m, 3H), 3.53-3.51 (m, 1H), 3.21-2.58 (m, 9H), 2.11-1.92 (m, 8H), 1.78-1.66 (m, 7H), 1.40-1.30 (m, 2H). | 562.0 |
| 277 | 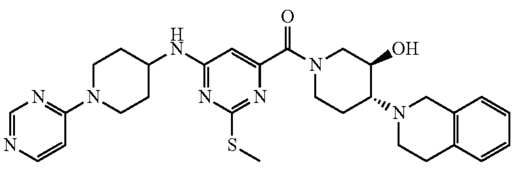 [SMILES: CSc1nc(NC2CCN(c3ccncn3)CC2)cc(C(=O)N2CC[C@@H](N3CCc4ccccc4C3)[C@H](O)C2)n1] | (400 MHz, DMSO-$d_6$) δ 8.49 (s, 1H), 8.16 (d, J = 6.0Hz, 1H), 7.72-7.68 (m, 1H), 7.08-7.03 (m, 4H), 6.86 (d, J = 6.4Hz, 1H), 6.24-6.18 (m, 1H), 4.81-4.72 (m, 1H), 4.46-4.16 (m, 4H), 3.86-3.71 (m, 3H), 3.61 (s, 1H), 3.18-3.13 (m, 2H), 2.91-2.79 (m, 6H), 2.67-2.66 (m, 1H), 2.43 (d, J = 7.6Hz, 3H), 1.99-1.73 (m, 3H), 1.54-1.37 (m, 3H). | 561.0 |

-continued

| Ex. | Structure | $^1$H NMR | LC-MS (ESI) [M + H]$^+$ |
| --- | --- | --- | --- |
| 278 | 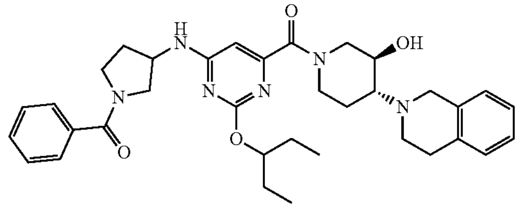 [SMILES: CCC(CC)Oc1nc(NC2CCN(C(=O)c3ccccc3)C2)cc(C(=O)N2CC[C@@H](N3CCc4ccccc4C3)[C@H](O)C2)n1] | (400 MHz, $CD_3OD$) δ 7.56-7.41 (m, 5H), 7.09-7.00 (m, 4H), 6.24-6.17 (m, 1H), 4.70-4.40 (m, 2H), 4.00-3.43 (m, 8H), 3.15-2.64 (m, 8H), 2.39-2.25 (m, 1H), 2.12-1.85 (m, 2H), 1.76-1.51 (m, 5H), 1.01-0.72 (m, 6H). | 613.4 |
| 279 | 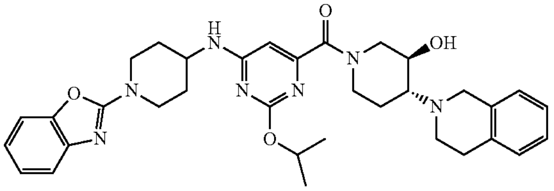 [SMILES: CC(C)Oc1nc(NC2CCN(c3nc4ccccc4o3)CC2)cc(C(=O)N2CC[C@@H](N3CCc4ccccc4C3)[C@H](O)C2)n1] | (400MHz, DMSO-$d_6$) δ 7.73-7.58 (m, 1H), 7.40 (d, J = 7.9 Hz, 1H), 7.29 (d, J = 7.8 Hz, 1H), 7.15 (t, J = 7.6 Hz, 1H), 7.10-6.98 (m, 5H), 6.42-6.01 (m, 1H), 5.17-5.00 (m, 1H), 4.88-4.67 (m, 1H), 4.52-4.27 (m, 1H), 4.20-4.02 (m, 3H), 3.90-3.69 (m, 3H), 3.68-3.54 (m, 1H), 3.45-3.36 (m, 1H), 3.05-2.72 (m, 6H), 2.68-2.54 (m, 2H), 2.10-1.92 (m, 2H), 1.88-1.69 (m, 1H), 1.62-1.42 (m, 3H), 1.33-1.20 (m, 6H). | 612.0 |
| 280 | 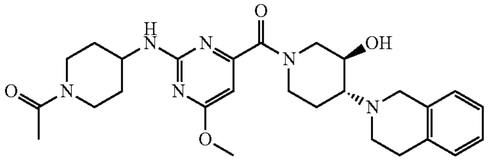 [SMILES: COc1cc(C(=O)N2CC[C@@H](N3CCc4ccccc4C3)[C@H](O)C2)nc(NC2CCN(C(C)=O)CC2)n1] | (400 MHz, DMSO-$d_6$) δ 7.48-7.33 (m, 1H), 7.09-7.01 (m, 4H), 6.10 (s, 1H), 4.81-4.64 (m, 1H), 4.47-4.23 (m, 2H), 3.96-3.59 (m, 9H), 3.17-3.11 (m, 1H), 3.01-2.89 (m, 1.5H), 2.78-2.54 (m, 6.5H), 1.99-1.71 (m, 6H), 1.49-1.28 (m, 3H). | 509.2 |
| 281 | 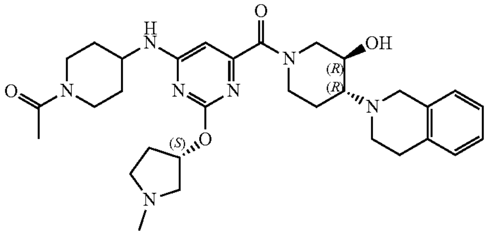 | (400 MHz, $CD_3OD$) δ 7.11-7.06 (m, 4H), 6.23 (d, J = 8.8 Hz, 1H), 5.40 (s, 1H), 4.71-4.54 (m, 1H), 4.43 (d, J = 12.4Hz, 1H), 4.19 (s, 1H), 3.97-3.79 (m, 5H), 3.14-2.73 (m, 12H), 2.64-2.56 (m, 1H), 2.44-2.35 (m, 4H), 2.14-2.03 (m, 7H), 1.72-1.64 (m, 1H), 1.55-1.42 (m, 2H). | 578.4 |
| 282 | 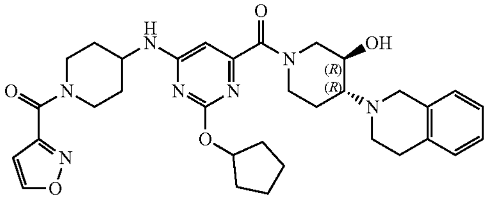 | (400 MHz, $CD_3OD$) δ 8.80-8.79 (m, 1H), 7.10-7.02 (m, 4H), 6.71-6.70 (m, 1H), 6.21-6.12 (m, 1H), 5.40-5.34 (m, 1H), 4.70-4.50 (m, 2H), 4.26-4.13 (m, 2H), 3.96-3.75 (m, 4H), 3.42-3.33 (m, 1H), 3.20-2.85 (m, 7H), 2.79-2.65 (m, 1H), 2.16-2.07 (m, 2H), 2.03-1.81 (m, 7H), 1.72-1.52 (m, 5H). | 616.3 |
| 283 | 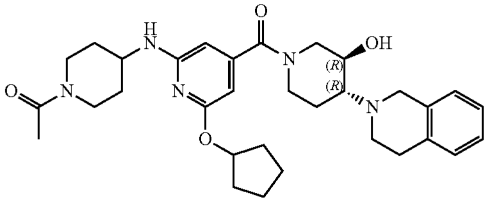 | (400 MHz, $CDCl_3$) δ 7.22-7.10 (m, 3H), 7.07-7.01 (m, 1H), 5.99-5.79 (m, 2H), 5.30-5.19 (m, 1H), 5.06-4.81 (m, 1H), 4.54-4.33 (m, 2H), 4.17-4.06 (m, 1H), 3.93-3.48 (m, 5H), 3.33-2.52 (m, 9H), 2.19-2.10 (m, 4H), 2.10-1.88 (m, 4H), 1.84-1.75 (m, 4H), 1.66-1.55 (m, 3H), 1.45-1.35 (m, 2H). | 562.00 |
| 284 | HCl 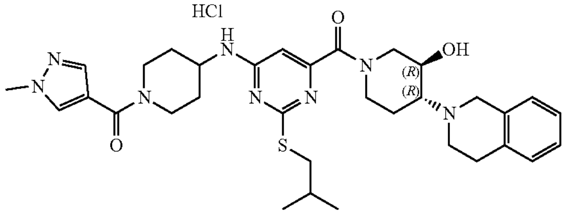 | (400 MHz, $(CD_3)_2SO$) δ 10.43-9.94 (m, 1H), 8.10-7.61 (m, 3H), 7.35-7.13 (m, 4H), 6.57-5.84 (m, 2H), 4.73-4.37 (m, 5H), 4.31-4.02 (m, 3H), 4.00-3.73 (m, 6H), 3.59-3.51 (m, 1H), 3.43-3.32 (m, 1H), 3.16-3.08 (m, 1H), 3.05-2.85 (m, 4H), 2.80-2.63 (m, 1H), 2.34-2.15 (m, 1H), 2.00-1.69 (m, 4H), 1.52-1.28 (m, 2H), 1.07-0.89 (m, 6H). | 633.2 |

-continued
| Ex. | Structure | $^1$H NMR | LC-MS (ESI) [M + H]$^+$ |
| --- | --- | --- | --- |
| 285 | 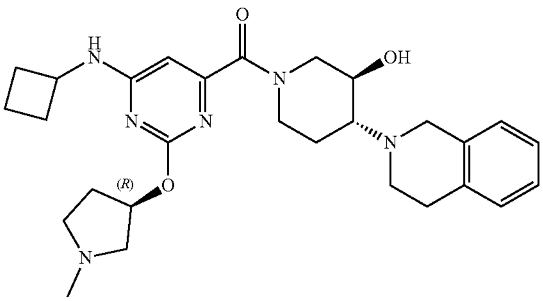 | (400 MHz, $CDCl_3$) δ 7.17-7.10 (m, 3H), 7.04-7.02 (m, 1H), 6.18-6.14 (m, 1H), 5.36-4.99 (m, 2H), 4.78-4.75 (m, 1H), 4.28-4.12 (m, 1H), 3.95-3.92 (m, 1H), 3.71-3.62 (m, 3H), 3.22-2.98 (m, 2H), 2.92-2.87 (m, 3H), 2.79-2.55 (m, 6H), 2.45-2.38 (m, 5H), 2.35-2.28 (m, 1H), 1.98-1.56 (m, 7H). | 507.4 |
| 286 | 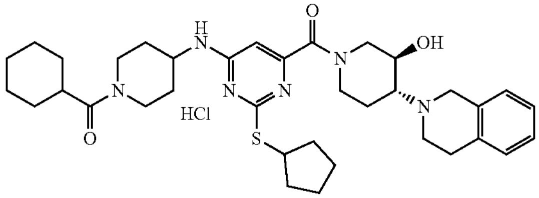 [SMILES: O=C(c1cc(NC2CCN(C(=O)C3CCCCC3)CC2)nc(SC2CCCC2)n1)N1CC[C@@H](N2CCc3ccccc3C2)[C@H](O)C1 ; Cl] | (400 MHz, $(CD_3)_2SO$) δ 10.52-10.06 (m, 1H), 8.02-7.65 (m, 1H), 7.33-7.15 (m, 4H), 6.56-5.88 (m, 2H), 4.73-4.39 (m, 3H), 4.35-4.19 (m, 1H), 4.07 (s, 1H), 3.99-3.84 (m, 4H), 3.46-2.93 (m, 6H), 2.89-2.56 (m, 4H), 2.31-2.07 (m, 3H), 2.01-1.83 (m, 2H), 1.80-1.50 (m, 12H), 1.46-1.24 (m, 6H), 1.21-1.07 (m, 1H). | 645.2 |
| 287 | 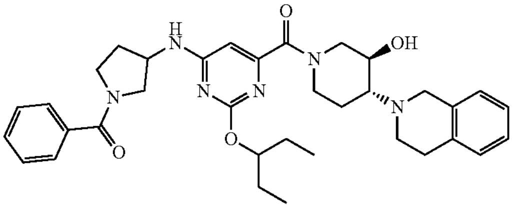 [SMILES: CCC(CC)Oc1nc(NC2CCN(C(=O)c3ccccc3)C2)cc(C(=O)N2CC[C@@H](N3CCc4ccccc4C3)[C@H](O)C2)n1] | (400 MHz, $CD_3OD$) δ 7.56-7.40 (m, 5H), 7.09-7.01 (m, 4H), 6.25-6.17 (m, 1H), 4.67-4.41 (m, 2H), 3.99-3.57 (m, 8H), 3.10-2.64 (m, 8H), 2.37-2.25 (m, 1H), 2.13-1.84 (m, 2H), 1.75-1.48 (m, 5H), 1.01-0.72 (m, 6H). | 613.4 |
| 288 | 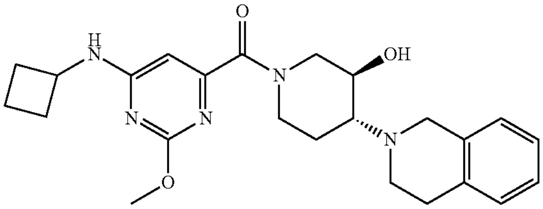 [SMILES: COc1nc(NC2CCC2)cc(C(=O)N2CC[C@@H](N3CCc4ccccc4C3)[C@H](O)C2)n1] | (400 MHz, $CD_3OD$) δ 7.13-7.04 (m, 4H), 6.15 (d, J = 9.2 Hz, 1H), 4.70-4.53 (m, 2H), 4.01-3.77 (m, 7H), 3.13-3.07 (m, 1H), 2.99-2.92 (m, 4H), 2.88-2.81 (m, 1H), 2.71-2.65 (m, 1H), 2.40-2.38 (m, 2H), 2.04-1.64 (m, 6H). | 438.2 |
| 289 | 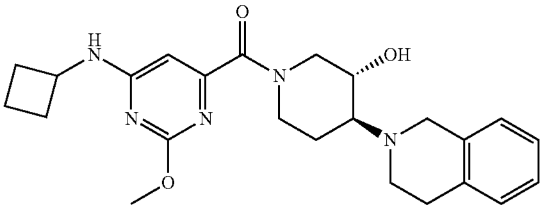 [SMILES: COc1nc(NC2CCC2)cc(C(=O)N2CC[C@H](N3CCc4ccccc4C3)[C@@H](O)C2)n1] | (400 MHz, $CD_3OD$) δ 7.10-7.03 (m, 4H), 6.15 (d, J = 9.6 Hz, 1H), 4.70-4.51 (m, 2H), 3.96-3.75 (m, 7H), 3.13-2.65 (m, 7H), 2.40-2.38 (m, 2H), 2.01-1.62 (m, 6H). | 438.2 |

-continued
| Ex. | Structure | $^1$H NMR | LC-MS (ESI) [M + H]$^+$ |
|---|---|---|---|
| 290 | 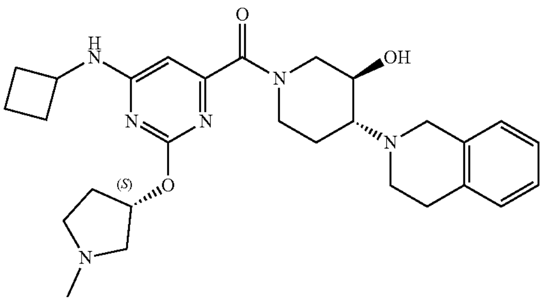 | (400 MHz, $CD_3OD$) δ 7.11-7.05 (m, 4H), 6.17 (d, J = 9.6 Hz, 1H), 5.40 (s, 1H), 4.71-4.54 (m, 2H), 3.98-3.78 (m, 4H), 3.10-2.97 (m, 3H), 2.96-2.84 (m, 4H), 2.80-2.73 (m, 3H), 2.63-2.59 (m, 1H), 2.41-2.36 (m, 6H), 2.04-1.91 (m, 4H), 1.85-1.80 (m, 2H), 1.69-1.66 (m, 1H). | 507.4 |
| 291 | 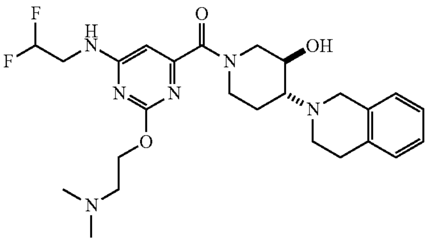 [SMILES: CN(C)CCOc1nc(NCC(F)F)cc(C(=O)N2CC[C@@H](N3CCc4ccccc4C3)[C@H](O)C2)n1] | (400 MHz, DMSO-$d_6$) δ 8.03 (s, 1H), 7.18-6.99 (m, 4H), 6.44-5.91 (m, 2H), 4.86-4.19 (m, 1H), 4.52-4.23 (m, 3H), 3.87-3.80 (m, 2H), 3.77-3.53 (m, 4H), 3.10-2.77 (m, 5H), 2.76-2.60 (m, 2H), 2.58-2.53 (m, 2H), 2.23-2.14 (m, 6H), 1.86-1.70 (m, 1H), 1.56-1.44 (m, 1H). | 505.5 |
| 292 | 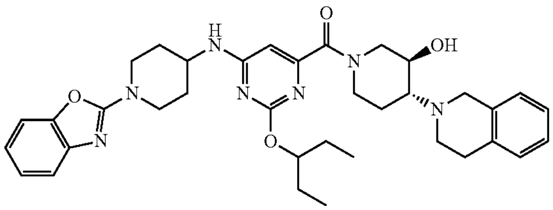 [SMILES: CCC(CC)Oc1nc(NC2CCN(c3nc4ccccc4o3)CC2)cc(C(=O)N2CC[C@@H](N3CCc4ccccc4C3)[C@H](O)C2)n1] | (400 MHz, DMSO-$d_6$) δ 10.31-9.86 (m, 1H), 8.08-7.75 (m, 1H), 7.41 (d, J = 8.0 Hz, 1H), 7.30-7.12 (m, 6H), 7.05-6.99 (m, 1H), 6.29-6.20 (m, 1H), 4.91-4.90 (m, 1H), 4.71-4.36 (m, 3H), 4.00-4.20 (m, 3H), 4.06-3.70 (m, 5H), 3.33-2.95 (m, 4H), 2.86-2.65 (m, 1H), 2.38-1.48 (m, 12H), 0.92-0.89 (m, 6H). | 640.0 |
| 293 | 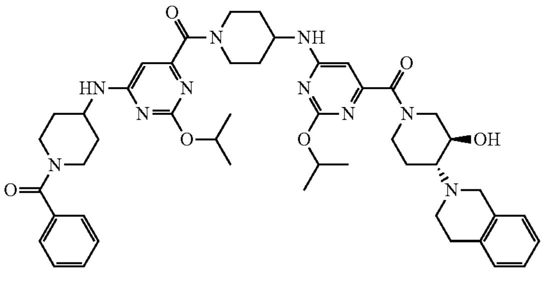 [SMILES: CC(C)Oc1nc(NC2CCN(C(=O)c3ccccc3)CC2)cc(C(=O)N2CCC(Nc3cc(C(=O)N4CC[C@@H](N5CCc6ccccc6C5)[C@H](O)C4)nc(OC(C)C)n3)CC2)n1] | (400 MHz, $CDCl_3$) δ 7.48-7.34 (m, 5H), 7.14 (m, 3H), 7.08-6.96 (m, 1H), 6.27-6.24 (m, 2H), 5.33-5.19 (m, 3H), 5.19-5.16 (m, 1H), 4.58-4.55 (m, 2H), 4.30-4.28 (m, 2H), 4.06-4.03 (m, 2H), 3.74-3.73 (m, 3H), 3.21-2.76 (m, 11H), 2.08-1.98 (m, 5H), 1.66-1.56 (m, 3H), 1.37-1.33 (m, 14H). | 861.6 |
| 294 | 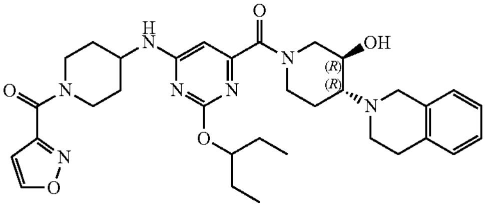 | (400 MHz, $CD_3OD$) δ 8.80-8.79 (m, 1H), 7.10-7.02 (m, 4H), 6.70 (t, J = 1.2 Hz, 1H), 6.12-6.21 (m, 1H), 5.02-4.97 (m, 1H), 4.70-4.53 (m, 2H), 4.24-4.14 (m, 2H), 3.96-3.75 (m, 4H), 3.42-3.32 (m, 1H), 3.17-2.66 (m, 8H), 2.16-1.86 (m, 3H), 1.73-1.52 (m, 7H), 0.99-0.93 (m, 6H). | 618.3 |

Example 295: Preparation of 1-(4-((6-((3R,4R)-4-(3,4-dihydroisoquinoline-2(1H)-yl)-3-hydroxypiperidine-1-carbonyl)-2-isopropoxypyrimidine-4-yl)amino)piperidine-1-yl)ethane-1-one Step 1: Preparation of 6-((1-acetylpiperidine-4-yl)amino)-2-isopropoxypyrimidine-4-carboxylic acid

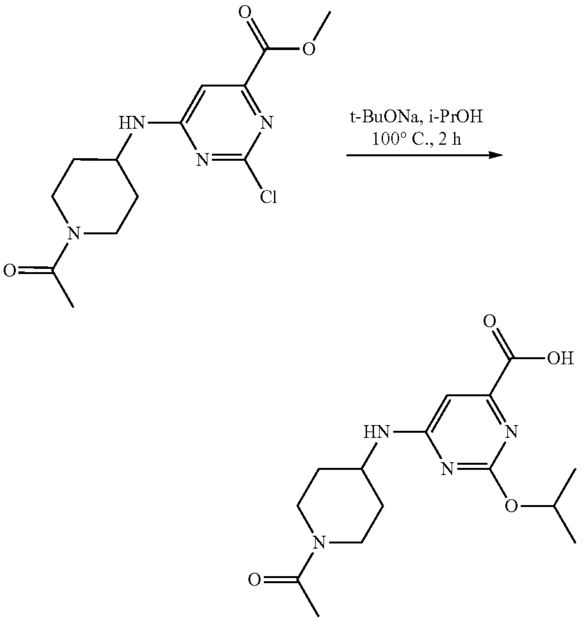

6-((1-acetylpiperidine-4-yl)amino)-2-chloropyrimidine-4-carboxylic acid methyl ester (3.25 g, purity: 50% (containing 50% DIPEA hydrochloride), 5.196 mmol, 1.0 equiv.) and sodium tert-butoxide (4.0 g, 41.62 mmol, 8.01 equiv.) were placed in a single-necked bottle. Anhydrous isopropanol (104 mL) was added. The reaction was performed under the protection of nitrogen gas at 100° C. for 2 hours. The completion of the reaction was monitored with LC-MS. The reaction system was adjusted to pH=3-4, and filtered. The solvent was removed by rotary drying to produce a crude product (110 mg), which was purified with reverse phase HPLC (C18, 10 mmol/L aqueous $NH_4HCO_3$ solution/acetonitrile) to produce the title compound (755 mg, yield: 44.6%).

LC-MS (ESI) $[M+H]^+$=323.3.

Step 2: Preparation of 1-(4-((6-((3R,4R)-4-(3,4-dihydroisoquinoline-2(1H)-yl)-3-hydroxypiperidine-1-carbonyl)-2-isopropoxypyrimidine-4-yl)amino)piperidine-1-yl)ethane-1-one

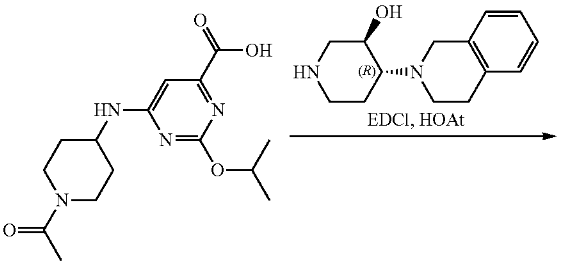

-continued

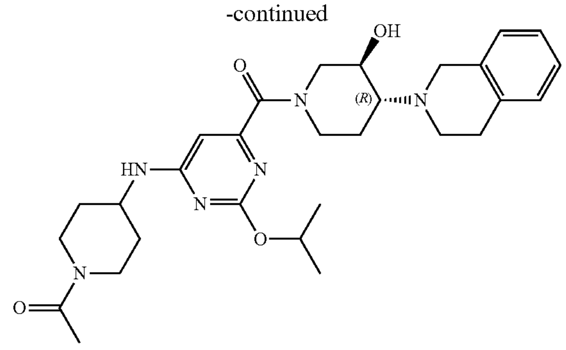

6-((1-acetylpiperidine-4-yl)amino)-2-isopropoxypyrimidine-4-carboxylic acid (550 mg, 1.706 mmol, 1 equiv.), EDCI (1-(3-dimethylaminopropyl)-3-ethylcarbodiimide hydrochloride)(495 mg, 2.582 mmol, 1.51 equiv.) and HOAt (N-hydroxy-7-aza-benzotriazole)(352 mg, 2.586 mmol, 1.52 equiv.) were dissolved in DMF (5.5 mL). The resulting mixture was stirred for 5 minutes, and a solution of (3R,4R)-4-(3,4-dihydroisoquinoline-2(1H)-yl)piperidine-3-ol (396 mg, 1.534 mmol, 0.9 equiv.) in DMF (3.5 mL) was added. The reaction was performed under stirring at room temperature for 1 hour. The solvent was removed by rotary drying to obtain a crude product, which was purified with reverse phase HPLC (C18, 10 mmol/L aqueous $NH_4HCO_3$ solution/acetonitrile) to produce the target compound (536 mg, yield: 58.6%).

LC-MS (ESI) $[M+H]^+$=537.3; $^1$H NMR (400 MHz, $CDCl_3$) δ 7.19-7.08 (m, 3H), 7.07-6.99 (m, 1H), 6.28-6.14 (m, 1H), 5.69-5.28 (m, 1H), 5.26-5.14 (m, 1H), 5.03-4.94 (m, 0.37H), 4.80-4.70 (m, 0.64H), 4.55-4.44 (m, 1H), 4.30-4.13 (m, 1H), 3.99-3.91 (m, 1H), 3.90-3.61 (m, 4H), 3.26-3.15 (m, 1H), 3.10-2.56 (m, 8H), 2.14-1.88 (m, 6H), 1.72-1.58 (m, 1H), 1.46-1.30 (m, 8H).

Example 296: Preparation of 1-(4-((6-(trans-4-(3,4-dihydroisoquinoline-2(1H)-yl)-3-hydroxypiperidine-1-carbonyl)-2-(pyrrolidin-1-yl)pyrimidine-4-yl)amino)piperidine-1-yl)ethane-1-one Step 1: Preparation of 6-((1-acetylpiperidine-4-yl)amino)-2-chloropyrimidine-4-carboxylic acid methyl ester

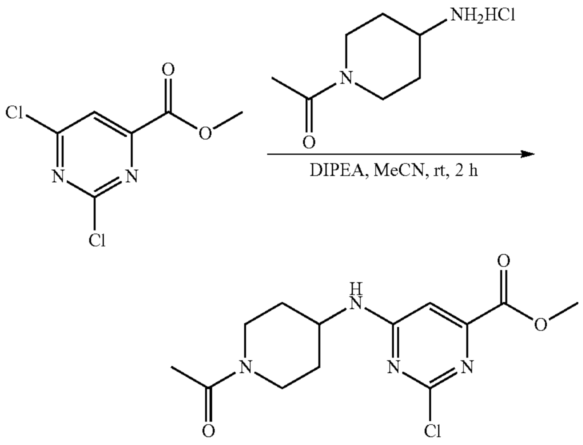

2,6-dichloropyrimidine-4-carboxylic acid methyl ester (6 g, 28.98 mmol), 1-acetylpiperidine-4-amine hydrochloride (5.7 g, 31.88 mmol) and DIPEA (14.98 g, 115.94 mmol) were dissolved in acetonitrile (50 mL). The resulting mixture was stirred at room temperature (25-30° C.) for 2 hours, and extracted with ethyl acetate three times, each time 100 mL. The ethyl acetate phases were combined, washed with water (50 mL) once, washed with saturated brine (50 mL) once, dried over anhydrous sodium sulfate for 10 minutes, and filtered to obtain a crude product, which was separated and purified with a column chromatography (DCM: MeOH=100:1) to produce a product (5.8 g, yield: 64%).

LC-MS (ESI) $[M+H]^+$=313.2.

Step 2: Preparation of 6-((1-acetylpiperidine-4-yl) amino)-2-chloropyrimidine-4-carboxylic acid hydrochloride

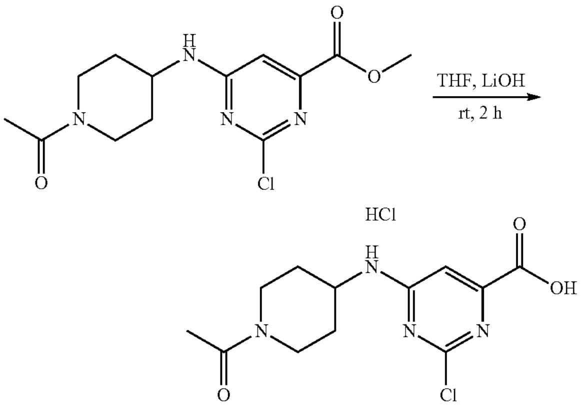

6-((1-acetylpiperidine-4-yl)amino)-2-chloropyrimidine-4-carboxylic acid methyl ester (5 g, 16.02 mmol) was dissolved in THF (36 mL) and methanol (36 mL). Then aqueous lithium hydroxide solution (16 mL, 32 mmol, 2M) was added. The reaction solution was stirred at room temperature (25-30° C.) for 2 hours. TLC indicated the completion of the reaction. The reaction system was adjusted with 1M (molar concentration) hydrochloric acid to pH=6-7, and directly rotary dried to obtain a crude product (5.8 g).

LC-MS (ESI) $[M+H]^+$=299.0.

Step 3: Preparation of 1-(4-((2-chloro-6-((trans)-4-(3,4-dihydroisoquinoline-2(1H)-yl)-3-hydroxypiperidine-1-carbonyl)pyrimidine-4-yl)amino)piperidine-1-yl)ethane-1-one

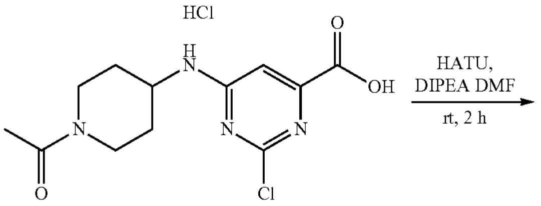

-continued

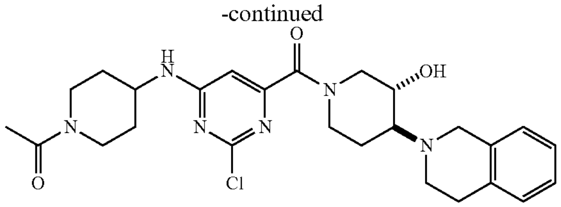

6-((1-acetylpiperidine-4-yl)amino)-2-chloropyrimidine-4-carboxylic acid hydrochloride (500 mg, 1.67 mmol), HATU (636.4 mg, 1.67 mmol), trans-4-(3,4-dihydroisoquinoline-2(1H)-yl)piperidine-3-ol (388.8 mg, 1.67 mmol) and DIPEA (1.08 g, 8.37 mmol) were dissolved in DMF (6.5 mL), The reaction solution was stirred at room temperature (25-30° C.) for 2 hours. LC-MS indicated the completion of the reaction. The reaction system was extracted with ethyl acetate three times, each time 20 mL. The ethyl acetate phases were combined, washed with water (10 mL) once, washed with saturated brine (10 mL) once, dried over anhydrous sodium sulfate for 10 minutes, and filtered to obtain a crude product, which was separated and purified with a column chromatography (DCM:MeOH=20:1) to produce the title compound (200 mg).

LC-MS (ESI) $[M+H]^+$=513.2.

Step 4: Preparation of 1-(4-((6-(trans-4-(3,4-dihydroisoquinoline-2(1H)-yl)-3-hydroxypiperidine-1-carbonyl)-2-(pyrrolidin-1-yl)pyrimidine-4-yl)amino) piperidine-1-yl)ethane-1-one

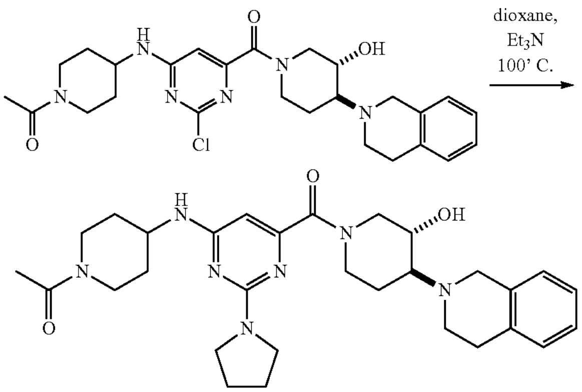

1-(4-((2-chloro-6-((trans)-4-(3,4-dihydroisoquinoline-2(1H)-yl)-3-hydroxypiperidine-1-carbonyl)pyrimidine-4-yl)amino)piperidine-1-yl)ethane-1-one (133 mg, 0.195 mmol) and tetrahydropyrrole (55 mg, 0.78 mmol) were dissolved in 1,4-dioxane (2 mL). $Et_3N$ (0.3 mL) was added. The resulting mixture was stirred at 100° C. for 2 hours. LC-MS indicated the completion of the reaction. The reaction system was extracted with EA (3*10 mL). The EA phases were combined, washed with water (1*10 mL) and saturated brine (1*10 mL), dried over anhydrous sodium sulfate, filtered, and purified with reverse phase Prep-HPLC (C18, 10 mmol/L aqueous $NH_4HCO_3$ solution/acetonitrile) to produce the title compound (77.47 mg, yield: 72%).

LC-MS (ESI) $[M+H]^+$=548.3; $^1H$ NMR (400 MHz, $CDCl_3$) δ 7.18-7.10 (m, 3H), 7.04-7.02 (m, 1H), 5.89-5.86 (m, 1H), 5.03 (m, 0.3H), 4.67 (s, 1H), 4.60-4.44 (m, 1.7H), 4.42-4.27 (m, 1H), 4.19 (s, 1H), 4.04-3.64 (m, 5H), 3.52 (s,

4H), 3.19 (t, J=12.6 Hz, 1H), 3.12-2.88 (m, 5H), 2.88-2.51 (m, 3H), 2.19-2.08 (m, 4H), 2.08-1.90 (m, 6H), 1.90-1.73 (m, 1H), 1.48-1.31 (m, 2H).

Example 297: Preparation of 1-(4-((6-(trans-4-(3,4-dihydroisoquinoline-2(1H)-yl)-3-hydroxypiperidine-1-carbonyl)-2-(trifluoromethyl)pyrimidine-4-yl)amino)piperidine-1-yl)ethane-1-one Step 1: Preparation of 1-(4-((6-chloro-2-(trifluoromethyl)pyrimidine-4-yl)amino)piperidine-1-yl)ethane-1-one

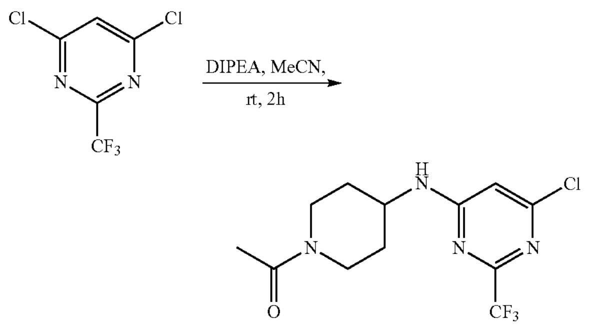

4,6-dichloro-2-(trifluoromethyl)pyrimidine (1.09 g, 5.02 mmol), 1-acetylpiperidine-4-amine hydrochloride (0.89 g, 5.02 mmol) and DIPEA (1.95 g, 15.07 mmol) were dissolved in acetonitrile (10 mL). The resulting mixture was stirred at room temperature for 2 hours. LC-MS monitored the completion of the reaction. The reaction system The reaction system was extracted with EA (3*20 mL). EA phases were combined, washed with water (1*20 mL) mL and saturated brine (1*20 mL) mL, dried over anhydrous sodium sulfate, and filtered to obtain a crude product, which was separated and purified with a column chromatography (DCM:MeOH=50:1) to produce the title compound (1.174 g, yield: 54%).

LC-MS (ESI) $[M+H]^+$=323.1.

Step 2: Preparation of 6-((1-acetylpiperidine-4-yl)amino)-2-(trifluoromethyl)pyrimidine-4-carboxylic acid methyl ester

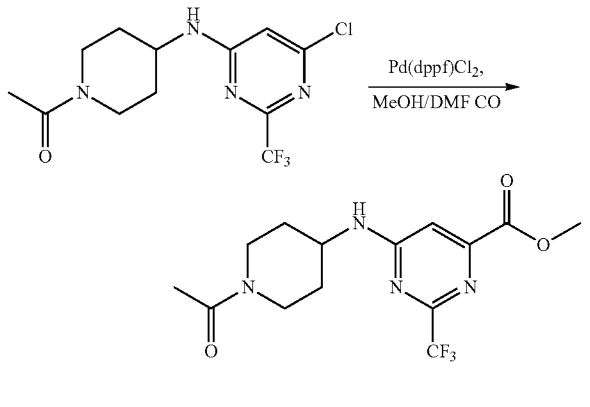

1-(4-((6-chloro-2-(trifluoromethyl)pyrimidine-4-yl)amino)piperidine-1-yl)ethane-1-one (0.3 g, 0.93 mmol), $Et_3N$ (282 mg, 2.79 mmol) and $Pd(dppf)Cl_2$ (68 mg, 0.093 mmol) were dissolved in a mixed solution of methanol (15 mL) and DMF (15 mL). The reaction was performed in an atmosphere of CO of 2 atms under heating at 100° C. for 30 hours. LC-MS indicated that a part of starting materials were converted into the product. The solvent was removed by rotary drying, The reaction system was extracted with EA (3*20 mL). EA phases were combined, washed with water (1*20 mL) mL and saturated brine (1*20 mL) mL, dried over anhydrous sodium sulfate, and filtered to obtain a crude product, which was separated and purified with a column chromatography (DCM:MeOH=50:1) to produce the title compound (100 mg, yield: 31%).

LC-MS (ESI) $[M+H]^+$=347.2.

Step 3: Preparation of 6-((1-acetylpiperidine-4-yl)amino)-2-(trifluoromethyl)pyrimidine-4-carboxylic acid hydrochloride

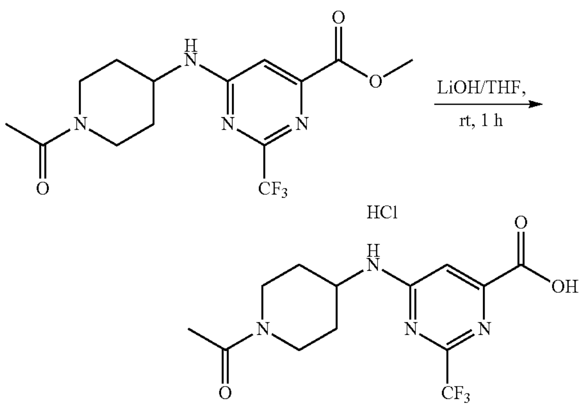

6-((1-acetylpiperidine-4-yl)amino)-2-(trifluoromethyl)pyrimidine-4-carboxylic acid methyl ester (100 mg, 0.289 mmol) were dissolved in THF (4 mL). Then aqueous lithium hydroxide solution (0.43 mL, 0.87 mmol, 2M) were added. The resulting mixture was stirred at room temperature for 1 hour. LC-MS indicated the completion of the reaction. The reaction system was extracted with EA (3*10 mL). The aqueous phase was retained. The reaction system was adjusted with 1 M (molar concentration) of hydrochloric acid to pH=6-7, and directly rotary dried to obtain a crude product (120 mg).

LC-MS (ESI) $[M+H]^+$=333.2.

Step 4: Preparation of 1-(4-((6-(trans-4-(3,4-dihydroisoquinoline-2(1H)-yl)-3-hydroxypiperidine-1-carbonyl)-2-(trifluoromethyl)pyrimidine-4-yl)amino)piperidine-1-yl)ethane-1-one

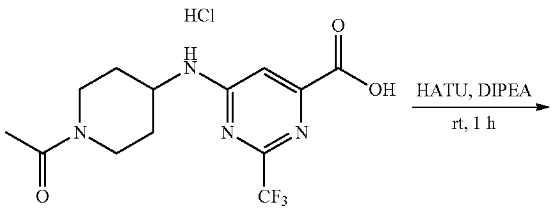

-continued

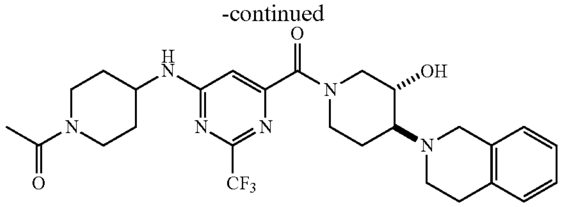

According to the process in step 2 of Example 5, 6-((1-acetylpiperidine-4-yl)amino)-2-(trifluoromethyl)pyrimidine-4-carboxylic acid hydrochloride (100 mg, 0.27 mmol, 1.0 equiv.) and trans-4-(3,4-dihydroisoquinoline-2(1H)-yl)piperidine-3-ol (66 mg, 0.28 mmol, 1.04 equiv.) were subjected to condensation reaction to obtain a crude product, which was separated and purified with reverse phase preparative HPLC (C18, 10 mmol/L aqueous $NH_4HCO_3$ solution/acetonitrile) to produce the title compound (104.56 mg, yield: 70%).

LC-MS (ESI) $[M+H]^+=547.2$; $^1H$ NMR (400 MHz, $CDCl_3$) δ 7.19-7.11 (m, 3H), 7.05-7.03 (m, 1H), 6.82-6.72 (m, 1H), 5.90-5.66 (m, 1H), 5.00-4.71 (m, 1H), 4.57 (d, J=13.0 Hz, 1H), 4.35-3.94 (m, 3H), 3.90-3.65 (m, 4H), 3.24 (t, J=13.2 Hz, 1H), 3.16-3.00 (m, 2H), 3.00-2.92 (m, 2H), 2.92-2.59 (m, 4H), 2.12 (d, J=2.4 Hz, 4H), 2.08-1.97 (m, 2H), 1.94-1.76 (m, 1H), 1.53-1.31 (m, 2H).

Example 298: Preparation of trans-1-(4-((6-(4-(3,4-dihydroisoquinoline-2(1H)-yl)-3-hydroxypiperidine-1-carbonyl)-2-(1H-imidazole-1-yl)pyrimidine-4-yl)amino)piperidine-1-yl)ethane-1-one

Step 1: Preparation of 6-((1-acetylpiperidine-4-yl)amino)-2-(1H-imidazole-1-yl)pyrimidine-4-carboxylic acid

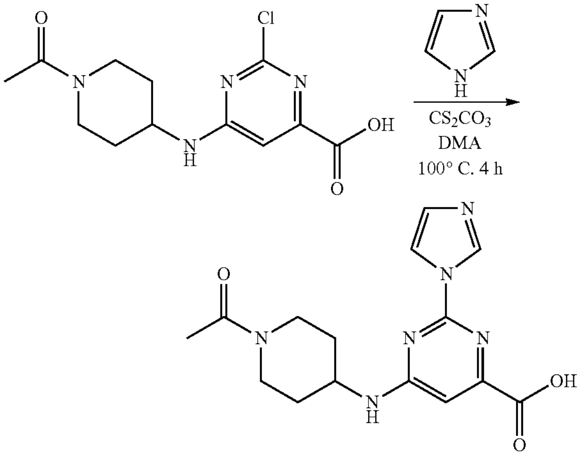

6-((1-acetylpiperidine-4-yl)amino)-2-chloropyrimidine-4-carboxylic acid (400 mg, 1.339 mmol, 1 equiv.) and imidazole (182 mg, 2.678 mmol, 2 equiv.) were dissolved in DMA (20 mL). Then cesium carbonate (1.31 g, 4.017 mmol, 3 equiv.) was added. The resulting mixture was stirred at 100° C. for 4 hours. The completion of the reaction was monitored with LC-MS. The reaction solution was quenched with water (10 mL), and extracted with DCM several times. The organic phases were dried, and concentrated to produce the title compound (3.0 g, crude).

LC-MS (ESI) $[M+H]^+=331.2$.

Step 2: Preparation of trans-1-(4-((6-(4-(3,4-dihydroisoquinoline-2(1H)-yl)-3-hydroxypiperidine-1-carbonyl)-2-(1H-imidazole-1-yl)pyrimidine-4-yl)amino)piperidine-1-yl)ethane-1-one

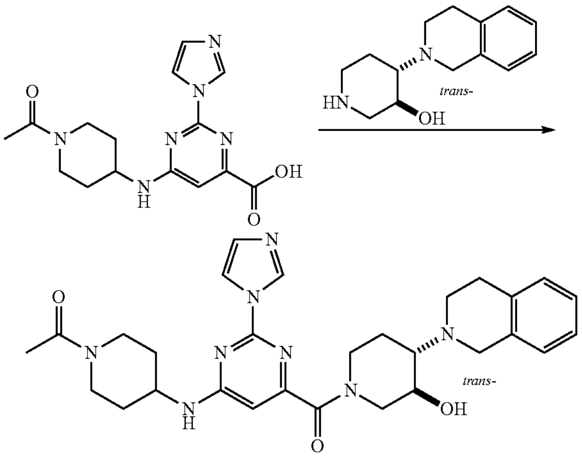

According to the process in step 2 of Example 5, 6-((1-acetylpiperidine-4-yl)amino)-2-(1H-imidazole-1-yl)pyrimidine-4-carboxylic acid (crude, 420 mg, 1.272 mmol, 1 equiv.) and trans-4-(3,4-dihydroisoquinoline-2(1H)-yl)piperidine-3-ol (325 mg, 1.399 mmol, 1.1 equiv.) were subjected to condensation reaction to obtain a crude product, which was separated and purified with reverse phase preparative HPLC (C18, aqueous $NH_4HCO_3$ solution/acetonitrile) to produce the title compound (75.42 mg, yield: 10.9%).

LC-MS (ESI) $[M+H]^+=545.3$; $^1H$ NMR (400 MHz, DMSO-$d_6$) δ 8.53-8.40 (m, 1H), 8.09 (t, J=8.1 Hz, 1H), 7.87-7.80 (m, 1H), 7.17-7.03 (m, 5H), 6.74-8.47 (m, 1H), 4.84-4.74 (m, 1H), 4.56-4.14 (m, 3H), 3.84-3.79 (m, 4H), 3.69-3.65 (m, 1H), 3.08-3.02 (m, 1H), 2.97-2.76 (m, 6H), 2.71-2.57 (m, 2H), 2.02 (s, 3H), 1.94-1.79 (m, 2H), 1.79-1.48 (m, 2H), 1.43-1.29 (m, 2H).

Example 299: Preparation of 1-(4-((6-(trans-4-(3,4-dihydroisoquinoline-2(1H)-yl)-3-hydroxypiperidine-1-carbonyl)-2-morpholinopyrimidine-4-yl)amino)piperidine-1-yl)ethane-1-one

Step 1: Preparation of 6-((1-acetylpiperidine-4-yl)amino)-2-chloropyrimidine-4-carboxylic acid methyl ester

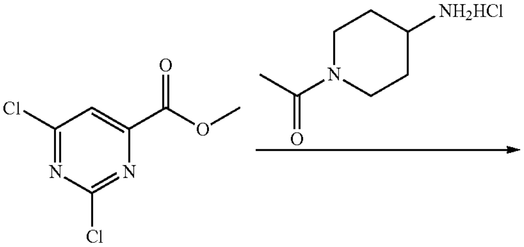

-continued

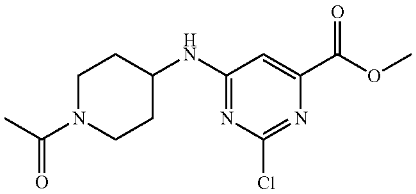

2,6-dichloropyridimine-4-carboxylic acid methyl ester (2 g, 9.66 mmol), 1-acetylpiperidine-4-amine hydrochloride (1.9 g, 10.63 mmol) and N,N-diisopropylethylamine (4.99 g, 38.65 mmol) were dissolved in acetonitrile (50 mL). The resulting mixture was stirred at 25° C. for 2 hours, and extracted with ethyl acetate three times, each time 50 mL. The ethyl acetate phases were combined, washed with water (20 mL) once, washed with saturated brine (20 mL) once, dried over anhydrous sodium sulfate for 10 minutes, and filtered to obtain a crude product, which was separated and purified with a column chromatography (DCM:MeOH=100:1) to produce 6-((1-acetylpiperidine-4-yl)amino)-2-chloropyrimidine-4-carboxylic acid methyl ester (2.8 g, yield: 92%).

LC-MS (ESI) $[M+H]^+$=313.2.

Step 2: Preparation of 6-((1-acetylpiperidine-4-yl)amino)-2-chloropyrimidine-4-carboxylic acid

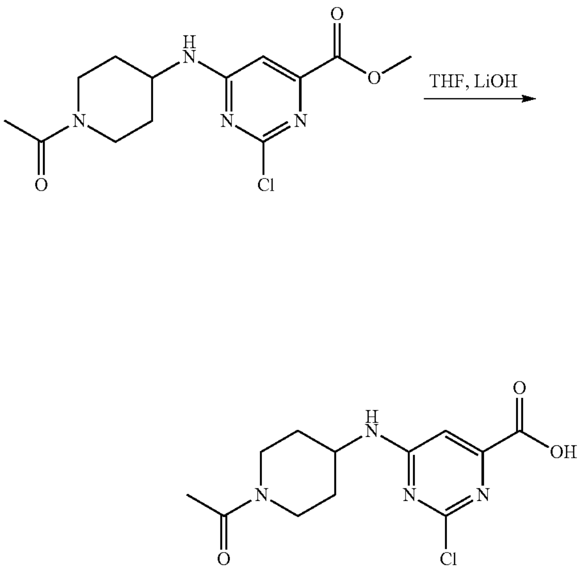

6-((1-acetylpiperidine-4-yl)amino)-2-methylpyrimidine-4-carboxylic acid methyl ester (200 mg, 0.639 mmol) was dissolved in THF (4 mL). Then 2M (molar concentration) of aqueous lithium hydroxide solution (0.64 mL, 1.28 mmol, 2 equiv.) was added. The reaction solution was stirred at room temperature (25° C.) for 2 hours. TLC indicated the completion of the reaction. The reaction system was adjusted with 1M (molar concentration) of hydrochloric acid to pH=6-7, and directly rotary dried to obtain a crude product (400 mg).

LC-MS (ESI) $[M+H]^+$=299.2.

Step 3: Preparation of 1-(4-((2-((3H-[1,2,3]triazolo[4,5-b]pyridine-3-yl)oxy)-6-(trans-4-(3,4-dihydroisoquinoline-2(1H)-yl)-3-hydroxypiperidine-1-carbonyl)pyrimidine-4-yl)amino)piperidine-1-yl)ethane-1-one

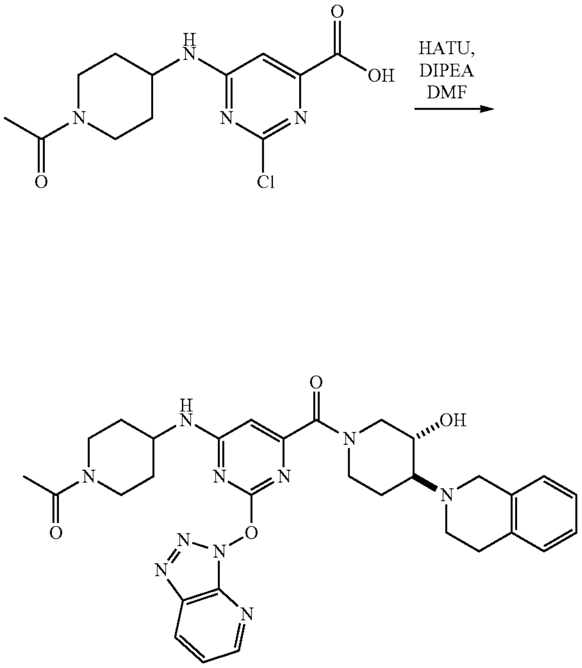

6-((1-acetylpiperidine-4-yl)amino)-2-chloropyrimidine-4-carboxylic acid (380 mg, 1.27 mmol), HATU (2-(7-azabenzotriazol-1-yl)-N,N,N',N'-tetramethyluronium hexafluorophosphate) (725.5 mg, 1.91 mmol), trans-4-(3,4-dihydroisoquinoline-2(1H)-yl)piperidine-3-ol (265 mg, 1.14 mmol) and DIPEA (N,N-diisopropylethylamine)(0.822 g, 6.36 mmol) were dissolved in DMF (N,N-dimethyl formamide)(5 mL). The reaction solution was stirred at room temperature (25° C.) for 2 hours. LC-MS indicated the completion of the reaction. The reaction system was extracted with ethyl acetate three times, each time 20 mL. The ethyl acetate phases were combined, washed with water (10 mL) once, washed with saturated brine (10 mL) once, dried over anhydrous sodium sulfate for 10 minutes, and filtered to obtain a crude product, which was separated and purified with a column chromatography (DCM:MeOH=20:1) to produce the title compound (200 mg).

LC-MS (ESI) $[M+H]^+$=613.3.

Step 4: Preparation of 1-(4-((6-(trans-4-(3,4-dihydroisoquinoline-2(1H)-yl)-3-hydroxypiperidine-1-carbonyl)-2-morpholinopyrimidine-4-yl)amino)piperidine-1-yl)ethane-1-one

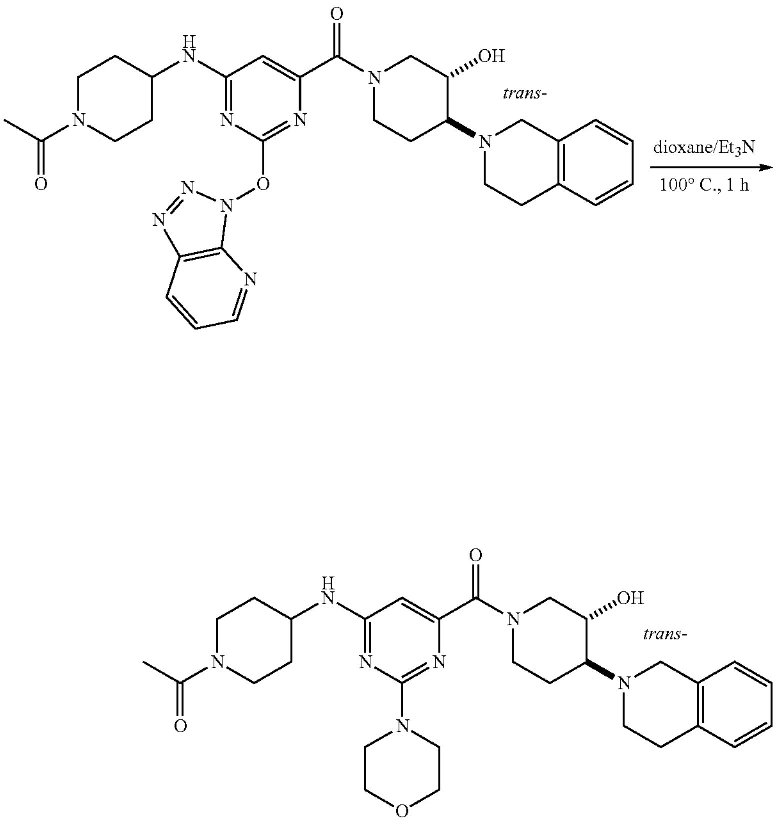 [SMILES: CC(=O)N1CCC(Nc2cc(C(=O)N3CC[C@H](N4CCc5ccccc5C4)[C@@H](O)C3)nc(On3nnc4cccnc43)n2)CC1 ; CC(=O)N1CCC(Nc2cc(C(=O)N3CC[C@H](N4CCc5ccccc5C4)[C@@H](O)C3)nc(N3CCOCC3)n2)CC1]

1-(4-((2-((3H-[1,2,3]triazolo[4,5-b]pyridine-3-yl)oxy)-6-(trans-4-(3,4-dihydroisoquinoline-2(1H)-yl)-3-hydroxypiperidine-1-carbonyl)pyrimidine-4-yl)amino)piperidine-1-yl)ethane-1-one (40 mg, 0.64 mmol) was dissolved in 1,4-dioxane (1.5 mL). $Et_3N$ (19.2 mg, 0.192 mmol) and morpholine (16 mg, 0.192 mmol) were added. The resulting mixture was stirred at 100° C. for 1 hour. LC-MS indicated the completion of the reaction. The reaction system was extracted with EA three times, each time 10 mL. The ethyl acetate phases were combined, washed with water (1*10 mL) and saturated brine (1*10 mL), dried over anhydrous sodium sulfate, filtered, and purified with reverse phase Prep-HPLC (crude, C18, 10 mmol/L aqueous $NH_4HCO_3$ solution/acetonitrile) to produce the title compound (25.59 mg, yield: 69%).

LC-MS (ESI) $[M+H]^+$=564.4; $^1H$ NMR (400 MHz, DMSO-$d_6$) δ 7.25 (s, 1H), 7.13-6.99 (m, 4H), 5.86 (s, 1H), 4.83-4.63 (m, 1H), 4.52-4.28 (m, 1H), 4.19 (d, J=12.6 Hz, 1H), 4.02 (s, 1H), 3.89-3.70 (m, 4H), 3.70-3.51 (m, 9H), 3.17 (t, J=12.4 Hz, 1H), 3.02-2.87 (m, 15H), 2.87-2.69 (m, 5H), 2.69-2.53 (m, 1.5H), 2.05-1.97 (m, 3H), 1.97-1.69 (m, 3H), 1.56-1.44 (m, 1H), 1.44-1.32 (m, 1H), 1.32-1.18 (m, 1H).

Example 300: Preparation of trans-1-(4-(3,4-dihydroisoquinoline-2(1H)-yl)-3-hydroxypiperidine-1-yl)(2-morpholino-6-((tetrahydro-2H-pyran-4-yl)amino)pyrimidine-4-yl)methanone Step 1: Preparation of 2-chloro-6-((tetrahydro-2H-pyran-4-yl)amino)pyrimidine-4-carboxylic acid methyl ester

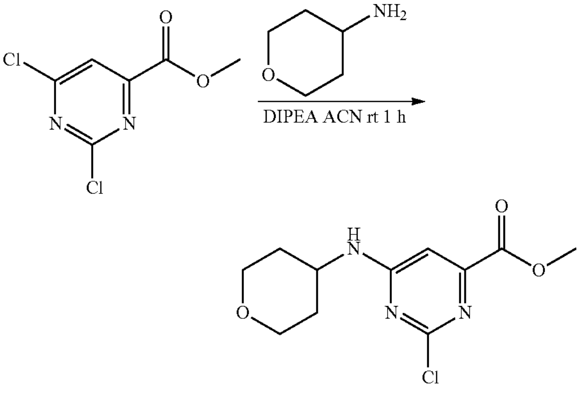

2,6-dichloropyridimine-4-carboxylic acid methyl ester (500 mg, 2.414 mmol, 1 equiv.) and tetrahydro-2H-pyran-4-amine (240 mg, 2.373 mmol, 3 equiv.) were dissolved in acetonitrile (12 mL). DIPEA (920 mg, 7.116 mmol, 3 equiv.) was added. The resulting mixture was stirred at 25° C. for 2 hours. The completion of the reaction was monitored with LC-MS. The reaction solution was quenched with water, and extracted with EA. The organic phases were combined, then washed with saturated sodium chloride, dried over anhydrous sodium sulfate, filtered, and concentrated to obtain a crude product, which was separated with flash chromatography (silica gel, PE:EA=1:10) to produce the title compound (720 mg, crude).

LC-MS (ESI) $[M+H]^+$=272.1.

Step 2: Preparation of 2-morpholino-6-((tetrahydro-2H-pyran-4-yl)amino)pyrimidine-4-carboxylic acid methyl ester

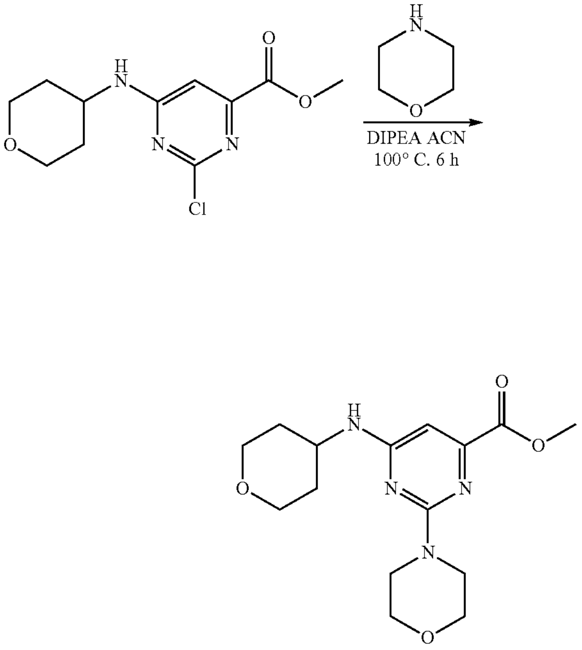

2-chloro-6-((tetrahydro-2H-pyran-4-yl)amino)pyrimidine-4-carboxylic acid methyl ester (720 mg, 2.582 mmol, 1 equiv.) and morpholine (247 mg, 2.840 mmol, 1.1 equiv.) were dissolved in acetonitrile (12 mL). DIPEA (1 g, 7.746 mmol, 3 equiv.) was added. The resulting mixture was stirred at 100° C. for 6 hours. The completion of the reaction was monitored with LC-MS. The reaction solution was quenched with water, and extracted with EA. The organic phases were combined, then washed with saturated sodium chloride, dried over anhydrous sodium sulfate, filtered, and concentrated to produce the title compound (900 g, crude).

LC-MS (ESI) $[M+H]^+$=323.3.

Step 3 Preparation of 2-morpholino-6-((tetrahydro-2H-pyran-4-yl)amino)pyrimidine-4-carboxylic acid

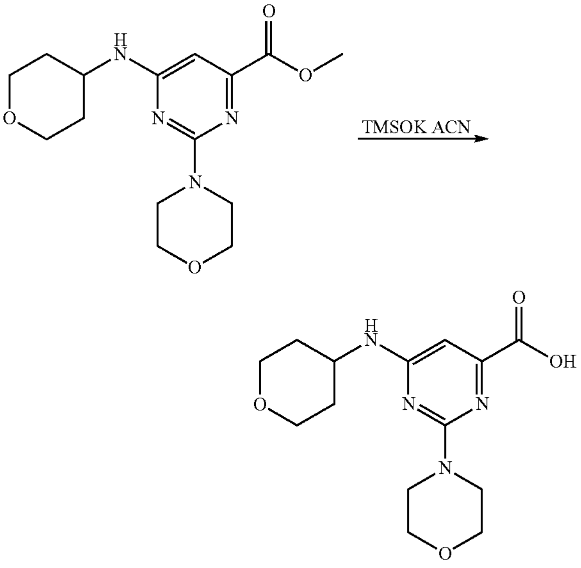

2-morpholino-6-((tetrahydro-2H-pyran-4-yl)amino)pyrimidine-4-carboxylic acid methyl ester (900 mg, 2.792 mmol, 1 equiv.) was dissolved in acetonitrile (30 mL). TMSOK (potassium trimethylsilanol)(394 mg, 3.071 mmol, 1.1 equiv.) was added. The resulting mixture was stirred at room temperature for 1 hour. The completion of the reaction was monitored with TLC. The reaction mixture was filtered. The filter cake was collected, and dissolved in water. The resulting mixture was adjusted with 1M (molar concentration) hydrochloric acid to pH=5-6. After the resulting solution was rotary dried, the resulting solid was dissolved in dichloromethane and methanol. The solid impurity was removed by filtering, and the resulting filtrate was concentrated to produce the title compound (1 g, crude).

LC-MS (ESI) $[M+H]^+$=309.2.

Step 4: Preparation of trans-1-(4-(3,4-dihydroisoquinoline-2(1H)-yl)-3-hydroxypiperidine-1-yl)(2-morpholino-6-((tetrahydro-2H-pyran-4-yl)amino)pyrimidine-4-yl)methanone

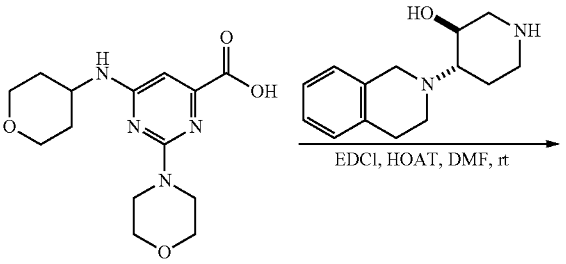

-continued

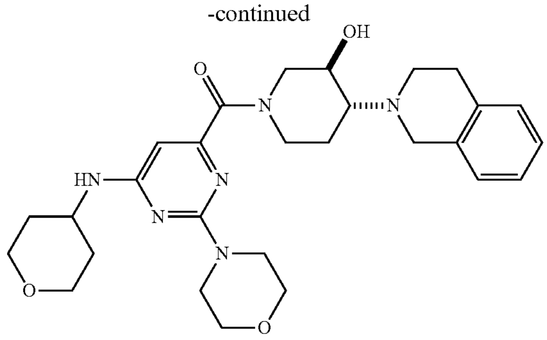

According to the process in step 2 of Example 5, 2-morpholino-6-((tetrahydro-2H-pyran-4-yl)amino)pyrimidine-4-carboxylic acid (200 mg, 0.649 mmol, 1 equiv.) and trans-4-(3,4-dihydroisoquinoline-2(1H)-yl)piperidine-3-ol (180 mg, 0.778 mmol, 1.2 equiv.) were subjected to condensation reaction to obtain a crude product, which was separated and purified with reverse phase HPLC (C18, aqueous $NH_4HCO_3$ solution/acetonitrile) to produce the title compound (106.9 mg, yield: 31.5%/).

LC-MS (ESI) $[M+H]^+$=523.6; $^1$H NMR (400 MHz, DMSO-$d_6$) δ 7.25 (s, 1H), 7.11-7.01 (m, 4H), 5.86 (s, 1H), 4.74 (dd, J=36.0, 3.8 Hz, 1H), 4.51-4.25 (m, 1H), 3.98 (s, 1H), 3.91-3.72 (m, 5H), 3.67-3.52 (m, 9H), 3.46-3.35 (m, 2H), 3.03-2.55 (m, 7H), 1.92-1.69 (m, 3H), 1.61-1.34 (m, 3H).

Example 301: Preparation of 1-(4-((6-((3R,4R)-4-(3,4-dihydroisoquinoline-2(1H)-yl)-3-hydroxypiperidine-1-carbonyl)-2-(pyrido[3,4-d]pyrimidine-7(8H)-yl)pyrimidine-4-yl)amino)piperidine-1-yl)ethane-1-one Using the same process as in Example 297, the compound of Example 301 (2.0 mg, yield: 1.2%) was synthesized.

LC-MS (ESI) $[M+H]^+$=610.4.

Examples 302-3531

Using the same process as in Example 297, the compounds of Examples 302-351 were synthesized. The compound structures and specific characterization data (LC-MS and $^1$H NMR) were as follows:

| Ex. | Structure | $^1$H NMR | LC-MS (ESI) $[M + H]^+$ |
|---|---|---|---|
| 302 | 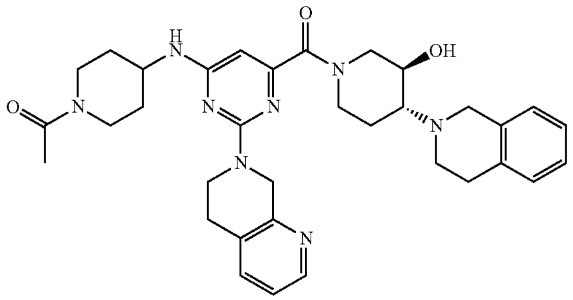 [SMILES: CC(=O)N1CCC(Nc2cc(C(=O)N3CC[C@@H](N4CCc5ccccc5C4)[C@H](O)C3)nc(N3CCc4cccnc4C3)n2)CC1] | (400 MHz, $CDCl_3$) δ 8.43-8.41 (m, 1H), 7.45-7.43 (m, 1H), 7.16-7.04 (m, 5H), 5.93-5.89 (m, 1H), 5.04-4.96 (m, 2H), 4.78-4.74 (m, 1H), 4.50-4.47 (m, 1H), 4.40-4.24 (m, 1H), 4.08-3.95 (m, 4H), 3.81-3.69 (m, 4H), 3.27-3.21 (m, 1H), 3.06-2.56 (m, 10H), 2.11-1.82 (m, 6H), 1.71-1.63 (m, 1H), 1.44-1.36 (m, 2H). | 611.0 |
| 303 | 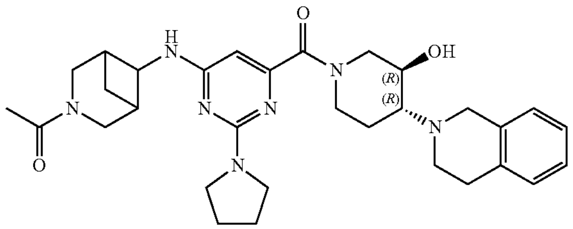 | (400 MHz, $CDCl_3$) δ 7.20-7.07 (m, 3H), 7.07-7.01 (m, 1H), 5.98-5.84 (m, 1H), 5.07-4.83 (m, 1H), 4.62-4.11 (m, 3H), 4.04-3.91 (m, 1H), 3.80-3.69 (m, 3H), 3.69-3.59 (m, 3H), 3.52 (s, 4H), 3.06-2.91 (m, 4H), 2.79-2.69 (m, 3H), 2.11 (s, 3H), 2.03-1.83 (m, 6H), 1.79-1.56 (m, 3H), 1.48-1.34 (m, 1H). | 560.0 |
| 304 | 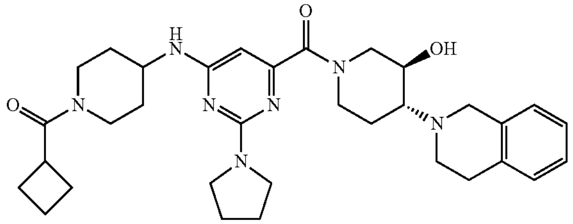 [SMILES: O=C(c1cc(NC2CCN(C(=O)C3CCC3)CC2)nc(N2CCCC2)n1)N1CC[C@@H](N2CCc3ccccc3C2)[C@H](O)C1] | (400 MHz, $CDCl_3$) δ 7.16-7.10 (m, 3H), 7.04-7.0 (m, 1H), 5.88-5.85 (m, 1H), 5.05-5.01 (m, 1H), 4.56-4.48 (m, 2H), 4.38-4.32 (m, 1H), 4.23-4.17 (m, 1H), 4.14-3.92 (m, 1H), 3.71-3.68 (m, 3H), 3.53-3.51 (m, 4H), 3.31-3.22 (m, 1H), 3.10-2.92 (m, 5H), 2.82-2.67 (m, 1H), 2.61-2.55 (m, 1H), 2.38-2.30 (m, 2H), 2.17-1.93 (m, 12H), 1.57-1.53 (m, 1H), 1.46-1.44 (m, 1H), 1.39-1.31 (m, 2H). | 588.6 |

-continued
| Ex. | Structure | $^1$H NMR | LC-MS (ESI) [M + H]$^+$ |
| --- | --- | --- | --- |
| 305 | 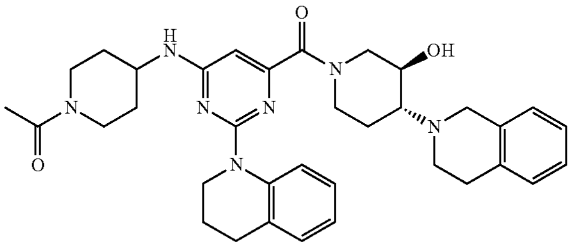 [SMILES: CC(=O)N1CCC(Nc2cc(C(=O)N3CC[C@@H](N4CCc5ccccc5C4)[C@H](O)C3)nc(N3CCCc4ccccc43)n2)CC1] | (400 MHz, DMSO-$d_6$) δ 7.75-7.70 (m, 1H), 7.36 (s, 1H), 7.11-7.03 (m, 6H), 6.95-6.89 (m, 1H), 5.99 (s, 1H), 4.79-4.69 (m, 1H), 4.48-4.33 (m, 1H), 4.27-4.24 (m, 1H), 4.04-3.77 (m, 7H), 3.64-3.57 (m, 1H), 3.12-3.04 (m, 1H), 3.02-2.82 (m, 2H), 2.80-2.53 (m, 8H), 2.00 (s, 3H), 1.89-1.74 (m, 5H), 1.55-1.43 (m, 1H), 1.37-1.23 (m, 2H). | 610.0 |
| 306 | 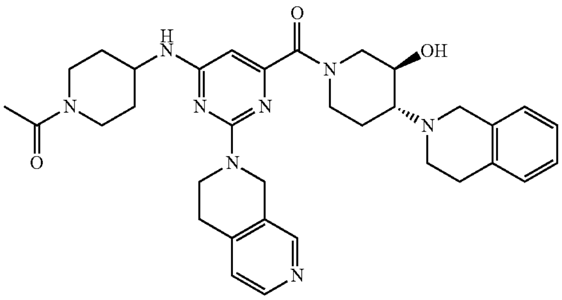 [SMILES: CC(=O)N1CCC(Nc2cc(C(=O)N3CC[C@@H](N4CCc5ccccc5C4)[C@H](O)C3)nc(N3CCc4ccncc4C3)n2)CC1] | (400 MHz, $CDCl_3$) δ 8.45-8.39 (m, 1H), 8.36 (d, J = 5.1 Hz, 1H), 7.23-6.93 (m, 6H), 6.05-5.81 (m, 1H), 5.10-4.63 (m, 4H), 4.58-4.31 (m, 2H), 4.27-3.95 (m, 4H), 3.87-3.69 (m, 3H), 3.30-3.07 (m, 2H), 3.04-2.95 (m, 2H), 2.93-2.69 (m, 6H), 2.18-1.95 (m, 6H), 1.91-1.71 (m, 1H), 1.49-1.35 (m, 2H). | 611.0 |
| 307 | 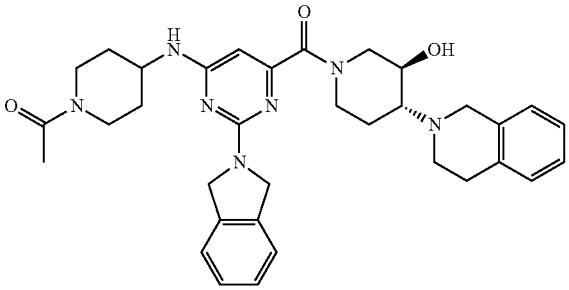 [SMILES: CC(=O)N1CCC(Nc2cc(C(=O)N3CC[C@@H](N4CCc5ccccc5C4)[C@H](O)C3)nc(N3Cc4ccccc4C3)n2)CC1] | (400 MHz, $CDCl_3$) δ 7.33-7.28 (m, 4H), 7.17-7.14 (m, 3H), 7.13-7.04 (m, 1H), 5.98-5.94 (m, 1H), 4.84-4.81 (m, 4H), 4.64-4.51 (m, 2H), 4.41-4.38 (m, 1H), 4.00-3.74 (m, 5H), 3.28-3.22 (m, 1H), 3.07-2.86 (m, 6H), 2.72-2.62 (m, 2H), 2.13 (s, 3H), 2.10-2.01 (m, 2H), 1.74-1.61 (m, 2H), 1.49-1.40 (m, 2H). | 596.4 |
| 308 | 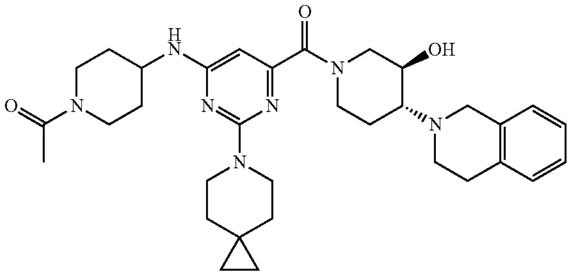 [SMILES: CC(=O)N1CCC(Nc2cc(C(=O)N3CC[C@@H](N4CCc5ccccc5C4)[C@H](O)C3)nc(N3CCC4(CC3)CC4)n2)CC1] | (400 MHz, $CDCl_3$) δ 7.19-7.09 (m, 3H), 7.05-7.00 (m, 1H), 5.93-5.78 (m, 1H), 5.09-4.58 (m, 2H), 4.54-4.46 (m, 1H), 4.44-4.24 (m, 1H), 4.02-3.88 (m, 2H), 3.84-3.64 (m, 7H), 3.25-3.15 (m, 1H), 3.12-3.02 (m, 1H), 2.98-2.53 (m, 7H), 2.15-2.08 (m, 4H), 2.06-1.81 (m, 2H), 1.74-1.60 (m, 1H), 1.47-1.31 (m, 6H), 0.35 (s, 4H). | 588.19 |
| 309 | 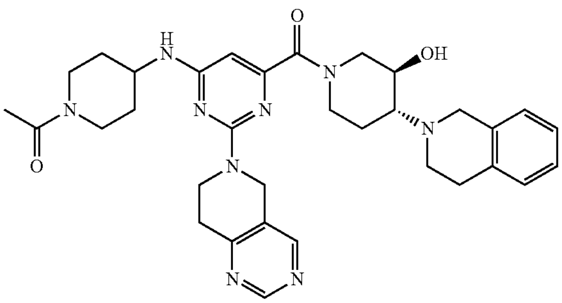 [SMILES: CC(=O)N1CCC(Nc2cc(C(=O)N3CC[C@@H](N4CCc5ccccc5C4)[C@H](O)C3)nc(N3CCc4ncncc4C3)n2)CC1] | (400 MHz, DMSO-$d_6$) δ 8.94 (d, J = 3.6 Hz, 1H), 8.67 (d, J = 8.8 Hz, 1H), 7.33 (s, 1H), 7.11-7.04 m, 4H), 5.89-5.87 (m, 1H), 4.87 (d, J = 6.8 Hz, 2H), 4.81-4.70 (m, 1H), 4.48-4.33 (m, 1H), 4.21 (m, 1H), 4.06-4.03 (m, 3H), 3.87-3.77 (m, 4H), 3.63 (s, 1H), 3.27-3.19 (m, 1H), 3.01-2.89 (m, 4H), 2.83-2.74 (m, 5H), 2.67-2.63 (m, 1H), 2.02 (s, 3H), 1.93-1.71 (m, 3H), 1.54-1.48 (m, 1H), 1.40-1.26 (m, 2H). | 612.4 |

-continued
| Ex. | Structure | $^1$H NMR | LC-MS (ESI) [M + H]$^+$ |
|---|---|---|---|
| 310 | 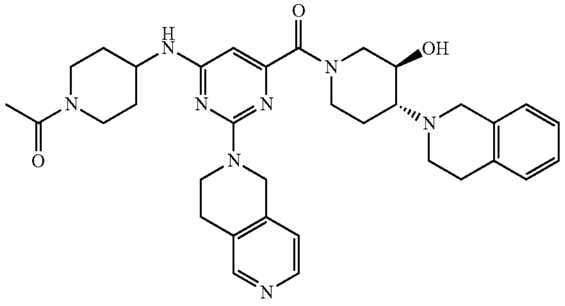 [SMILES: CC(=O)N1CCC(Nc2cc(C(=O)N3CC[C@@H](N4CCc5ccccc5C4)[C@H](O)C3)nc(N3CCc4cnccc4C3)n2)CC1] | (400 MHz, DMSO-$d_6$) δ 8.37 (d, J = 4.8 Hz, 1H), 8.33 (t, J = 5.6 Hz, 1H), 7.30 (s, 1H), 7.26-7.22 (m, 1H), 7.11-7.05 (m, 4H), 5.87 (s, 1H), 4.82-4.70 (m, 3H), 4.48-4.33 (m, 1H), 4.22 (s, 1H), 4.08-3.96 (m, 3H), 3.99-3.77 (m, 4H), 3.63-3.61 (m, 1H), 3.22-3.19 (m, 1H), 3.01-2.81 (m, 9H), 2.67-2.52 (m, 1H), 2.02 (s, 3H), 1.93-1.72 (m, 3H), 1.51-1.48 (m, 1H), 1.40-1.24 (m, 2H). | 612.4 |
| 311 | 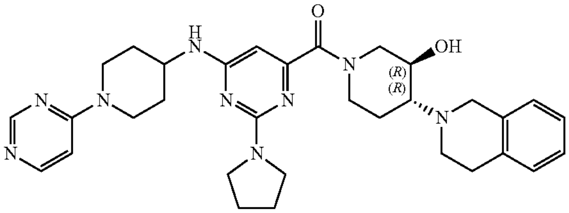 | (400 MHz, $CD_3OD$) δ 8.43 (s, 1H), 8.09 (d, J = 6.4 Hz, 1H), 7.11-7.00 (m, 4H), 6.83-6.75 (m, 1H), 5.89-5.75 (m, 1H), 4.75-4.46 (m, 1H), 4.43-4.32 (m, 2H), 4.27-4.16 (m, 1H), 4.05-3.85 (m, 3H), 3.85-3.75 (m, 1H), 3.57-3.45 (m, 4H), 3.25-3.14 (m, 2H), 3.14-2.96 (m, 2H), 2.96-2.86 (m, 3H), 2.86-2.62 (m, 2H), 2.15-2.09 (m, 2H), 2.04-1.82 (m, 5H), 1.77-1.60 (m, 1H), 1.58-1.45 (m, 2H). | 584.4 |
| 312 | 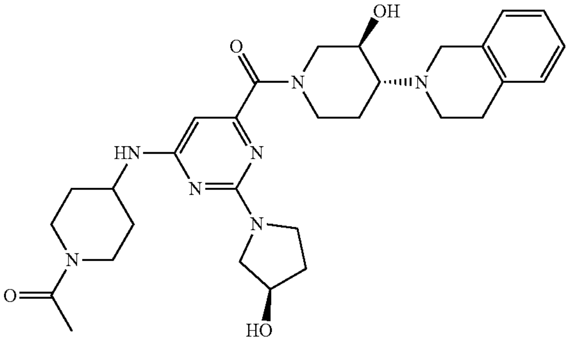 [SMILES: CC(=O)N1CCC(Nc2cc(C(=O)N3CC[C@@H](N4CCc5ccccc5C4)[C@H](O)C3)nc(N3CC[C@@H](O)C3)n2)CC1] | (400 MHz, DMSO-$d_6$) δ 7.10-7.02 (m, 5H), 5.79 (s, 1H), 4.88 (s, 1H), 4.78-4.73 (m, 1H), 4.48-4.32 (m, 2H), 4.22-4.19 (m, 1H), 4.04-3.75 (m, 5H), 3.61-3.49 (m, 4H), 3.19-3.13 (m, 1H), 2.98-2.79 (m, 7H), 2.67-2.56 (m, 1H), 2.00-1.72 (m, 8H) 1.51-1.25 (m, 3H). | 564.7 |
| 313 | 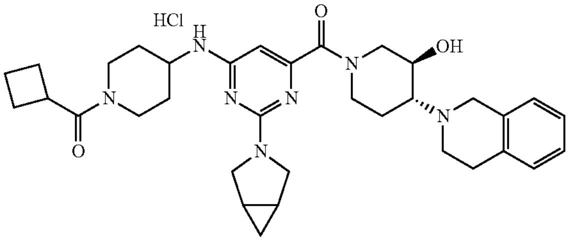 [SMILES: O=C(c1cc(NC2CCN(C(=O)C3CCC3)CC2)nc(N2CC3CC3C2)n1)N1CC[C@@H](N2CCc3ccccc3C2)[C@H](O)C1 ; Cl] | (400 MHz, $(CD_3)_2SO$) δ 10.30-9.88 (m, 1H), 7.31-7.19 (m, 5H), 6.26-5.98 (m, 2H), 4.68-4.19 (m, 5H), 4.08-3.89 (m, 3H), 3.79-3.63 (m, 5H), 3.22-2.78 (m, 6H), 2.18-2.07 (m, 6H), 1.95-1.86 (m, 4H), 1.81-1.24 (m, 7H), 0.77-0.69 (m, 1H), 0.20-0.10 (m, 1H). | 600.4 |
| 314 | 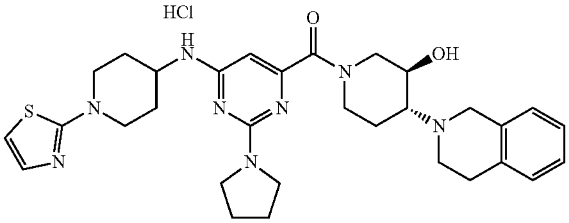 [SMILES: Cl ; O=C(c1cc(NC2CCN(c3nccs3)CC2)nc(N2CCCC2)n1)N1CC[C@@H](N2CCc3ccccc3C2)[C@H](O)C1] | (400 MHz, $(CD_3)_2SO$) δ 10.49-9.72 (m, 1H), 7.31-7.14 (m, 6H), 6.84 (d, J = 3.2 Hz, 1H), 6.25-5.89 (m, 2H), 4.69-4.39 (m, 3H), 4.12-3.82 (m, 5H), 3.74-3.40 (m, 8H), 3.25-3.17 (m, 3H), 3.09-2.94 (m, 2H), 1.99-1.81 (m, 8H), 1.64-1.50 (m, 2H). | 589.4 |
| 315 | 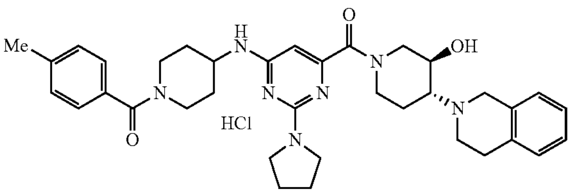 [SMILES: Cc1ccc(C(=O)N2CCC(Nc3cc(C(=O)N4CC[C@@H](N5CCc6ccccc6C5)[C@H](O)C4)nc(N4CCCC4)n3)CC2)cc1 ; Cl] | (400 MHz, $(CD_3)_2SO$) δ 10.67-10.18 (m, 1H), 7.35-7.14 (m, 9H), 6.42-5.75 (m, 2H), 4.79-4.40 (m, 3H), 4.34-3.69 (m, 6H), 3.43-3.25 (m, 6H), 3.22-2.59 (m, 6H), 2.34 (s, 3H), 2.26-1.83 (m, 8H), 1.59-1.32 (m, 2H). | 577.2 |

-continued
| Ex. | Structure | $^1$H NMR | LC-MS (ESI) $[M + H]^+$ |
| --- | --- | --- | --- |
| 316 | 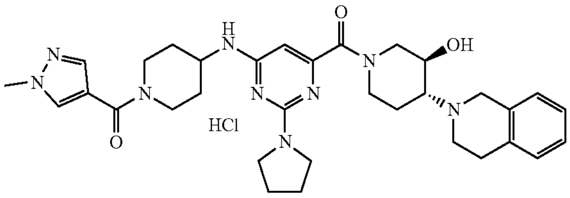 [SMILES: Cn1cc(C(=O)N2CCC(Nc3cc(C(=O)N4CC[C@@H](N5CCc6ccccc6C5)[C@H](O)C4)nc(N4CCCC4)n3)CC2)cn1 ; Cl] | (400 MHz, $(CD_3)_2SO$) δ 10.66-10.22 (m, 1H), 8.05 (s, 1H), 7.64 (s, 1H), 7.34-7.14 (m, 5H), 6.42-5.81 (m, 2H), 4.80-4.39 (m, 3H), 4.33-3.96 (m, 5H), 3.87-3.65 (m, 5H), 3.41-3.29 (m, 5H), 3.26-2.59 (m, 6H), 2.26-2.09 (m, 1H), 2.02-1.79 (m, 7H), 1.55-1.25 (m, 2H). | 613.2 |
| 317 | 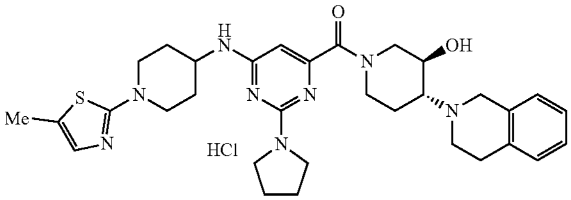 [SMILES: Cc1cnc(N2CCC(Nc3cc(C(=O)N4CC[C@@H](N5CCc6ccccc6C5)[C@H](O)C4)nc(N4CCCC4)n3)CC2)s1 ; Cl] | (400 MHz, $(CD_3)_2SO$) δ 8.96 (s, 2H), 7.51-6.56 (m, 6H), 6.07-5.74 (m, 1H), 5.50-5.00 (m, 1H), 4.87-4.39 (m, 1H), 4.37-4.00 (m, 2H), 3.93-3.66 (m, 2H), 3.40-3.23 (m, 6H), 3.20-2.83 (m, 6H), 2.80-2.56 (m, 2H), 2.37-1.99 (m, 6H), 1.97-1.56 (m, 8H). | 603.2 |
| 318 | 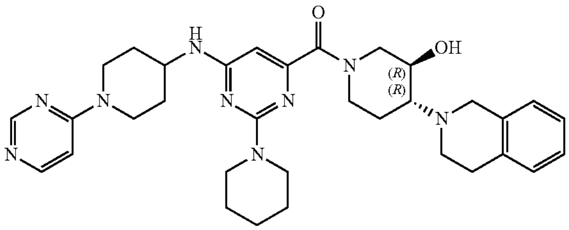 | (400 MHz, DMSO-$d_6$) δ 10.62-10.48 (m, 1H), 8.83 (s, 1H), 8.35-8.33 (m, 1H), 7.29-7.20 (m, 6H), 6.25 (s, 1H), 4.47-4.44 (m, 5H), 4.30-4.19 (m, 4H), 3.80-3.59 (m, 4H), 3.50-3.39 (m, 2H), 3.17-2.89 (m, 4H), 2.81-2.67 (m, 1H), 2.52-2.51 (m, 1H), 2.49-1.83 (m, 6H), 1.73-1.60 (m, 6H). | 598.5 |
| 319 | 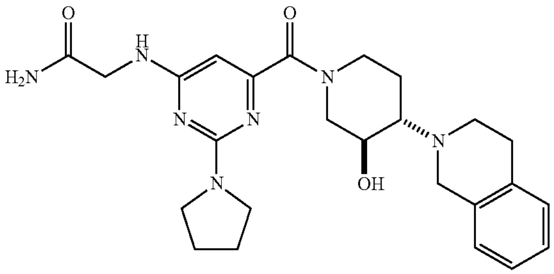 [SMILES: NC(=O)CNc1cc(C(=O)N2CC[C@H](N3CCc4ccccc4C3)[C@@H](O)C2)nc(N2CCCC2)n1] | (400 MHz, DMSO-$d_6$) δ 7.33 (d, J = 5.6 Hz, 2H), 7.12-7.00 (m, 4H), 6.98 (s, 1H), 5.88 (s, 1H), 4.83-4.69 (m, 1H), 4.52-4.25 (m, 1H), 3.95-3.70 (m, 5H), 3.69-3.51 (m, 1H), 3.69-3.51 (m, 1H), 3.43-3.40 (m, 4H), 2.97-2.85 (m, 1.5H), 2.85-2.69 (m, 4H), 2.69-2.55 (m, 1.5H), 1.94-1.67 (m, 5H), 1.58-1.39 (m, 1H). | 480.2 |
| 320 | 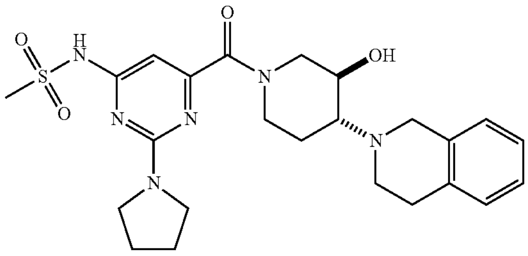 [SMILES: CS(=O)(=O)Nc1cc(C(=O)N2CC[C@@H](N3CCc4ccccc4C3)[C@H](O)C2)nc(N2CCCC2)n1] | (400 MHz, $CDCl_3$) δ 7.18-7.09 (m, 3H), 7.06-7.01 (m, 1H), 6.36-6.22 (m, 1H), 5.11-4.62 (m, 1H), 4.36-4.07 (m, 1H), 4.00-3.88 (m, 1H), 3.75-3.64 (m, 2H), 3.60-3.47 (m, 4H), 3.35-3.29 (m, 3H), 3.28-3.24 (m, 1H), 3.08-2.96 (m, 2H), 2.95-2.89 (m, 2H), 2.91-2.79 (m, 1H), 2.75-2.57 (m, 3H), 2.02-1.94 (m, 4H), 1.87-1.80 (m, 1H), 1.75-1.61 (m, 1H). | 501.24 |
| 321 | 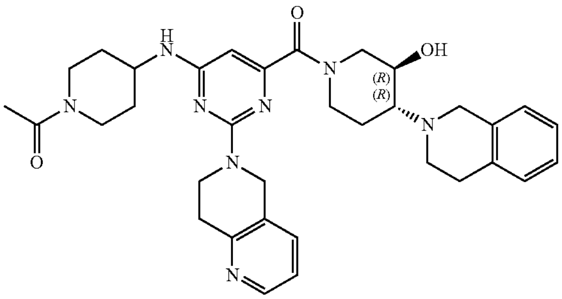 | (400 MHz, DMSO-$d_6$) δ 8.37-8.35 (m, 1H), 7.63 (t, J = 8.0 Hz, 1H), 7.28-7.19 (m, 2H), 7.11-7.04 (m, 4H), 5.87 (s, 1H), 4.85-4.83 (m, 2H), 4.80-4.68 (m, 1H), 4.38-4.34 (m, 1H), 4.22-4.20 (m, 1H), 4.07-4.01 (m, 3H), 3.88-3.77 (m, 4H), 3.64-3.59 (m, 1H), 3.25-3.19 (m, 1H), 3.01-2.86 (m, 4H), 2.83-2.74 (m, 4H), 2.67-2.51 (m, 2H), 2.01 (s, 3H), 1.94-1.72 (m, 3H), 1.51-1.28 (m, 3H). | 611.4 |

-continued
| Ex. | Structure | $^1$H NMR | LC-MS (ESI) [M + H]$^+$ |
|---|---|---|---|
| 322 | 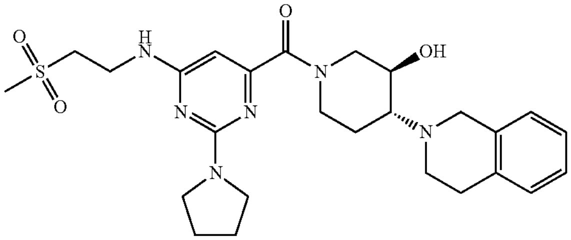 [SMILES: CS(=O)(=O)CCNc1cc(C(=O)N2CC[C@@H](N3CCc4ccccc4C3)[C@H](O)C2)nc(N2CCCC2)n1] | (400 MHz, $CDCl_3$) δ 7.19-7.08 (m, 3H), 7.07-6.99 (m, 1H), 6.01-5.82 (m, 1H), 5.39-5.15 (m, 1H), 5.06-4.52 (m, 1H), 4.41-4.22 (m, 1H), 4.10 (s, 1H), 4.03-3.85 (m, 3H), 3.79-3.63 (m, 2H), 3.61-3.45 (m, 4H), 3.44-3.32 (m, 2H), 3.15-2.79 (m, 8H), 2.78-2.55 (m, 2H), 2.03-1.81 (m, 5H), 1.74-1.65 (m, 1H). | 529.29 |
| 323 | HCl 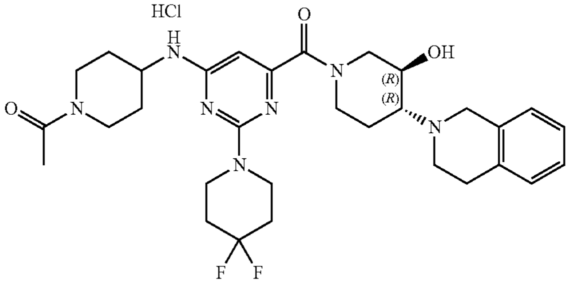 | (400 MHz, DMSO-$d_6$) δ 10.32-9.90 (m, 1H), 7.41 (s, 1H), 7.34-7.10 (m, 4H), 6.31-6.00 (m, 1H), 5.95 (s, 1H), 4.75-4.34 (m, 3H), 4.33-3.86 (m, 4H), 3.87-3.65 (m, 6H), 3.60-3.40 (m, 2H), 3.28-3.00 (m, 3H), 3.00-2.54 (m, 3H), 2.36-2.12 (m, 1H), 2.07-1.56 (m, 10H), 1.43-1.22 (m, 2H). | 598.29 |
| 324 | 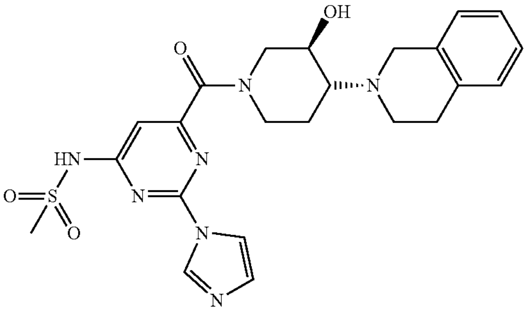 | (400 MHz, $CD_3OD$) δ 8.64 (d, J = 9.2 Hz, 1H), 7.97 (d, J = 9.2 Hz, 1H), 7.28-7.18 (m, 4H), 7.12 (s, 1H), 6.73 (d, J = 2.8 Hz, 1H), 4.84-4.71 (m, 1H), 4.47-4.39 (m, 2H), 4.14-4.00 (m, 2H), 3.58-3.37 (m, 3H), 3.32-3.17 (m, 5H), 2.08-2.77 (m, 2H), 2.25-2.10 (m, 1H), 1.93-1.87 (m, 1H). | 466.3 |
| 325 | 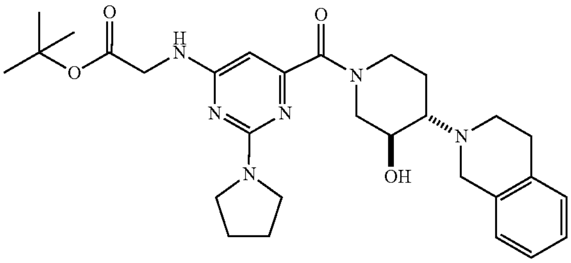 [SMILES: CC(C)(C)OC(=O)CNc1cc(C(=O)N2CC[C@H](N3CCc4ccccc4C3)[C@@H](O)C2)nc(N2CCCC2)n1] | (400 MHz, DMSO-$d_6$) δ 7.48 (s, 1H), 7.13-6.99 (m, 4H), 5.95-5.83 (m, 1H), 4.82-4.66 (m, 1H), 4.51-4.26 (m, 1H), 3.99-3.84 (m, 2.7H), 3.85-3.73 (m, 2.3H), 3.68-3.52 (m, 1H), 3.46-3.34 (m, 4H), 3.02-2.86 (m, 1.5H), 2.84-2.69 (m, 4H), 2.69-2.57 (m, 1.5H), 1.94-1.68 (m, 5H), 1.61-1.44 (m, 1H), 1.44-1.35 (m, 9H). | 357.3 |
| 326 | HCl 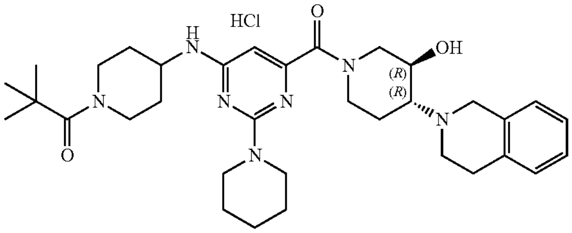 | (400 MHz, DMSO-$d_6$) δ 10.47 and 10.23 (s, 1H), 7.28-7.20 (m, 4H), 6.12-6.10 (m, 2H), 4.74-4.56 (m, 3H), 4.52-4.45 (m, 4H), 4.18-4.15 (m, 1H), 3.86-3.04 (m, 8H), 2.85-2.51 (m, 4H), 2.50-2.10 (m, 4H), 1.91-1.63 (m, 6H), 1.58-1.40 (m, 2H), 1.38-1.20 (m, 9H). | 604.5 |

-continued

| Ex. | Structure | $^1$H NMR | LC-MS (ESI) $[M + H]^+$ |
| --- | --- | --- | --- |
| 327 | 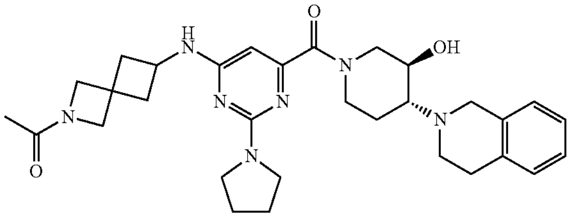 [SMILES: CC(=O)N1CC2(CC(Nc3cc(C(=O)N4CC[C@@H](N5CCc6ccccc6C5)[C@H](O)C4)nc(N4CCCC4)n3)C2)C1] | (400 MHz, $CDCl_3$) δ 7.18-7.09 (m, 3H), 7.06-6.99 (m, 1H), 5.86-5.79 (m, 1H), 5.09-4.49 (m, 2H), 4.42-4.27 (m, 1H), 4.23-4.11 (m, 2H), 4.09-4.02 (m, 2H), 4.01-3.88 (m, 2H), 3.82-3.65 (m, 2H), 3.58-3.42 (m, 4H), 3.10-2.96 (m, 2H), 2.96-2.87 (m, 2H), 2.81-2.50 (m, 4H), 2.19-2.07 (m, 2H), 2.04-1.90 (m, 5H), 1.88-1.83 (m, 3H), 1.82-1.59 (m, 3H). | 560.3 |
| 328 | 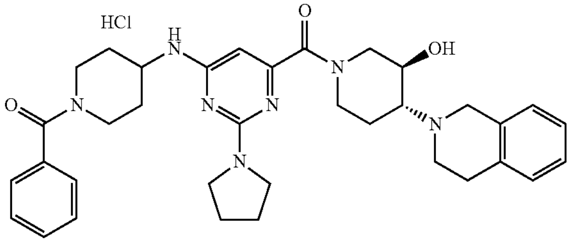 [SMILES: O=C(c1ccccc1)N1CCC(Nc2cc(C(=O)N3CC[C@@H](N4CCc5ccccc5C4)[C@H](O)C3)nc(N3CCCC3)n2)CC1 ; Cl] | (400 MHz, $CDCl_3$) δ 7.42-7.39 (m, 5H), 7.16-7.13 (m, 3H), 7.10-7.03 (m, 1H), 5.90-5.87 (m, 1H), 4.61-4.52 (m, 2H), 4.38-4.36 (m, 1H), 4.10-3.95 (m, 2H), 3.74-3.72 (m, 3H), 3.71-3.52 (m, 4H), 3.02-2.93 (m, 7H), 2.74-2.68 (m, 2H), 2.03-1.94 (m, 7H), 1.93-1.71 (m, 2H), 1.67-1.56 (m, 1H). | 610.4 |
| 329 | 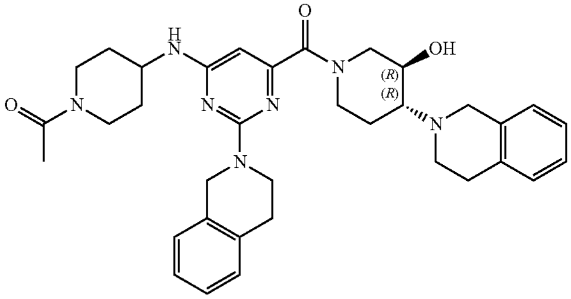 | (400 MHz, $CDCl_3$) δ 7.20-7.09 (m, 7H), 7.11-7.00 (m, 1H), 5.95-5.85 (m, 1H), 5.09-4.63 (m, 4H), 4.56-4.22 (m, 2H), 4.13-3.91 (m, 4H), 3.86-3.61 (m, 4H), 3.29-3.18 (m, 1H), 3.15-3.03 (m, 1H), 2.99-2.79 (m, 7H), 2.73-2.65 (m, 1H), 2.19-2.10 (m, 4H), 2.08-1.83 (m, 2H), 1.77-1.67 (m, 1H), 1.48-1.36 (m, 2H). | 610.45 |
| 330 | 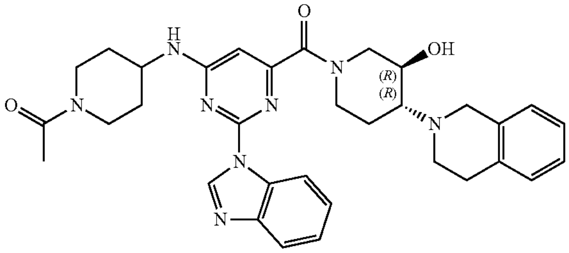 | (400 MHz, $CDCl_3$) δ 9.08-8.88 (m, 1H), 8.57-8.41 (m, 1H), 7.90-7.75 (m, 1H), 7.41-7.30 (m, 2H), 7.19-7.10 (m, 3H), 7.08-7.00 (m, 1H), 6.64-6.39 (m, 1H), 5.82-5.46 (m, 1H), 5.17-4.81 (m, 1H), 4.61 (d, J=13.2 Hz, 1H), 4.52-4.06 (m, 2H), 4.05-3.94 (m, 1H), 3.93-3.63 (m, 4H), 3.34-3.23 (m, 1H), 3.14-3.06 (m, 1H), 3.01-2.80 (m, 4H), 2.77-2.67 (m, 2H), 2.30-2.20 (m, 1H), 2.19-2.09 (m, 4H), 2.08-1.86 (m, 1H), 1.77-1.70 (m, 1H), 1.58-1.46 (m, 2H). | 595.36 |
| 331 | 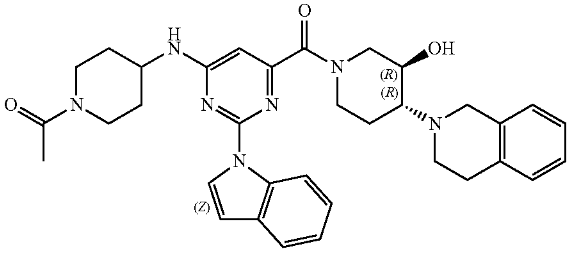 | (400 MHz, $CD_3OD$) δ 8.76 (s, 1H), 8.25-8.23 (m, 1H), 7.58 (d, J = 7.6 Hz, 1H), 7.31-7.26 (m, 1H), 7.21-7.16 (m, 1H), 7.11-7.03 (m, 4H), 6.68-6.61 (m, 1H), 6.43-6.36 (m, 1H), 4.80-4.60 (m, 1H), 4.81-4.59 (m, 1H), 4.40-4.23 (m, 1H), 4.12-3.80 (m, 5H), 3.38-3.35 (m, 1H), 3.16-2.72 (m, 8H), 2.23-2.13 (m, 5H), 2.05-1.84 (m, 1H), 1.74-1.67 (m, 1H), 1.61-1.45 (m, 2H). | 594.3 |
| 332 | 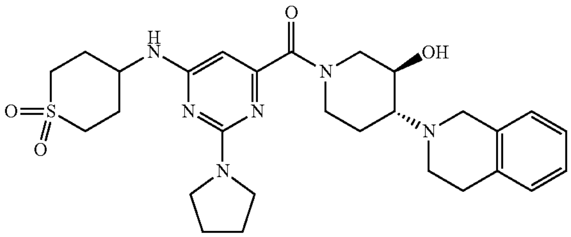 [SMILES: O=C(c1cc(NC2CCS(=O)(=O)CC2)nc(N2CCCC2)n1)N1CC[C@@H](N2CCc3ccccc3C2)[C@H](O)C1] | (400 MHz, $CDCl_3$) δ 7.18-7.09 (m, 3H), 7.06-7.01 (m, 1H), 6.00-5.82 (m, 1H), 5.11-4.85 (m, 1H), 4.62-4.52 (m, 1H), 4.40-4.25 (m, 1H), 4.21-4.09 (m, 1H), 4.02-3.90 (m, 1H), 3.80-3.67 (m, 2H), 3.56-3.44 (m, 4H), 3.22-2.89 (m, 9H), 2.80-2.55 (m, 2H), 2.48-2.36 (m, 2H), 2.30-2.15 (m, 2H), 2.10-1.90 (m, 5H), 1.89-1.67 (m, 1H). | 555.27 |

-continued
| Ex. | Structure | $^1$H NMR | LC-MS (ESI) $[M + H]^+$ |
|---|---|---|---|
| 333 | 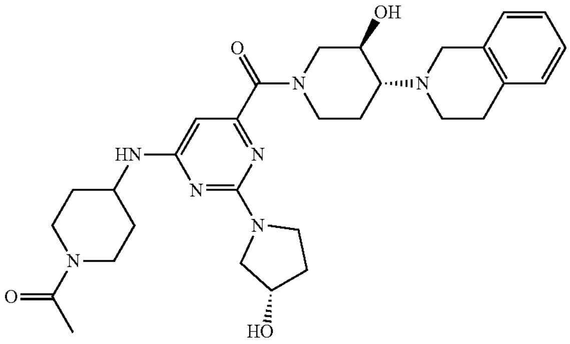 [SMILES: CC(=O)N1CCC(Nc2cc(C(=O)N3CC[C@@H](N4CCc5ccccc5C4)[C@H](O)C3)nc(N3CC[C@H](O)C3)n2)CC1] | (400 MHz, DMSO-$d_6$) δ 7.10-7.03 (m, 5H), 5.79 (s, 1H), 4.90-4.87 (m, 1H), 4.78-4.72 (m, 1H), 4.48-4.31 (m, 2H), 4.21-4.19 (m, 1H), 4.04-3.75 (m, 5H), 3.61-3.42 (m, 4H), 3.19-3.13 (m, 1H), 2.98-2.79 (m, 7H), 2.67-2.56 (m, 1H), 2.00-1.72 (m, 8H) 1.51-1.25 (m, 3H). | 564.7 |
| 334 | 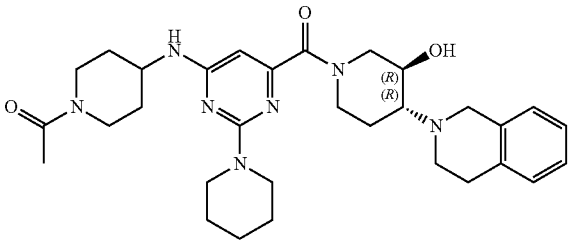 | (400 MHz, $CDCl_3$) δ 7.19-7.08 (m, 3H), 7.06-6.99 (m, 1H), 5.91-5.76 (m, 1H), 5.12-4.69 (m, 1H), 4.59 (s, 1H), 4.53-4.24 (m, 2H), 4.02-3.86 (m, 2H), 3.84-3.77 (m, 1H), 3.76-3.64 (m, 6H), 3.28-3.17 (m, 1H), 3.12-3.00 (m, 1H), 3.00-2.51 (m, 7H), 2.17-2.07 (m, 4H), 2.05-1.79 (m, 2H), 1.67-1.56 (m, 7H), 1.47-1.31 (m, 2H). | 562.53 |
| 335 | 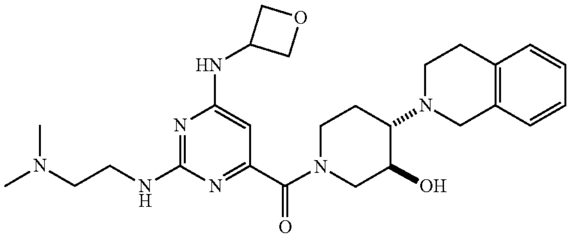 [SMILES: CN(C)CCNc1nc(NC2COC2)cc(C(=O)N2CC[C@H](N3CCc4ccccc4C3)[C@@H](O)C2)n1] | (400 MHz, $CDCl_3$) δ 7.16-7.10 (m, 3H), 7.04-7.00 (m, 1H), 5.88 (s, 1H), 5.51-4.91 (m, 5H), 4.79-4.50 (m, 3H), 4.38-4.10 (m, 1H), 4.07-3.75 (m, 2H), 3.72-3.62 (m, 2H), 3.50-3.38 (m, 2H), 3.07-2.94 (m, 2H), 2.94-2.84 (m, 3H), 2.72-2.58 (m, 2H), 2.57-2.46 (m, 2H), 2.38-2.13 (m, 6H), 2.02-1.92 (m, 1H), 1.79-1.68 (m, 1H). | 496.57 |
| 336 | 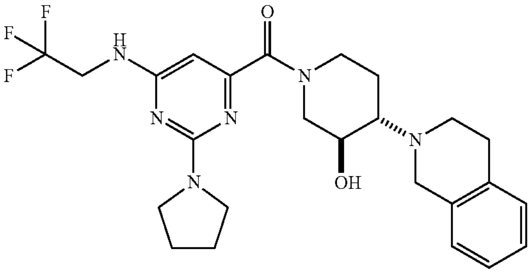 [SMILES: O=C(c1cc(NCC(F)(F)F)nc(N2CCCC2)n1)N1CC[C@H](N2CCc3ccccc3C2)[C@@H](O)C1] | (400 MHz, DMSO-$d_6$) δ 7.78-7.57 (m, 1H), 7.14-6.96 (m, 4H), 6.01-5.83 (m, 1H), 4.84-4.67 (m, 1H), 4.54-4.29 (m, 1H), 4.20 (s, 2H), 3.92-3.72 (m, 3H), 3.70-3.52 (m, 1H), 3.44-3.36 (m, 4H), 3.05-2.84 (m, 1.5H), 2.85-2.70 (m, 4H), 2.69-2.53 (m, 1.5H), 1.95-1.68 (m, 5H), 1.58-1.39 (m, 1H). | 505.2 |
| 337 | 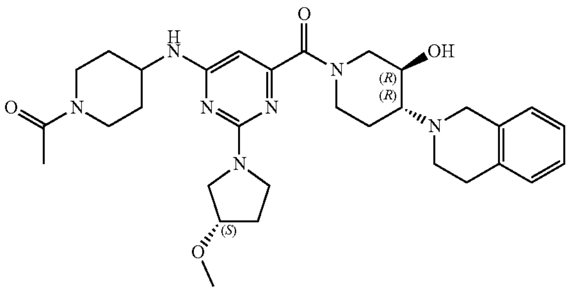 | (400 MHz, $CDCl_3$) δ 7.19-7.09 (m, 3H), 7.06-6.99 (m, 1H), 6.04-5.73 (m, 1H), 5.08-4.28 (m, 4H), 4.06-3.90 (m, 3H), 3.85-3.58 (m, 7H), 3.43-3.30 (m, 3H), 3.28-3.14 (m, 1H), 3.09-2.57 (m, 8H), 2.23-1.82 (m, 8H), 1.74-1.66 (m, 1H), 1.46-1.32 (m, 2H). | 578.32 |

-continued
| Ex. | Structure | $^1$H NMR | LC-MS (ESI) $[M + H]^+$ |
|---|---|---|---|
| 338 | 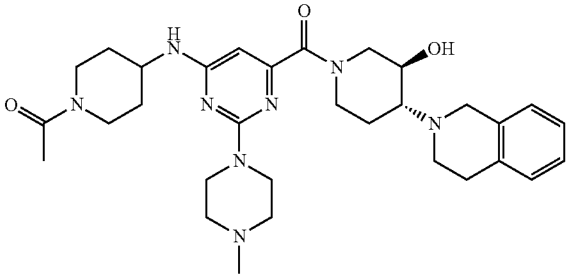 [SMILES: CC(=O)N1CCC(Nc2cc(C(=O)N3CC[C@@H](N4CCc5ccccc5C4)[C@H](O)C3)nc(N3CCN(C)CC3)n2)CC1] | (400 MHz, $CDCl_3$) δ 7.19-7.08 (m, 3H), 7.06-6.99 (m, 1H), 5.93-5.84 (m, 1H), 5.06-4.62 (m, 2H), 4.54-4.45 (m, 1H), 4.40-4.16 (m, 1H), 4.00-3.89 (m, 1H), 3.88-3.57 (m, 8H), 3.27-3.15 (m, 1H), 3.08-2.45 (m, 13H), 2.38 (s, 3H), 2.16-2.08 (m, 4H), 2.07-1.92 (m, 2H), 1.87-1.79 (m, 1H), 1.47-1.32 (m, 2H). | 577.39 |
| 339 | 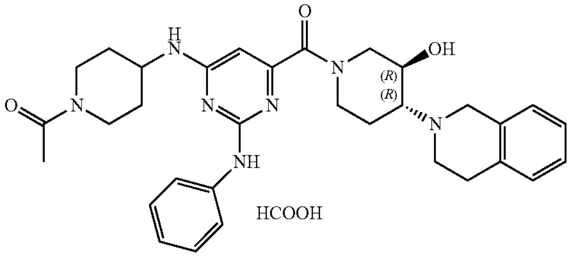 HCOOH | (400 MHz, DMSO-$d_6$) δ 9.20 (d, J = 10.8 Hz, 1H), 8.15 (s, 0.23H), 7.78-7.75 (m, 2H), 7.43 (brs, 1H), 7.27-7.21 (m, 2H), 7.11-7.04 (m, 4H), 6.92-6.89 (m, 1H), 5.97 (s, 1H), 4.75 (d, J=32.0Hz, 1H), 4.50-4.29 (m, 2H), 4.09 (brs, 1H), 3.88-3.77 (m, 4H), 3.61 (brs, 1H), 3.18 (t, J = 11.6Hz, 1H), 3.01-2.75 (m, 6H), 2.68-2.56 (m, 2H), 2.03-1.95 (m, 5H), 1.83-1.74 (m, 1H), 1.49-1.29 (m, 3H). | 570.4 |
| 340 | 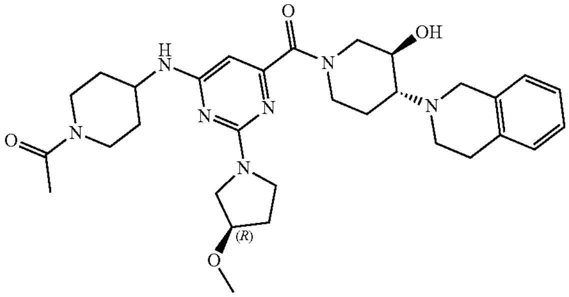 | (400 MHz, $CDCl_3$) δ 7.17-7.10 (m, 3H), 7.04-7.01 (m, 1H), 5.89-5.87 (m, 1H), 5.03-4.65 (m, 1H), 4.51-4.48 (m, 2H), 4.36-4.28 (m, 1H), 4.03-3.90 (m, 3H), 3.81-3.56 (m, 7H), 3.36 (s, 3H), 3.22-3.15 (m, 1H), 3.06-2.58 (m, 8H), 2.11-1.99 (m, 8H), 1.82-1.80 (m, 1H), 1.44-1.38 (m, 2H). | 578.4 |
| 341 | 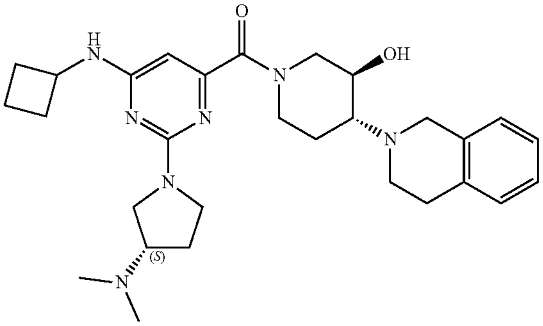 | (400 MHz, $CDCl_3$) δ 7.16-7.09 (m, 3H), 7.03-6.99 (m, 1H), 5.83 (s, 1H), 5.05-4.88 (m, 1H), 4.61-4.58 (m, 1H), 4.37-4.21 (m, 2H), 3.95-3.88 (m, 2H), 3.78-3.63 (m, 4H), 3.49-3.27 (m, 2H), 3.25-2.90 (m, 5H), 2.73-2.54 (m, 2H), 2.43-2.33 (m, 7H), 2.20-2.14 (m, 1H), 2.00-1.63 (m, 8H). | 520.4 |
| 342 | 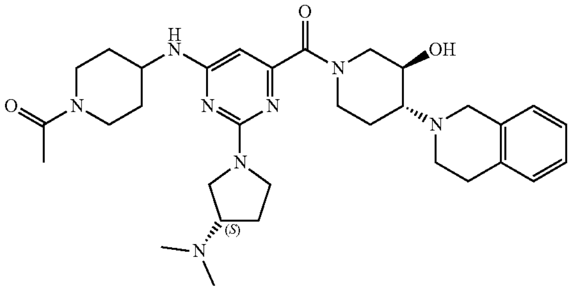 | (400 MHz, $CDCl_3$) δ 7.19-7.07 (m, 3H), 7.07-6.98 (m, 1H), 6.02-5.76 (m, 1H), 5.14-4.54 (m, 2H), 4.54-4.46 (m, 1H), 4.43-4.24 (m, 1H), 3.98-3.85 (m, 3H), 3.84-3.72 (m, 3H), 3.72-3.64 (m, 1H), 3.52-3.37 (m, 1H), 3.34-3.14 (m, 2H), 3.09-2.99 (m, 1H), 2.95-2.87 (m, 3H), 2.87-2.74 (m, 2H), 2.74-2.60 (m, 2H), 2.33 (s, 6H), 2.22-2.08 (m, 5H), 2.08-1.94 (m, 2H), 1.94-1.79 (m, 1H), 1.78-1.52 (m, 3H), 1.50-1.33 (m, 2H). | 591.33 |

-continued
| Ex. | Structure | $^1$H NMR | LC-MS (ESI) $[M + H]^+$ |
|---|---|---|---|
| 343 | 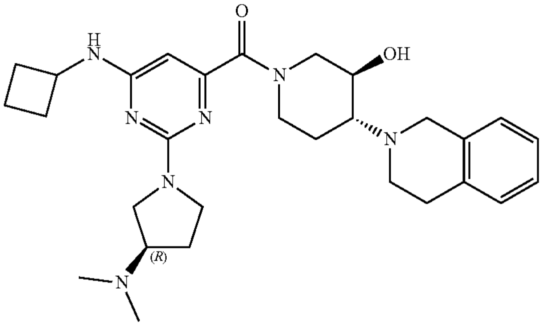 | (400 MHz, $CDCl_3$) δ 7.19-7.08 (m, 3H), 7.05-6.99 (m, 1H), 5.86-5.81 (m, 1H), 5.09-4.86 (m, 1H), 4.63 (s, 1H), 4.39-4.09 (m, 2H), 3.98-3.60 (m, 6H), 3.53-3.39 (m, 1H), 3.28 (s, 1H), 3.09-2.52 (m, 8H), 2.45-2.28 (m, 7H), 2.24-2.10 (m, 1H), 2.02-1.56 (m, 8H). | 520.31 |
| 344 | HCl 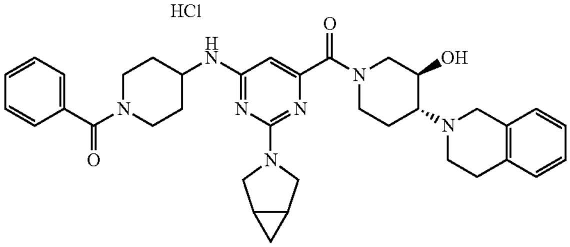 [SMILES: Cl ; O=C(c1ccccc1)N1CCC(Nc2cc(C(=O)N3CC[C@@H](N4CCc5ccccc5C4)[C@H](O)C3)nc(N3CC4CC4C3)n2)CC1] | (400 MHz, $(CD_3)_2SO$) δ 10.26-9.85 (m, 1H), 7.46-7.45 (m, 3H), 7.39-7.38 (m, 2H), 7.31-7.17 (m, 5H), 6.26-5.90 (m, 2H), 4.69-4.32 (m, 4H), 4.09-3.80 (m, 3H), 3.74-3.43 (m, 9H), 3.08-2.89 (m, 3H), 2.16-1.91 (m, 5H), 1.77-1.33 (m, 5H), 0.76-0.68 (m, 1H), 0.18-0.11 (m, 1H). | 622.4 |
| 345 | 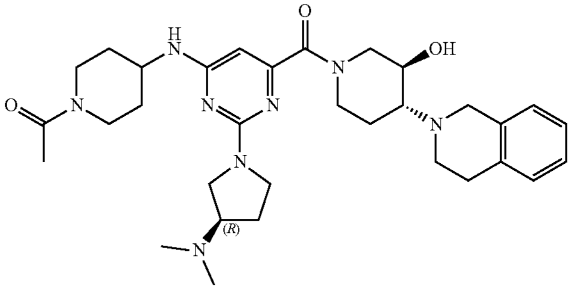 | (400 MHz, $CDCl_3$) δ 7.17-7.09 (m, 3H), 7.05-6.98 (m, 1H), 5.92-5.86 (m, 1H), 5.08-4.58 (m, 2H), 4.54-4.46 (m, 1H), 4.43-4.25 (m, 1H), 3.99-3.60 (m, 8H), 3.51-3.40 (m, 1H), 3.35-3.15 (m, 2H), 3.08-2.76 (m, 7H), 2.73-2.55 (m, 2H), 2.33 (s, 6H), 2.22-2.09 (m, 5H), 2.07-1.95 (m, 2H), 1.93-1.77 (m, 1H), 1.74-1.61 (m, 1H), 1.46-1.33 (m, 2H). | 591.33 |
| 346 | 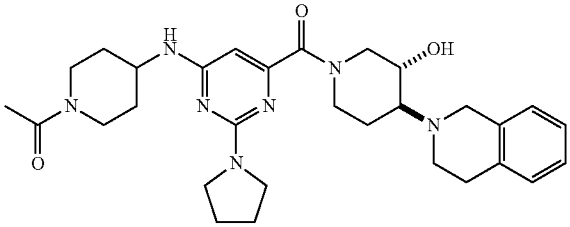 [SMILES: CC(=O)N1CCC(Nc2cc(C(=O)N3CC[C@H](N4CCc5ccccc5C4)[C@@H](O)C3)nc(N3CCCC3)n2)CC1] | (400 MHz, DMSO-$d_6$) δ 7.18-6.99 (m, 4H), 5.80 (s, 1H), 4.54-4.29 (m, 1H), 4.20 (d, J = 12.7 Hz, 1H), 4.15-3.81 (m, 4H), 3.81-3.73 (m, 1H), 3.65-3.34 (m, 10H), 3.24-3.08 (m, 1.5H), 3.03-2.65 (m, 6.5H), 2.06-1.96 (m, 3H), 1.95-1.72 (m, 5H), 1.57-1.47 (m, 1H), 1.40-1.23 (m, 2H). | 548.4 |
| 347 | 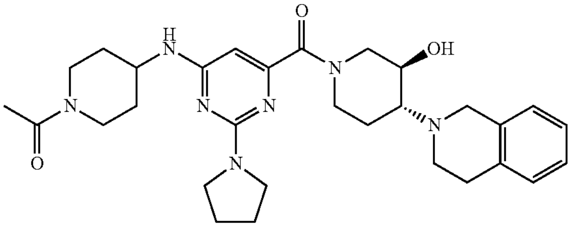 [SMILES: CC(=O)N1CCC(Nc2cc(C(=O)N3CC[C@@H](N4CCc5ccccc5C4)[C@H](O)C3)nc(N3CCCC3)n2)CC1] | (400 MHz, DMSO-$d_6$) δ 7.18-6.99 (m, 4H), 5.80 (s, 1H), 4.54-4.29 (m, 1H), 4.20 (d, J = 12.7 Hz, 1H), 4.15-3.81 (m, 4H), 3.81-3.73 (m, 1H), 3.65-3.34 (m, 10H), 3.24-3.08 (m, 1.5H), 3.03-2.65 (m, 6.5H), 2.06-1.96 (m, 3H), 1.95-1.72 (m, 5H), 1.57-1.47 (m, 1H), 1.40-1.23 (m, 2H). | 548.4 |

-continued
| Ex. | Structure | $^1$H NMR | LC-MS (ESI) $[M + H]^+$ |
|---|---|---|---|
| 348 | 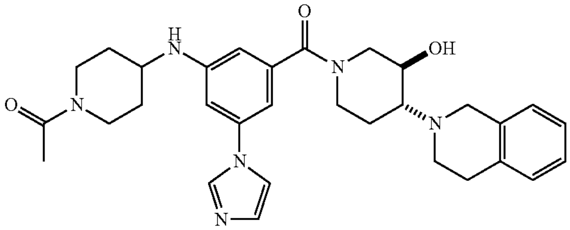 [SMILES: CC(=O)N1CCC(Nc2cc(C(=O)N3CC[C@@H](N4CCc5ccccc5C4)[C@H](O)C3)cc(-n3ccnc3)c2)CC1] | (400 MHz, DMSO-$d_6$) δ 8.24 (s, 1H), 7.72 (s, 1H), 7.27-6.98 (m, 5H), 6.83 (s, 1H), 6.75 (s, 1H), 6.57 (s, 1H), 6.09 (d, J = 8.1 Hz, 1H), 4.88-4.65 (m, 1H), 4.60-4.33 (m, 1H), 4.33-4.16 (m, 1H), 3.89-3.74 (m, 3H), 3.75-3.57 (m, 3H), 3.29-3.12 (m, 1H), 3.07-2.72 (m, 6.5H), 2.62 (s, 1.5H), 2.06-1.65 (m, 6H), 1.60-1.40 (m, 1H), 1.37-1.10 (m, 2H). | 543.3 |
| 349 | 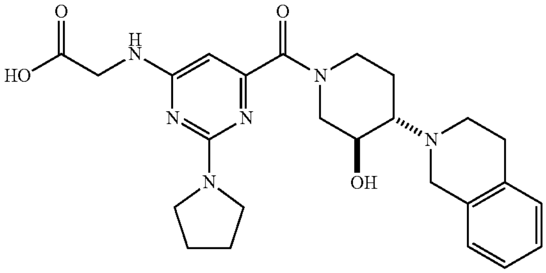 [SMILES: O=C(O)CNc1cc(C(=O)N2CC[C@H](N3CCc4ccccc4C3)[C@@H](O)C2)nc(N2CCCC2)n1] | (400 MHz, DMSO-$d_6$) δ 7.43 (s, 1H), 7.15-6.98 (m, 4H), 6.00-5.80 (m, 1H), 4.77 (s, 1H), 4.51-4.29 (m, 1H), 4.00-3.88 (m, 3H), 3.88-3.75 (m, 4H), 3.64-3.60 (m, 2H), 3.01-2.86 (m, 2H), 2.86-2.73 (m, 4H), 2.71-2.52 (m, 2H), 1.94-1.66 (m, 5H), 1.60-1.39 (m, 1H). | 481.20 |
| 350 | 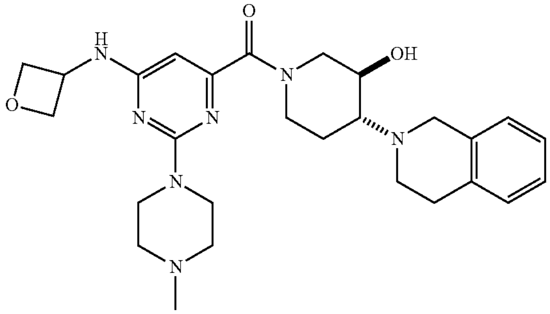 [SMILES: CN1CCN(c2nc(NC3COC3)cc(C(=O)N3CC[C@@H](N4CCc5ccccc5C4)[C@H](O)C3)n2)CC1] | (400 MHz, $CDCl_3$) δ 7.17-7.09 (m, 3H), 7.05-7.01 (m, 1H), 5.94-5.82 (m, 1H), 5.24-5.15 (m, 1H), 5.07-4.71 (m, 4H), 4.63-4.53 (m, 2H), 4.40-4.12 (m, 1H), 3.98-3.89 (m, 1H), 3.85-3.57 (m, 7H), 3.08-2.85 (m, 4H), 2.83-2.55 (m, 3H), 2.49-2.42 (m, 4H), 2.37-2.30 (m, 3H), 2.01-1.79 (m, 1H), 1.72-1.52 (m, 1H). | 508.56 |
| 351 | 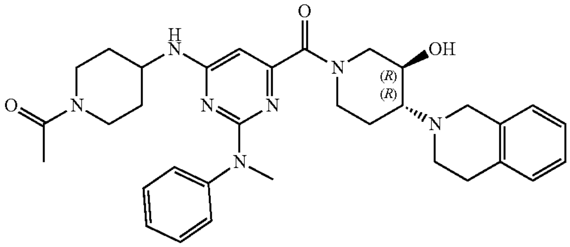 | (400 MHz, $CD_3OD$) δ 7.43-7.30 (m, 4H), 7.18-7.11 (m, 1H), 7.06-7.05 (m, 4H), 5.96 (s, 1H), 4.70-4.52 (m, 1H), 4.37 (d, J = 13.6 Hz, 1H), 3.94-3.84 (m, 5H), 3.74-3.68 (m, 1H), 3.49 (d, J = 10.8 Hz, 3H), 4.37 (t, J = 11.2 Hz, 1H), 2.99-2.89 (m, 4H), 2.83-2.74 (m, 4H), 2.12 (s, 3H), 1.98-1.77 (m, 3H), 1.61-1.31 (m, 3H). | 584.4 |

Examples 352-374

Using the same process as in Example 297, the compounds of Examples 352-374 were synthesized. The compound structures and specific characterization data (LC-MS and $^{1}$H NMR) were as follows:

| Ex. | Structure | $^{1}$H NMR | LC-MS (ESI) $[M + H]^+$ |
|---|---|---|---|
| 352 | 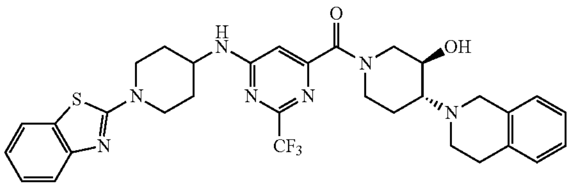 [SMILES: O=C(c1cc(NC2CCN(c3nc4ccccc4s3)CC2)nc(C(F)(F)F)n1)N1CC[C@@H](N2CCc3ccccc3C2)[C@H](O)C1] | (400 MHz, $(CD_3)_2SO$) δ 8.50-8.28 (m, 1H), 7.77-7.75 (d, J = 8, 1H), 7.46-7.44 (d, J = 8, 1H), 7.29-7.25 (m, 1H), 7.09-7.03 (m, 5H), 6.74-6.72 (m, 1H), 4.85-4.70 (m, 1H), 4.50-4.25 (m, 1H), 4.25-4.14 (m, 1H), 4.08-3.99 (m, 2H), 3.86-3.76 (m, 2H), 3.68-3.57 (m, 2H), 3.43-3.37 (m, 2H), 3.08-3.02 (m, 0.5H), 2.93-2.87 (m, 2H), 2.78-2.78 (m, 3H), 2.67-2.62 (m, 1.5H), 2.07-1.97 (m, 2H), 1.86-1.72 (m, 1H), 1.59-1.47 (m, 3H). | 638.0 |
| 353 | 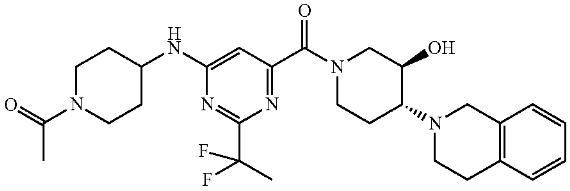 [SMILES: CC(=O)N1CCC(Nc2cc(C(=O)N3CC[C@@H](N4CCc5ccccc5C4)[C@H](O)C3)nc(C(C)(F)F)n2)CC1] | (400 MHz, $CDCl_3$) δ 7.20-7.11 (m, 3H), 7.08-7.02 (m, 1H), 6.70 (s, 1H), 5.42 (s, 1H), 5.06-4.64 (m, 1H), 4.59-4.47 (m, 1H), 4.30-3.94 (m, 3H), 3.88-3.71 (m, 3H), 3.29-2.69 (m, 9H), 2.12 (s, 3H), 2.09-2.02 (m, 2H), 2.01-1.91 (m, 3H), 1.80-1.69 (m, 1H), 1.59-1.39 (m, 3H). | 543.4 |
| 354 | 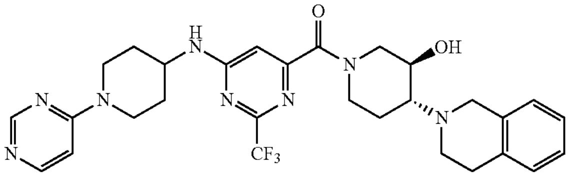 [SMILES: O=C(c1cc(NC2CCN(c3ccncn3)CC2)nc(C(F)(F)F)n1)N1CC[C@@H](N2CCc3ccccc3C2)[C@H](O)C1] | (400 MHz, DMSO-$d_6$) δ 8.14 (s, 1H), 8.49-8.24 (m, 1H), 8.18-8.16 (m, 1H), 7.09-7.01 (m, 4H), 6.88-6.86 (m, 1H), 6.72-6.71 (m, 1H), 4.84-4.70 (m, 1H), 4.46-4.29 (m, 3H), 4.19 (s, 1H), 3.86-3.75 (m, 2H), 3.68-3.56 (m, 2H), 3.21-3.07 (m, 2.5H), 2.92-2.78 (m, 5H), 2.67-2.61 (m, 1.5H), 2.01-1.71 (m, 3H), 1.57-1.37 (m, 3H). | 583.3 |
| 355 | 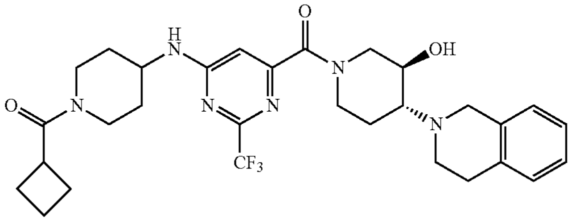 [SMILES: O=C(c1cc(NC2CCN(C(=O)C3CCC3)CC2)nc(C(F)(F)F)n1)N1CC[C@@H](N2CCc3ccccc3C2)[C@H](O)C1] | (400 MHz, DMSO-$d_6$) δ 8.14-8.22 (m, 1H), 7.09-6.93 (m, 4H), 6.72-6.71 (m, 1H), 4.84-4.69 (m, 1H), 4.49-4.19 (m, 2H), 4.08 (s, 1H), 3.82-3.61 (m, 2H), 3.67-3.61 (m, 3H), 3.37-3.32 (m, 1H), 3.14-3.01 (m, 1.5H), 2.89-2.73 (m, 6H), 2.67-2.61 (m, 1.5H), 2.18-2.06 (m, 4H), 1.94-1.71 (m, 5H), 1.55-1.47 (m, 1H), 1.34-1.28 (m, 2H). | 587.3 |
| 356 | 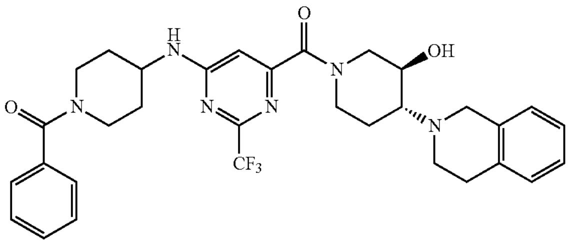 [SMILES: O=C(c1ccccc1)N1CCC(Nc2cc(C(=O)N3CC[C@@H](N4CCc5ccccc5C4)[C@H](O)C3)nc(C(F)(F)F)n2)CC1] | (400 MHz, DMSO-$d_6$) δ 8.45-8.26 (m, 1H), 7.45-7.44 (m, 3H), 7.39-7.38 (m, 2H), 7.09-7.00 (m, 4H), 6.75-6.73 (m, 1H), 4.85-4.69 (m, 1H), 4.49-4.25 (m, 2H), 4.15 (s, 1H), 3.86-3.67 (m, 2H), 3.64-3.54 (m, 3H), 3.23-3.04 (m, 2.5H), 2.90-2.78 (m, 2H), 2.81-2.78 (m, 3H), 2.67-2.61 (m, 1.5H), 2.01-1.71 (m, 3H), 1.56-1.38 (m, 3H) | 609.2 |
| 357 | 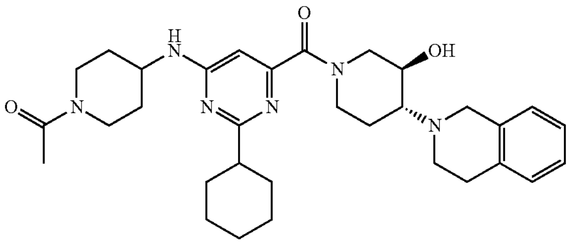 [SMILES: CC(=O)N1CCC(Nc2cc(C(=O)N3CC[C@@H](N4CCc5ccccc5C4)[C@H](O)C3)nc(C3CCCCC3)n2)CC1] | (400 MHz, DMSO-$d_6$) δ 10.66-10.42 (m, 1H), 7.42 (s, 1H), 7.30-7.17 (m, 4H), 6.88-6.80 (m, 1H), 4.87-4.56 (m, 1H), 4.54-4.38 (m, 2H), 4.35-4.09 (m, 3H), 3.61-3.51 (m, 2H), 3.40-3.17 (m, 3H), 3.11-2.66 (m, 5H), 2.36-2.14 (m, 2H), 2.02 (s, 3H), 1.94-1.68 (m, 8H), 1.63-1.22 (m, 8H). | 561.3 |

-continued
| Ex. | Structure | $^1$H NMR | LC-MS (ESI) $[M + H]^+$ |
|---|---|---|---|
| 358 | 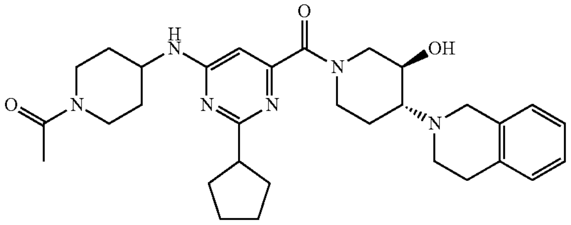 [SMILES: CC(=O)N1CCC(Nc2cc(C(=O)N3CC[C@@H](N4CCc5ccccc5C4)[C@H](O)C3)nc(C3CCCC3)n2)CC1] | (400 MHz, DMSO-$d_6$) δ 10.49-10.24 (m, 1H), 7.30-7.16 (m, 4H), 6.74-6.53 (m, 1H), 6.38-6.10 (m, 1H), 4.74-4.42 (m, 3H), 4.22-4.05 (m, 2H), 3.90-3.79 (m, 3H), 3.67-3.28 (m, 7H), 3.09-2.67 (m, 4H), 2.33-2.10 (m, 1H), 2.01-1.97 (m, 6H), 1.87-1.63 (m, 8H), 1.54-1.22 (m, 6H). | 547.2 |
| 359 | 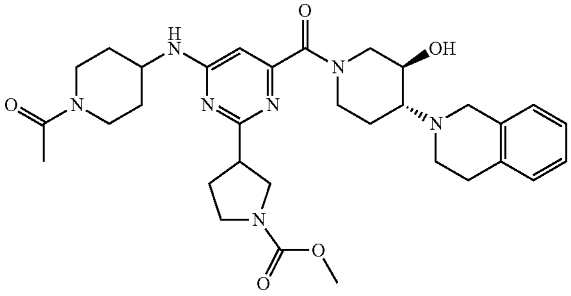 [SMILES: COC(=O)N1CCC(c2nc(NC3CCN(C(C)=O)CC3)cc(C(=O)N3CC[C@@H](N4CCc5ccccc5C4)[C@H](O)C3)n2)C1] | (400 MHz, DMSO-$d_6$) δ 7.08-7.04 (m, 4H), 6.42 (s, 1H), 4.71-4.39 (m, 3H), 4.18 (s, 1H), 3.95-3.68 (m, 11H), 3.49-3.47 (m, 2H), 3.12-2.88 (m, 7H), 2.76-2.67 (m, 1H), 2.30-2.19 (m, 2H), 2.12-2.00 (m, 4H), 1.88-1.86 (m, 2H), 1.68-1.65 (m, 1H), 1.50-1.39 (m, 2H). | 606.5 |
| 360 | 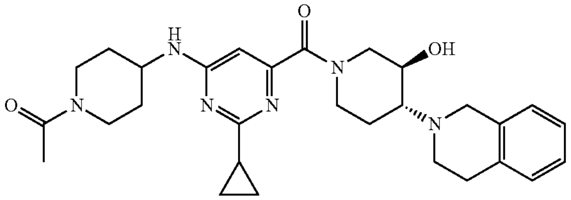 [SMILES: CC(=O)N1CCC(Nc2cc(C(=O)N3CC[C@@H](N4CCc5ccccc5C4)[C@H](O)C3)nc(C3CC3)n2)CC1] | (400 MHz, $CDCl_3$) δ 7.16-7.10 (m, 3H), 7.04-6.99 (m, 1H), 6.37-6.33 (m, 1H), 5.04-4.99 (m, 0.3H), 4.88 (s, 1H), 4.67-4.64 (m, 0.7H), 4.53-4.50 (m, 1H), 4.24-4.15 (m, 1H), 3.99-3.68 (m, 6H), 3.24-3.17 (m, 1H), 3.04-2.98 (m, 2H), 2.93-2.57 (m, 6H), 2.12 (s, 4H), 2.07-1.97 (m, 3H), 1.85-1.69 (m, 1H), 1.44-1.35 (m, 2H), 1.06-0.94 (m, 4H). | 519.2 |
| 361 | 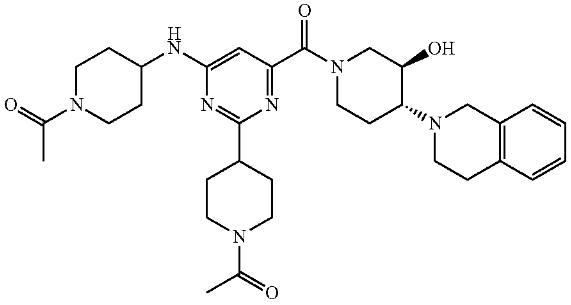 [SMILES: CC(=O)N1CCC(Nc2cc(C(=O)N3CC[C@@H](N4CCc5ccccc5C4)[C@H](O)C3)nc(C3CCN(C(C)=O)CC3)n2)CC1] | (400 MHz, $CD_3OD$) δ 7.11-7.06 (m, 4H), 6.41 (d, J = 8 Hz, 1H), 4.74-4.59 (m, 2H), 4.43-4.24 (m, 2H), 4.03-3.75 (m, 6H), 3.29-3.24 (m, 2H), 3.12-2.72 (m, 10H), 2.15-2.02 (m, 11H), 1.91-1.68 (m, 3H), 1.54-1.43 (m, 2H). | 604.4 |
| 362 | 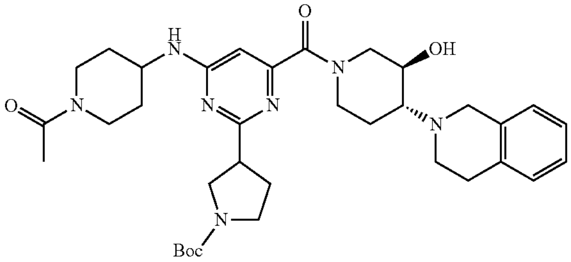 [SMILES: CC(=O)N1CCC(Nc2cc(C(=O)N3CC[C@@H](N4CCc5ccccc5C4)[C@H](O)C3)nc(C3CCN(C(=O)OC(C)(C)C)C3)n2)CC1] | (400 MHz, $CD_3OD$) δ 7.10-7.04 (m, 4H), 6.43-6.37 (m, 1H), 4.72-4.22 (m, 3H), 3.96-3.40 (m, 11H), 3.13-2.68 (m, 8H), 2.27-2.24 (m, 2H), 2.12-2.87 (m, 6H), 1.72-1.60 (m, 1H), 1.50-1.37 (m, 11H). | 648.4 |

-continued
| Ex. | Structure | $^1$H NMR | LC-MS (ESI) $[M + H]^+$ |
|---|---|---|---|
| 363 | 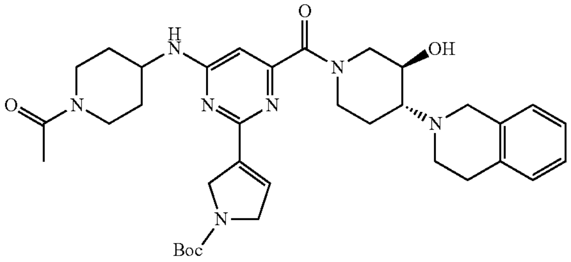 [SMILES: CC(=O)N1CCC(Nc2cc(C(=O)N3CC[C@@H](N4CCc5ccccc5C4)[C@H](O)C3)nc(C3=CCN(C(=O)OC(C)(C)C)C3)n2)CC1] | (400 MHz, $CD_3OD$) δ 7.10-7.04 (m, 4H), 6.86-6.80 (m, 1H), 6.47 (s, 1H), 4.73-4.48 (m, 3H), 4.43-4.25 (m, 4H), 3.98-3.78 (m, 5H), 3.13-2.68 (m, 9H), 2.12 (s, 4H), 2.04-1.89 (m, 2H), 1.74-1.67 (m, 1H), 1.51-1.29 (m, 11H). | 646.5 |
| 364 | 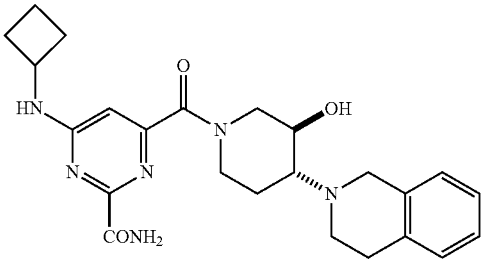 [SMILES: NC(=O)c1nc(NC2CCC2)cc(C(=O)N2CC[C@@H](N3CCc4ccccc4C3)[C@H](O)C2)n1] | (400 MHz, $CD_3OD$) δ 7.11-7.03 (m, 4H), 6.61-6.58 (m, 1H), 4.81-4.50 (m, 2H), 4.10-3.73 (m, 4H), 3.15-2.71 (m, 7H), 2.43 (s, 2H), 2.04-1.67 (m, 6H) | 451.3 |
| 365 | 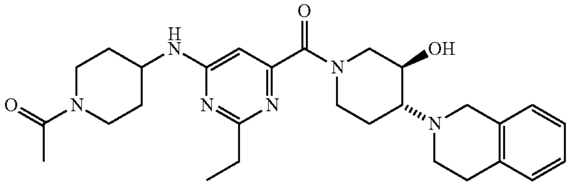 [SMILES: CCc1nc(NC2CCN(C(C)=O)CC2)cc(C(=O)N2CC[C@@H](N3CCc4ccccc4C3)[C@H](O)C2)n1] | (400 MHz, DMSO-$d_6$) δ 7.0.9-7.04 (m, 4H), 6.37 (s, 1H), 4.86-4.40 (m, 3H), 4.27 (s, 1H), 3.96-3.68 (m, 6H), 3.07-3.01 (m, 2H), 2.97-2.94 (m, 5H), 2.98-2.85 (m, 4H), 2.12 (s, 1H), 2.03-1.85 (m, 3H), 1.71-1.69 (m, 1H), 1.51-1.40 (m, 2H), 1.38-1.26 (m, 3H). | 507.6 |
| 366 | 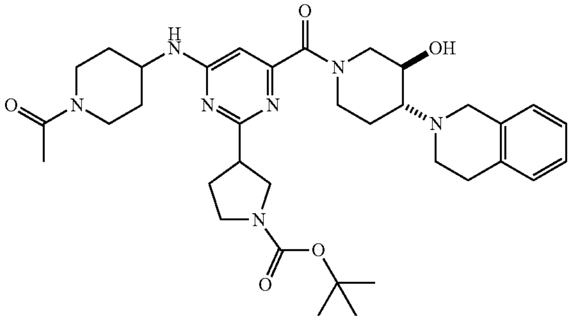 [SMILES: CC(=O)N1CCC(Nc2cc(C(=O)N3CC[C@@H](N4CCc5ccccc5C4)[C@H](O)C3)nc(C3CCN(C(=O)OC(C)(C)C)C3)n2)CC1] | (400 MHz, $CD_3OD$) δ 7.09-7.04 (m, 4H), 6.42 (s, 1H), 4.79-4.36 (m, 3H), 4.26-4.12 (m, 1H), 3.96-3.50 (m, 10H), 3.13-2.86 (m, 7H), 2.82-2.68 (m, 2H), 2.27-2.18 (m, 2H), 2.12-2.00 (m, 5H), 1.89-1.57 (m, 2H), 1.46-1.40 (m, 9H), 1.37-1.26 (m, 2H). | 648.4 |
| 367 | 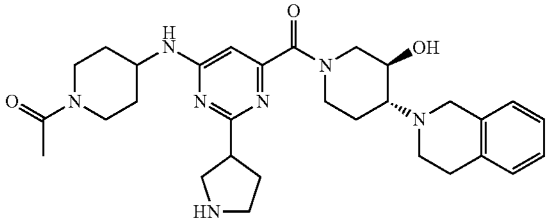 [SMILES: CC(=O)N1CCC(Nc2cc(C(=O)N3CC[C@@H](N4CCc5ccccc5C4)[C@H](O)C3)nc(C3CCNC3)n2)CC1] | (400 MHz, $CD_3OD$) δ 7.16-7.03 (m, 4H), 6.43-6.39 (m, 1H), 4.77-4.12 (m, 4H), 3.96-3.73 (m, 5H), 3.53-3.43 (m, 1H), 3.16-2.69 (m, 11H), 2.35-1.87 (m, 9H), 1.73-1.38 (m, 3H). | 548.4 |
| 368 | 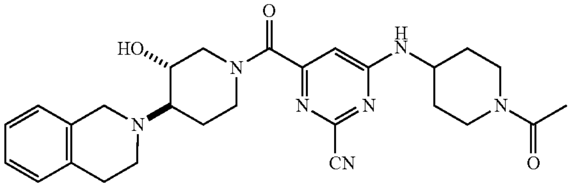 [SMILES: CC(=O)N1CCC(Nc2cc(C(=O)N3CC[C@@H](N4CCc5ccccc5C4)[C@H](O)C3)nc(C#N)n2)CC1] | (400 MHz, $CD_3OD$) δ 7.10-7.04 (m, 4H), 6.71 (d, J = 7.6 Hz, 1H), 4.68-4.42 (m, 2H), 4.26-4.20 (m, 1H), 3.96-3.76 (m, 5H), 3.15-2.70 (m, 9H), 2.12-2.08 (m, 4H), 2.03-1.89 (m, 2H), 1.71-1.62 (m, 1H), 1.53-1.37 (m, 2H). | 504.5 |

-continued
| Ex. | Structure | $^1$H NMR | LC-MS (ESI) [M + H]$^+$ |
| --- | --- | --- | --- |
| 369 | 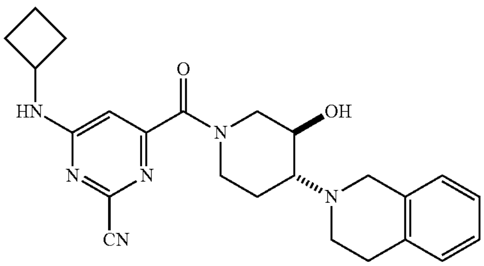 | (400 MHz, $CD_3OD$) δ 7.10-7.04 (m, 4H), 6.72-6.66 (m, 1H), 4.48-4.69 (m, 2H), 4.08-3.78 (m, 4H), 3.15-2.69 (m, 7H), 2.40 (s, 2H), 2.04-1.81 (m, 5H), 1.71-1.62 (m, 1H). | 433.3 |
| 370 | 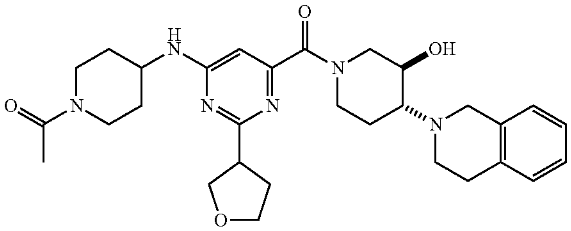 [SMILES: CC(=O)N1CCC(Nc2cc(C(=O)N3CC[C@@H](N4CCc5ccccc5C4)[C@H](O)C3)nc(C3CCOC3)n2)CC1] | (400 MHz, $CD_3OD$) δ 7.10-7.04 (m, 4H), 6.41-6.39 (m, 1H), 4.72-4.51 (m, 1H), 4.40 (d, J = 13.6 Hz, 1H), 4.24 (s, 1H), 4.12 (q, J = 8.0 Hz, 1H), 4.03-3.73 (m, 8H), 3.56-3.47 (m, 1H), 3.14-2.84 (m, 7H), 2.79-2.68 (m, 2H), 2.37-2.26 (m, 2H), 2.12-2.08 (m, 4H), 2.04-1.85 (m, 2H), 1.73-1.63 (m, 1H), 1.54-1.37 (m, 2H). | 549.6 |
| 371 | 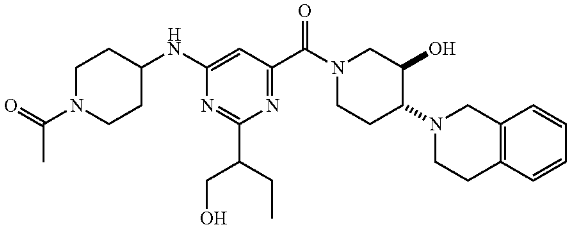 [SMILES: CCC(CO)c1nc(NC2CCN(C(C)=O)CC2)cc(C(=O)N2CC[C@@H](N3CCc4ccccc4C3)[C@H](O)C2)n1] | (400 MHz, $CD_3OD$) δ 7.16-7.06 (m, 4H), 6.40-5.18 (m, 1H), 4.59-4.15 (m, 6H), 4.13-3.87 (m, 5H), 3.84-3.66 (m, 1H), 3.55-3.38 (m, 1H), 3.13-3.03 (m, 1H), 2.98-2.83 (m, 5H), 2.80-2.72 (m, 1H), 2.69-2.59 (m, 1H), 2.37-2.33 (m, 3H), 2.31-2.24 (m, 1H), 2.12-2.07 (m, 4H), 2.02-1.95 (m, 1H), 1.53-1.37 (m, 2H), 1.34-1.26 (m, 2H). | 551.6 |
| 372 | 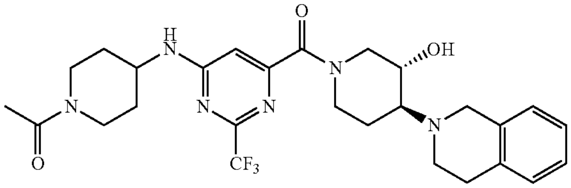 [SMILES: CC(=O)N1CCC(Nc2cc(C(=O)N3CC[C@H](N4CCc5ccccc5C4)[C@@H](O)C3)nc(C(F)(F)F)n2)CC1] | (400 MHz, DMSO-$d_6$) δ 8.49-8.20 (m, 1H), 7.15-6.94 (m, 4H), 6.73 (d, J = 6.8 Hz, 1H), 4.78 (dd, J = 56.9, 3.9 Hz, 1H), 4.54-4.17 (m, 2H), 4.15-3.73 (m, 4H), 3.73-3.49 (m, 2H), 3.27-3.13 (m, 1H), 3.10-2.73 (m, 6H), 2.74-2.57 (m, 2H), 2.04-1.68 (m, 6H), 1.61-1.25 (m, 3H). | 546.6 |
| 373 | 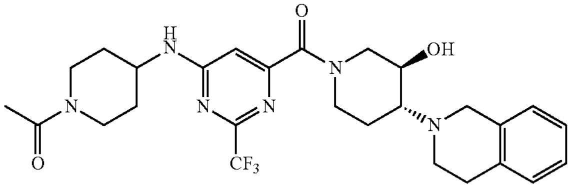 [SMILES: CC(=O)N1CCC(Nc2cc(C(=O)N3CC[C@@H](N4CCc5ccccc5C4)[C@H](O)C3)nc(C(F)(F)F)n2)CC1] | (400 MHz, DMSO-$d_6$) δ 8.49-8.21 (m, 1H), 7.17-6.95 (m, 4H), 6.73 (d, J = 6.9 Hz, 1H), 4.94-4.65 (m, 1H), 4.54-4.16 (m, 2H), 4.14-3.72 (m, 4H), 3.64 (d, J = 12.4 Hz, 2H), 3.20 (d, J = 12.4 Hz, 1H), 3.10-2.75 (m, 6H), 2.72-2.57 (m, 2H), 2.05-1.69 (m, 6H), 1.62-1.18 (m, 3H). | 546.6 |
| 374 | 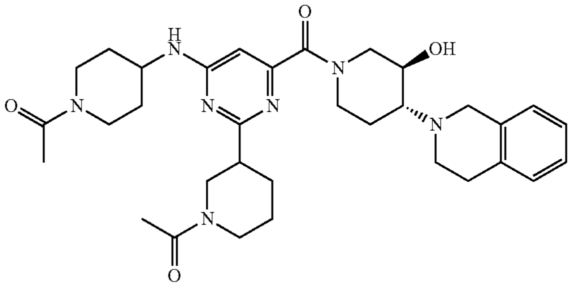 [SMILES: CC(=O)N1CCC(Nc2cc(C(=O)N3CC[C@@H](N4CCc5ccccc5C4)[C@H](O)C3)nc(C3CCCN(C(C)=O)C3)n2)CC1] | (400 MHz, $CD_3OD$) δ 7.11-7.06 (m, 4H), 6.44 (s, 1H), 4.74-4.60 (m, 2H), 4.44-4.29 (m, 2H), 4.08-3.81 (m, 6H), 3.60-3.48 (m, 1H), 3.21-3.04 (m, 3H), 2.99-2.91 (m, 6H), 2.78-2.71 (m, 2H), 2.20-2.13 (m, 8H), 2.06-1.85 (m, 4H), 1.72-1.44 (m, 4H). | 604.4 |

Example 375: Preparation of 4-((1-acetylpiperidine-4-yl)amino)-6-((3R,4R)-4-(3,4-dihydroisoquinoline-2(1H)-yl)-3-hydroxypiperidine-1-carbonyl)pyrimidine-2-carboxylic acid methyl ester

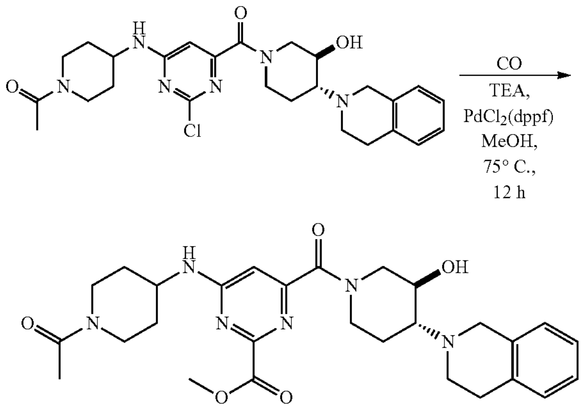

1,1-bis(diphenylphosphino)ferrocene palladium dichloride (104.4 mg, 0.14 mmol, 0.1 equiv.) was added to a solution of 1-(4-((2-chloro-6-((3R,4R)-4-(3,4-dihydroisoquinoline-2(1H)-yl)-3-hydroxypiperidine-11-carbonyl)pyrimidine-4-yl)amino)piperidine-1-yl)ethane-1-one (700 mg, 1.36 mmol, 1 equiv.) in methanol (15 mL, 100%). The atmosphere was replaced with CO gas three times. The reaction was performed at 75° C. for 12 hours. After the completion of the reaction was detected with LC-MC, the system was filtered. The filter cake was washed with DCM: MeOH=10:1 (20 mL) twice. The filtrate was concentrated to dryness to obtain a crude product, which was purified with column chromatography (DCM:MeOH=10:1) to produce a crude product of the title compound (500 mg), a part of which (400 mg) was purified with reverse phase preparative HPLC (C18, 10 mmol/L aqueous FA solution/acetonitrile) to produce the title compound (202.2 mg).

LC-MS (ESI) $[M+H]^+$=537.3; $^1$H NMR (400 MHz, $CD_3OD$) δ 8.42 (s, 1H), 7.25-7.11 (m, 4H), 6.68 (d, J=5.4 Hz, 1H), 4.80-4.56 (m, 2H), 4.48-4.32 (m, 2H), 4.31-4.18 (m, 2H), 4.06-3.97 (m, 1H), 3.95 (d, J=9.2 Hz, 3H), 3.93-3.77 (m, 2H), 3.43-3.33 (m, 1H), 3.27-3.12 (m, 2H), 3.11-2.70 (m, 5H), 2.16 (s, 1H), 2.12 (d, J=1.2 Hz, 3H), 2.10-1.94 (m, 2H), 1.94-1.77 (m, 1H), 1.59-1.35 (m, 2H).

Example 376: Preparation of (3S,4S)-4-(3,4-dihydroisoquinoline-2(1H)-yl)-1-(phenylsulfonyl)piperidine-3-ol

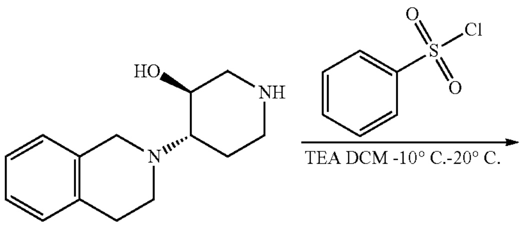

-continued

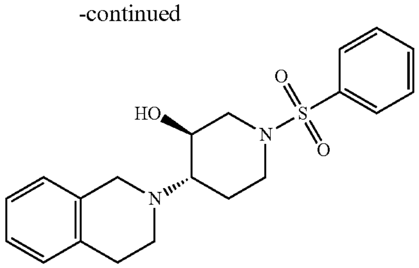

(3S,4S)-4-(3,4-dihydroisoquinoline-2(1H)-yl)piperidine-3-ol (168 mg, 0.724 mmol, 1.0 equiv.) was dissolved in dichloromethane (10 ml). Triethylamine (83 mg, 0.826 mmol, 1.2 equiv.) was added. The resulting mixture was cooled down to about −10° C. in an ice-salt bath. To the reaction solution was slowly added a solution of phenylsulfonyl chloride (CAS:98-09-9)(128 mg, 0.724 mmol, 1.0 equiv.) in dichloromethane (2 mL). After the completion of the addition, the resulting mixture was warmed up to room temperature (20° C.) and stirred for half a hour. LC-MS detected that the raw materials disappeared. The reaction solution was quenched with water, and then extracted with dichloromethane. The organic phases were combined, then washed with saturated sodium chloride, dried over anhydrous sodium sulfate, filtered, and concentrated to obtain a crude product, which was separated and purified with reverse phase HPLC (C18, aqueous $NH_4HCO_3$ solution/acetonitrile) to produce the title compound (48.5 mg, yield: 18.03%).

LC-MS (ESI) $[M+H]^+$=373.2; $^1$H NMR (400 MHz, $(CD_3)_2SO$) δ 7.82-7.71 (m, 3H), 7.67 (t, J=7.3 Hz, 2H), 7.10-7.02 (m, 3H), 7.01-6.96 (m, 1H), 4.80 (d, J=3.9 Hz, 1H), 3.80-3.57 (m, 5H), 2.89-2.79 (m, 1H), 2.78-2.65 (m, 3H), 2.40-2.25 (m, 2H), 2.09-1.98 (m, 1H), 1.82-1.71 (m, 1H), 1.65-1.49 (m, 1H).

Example 377: Preparation of (3R,4R)-4-(3,4-dihydroisoquinoline-2(1H)-yl)-1-(phenylsulfonyl)piperidine-3-ol

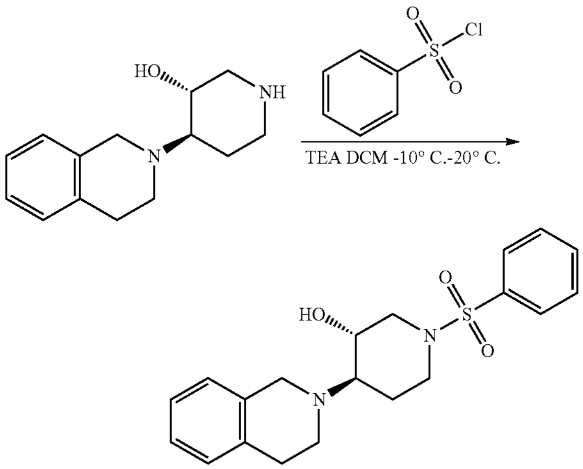

(3R,4R)-4-(3,4-dihydroisoquinoline-2(1H)-yl)piperidine-3-ol (200 mg, 0.861 mmol, 1.0 equiv.) was dissolved in dichloromethane (5 mL). Triethylamine (105 mg, 1.033 mmol, 1.2 equiv.) was added. The resulting mixture was cooled down to about −10° C. in an ice-salt bath. To the reaction solution was slowly added a solution of phenylsulfonyl chloride (160 mg, 0.904 mmol, 1.05 equiv.) in dichloromethane (5 mL). After the completion of the addition, the resulting mixture was warmed up to room temperature (20° C.) and stirred for half a hour. LC-MS detected that the raw materials disappeared. The reaction solution was quenched with water, and then extracted with dichloromethane. The organic phases were combined, then washed with saturated sodium chloride, dried over anhydrous sodium sulfate, and filtered. The filtrate was concentrated to obtain a crude product, which was separated and purified with reverse phase HPLC (C18, aqueous $NH_4HCO_3$ solution/acetonitrile) to produce the title compound (49.83 mg, yield: 15.6%).

LC-MS (ESI) $[M+H]^+$=373.2; $^1H$ NMR (400 MHz, $(CD_3)_2SO$) δ 7.81-7.59 (m, 5H), 7.13-6.93 (m, 4H), 4.80 (d, J=4.1 Hz, 1H), 3.81-3.57 (m, 5H), 2.87-2.64 (m, 4H), 2.41-2.21 (m, 2H), 2.04 (t, J=11.9 Hz, 1H), 1.81-1.72 (m, 1H), 1.63-1.48 (m, 1H).

Example 378: Preparation of 1-(4-((6-((3R,4R,5S)-4-(3,4-dihydroisoquinoline-2(1H)-yl)-3,5-dihydroxypiperidine-1-carbonyl)pyrimidine-4-yl)amino)piperidine-1-yl)ethane-1-one Step 1: Preparation of (3aR,5R,6R,6aR)-5-((R)-2,2-dimethyl-1,3-dioxolane-4-yl)-2,2-dimethyltetrahydrofuro[2,3-d][1,3]dioxolane-6-yl trifluoromethanesulfonate

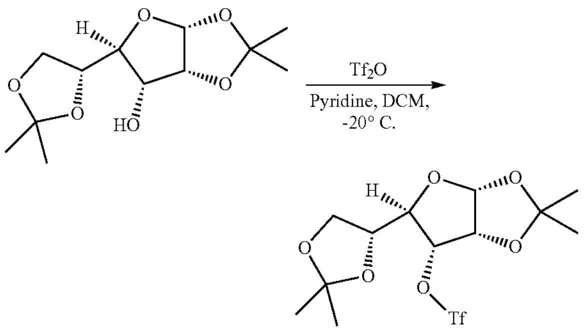

(3aR,5S,6R,6aR)-5-((R)-2,2-dimethyl-1,3-dioxolane-4-yl)-2,2-dimethyltetrahydrofuro[2,3-d][1,3]dioxolane-6-ol (10 g, 3.842 mmol, 1.0 equiv.) and pyridine (11.55 g, 14.6 mmol, 3.8 equiv.) were dissolved in dichloromethane (600 mL). The system was cooled down to −17° C. Trifluoromethanesulfonic anhydride (13 g, 4.61 mmol, 1.2 equiv.) was added to a 100 mL normal pressure dropping funnel, and added dropwise to the system at −20° C. After the dropwise addition, the reaction was continued at −20° C. for 2 hours. After the completion of the reaction, the reaction solution was poured into ice-saturated $NaHCO_3$ (100 mL). The extraction was performed, and two phases were separated. Then the aqueous phase was washed with dichloromethane two times (50 mL/each time). The organic phases were combined, dried over $Na_2SO_4$, and filtered by suction. The filtrate was concentrated, and toluene (150 mL) was added to the residue. The resulting mixture was concentrated. This operation was repeated twice. n-hexane (160 mL) was added to the residue. The hexane solution was filtered. The filtrate was concentrated again to produce the title compound (14.72 g, yield: 97.7%).

$^1H$ NMR (400 MHz, $CDCl_3$) δ 5.84 (d, J=3.8 Hz, 1H), 4.92-4.89 (m, 1H), 4.78-4.76 (m, 1H), 4.23-4.10 (m, 3H), 3.93-3.89 (m, 1H), 1.59 (s, 3H), 1.45 (s, 3H), 1.39 (s, 3H), 1.35 (s, 3H).

Step 2: Preparation of (3aR,5S,6S,6aR)-6-azido-5-((R)-2,2-dimethyl-1,3-dioxolane-4-yl)-2,2-dimethyltetrahydrofuro[2,3-d][1,3]dioxole

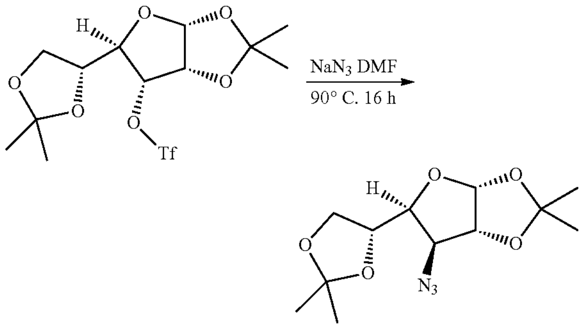

(3aR,5R,6R,6aR)-5-((R)-2,2-dimethyl-1,3-dioxolane-4-yl)-2,2-dimethyltetrahydrofuro[2,3-d][1,3]dioxolane-6-yl trifluoromethanesulfonate (14.7 g, 37.47 mmol, 1.0 equiv.) was dissolved in DMF (100 mL). Sodium azide (4.87 g, 74.94 mmol, 2.0 equiv.) was added to the system. The reaction solution was reacted at 90° C. for 16 hours, and TLC (petroleum ether:ethyl acetate=10:1) was used to determine the endpoint of the reaction. Most of the reaction solution was concentrated. 100 mL ethyl acetate was added to the solution. The ethyl acetate solution was extracted with water (washed with water three times, 50 mL/each time). The organic phase was washed with saturated brine (100 mL) once. The organic phase was dried over Na2SO4, and filtered by suction. The organic phase was concentrated to produce a crude product, which was purified with silicagel column chromatography (normal phase)(PE:EA=10:1) to produce the title compound (8.45 g, yield: 79.1%).

$^1H$ NMR (400 MHz, $CDCl_3$) δ 5.86 (d, J=3.6 Hz, 1H), 4.62 (d, J=3.6 Hz, 1H), 4.28-4.21 (m, 1H), 4.17-4.07 (m, 3H), 4.00- 3.97 (m, 1H), 1.51 (s, 3H), 1.44 (s, 3H), 1.37 (s, 3H), 1.33 (s, 3H).

Step 3: Preparation of (3aR,5S,6S,6aR)-5-((R)-2,2-dimethyl-1,3-dioxolane-4-yl)-2,2-dimethyltetrahydrofuro[2,3-d][1,3]dioxolane-6-amine

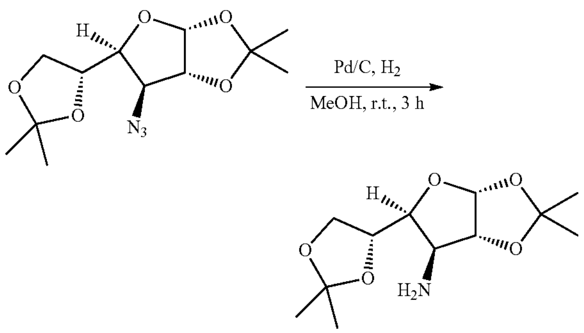

(3aR,5S,6S,6aR)-6-azido-5-((R)-2,2-dimethyl-1,3-dioxolane-4-yl)-2,2-dimethyltetrahydrofuro[2,3-d][1,3]dioxole (200 mg, 0.701 mol, 1 equiv.) was dissolved in methanol (5 mL). 50 mg 10% Pd/C was added. The reaction solution was stirred under hydrogen gas at 16° C. for 3 hours. The completion of the reaction was detected with TLC and LC-MS. Pd/C was removed by filtering. The filtrate was rotary dried to remove the solvent, and purified with column chromatography (DCM:MeOH=98:2) to produce the title compound (160 mg, yield: 88%).

LC-MS (ESI) $[M+H]^+$=260.2; $^1H$ NMR (400 MHz) δ 5.89 (d, J=3.6 Hz, 1H), 4.40 (d, J=3.6 Hz, 1H), 4.23-4.18 (m, 1H), 4.18-4.14 (m, 1H), 4.06-4.01 (m, 1H), 4.00-3.96 (m, 1H), 3.56 (d, J=3.4 Hz, 1H), 1.51 (s, 3H), 1.42 (s, 3H), 1.35 (s, 3H), 1.31 (s, 3H).

Step 4: Preparation of 2-((3aR,5S,6S,6aR)-5-((R)-2,2-dimethyl-1,3-dioxolane-4-yl)-2,2-dimethyltetrahydrofuro[2,3-d][1,3]dioxolane-6-yl)-1,2,3,4-tetrahydroisoquinoline

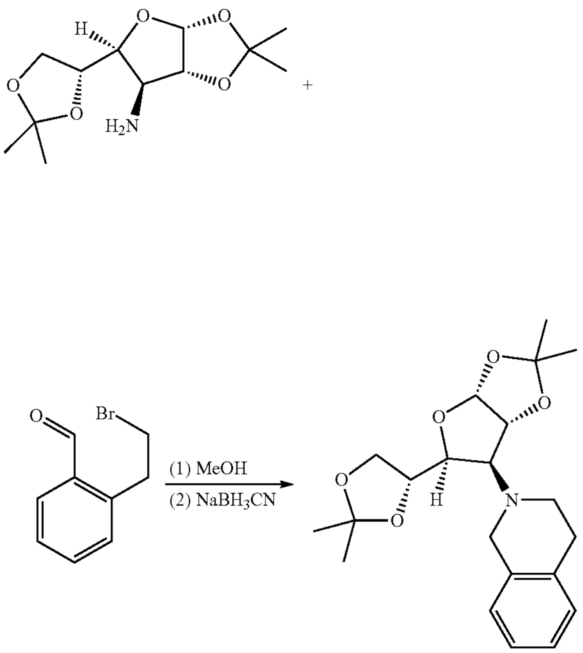

(3aR,5S,6S,6aR)-5-((R)-2,2-dimethyl-1,3-dioxolane-4-yl)-2,2-dimethyltetrahydrofuro[2,3-d][1,3]dioxolane-6-amine (60 mg, 0.232 mmol, 1.0 equiv.) was dissolved in methanol (1 mL). 2-(2-bromoethyl)benzaldehyde (54 mg, 0.255 mmol, 1.1 equiv) was added. The resulting mixture was stirred at 16° C. under the protection of $N_2$ for 1 hour. LC-MS detected the formation of the intermediate state. Then sodium cyanoborohydride (41 mg, 0.696 mmol, 3.0 equiv.) was added at 0° C. The stirring was continued at 16° C. for 1 hour. TLC and LC-MS detected the completion of the reaction. To the reaction solution were added appropriate amounts of water and dichloromethane. The organic phase was washed with water and saturated NaCl solution each once, dried over anhydrous sodium sulfate, rotary dried to remove the solvent, and purified with column chromatography (PE:EA=2:1) to produce the title compound (18 mg, yield: 20.7%).

LC-MS (ESI) $[M+H]^+$=376.2; $^1H$ NMR (400 MHz, $CDCl_3$) δ 7.08-6.99 (m, 3H), 6.97-6.89 (m, 1H), 5.78 (d, J=3.8 Hz, 1H), 4.79 (d, J=3.7 Hz, 1H), 4.33-4.25 (m, 1H), 4.14-4.07 (m, 1H), 4.06-3.95 (m, 2H), 3.88 (d, J=14.8 Hz, 1H), 3.70 (d, J=14.8 Hz, 1H), 3.34 (d, J=4.7 Hz, 1H), 3.01-2.91 (m, 1H), 2.88-2.79 (m, 1H), 2.78-2.61 (m, 2H), 1.46 (s, 3H), 1.35 (s, 3H), 1.26 (s, 3H), 1.25 (s, 3H).

Step 5: Preparation of (R)-1-((3aR,5S,6S,6aR)-6-(3,4-dihydroisoquinoline-2(1H)-yl)-2,2-dimethyltetrahydrofuro[2,3-d][1,3]dioxolane-5-yl)ethane-1,2-diol

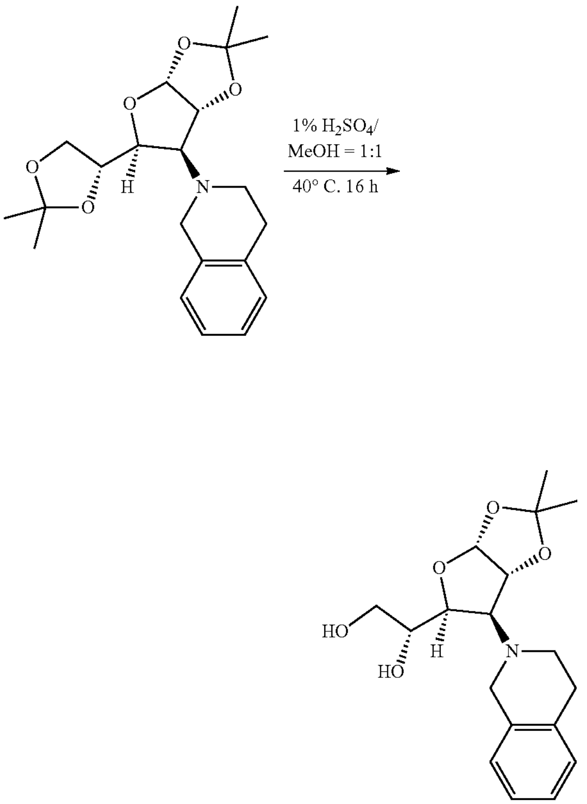

2-((3aR,5S,6S,6aR)-5-((R)-2,2-dimethyl-1,3-dioxolane-4-yl)-2,2-dimethyltetrahydrofuro[2,3-d][1,3]dioxolane-6-yl)-1,2,3,4-tetrahydroisoquinoline (180 mg, 0.48 mmol, 1.0 equiv.) was dissolved in methanol (1 mL). 1% $H_2SO_4$ (1 mL) was added. The resulting mixture was stirred at 40° C. for 16 hours. LC-MS detected the formation of the target product. The reaction solution was adjusted with saturated $NaHCO_3$ solution to pH=8, rotary dried to remove the solvent, and purified with column chromatography (DCM:MeOH=98:2) to produce the title compound (82 mg, yield: 51%).

LC-MS (ESI) $[M+H]^+$=336.2; $^1H$ NMR (400 MHz, $CD_3OD$) δ 7.12-7.05 (m, 3H), 7.05-7.00 (m, 1H), 5.92 (d, J=3.8 Hz, 1H), 5.01 (d, J=3.8 Hz, 1H), 4.23-4.12 (m, 1H), 4.01-3.90 (m, 2H), 3.83-3.73 (m, 2H), 3.65-3.56 (m, 1H), 3.45 (d, J=5.0 Hz, 1H), 3.21-3.09 (m, 1H), 2.99-2.87 (m, 1H), 2.86-2.71 (m, 2H), 1.48 (s, 3H), 1.32 (s, 3H).

Step 6: Preparation of (3aR,5S,6S,6aR)-6-(3,4-dihydroisoquinoline-2(1H)-yl)-2,2-dimethyltetrahydrofuro[2,3-d][1,3]dioxolane-5-carbaldehyde

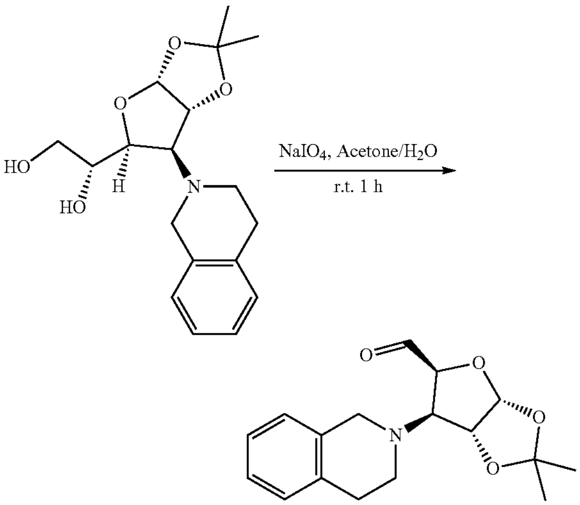

(R)-1-((3aR,5S,6S,6aR)-6-(3,4-dihydroisoquinoline-2(1H)-yl)-2,2-dimethyltetrahydrofuro[2,3-d][1,3]dioxolane-5-yl)ethane-1,2-diol (60 mg, 0.15 mmol, 1.0 equiv.) was dissolved in acetone/water (1.2 mL, 5:1). $NaIO_4$ (48 mg, 0.224 mmol, 1.5 equiv) was added at 0° C. The stirring was continued at 16° C. for 1 hour. Cyclobutanecarbonyl chloride (21.29 mg, 0.18 mmol, 1.1 equiv) was added dropwise in an ice bath. The resulting mixture was stirred for 1 hour. TLC (PE:EA=2:1, $R_f$=0.5, $H_2SO_4$/EtOH as chromogenic reagent) detected the completion of the reaction. The reaction system was rotary dried to remove the solvent. The residue was dissolved in dichloromethane, and filtered by suction. The resulting filtrate was rotary dried to remove the solvent to obtain a crude product, which was directly used in the next step.

Step 7: Preparation of ((3aR,5S,6S,6aR)-6-(3,4-dihydroisoquinoline-2(1H)-yl)-2,2-dimethyltetrahydrofuro[2,3-d][1,3]dioxolane-5-yl)methanol

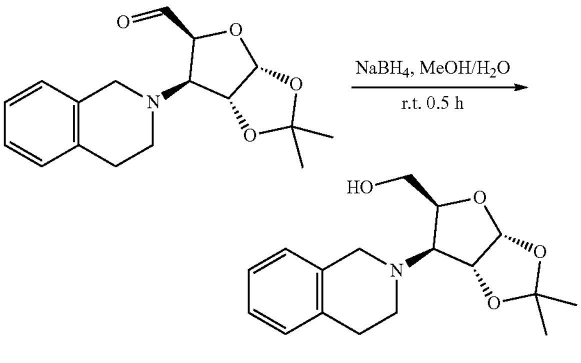

(3aR,5S,6S,6aR)-6-(3,4-dihydroisoquinoline-2(1H)-yl)-2,2-dimethyltetrahydrofuro[2,3-d][1,3]dioxolane-5-carbaldehyde (crude, 50 mg, 0.165 mmol, 1.0 equiv.) was dissolved in methanol/water (1 mL, 4:1). $NaBH_4$ (10 mg, 0.248 mmol, 1.5 equiv) was added at 0° C. The stirring was continued at 16° C. for 0.5 hours. TLC (DCM:MeOH=20:1, $H_2SO_4$/EtOH as chromogenic reagent) detected the completion of the reaction. To the reaction solution was added saturated ammonium chloride solution (1 mL). The resulting mixture was extracted with DCM. The organic phase was washed with water and saturated NaCl solution each once, dried over anhydrous sodium sulfate, rotary dried to remove the solvent, and purified with column chromatography (DCM:MeOH=98:2) to produce the target compound (32 mg, yield: 63.5%).

LC-MS (ESI) $[M+H]^+$=306.1; $^1H$ NMR (400 MHz, $CDCl_3$) δ 7.13 (dt, J=8.5, 4.7 Hz, 3H), 7.06-7.00 (m, 1H), 5.97 (d, J=4.0 Hz, 1H), 4.91 (d, J=3.3 Hz, 1H), 4.49 (q, J=5.7 Hz, 1H), 4.00 (dd, J=12.1, 6.0 Hz, 2H), 3.88 (dd, J=12.2, 5.8 Hz, 1H), 3.75 (d, J=14.3 Hz, 1H), 3.43 (d, J=4.1 Hz, 1H), 3.16 (s, 2H), 2.93 (d, J=7.2 Hz, 1H), 2.88-2.68 (m, 2H), 1.54 (s, 3H), 1.36 (s, 3H).

Step 8: Preparation of ((3aR,5S,6S,6aR)-6-(3,4-dihydroisoquinoline-2(1H)-yl)-2,2-dimethyltetrahydrofuro[2,3-d][1,3]dioxolane-5-yl)methyl 4-methylbenzenesulfonate

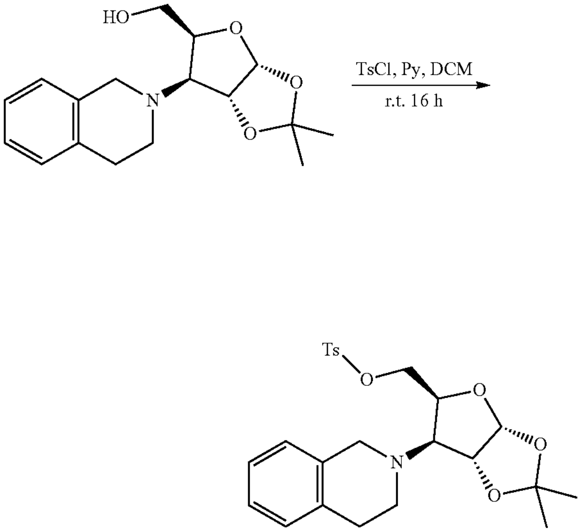 [SMILES: CC1(C)O[C@H]2O[C@H](CO)[C@H](N3CCc4ccccc4C3)[C@H]2O1 ; Cc1ccc(S(=O)(=O)OC[C@H]2O[C@@H]3OC(C)(C)O[C@@H]3[C@H]2N2CCc3ccccc3C2)cc1]

((3aR,5S,6S,6aR)-6-(3,4-dihydroisoquinoline-2(1H)-yl)-2,2-dimethyltetrahydrofuro[2,3-d][1,3]dioxolane-5-yl)methanol (250 mg, 0.819 mmol, 1.0 equiv.) was dissolved in dichloromethane (4 mL). Para-methylbenzenesulfonyl chloride (312.2 mg, 1.64 mmol, 2.0 equiv) and pyridine (0.5 mL) were added. The resulting mixture was stirred at 16° C. for 16 hours, rotary dried to remove the solvent, and purified with column chromatography (PE:EA=93:7) to produce the title compound (125 mg, yield: 33.2%).

LC-MS (ESI) $[M+H]^+$=460.4; $^1H$ NMR (400 MHz, $CDCl_3$) δ 7.77-7.71 (m, 2H), 7.18-7.12 (m, 4H), 7.08-7.04 (m, 1H), 7.01-6.94 (m, 1H), 5.85 (d, J=3.7 Hz, 1H), 4.87-4.78 (m, 1H), 4.54-4.47 (m, 1H), 4.37-4.28 (m, 1H), 4.26-4.18 (m, 1H), 3.93-3.81 (m, 1H), 3.74-3.54 (m, 1H), 3.45-3.28 (m, 1H), 3.00-2.85 (m, 1H), 2.75-2.49 (m, 3H), 2.35 (s, 3H), 1.50 (s, 3H), 1.32 (s, 3H).

Step 9: Preparation of 2-((3aR,5R,6S,6aR)-5-(azidomethyl)-2,2-dimethyltetrahydrofuro[2,3-d][1,3]dioxolane-6-yl)-1,2,3,4-tetrahydroisoquinoline

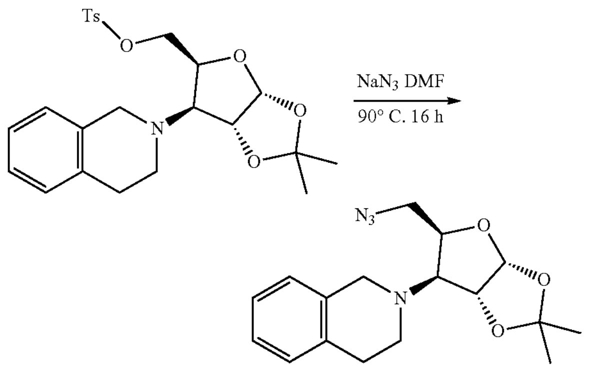

((3aR,5S,6S,6aR)-6-(3,4-dihydroisoquinoline-2(1H)-yl)-2,2-dimethyltetrahydrofuro[2,3-d][1,3]dioxolane-5-yl)methyl 4-methylbenzenesulfonate (126 mg, 0.274 mmol, 1.0 equiv.) was dissolved in N,N-dimethyl formamide (1.0 mL). Sodium azide (54 mg, 0.822 mmol, 3.0 equiv) was added. The resulting mixture was stirred at 90° C. and under nitrogen gas for 16 hours. The completion of the reaction was monitored with TLC and LC-MS. To the reaction system were added water and ethyl acetate. The organic phase was washed with water and saturated NaCl solution each once, dried over anhydrous sodium sulfate, rotary dried to remove the solvent, and purified with column chromatography (PE:EA=2:1) to produce the title compound (62 mg, yield: 68.4%). LC-MS (ESI) $[M+H]^+$=331.1.

Step 10: Preparation of (2S,3R,4R,5R)-5-(azidomethyl)-4-(3,4-dihydroisoquinoline-2(1H)-yl)tetrahydrofuran-2,3-diol

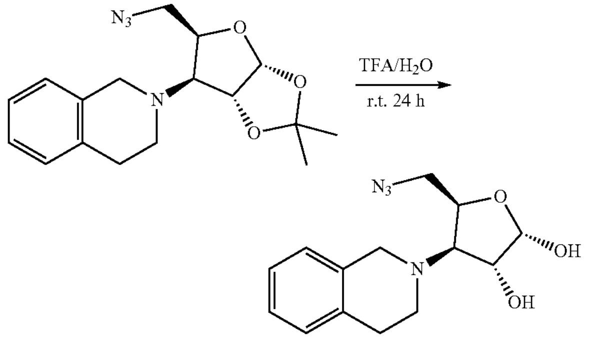

To 2-((3aR,5R,6S,6aR)-5-(azidomethyl)-2,2-dimethyltetrahydrofuro[2,3-d][1,3]dioxolane-6-yl)-1,2,3,4-tetrahydroisoquinoline (100 mg, 0.302 mmol, 1.0 equiv.) was added trifluoroacetic acid/water (0.5 mL, 3:2). The reaction solution was stirred at 16° C. for 24 hours. The completion of the reaction was monitored with TLC and LC-MS. To the system was added toluene and the solvent was removed by rotary drying to obtain a crude product, which was directly used in the next step.

Step 11; Preparation of (3S,4r,5R)-4 (3,4-dihydroisoquinoline-2(1H)-yl)piperidine-3,5-diol

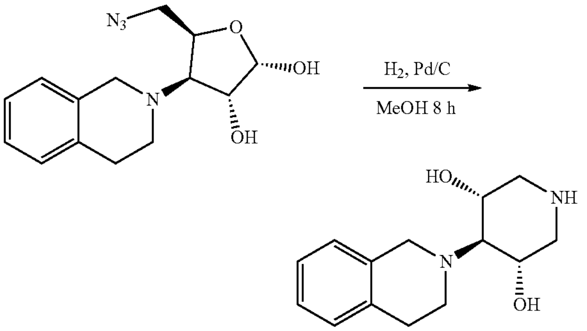

To (2S,3R,4R,5R)-5-(azidomethyl)-4-(3,4-dihydroisoquinoline-2(1H)-yl)tetrahydrofuran-2,3-diol (85 mg, 0.292 mmol, 1.0 equiv.) were added methanol (10 mL) and 10% Pd/C (30 mg). The reaction solution was stirred under hydrogen gas at 16° C. for 8 hours. The completion of the reaction was monitored with TLC and LC-MS. The reaction system was filtered, and rotary dried to remove the solvent to obtain a crude product, which was separated and purified with Prep-HPLC (C18, 10 mmol/L aqueous solution, MeCN) to produce the target product (67 mg).

LC-MS (ESI) $[M+H]^+$=249.1; $^1H$ NMR (400 MHz, $CDCl_3$) δ 7.18-7.09 (m, 3H), 7.06-6.98 (m, 1H), 4.10 (s, 2H), 3.79-3.65 (m, 2H), 3.28 (dd, J=11.5, 4.6 Hz, 2H), 3.21-3.11 (m, 2H), 2.96-2.87 (m, 2H), 2.62-2.47 (m, 4H), 2.43 (t, J=9.9 Hz, 1H).

Step 12: 1-(4-((6-((3R,4R,5S)-4-(3,4-dihydroisoquinoline-2(1H)-yl)-3,5-dihydroxypiperidine-1-carbonyl)pyrimidine-4-yl)amino)piperidine-1-yl)ethane-1-one

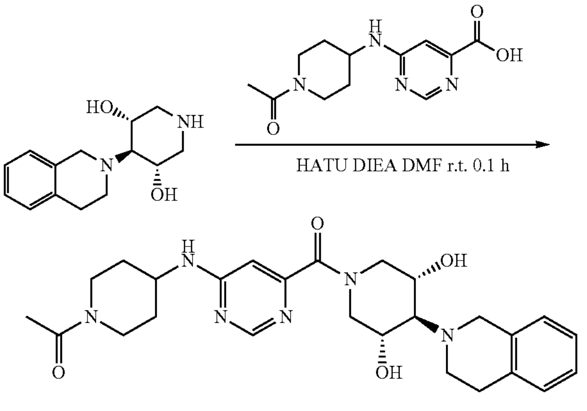

(3S,4r,5R)-4-(3,4-dihydroisoquinoline-2(1H)-yl)piperidine-3,5-diol (50 mg, 0.2 mmol, 1.0 equiv.), 6-((1-acetylpiperidine-4-yl)amino)pyrimidine-4-carboxylic acid (58 mg, 0.22 mmol, 1.1 equiv.) and O-(7-azabenzotriazol-1-yl)-N,N,N',N'-tetramethyluronium hexafluorophosphate (114 mg, 0.3 mmol, 1.5 equiv.) were added to N,N-dimethyl formamide (0.6 mL). Then N,N-diisopropylethylamine (78 mg, 0.6 mmol, 3.0 equiv.) was added. The resulting mixture was stirred at 16° C. for 0.5 hours. TLC detected the reaction of raw materials was completed. To the reaction system was added water (15 mL), and the resulting mixture was extracted with ethyl acetate three times (3×15 mL). The organic phases were combined, washed with saturated sodium chloride solution (20 mL) once, dried over anhydrous sodium sulfate, and filtered by suction. The filtrate was concentrated to remove the solvent, and separated and purified with Prep-HPLC (C18, 10 mmol/L aqueous solution, MeCN) to produce the target product (18.29 mg, yield: 18.6%).

LC-MS (ESI) $[M+H]^+$=495.3; $^1H$ NMR (400 MHz, $CDCl_3$) δ 8.53 (s, 1H), 7.19-7.09 (m, 3H), 7.04-6.98 (m, 1H), 6.69 (s, 1H), 5.48 (s, 1H), 4.63-4.49 (m, 2H), 4.23-3.95 (m, 5H), 3.92-3.77 (m, 2H), 3.30-3.08 (m, 4H), 3.05-2.88 (m, 3H), 2.86-2.67 (m, 2H), 2.17-2.12 (m, 1H), 2.11 (s, 3H), 2.06-1.98 (m, 1H), 1.45 (m, 2H).

Example 379: Preparation of trans-1-(4-((6-(4-amino-3-(3,4-dihydroisoquinoline-2(1H)-yl)piperidine-1-carbonyl)pyrimidine-4-yl)amino)piperidine-1-yl)ethane-1-one

Step 1: Preparation of 4-amino-3-hydroxypiperidine-1-carboxylic acid benzyl ester and 3-amino-4-hydroxypiperidine-1-carboxylic acid benzyl ester

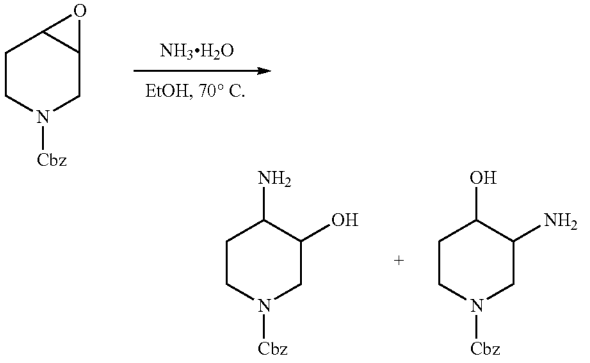

7-oxa-3-azabicyclo[4.1.0]heptane-3-carboxylic acid benzyl ester (2.5 g, 10.72 mmol, 1 equiv.) was dissolved in ethanol (5 mL). Concentrated ammonia (15 mL, 25-28%, 210 mmol, 19.6 equiv.) was added. The reaction was performed at 70° C. under stirring overnight (16 hours). TLC monitored the completion of the reaction (PE:EA=2:1). The reaction solution was rotary dried to obtain a crude product (2.8 g), which was directly used in the next step.

LC-MS (ESI) $[M+H]^+$=251.2.

Step 2: Preparation of 4-((tert-butoxycarbonyl)amino)-3-hydroxypiperidine-1-carboxylic acid benzyl ester and 3-((tert-butoxycarbonyl)amino)-4-hydroxypiperidine-1-carboxylic acid benzyl ester

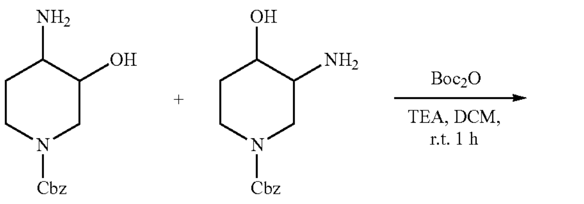

-continued

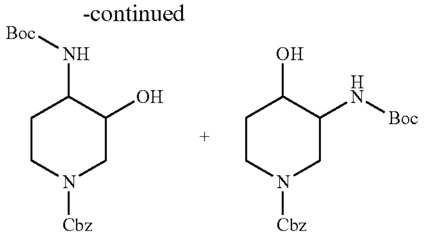

The crude product from the previous step (2.8 g, 10.72 mmol, 1 equiv.) was dissolved in dichloromethane (25 mL). Triethylamine (1.63 g, 16.11 mmol, 1.5 equiv.) and di-tert-butyl dicarbonate (2.8 g, 12.83 mmol, 1.2 equiv.) were added. The resulting mixture was stirred at room temperature for 1 hour. The completion of the reaction was monitored with LC-MS. The reaction solution was not purified and directly used in the next step.

LC-MS (ESI) $[(M-100)+1]^+$=251.20, $[(M-56)+1]^+$=295.20.

Step 3: Preparation of 4-((tert-butoxycarbonyl)amino)-3-(para-toluenesulfonyloxy)piperidine-1-carboxylic acid benzyl ester and 3-((tert-butoxycarbonyl)amino)-4-(para-toluenesulfonyloxy)piperidine-1-carboxylic acid benzyl ester

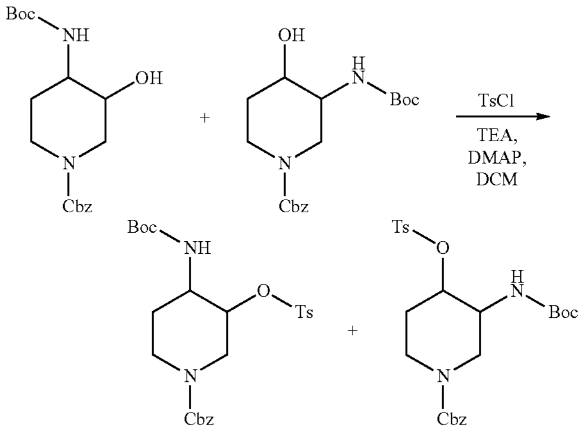

To the reaction solution from the previous step (10.72 mmol raw material) were successively added triethylamine (2.17 g, 21.44 mmol, 2 equiv.), 4-toluenesulfonyl chloride (4.09 g, 21.45 mmol, 2 equiv.) and 4-dimethylaminopyridine (131 mg, 1.072 mmol, 0.1 equiv.). The resulting mixture was stirred at room temperature for 16 hours. TLC monitored the completion of the reaction. The solvent was removed by rotary drying to obtain a crude product, which was separated and purified with flash chromatography (silica gel, 0-27% EA/PE solution) to produce a product (3.317 g, total yield of three steps: 61.4%).

LC-MS (ESI) $[M+H]^+$=348.0; $^1H$ NMR (400 MHz, $CDCl_3$) δ 7.88-7.66 (m, 2H), 7.43-7.17 (m, 7H), 5.16-5.04 (m, 2H), 4.73-4.44 (m, 1H), 4.32-4.08 (m, 1H), 4.04-3.76 (m, 1H), 3.74-3.54 (m, 1H), 3.43-2.75 (m, 2H), 2.49-2.34 (m, 3H), 2.16-2.07 (m, 0.7H), 1.96-1.85 (m, 0.3H), 1.51-1.35 (m, 10H).

Step 4: Preparation of 3-benzyl 7-tert-butyl 3,7-diazabicyclo[4.1.0]heptane-3,7-dicarboxylate

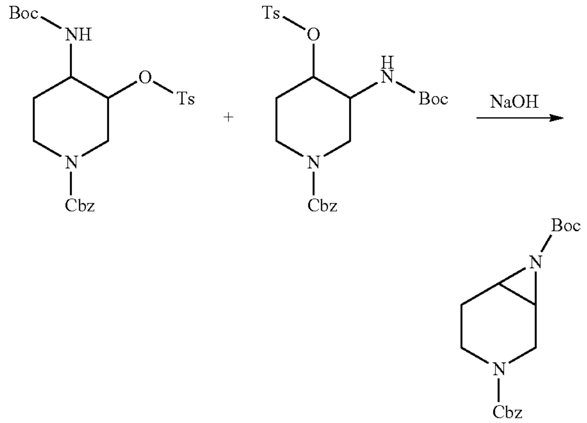

The product from step 3 (3.317 g, 6.574 mmol, 1 equiv.) was dissolved in DMF (28 mL). Aqueous sodium hydroxide solution (526 mg/7 mL, 13.15 mmol, 2 equiv.) was added. The resulting mixture was stirred under heating at 50° C. for 1 hour. The completion of the reaction was monitored with LC-MS. The reaction solution was diluted with ethyl acetate, and washed with water. The phases were separated. The organic phase was washed with saturated brine once, dried over anhydrous sodium sulfate, and rotary dried to obtain a crude product, which was separated and purified with flash chromatography (silica gel, 0-20% EA/PE solution) to produce the title compound (2.0 g, yield: 91.5%) as colorless oil.

LC-MS (ESI) $[(M-100)+1]^+$=233.20, $[(M-56)+1]^+$=277.20.

Step 5: Preparation of trans-4-((tert-butoxycarbonyl)amino)-3-(3,4-dihydroisoquinoline-2(1H)-yl) piperidine-1-carboxylic acid benzylester

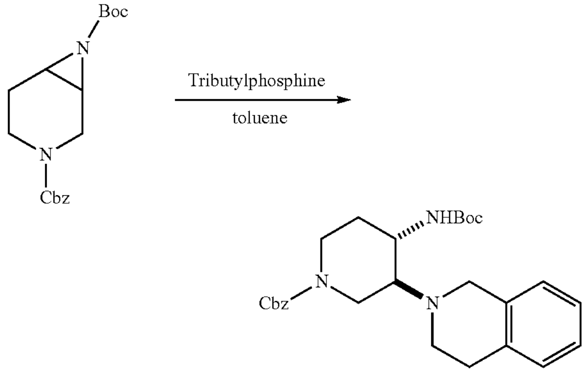

3-benzyl 7-tert-butyl 3,7-diazabicyclo[4.1.0]heptane-3,7-dicarboxylate (200 mg, 0.602 mmol, 1 equiv.) and 1,2,3,4-tetrahydroisoquinoline (120 mg, 0.901 mmol, 1.5 equiv.) were dissolved in toluene (3 mL). Tributylphosphine (13 mg, 0.0643 mmol, 0.11 equiv.) was added. The reaction was performed under nitrogen gas at reflux overnight (16 hours). LC-MS monitored the remained raw material. Tetrahydroisoquinoline (96 mg, 0.722 mmol, 1.2 equiv.) and tributylphosphine (24 mg, 0.120 mmol, 0.2 equiv.) were supplemented. The reaction was continued at 110° C. for 1 day (24 hours), and rotary dried to remove the solvent to obtain a crude product, which was separated and purified with flash chromatography (silica gel, 0-15% EA/PE solution) to produce trans-4-((tert-butoxycarbonyl)amino)-3-(3,4-dihydroisoquinoline-2(1H)-yl)piperidine-1-carboxylic acid benzyl ester (crude, 166 mg), which was purified with reverse phase column chromatography (C18, 10 mmol/L aqueous $NH_4HCO_3$ solution, 30%-90% MeCN) to produce the title compound (97 mg, yield: 34.7%).

LC-MS (ESI) $[M+H]^+$=466.2; $^1H$ NMR (400 MHz, DMSO-$d_6$) δ 7.44-7.26 (m, 5H), 7.11-6.93 (m, 4H), 6.61 (d, J=8.8 Hz, 1H), 5.09 (s, 2H), 4.18-4.04 (m, 1H), 3.97-3.82 (m, 2H), 3.80-3.63 (m, 2H), 3.11-3.00 (m, 1H), 2.97-2.57 (m, 5H), 2.54-2.46 (m, 1H), 1.86-1.76 (m, 1H), 1.45-1.25 (m, 10H).

Step 6: Preparation of trans-(3-(3,4-dihydroisoquinoline-2(1H)-yl)piperidine-4-yl)carbamic acid tert-butyl ester

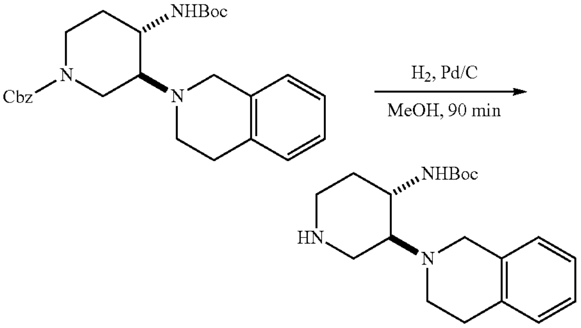

trans-4-((tert-butoxycarbonyl)amino)-3-(3,4-dihydroisoquinoline-2(1H)-yl)piperidine-1-carboxylic acid benzyl ester (87 mg, 0.187 mmol, 1 equiv.) was dissolved in methanol (chromatographic grade, 5 mL). Pd/C (10%, 90 mg) was added. The resulting mixture was stirred under $H_2$ for 1.5 hours. TLC monitored the completion of the reaction. The reaction solution was filtered, and rotary dried to obtain a crude product (60 mg, yield: 96.9%), which was directly used in the next step.

LC-MS (ESI) $[M+H]^+$=332.25.

Step 7: Preparation of trans-(1-(6-((1-acetylpiperidine-4-yl)amino)pyrimidine-4-carbonyl)-3-(3,4-dihydroisoquinoline-2(1H)-yl)piperidine-4-yl)carbamic acid tert-butyl ester

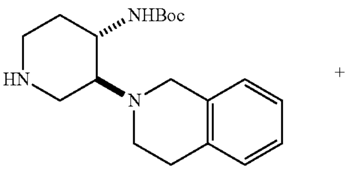

-continued

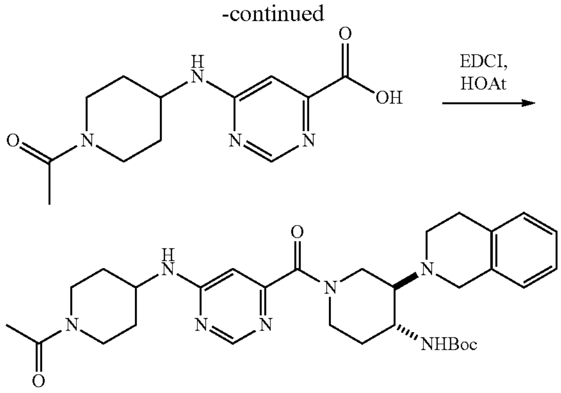

6-((1-acetylpiperidine-4-yl)amino)pyrimidine-4-carboxylic acid (48 mg, 0.182 mmol, 1 equiv.), EDCI (53 mg, 0.276 mmol, 1.52 equiv.) and HOAt (37 mg, 0.271839 mmol, 1.5 equiv.) were dissolved in DMF (2 mL). The resulting mixture was stirred for 5 minutes. A solution of trans-(3-(3,4-dihydroisoquinoline-2(1H)-yl)piperidine-4-yl)carbamic acid tert-butyl ester (45 mg, 0.174 mmol, 1.7 equiv.) in DMF (1 mL) was added. The reaction was performed under stirring at room temperature for 1.5 hours. The solvent was removed by rotary drying to obtain a crude product, which was separated and purified with flash chromatography (silica gel, 0-5% MeOH/DCM solution) to produce the title compound (115 mg, purity: 80%, yield: 91.6%).

LC-MS (ESI) $[M+H]^+$=578.2.

Step 8: Preparation of trans-1-(4-((6-(4-amino-3-(3,4-dihydroisoquinoline-2(1H)-yl)piperidine-1-carbonyl)pyrimidine-4-yl)amino)piperidine-1-yl)ethane-1-one

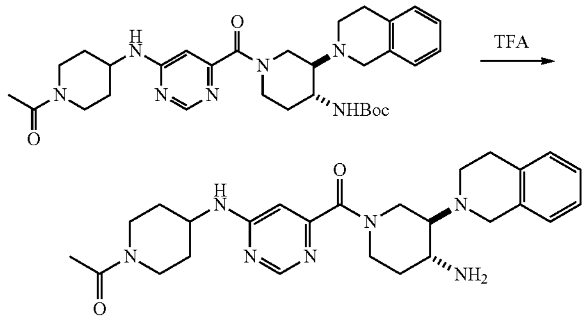

trans-(1-(6-((1-acetylpiperidine-4-yl)amino)pyrimidine-4-carbonyl)-3-(3,4-dihydroisoquinoline-2(1H)-yl)piperidine-4-yl)carbamic acid tert-butyl ester (115 mg, 80%, 0.159 mmol, 1 equiv.) was dissolved in dichloromethane (4 mL). Trifluoroacetic acid (2 mL) was added. The resulting mixture was stirred at room temperature for 1 hour. The completion of the reaction was monitored with LC-MS. The system was rotary dried to remove dichloromethane and trifluoroacetic acid to obtain a crude product, which was dissolved in methanol. The resulting mixture was adjusted with a strongly basic anion exchange resin to pH=8-9, filtered, rotary dried, and purified with reverse phase column preparative chromatography (C18, 10 mmol/L aqueous $NH_{40}H$ solution/acetonitrile) to produce the title compound (19.46 mg, yield: 25.1%).

LC-MS (ESI) $[M+H]^+$=478.4; $^1H$ NMR (400 MHz, $CDCl_3$) δ 8.58-8.51 (m, 1H), 7.18-6.95 (m, 4H), 6.68-6.56 (m, 1H), 5.34-5.13 (m, 1H), 4.93-4.66 (m, 1H), 4.61-4.50 (m, 1H), 4.27-4.20 (m, 0.4H), 4.13-4.08 (m, 0.6H), 4.05-3.97 (m, 0.6H), 3.91-3.70 (m, 2.4H), 3.28-3.03 (m, 3H), 3.03-2.88 (m, 2H), 2.87-2.61 (m, 4.4H), 2.55-2.46 (m, 0.6H), 2.19-1.95 (m, 6H), 1.58-1.35 (m, 3H).

Example 380: Preparation of 1-(4-((6-((3R,4R)-4-(3,4-dihydroisoquinoline-2(1H)-yl)-3-hydroxypiperidine-1-carbonyl)-2-(isopropylsulfinyl)pyrimidine-4-yl)amino)piperidine-1-yl)ethane-1-one

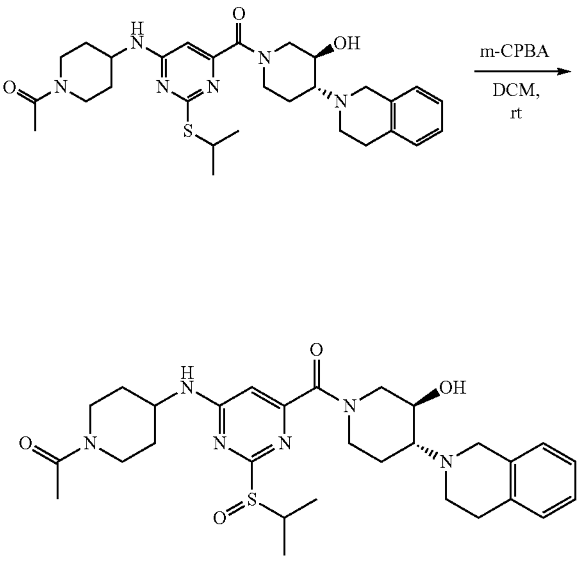

1-(4-((6-((3R,4R)-4-(3,4-dihydroisoquinoline-2(1H)-yl)-3-hydroxypiperidine-1-carbonyl)-2-(isopropylthio)pyrimidine-4-yl)amino)piperidine-1-yl)ethane-1-one (40 mg, 0.072368 mmol, 1 equiv.) and m-CPBA (13.7374 mg, 0.079605 mmol, 1.1 equiv.) were dissolved in dichloromethane (2 mL). The reaction solution was stirred at room temperature for 2 hours. The reaction solution was rotary dried with a rotary evaporator to produce a crude product, which was separated and purified with reverse phase HPLC (C18, aqueous $NH_4HCO_3$ solution/acetonitrile) to produce the title compound (15 mg).

LC-MS (ESI) $[M+H]^+$=569.0; $^1H$ NMR (400 MHz, DMSO) δ 8.48-7.45 (m, 1H), 7.17-6.99 (m, 4H), 6.81-6.56 (m, 1H), 4.85-4.69 (m, 1H), 4.46-4.09 (m, 3H), 3.86-3.76 (m, 3H), 3.69-3.59 (m, 2H), 3.26-3.13 (m, 2H), 3.08-2.73 (m, 6H), 2.70-2.59 (m, 2H), 2.07-1.66 (m, 6H), 1.55-1.25 (m, 6H), 1.11-0.96 (m, 2H).

Examples 381-384

Using the same process as in Example 378, the compounds of Examples 381-384 were synthesized. The compound structures and specific characterization data (LC-MS and $^1H$ NMR) were as follows:

| Ex | Structure | ¹H NMR | LC-MS (ESI) $[M + H]^+$ |
|---|---|---|---|
| 381 | 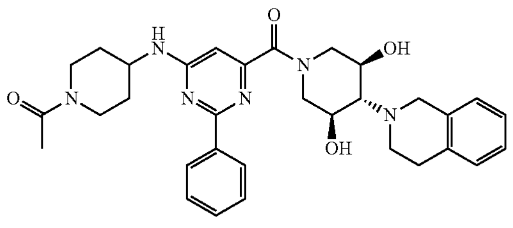 [SMILES: CC(=O)N1CCC(Nc2cc(C(=O)N3C[C@@H](O)[C@H](N4CCc5ccccc5C4)[C@@H](O)C3)nc(-c3ccccc3)n2)CC1] | (400 MHz, $CDCl_3$) δ 8.36-8.27 (m, 2H), 7.50-7.43 (m, 3H), 7.18-7.09 (m, 3H), 7.05-6.99 (m, 1H), 6.61 (s, 1H), 5.39 (s, 1H), 4.78-4.64 (m, 1H), 4.59-4.50 (m, 1H), 4.48-4.39 (m, 1H), 4.17-3.57 (m, 6H), 3.30-3.08 (m, 4H), 3.04-2.82 (m, 4H), 2.77-2.56 (m, 1H), 2.25-2.15 (m, 1H), 2.12 (s, 3H), 2.11-2.03 (m, 1H), 1.54-1.42 (m, 2H). | 571.4 |
| 382 | 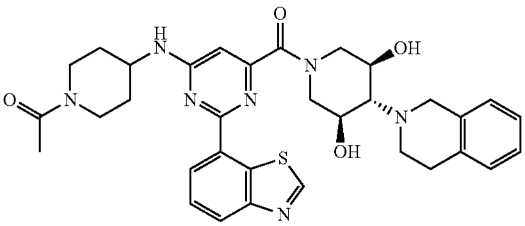 [SMILES: CC(=O)N1CCC(Nc2cc(C(=O)N3C[C@@H](O)[C@H](N4CCc5ccccc5C4)[C@@H](O)C3)nc(-c3cccc4ncsc34)n2)CC1] | (400 MHz, DMSO-$d_6$) δ 9.48 (s, 1H), 8.63 (d, J = 7.6 Hz, 1H), 8.25 (d, J = 7.9 Hz, 1H), 7.96 (d, J = 7.3 Hz, 1H), 7.71 (t, J = 7.8 Hz, 1H), 7.12-7.07 (m, 3H), 7.06-7.02 (m, 1H), 6.57 (s, 1H), 4.86 (d, J = 3.5 Hz, 1H), 4.69-4.62 (m, 1H), 4.60-4.30 (m, 3H), 4.10-3.96 (m, 2H), 3.94-3.81 (m, 2H), 3.76-3.61 (m, 2H), 3.41-3.33 (m, 1H), 3.13-3.02 (m, 2H), 3.01-2.89 (m, 2H), 2.86-2.76 (m, 2H), 2.69-2.61 (m, 1H), 2.46 (s, 1H), 2.18-2.06 (m, 2H), 2.05 (s, 3H), 1.57-1.45 (m, 1H), 1.43-1.32 (m, 1H). | 628.4 |
| 383 | 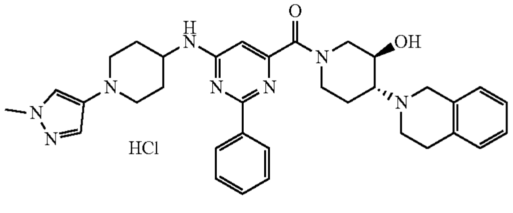 [SMILES: Cn1cc(N2CCC(Nc3cc(C(=O)N4CC[C@@H](N5CCc6ccccc6C5)[C@H](O)C4)nc(-c4ccccc4)n3)CC2)cn1 ; Cl] HCl | ¹H NMR (400 MHz, $(CD_3)_2SO$) δ 10.55-9.96 (m, 1H), 8.41-8.07 (m, 2H), 7.92-7.65 (m, 1H), 7.57-7.42 (m, 3H), 7.32-7.07 (m, 6H), 6.75-6.50 (m, 1H), 6.36-5.96 (m, 1H), 4.74-4.40 (m, 3H), 4.21-3.90 (m, 3H), 3.85-3.68 (m, 4H), 3.64-3.35 (m, 3H), 3.31-3.26 (m, 1H), 3.21-2.84 (m, 3H), 2.78-2.59 (m, 3H), 2.38-1.79 (m, 4H), 1.74-1.53 (m, 2H). | 593.2 |
| 384 | 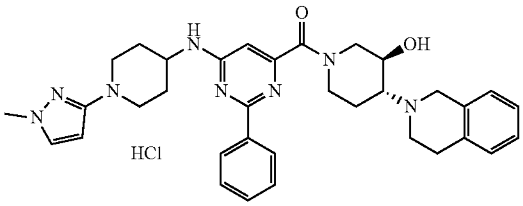 [SMILES: Cn1ccc(N2CCC(Nc3cc(C(=O)N4CC[C@@H](N5CCc6ccccc6C5)[C@H](O)C4)nc(-c4ccccc4)n3)CC2)n1 ; Cl] HCl | (400 MHz, $(CD_3)_2SO$) δ 10.34-9.93 (m, 1H), 8.46-8.24 (m, 2H), 7.82 (s, 1H), 7.57-7.39 (m, 4H), 7.35-7.14 (m, 4H), 6.73-6.52 (m, 1H), 6.39-5.92 (m, 1H), 5.72 (s, 1H), 4.74-4.40 (m, 3H), 4.27-3.91 (m, 3H), 3.87-3.71 (m, 1H), 3.68-3.63 (m, 5H), 3.40-2.98 (m, 5H), 2.96-2.80 (m, 2H), 2.79-2.63 (m, 1H), 2.24-1.97 (m, 3H), 1.93-1.77 (m, 1H), 1.68-1.53 (m, 2H). | 593.2 |

Example 385 and Example 386: Preparation of (E)-1-(4-((6-((3R,4R)-4-(3,4-dihydroisoquinoline-2(1H)-yl)-3-hydroxypiperidine-1-carbonyl)pyrimidine-4-yl)amino)piperidine-1-yl)-2-(methoxyimino)propane-1-one (compound of Example 385) and (Z)-1-(4-((6-((3R,4R)-4-(3,4-dihydroisoquinoline-2(1H)-yl)-3-hydroxypiperidine-1-carbonyl)pyrimidine-4-yl)amino)piperidine-1-yl)-2-(methoxyimino)propane-1-one (compound of Example 386)

Step 1: Preparation of (1-(2-oxopropanoyl)piperidine-4-yl)carbamic acid tert-butyl ester

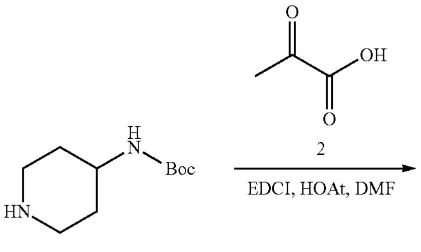

-continued

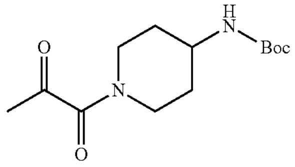

Piperidine-4-ylcarbamic acid tert-butyl ester (1 g, 5 mmol, 1 equiv.), EDCI (1.15 g, 6 mmol, 1.2 equiv.), and HOAt (0.815 g, 6 mmol, 1.2 equiv.) were dissolved in DMF (10 mL). 2-oxopropanoic acid (0.44 g, 5 mmol, 1.0 equiv.) was added. The reaction was performed at room temperature (20° C.) under stirring for 1 hour. After the completion of the reaction was detected with LC-MC, the resulting mixture was concentrated. Water was added (20 mL). The resulting mixture was extracted with ethyl acetate three times, each time 20 mL. The organic phases were combined and rotary dried to obtain a crude product, which was purified with a column chromatography (PE:EA=1:1) to produce the title compound (1.1 g, yield: 81.5%).

LC-MS (ESI) $[M+H]^+$=215.0.

Step 2: Preparation of (1-(2-(methoxyimino)propanoyl)piperidine-4-yl)carbamic acid tert-butyl ester

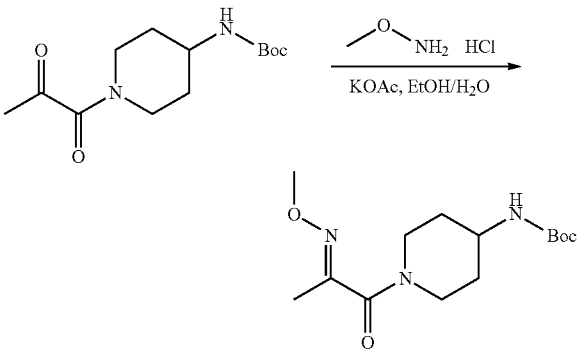

(1-(2-oxopropanoyl)piperidine-4-yl)carbamic acid tert-butyl ester (600 mg, 2.2 mmol, 1 equiv.), and methoxyamine hydrochloride (407.8 mg, 4.8 mmol, 2.2 equiv.) were dissolved in ethanol (6 mL) and water (1.5 mL). Potassium acetate (958 mg, 9.6 mmol, 4.4 equiv.) was added. The reaction was performed at room temperature 80° C. under stirring for 16 hours. After the completion of the reaction was detected with LC-MC, the resulting mixture was concentrated. Water (20 mL) was added. The resulting mixture was extracted with ethyl acetate three times, each time 20 mL. The organic phases were combined, and rotary dried to obtain a crude product, which was purified with a column chromatography to produce compounds (E)-(1-(2-(methoxyimino)propanoyl)piperidine-4-yl)carbamic acid tert-butyl ester (290 mg) and (Z)-(1-(2-(methoxyimino)propanoyl)piperidine-4-yl)carbamic acid tert-butyl ester (337 mg).

LC-MS (ESI) $[M+H]^+$=244.0.

Step 3: Preparation of 1-(4-aminopiperidine-1-yl)-2-(methoxyimino)propane-1-one

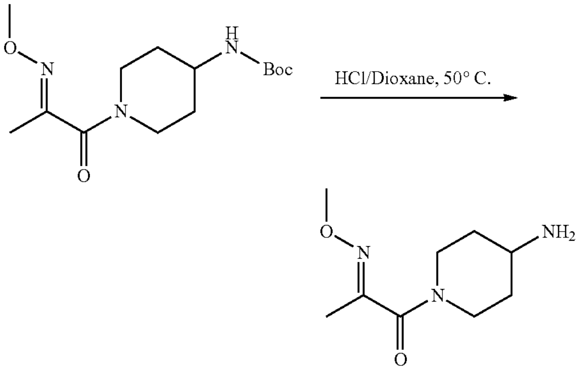

(E)-(1-(2-(methoxyimino)propanoyl)piperidine-4-yl)carbamic acid tert-butyl ester and (Z)-(1-(2-(methoxyimino) propanoyl)piperidine-4-yl)carbamic acid tert-butyl ester (600 mg, 2 mmol, 1 equiv.) were dissolved in 1,4-dioxane (5 mL). A solution of hydrochloric acid in 1,4-dioxane (2.5 mL, 10 mmol, 4M) was added. The reaction was performed at room temperature 50° C. under stirring for 1 hour. After the completion of the reaction was detected with LC-MC, the resulting mixture was concentrated, and rotary dried to obtain a crude product (584 mg), which was directly used in the next step.

LC-MS (ESI) $[M+H]^+$=200.2.

Step 4: Preparation of 6-((1-(2-(methoxyimino)propanoyl)piperidine-4-yl)amino)pyrimidine-4-carboxylic acid methyl ester

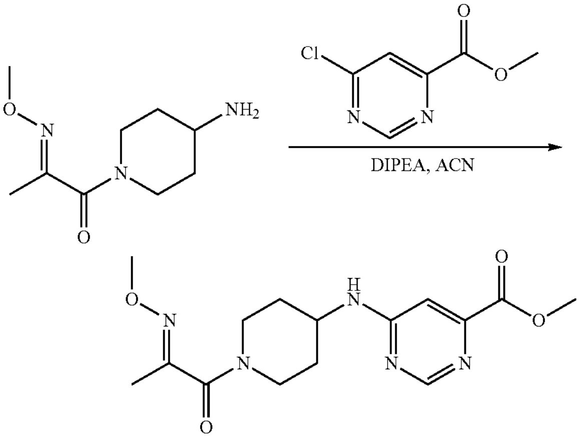

1-(4-aminopiperidine-1-yl)-2-(methoxyimino)propane-1-one (550 mg, 1.96 mmol, 1 equiv.), and 6-chloropyrimidine-4-carboxylic acid methyl ester (338 mg, 1.96 mmol, 1.0 equiv.) were dissolved in acetonitrile (6 mL). DIPEA (1.01 g, 7.84 mmol, 4.0 equiv.) was added. The reaction was performed at room temperature 90° C. under stirring for 2 hours. After the completion of the reaction was detected with LC-MC, the resulting mixture was concentrated. Water (20 mL) was added. The resulting mixture was extracted with ethyl acetate, each time 20 mL. The organic phases were combined, and rotary dried to obtain a crude product, which was purified with a column chromatography to produce the target compound (438 mg, yield: 66%).

LC-MS (ESI) $[M+H]^+$=336.2.

Step 5: Preparation of 6-((1-(2-(methoxyimino)propanoyl)piperidine-4-yl)amino)pyrimidine-4-carboxylic acid

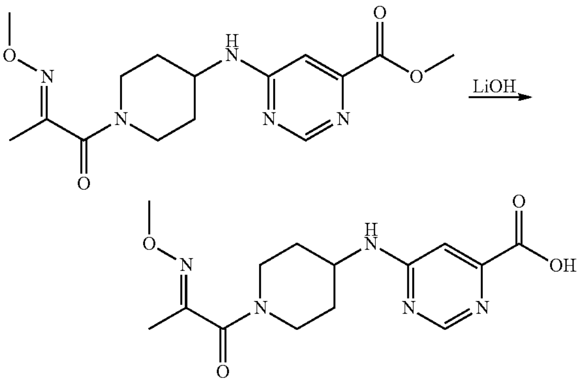

6-((1-(2-(methoxyimino)propanoyl)piperidine-4-yl)amino)pyrimidine-4-carboxylic acid methyl ester (470 mg, 1.4 mmol, 1 equiv.) was dissolved in THF (4 mL) and $H_2O$ (4 mL). Lithium hydroxide (2.8 mL, 2.8 mmol, 2.0 equiv., 2M) was added. The reaction was performed at room temperature 25° C. under stirring for 1 hour. After the completion of the reaction was detected with LC-MC, the reaction system was adjusted with 1M aqueous hydrochloric acid solution to pH=5-6, concentrated, and rotary dried to obtain a crude product (450 mg), which was directly used in the next step.

LC-MS (ESI) $[M+H]^+$=322.2.

Step 6: Preparation of (E)-1-(4-((6-((3R,4R)-4-(3,4-dihydroisoquinoline-2(1H)-yl)-3-hydroxypiperidine-1-carbonyl)pyrimidine-4-yl)amino)piperidine-1-yl)-2-(methoxyimino)propane-1-one (compound of Example 385) and (Z)-1-(4-((6-((3R,4R)-4-(3,4-dihydroisoquinoline-2(1H)-yl)-3-hydroxypiperidine-1-carbonyl)pyrimidine-4-yl)amino)piperidine-1-yl)-2-(methoxyimino)propane-1-one (compound of Example 386)

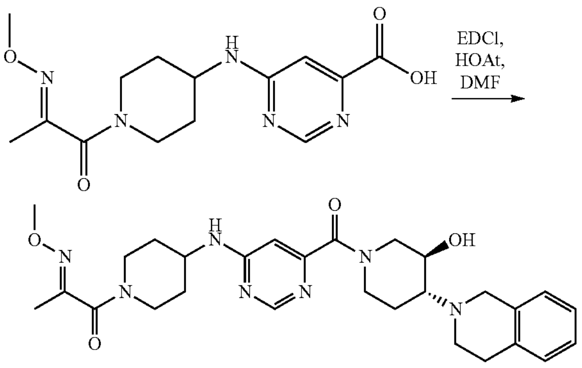

6-((1-(2-(methoxyimino)propanoyl)piperidine-4-yl)amino)pyrimidine-4-carboxylic acid (420 mg, 1.3 mmol, 1 equiv.), EDCI (325 mg, 1.7 mmol, 1.3 equiv.), and HOAt (231 mg, 1.7 mmol, 1.3 equiv.) were dissolved in DMF (5 mL). (3R,4R)-4-(3,4-dihydroisoquinoline-2(1H)-yl)piperidine-3-ol (334 mg, 1.4 mmol, 1.1 equiv.) was added. The reaction was performed at room temperature (20° C.) under stirring for 1 hour. After the completion of the reaction was detected with LC-MC, the reaction system was concentrated to obtain a crude product, which was separated and purified with reverse phase HPLC (C18, 10 mmol/L aqueous $NH_4HCO_3$ solution/acetonitrile) to produce two compounds:

Title compound (compound of Example 385)(184 mg). LC-MS (ESI) $[M+H]^+$=536.0; $^1H$ NMR (400 MHz, $(CD_3)_2SO$) δ 8.45-8.43 (m, 1H), 7.69-7.63 (m, 1H), 7.09-7.02 (m, 4H), 6.53 (s, 1H), 4.81-4.72 (m, 1H), 4.49-4.31 (m, 1H), 4.18-4.13 (m, 2H), 3.85-3.58 (m, 7H), 3.47-3.40 (m, 1H), 3.20-3.14 (m, 1H), 3.02-2.55 (m, 8H), 1.95-1.93 (m, 5H), 1.85-1.71 (m, 1H), 1.52-1.30 (m, 3H).

Title compound (compound of Example 386)(301.72 mg). LC-MS (ESI) $[M+H]^+$=536.0; $^1H$ NMR (400 MHz, $(CD_3)_2SO$) δ 8.45-8.43 (m, 1H), 7.68-7.64 (m, 1H), 7.09-7.02 (m, 4H), 6.52 (s, 1H), 4.81-4.72 (m, 1H), 4.49-4.31 (m, 1H), 4.25- 4.17 (m, 2H), 3.88-3.59 (m, 8H), 3.25-3.19 (m, 1H), 3.02-2.76 (m, 6.5H), 2.67-2.55 (m, 1.5H), 1.93-1.93 (m, 5H), 1.84-1.71 (m, 1H), 1.51-1.32 (m, 3H).

Example 387 and Example 388: Preparation of (E)-1-(6-((6-((3R,4R)-4-(3,4-dihydroisoquinoline-2(1H)-yl)-3-hydroxypiperidine-1-carbonyl)pyrimidine-4-yl)amino)-3-azabicyclo[3.1.1]heptan-3-yl)-2-(methoxyimino)propane-1-one (the compound of Example 387) and (Z)-1-(6-((6-((3R,4R)-4-(3,4-dihydroisoquinoline-2(1H)-yl)-3-hydroxypiperidine-1-carbonyl)pyrimidine-4-yl)amino)-3-azabicyclo[3.1.1]heptan-3-yl)-2-(methoxyimino)propane-1-one (the compound of Example 388)

Step 1: Preparation of (3-(2-oxopropanoyl)-3-azabicyclo[3.1.1]heptan-6-yl)carbamic acid tert-butyl ester

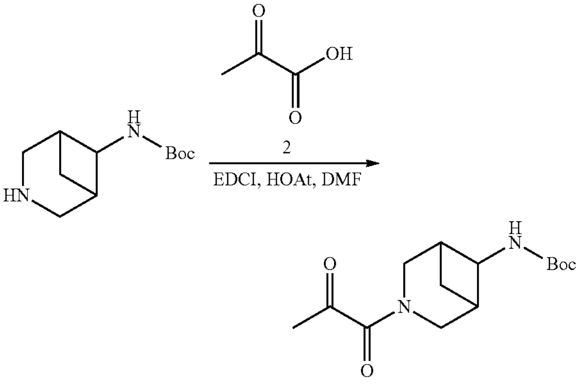

(3-azabicyclo[3.1.1]heptan-6-yl)carbamic acid tert-butyl ester (460 mg, 2.17 mmol, 1 equiv.), EDCI (498 mg, 2.6 mmol, 1.2 equiv.) and HOAt (354 mg, 2.6 mmol, 1.2 equiv.) were dissolved in DMF (5 mL). 2-oxopropanoic acid (209.9 mg, 2.38 mmol, 1.1 equiv.) was added. The reaction was performed at room temperature (20° C.) under stirring for 1 hour. After the completion of the reaction was detected with LC-MC, the resulting mixture was concentrated. Water (20 mL) was added. The resulting mixture was extracted with ethyl acetate, each time 20 mL. The organic phases were combined, and rotary dried to obtain a crude product, which was purified with a column chromatography (PE:EA=1:1) to produce the title compound (412 mg, yield: 67%).

LC-MS (ESI) $[M+H]^+$=227.0.

Step 2: Preparation of (3-(2-(methoxyimino)propanoyl)-3-azabicyclo[3.1.1]heptan-6-yl)carbamic acid tert-butyl ester

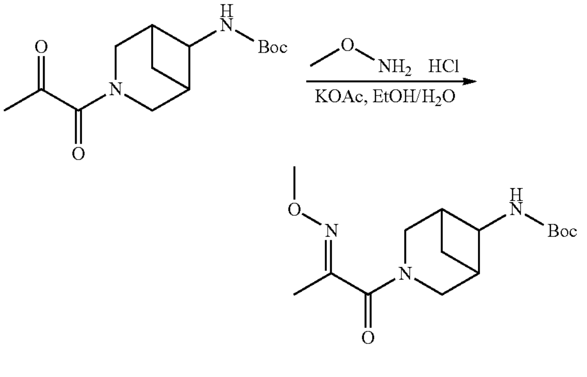

(3-(2-oxopropanoyl)-3-azabicyclo[3.1.1]heptan-6-yl)carbamic acid tert-butyl ester (400 mg, 1.4 mmol, 1 equiv.), and methoxyamine hydrochloride (260 mg, 3.1 mmol, 2.2 equiv.) were dissolved in ethanol (4 mL) and water (1 mL). Potassium acetate (611.8 mg, 6.2 mmol, 4.4 equiv.) was added. The reaction was performed at room temperature 80° C. under stirring for 16 hours. After the completion of the reaction was detected with LC-MC, the resulting mixture was concentrated. Water (20 mL) was added. The resulting mixture was extracted with ethyl acetate, each time 20 mL. The organic phases were combined, and rotary dried to obtain a crude product, which was purified with a column chromatography to produce the target compound (440 mg).

LC-MS (ESI) $[M+H]^+$=256.1.

Step 3: Preparation of 1-6-amino-3-azabicyclo[3.1.1]heptan-3-yl)-2-(methoxyimino)propane-1-one

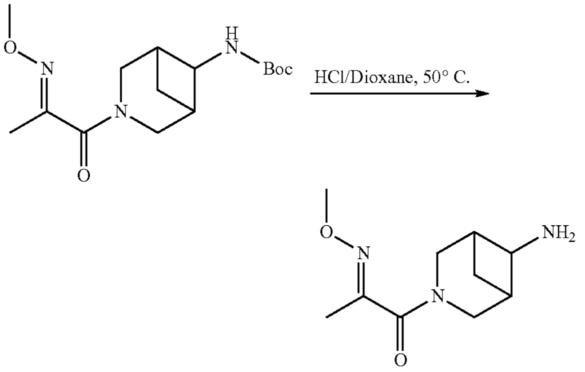

(3-(2-(methoxyimino)propanoyl)-3-azabicyclo[3.1.1]heptan-6-yl)carbamic acid tert-butyl ester (400 mg, 1.28 mmol, 1 equiv.) was dissolved in 1,4-dioxane (5 mL). A solution of hydrochloric acid in 1,4-dioxane (2.5 mL, 10 mmol, 4M) was added. The reaction was performed at room temperature 50° C. under stirring for 1 hour. After the completion of the reaction was detected with LC-MC, the resulting mixture was concentrated, and rotary dried to obtain a crude product (360 mg), which was directly used in the next step.

LC-MS (ESI) $[M+H]^+$=212.0.

Step 4: Preparation of 6-((3-(2-(methoxyimino)propanoyl)-3-azabicyclo[3.1.1]heptan-6-yl)amino)pyrimidine-4-carboxylic acid methyl ester

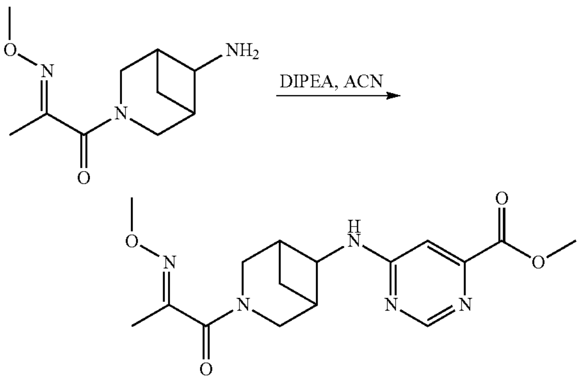

1-(6-amino-3-azabicyclo[3.1.1]heptan-3-yl)-2-(methoxyimino)propane-1-one (320 mg, 1.5 mmol, 1 equiv.), and 6-chloropyrimidine-4-carboxylic acid methyl ester (287 mg, 1.6 mmol, 1.1 equiv.) were dissolved in acetonitrile (5 mL). DIPEA (783 mg, 6.0 mmol, 4.0 equiv.) was added. The reaction was performed at room temperature 90° C. under stirring for 2 hours. After the completion of the reaction was detected with LC-MC, the resulting mixture was concentrated. Water (20 mL) was added. The resulting mixture was extracted with ethyl acetate, each time 20 mL. The organic phases were combined, and rotary dried to obtain a crude product, which was purified with a column chromatography to produce the target compound (266 mg, yield: 51%).

LC-MS (ESI) $[M+H]^+$=348.2.

Step 5: Preparation of 6-((3-(2-(methoxyimino)propanoyl)-3-azabicyclo[3.1.1]heptan-6-yl)amino)pyrimidine-4-carboxylic acid

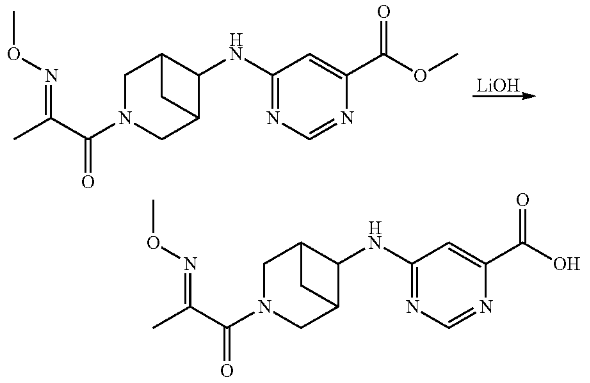

6-((3-(2-(methoxyimino)propanoyl)-3-azabicyclo[3.1.1]heptan-6-yl)amino)pyrimidine-4-carboxylic acid methyl ester (240 mg, 0.69 mmol, 1 equiv.) was dissolved in THF (4 mL) and $H_2O$ (4 mL). Lithium hydroxide (0.34 mL, 1.38 mmol, 2.0 equiv., 2M) was added. The reaction was performed at room temperature 25° C. under stirring for 1 hour. After the completion of the reaction was detected with LC-MC, the reaction system was adjusted with 1M aqueous hydrochloric acid solution to pH=5~6, concentrated, and rotary dried to obtain a crude product (250 mg), which was directly used in the next step.

LC-MS (ESI) $[M+H]^+$=334.20.

Step 6: Preparation of (E)-1-(6-((6-((3R,4R)-4-(3,4-dihydroisoquinoline-2(1H)-yl)-3-hydroxypiperidine-1-carbonyl)pyrimidine-4-yl)amino)-3-azabicyclo[3.1.1]heptan-3-yl)-2-(methoxyimino)propane-1-one (compound of Example 387) and (Z)-1-(6-((6-((3R,4R)-4-(3,4-dihydroisoquinoline-2(1H)-yl)-3-hydroxypiperidine-1-carbonyl)pyrimidine-4-yl)amino)-3-azabicyclo[3.1.1]heptan-3-yl)-2-(methoxyimino)propane-1-one (compound of Example 388)

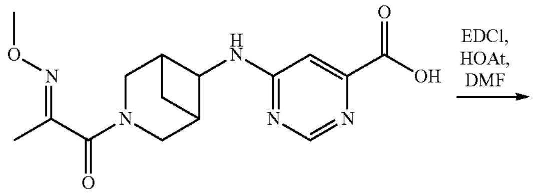

-continued

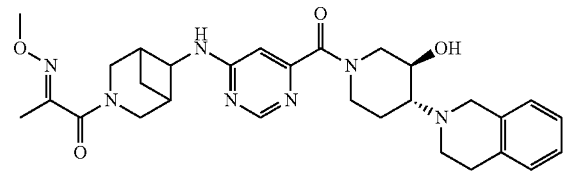

6-((3-(2-(methoxyimino)propanoyl)-3-azabicyclo[3.1.1]heptan-6-yl)amino)pyrimidine-4-carboxylic acid (220 mg, 0.66 mmol, 1 equiv.), EDCI (164.5 mg, 0.86 mmol, 1.3 equiv.) and HOAt (117 mg, 0.86 mmol, 1.3 equiv.) were dissolved in DMF (3 mL). (3R,4R)-4-(3,4-dihydroisoquinoline-2(1H)-yl)piperidine-3-ol (169 mg, 0.72 mmol, 1.1 equiv.) was added. The reaction was performed at room temperature (20° C.) under stirring for 1 hour. After the completion of the reaction was detected with LC-MC, the reaction system was concentrated to obtain a crude product, which was separated and purified with reverse phase HPLC (C18, 10 mmol/L aqueous $NH_4HCO_3$ solution/acetonitrile) to produce two compounds:

Title compound (compound of Example 387)(63.15 mg). LC-MS (ESI) $[M+H]^+$=548.0; $^1$H NMR (400 MHz, $(CD_3)_2SO$) δ 8.47-8.45 (m, 1H), 7.63-7.59 (m, 1H), 7.09-7.01 (m, 4H), 6.71 (s, 1H), 4.82-4.70 (m, 1H), 4.48-4.07 (m, 2H), 3.85-3.70 (m, 5H), 3.62-3.40 (m, 6H), 3.03-2.85 (m, 2H), 2.81-2.51 (m, 7H), 1.93-1.93 (m, 4H), 1.85-1.70 (m, 1H), 1.53-1.32 (m, 2H).

Title compound (compound of Example 388)(206.44 mg). LC-MS (ESI) $[M+H]^+$=548.0; $^1$H NMR (400 MHz, $(CD_3)_2SO$) δ 8.47-8.45 (m, 1H), 7.67 (s, 1H), 7.09-7.02 (m, 4H), 6.75 (s, 1H), 4.82-4.71 (m, 1H), 4.49-4.26 (m, 2H), 3.85-3.79 (m, 6H), 3.75-3.57 (m, 4H), 3.53-3.50 (m, 1H), 3.03-2.86 (m, 2H), 2.82-2.59 (m, 7H), 1.94-1.91 (m, 4H), 1.85-1.71 (m, 1H), 1.51-1.45 (m, 1H), 1.40-1.37 (m, 1H).

Example 389: Preparation of 1-(4-((4-benzyl-5-((3R,4R)-4-(3,4-dihydroisoquinoline-2(1H)-yl)-3-hydroxypiperidine-1-carbonyl)thiazole-2-yl)amino)piperidine-1-yl)ethane-1-one

Step 1: Preparation of N-((1-acetylpiperidine-4-yl)carbamothioyl)benzamide

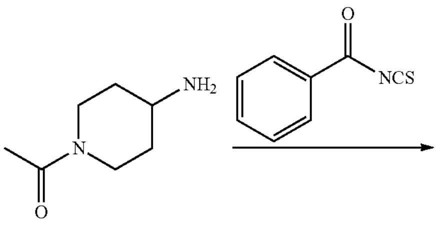

-continued

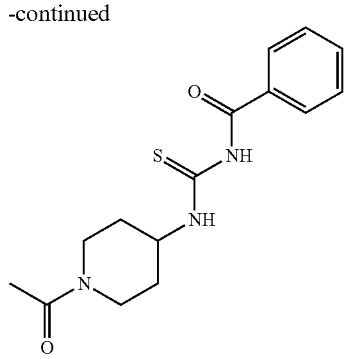

1-(4-aminopiperidine-1-yl)ethane-1-one (100 mg, 0.56 mmol, 1.0 equiv.) and benzoyl isothiocyanate (91 mg, 0.56 mmol, 1.0 equiv.) were added to dichloromethane (2.6 mL). The mixture was stirred under nitrogen gas at 16° C. for 48 hours. TLC detected the reaction of raw materials was completed. To the reaction system was added water (15 mL). The resulting mixture was extracted ethyl acetate three times (3×15 mL). The organic phases were combined, washed with saturated sodium chloride solution (20 mL) once, dried over anhydrous sodium sulfate, filtered by suction, concentrated to remove the solvent, and purified with column chromatography (DCM:MeOH=98:2) to produce the target product (70 mg, yield: 32.6%).

LC-MS (ESI) $[M+H]^+$=306.2; $^1$H NMR (400 MHz, DMSO-$d_6$) δ 11.35 (s, 1H), 10.91 (d, J=7.6 Hz, 1H), 7.95-7.89 (m, 2H), 7.64 (t, J=7.4 Hz, 1H), 7.51 (t, J=7.7 Hz, 2H), 4.49-4.35 (m, 1H), 4.23-4.12 (m, 1H), 3.82-3.70 (m, 1H), 3.27-3.16 (m, 1H), 2.91-2.79 (m, 1H), 2.10-2.03 (m, 1H), 2.02 (s, 3H), 2.01-1.95 (m, 1H), 1.65-1.51 (m, 1H), 1.49-1.35 (m, 1H).

Step 2: Preparation of 1-(1-acetylpiperidine-4-yl)thiourea

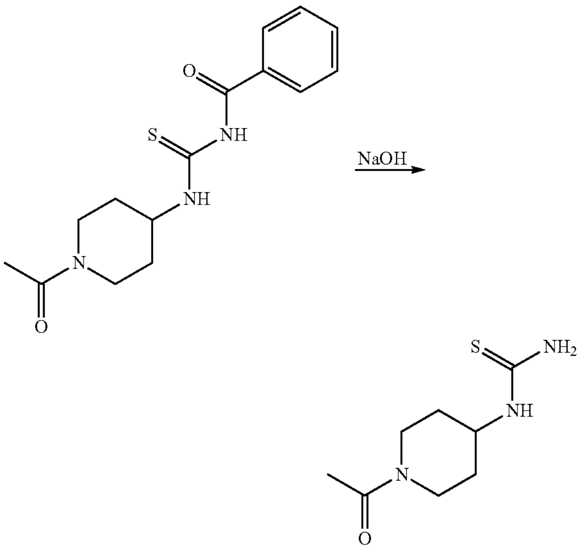

N-((1-acetylpiperidine-4-yl)carbamothioyl)benzamide (402 mg, 1.32 mmol, 1.0 equiv.) was added to methanol (6.6 mL). Sodium hydroxide (63 mg, 1.58 mmol, 1.2 equiv. 1.5 M) solution was added. The mixture was stirred at 80° C. for 2 hours. TLC detected the reaction of raw materials was completed. The reaction system was concentrated to remove the solvent to obtain a crude product of the title compound (410 mg), which was directly used in the next reaction.

LC-MS (ESI) $[M+H]^+$=202.1.

Step 3: Preparation of 2-chloro-3-oxo-4-phenylbutanoic acid methyl ester

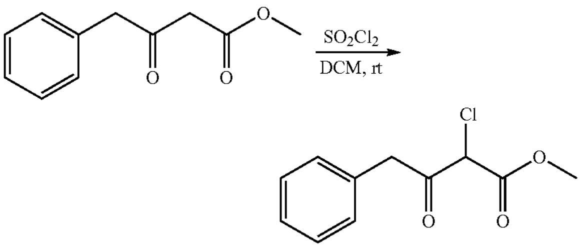

3-oxo-4-phenylbutanoic acid methyl ester (100 mg, 0.521 mmol, 1.0 equiv.) was added to dichloromethane (2.6 mL). Then a mixed solution of sulfonyl chloride (85 mg, 0.625 mmol, 1.2 equiv.)/dichloromethane (1.0 mL) was added dropwise. The mixture was stirred at 16° C. for 2 hours. TLC detected the reaction of raw materials was completed. To the reaction system was added water (15 mL). The mixture was extracted with ethyl acetate three times (3×15 mL). The organic phases were combined, washed with saturated sodium chloride solution (20 mL) once, dried over anhydrous sodium sulfate, filtered by suction, concentrated to remove the solvent, and purified with column chromatography (PE:EA=90:10) to produce the target product (100 mg, yield: 84.8%).

$^1$H NMR (400 MHz, DMSO-$d_6$) δ 7.36-7.30 (m, 2H), 7.29-7.26 (m, 1H), 7.23-7.17 (m, 2H), 5.76 (s, 1H), 4.07 (s, 2H), 3.75 (s, 3H).

Step 4: Preparation of 2-((1-acetylpiperidine-4-yl) amino)-4-benzylthiazole-5-carboxylic acid methyl ester

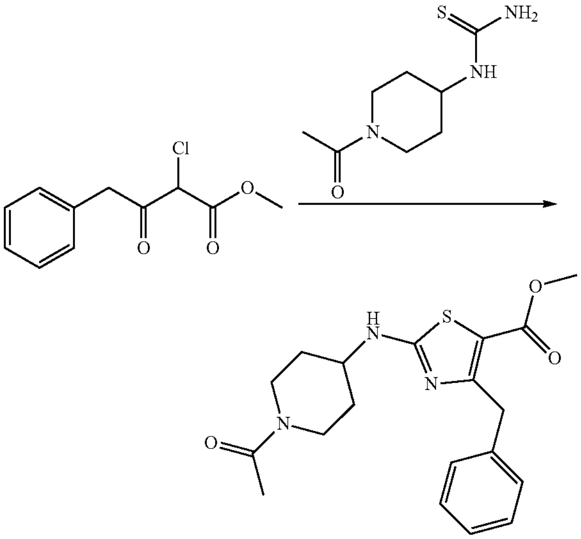

2-chloro-3-oxo-4-phenylbutanoic acid methyl ester (200 mg, 1.0 mmol, 1.0 equiv.) and 1-(1-acetylpiperidine-4-yl) thiourea (226 mg, 1.0 mmol, 1.0 equiv.) were added to ethanol (5.0 mL). The mixture was stirred under nitrogen gas at 85° C. for 1 hour. TLC detected the reaction of raw materials was completed. To the reaction system was added water (15 mL). The mixture was extracted with ethyl acetate three times (3×15 mL). The organic phases were combined, washed with saturated sodium chloride solution (20 mL) once, dried over anhydrous sodium sulfate, filtered by suction, concentrated to remove the solvent, and purified with column chromatography (DCM:MeOH=98:2) to produce the target product (140 mg, yield: 37.5%).

LC-MS (ESI) $[M+H]^+$=374.2; $^1$H NMR (400 MHz, DMSO-$d_6$) δ 8.56 (d, J=7.4 Hz, 1H), 7.33-7.28 (m, 4H), 7.26-7.20 (m, 1H), 4.27 (s, 2H), 4.25-4.18 (m, 1H), 3.85-3.79 (m, 1H), 3.77 (s, 3H), 3.75-3.63 (m, 1H), 3.26-3.20 (m, 1H), 2.91-2.80 (m, 1H), 2.04 (s, 3H), 2.02-1.89 (m, 2H), 1.49-1.37 (m, 1H), 1.37-1.26 (m, 1H).

Step 5: Preparation of 2-((1-acetylpiperidine-4-yl) amino)-4-benzylthiazole-5-carboxylic acid

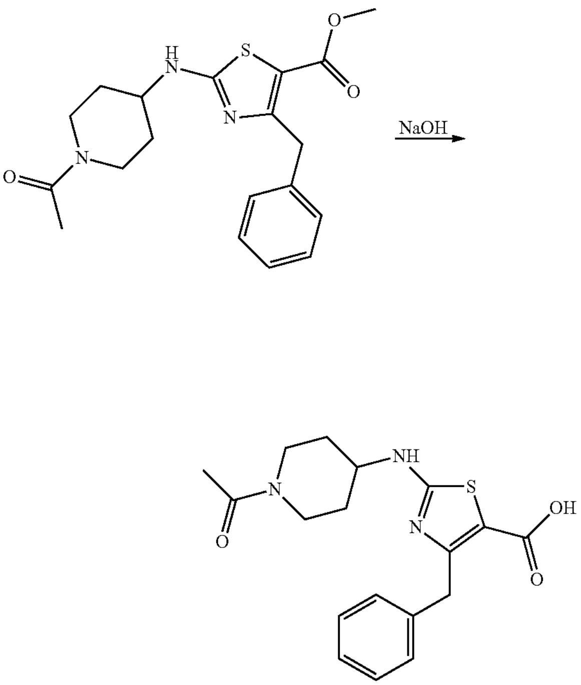

To a solution of 2-((1-acetylpiperidine-4-yl)amino)-4-benzylthiazole-5-carboxylic acid methyl ester (22 mg, 0.059 mmol, 1.0 equiv.) in methanol (0.3 mL) was added NaOH solution (9.5 mg, 0.236 mmol, 4.0 equiv., 1 M). The mixture was stirred at 16° C. for 16 hours. TLC detected the complete reaction of raw materials. The reaction system was adjusted with diluted hydrochloric acid solution to pH=3. Water (15 mL) was added to the reaction system. The resulting mixture was extracted with ethyl acetate three times (3×15 mL). The organic phases were combined, washed with saturated sodium chloride solution (20 mL) once, dried over anhydrous sodium sulfate, filtered by suction, and concentrated to remove the solvent to produce the title compound (20 mg, crude), which was directly used in the next reaction.

Step 6: Preparation of 1-(4-((4-benzyl-5-((3R,4R)-4-(3,4-dihydroisoquinoline-2(1H)-yl)-3-hydroxypiperidine-1-carbonyl)thiazole-2-yl)amino)piperidine-1-yl)ethane-1-one

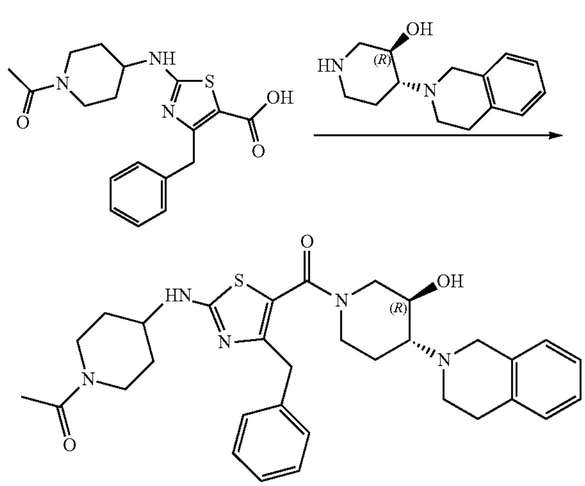

2-((1-acetylpiperidine-4-yl)amino)-4-benzylthiazole-5-carboxylic acid (20 mg, 0.056 mmol, 1.0 equiv.), (3R,4R)-3-(3,4-dihydroisoquinoline-2(1H)-yl)piperidine-4-ol (13 mg, 0.056 mmol, 1.0 equiv.) and O-(7-azabenzotriazol-1-yl)-N,N,N',N'-tetramethyluronium hexafluorophosphate (32 mg, 0.084 mmol, 1.5 equiv.) were added to N,N-dimethyl formamide (0.2 mL). N,N-diisopropylethylamine (22 mg, 0.168 mmol, 3.0 equiv.) was added. The mixture was stirred at 16° C. for 0.5 hours. TLC detected the reaction of raw materials was completed. To the reaction system was added water (15 mL). The resulting mixture was extracted with ethyl acetate three times (3×15 mL). The organic phases were combined, washed with saturated sodium chloride solution (20 mL) once, dried over anhydrous sodium sulfate, filtered by suction, and concentrated to remove the solvent to obtain a crude product, which was separated and purified with Prep-HPLC (C18, 10 mmol/L aqueous solution/acetonitrile) to produce the target product (2.06 mg, yield: 6.4%).

LC-MS (ESI) $[M+H]^+$=574.5; $^1H$ NMR (400 MHz, $CD_3OD$) δ 7.31-7.14 (m, 5H), 7.12-7.05 (m, 3H), 7.04-7.00 (m, 1H), 4.39-4.32 (m, 1H), 4.32-4.10 (m, 2H), 3.95 (s, 2H), 3.92-3.74 (m, 4H), 3.53-3.45 (m, 1H), 3.28-3.21 (m, 1H), 2.95-2.84 (m, 5H), 2.80-2.62 (m, 3H), 2.17-2.11 (m, 1H), 2.10 (s, 3H), 2.07-1.99 (m, 1H), 1.88-1.78 (m, 1H), 1.54-1.29 (m, 3H).

Example 390: Preparation of (4-bromophenyl)((3R,4R)-4-(3,4-dihydroisoquinoline-2(1H)-yl)-3-hydroxypiperidine-1-yl)methanone

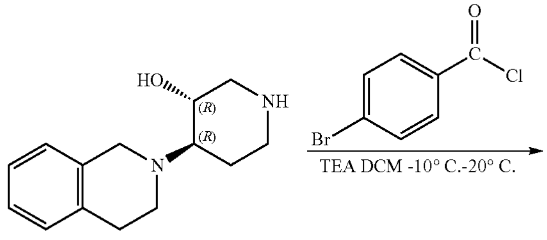

-continued

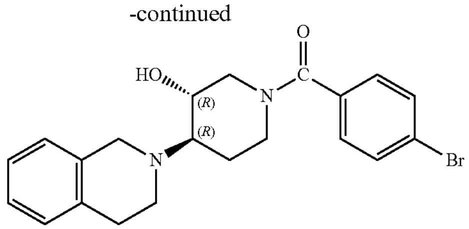

(3R,4R)-4-(3,4-dihydroisoquinoline-2(1H)-yl)piperidine-3-ol (500 mg, 2.152 mmol, 1.0 equiv.) was dissolved in dichloromethane (20 mL). Triethylamine (330 mg, 3.229 mmol, 1.5 equiv.) was added. The mixture was cooled down to about −10° C. in an ice-salt bath. Then a solution of para-bromobenzoyl chloride (520 mg, 2.368 mmol, 1.1 equiv.) in dichloromethane (5 mL) was slowly added to the reaction solution. After the completion of the addition, the reaction mixture was warmed up to room temperature (20° C.) and stirred for 0.5 hours. LC-MS detected raw materials disappeared. The reaction solution was quenched with water, and then extracted with dichloromethane. The organic phases were combined, then washed with saturated sodium chloride, dried over anhydrous sodium sulfate, and filtered. The filtrate was concentrated to produce a crude product, which was separated and purified with reverse phase HPLC (C18, aqueous $NH_4HCO_3$ solution/acetonitrile) to produce the title compound (697.22 mg, yield: 77.9%).

LC-MS (ESI) $[M+H]^+$=416.0; $^1H$ NMR (400 MHz, $(CD_3)_2SO$) δ 7.58-7.49 (m, 2H), 7.34-7.28 (m, 2H), 7.19-7.09 (m, 3H), 7.07-6.98 (m, 1H), 5.20-4.73 (m, 1H), 4.18-3.80 (m, 2H), 3.78-3.39 (m, 3H), 3.17-3.01 (m, 1H), 2.99-2.56 (m, 6H), 2.05-1.35 (m, 2H).

Example 391: Preparation of ((3R,4R)-4-(3,4-dihydroisoquinoline-2(1H)-yl)-3-hydroxypiperidine-1-yl)(2-isobutoxy-6-((1-(thiazole-2-yl)piperidine-4-yl)amino)pyrimidine-4-yl)methanone hydrochloride Step 1: Preparation of ((3R,4R)-4-(3,4-dihydroisoquinoline-2(1H)-yl)-3-hydroxypiperidine-1-yl)(2-isobutoxy-6-((1-(thiazole-2-yl)piperidine-4-yl)amino)pyrimidine-4-yl)methanone

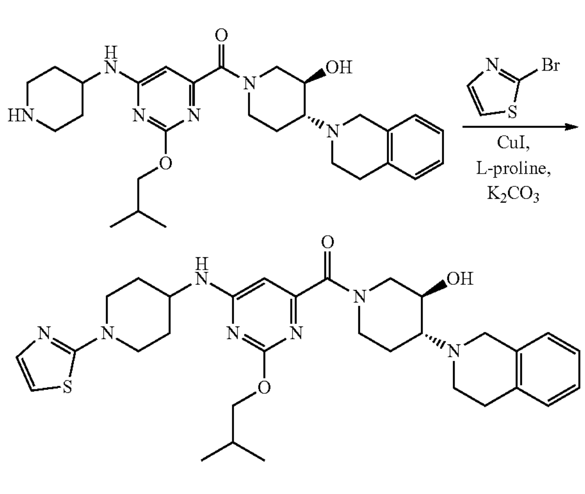

((3R,4R)-4-(3,4-dihydroisoquinoline-2(1H)-yl)-3-hydroxypiperidine-1-yl)(2-isobutoxy-6-(piperidine-4- ylamino)pyrimidine-4-yl)methanone (1 g, 1.97 mmol, 1.0 equiv.), 2-bromothiazole (387 mg, 2.36 mmol, 1.2 equiv.), CuI (37.44 mg, 0.2 mmol, 0.1 equiv.), L-proline (45.27 mg, 0.4 mmol, 0.2 equiv.) and $K_2CO_3$ (543 mg, 3.93 mmol, 2.0 equiv.) were dissolved in DMSO (10 mL). The reaction was performed at 100° C. for 16 hours. The reaction solution was quenched with saturated aqueous sodium bicarbonate solution, and extracted with ethyl acetate. The organic phase was concentrated, and the solvent was removed by rotary drying to obtain a crude product, which was purified with prep-HPLC (C18, 10 mmol/L aqueous $NH_{40}H$ solution/acetonitrile) to produce the target compound (310 mg, yield: 26.6%).

LC-MS (ESI) $[M+H]^+$=592.2.

Step 2: Preparation of ((3R,4R)-4-(3,4-dihydroisoquinoline-2(1H)-yl)-3-hydroxypiperidine-1-yl)(2-isobutoxy-6-((1-(thiazole-2-yl)piperidine-4-yl)amino)pyrimidine-4-yl)methanone hydrochloride

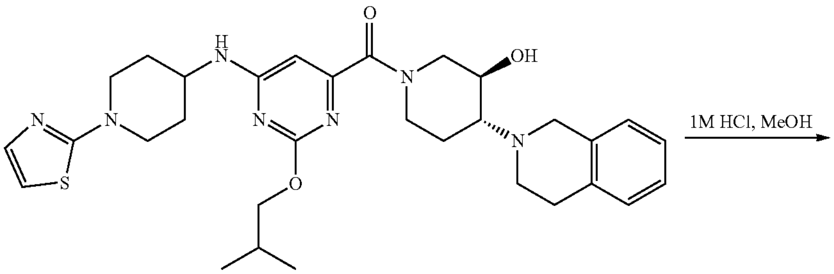

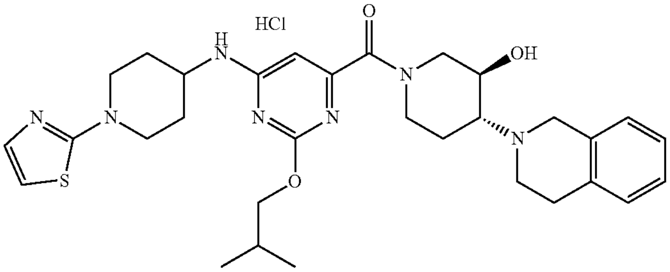

((3R,4R)-4-(3,4-dihydroisoquinoline-2(1H)-yl)-3-hydroxypiperidine-1-yl)(2-isobutoxy-6-((1-(thiazole-2-yl)piperidine-4-yl)amino)pyrimidine-4-yl)methanone (310 mg, 0.524 mmol, 1.0 equiv.) and hydrochloric acid (1 M)(0.55 mL, 0.55 mmol, 1.05 equiv.) were dissolved in MeOH (10 mL). The reaction was performed at 20° C. for 0.5 hours. The reaction solution was concentrated to produce the target compound (310.18 mg, yield: 95%).

LC-MS (ESI) $[M+H]^+$=592.2; $^1H$ NMR (400 MHz, $(CD_3)_2SO$) δ 10.56-10.37 (m, 1H), 8.18 (s, 1H), 7.28-7.18 (m, 5H), 6.89-6.88 (m, 1H), 6.47-6.09 (m, 2H), 4.74-4.41 (m, 3H), 4.13 (s, 1H), 4.03-3.89 (m, 6H), 3.78-3.55 (m, 3H), 3.35-3.26 (m, 3H), 3.14-2.98 (m, 2H), 2.86-2.65 (m, 1H), 2.26-2.15 (m, 1H), 2.03-1.98 (m, 3H), 1.84-1.75 (m, 1H), 1.62-1.50 (m, 2H), 1.61-1.53 (m, 6H).

Example 392: Preparation of ((3R,4R)-4-(3,4-dihydroisoquinoline-2(1H)-yl)-3-hydroxypiperidine-1-yl)(2-methoxy-6-((1-(4-methylbenzoyl)piperidine-4-yl)amino)pyrimidine-4-yl)methanone hydrochloride Step 1: Preparation of 6-((1-(tert-butoxycarbonyl)piperidine-4-yl)amino)-2-methoxypyrimidine-4-carboxylic acid

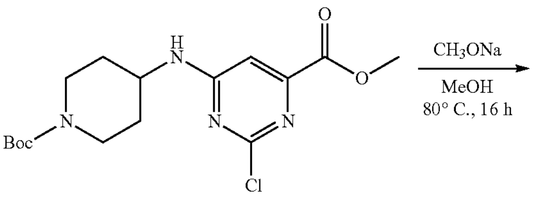

-continued

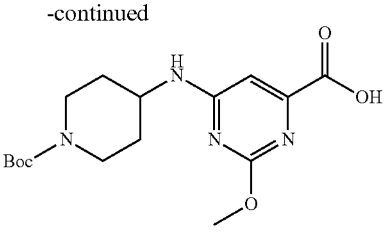

6-((1-(tert-butoxycarbonyl)piperidine-4-yl)amino)-2-chloropyrimidine-4-carboxylic acid methyl ester (2.0 g, 5.4 mmol, 1.0 equiv.) and sodium methoxide (1.16 g, 21.6 mmol, 4.0 equiv.) were dissolved in methanol (20 mL). The reaction was performed at 80° C. under stirring for 16 hours. The completion of the reaction was monitored with LC-MS. The reaction solution was adjusted with diluted hydrochloric acid to pH=5. The solvent was removed by rotary drying.

The resulting crude product was dissolved in methanol, and filtered. The filtrate was rotary dried to produce a crude product of the title compound (2.5 g), which was directly used in the next reaction.

LC-MS (ESI) $[M+H]^+$=353.2.

Step 2: Preparation of 4-((6-((3R,4R)-4-(3,4-dihydroisoquinoline-2(1H)-yl)-3-hydroxypiperidine-1-carbonyl)-2-methoxypyrimidine-4-yl)amino)piperidine-1-carboxylic acid tert-butyl ester

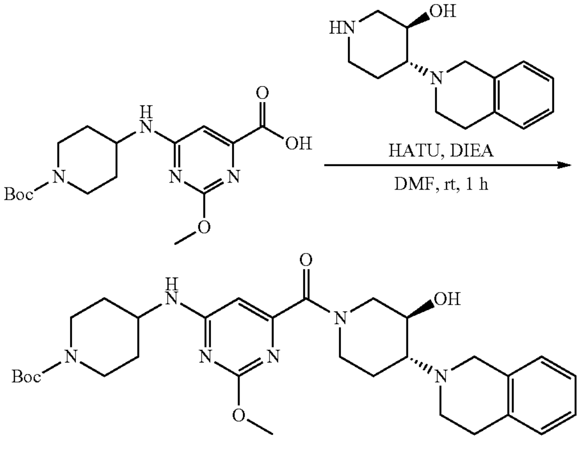

6-((1-(tert-butoxycarbonyl)piperidine-4-yl)amino)-2-methoxypyrimidine-4-carboxylic acid (2.2 g, 6.77 mmol, 1.0 equiv.), (3R,4R)-4-(3,4-dihydroisoquinoline-2(1H)-yl)piperidine-3-ol (1.7 g, 7.45 mmol, 1.1 equiv.), HATU (3.86 g, 10.1 mmol, 1.5 equiv.) and DIPEA (2.62 g, 20.3 mmol, 3.0 equiv.) were dissolved in DMF (20 mL). The reaction solution was stirred at 25° C. for 1 hour. LC-MS indicated the completion of the reaction. The reaction solution was quenched with water, and then extracted with ethyl acetate. The organic phases were combined, dried over anhydrous sodium sulfate, filtered, and concentrated to obtain a crude product, which was purified with flash column chromatography to produce the title compound (3.0 g, yield: 84%).

LC-MS (ESI) $[M+H]^+$=567.2.

Step 3: Preparation of ((3R,4R)-4-(3,4-dihydroisoquinoline-2(1H)-yl)-3-hydroxypiperidine-1-yl)(2-methoxy-6-(piperidine-4-ylamino)pyrimidine-4-yl)methanone

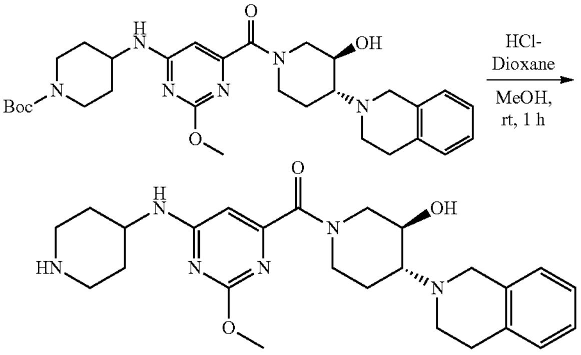

4-((6-((3R,4R)-4-(3,4-dihydroisoquinoline-2(1H)-yl)-3-hydroxypiperidine-1-carbonyl)-2-methoxypyrimidine-4-yl)amino)piperidine-1-carboxylic acid tert-butyl ester (2.5 g, 4.41 mmol, 1.0 equiv.) was dissolved in methanol (10 mL). HCl/1,4-dioxane (5 mL) was added. The reaction was performed at 20° C. under stirring for 1 hour. The completion of the reaction was monitored with LC-MS. The solvent was removed by rotary drying to produce a crude product of the title compound (2.2 g).

LC-MS (ESI) $[M+H]^+$=467.3.

Step 4: Preparation of ((3R,4R)-4-(3,4-dihydroisoquinoline-2(1H)-yl)-3-hydroxypiperidine-1-yl)(2-methoxy-6-((1-(4-methylbenzoyl)piperidine-4-yl)amino)pyrimidine-4-yl)methanone

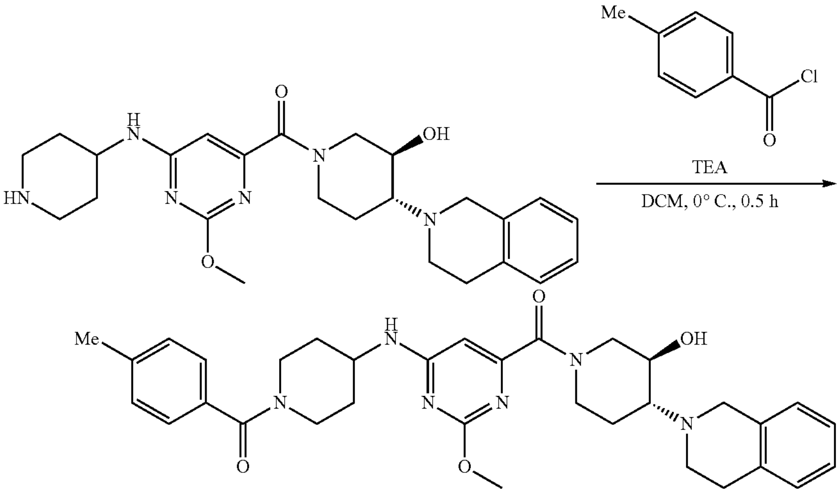

((3R,4R)-4-(3,4-dihydroisoquinoline-2(1H)-yl)-3-hydroxypiperidine-1-yl)(2-methoxy-6-(piperidine-4-ylamino)pyrimidine-4-yl)methanone (1.0 g, 2.14 mmol, 1.0 equiv.) was dissolved in dichloromethane (10 mL). Then triethylamine (1.7 g, 17.1 mmol, 8.0 equiv.) was added. The reaction was cooled down to about 0° C., and then to the reaction solution was slowly added 4-methylbenzoyl chloride (329 mg, 2.14 mmol, 1.0 equiv.). The mixture was stirred for 1 hour. Then LC-MS indicated the completion of the reaction. The reaction solution was quenched with water, and then extracted with dichloromethane. The organic phases were combined, then dried over anhydrous sodium sulfate, then filtered, and concentrated to obtain a crude product, which was separated and purified with reverse phase HPLC (C18, 10 mmol/L aqueous $NH_4HCO_3$ solution/acetonitrile) to produce the title compound (820 mg, yield: 65.5%).

LC-MS (ESI) $[M+H]^+$=585.2.

Step 5: Preparation of ((3R,4R)-4-(3,4-dihydroisoquinoline-2(1H)-yl)-3-hydroxypiperidine-1-yl)(2-methoxy-6-((1-(4-methylbenzoyl)piperidine-4-yl)amino)pyrimidine-4-yl)methanone hydrochloride

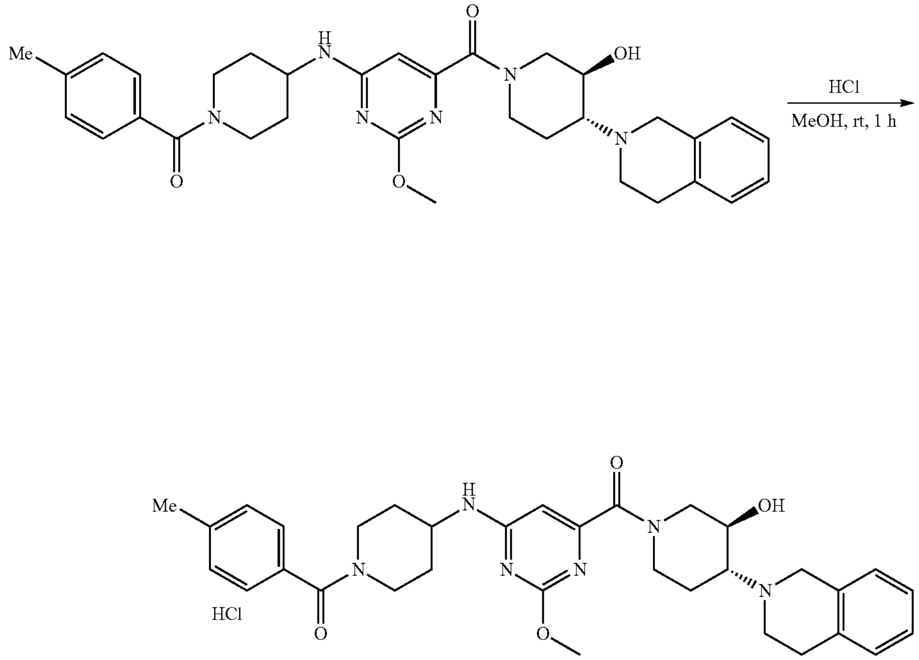

((3R,4R)-4-(3,4-dihydroisoquinoline-2(1H)-yl)-3-hydroxypiperidine-1-yl)(2-methoxy-6-((1-(4-methylbenzoyl)piperidine-4-yl)amino)pyrimidine-4-yl)methanone (820 mg, 1.40 mmol, 1.0 equiv.) was dissolved in methanol (10 mL). Then HCl (1 mol/L)(1.47 mL, 1.47 mmol, 1.05 equiv.) was added. The reaction solution was stirred at 25° C. for 1 hour. The reaction solution was concentrated, and after adding pure water for dissolving, lyophilized to produce the title compound (747.47 mg, yield: 86%).

LC-MS (ESI) $[M+H]^+$=585.2; $^1H$ NMR (400 MHz, $(CD_3)_2SO$) δ 10.58-10.47 (m, 1H), 8.10 (s, 1H), 7.29-7.20 (m, 8H), 6.49-6.14 (m, 2H), 4.70-4.32 (m, 4H), 4.13-3.98 (m, 3H), 3.84-3.75 (m, 4H), 3.56-2.65 (m, 9H), 2.39-2.17 (m, 4H), 1.92-1.81 (m, 3H), 1.43-1.42 (m, 2H).

Example 393: Preparation of ((3R,4R)-4-(3,4-dihydroisoquinoline-2(1H)-yl)-3-hydroxypiperidine-1-yl)(2-methoxy-6-((1-(1-methyl-1H-pyrazole-4-carbonyl)piperidine-4-yl)amino)pyrimidine-4-yl)methanone hydrochloride Step 1: Preparation of ((3R,4R)-4-(3,4-dihydroisoquinoline-2(1H)-yl)-3-hydroxypiperidine-1-yl)(2-methoxy-6-((1-(1-methyl-1H-pyrazole-4-carbonyl)piperidine-4-yl)amino)pyrimidine-4-yl)methanone

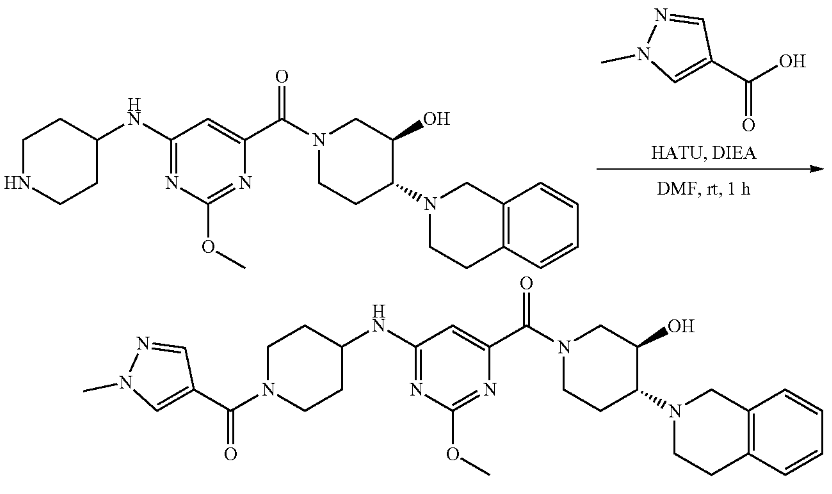

((3R,4R)-4-(3,4-dihydroisoquinoline-2(1H)-yl)-3-hydroxypiperidine-1-yl)(2-methoxy-6-(piperidine-4-ylamino)pyrimidine-4-yl)methanone (1.0 g, 2.14 mmol, 1.0 equiv.), 1-methylpyrazole-4-carboxylic acid (297 mg, 2.36 mmol, 1.1 equiv.), HATU (1.22 g, 3.21 mmol, 1.5 equiv.) and DIPEA (831 mg, 6.43 mmol, 3.0 equiv.) were dissolved in DMF (10 mL). The reaction was performed at 20° C. for 1 hour. The reaction solution was concentrated to obtain a crude product, which was separated and purified with reverse phase HPLC (C18, 10 mmol/L aqueous $NH_4HCO_3$ solution/acetonitrile) to produce the title compound (709 mg, yield: 57.7%).

LC-MS (ESI) $[M+H]^+$=575.2.

Step 2: Preparation of ((3R,4R)-4-(3,4-dihydroisoquinoline-2(1H)-yl)-3-hydroxypiperidine-1-yl)(2-methoxy-6-((1-(1-methyl-1H-pyrazole-4-carbonyl)piperidine-4-yl)aminopyrimidine-4-yl)methanone hydrochloride

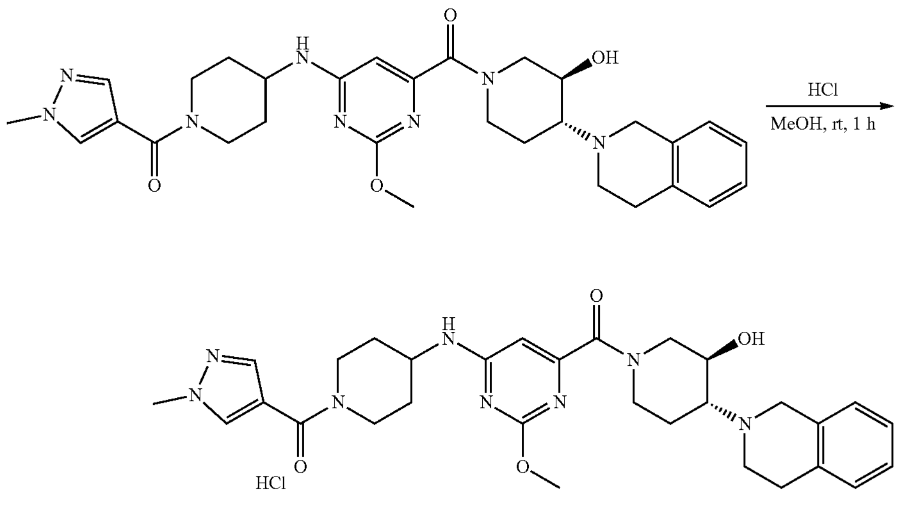

((3R,4R)-4-(3,4-dihydroisoquinoline-2(1H)-yl)-3-hydroxypiperidine-1-yl)(2-methoxy-6-((1-(1-methyl-1H-pyrazole-4-carbonyl)piperidine-4-yl)amino)pyrimidine-4-yl) methanone (709 mg, 1.23 mmol, 1.0 equiv.) was dissolved in methanol (10 mL). Then HCl (1 mol/L)(1.29 mL, 1.29 mmol, 1.05 equiv.) was added. The reaction solution was stirred at 25° C. for 1 hour. The reaction solution was concentrated, after adding pure water for dissolving, lyophilized to produce the title compound (694.42 mg, yield: 92.4%).

LC-MS (ESI) $[M+H]^+$=575.2; $^1H$ NMR (400 MHz, $(CD_3)_2SO$) δ 10.75-10.34 (m, 1H), 8.35-8.05 (m, 2H), 7.64 (s, 1H), 7.27-7.20 (m, 4H), 6.37-6.11 (m, 2H), 4.68-4.46 (m, 3H), 4.13-3.96 (m, 5H), 3.85-3.81 (m, 6H), 3.55-2.64 (m, 9H), 2.33-2.13 (m, 1H), 1.96-1.80 (m, 3H), 1.42-1.39 (m, 2H).

Example 394: Preparation of ((3R,4R)-4-(3,4-dihydroisoquinoline-2(1H)-yl)-3-hydroxypiperidine-1-yl)(6-((1-(5-methylthiazole-2-yl)piperidine-4-yl)amino)pyrimidine-4-yl)methanone hydrochloride Step 1: Preparation of ((3R,4R)-4-(3,4-dihydroisoquinoline-2(1H)-yl)-3-hydroxypiperidine-1-yl)(6-((1-(5-methylthiazole-2-yl)piperidine-4-yl)amino)pyrimidine-4-yl)methanone

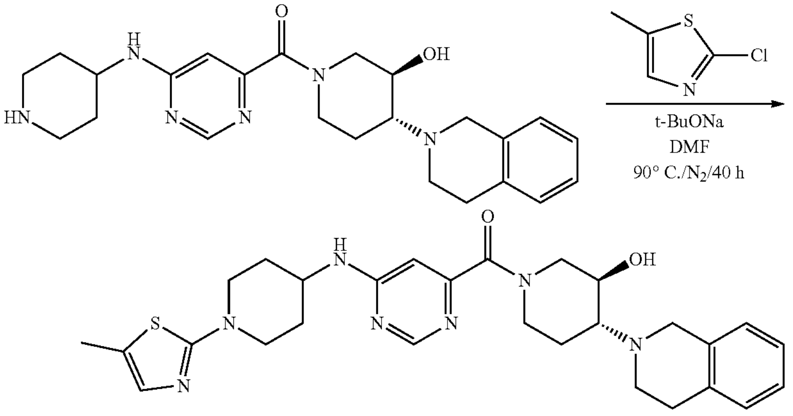

((3R,4R)-4-(3,4-dihydroisoquinoline-2(1H)-yl)-3-hydroxypiperidine-1-yl)(6-(piperidine-4-ylamino)pyrimidine-4-yl)methanone (0.52 g, 0.87 mmol, 1.0 equiv.), 2-chloro-5-methylthiazole (139 mg, 1.04 mmol, 1.2 equiv.) and sodium tert-butoxide (418 mg, 4.35 mmol, 5.0 equiv.) were dissolved in DMF (5 mL). The reaction was performed in the protection of nitrogen gas at 90° C. for 40 hours. The reaction solution was concentrated to obtain a crude product, which was purified with reverse phase Prep-HPLC (C18, 10 mmol/L aqueous $NH_4HCO_3$ solution/acetonitrile) to produce the target compound (92 mg, yield: 19.8%).

LC-MS (ESI) $[M+H]^+$=534.2.

Step 2: Preparation of ((3R,4R)-4-(3,4-dihydroisoquinoline-2(1H)-yl)-3-hydroxypiperidine-1-yl)(6-((1-(5-methylthiazole-2-yl)piperidine-4-yl)amino)pyrimidine-4-yl)methanone hydrochloride

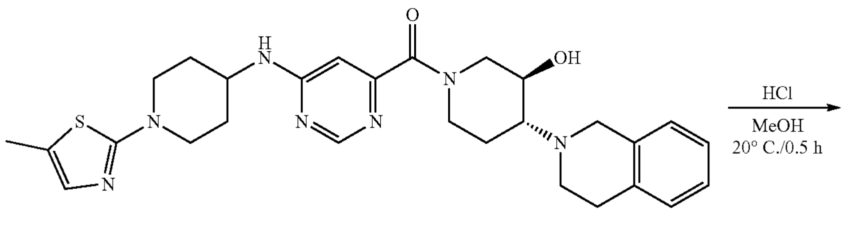

-continued

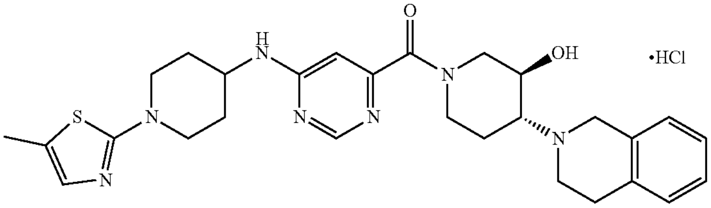

((3R,4R)-4-(3,4-dihydroisoquinoline-2(1H)-yl)-3-hydroxypiperidine-1-yl)(6-((1-(5-methylthiazole-2-yl)piperidine-4-yl)amino)pyrimidine-4-yl)methanone (92 mg, 0.17 mmol, 1.0 equiv.) and hydrochloric acid (0.1 M)(1.9 mL, 0.19 mmol, 1.1 equiv.) were dissolved in MeOH (3 mL). The reaction was performed at 20° C. for 0.5 hours. The reaction solution was concentrated to produce the target compound (83.06 mg, yield: 85.7%).

LC-MS (ESI) $[M-Cl]^+$=534.2; $^1$H NMR (400 MHz, $(CD_3)_2SO$) δ 9.11-8.85 (m, 2H), 8.54-8.31 (m, 1H), 8.07-7.82 (m, 1H), 7.30-6.96 (m, 4H), 6.92-6.57 (m, 2H), 5.22-5.01 (m, 1H), 4.81-4.36 (m, 1H), 4.25-3.96 (m, 2H), 3.89-3.61 (m, 2H), 3.32-3.25 (m, 3H), 3.20-2.87 (m, 6H), 2.82-2.59 (m, 2H), 2.28-2.19 (m, 3H), 2.09-1.65 (m, 6H).

Example 395: Preparation of ((3R,4R)-4-(3,4-dihydroisoquinoline-2(1H)-yl)-3-hydroxypiperidine-1-yl)(6-((1-(phenylsulfonyl)piperidine-4-yl)amino)pyrimidine-4-yl)methanone

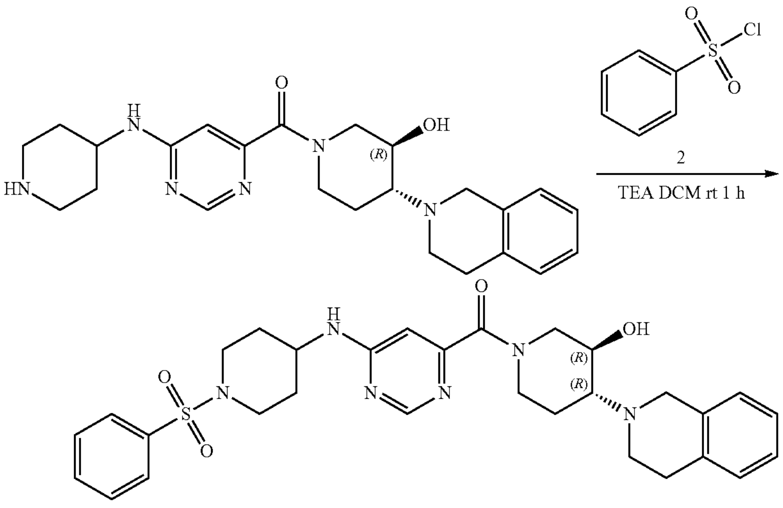

((3R,4R)-4-(3,4-dihydroisoquinoline-2(1H)-yl)-3-hydroxypiperidine-1-yl)(6-(piperidine-4-ylamino)pyrimidine-4-yl)methanone (150 mg, 0.343 mmol, 1.0 equiv.) was dissolved in dichloromethane (5 mL). Then triethylamine (42 mg, 0.412 mmol, 1.2 equiv.) was added. The reaction was cooled down to about −10° C., and then to the reaction solution was slowly added benzenesulfonyl chloride (67 mg, 0.378 mmol, 1.1 equiv.), and the temperature of the reaction system was maintained at no more than 0° C. After the completion of the addition, the reaction was gradually warmed up to room temperature (20° C.). The reaction system was stirred for 1 hour. LC-MS indicated the completion of the reaction. The reaction solution was quenched with water, and then the reaction system was concentrated to produce a crude product, which was separated and purified with reverse phase HPLC (C18, aqueous $NH_4HCO_3$ solution/acetonitrile) to produce the title compound (42 mg, yield: 21.2%).

LC-MS (ESI) $[M+H]^+$=577.2.

Example 396: Preparation of (6-((1-(cyclohexylcarbonyl)piperidine-4-yl)amino)-2-(cyclopentylthio) pyrimidine-4-yl)((3R,4R)-4-(3,4-dihydroisoquinoline-2(1H)-yl)-3-hydroxypiperidine-1-yl)methanone

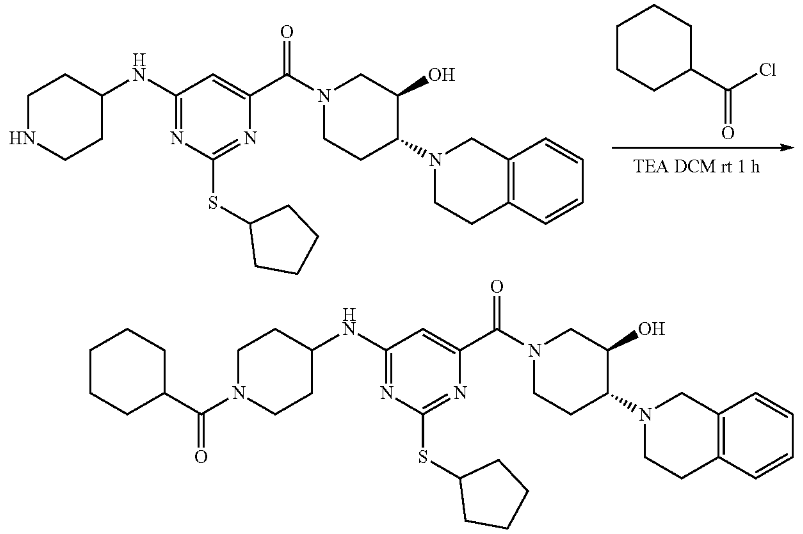

(2-(cyclopentylthio)-6-(piperidine-4-ylamino)pyrimidine-4-yl)((3R,4R)-4-(3,4-dihydroisoquinoline-2(1H)-yl)-3-hydroxypiperidine-1-yl)methanone (150 mg, 0.280 mmol, 1.0 equiv.) was dissolved in dichloromethane (5 mL). Then triethylamine (86 mg, 0.839 mmol, 3.0 equiv.) was added. The reaction was cooled down to about −10° C. Then to the reaction solution was slowly added cyclohexanecarbonyl chloride (45 mg, 0.308 mmol, 1.1 equiv.), and the temperature of the reaction system was maintained at no more than 0° C. After the completion of the addition, the reaction was gradually warmed up to room temperature (20° C.). The mixture was stirred for 1 hour. LC-MS indicated the completion of the reaction. The reaction solution was quenched with water, and then the reaction solution was concentrated to obtain a crude product, which was separated and purified with reverse phase HPLC (C18, aqueous $NH_4HCO_3$ solution/acetonitrile) to produce the title compound (50 mg, yield: 27.8%).

LC-MS (ESI) $[M+H]^+$=647.0.

Example 397: Preparation of (6-(cyclobutylamino)-2-((1-(dimethylamino)propane-2-yl)oxy)pyrimidine-4-yl)((3R,4R)-4-(3,4-dihydroisoquinoline-2(1H)-yl)-3-hydroxypiperidine-1-yl)methanone Step 1: Preparation of 6-(cyclobutylamino)-2-((1-(dimethylamino)propane-2-yl)oxy)pyrimidine-4-carboxylic acid

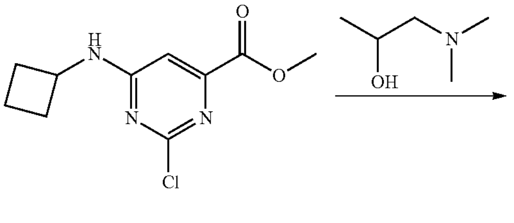

-continued

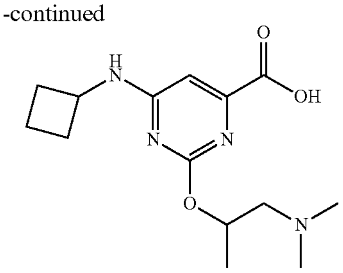

2-chloro-6-(cyclobutylamino)pyrimidine-4-carboxylic acid methyl ester (60 mg, 0.25 mmol) was dissolved in 1-(dimethylamino)propane-2-ol (770 mg, 7.50 mmol). At room temperature, para-toluene sulfonic acid (43 mg, 0.25 mmol) was added. The reaction solution was heated to 110° C., and reacted for 16 hours. After the completion of the reaction was detected with TLC, the reaction solution was purified with medium-pressure preparative chromatography to produce the title compound (30 mg, yield: 38.9%).

LC-MS (ESI) $[M+H]^+$=295.2.

Step 2: Preparation of (6-(cyclobutylamino)-2-((1-(dimethylamino)propane-2-yl)oxy)pyrimidine-4-yl) ((3R,4R)-4-(3,4-dihy droisoquinoline-2(1H)-yl)-3-hydroxypiperidine-1-yl)methanone

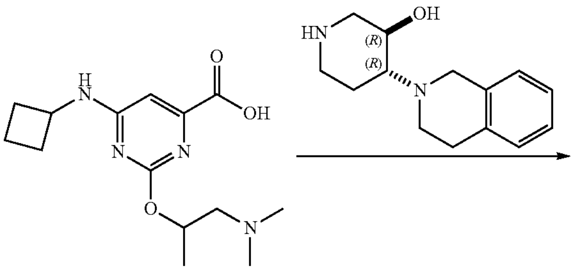

-continued

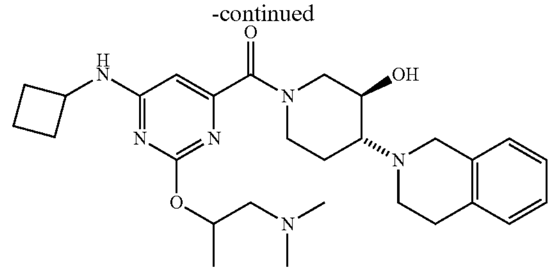

6-(cyclobutylamino)-2-((1-(dimethylamino)propane-2-yl)oxy)pyrimidine-4-carboxylic acid (30 mg, 0.102 mmol) and triethylamine (31 mg, 0.306 mmol) were dissolved in N,N-dimethyl formamide (3 mL). At room temperature, N,N,N',N'-tetramethyl-O-(7-azabenzotriazol-1-yl)uronium hexafluorophosphate (46 mg, 0.122 mmol) was added. The resulting mixture was stirred at room temperature for 10 minutes. (3R,4R)-4-(3,4-dihydroisoquinoline-2(1H)-yl)piperidine-3-ol (35.5 mg, 0.153 mmol) was added. After the completion of the addition, the resulting mixture was stirred at room temperature for 16 hours. TLC indicated the complete reaction of raw materials. Water (20 mL) and dichloromethane (20 mL) were added to the reaction system. The mixture was extracted and allowed to stand for the separation of the organic phase. The organic phase was washed with saturated brine solution three times, and then dried over anhydrous sodium sulfate to obtain a crude product, which was purified with medium-pressure preparative chromatography to produce the title compound (4.11 mg, yield: 8.1%).

LC-MS (ESI) $[M+H]^+$=509.3.

Example 398: Preparation of 1-(4-((6-((3R,4R)-4-(3,4-dihydroisoquinoline-2(1H)-yl-4',4'-dideuterium)-3-hydroxypiperidine-1-carbonyl)-2-isobutoxypyrimidine-4-yl)amino)piperidine-1-yl)ethane-1-one Step 1: Preparation of (3R,4R)-3-((tert-butoxycarbonyl)oxy)-4-(3,4-dihydroisoquinoline-2(1H)-yl) piperidine-1-carboxylic acid tert-butyl ester

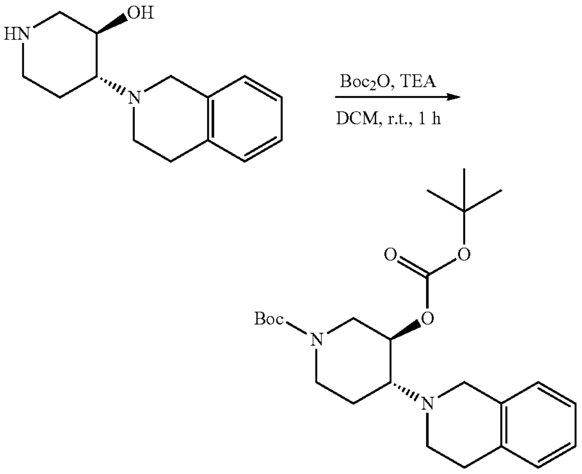

(3R,4)-4-3,4-dihydroisoquinoline-2(1H)-yl)piperidine-3-ol (I g, 4.3 mmol, 1.0 equiv.), triethylamine (1.3 g, 12.9 mmol, 3.0 equiv.) and DMAP (105 mg, 0.86 mmol, 0.2 equiv.) were dissolved in THF (20 mL). Under stirring, $Boc_2O$ (1.88 g, 8.6 mmol, 2.0 equiv.) was added. The reaction was performed at 20° C. for 1 hour. The reaction solution was concentrated, and separated and purified with column chromatography (silica gel, PE:EA=20:1) to produce the target compound (1.12 g, yield: 60%).

LC-MS (ESI) $[M+H]^+$=433.3.

Step 2: Preparation of (3R,4R)-3-((tert-butoxycarbonyl)oxy)-4-(4-oxo-3,4-dihydroisoquinoline-2(1H)-yl)piperidine-1-carboxylic acid tert-butyl ester

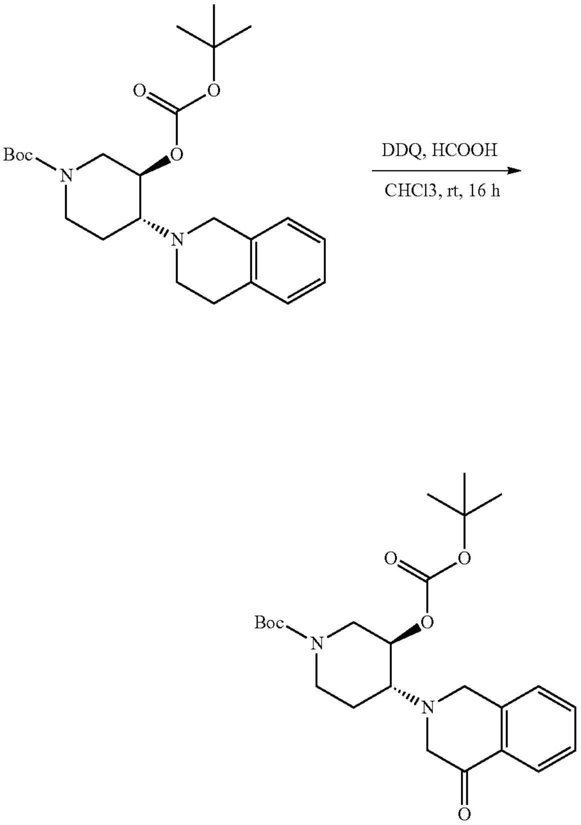 [SMILES: CC(C)(C)OC(=O)O[C@@H]1CN(C(=O)OC(C)(C)C)CC[C@H]1N1CCc2ccccc2C1 ; CC(C)(C)OC(=O)O[C@@H]1CN(C(=O)OC(C)(C)C)CC[C@H]1N1CC(=O)c2ccccc2C1]

(3R,4R)-3-((tert-butoxycarbonyl)oxy)-4-(3,4-dihydroisoquinoline-2(1H)-yl)piperidine-1-carboxylic acid tert-butyl ester (300 mg, 0.49 mmol, 1.0 equiv.) was dissolved in $CHCl_3$ (10 mL). Formic acid (451 mg, 9.8 mmol, 20.0 equiv.) and DDQ (473 mg, 2.08 mmol, 3.0 equiv.) were added. The reaction was performed at 20° C. for 16 hours. To the reaction solution was added aqueous saturated sodium carbonate solution (5 mL). The mixture was extracted with water and DCM. The organic phase was concentrated to obtain a crude product, which was separated and purified with column chromatography (silica gel, DCM: MeOH=50:1) to produce the target compound (46 mg, yield: 18%).

LC-MS (ESI) $[M+Na]^+$=469.3.

Step 3: Preparation of 2-((3R,4R)-3-hydroxypiperidine-4-yl)-2,3-dihydroisoquinoline-4(1H)-one

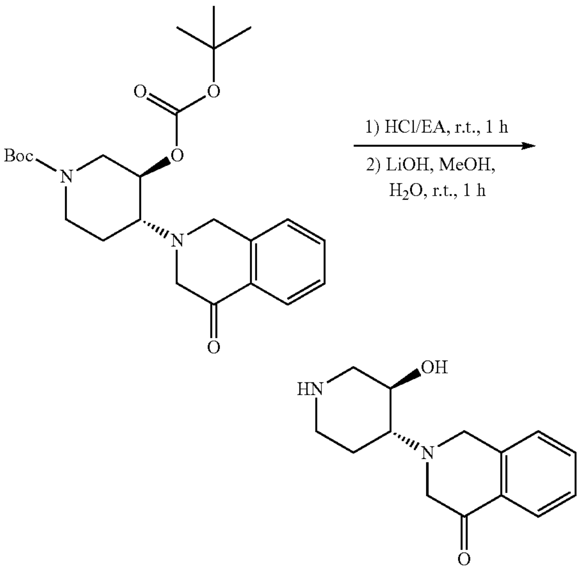

(3R,4R)-3-((tert-butoxycarbonyl)oxy)-4-(4-oxo-3,4-dihydroisoquinoline-2(1H)-yl)piperidine-1-carboxylic acid tert-butyl ester (46 mg, 0.1 mmol, 1.0 equiv.) was dissolved in EA (0.5 mL). Ethyl acetate-hydrochloric acid gas (5 mL, 4M) was added. The reaction was performed at 20° C. for 1 hour. The reaction solution was concentrated to obtain a crude product, which was dissolved in MeOH:$H_2O$ (1 mL: 1 mL). Lithium hydroxide (7 mg, 0.3 mmol, 3.0 equiv.) was added. The reaction was performed at 20° C. for 1 hour. The reaction solution was concentrated, and purified with pre-TL (silica gel, DCM:MeOH=5:1) to produce the target compound (12 mg, yield: 48%).

LC-MS (ESI) $[M+H]^+$=247.3.

Step 4: Preparation of (3R,4R)-4-(4,4-dideuterium-3,4-dihydroisoquinoline-2(1H)-yl)piperidine-3-ol

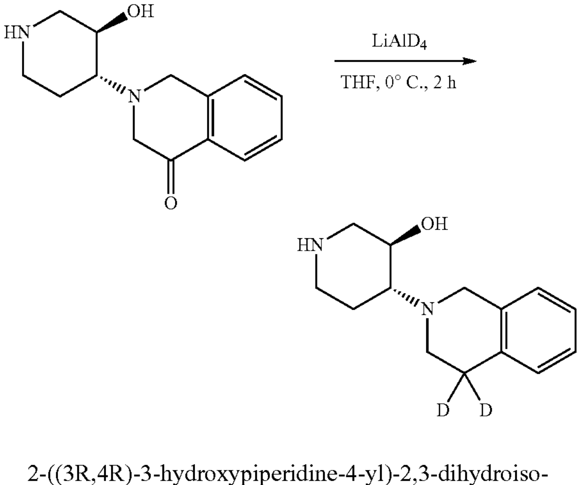

2-((3R,4R)-3-hydroxypiperidine-4-yl)-2,3-dihydroisoquinoline-4(1H)-one (4 mg, 0.016 mmol, 1.0 equiv.) was dissolved in dry THF (1 mL). $LiAlD_4$ (1.3 mg, 0.032 mmol, 2.0 equiv.) was added. The reaction was performed at 20° C. for 2 hours. The reaction solution was quenched with heavy water, and concentrated to produce the title compound (6 mg, crude).

LC-MS (ESI) $[M+H]^+$=235.1.

Step 5: Preparation of 1-(4-((6-((3R,4R)-4-(3,4-dihydroisoquinoline-2(1H)-yl-4',4'-dideuterium)-3-hydroxypiperidine-1-carbonyl)-2-isobutoxypyrimidine-4-yl)amino)piperidine-1-yl)ethane-1-one

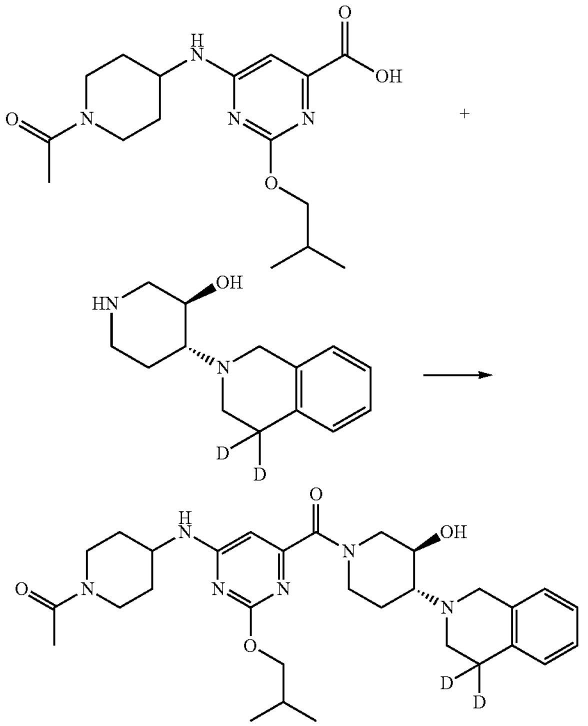

The title compound was synthesized with the process in step 3 of Example 187.

LC-MS (ESI) $[M+H]^+$=553.3.

Example 399: Preparation of 1-(4-((6-((3R,4R)-4-(3,4-dihydroisoquinoline-2(1H)-yl-4',4'-dideuterium)-3-hydroxypiperidine-1-carbonyl)-2-(pentane 3-oxy)pyrimidine-4-yl)amino)piperidine-1-yl)ethane-1-one

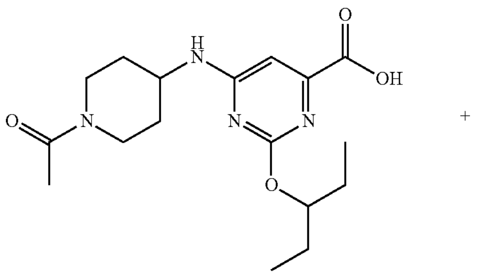

-continued

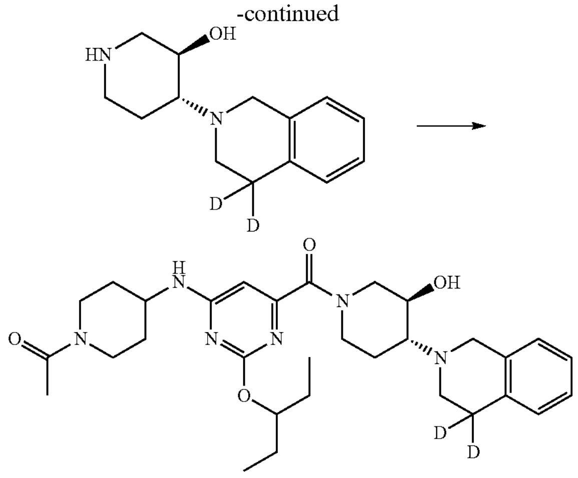

The title compound was synthesized with the intermediates and process in step 2 of Example 188.

LC-MS (ESI) $[M+H]^+$=567.4.

Example 400: Preparation of (6-((1-(cyclobutylcarbonyl)piperidine-4-yl)amino)-2-isopropoxypyrimidine-4-yl)((3R,4R)-4-(3,4-dihydroisoquinoline-2(1H)-yl-4,4-$d_2$)-3-hydroxypiperidine-1-yl)methanone

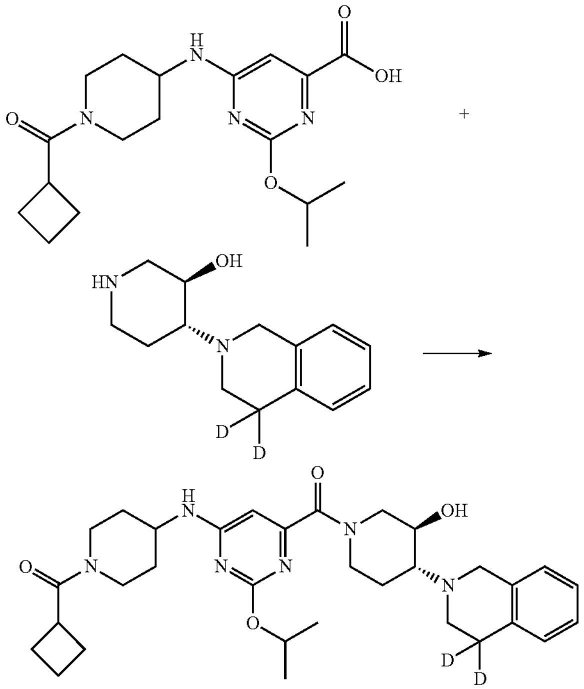

The intermediate (3R,4R)-4-(3,4-dihydroisoquinoline-2(1H)-yl)piperidine-3-ol was replaced with (3R,4R)-4-(3,4-dihydroisoquinoline-2(1H)-yl-4,4-$d_2$)piperidine-3-ol, and the title compound was synthesized with the process of Example 189.

LC-MS (ESI) $[M+H]^+$=579.4.

Example 401: Preparation of (6-((1-(benzoyl)piperidine-4-yl)amino)-2-isopropoxypyrimidine-4-yl)((3R,4R)-4-(3,4-dihydroisoquinoline-2(1H)-yl-4,4-$d_2$)-3-hydroxypiperidine-1-1)methanone

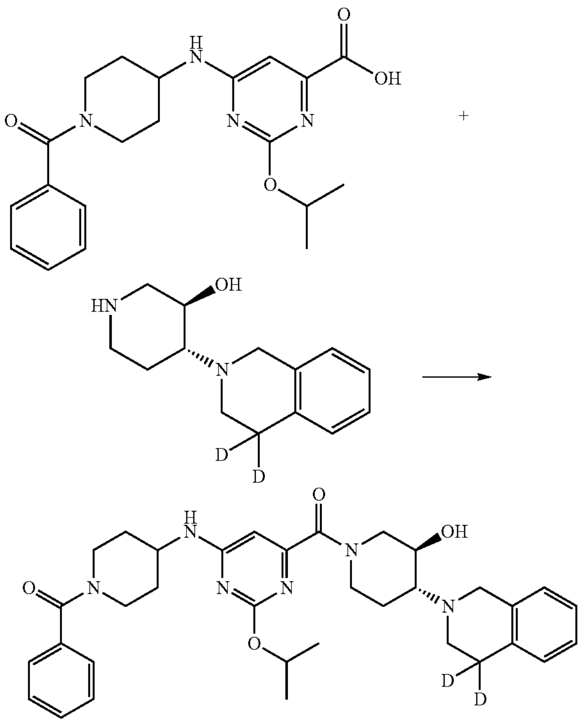

The intermediate (3R,4R)-4-(3,4-dihydroisoquinoline-2(1H)-yl)piperidine-3-ol was replaced with (3R,4R)-4-(3,4-dihydroisoquinoline-2(1H)-yl-4,4-$d_2$)piperidine-3-ol, and the title compound was synthesized with the same process of Example 183.

LC-MS (ESI) $[M+H]^+$=601.3.

Example 402: Preparation of 1-(4-((2-(tert-butylthio)-6-((3R,4R)-4-(3,4-dihydroisoquinoline-2(1H)-yl-4,4-$d_2$)-3-hydroxypiperidine-1-carbonyl)pyrimidine-4-yl)amino)piperidine-1-yl)ethane-1-one

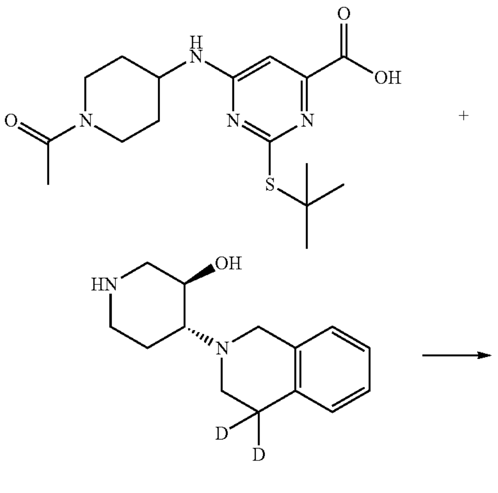

-continued

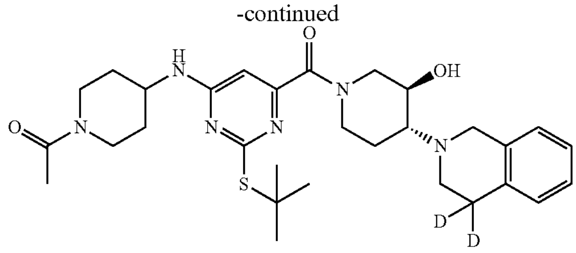

The process in step 3 of Example 187 was used, and the intermediate of Preparation Example 38 was used to produce the title compound.

LC-MS (ESI) $[M+H]^+$=569.3.

Comparative Example 1: The compound of Comparative Example 1 (1.67 g, yield: 50.0%) was obtained according to the preparation process in Example 13 of WO2020182018A1

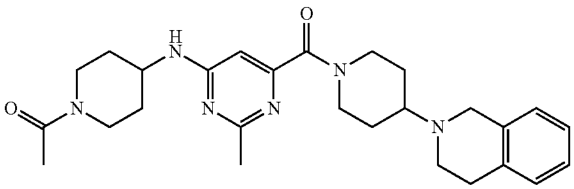 [SMILES: CC(=O)N1CCC(Nc2cc(C(=O)N3CCC(N4CCc5ccccc5C4)CC3)nc(C)n2)CC1]

LC-MS (ESI) $[M+H]^+$=477.4; $^1$H NMR (400 MHz, $CDCl_3$) δ 7.12 (dd, J=7.9, 4.6 Hz, 3H), 7.02 (d, J=5.7 Hz, 1H), 6.36 (s, 1H), 5.19 (d, J=7.7 Hz, 1H), 4.72 (d, J=13.4 Hz, 1H), 4.51 (d, J=13.3 Hz, 1H), 3.99 (d, J=13.5 Hz, 1H), 3.84 (s, 2H), 3.79 (s, 1H), 3.21 (t, J=11.8 Hz, 1H), 3.10 (t, J=12.1 Hz, 1H), 2.91 (d, J=4.1 Hz, 3H), 2.80 (d, J=10.8 Hz, 3H), 2.50 (s, 3H), 2.11 (s, 3H), 2.05 (d, J=13.7 Hz, 3H), 2.00 (s, 1H), 1.93 (d, J=11.9 Hz, 1H), 1.70 (dd, J=23.6, 11.7 Hz, 2H), 1.39 (d, J=11.3 Hz, 2H).

Comparative Example 2 (Example 403): 1-(4-((6-((3R,4R)-4-(3,4-dihydroisoquinoline-2(1H)-yl)-3-hydroxypiperidine-1-carbonyl)-2-methylpyrimidine-4-yl)amino)piperidine-1-yl)ethanone Step 1: Preparation of 6-hydroxy-2-methylpyrimidine-4-carboxylic acid

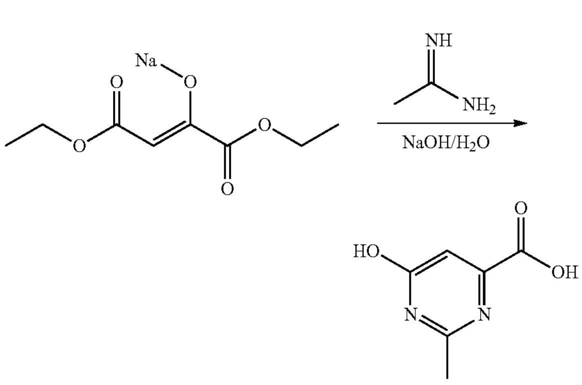

Sodium (Z)-1,4-diethoxy-1,4-dioxobut-2-en-2-olate (30 g, 142.75 mmol, 1 equiv.) was dissolved in water (50 mL). At room temperature, aqueous sodium hydroxide solution (23.6 mL, 6 mol/L) was added dropwise. At 25° C., the mixture was stirred for 1 hour. Acetimidamide (18.2 g, 314.05 mmol, 2.2 equiv.) was dissolved in water (40 mL), and then added to the reaction system. The resulting system was adjusted under ice bath with aqueous sodium hydroxide solution (6 mol/L) to pH=11. At this temperature, the stirring was continued for 40 minutes. The system was adjusted with hydrochloric acid aqueous solution (12 mol/L) to pH=1, and then filtered by suction under reduced pressure. The filter cake was washed with aqueous hydrochloric acid solution (2×50 mL, 0.1 mol/L), and dried to the target compound (9.5 g, yield: 43.2%).

LC-MS (ESI) $[M+H]^+$=155.2.

Step 2: Preparation of 6-chloro-2-methylpyrimidine-4-carbonyl chloride

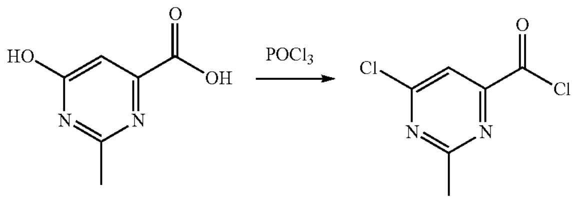

6-hydroxy-2-methylpyrimidine-4-carboxylic acid (1.5 g, 9.73 mmol, 1.0 equiv.) was added to phosphorus oxychloride (20 ml). The mixture was warmed up to 110° C. and reacted for 1 hour until the solid was completely dissolved. LC-MS detected the completion of the reaction. The system was cooled down to room temperature, and the reaction solution was concentrated under reduced pressure to obtain a crude product, which was directly used in the next reaction.

LC-MS (ESI) $[M+H]^+$=183.1.

Step 3: Preparation of (6-chloro-2-methylpyrimidine-4-yl)((3R,4R)-4-(3,4-dihydroisoquinoline-2(1H)-yl)-3-hydroxypiperidine-1-yl) methanone

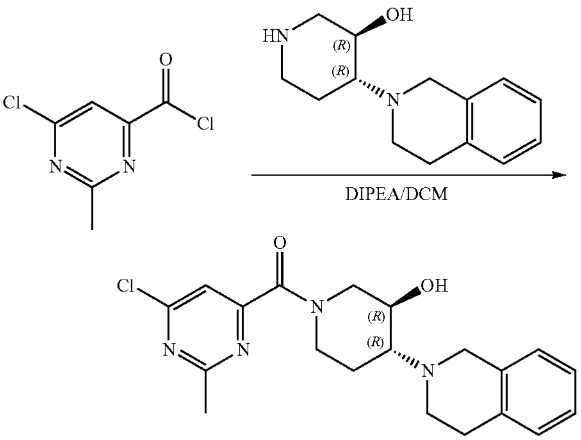

(3R,4R)-4-(3,4-dihydroisoquinoline-2(1H)-yl)piperidine-3-ol (2.19 g, 9.42 mmol, 1.2 equiv.) and DIEA (8.12 g, 62.8 mmol, 8 equiv.) were dissolved in dichloromethane (30 mL). Under ice bath, 6-chloro-2-methylpyrimidine-4-carbonyl chloride (1.5 g, 7.85 mmol, 1 equiv.)(dissolved in dichloromethane in advance) was slowly added. The mixture was stirred at 25° C. for 2 hours. Water (50 mL) was added to the reaction system. The mixture was extracted, and separated into two phases. The organic phase was concentrated. The residue was purified with column chromatography (petroleum ether:ethyl acetate=1:1) to produce the target compound (230 mg, yield: 7.5%).

LC-MS (ESI) $[M+H]^+$=387.2.

Step 4: Preparation of 1-(4-((6-((3R,4R)-4-(3,4-dihydroisoquinoline-2(1H)-yl)-3-hydroxypiperidine-1-carbonyl)-2-methylpyrimidine-4-yl)amino)piperidine-1-ylethanone

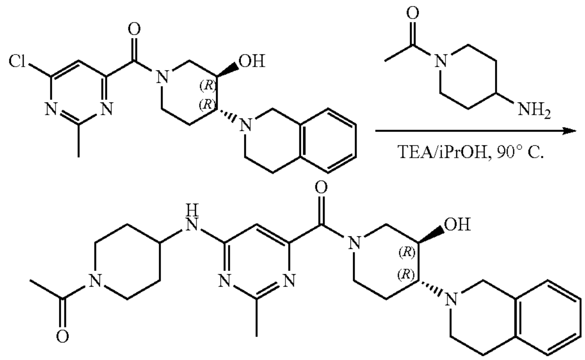

(6-chloro-2-methylpyrimidine-4-yl)((3R,4R)-4-(3,4-dihydroisoquinoline-2(1H)-yl)-3-hydroxypiperidine-1-yl) methanone (230 mg, 0.59 mmol, 1.0 equiv.), (4-aminopiperidine-1-yl)ethane-1-one (170 mg, 1.196 mmol, 2.0 equiv.) and triethylamine (421.1 mg, 4.16 mmol, 7.0 equiv.) were dissolved in isopropanol (10 mL). Then the mixture was heated to 90° C. and reacted for 2 hours. LC-MS detected the completion of the reaction. The reaction solution was extracted with ethyl acetate and water. The organic phases were combined, dried, concentrated, and purified with preparative chromatography to produce the target compound (83.7 mg, yield: 28.6%).

LC-MS (ESI) $[M+H]^+$=493.4; $^1$H NMR (400 MHz, CD3OD) δ 8.44 (s, 1H), 7.11 (d, J=18.3 Hz, 5H), 6.36 (s, 1H), 4.57 (d, J=12.5 Hz, 1H), 4.40 (d, J=12.3 Hz, 1H), 4.09 (d, J=14.8 Hz, 2H), 3.94-3.70 (m, 4H), 3.24 (s, 1H), 3.15-3.05 (m, 2H), 2.98 (s, 4H), 2.93-2.84 (m, 2H), 2.76-2.64 (m, 1H), 2.44 (d, J=8.4 Hz, 3H), 2.10 (s, 3H), 1.98 (dd, J=35.5, 21.9 Hz, 3H), 1.79-1.69 (m, 1H), 1.43 (dd, J=30.9, 12.2 Hz, 2H).

Biological Assay and Evaluation

The present invention will be further described hereinafter in combination with assay examples, but the examples are not intended to limit the scope of the present invention.

Assay Example 1. Evaluation of the inhibitory activity against PRMT5 enzyme activity 1. Assay Method:

A 1× enzyme reaction buffer (10 mM Tris 8.0 (Sigma, Cat. No. T2694-1L), 0.01% Tween-20 (Sigma, Cat. No. P2287-100ML), and 1 mM DTT (Sigma, Cat. No. D0632-10G)) was prepared. PRMT5 (Active Motif, Cat. No. 31921) and [3H]-SAM (PerkinElmer, Cat. No. NET155V001MC) were added to the 1× enzyme reactionbuffer, to prepare a 25/15× mixed solution (PRMT5 final concentration: 5 nM, [3H]-SAM final concentration: 0.3 μM). 15 L of this solution was transferred into a 384-well microplate (Corning 384-well Polypropylene Storage Microplates, Cat. No. 3657) with various concentrations of the compounds (DMSO final concentration 1%), and incubated at room temperature for 60 minutes. A polypeptide substrate, GL-27 (Ac-SGRGKGGKGLGKGGAKRHRKVGG-K) (Biotin) (GL Biochem, Cat. No. 342095), was added into the 1× enzyme reaction buffer to prepare a 25/10× substrate solution. Then 10 μL of the polypeptide substrate solution (final concentration of the polypeptide substrate: 100 nM) was added, the reaction was performed at room temperature for 120 minutes, and then 5 μL 6× ice cold SAM (Sigma, Cat. No. A7007-100MG) solution was added to stop the reaction (SAM final concentration: 0.125 mM). 25 μL of the reaction system was transferred into a FlashPlate (Streptavidin FlashPlate HTS PLUS, High Capacity, 384-well, Perkin Elmer, Cat. No. SMP410A001PK), and incubated at room temperature for 1 hour. After washed three times with distilled water containing 0.1% Tween-20, the microplate was read on a MicroBeta reader for CPM data (Counts Per Minute). After the CPM original data of the compounds at various concentrations were obtained, the data were normalized according to Inh %=(Max−Sample)/(Max−Min)*100%, and the enzyme activity inhibition rate Inh % at each concentration point was obtained (wherein Max was the CPM value of a positive well with the enzyme, Min was the CPM value of a negative well without the enzyme, and Sample was the CPM value of the sample well treated with the compounds). Then the inhibition rate Inh % (Y) corresponding to each concentration (X) was input in EXCEL, and the IC 50 value (the half inhibitory concentration) of each compound was calculated with the XLfit plug-in according to the built-in four-parameter fitting equation Y=Bottom+(Top−Bottom)/ $(1+(IC_{50}/X)*HillSlope)$.

2. Assay Results:

The compounds of examples according to the present invention had the biological activities in the PRMT5 enzymatic activity inhibition assay as showed in Table 1 below.

TABLE 1

$IC_{50}$ values of compounds inhibiting against PRMT5 enzyme activity

| Ex. | $IC_{50}$ |
|---|---|
| 1 | C |
| 2 | A |
| 3 | B |
| 4 | B |
| 5 | A |
| 6 | A |
| 7 | A |
| 8 | A |
| 9 | A |
| 10 | B |
| 11 | A |
| 12 | B |
| 13 | A |
| 14 | C |
| 15 | C |
| 16 | B |
| 17 | C |
| 18 | B |
| 19 | A |

TABLE 1-continued

| IC$_{50}$ values of compounds inhibiting against PRMT5 enzyme activity | |
|---|---|
| Ex. | IC$_{50}$ |
| 20 | A |
| 21 | A |
| 22 | A |
| 23 | B |
| 24 | B |
| 25 | A |
| 26 | B |
| 27 | A |
| 28 | A |
| 29 | B |
| 30 | B |
| 31 | D |
| 32 | B |
| 33 | A |
| 34 | A |
| 35 | A |
| 36 | B |
| 38 | A |
| 39 | A |
| 40 | A |
| 41 | A |
| 42 | A |
| 43 | B |
| 44 | A |
| 45 | B |
| 46 | B |
| 47 | D |
| 48 | A |
| 49 | A |
| 50 | A |
| 52 | B |
| 53 | C |
| 54 | B |
| 55 | B |
| 56 | B |
| 57 | D |
| 58 | C |
| 60 | C |
| 61 | A |
| 62 | A |
| 63 | A |
| 64 | D |
| 65 | B |
| 66 | B |
| 67 | B |
| 68 | A |
| 69 | A |
| 70 | C |
| 71 | B |
| 72 | A |
| 74 | B |
| 75 | B |
| 76 | C |
| 77 | C |
| 78 | C |
| 79 | B |
| 80 | C |
| 81 | C |
| 82 | A |
| 83 | A |
| 84 | B |
| 85 | B |
| 86 | B |
| 87 | B |
| 88 | A |
| 89 | B |
| 90 | B |
| 91 | D |
| 92 | B |
| 93 | A |
| 94 | B |
| 95 | B |
| 96 | A |
| 97 | A |
| 98 | B |

TABLE 1-continued

| IC$_{50}$ values of compounds inhibiting against PRMT5 enzyme activity | |
|---|---|
| Ex. | IC$_{50}$ |
| 99 | C |
| 100 | D |
| 101 | D |
| 102 | D |
| 103 | D |
| 104 | D |
| 105 | D |
| 106 | D |
| 107 | B |
| 108 | D |
| 109 | D |
| 110 | D |
| 111 | D |
| 112 | B |
| 113 | B |
| 114 | A |
| 115 | D |
| 116 | D |
| 117 | D |
| 118 | D |
| 119 | D |
| 120 | D |
| 121 | D |
| 122 | D |
| 123 | D |
| 124 | D |
| 125 | D |
| 126 | B |
| 127 | D |
| 128 | D |
| 129 | A |
| 130 | D |
| 131 | A |
| 132 | B |
| 133 | D |
| 134 | B |
| 135 | D |
| 136 | B |
| 138 | D |
| 139 | A |
| 140 | B |
| 141 | C |
| 142 | A |
| 143 | A |
| 144 | A |
| 145 | A |
| 146 | B |
| 147 | B |
| 148 | B |
| 149 | B |
| 150 | A |
| 151 | C |
| 152 | C |
| 153 | A |
| 154 | C |
| 155 | A |
| 156 | A |
| 157 | B |
| 158 | A |
| 159 | B |
| 160 | A |
| 161 | B |
| 162 | A |
| 163 | A |
| 164 | C |
| 165 | B |
| 166 | B |
| 167 | B |
| 168 | B |
| 169 | B |
| 170 | B |
| 171 | A |
| 172 | B |
| 173 | C |
| 174 | A |

TABLE 1-continued

| IC$_{50}$ values of compounds inhibiting against PRMT5 enzyme activity | |
|---|---|
| Ex. | IC$_{50}$ |
| 176 | B |
| 177 | B |
| 178 | A |
| 179 | B |
| 180 | A |
| 182 | B |
| 183 | A |
| 184 | B |
| 185 | A |
| 186 | B |
| 187 | A |
| 188 | A |
| 189 | A |
| 190 | A |
| 191 | A |
| 192 | A |
| 193 | A |
| 194 | A |
| 195 | B |
| 196 | A |
| 197 | A |
| 198 | A |
| 199 | A |
| 200 | A |
| 201 | B |
| 202 | A |
| 203 | B |
| 204 | A |
| 205 | A |
| 206 | A |
| 207 | A |
| 208 | A |
| 209 | A |
| 210 | A |
| 211 | B |
| 212 | A |
| 213 | A |
| 214 | A |
| 215 | A |
| 216 | A |
| 217 | A |
| 218 | A |
| 219 | A |
| 220 | A |
| 221 | C |
| 222 | B |
| 223 | A |
| 224 | B |
| 225 | A |
| 226 | A |
| 227 | A |
| 228 | A |
| 229 | B |
| 230 | B |
| 231 | B |
| 232 | A |
| 233 | A |
| 234 | B |
| 235 | B |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | A |
| 249 | B |
| 250 | A |
| 251 | A |

TABLE 1-continued

| IC$_{50}$ values of compounds inhibiting against PRMT5 enzyme activity | |
|---|---|
| Ex. | IC$_{50}$ |
| 252 | D |
| 253 | A |
| 254 | D |
| 255 | A |
| 256 | A |
| 257 | A |
| 258 | D |
| 259 | A |
| 260 | B |
| 261 | B |
| 262 | D |
| 263 | D |
| 264 | A |
| 265 | C |
| 266 | A |
| 267 | B |
| 268 | C |
| 269 | A |
| 270 | C |
| 271 | A |
| 272 | A |
| 273 | A |
| 274 | A |
| 275 | A |
| 276 | A |
| 277 | A |
| 278 | A |
| 279 | A |
| 281 | A |
| 282 | A |
| 283 | A |
| 284 | A |
| 285 | A |
| 286 | B |
| 287 | A |
| 288 | A |
| 289 | D |
| 290 | A |
| 291 | B |
| 292 | A |
| 293 | A |
| 294 | A |
| 295 | A |
| 296 | A |
| 297 | A |
| 298 | A |
| 299 | B |
| 301 | B |
| 302 | A |
| 303 | D |
| 304 | A |
| 305 | A |
| 306 | A |
| 307 | B |
| 308 | A |
| 309 | A |
| 310 | A |
| 311 | A |
| 313 | A |
| 314 | A |
| 315 | A |
| 316 | A |
| 318 | A |
| 319 | D |
| 320 | D |
| 321 | A |
| 322 | C |
| 323 | B |
| 324 | D |
| 325 | D |
| 326 | B |
| 327 | B |
| 328 | A |
| 329 | A |
| 330 | A |

TABLE 1-continued

| IC$_{50}$ values of compounds inhibiting against PRMT5 enzyme activity | |
|---|---|
| Ex. | IC$_{50}$ |
| 331 | B |
| 332 | B |
| 334 | A |
| 335 | B |
| 336 | C |
| 337 | C |
| 338 | A |
| 339 | A |
| 340 | B |
| 341 | A |
| 342 | A |
| 343 | A |
| 344 | A |
| 345 | A |
| 347 | B |
| 348 | B |
| 349 | D |
| 350 | C |
| 351 | A |
| 352 | B |
| 353 | A |
| 354 | A |
| 355 | A |
| 356 | A |
| 357 | A |
| 358 | A |
| 359 | A |
| 360 | B |
| 361 | B |
| 362 | A |
| 363 | B |
| 364 | C |
| 365 | B |
| 366 | A |
| 367 | A |
| 368 | B |
| 369 | B |
| 370 | B |
| 372 | C |
| 373 | B |
| 374 | B |
| 375 | C |
| 376 | D |
| 377 | D |
| 378 | D |
| 379 | D |
| 380 | A |
| 381 | D |
| 382 | B |
| 383 | B |
| 384 | B |
| 385 | B |
| 386 | B |
| 387 | D |
| 388 | D |
| 389 | A |
| 391 | A |
| 392 | A |
| 393 | A |
| 398 | A |
| 400 | A |

TABLE 1-continued

| IC$_{50}$ values of compounds inhibiting against PRMT5 enzyme activity | |
|---|---|
| Ex. | IC$_{50}$ |
| 401 | A |
| 402 | A |
| Comp. 1 | D |
| Comp. 2 | B |

Note:
A represents IC$_{50}$ ≤ 20 nM; B represents 20 nM < IC$_{50}$ ≤ 50 nM; C represents 50 nM < IC$_{50}$ ≤ 100 nM; D represents IC$_{50}$ > 100 nM.

3. Assay conclusion:

As shown in the table above, the compounds of the present invention exhibited different inhibitory activities on the PRMT5 enzyme activity. some compounds could have level D of the measured enzyme inhibitory IC$_{50}$ values (for example, 99.80 nM for compound of Example 37, 107.00 nM for compound of Example 59, and 110.00 nM for compound of Example 73), some compounds could have level C of the measured enzyme inhibitory IC$_{50}$ values (for example, 65.00 nM for compound of Example 1, 66.40 nM for compound of Example 70, and 51.25 nM for compound of Example 173), some compounds could have level B of the measured enzyme inhibitory IC$_{50}$ values (for example, 35.20 nM for compound of Example 12, 29.15 nM for compound of Example 46, and 20.54 nM for compound of Example 172), and some compounds could even have level A of the measured enzyme inhibitory IC$_{50}$ values (for example, 6.97 nM for compound of Example 153, 6.40 nM for compound of Example 183, 6.40 nM for compound of Example 193, 4.50 nM for compound of Example 194, 5.20 nM for compound of Example 202, 3.90 nM for compound of Example 207, 4.50 nM for compound of Example 213, 4.70 nM for compound of Example 315, 2.80 nM for compound of Example 392, and 7.90 nM for compound of Example 401), all of which were significantly better than or equivalent to the compound of Control Example 1 that reached level D (i.e., compound 13 of WO2020182018A1, which had a measured IC$_{50}$ value of 115.00 nM).

In addition, compared with the compound of Control Example 1, the compound of Control Example 2 could reached level B of the measured enzyme inhibitory IC$_{50}$ values (its measured IC$_{50}$ value was 36.00 nM), indicating that the hydroxyl substitution at the specific position of the piperidine ring and trans-type disubstitution configuration at 3,4-positions are the key for the compounds of the present invention to exhibit excellent the inhibitory activity on the enzyme activity. Assay

Example 2: Evaluation of Growth Inhibitory Activity of Human B-Cell Non-Hodgkin Lymphoma Z-138 Cells

1. Experimental Materials and Instruments

1) Cell Lines and Culture Methods

| Cell line | Supplier | Catalog number | Tumor type | Characteristics of growth | Culture method |
|---|---|---|---|---|---|
| Z-138 | ATCC | CRL-3001 | Mantle cell lymphoma (B-cell non-Hodgkin lymphoma) | Suspension | IMDM + 10% FBS |

2) Culture Medium and Reagent

| Culture medium and reagent | Manufacturer | Catalog number |
|---|---|---|
| IMDM | GIBCO | 31980048 |
| FBS | Hyclone | SH30084.03 |
| penicillin streptomycin | Thermo | SV30010 |
| DMSO | SIGMA | D2650 |
| Promega CellTiter-Glo Luminescence Cell Viability Detection Kit | Promega | Promega-G7573 |

3) 384-Well Plate

Corning® 384-well clear flat-bottom white polystyrene microplate (lidded, sterile), Corning, Cat. No. 3765.

4) Instruments

2104 EnVision plate reader, PerkinElmer;

Vi-Cell XR cell counter, Beckmancoulter.

2. Experimental Methods and Procedures

1) Cell Culture

Cells were revived and cultured in an incubator at 37° C./5% CO2 according to the above-mentioned culturing conditions.

Periodical passaging was performed, and cell lines with good growth status in about two generations were taken for plating.

2) Cell Plating

I. Cells were taken from the incubator. The cell suspension was transferred to a 50 mL centrifuge tube, and centrifuged at 800-1000 rpm for 3-5 minutes. The supernatant was discarded. An appropriate volume of culture medium was added to the centrifuge tube and gently beated to resuspend the cells evenly. Cells were counted using a Vi-Cell XR cell counter.

II. According to the measured cell density, the cell suspension was adjusted to an appropriate concentration.

III. The cell suspension was added into the 384-well plate, 40 μL/well, containing 700 cells/well, and an equal volume of culture medium without cells was added to the blank control well.

3) Formulating and Dosing the Compounds

I. A compound was dissolved in 100% DMSO to formulate a 10 mM stock solution.

II. The stock solution with a concentration of 10 mM was taken, diluted with DMSO to a 2 mM solution, which was used as the starting concentration to perform a 4× gradient dilution with DMSO for 9 points.

III. 200 nL of the above compound solutions in gradient concentrations were taken and added to each well respectively. To the blank control well and the DMSO control well were respectively added 200 nL DMSO solutions, and the final concentration of DMSO was 0.5%.

IV. The cell plate was incubated in a carbon dioxide incubator for 5 days (120H).

4) Reagent Preparation and Testing

Detection was performed according to the operation instructions of Promega CellTiter-Glo Luminescence Cell Viability Detection Kit (Promega-$G^{7573}$):

I. CellTiter-Glo buffer was thawed and allowed to come to room temperature.

II. A lyophilized CellTiter-Glo substrate was allowed to come to room temperature.

III. CellTiter-Glo buffer was added to a bottle of CellTiter-Glo substrate to dissolve the substrate to formulate a CellTiter-Glo working solution.

IV. The working solution was slowly vortexed to fully dissolve the contents.

V. The cell culture plate was taken and allowed to equilibrate to room temperature.

VI. 25 μl of a mixed CellTiter Glo reagent was added to each well, oscillated for 10 minutes in the dark, and incubated for 10 minutes.

VII. The luminescence signal was detected on the 2104 EnVision plate reader.

3. Data Analysis

The inhibition rates (IRs) of the detected compounds were calculated according to the following formula:

$$IR\ (\%)=(1-(RLU_{compound}-RLU_{blank\ control})/(RLU_{DMSO}-RLU_{blank\ control}))*100\%,$$

XLFit was used to plot the efficacy inhibition rate curve, and the $IC_{50}$ value was calculated using the following 4-parameter model: [fit=(A±((B−A)/(1+((C/x)^D))))].

4. Experimental Results

The compounds of examples according to the present invention had the biological activities in the Z-138 cell growth inhibition assay as showed in Table 2 below.

TABLE 2

$IC_{50}$ values of compounds inhibiting against Z-138 cell growth

| Ex. | $IC_{50}$ |
|---|---|
| 5 | A |
| 6 | D |
| 8 | A |
| 9 | A |
| 10 | D |
| 11 | B |
| 12 | E |
| 13 | A |
| 19 | B |
| 20 | B |
| 21 | B |
| 22 | B |
| 23 | C |
| 25 | A |
| 26 | B |
| 27 | B |
| 28 | B |
| 29 | E |
| 30 | C |
| 31 | D |
| 32 | C |
| 33 | C |
| 34 | B |
| 35 | B |
| 36 | D |
| 37 | D |
| 38 | C |
| 39 | D |
| 40 | B |
| 41 | D |

TABLE 2-continued

| IC$_{50}$ values of compounds inhibiting against Z-138 cell growth | |
|---|---|
| Ex. | IC$_{50}$ |
| 42 | B |
| 43 | C |
| 44 | B |
| 45 | E |
| 46 | B |
| 48 | B |
| 49 | C |
| 50 | B |
| 54 | D |
| 55 | C |
| 56 | C |
| 60 | C |
| 61 | A |
| 62 | A |
| 63 | A |
| 64 | E |
| Comp. 1 | E |
| 65 | C |
| 67 | D |
| 68 | A |
| 69 | A |
| 70 | E |
| 71 | D |
| 90 | B |
| 110 | B |
| 129 | E |
| 136 | D |
| 138 | E |
| 140 | C |
| 142 | A |
| 143 | B |
| 144 | A |
| 145 | B |
| 146 | C |
| 147 | D |
| 148 | D |
| 149 | D |
| 150 | A |
| 151 | E |
| 153 | A |
| 154 | E |
| 155 | D |
| 156 | B |
| 157 | C |
| 158 | A |
| 159 | D |
| 160 | C |
| 161 | B |
| 162 | A |
| 163 | A |
| 164 | E |
| 165 | B |
| 166 | A |
| 167 | B |
| 168 | B |
| 169 | B |
| 170 | C |
| 171 | A |
| 172 | A |
| 173 | B |
| 174 | B |
| 176 | E |
| 177 | B |
| Comp. 2 | \ |
| 178 | B |
| 179 | C |
| 180 | A |
| 182 | C |
| 183 | B |
| 184 | D |
| 185 | D |
| 187 | A |
| 188 | A |
| 189 | A |
| 190 | A |
| 191 | A |

TABLE 2-continued

| IC$_{50}$ values of compounds inhibiting against Z-138 cell growth | |
|---|---|
| Ex. | IC$_{50}$ |
| 192 | A |
| 193 | A |
| 194 | A |
| 195 | B |
| 196 | A |
| 197 | A |
| 198 | A |
| 199 | A |
| 200 | A |
| 201 | C |
| 202 | A |
| 203 | A |
| 204 | A |
| 205 | B |
| 206 | B |
| 207 | A |
| 208 | A |
| 209 | A |
| 210 | A |
| 211 | D |
| 212 | B |
| 213 | A |
| 214 | B |
| 215 | D |
| 216 | A |
| 217 | C |
| 218 | B |
| 219 | D |
| 220 | A |
| 221 | D |
| 222 | B |
| 223 | A |
| 224 | C |
| 225 | A |
| 226 | B |
| 227 | A |
| 228 | A |
| 229 | C |
| 230 | C |
| 231 | B |
| 232 | B |
| 233 | D |
| 234 | B |
| 235 | B |
| 236 | B |
| 237 | D |
| 238 | D |
| 241 | A |
| 242 | A |
| 243 | A |
| 244 | A |
| 245 | A |
| 246 | A |
| 247 | A |
| 248 | B |
| 249 | E |
| 250 | A |
| 251 | B |
| 253 | A |
| 255 | A |
| 256 | B |
| 257 | E |
| 259 | E |
| 260 | E |
| 261 | C |
| 263 | E |
| 264 | D |
| 267 | C |
| 269 | C |
| 271 | A |
| 272 | D |
| 273 | A |
| 274 | B |
| 275 | A |
| 276 | D |
| 277 | A |

TABLE 2-continued

IC$_{50}$ values of compounds inhibiting against Z-138 cell growth

| Ex. | IC$_{50}$ |
|---|---|
| 278 | B |
| 279 | A |
| 281 | D |
| 282 | A |
| 283 | B |
| 284 | A |
| 285 | D |
| 286 | B |
| 287 | B |
| 288 | D |
| 289 | E |
| 290 | D |
| 291 | E |
| 292 | A |
| 293 | B |
| 294 | A |
| 295 | B |
| 301 | D |
| 302 | A |
| 303 | E |
| 304 | B |
| 305 | B |
| 306 | A |
| 307 | D |
| 308 | B |
| 309 | A |
| 310 | A |
| 311 | A |
| 313 | C |
| 314 | D |
| 315 | B |
| 316 | B |
| 318 | A |
| 321 | A |
| 323 | B |
| 326 | B |
| 327 | C |
| 328 | A |
| 329 | A |
| 330 | B |
| 331 | C |
| 332 | D |
| 334 | B |
| 335 | E |
| 336 | D |
| 337 | D |
| 338 | D |
| 339 | C |
| 340 | D |
| 341 | D |
| 342 | D |
| 343 | D |
| 344 | B |
| 345 | D |
| 348 | D |
| 350 | E |
| 351 | D |
| 352 | B |
| 353 | B |
| 354 | A |
| 355 | A |
| 356 | A |
| 357 | A |
| 358 | A |
| 359 | C |
| 360 | B |
| 361 | D |
| 362 | A |
| 363 | D |
| 365 | D |
| 366 | B |
| 368 | D |
| 369 | D |
| 370 | D |
| 373 | C |
| 374 | D |
| 376 | E |
| 377 | E |
| 378 | D |
| 379 | E |
| 380 | D |
| 381 | D |
| 382 | D |
| 383 | D |
| 384 | D |
| 385 | D |
| 386 | C |
| 387 | E |
| 388 | E |
| 389 | D |
| 391 | C |
| 392 | A |
| 393 | B |
| 398 | B |
| 400 | B |
| 401 | A |
| 402 | B |

Note:
A represents IC$_{50}$ ≤ 20 nM; B represents 20 nM < IC$_{50}$ ≤ 50 nM; C represents 50 nM < IC$_{50}$ ≤ 100 nM; D represents represents 100 nM < IC$_{50}$ ≤ 1000 nM; E represents IC$_{50}$ > 1000 nM; \ represents NOT measured.

5. Assay Conclusion

As shown in the table above, the compounds of the present invention exhibited different inhibitory activities on the Z-138 cell growth. Some compounds could have level E of the measured cell growth inhibitory IC$_{50}$ values (for example, 1325.00 nM for compound of Example 45, 1358.00 nM for compound of Example 66, and 1190.00 nM for compound of Example 259), some compounds could have level D of the measured cell growth inhibitory IC$_{50}$ values (for example, 134.70 nM for compound of Example 39, 157.00 nM for compound of Example 215, and 111.00 nM for compound of Example 276), some compounds could have level C of the measured cell growth inhibitory IC$_{50}$ values (for example, 62.80 nM for compound of Example 170, 60.50 nM for compound of Example 217, and 65.30 nM for compound of Example 339), some compounds could have level B of the measured cell growth inhibitory IC$_{50}$ values (for example, 33.70 nM for compound of Example 165, 46.60 nM for compound of Example 183, and 22.22 nM for compound of Example 212), some compounds could even have level A of the measured cell growth inhibitory IC$_{50}$ values (for example, 13.75 nM for compound of Example 153, 19.00 nM for compound of Example 158, 11.50 nM for compound of Example 171, 11.00 nM for compound of Example 194, 8.00 nM for compound of Example 202, 12.00 nM for compound of Example 207, 5.80 nM for compound of Example 243, 7.40 nM for compound of Example 253, 12.30 nM for compound of Example 392, and 16.00 nM for compound of Example 401), all of which were significantly better than or equivalent to the compound of Control Example 1 that reached level E (i.e., compound 13 of WO2020182018A1, which had a measured IC$_{50}$ value of 2709.60 nM).

The invention claimed is:

1. A compound represented by formula (III), or stereoisomer, geometric isomer, tautomer, pharmaceutical salt, prodrug, hydrate, solvate, or isotope-labeled analogue thereof:

(III)

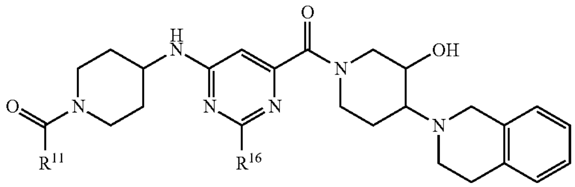

wherein, $R^{16}$ is selected from hydrogen, deuterium, halogen, hydroxy, mercapto, amino, cyano, —$R^9$, —$OR^9$, —$SR^9$, —$NH(R^9)$ and —$N(R^9)(R^{10})$;

at each occurrence, $R^9$ and $R^{10}$ are each independently selected from C1-6alkyl and C3-6cycloalkyl, or $R^9$ and $R^{10}$ together with the N atom to which they are connected form 4-6 membered heterocyclyl;

$R^{11}$ is selected from C6-8aryl and 5-6 membered heteroaryl, and the aryl or heteroaryl is optionally substituted by one or more of halogen, C1-6alkyl, and trifluoromethyl;

the heterocyclyl or heteroaryl contains 1, 2 or 3 heteroatoms, which are each independently selected from N, O and S.

2. The compound represented by formula (III) according to claim 1, or stereoisomer, geometric isomer, tautomer, pharmaceutical salt, hydrate, solvate, or isotope-labeled analogue thereof, wherein $R^{16}$ is selected from hydrogen, deuterium, —$R^9$, —$OR^9$, —$SR^9$ and —$N(R^9)(R^{10})$, wherein $R^9$ and $R^{10}$ are as defined in claim 1.

3. The compound represented by formula (III) according to claim 1, or stereoisomer, geometric isomer, tautomer, pharmaceutical salt, hydrate, solvate, or isotope-labeled analogue thereof, wherein $R^{11}$ is selected from phenyl, pyrrolyl, furyl, thienyl, imidazolyl, pyrazolyl, oxazolyl, isoxazolyl, thiazolyl, isothiazolyl, pyridyl, pyrimidinyl, pyridazinyl and pyrazinyl, wherein the phenyl, pyrrolyl, furyl, thienyl, imidazolyl, pyrazolyl, oxazolyl, isoxazolyl, thiazolyl, isothiazolyl, pyridyl, pyrimidinyl, pyridazinyl or pyrazinyl is optionally substituted by one or more of halogen, methyl, and trifluoromethyl.

4. The compound represented by formula (III) according to claim 1, or stereoisomer, geometric isomer, tautomer, pharmaceutical salt, hydrate, solvate, or isotope-labeled analogue thereof, wherein the compound represented by formula (III) has a structure represented by formula (III)A or formula (III)B:

(III)A

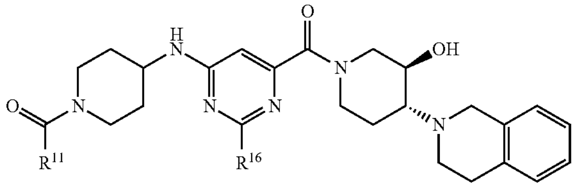

-continued (III)B

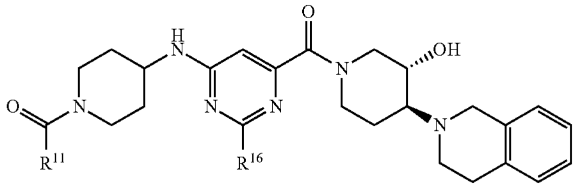

wherein $R^{11}$ and $R^{16}$ are as defined in claim 1.

5. A pharmaceutical composition, which contains a compound according to claim 1, or stereoisomer, geometric isomer, tautomer, pharmaceutical salt, hydrate, solvate, or isotope-labeled analogue thereof.

6. A method for preventing and/or treating PRMT5-mediated diseases, which includes administering a therapeutically effective dose of the compound according to claim 1, or stereoisomer, geometric isomer, tautomer, pharmaceutical salt, hydrate, solvate, or isotope-labeled analogue thereof to a patient.

7. A pharmaceutical combination, comprising the compound according to claim 1, or stereoisomer, geometric isomer, tautomer, pharmaceutical salt, hydrate, solvate, or isotope-labeled analogue thereof, and an additional anticancer agent or immune checkpoint inhibitor.

8. The compound represented by formula (III) according to claim 1, or stereoisomer, geometric isomer, tautomer, pharmaceutical salt, hydrate, solvate, or isotope-labeled analogue thereof, wherein $R^{16}$ is selected from hydrogen, deuterium, —$OCH_3$, —$OCH_2CH_3$, —$OCH(CH_3)_2$, —$OCH_2CH(CH_3)_2$, —$OC(CH_3)_3$, —$OCH(CH_2CH_3)_2$, —O-cyclopropyl, —O-cyclobutyl, —O-cyclopentyl, —O-cyclohexyl, —$SCH_3$, —$SCH_2CH_3$, —$SCH(CH_3)_2$, —$SCH_2CH(CH_3)_2$, —$SC(CH_3)_3$, —$SCH(CH_2CH_3)_2$, —S-cyclopropyl, —S-cyclobutyl, —S-cyclopentyl, —S-cyclohexyl, azetidin-1-yl, pyrrolidin-1-yl, piperidine-1-yl and 3-azabicyclo [3.1.0] hexan-3-yl.

9. The compound represented by formula (III) according to claim 1, or stereoisomer, geometric isomer, tautomer, pharmaceutical salt, hydrate, solvate, or isotope-labeled analogue thereof, wherein $R^{11}$ is selected from phenyl, 2-fluorophenyl, 3-fluorophenyl, 4-fluorophenyl, 2-methylphenyl, 3-methylphenyl, 4-methylphenyl, 2-(trifluoromethyl)phenyl, 3-(trifluoromethyl)phenyl, 4-(trifluoromethyl)phenyl, thien-2-yl, thien-3-yl, 1-methyl-1H-pyrazol-3-yl, 1-methyl-1H-pyrazol-4-yl, 1-methyl-1H-pyrazol-5-yl, isoxazol-3-yl, isoxazol-4-yl, isoxazol-5-yl, thiazol-2-yl, thiazol-4-yl, thiazol-5-yl, pyridin-2-yl, pyridin-3-yl, pyridin-4-yl, pyrimidin-2-yl, pyrimidin-4-yl and pyrimidin-5-yl.

10. The compound represented by formula (III) according to claim 1, or stereoisomer, geometric isomer, tautomer, pharmaceutical salt, hydrate, solvate, or isotope-labeled analogue thereof, wherein the compound is selected from compounds 183, 193, 194, 202, 207, 212, 213, 214, 216, 217, 218, 220, 223, 228, 236, 243, 245, 247, 253, 269, 274, 275, 282, 284, 287, 293, 294, 315, 316, 328, 344, 356, 392, 393, and 401:

| No. | Structures |
|---|---|
| 183 | 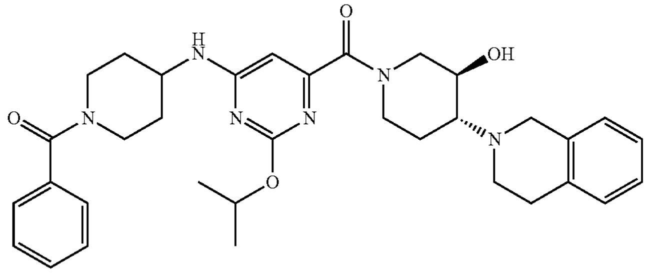 [SMILES: CC(C)Oc1nc(NC2CCN(C(=O)c3ccccc3)CC2)cc(C(=O)N2CC[C@@H](N3CCc4ccccc4C3)[C@H](O)C2)n1] |
| 193 | 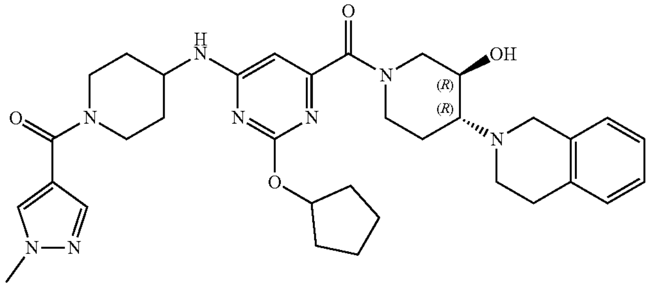 |
| 194 | 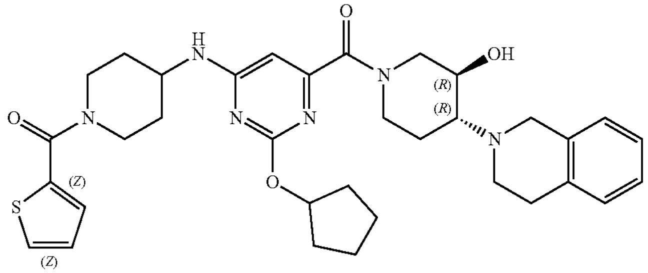 |
| 202 | 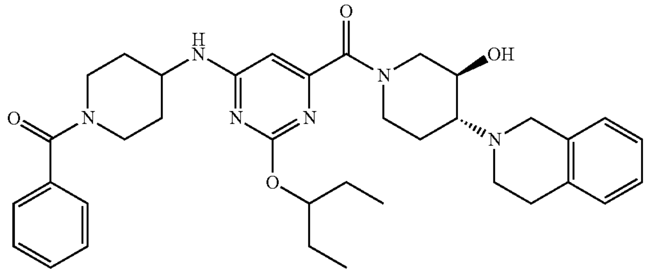 [SMILES: CCC(CC)Oc1nc(NC2CCN(C(=O)c3ccccc3)CC2)cc(C(=O)N2CC[C@@H](N3CCc4ccccc4C3)[C@H](O)C2)n1] |
| 207 | 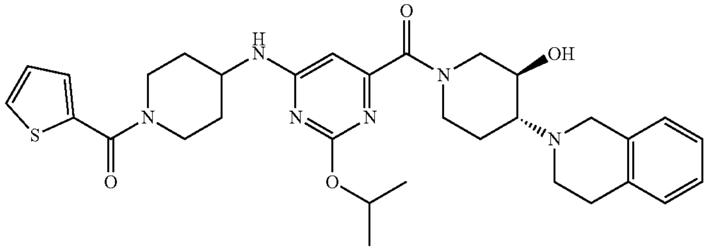 [SMILES: CC(C)Oc1nc(NC2CCN(C(=O)c3cccs3)CC2)cc(C(=O)N2CC[C@@H](N3CCc4ccccc4C3)[C@H](O)C2)n1] |

-continued
| No. | Structures |
|---|---|
| 212 | 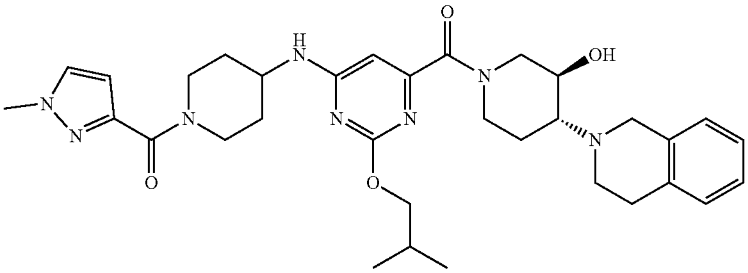 [SMILES: CC(C)COc1nc(NC2CCN(C(=O)c3ccn(C)n3)CC2)cc(C(=O)N2CC[C@@H](N3CCc4ccccc4C3)[C@H](O)C2)n1] |
| 213 | 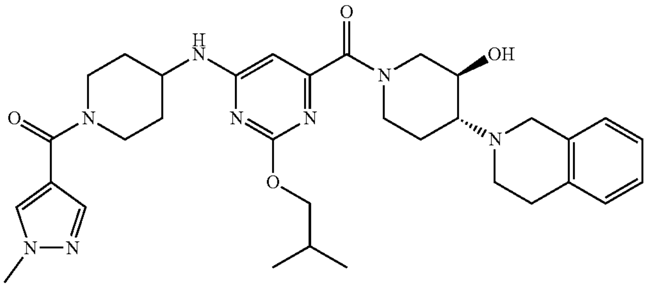 [SMILES: CC(C)COc1nc(NC2CCN(C(=O)c3cnn(C)c3)CC2)cc(C(=O)N2CC[C@@H](N3CCc4ccccc4C3)[C@H](O)C2)n1] |
| 214 | 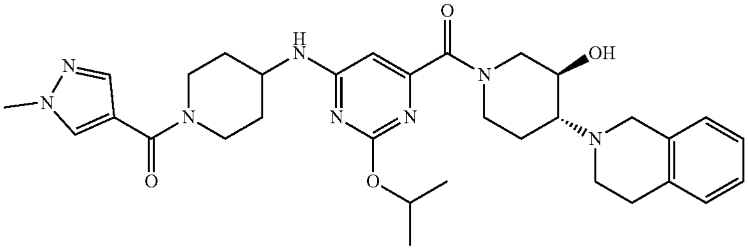 [SMILES: CC(C)Oc1nc(NC2CCN(C(=O)c3cnn(C)c3)CC2)cc(C(=O)N2CC[C@@H](N3CCc4ccccc4C3)[C@H](O)C2)n1] |
| 216 | 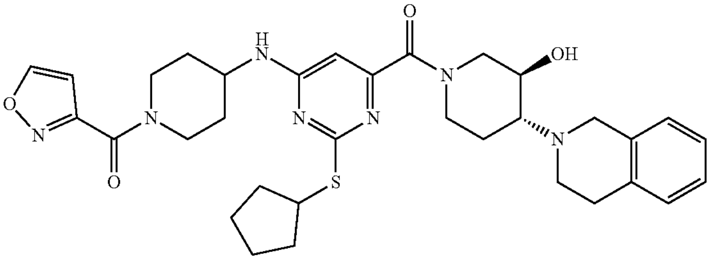 [SMILES: O=C(c1ccon1)N1CCC(Nc2cc(C(=O)N3CC[C@@H](N4CCc5ccccc5C4)[C@H](O)C3)nc(SC3CCCC3)n2)CC1] |
| 217 | 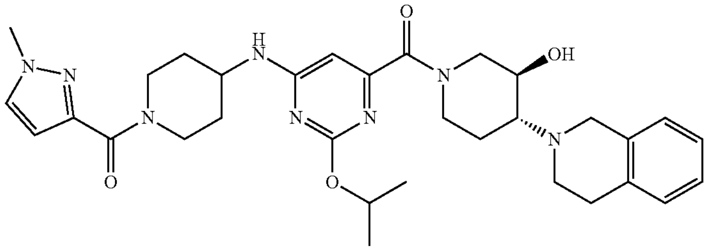 [SMILES: CC(C)Oc1nc(NC2CCN(C(=O)c3ccn(C)n3)CC2)cc(C(=O)N2CC[C@@H](N3CCc4ccccc4C3)[C@H](O)C2)n1] |

-continued
| No. | Structures |
| --- | --- |
| 218 | 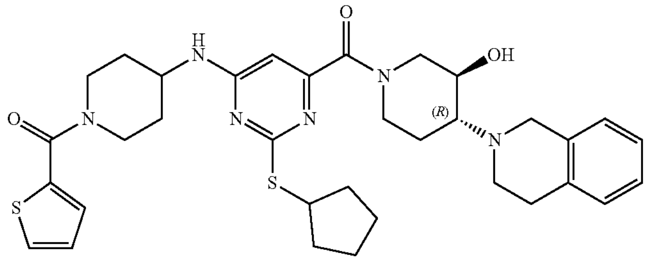 |
| 220 | 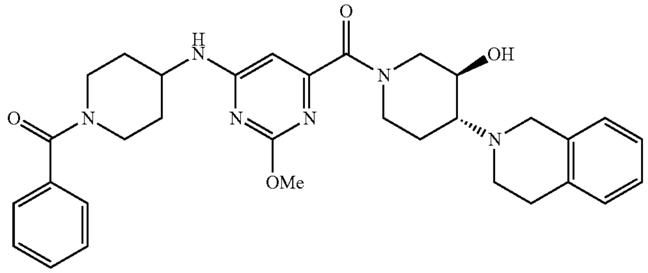 [SMILES: COc1nc(NC2CCN(C(=O)c3ccccc3)CC2)cc(C(=O)N2CC[C@@H](N3CCc4ccccc4C3)[C@H](O)C2)n1] |
| 223 | 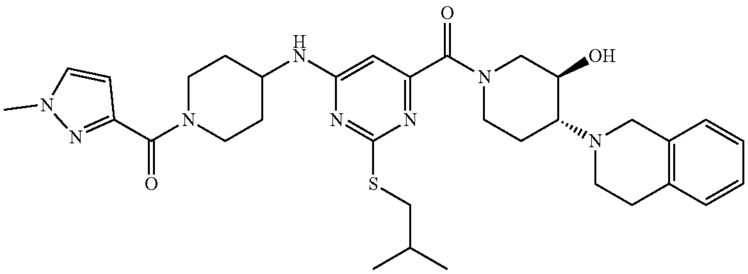 |
| 228 | 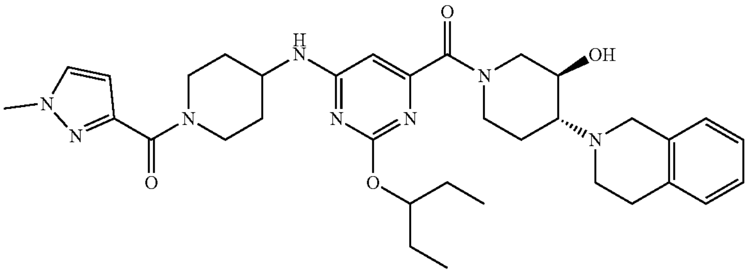 [SMILES: CCC(CC)Oc1nc(NC2CCN(C(=O)c3ccn(C)n3)CC2)cc(C(=O)N2CC[C@@H](N3CCc4ccccc4C3)[C@H](O)C2)n1] |
| 236 | 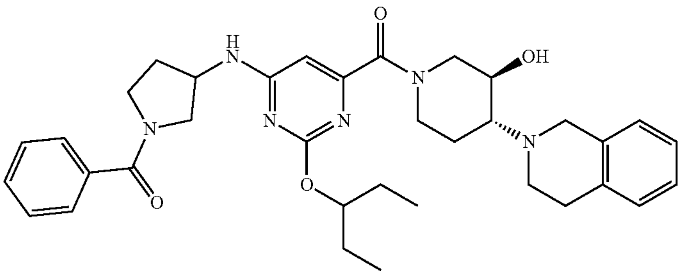 [SMILES: CCC(CC)Oc1nc(NC2CCN(C(=O)c3ccccc3)C2)cc(C(=O)N2CC[C@@H](N3CCc4ccccc4C3)[C@H](O)C2)n1] |

-continued
| No. | Structures |
|---|---|
| 243 | 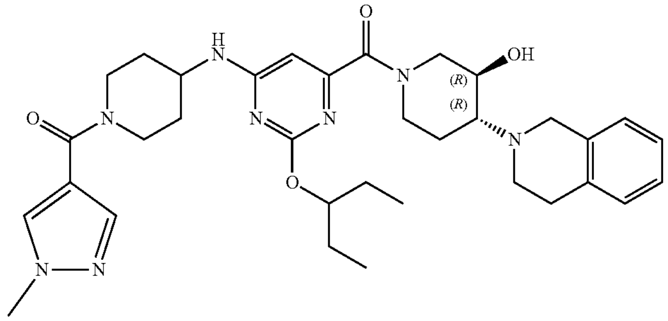 |
| 245 | 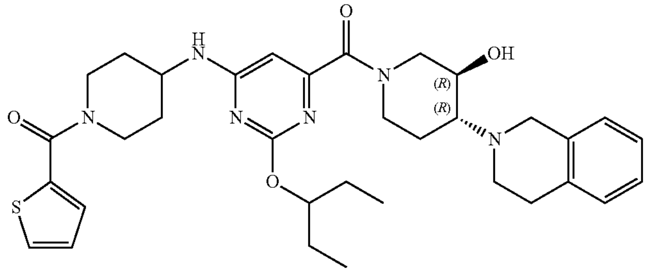 |
| 247 | 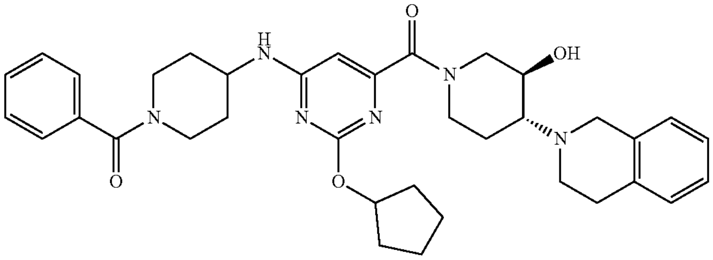 [SMILES: O=C(c1ccccc1)N1CCC(Nc2cc(C(=O)N3CC[C@@H](N4CCc5ccccc5C4)[C@H](O)C3)nc(OC3CCCC3)n2)CC1] |
| 253 | 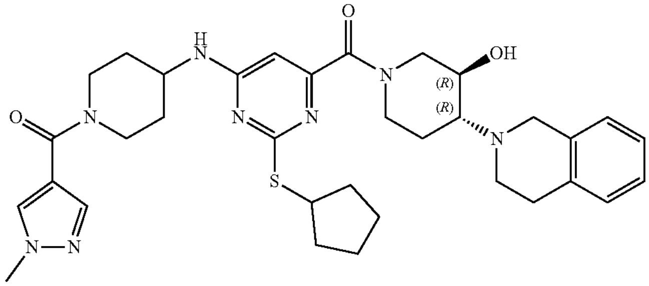 |
| 269 | 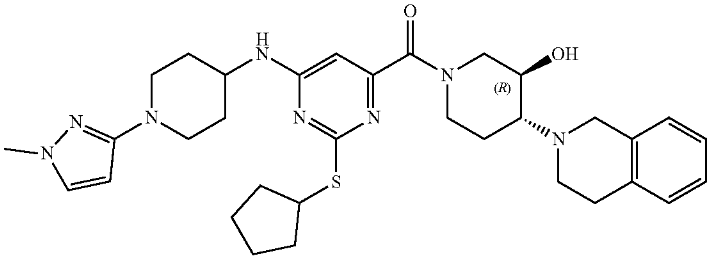 |

-continued
| No. | Structures |
|---|---|
| 274 | 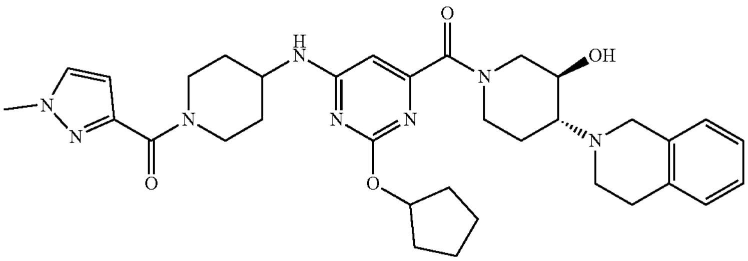 |
| 275 | 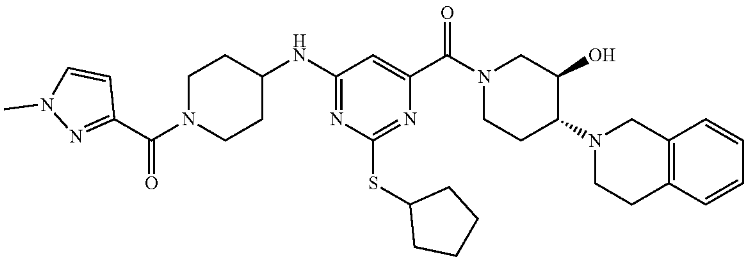 |
| 282 | 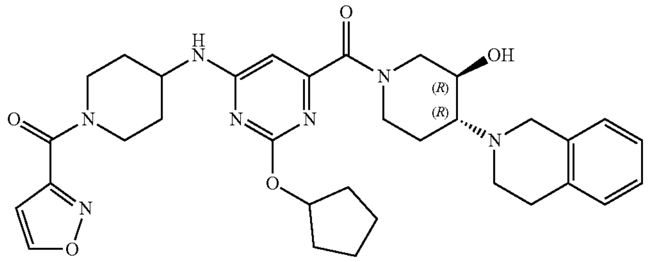 |
| 284 | 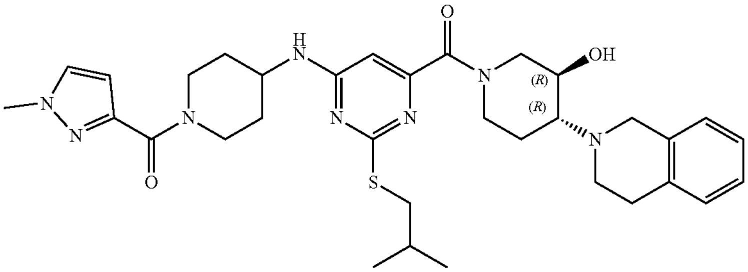 |
| 287 | 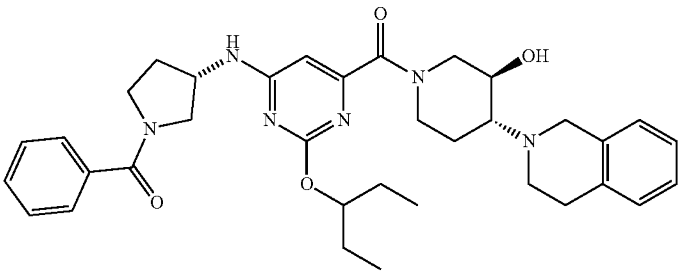 [SMILES: CCC(CC)Oc1nc(N[C@H]2CCN(C(=O)c3ccccc3)C2)cc(C(=O)N2CC[C@@H](N3CCc4ccccc4C3)[C@H](O)C2)n1] |

-continued
| No. | Structures |
| --- | --- |
| 293 | 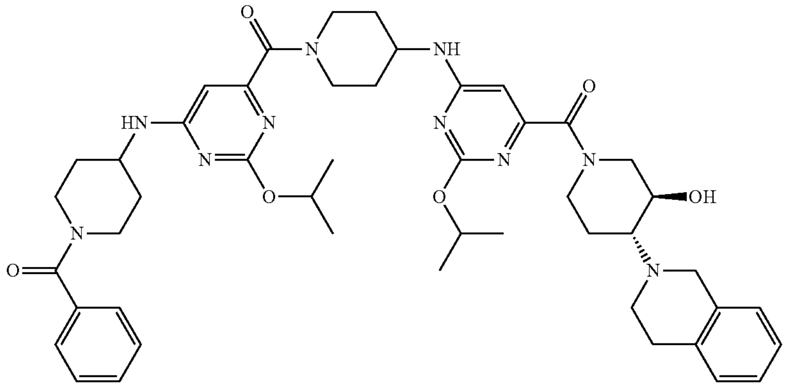 [SMILES: CC(C)Oc1nc(NC2CCN(C(=O)c3ccccc3)CC2)cc(C(=O)N2CCC(Nc3cc(C(=O)N4CC[C@@H](N5CCc6ccccc6C5)[C@H](O)C4)nc(OC(C)C)n3)CC2)n1] |
| 294 | 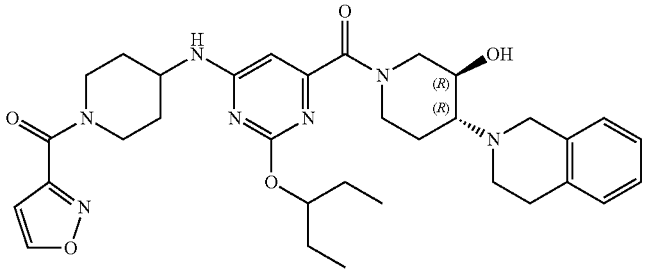 |
| 315 | 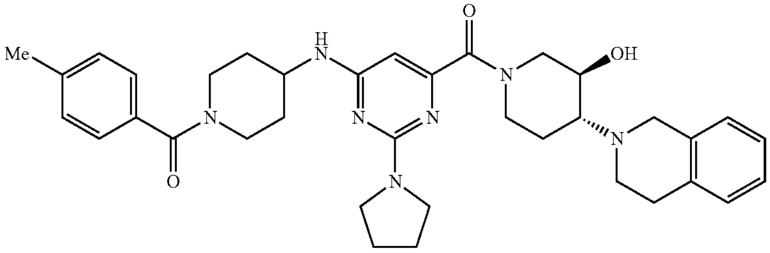 [SMILES: Cc1ccc(C(=O)N2CCC(Nc3cc(C(=O)N4CC[C@@H](N5CCc6ccccc6C5)[C@H](O)C4)nc(N4CCCC4)n3)CC2)cc1] |
| 316 | 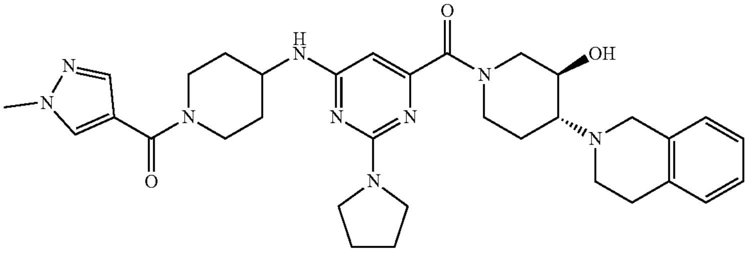 [SMILES: Cn1cc(C(=O)N2CCC(Nc3cc(C(=O)N4CC[C@@H](N5CCc6ccccc6C5)[C@H](O)C4)nc(N4CCCC4)n3)CC2)cn1] |
| 328 | 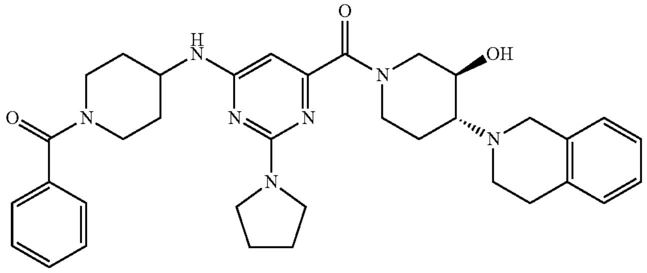 [SMILES: O=C(c1ccccc1)N1CCC(Nc2cc(C(=O)N3CC[C@@H](N4CCc5ccccc5C4)[C@H](O)C3)nc(N3CCCC3)n2)CC1] |

-continued
| No. | Structures |
| --- | --- |
| 344 | 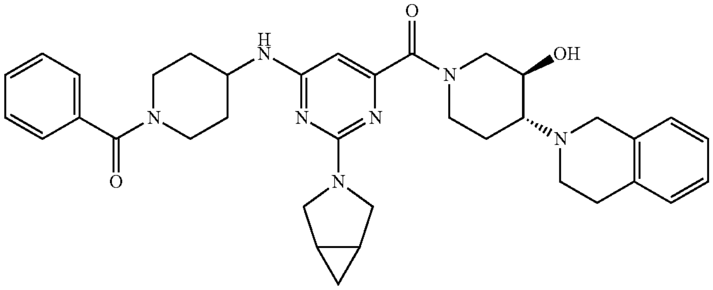 [SMILES: O=C(c1ccccc1)N1CCC(Nc2cc(C(=O)N3CC[C@@H](N4CCc5ccccc5C4)[C@H](O)C3)nc(N3CC4CC4C3)n2)CC1] |
| 356 | 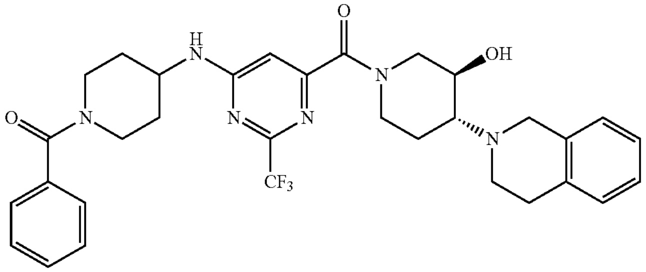 [SMILES: O=C(c1ccccc1)N1CCC(Nc2cc(C(=O)N3CC[C@@H](N4CCc5ccccc5C4)[C@H](O)C3)nc(C(F)(F)F)n2)CC1] |
| 392 | 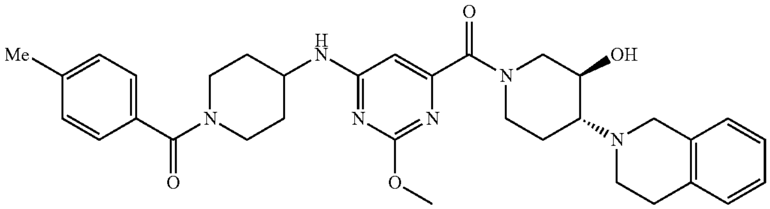 [SMILES: COc1nc(NC2CCN(C(=O)c3ccc(C)cc3)CC2)cc(C(=O)N2CC[C@@H](N3CCc4ccccc4C3)[C@H](O)C2)n1] |
| 393 | 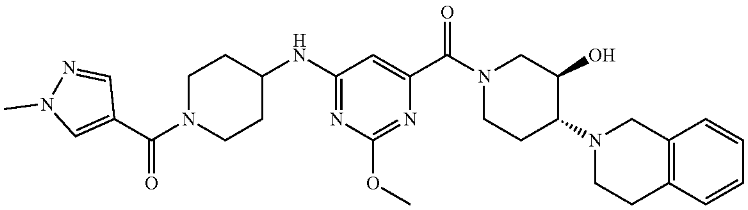 [SMILES: COc1nc(NC2CCN(C(=O)c3cnn(C)c3)CC2)cc(C(=O)N2CC[C@@H](N3CCc4ccccc4C3)[C@H](O)C2)n1] |
| 401 | 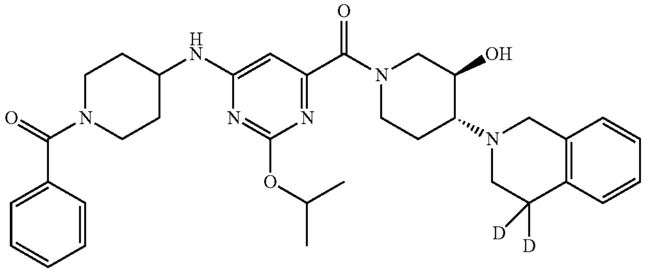 [SMILES: [2H]C1([2H])CN([C@@H]2CCN(C(=O)c3cc(NC4CCN(C(=O)c5ccccc5)CC4)nc(OC(C)C)n3)C[C@H]2O)Cc2ccccc21] |
11. The method of claim 6, wherein the PRMT5-mediated disease is cancer or a tumor-related disease.
12. The method of claim 6, wherein the PRMT5-mediated disease is lymphoma.
* * * * *